US011896615B2

United States Patent
Ports et al.

(10) Patent No.: US 11,896,615 B2
(45) Date of Patent: Feb. 13, 2024

(54) IMMUNOTHERAPY METHODS AND COMPOSITIONS INVOLVING TRYPTOPHAN METABOLIC PATHWAY MODULATORS

(71) Applicant: Juno Therapeutics, Inc., Seattle, WA (US)

(72) Inventors: Michael Ports, Seattle, WA (US); Evan Paul Thomas, Seattle, WA (US); Hyam I. Levitsky, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 551 days.

(21) Appl. No.: 16/340,085

(22) PCT Filed: Oct. 13, 2017

(86) PCT No.: PCT/US2017/056680
§ 371 (c)(1),
(2) Date: Apr. 5, 2019

(87) PCT Pub. No.: WO2018/071873
PCT Pub. Date: Apr. 19, 2018

(65) Prior Publication Data
US 2020/0054673 A1 Feb. 20, 2020

Related U.S. Application Data

(60) Provisional application No. 62/514,767, filed on Jun. 2, 2017, provisional application No. 62/407,776, filed on Oct. 13, 2016.

(51) Int. Cl.
| | |
|---|---|
| *C12N 5/07* | (2010.01) |
| *A61K 35/17* | (2015.01) |
| *A61K 31/4245* | (2006.01) |
| *C07K 14/725* | (2006.01) |
| *C12N 5/0783* | (2010.01) |
| *C12N 15/90* | (2006.01) |
| *G01N 33/574* | (2006.01) |

(52) U.S. Cl.
CPC .......... *A61K 35/17* (2013.01); *A61K 31/4245* (2013.01); *C07K 14/7051* (2013.01); *C12N 5/0636* (2013.01); *C12N 15/907* (2013.01); *G01N 33/57496* (2013.01); *C07K 2319/03* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,452,773 A | 6/1984 | Molday | |
| 4,501,728 A | 2/1985 | Geho et al. | |
| 4,690,915 A | 9/1987 | Rosenberg | |
| 4,795,698 A | 1/1989 | Owen et al. | |
| 4,837,028 A | 6/1989 | Allen | |
| 4,897,355 A | 1/1990 | Eppstein et al. | |
| 4,946,787 A | 8/1990 | Eppstein et al. | |
| 5,019,369 A | 5/1991 | Presant et al. | |
| 5,049,386 A | 9/1991 | Eppstein et al. | |
| 5,200,084 A | 4/1993 | Liberti et al. | |
| 5,219,740 A | 6/1993 | Miller et al. | |
| 5,356,802 A | 10/1994 | Chandrasegaran et al. | |
| 5,436,150 A | 7/1995 | Chandrasegaran | |
| 5,487,994 A | 1/1996 | Chandrasegaran | |
| 6,040,177 A | 3/2000 | Riddell et al. | |
| 6,140,081 A | 10/2000 | Barbas | |
| 6,207,453 B1 | 3/2001 | Maass et al. | |
| 6,410,319 B1 | 6/2002 | Raubitschek et al. | |
| 6,451,995 B1 | 9/2002 | Cheung et al. | |
| 6,453,242 B1 | 9/2002 | Eisenberg et al. | |
| 6,503,717 B2 | 1/2003 | Case et al. | |
| 6,534,261 B1 | 3/2003 | Cox et al. | |

(Continued)

FOREIGN PATENT DOCUMENTS

| | | |
|---|---|---|
| CN | 102579452 | 7/2012 |
| CN | 103070868 | 5/2013 |

(Continued)

OTHER PUBLICATIONS

US 8,252,592 B2, 08/2012, Sadelain (withdrawn)

(Continued)

*Primary Examiner* — Maria G Leavitt
(74) *Attorney, Agent, or Firm* — Morrison & Foerster LLP

(57) ABSTRACT

Provided are methods of treatment involving immunotherapy, such as T cell therapy, and administration of a tryptophan metabolism and/or kynurenine pathway modulator. In some embodiments, the method includes a combination therapy that involves administration of engineered T cells, such as chimeric antigen receptor (CAR)-expressing cells, and a tryptophan metabolism and/or kynurenine pathway modulator, such as an inhibitor of an enzyme. Also provided are engineered cells in which the expression of a molecule involved in the kynurenine pathway is modified. Also provided are methods of manufacturing engineered cells, cells, compositions, methods of administration to subjects, nucleic acids and kits for use in the methods. In some aspects, features of the methods and cells provide for increased or improved activity, activity, outcome, function, response, persistence, expansion and/or proliferation of cells for adoptive cell therapy.

22 Claims, 44 Drawing Sheets
Specification includes a Sequence Listing.

(56) References Cited

U.S. PATENT DOCUMENTS

| | | |
|---|---|---|
| 6,599,692 B1 | 7/2003 | Case et al. |
| 6,689,558 B2 | 2/2004 | Case |
| 6,794,136 B1 | 9/2004 | Eisenberg et al. |
| 7,030,215 B2 | 4/2006 | Liu et al. |
| 7,067,317 B2 | 6/2006 | Rebar et al. |
| 7,070,934 B2 | 7/2006 | Cox et al. |
| 7,070,995 B2 | 7/2006 | Jensen |
| 7,098,209 B2 | 8/2006 | Orme et al. |
| 7,253,273 B2 | 8/2007 | Collingwood |
| 7,262,054 B2 | 8/2007 | Jamieson et al. |
| 7,265,209 B2 | 9/2007 | Jensen |
| 7,354,762 B2 | 4/2008 | Jensen |
| 7,361,635 B2 | 4/2008 | Miller et al. |
| 7,446,179 B2 | 11/2008 | Jensen et al. |
| 7,446,190 B2 | 11/2008 | Sadelain et al. |
| 7,446,191 B2 | 11/2008 | Jensen |
| 8,324,353 B2 | 12/2012 | Jensen |
| 8,339,645 B2 | 12/2012 | Nakawaki |
| 8,389,282 B2 | 3/2013 | Sadelain et al. |
| 8,465,743 B2 | 6/2013 | Rosenberg et al. |
| 8,479,118 B2 | 7/2013 | Lindersay |
| 8,710,237 B2 | 4/2014 | Muchowski et al. |
| 8,802,374 B2 | 8/2014 | Jensen |
| 8,822,647 B2 | 9/2014 | Jensen |
| 8,911,993 B2 | 12/2014 | June et al. |
| 11,020,429 B2 | 6/2021 | Juno |
| 2002/0131960 A1 | 9/2002 | Sadelain et al. |
| 2003/0170238 A1 | 9/2003 | Gruenberg et al. |
| 2005/0064474 A1 | 3/2005 | Urnov et al. |
| 2005/0186289 A1 | 8/2005 | Munn et al. |
| 2005/0267061 A1 | 12/2005 | Martin |
| 2006/0188987 A1 | 8/2006 | Guschin et al. |
| 2006/0292618 A1 | 12/2006 | Mellor et al. |
| 2007/0105907 A1 | 5/2007 | Prendergast et al. |
| 2007/0116690 A1 | 5/2007 | Yang et al. |
| 2007/0218528 A1 | 9/2007 | Miller |
| 2011/0003380 A1 | 1/2011 | Miltenyi et al. |
| 2011/0059502 A1 | 3/2011 | Chalasani |
| 2011/0301073 A1 | 12/2011 | Gregory et al. |
| 2011/0305713 A1 | 12/2011 | Munn et al. |
| 2012/0046324 A1 | 2/2012 | Muchowski et al. |
| 2012/0329812 A1 | 12/2012 | Wityak et al. |
| 2012/0330185 A1 | 12/2012 | Coonahan et al. |
| 2013/0029988 A1 | 1/2013 | Dominguez et al. |
| 2013/0149337 A1 | 6/2013 | Cooper et al. |
| 2013/0287748 A1 | 10/2013 | June et al. |
| 2013/0331370 A1 | 12/2013 | Wityak et al. |
| 2014/0120622 A1 | 5/2014 | Gregory et al. |
| 2014/0271635 A1 | 9/2014 | Brogdon et al. |
| 2014/0329795 A1 | 11/2014 | Courtney et al. |
| 2014/0329816 A1 | 11/2014 | Dominguez et al. |
| 2015/0057238 A1 | 2/2015 | Toledo-Sherman et al. |
| 2015/0064154 A1 | 3/2015 | Georgiou et al. |
| 2015/0175712 A1 | 6/2015 | Bessede |
| 2016/0046596 A1 | 2/2016 | Banerjee et al. |
| 2016/0058845 A1 | 3/2016 | Georgiou et al. |
| 2016/0060266 A1 | 3/2016 | Kumar et al. |
| 2017/0051035 A1 | 2/2017 | Payne et al. |
| 2017/0137783 A1 | 5/2017 | Bedoya et al. |
| 2017/0174713 A1* | 6/2017 | Du .................... A61P 1/18 |
| 2017/0267668 A1* | 9/2017 | Cowley ............... A61K 31/41 |
| 2018/0142035 A1 | 5/2018 | Lobb et al. |
| 2018/0318349 A1 | 11/2018 | Thompson et al. |
| 2019/0358262 A1 | 11/2019 | Albertson |

FOREIGN PATENT DOCUMENTS

| | | |
|---|---|---|
| CN | 105567690 | 5/2016 |
| EP | 0 452 342 | 11/1994 |
| EP | 2 331 095 | 6/2011 |
| EP | 2 736 337 | 6/2014 |
| EP | 2 751 086 | 7/2014 |
| EP | 2 420 494 | 10/2014 |
| EP | 2 537 416 | 11/2014 |
| EP | 2 750 677 | 3/2017 |
| WO | WO 1991/016024 | 10/1991 |
| WO | WO 1991/017424 | 11/1991 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1998/053058 | 11/1998 |
| WO | WO 1998/053059 | 11/1998 |
| WO | WO 1998/053060 | 11/1998 |
| WO | WO 1999/018129 | 4/1999 |
| WO | WO 1999/060120 | 11/1999 |
| WO | WO 2000/014257 | 3/2000 |
| WO | WO 2002/016536 | 2/2002 |
| WO | WO 2003/016496 | 2/2003 |
| WO | WO 2003/020763 | 3/2003 |
| WO | WO 2004/033685 | 4/2004 |
| WO | WO 2004/045543 | 6/2004 |
| WO | WO 2004/048566 | 6/2004 |
| WO | WO 2004/093871 | 11/2004 |
| WO | WO 2004/094409 | 11/2004 |
| WO | WO 2006/000830 | 1/2006 |
| WO | WO 2008/022286 | 2/2008 |
| WO | WO 2008/052352 | 5/2008 |
| WO | WO 2008/058178 | 5/2008 |
| WO | WO 2010/033140 | 3/2009 |
| WO | WO 2009/072003 | 6/2009 |
| WO | WO 2009/073620 | 6/2009 |
| WO | WO 2010/005958 | 1/2010 |
| WO | WO 2010/008427 | 1/2010 |
| WO | WO 2010/017132 | 2/2010 |
| WO | WO 2010/017179 | 2/2010 |
| WO | WO 2011/044186 | 4/2011 |
| WO | WO 2011/045341 | 4/2011 |
| WO | WO 2011/056652 | 5/2011 |
| WO | WO 2011/091153 | 7/2011 |
| WO | WO 2012/031744 | 3/2012 |
| WO | WO 2012/079000 | 6/2012 |
| WO | WO 2012/129514 | 9/2012 |
| WO | WO 2012/142237 | 10/2012 |
| WO | WO 2013/016488 | 1/2013 |
| WO | WO 2013/026837 | 2/2013 |
| WO | WO 2013/033068 | 3/2013 |
| WO | WO 2013/033085 | 3/2013 |
| WO | WO 2013/059593 | 4/2013 |
| WO | WO 2013/071154 | 5/2013 |
| WO | WO 2013/123061 | 8/2013 |
| WO | WO 2013/126726 | 8/2013 |
| WO | WO 2013/151707 | 10/2013 |
| WO | WO 2013/166321 | 11/2013 |
| WO | WO 2014/018423 | 1/2014 |
| WO | WO 2014/031687 | 2/2014 |
| WO | WO 2014/055668 | 4/2014 |
| WO | WO 2014/150646 | 9/2014 |
| WO | WO 2014/150677 | 9/2014 |
| WO | WO 2014/159248 | 10/2014 |
| WO | WO 2014/186035 | 11/2014 |
| WO | WO 2014/186469 | 11/2014 |
| WO | WO 2014/188220 | 11/2014 |
| WO | WO 2015/002918 | 1/2015 |
| WO | WO 2015/006520 | 1/2015 |
| WO | WO 2015/047978 | 4/2015 |
| WO | WO 2015/082499 | 6/2015 |
| WO | WO 2015/119944 | 8/2015 |
| WO | WO 2016/026772 | 8/2015 |
| WO | WO 2015/142675 | 10/2015 |
| WO | WO 2015/155341 | 10/2015 |
| WO | WO 2015/157399 | 10/2015 |
| WO | WO 2015/161276 | 10/2015 |
| WO | WO 2006/005185 | 1/2016 |
| WO | WO 2016/012615 | 1/2016 |
| WO | WO 2016/024233 | 2/2016 |
| WO | WO 2016/051181 | 4/2016 |
| WO | WO 2016/061231 | 4/2016 |
| WO | WO 2016/073381 | 5/2016 |
| WO | WO 2016/146035 | 9/2016 |
| WO | WO 2017/079703 | 5/2017 |
| WO | WO 2017/153459 | 9/2017 |

(56) References Cited

FOREIGN PATENT DOCUMENTS

| | | |
|---|---|---|
| WO | WO 2017/210617 | 12/2017 |
| WO | WO 2018/023025 | 2/2018 |
| WO | WO 2018/102786 | 6/2018 |

OTHER PUBLICATIONS

Ninomiya, S, et al. (2015). Tumor indoleamine 2,3-dioxygenase (IDO) inhibits CD19-CAR T cells and is downregulated by lymphodepleting drugs. Blood 125: 3905-3916.*
Platten et al Tryptophan metabolism in brain tumors—IDO and beyond Current Opinion in Immunology 2021, 70:57-66.*
Savoldo B, CD28 costimulation improves expansion and persistence of chimeric antigen receptor-modified T cells in lymphoma patients. J Clin Invest. 2011.*
Dotti et al Design and Development of Therapies using Chimeric Antigen Receptor-Expressing T cells Immunol Rev. Jan. 2014; 257(1): pp. 1-24.*
Southan et al., 1996. Structural requirements of the competitive binding site of recombinant human indoleamine 2,3-dioxygenase. Medicinal Chemistry Research, 6(5), 343-352.*
Röhrig et al., 2015; Challenges in the Discovery of Indoleamine 2,3-Dioxygenase 1 (IDO1) Inhibitors J. Med. Chem., 58, 9421-9437.*
Vachelli et al., 2014, Trial watch: IDO inhibitors in cancer therapy, Oncolmmunology, 3:10 pp. 1-10.*
Vilgelm et al., "Combinatorial approach to cancer immunotherapy: strength in numbers," J Leukoc Biol (2016) 100(2):275-290.
"Database accession No. P14902," Retrieved from UNIPROT, http://www.uniprot.org/uniprot/P14902. Retrieved Sep. 28, 2016.
"Database accession No. Q01650," Retrieved from UNIPROT, http://www.uniprot.org/uniprot/Q01650. Retrieved Apr. 20, 2017.
Abdelrahim et al., "Aryl hydrocarbon receptor gene silencing with small inhibitory RNA differentially modulates Ah-responsiveness in MCF-7 and HepG2 cancer cells," Mol Pharmacol. (2003) 63(6): 1373-81.
Abken et al., "Costimulation Engages the Gear in Driving CARs," Immunity. Feb. 16, 2016;44(2):214-6.
Alford et al., "IDO1 inhibitors for cancer immunotherapy." Drugs Fut (2016) 41(9): 553-559.
Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.
Anderson, W.F. "Human Gene Therapy," Science (1992) 256: 808-813.
Anthony, et al., "Dissecting the T Cell Response: Proliferation Assays vs. Cytokine Signatures by ELISPO," Cells (2012) 1: 127-140.
Armstrong et al., "Regulation of endoplasmic reticulum stress-induced cell death by ATF4 in neuroectodermal tumor cells," J Biol Chem. Feb. 26, 2010;285(9): 6091-6100.
Bakmiwewa et al., "Identification of selective inhibitors of indoleamine 2,3-dioxygenase 2," Bioorg Med Chem Lett. (2012) 22(24): 7641-7646.
Barnes et al., "Amino acid deprivation links BLIMP-1 to the immunomodulatory enzyme indoleamine 2,3-dioxygenase," J Immunol. (2009) 183(9): 5768-5777.
Barollo et al., "Overexpression of L-Type Amino Acid Transporter 1 (LAT1) and 2 (LAT2): Novel Markers of Neuroendocrine Tumors," PLoS One. (2016) 11(5): e0156044.
Barrett et al., "Chimeric Antigen Receptor Therapy for Cancer," Annual Review of Medicine (2013) 65:333-347.
Beerli et al., "Engineering polydactyl zinc-finger transcription factors," Nat Biotechnol. (2002) 20(2): 135-41.
Belguise et al., "The PKCθ pathway participates in the aberrant accumulation of Fra-1 protein in invasive ER-negative breast cancer cells," Oncogene. (2012) 31(47): 4889-4897.

Bernstein et al., "Role for a bidentate ribonuclease in the initiation step of RNA interference," Nature. (2001) 409(6818): 363-366.
Bonanno et al., "Indoleamine 2,3-dioxygenase 1 (IDO1) activity correlates with immune system abnormalities in multiple myeloma." J Transl Med. Dec. 11, 2012;10:247.
Boris-Lawrie et al., "Recent advances in retrovirus vector technology," Current Opinion in Genetics & Development (1993) 3(1):102-109.
Boutla et al., Short 5'-phosphorylated double-stranded RNAs induce RNA interference in *Drosophila*, Curr Biol. (2001) 11(22): 1776-80.
Brahmandam et al., "Enhanced Functional Profile of CAR-T Cells Generated in the Presence of mTOR Kinase Inhibitor," SITC Annual Meeting 2017, Poster (P163).
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Brochez et al., "The rationale of indoleamine 2,3-dioxygenase inhibition for cancer therapy." Eur J Cancer. May 2017;76:167-182.
Broer et al., "The role of amino acid transporters in inherited and acquired diseases," Biochem J. (2011) 436(2): 193-211.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Campbell et al., "Overexpression of LAT1/CD98 Light Chain is Sufficient to Increase System L-amino Acid Transport Activity in Mouse Hepatocytes but Not Fibroblasts," J Biol Chem. (2001) 276 (20), 16877-84.
Cao et al., "Hypoxia-inducible transgene expression in differentiated human NT2N neurons—a cell culture model for gene therapy of postichemic neuronal loss," Gene Ther (2001) 8(17):1357-1362.
Caplen et al., "Specific inhibition of gene expression by small double-stranded RNAs in invertebrate and vertebrate systems," Proc Natl Acad Sci U S A. (2001) 98(17): 9742-9747.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carvalho et al., "Benzofuranquinones as inhibitors of indoleamine 2,3-dioxygenase (IDO). Synthesis and biological evaluation," Org Biomol Chem. (2014) 12(17): 2663-2674.
Cavalieri et al., "Human T lymphocytes transduced by lentiviral vectors in the absence of TCR activation maintain an intact immune competence," Blood (2003) 102(2): 497-505.
Chadwick et al., "A Syngeneic Mouse Model of CAR T-Mediated Toxicity and Neuroinflammation," SITC Annual Meeting 2017, (P372), poster.
Chang et al., "Immunomodulation of curcumin on adoptive therapy with T cell functional imaging in mice." Cancer Prev Res (Phila). (2012) 5(3):444-452.
Cheadle et al., "Chimeric antigen receptors for T-cell based therapy," Methods Mol Biol. (2012);907:645-66.
Chervin et al., "Engineering higher affinity T cell receptors using a T cell display system," J Immunol Methods (2008) 339(2):175-184.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Choo et al., "Advances in zinc finger engineering," Curr Opin Struct Biol. (2000) 10(4): 411-416.
Chothia et al., "The outline structure of the T-cell alpha beta receptor," EMBO J (1988) 7(12):3745-3755.

(56) References Cited

OTHER PUBLICATIONS

Chuang et al., "Serial low doses of sorafenib enhance therapeutic efficacy of adoptive T cell therapy in a murine model by improving tumor microenvironment." PLoS One. (2014) 9(10): e109992.
Clarke et al., "Immunomagnetic Cell Separation," in Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Clinicaltrials.gov Identifier NCT01822652. First posted Apr. 2, 2013. Last updated May 3, 2019.
Clinicaltrials.gov Identifier NCT02315612. First posted Dec. 12, 2014. Last updated Oct. 9, 2019.
Cooper et al., "T-cell clones can be rendered specific for CD19: toward the selective augmentation of the graft-versus-B-lineage leukemia effect," Blood (2003) 101:1637-1644.
Critchlow et al., "DNA end-joining: from yeast to man," Trends Biochem Sci. (1998) 23(10):394-398.
Cui et al., "IL-7-Induced Glycerol Transport and TAG Synthesis Promotes Memory CD8+ T Cell Longevity," Cell. (2015)161(4):750-61.
Dachs et al., "Hypoxia modulated gene expression: angiogenesis, netastasis and therapeutic exploitation," Eur J Cancer (2000) 36(13 Spec No):1649-1660.
Dai et al., "Tight transcriptional regulation of foreign genes in insect cells using an ecdysone receptor-based inducible system," Protein Expr Purif. (2005) 42(2): 236-245.
Davila et al., "CD19 CAR-Targeted T Cells Induce Long-Term Remission and B Cell Aplasia in an Immunocompetent Mouse Model of B Cell Acute Lymphoblastic Leukemia," PLOS One (2013) 8(4):e61338.
Davila et al., "How do CARs work?: Early insights from recent clinical studies targeting CD19," Oncoimmunology (2012) 1(9):1577-1583.
De Felipe et al., "Targeting of Proteins Derived from Self-Processing Polyproteins Containing Multiple Signal Sequences," Traffic (2004) 5(8):616-626.
De Felipe, "Skipping the co-expression problem: the new 2A "Chysel" technology," Genet Vaccines Ther (2004) 2:13.
Dhadialla et al., "New insecticides with ecdysteroidal and juvenile hormone activity," Annu Rev Entomol. (1998) 43: 545-569.
Dillon, "Regulating gene expression in gene therapy," Trends Biotechnol. (1993) 11(5):167-173.
Dolusic et al., "Tryptophan 2,3-dioxygenase (TDO) inhibitors. 3-(2-(pyridyl)ethenyl)indoles as potential anticancer immunomodulators," J Med Chem.( 2011) 54(15): 5320-5334.
Dreesen et al., "Ectopic expression of human mTOR increases viability, robustness, cell size, proliferation, and antibody production of Chinese hamster ovary cells," Biotechnol Bioeng. (2011) 108(4):853-866.
Dudley et al., "Cancer regression and autoimmunity in patients after clonal repopulation with antitumor lymphocytes," Science (2002) 298(5594):850-854.
Eguchi et al., "Inhibition of indoleamine 2,3-dioxygenase and tryptophan 2,3-dioxygenase by beta-carboline and indole derivatives," Arch Biochem Biophys. (1984) 232(2): 602-609.
Fan et al., "Icariin displays anticancer activity against human esophageal cancer cells via regulating endoplasmic reticulum stress-mediated apoptotic signaling," Sci Rep. (2016) 6:21145.
Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.
Gaj, T. et al. "ZFN, TALEN, and CRISPR/Cas-Based Methods for Genome Engineering," Trends Biotechnol. (2013) 31(7): 397-405.
Gajewski et al., "Overcoming immune resistance in the tumor microenvironment by blockade of indoleamine 2,3-dioxygenase and programmed death ligand 1." Curr Opin Investig Drugs. Dec. 2004;5(12):1279-83.
Gardner et al., "CD19CAR T Cell Products of Defined CD4:CD8 Composition and Transgene Expression Show Prolonged Persistence and Durable MRD-Negative Remission in Pediatric and Young Adult B-Cell ALL." Blood 2016 128:219.
Georgiou et al., "A Therapeutic Enzyme for Highly Effective Immune Checkpoint Inhibition in Cancer," Cancer Prevention & Research Institute of Texas, Nov. 10, 2015, Presentation, 19 pages.
Godin et al., "Microfluidics and photonics for Bio-System-on-a-Chip: a review of advancements in technology towards a microfluidic flow cytometry chip," J Biophotonics (2008) 1(5):355-376.
Gorman et al., "Site-specific gene targeting for gene expression in eukaryotes," Curr Opin Biotechnol (2000) 11(5):455-460.
Greco et al., "Novel chimeric gene promoters responsive to hypoxia and ionizing radiation," Gene Ther (2002) 9(20): 1403-1411.
Gros et al., "PD-1 identifies the patient-specific $CD8^+$ tumor-reactive repertoire infiltrating human tumors." J Clin Invest. May 2014;124(5):2246-59.
Han et al., "Chimeric antigen receptor-engineered T cells for cancer immunotherapy: progress and challenges," J Hematology & Oncology (2013) 6:47.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Ho et al., "Phosphoenolpyruvate is a Metabolic Checkpoint of Anti-tumor T Cell Responses," Cell. (Sep. 10, 2015);162(6):1217-28.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Holliger et al., "Specific killing of lymphoma cells by cytotoxic T-cells mediated by a bispecific diabody," Protein Engineering Design and Selection (1996) 9(3):299-305.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin Cancer Res (2013) 19(12):3153-3164.
Huss et al., "PSMA-Associated PET Imaging of CAR-T Cells," SITC Annual Meeting 2017, Poster (P300).
Isalan et al., "A rapid, generally applicable method to engineer zinc fingers illustrated by targeting the HIV-1 promoter," Nat Biotechnol. (Jul. 2001);19(7):656-660.
Ishida et al,. "Activation of the aryl hydrocarbon receptor pathway enhances cancer cell invasion by upregulating the MMP expression and is associated with poor prognosis in upper urinary tract urothelial cancer," Carcinogenesis. (2010) 31(2): 287-95.
Janeway et al., Immunobiology: The Immune System in Health and Disease, 3rd ED., Current Biology Publications (1997), p. 4:33.
Jensen et al., "Antitransgene rejection responses contribute to attenuated persistence of adoptively transferred CD20/CD19-specific chimeric antigen receptor redirected T cells in humans," Biol Blood Marrow Transplant (2010) 16(9):1245-1256.
Jiang et al., "T-cell exhaustion in the tumor microenvironment," Cell Death Dis (2015) 6:e1792.
Jin et al., Prospects to improve chimeric antigen receptor T-cell therapy for solid tumors, Immunotherapy (2016) 8(12): 1355-1361.
Jochems et al., "The IDO1 selective inhibitor epacadostat enhances dendritic cell immunogenicity and lytic ability of tumor antigen-specific T cells." Oncotarget. (2016) 7(25): 37762-37772.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity.," PNAS (1990) 87(23):9138-9142.
Kalos et al., "T cells with chimeric antigen receptors have potent antitumor effects and can establish memory in patients with advanced leukemia," Sci Transl Med (2011) 3(95):95ra73.
Kaper et al., "Nanosensor detection of an immunoregulatory tryptophan influx/kynurenine efflux cycle," PLoS Biol. (2007) 5(10): e257.

(56) References Cited

OTHER PUBLICATIONS

Karzenowski et al., "Inducible control of transgene expression with ecdysone receptor: gene switches with high sensitivity, robust expression, and reduced size," Biotechniques. (2005) 39(2): 191-200.
Karzenowski et al., "RheoSwitch® Therapeutic System-Inducible Recombinant AAV Vectors for Tightly Regulated Transgene Expression," Molecular Therapy (2006) 13:S194.
Katakam et al., "The RheoSwitch® Therapeutic System Precisely Regulates IL-2 Expression in Melanoma Cells and Supports Survival of NK Cells at the Tumor Site," Molecular Therapy. 2006 13:S103.
Kim et al., "A library of TAL effector nucleases spanning the human genome," Nat Biotechnol. (2013) 31(3):251-258.
Kim et al., "CCAAT/Enhancer-binding protein-homologous protein sensitizes to SU5416 by modulating p21 and PI3K/Akt signal pathway in FRO anaplastic thyroid carcinoma cells," Horm Metab Res. (2013) 45(1): 9-14.
Kim et al., "Chimeric restriction endonuclease," Proc Natl Acad Sci U S A. (1994) 91(3):883-887.
Kim et al., "Insertion and deletion mutants of FokI restriction endonuclease," J Biol Chem. (1994) 269(50):31978-31982.
Kipriyanov et al., "Bispecific tandem diabody for tumor therapy with improved antigen binding and pharmacokinetics," J Mol Biol (1999) 293(1):41-56.
Klebanoff et al., "Sorting through subsets: Which T cell populations mediate highly effective adoptive immunotherapy?" J Immunother (2012) 35(9):651-660.
Koblish et al., "Hydroxyamidine inhibitors of indoleamine-2,3-dioxygenase potently suppress systemic tryptophan catabolismand the growth of IDO-expressing tumors." Mol Cancer Ther. (2010) 9(2): 489-98.
Koblish, H. "Selective ID01 Inhibition: Pharmacodynamic and Antitumor Activity of INCB24360" Incyte Presentation, 18 pages.
Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol (2013) 10(5):267-276.
Kolb, "Genome engineering using site-specific recombinases," Cloning Stem Cells. (2002) 4(1): 65-80.
Koste et al., "T-cell receptor transfer into human T cells with ecotropic retroviral vectors," Gene Therapy (2014) 21:533-538.
Kotb et al., "Bacterial pyrogenic exotoxins as superantigens," Clinical Microbiology Reviews (1995) 8:411-426.
Kremer et al., "Adenovirus and adeno-associated virus mediated gene transfer," Br Med Bull. (1995) 51(1):31-44.
Kuhn et al., "Cre/loxP recombination system and gene targeting," Methods Mol Biol. (2002) 180: 175-204.
Kumar et al., "Highly flexible ligand binding pocket of ecdysone receptor: a single amino acid change leads to discrimination between two groups of nonsteroidal ecdysone agonists," J Biol Chem. (2004) 279(26): 27211-27218.
Kurucz et al., "A bacterially expressed single-chain Fv construct from the 2B4 T-cell receptor," PNAS (1993) 90(9):3830-3834.
Lamers et al., "Immune responses to transgene and retroviral vector in patients treated with ex vivo-engineered T cells," Blood (2011) 117(1):72-82.
Lee et al., "Novel antileukemic compound ingenol 3-angelate inhibits T cell apoptosis by activating protein kinase Ctheta," J Biol Chem. (2010) 285(31): 23889-23898.
Lee et al., "T cells expressing CD19 chimeric antigen receptors for acute lymphoblastic leukaemia in children and yound adults: a phase 1 dose escalation trial," The Lancet (2015) 385(9967): 517-528.

Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nat Biotechnol (2005) 23(3):349-354.
Li et al., "Functional domains in Fok I restriction endonuclease," Proc Natl Acad Sci U S A. (1992) 89(10):4275-4279.
Li et al.," Alteration of the cleavage distance of Fok I restriction endonuclease by insertion mutagenesis," Proc Natl Acad Sci U S A. (1993) 90(7):2764-2768.
Ligtenberg et al., "Coexpressed Catalase Protects Chimeric Antigen Receptor- Redirected T Cells as well as Bystander Cells from Oxidative Stress-Induced Loss of Antitumor Activity," J Immunol. (Jan. 15, 2016);196(2):759-66.
Lin et al., "L-type amino acid transporter-1 overexpression and melphalan sensitivity in Barrett's adenocarcinoma," Neoplasia. (2004) 6(1): 74-84.
Lindstrom et al., "Indoleamine 2,3-dioxygenase activity and expression in patients with chronic lymphocytic leukemia." Clin Lymphoma Myeloma Leuk. Oct. 2012;12(5):363-5.
Liu et al., "Selective inhibition of IDO1 effectively regulates mediators of antitumor immunity." Blood. Apr. 29, 2010;115(17):3520-30.
Lloyd et al., "Beyond the antigen receptor: editing the genome of T-cells for cancer adoptive cellular therapies," Front Immunol (2013) 4(221):1-7.
Lupton et al., "Dominant positive and negative selection using a hygromycin phosphotransferase-thymidine kinase fusion gene," Mol and Cell Biol (1991) 11(6):3374-3378.
Malmberg et al., "Insulin signaling and the general amino acid control response. Two distinct pathways to amino acid synthesis and uptake," J Biol Chem. (2008) 283(28):19229-19234.
Manuri et al., "piggyBac Transposon/Transposase System to Generate CD19-Specific T Cells for the Treatment of B-Lineage Malignancies," Hum Gene Ther (2010) 21(4):427-437.
McGaha et al., "Amino acid catabolisma pivotal regulator of innate and adaptive immunity," Immunol Rev. (2012) 249(1):135-57.
Meininger et al., "Purification and kinetic characterization of human indoleamine 2,3- dioxygenases 1 and 2 (IDO1 and IDO2) and discovery of selective IDO1 inhibitors," Biochim Biophys Acta. (2011) 1814(12): 1947-54.
Metz et al., "IDO inhibits a tryptophan sufficiency signal that stimulates mTOR: A novel IDO effector pathway targeted by D-1-methyl-tryptophan," Oncoimmunology. (2012) 1(9): 1460-1468.
Miller et al., "Improved retroviral vectors for gene transfer and expression," Biotechniques (1989) 7(9):980-982.
Miller, "Human gene therapy comes of age," Nature. (1992) 357(6378): 455-460.
Miller, "Retrovirus packaging cells," Hum Gene Ther (1990) 1(1):5-14.
Mitani et al., "Delivering therapeutic genes—matching approach and application," Trends Biotechnol. (1993) 11(5): 162-166.
Moon et al., "Targeting the indoleamine 2,3-dioxygenase pathway in cancer," J Immunother Cancer. (2015) 15; 3:51.
Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.
Munn et al., "GCN2 kinase in T cells mediates proliferative arrest and anergy induction in response to indoleamine 2,3-dioxygenase," Immunity. (2005) 22(5): 633-42.
Munn, D, "Small-molecule inhibitors of the IDO Pathway as immune modulators," presentation, 21 pages.
Munn, D., "IDO and Immune Suppression," SITC Annual Meeting, Oct. 2012, presentation, 37 pages.
Muranski et al., "Increased intensity lymphodepletion and adoptive immunotherapy—how far can we go?" Nat Clin Pract Oncol (2006) 3(12):668-681.
Nabel et al., "Direct gene transfer for immunotherapy and immunization," Trends Biotechnol. May 1993; 11(5):211-5.

(56) References Cited

OTHER PUBLICATIONS

Nagorsen et al., "Immunomodulatory therapy of cancer with T cell-engaging BITE antibody blinatumomab," Exp Cell Res (2011) 317(9):1255-1260.
Ninomiya et al., "Indoleamine 2,3-dioxygenase in tumor tissue indicates prognosis in patients with diffuse large B-cell lymphoma treated with R-CHOP." Ann Hematol. Apr. 2011;90(4):409-16.
Ninomiya et al., "T cells expressing CD19-specific chimeric antigen receptors are inhibited by indoleamine 2,3-dioxygenase in tumors," Blood 2014 124:2434.
Ninomiya et al., "Tumor indoleamine 2,3-dioxygenase (IDO) inhibits CD19-CAR T cells and is downregulated by lymphodepleting drugs." Blood. Jun. 18, 2015;125(25):3905-16.
O'Gorman et al., "Recombinase-mediated gene activation and site-specific integration in mammalian cells," Science. (1991) 251(4999): 1351-1355.
Okoye et al., "T cell metabolism. The protein LEM promotes CD8+ T cell immunity through effects on mitochondrial respiration," Science. (May 29, 2015);348(6238):995-1001.
Opitz et al., "The indoleamine-2,3-dioxygenase (IDO) inhibitor 1-methyl-D-tryptophan upregulates IDO1 in human cancer cell," PLoS One. 2011;6(5):e19823.
Ovrevik et al., "AhR and Arnt differentially regulate NF-κB signaling and chemokine responses in human bronchial epithelial cells," Cell Commun Signal. (2014) 12:48.
Pabo et al., "Design and selection of novel Cys2His2 zinc finger proteins," Annu Rev Biochem. (2001) 70: 313-340.
Palli et al., "Improved ecdysone receptor-based inducible gene regulation system," Eur J Biochem. (2003) 270(6): 1308-15.
Pardoll "The Blockade of Immune Checkpoints in Cancer Immunotherapy," Nat. Rev. Cancer (2012) 12(4): 252-264.
Park et al., "Adoptive transfer of chimeric antigen receptor re-directed cytolytic T lymphocyte clones in patients with neuroblastoma," Mol Ther (2007) 15(4):825-833.
Park et al., "Treating cancer with genetically engineered T cells," Trends Biotechnol (2011) 29(11):550-557.
Pauken et al., "Epigenetic stability of exhausted T cells limits durability of reinvigoration by PD-1 blockade." Science. Dec. 2, 2016;354(6316):1160-1165.
Peterson et al., "Evaluation of Substituted β-Carbolines as Non-competitive Indolamine 2,3-Dioxygenase Inhibitors," Med. Chem. Res. (1993) 3:473-482.
Platten et al., "Cancer Immunotherapy by Targeting IDO1/TDO and Their Downstream Effectors," Front Immunol. (2015) 5:673.
Qi et al., "Repurposing CRISPR as an RNA-guided platform for sequence-specific control of gene expression," Cell. Feb. 28, 2013;152(5):1173-83.
Ribas, A., "Adaptive Immune Resistance: How Cancer Protects from Immune Attack," Cancer Discov. (2015) 5(9):915-9.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.
Rohrig et al., "Challenges in the Discovery of Indoleamine 2,3-Dioxygenase 1 (IDO1) Inhibitors," J Med Chem. 2015 58(24): 9421-9437.
Rohrig et al., "Rational design of 4-aryl-1,2,3-triazoles for indoleamine 2,3-dioxygenase 1 inhibition," J Med Chem. (2012) 55(11): 5270-90.
Rosenberg et al., "Durable Complete Responses in Heavily Pre-treated Patients with Metastatic Melanoma Using T-Cell Transfer Immunotherapy," Clin Cancer Res (2011) 17(13):4550-4557.
Rosenberg, "Cell transfer immunotherapy for metastatic solid cancer—what clinicians need to know," Nat Rev Clin Oncol (2011) 8(10):577-585.
Rosilio et al., "L-type Amino-Acid Transporter 1 (LAT1): A Therapeutic Target Supporting Growth and Survival of T-cell Lymphoblastic lymphoma/T-cell Acute Lymphoblastic Leukemia," Leukemia (2015) 29(6): 1253-66.
Ryder et al., "Acidosis blocks CCAAT/enhancer-binding protein homologous protein (CHOP)- and c-Jun-mediated induction of p53-upregulated mediator of apoptosis (PUMA) during amino acid starvation," Biochem Biophys Res Commun. 2013 430(4): 1283-1288.
Sadelain et al., "The basic principles of chimeric antigen receptor (CAR) design," Cancer Discov (2013) 3(4):388-398.
Saito et al., "4-Chloro-3-hydroxyanthranilate, 6-chlorotryptophan and norharmane attenuate quinolinic acid formation by interferon-gamma-stimulated monocytes (THP-1 cells)," Biochem J. (1993) 291 (Pt 1): 11-14.
Sander et al., "CRISPR-Cas systems for editing, regulating and targeting genomes," Nat Biotechnol. (2014) 32(4): 347-355.
Sanjana et al., "Improved vectors and genome-wide libraries for CRISPR screening," Nat Methods. (2014) 11(8): 783-784.
Sauer et al., "Cre-stimulated recombination at loxP-containing DNA sequences placed into the mammalian genome," Nucleic Acids Res. (1989) 17(1): 147-61.
Savoldo et al., "CD28 costimulation improves expansion and persistence of chimeric antigen receptor-modified T cells in lymphoma patients," J Clin Invest (2011) 121(5):1822-1826.
Scarpa et al., "Characterization of recombinant helper retroviruses from Moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 256(5):859-869.
Schuler et al., "SYFPEITHI: database for searching and T-cell epitope prediction," Methods Mol Biol. (2007) 409: 75-93.
Segal et al., "Custom DNA-binding proteins come of age: polydactyl zinc-finger proteins," Curr Opin Biotechnol. (2001) 12(6): 632-637.
Seimetz et al., "Development and approval of the trifunctional antibody catumaxomab (anti-EpCAM x anti-CD3) as a targeted cancer immunotherapy," Cancer Treat Rev (2010) 36:458-467.
Sen et al., "The epigenetic landscape of T cell exhaustion." Science. Dec. 2, 2016;354(6316):1165-1169.
Seymour et al., "A high-affinity, tryptophan-selective amino acid transport system in human macrophages," J Leukoc Biol. Dec. 2006; 80(6):1320-1327.
Sharma et al., "Efficient Sleeping Beauty DNA Transposition From DNA Minicircles," Molec Ther Nucl Acids (2013) 2:e74.
Sheridan, C., "IDO inhibitors move center stage in immuno-oncology," Nat Biotechnol. (2015) 33(4): 321-322.
Singer et al.,"A distinct gene module for dysfunction uncoupled from activation in tumor-infiltrating T cells." Cell 2016;166:1500-1511.
Singh et al., "ProPred: prediction of HLA-DR binding sites," Bioinformatics (2001) 17(12):1236-1237.
Sono et al., "Enzyme kinetic and spectroscopic studies of inhibitor and effector interactions with indoleamine 2,3-dioxygenase. 1. Norharman and 4-phenylimidazole binding to the enzyme as inhibitors and heme ligands," Biochemistry. (1989) 28(13): 5392-5399.
Soo Hoo et al., "Characterization of a single-chain T-cell receptor expressed in *Escherichia coli*," PNAS (1992) 89(10):4759-4763.
Spranger et al., "Up-regulation of PD-L1, IDO, and T(regs) in the Melanoma Tumor Microenvironment is Driven by CD8(+) T Cells," Sci Transl Med (2013) 5(200): 200ra116.
Sucher et al., "IDO-Mediated Tryptophan Degradation in the Pathogenesis of Malignant Tumor Disease," Int J Tryptophan Res. (2010) 3:113-120.
Szoka et al., "Comparative properties and methods of preparation of lipid vesicles (liposomes)," Annu Rev Biophys Bioeng. (1980) 9:467-508.
Tang et al., "A Phase 2 Randomized Trial of the IDO Pathway Inhibitor Indoximod in Combination With Taxane-based Chemotherapy for Metastatic Breast Cancer: Preliminary Data," San Antonio Breast Cancer Symposium (SABCS) Dec. 2015, Poster (Abs #P2-11-09).
Terakura et al., "Generation of CD19-chimeric antigen receptor modified CD8+ T cells derived from virus-specific central memory T cells," Blood (2012) 119(1):72-82.
Themeli et al., "Generation of tumor-targeted human T lymphocytes from induced pluripotent stem cells for cancer therapy," Nat Biotechnol (2013) 31(10):928-933.

(56) References Cited

OTHER PUBLICATIONS

Thomas et al., "IDO1-Mediated Tryptophan Depletion Potently Inhibits CAR-T Functionality as Part of a CAR-T-Driven Adaptive Immune Resistance Response in the Tumor Microenvironment," 2017 SITC Annual Meeting, Poster P199.
Tojo et al., "Crystal Structures and Structure-Activity Relationships of Imidazothiazole Derivatives as IDO1 Inhibitors," ACS Med Chem Lett. (2014) 5(10): 1119-1123.
Tsukahara et al., "CD19 target-engineered T-cells accumulate at tumor lesions in human B-cell lymphoma xenograft mouse models," Biochem Biophys Res Commun (2013) 438(1):84-89.
Turtle et al., "Engineered T cells for anti-cancer therapy," Engineered T cells for anti-cancer therapy, Curr Opin Immunol (2012) 24(5):633-639.
Vacchelli et al., "Trial watch: IDO inhibitors in cancer therapy." Oncoimmunology. 2014 3(10):e957994.
Van Brunt, J. "Molecular Farming: Transgenic Animals as Bioreactors," Biotechnology (1988) 6(10): 1149-1154.
Van Tendeloo et al., "High-level transgene expression in primary human T lymphocytes and adult bone marrow CD34+ cells via electroporation-mediated gene delivery," Gene Therpay (2000) 7(16):1431-1437.
Verhaegen et al., "Recombinant Gaussia luciferase. Overexpression, purification, and analytical application of a bioluminescent reporter for DNA hybridization," Anal Chem. (2002) 74(17):4378-4385.
Verhoeyen et al., "Lentiviral vector gene transfer into human T cells," Methods Mol Biol (2009) 506:97-114.
Vigne et al., "Third-generation adenovectors for gene therapy," Restor Neurol Neurosci. (1995) 8(1): 35-36.
Wang et al., "A Critical Role of the mTOR/eIF2α Pathway in Hypoxia-Induced Pulmonary Hypertension," PLoS One. (2015) 10(6): e0130806.
Wang et al., "Genetic screens in human cells using the CRISPR-Cas9 system," Science. (2014) 343(6166): 80-84.
Wang et al., "L-type amino acid transport and cancer: targeting the mTORC1 pathway to inhibit neoplasia," Am J Cancer Res. (2015) 5(4): 1281-1294.
Wang et al., "Phenotypic and Functional Attributes of Lentivirus Modified CD19-specific Human CD8+ Central Memory T Cells Manufactured at Clinical Scale," J Immunother (2012) 35(9):689-701.
Weinmann, H. "Cancer Immunotherapy: Selected Targets and Small-Molecule Modulators," ChemMedChem. (2016) 11(5): 450-466.
Wigler et al., "Transfer of Purified Herpes Virus Thymidine Kinase Gene to Cultured Mouse Cells," Cell (1997) 2:223.
Wu et al., "Adoptive T-cell therapy using autologous tumor-infiltrating lymphocytes for metastatic melanoma: current status and future outlook," Cancer J (2012) 18(2):160-175.
Wulfing et al., "Correctly folded T-cell receptor fragments in the periplasm of *Escherichia coli*. Influence of folding catalysts," J Mol Biol (1994) 242(5):655-669.
Yan et al., "BLIMP1 regulates cell growth through repression of p53 transcription," Proc Natl Acad Sci U S A. (2007) 104(6): 1841-1846.
Yu et al., "Blimp1 activation by AP-1 in human lung cancer cells promotes a migratory phenotype and is inhibited by the lysyl oxidase propeptide," PLoS One. 2012;7(3):e33287, 15 pages.
Yu et al., "Progress towards gene therapy for HIV infection," Gene Ther. (1994) 1(1):13-26.
Zadori et al., "Inhibitors of the kynurenine pathway as neurotherapeutics: a patent review (2012-2015)," Expert Opinion on Therapeutic Patents, (2016) 26;(7); 815-832.
Zetche et al., "A split-Cas9 architecture for inducible genome editing and transcription modulation," Nat Biotechnol. (2015) 33(2): 139-142.
Zhai et al., "Molecular Pathways: Targeting IDO1 and Other Tryptophan Dioxygenases for Cancer Immunotherapy." Clin Cancer Res. (2015) 21(24): 5427-33.
Zhao et al., "miR-3188 regulates nasopharyngeal carcinoma proliferation and chemosensitivity through a FOXO1-modulated positive feedback loop with mTOR-p-PI3K/AKT-c-JUN," Nat Commun. (2016) 7: 11309. (13 pages).
Zhao et al., "Structural Design of Engineered Costimulation Determines Tumor Rejection Kinetics and Persistence of CAR T Cells," Cancer Cell (2015) 28(4):415-428.
Zhao-Emonet et al., "T cell-specific expression from Mo-MLV retroviral vectors containing a CD4 mini-promoter/enhancer," J Gene Med (Nov.-Dec. 2000);2(6):416-425.
Cherkassky et al., "Human Car T cells with cell-intrinsicPD-1 checkpoint blockade resist tumor-mediated inhibition. The Journal of Clinical Investigation," J Clin Invest (2016) 126(8):3130-3144.
Dammeijer et al., "Rationally combining immuotherapies to improve efficacy of immune checkpoint blockade in solid tumors," Cytokine & Growth Factor Reviews (2017) 36 pages.
Grushina et al., "Malignant tumours and physiotherapy," (2013) p. 70-79 (In Russian, but English abstract is on the first page of the reference).
Komatsu et al., "Particle radiotherapy, a novel external radiation therapy, versus liver resection for hepatocellular carcinoma accompanied with inferior vena cava tumor thrombus: A matched-pair analysis," Surgery (2017) 162:1241-1249.
Larson et al., "Preclinical Analyses Support Clinical Investigation of Combined PD-L1 Blockade and Anti-CD19 Car T Cell Therapy for the Treatment of NHL," Blood (2015) 126 (23): 5430.
Prendergast et al., "Indoleamine 2,3-dioxygenase pathways of pathgenic inflammation and immune escape in cancer," Cancer Immunol Immunother (2014) 63(7):721-735.
Blackburn et al., "Selective expansion of a subset of exhausted CD8 T cells by alphaPD-L1 blockade," Proc Natl Acad Sci U S A. (2008) 105(39):15016-21.
Lastwika, Kristin, "Regulation and Consequences of PD-Li Expression in Non-Small Cell Lung Cancer," ProQuest Dissertations and Theses (2014) 125 pages.
Long et al., "4-1BB costimulation ameliorates T cell exhaustion induced by tonic signaling of chimeric antigen receptors," Nat Med. (2015) 21(6):581-90.
Pauken et al., "Overcoming T cell exhaustion in infection and cancer," Trends Immunol. (2015) 36(4): 265-76.

\* cited by examiner

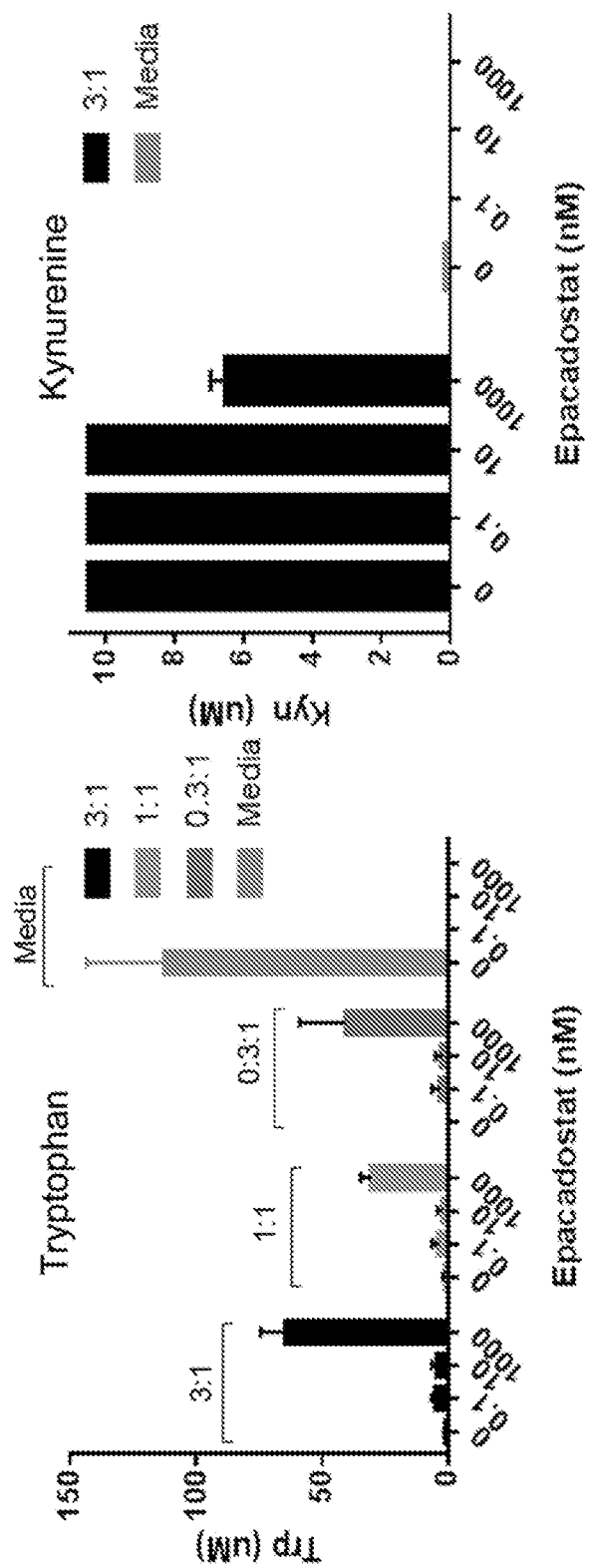
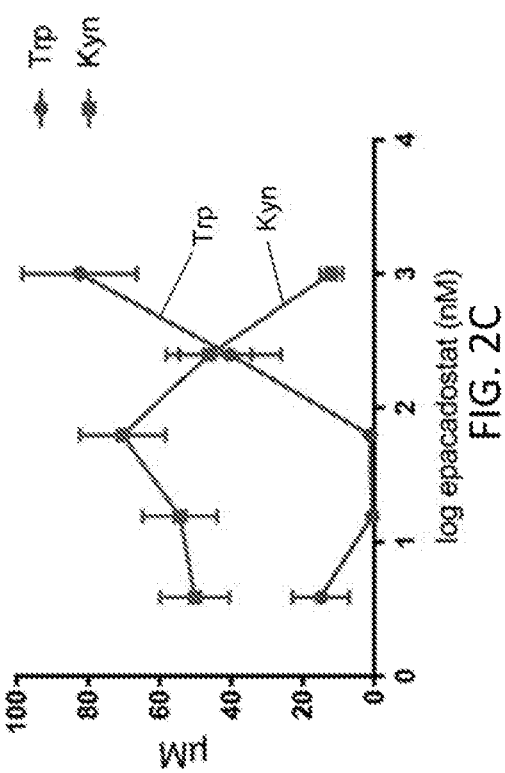
FIG. 2A
FIG. 2B
FIG. 2C

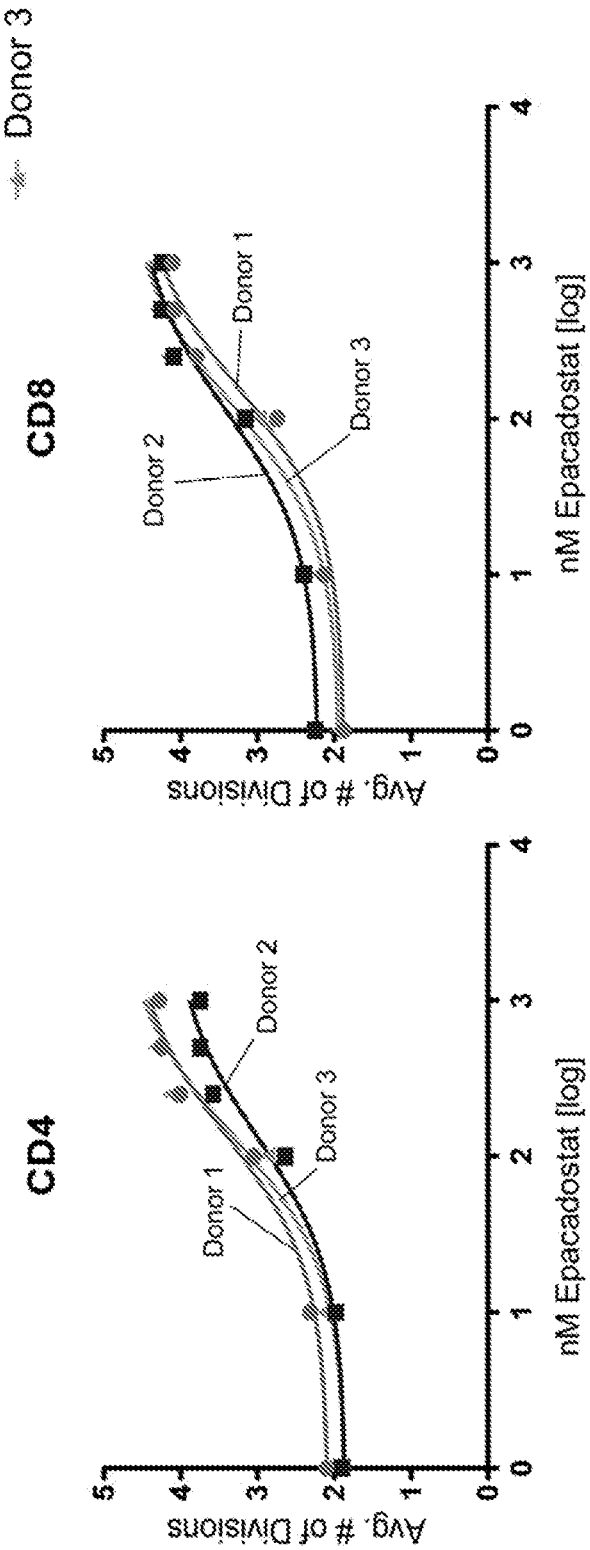

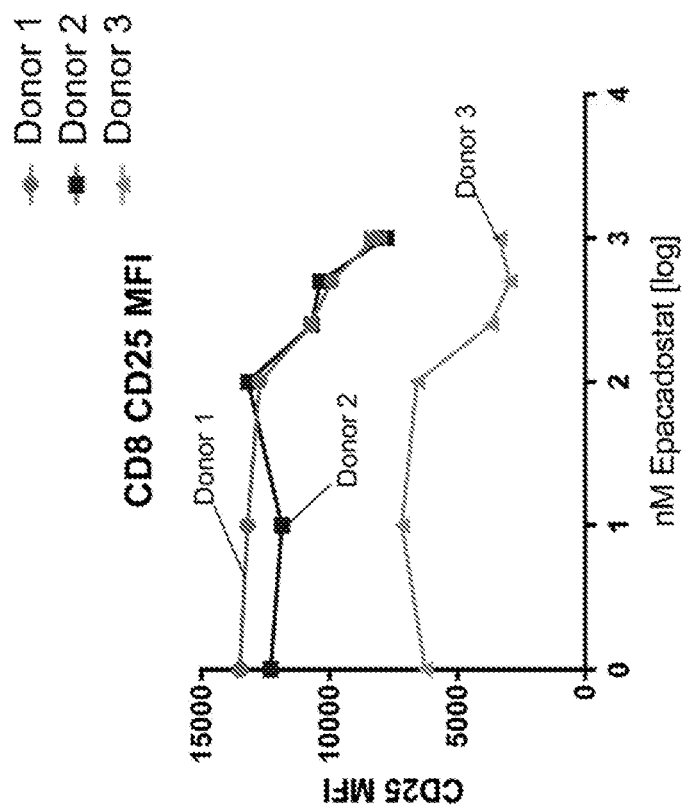
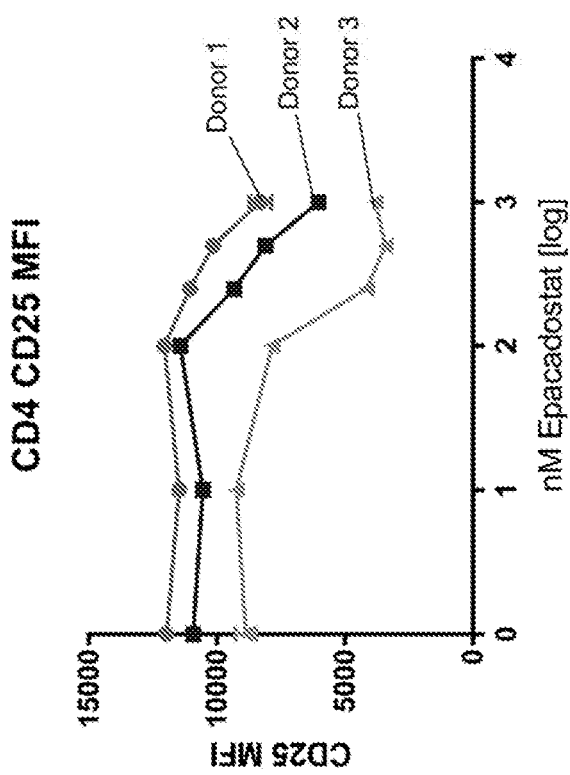
FIG. 8A
FIG. 8B

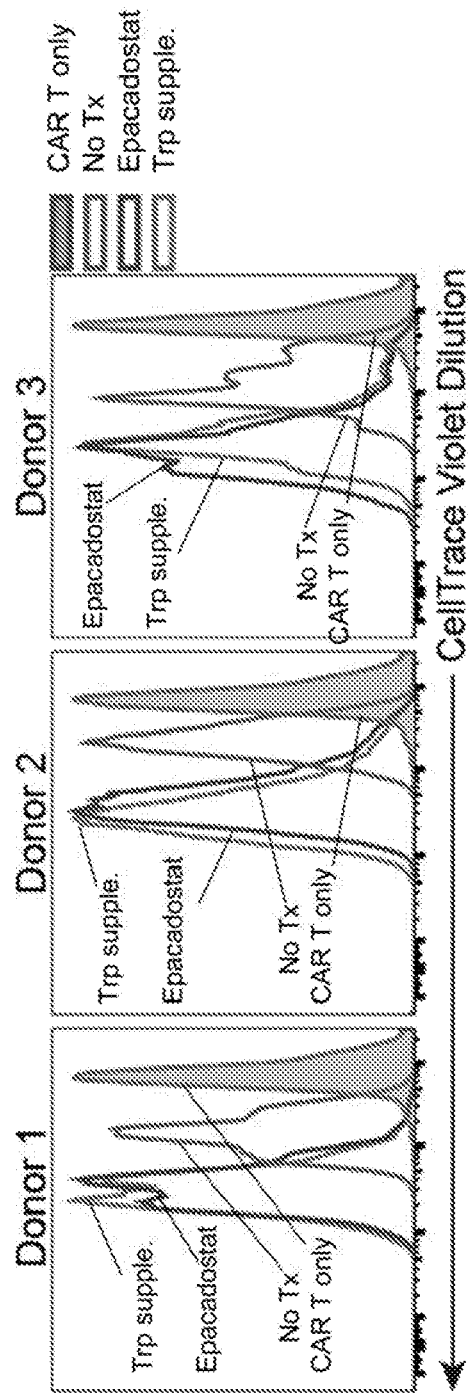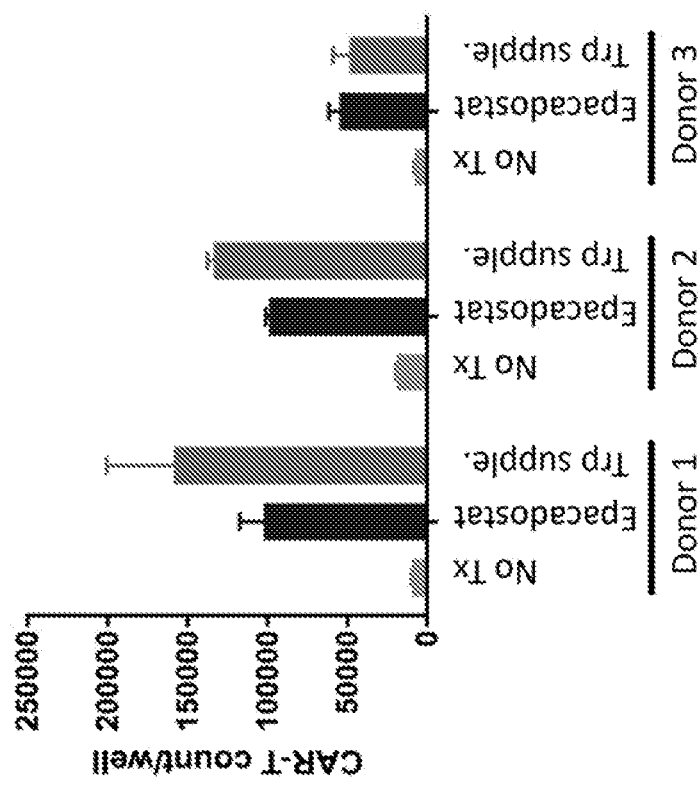
FIG. 14A
FIG. 14B

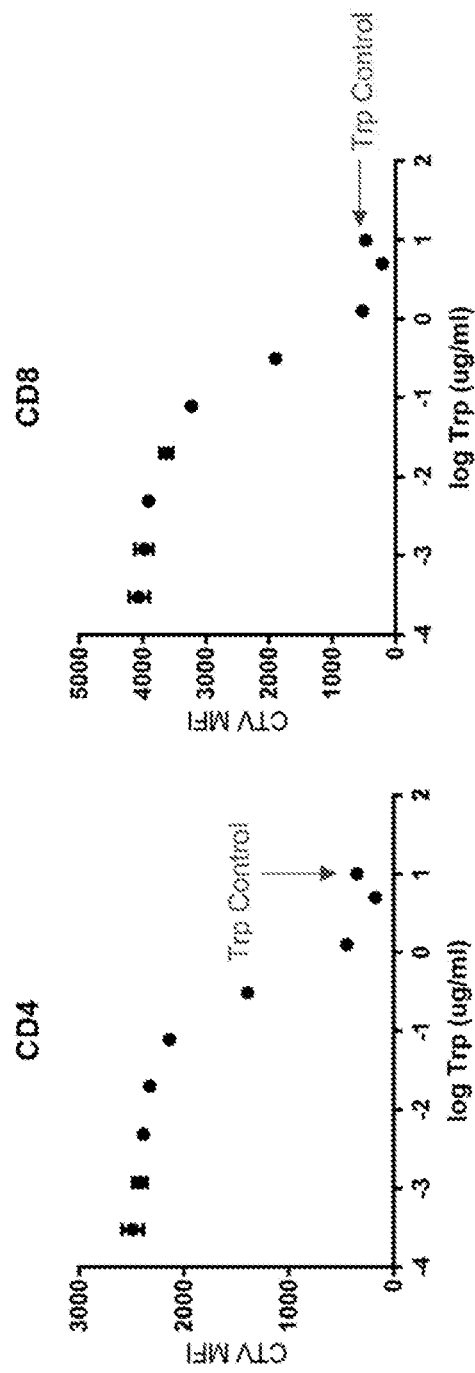
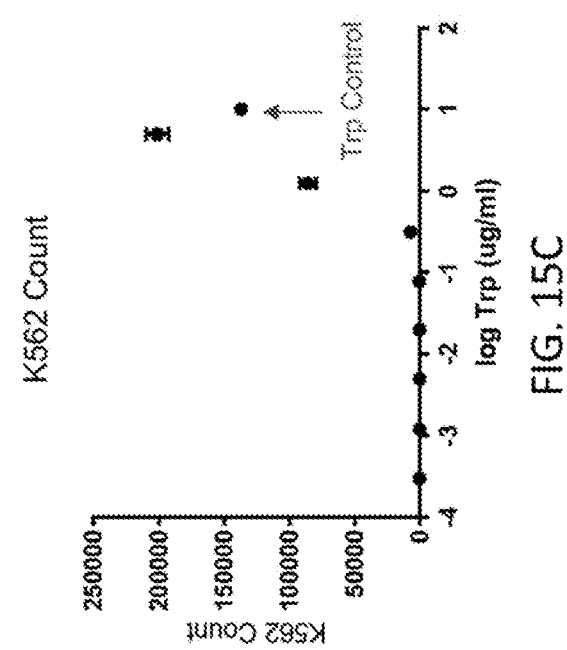

IMMUNOTHERAPY METHODS AND COMPOSITIONS INVOLVING TRYPTOPHAN METABOLIC PATHWAY MODULATORS

CROSS-REFERENCE TO RELATED APPLICATIONS

This application is a U.S. National Stage under 35 U.S.C. § 371 of International Application No. PCT/US2017/056680, filed Oct. 13, 2017, which claims the benefit of priority from U.S. provisional application No. No. 62/407,776, filed Oct. 13, 2016, entitled "IMMUNOTHERAPY METHODS AND COMPOSITIONS INVOLVING TRYPTOPHAN METABOLIC PATHWAY MODULATORS," and U.S. provisional application No. 62/514,767, filed Jun. 2, 2017, entitled "IMMUNOTHERAPY METHODS AND COMPOSITIONS INVOLVING TRYPTOPHAN METABOLIC PATHWAY MODULATORS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042007500SeqList.txt, created Apr. 5, 2019 which is 136 kilobytes in size. The information in the electronic format of the Sequence Listing is incorporated by reference in its entirety.

FIELD

The present disclosure relates in some aspects to methods, compositions and uses involving immunotherapies, such as adoptive cell therapy, e.g., T cell therapy, and modulator(s) of a pathway involved in the metabolism of tryptophan, such as an alternative tryptophan metabolic pathway, and/or a component or metabolite thereof. In some embodiments, the modulators include kynurenine pathway modulators, including modulators of one or more reactions or components promoting the metabolism of tryptophan via the kynurenine pathway, and/or metabolites thereof. The provided methods, compositions and uses include those for combination therapies involving the administration or use of one or more such modulator (e.g., inhibitor of an enzyme in such pathway(s)) in conjunction with another agent, such as an immunotherapeutic agent, such as a therapeutic antibody, e.g., a multi-specific (e.g., T cell engaging) antibody, and/or a cell therapy, such as chimeric antigen receptor (CAR)-expressing T cells. Also among the provided compositions and uses are one or more such immunotherapeutic agents, such as engineered cells, that are or have been treated, altered or engineered with or to include one or more such modulators. Also among engineered cells are cells in which the expression, activity, or function of a molecule such as a protein involved in immunosuppressive activity of the cells in response to tryptophan metabolism, such as tryptophan catabolism, is modified, altered, disrupted or affected. Also provided are methods of manufacturing engineered cells, cells, compositions, methods of administration to subjects, nucleic acids, articles of manufacture and kits for use in the methods. In some embodiments, combinations are provided including the immunotherapeutic agent, such as engineered cells, and kynurenine and/or tryptophan modulator and instructions for the administration thereof. In some aspects, features of the methods and cells provide for increased or improved activity, function, persistence, expansion and/or proliferation of cells for adoptive cell therapy or endogenous immune cells recruited by immunotherapeutic agents.

BACKGROUND

Various strategies are available for immunotherapy, for example administering engineered T cells for adoptive therapy. For example, strategies are available for engineering T cells expressing genetically engineered antigen receptors, such as CARs, and administering compositions containing such cells to subjects. Improved strategies for cell therapy are needed. For example, in some contexts, strategies are desired with improvements in one or more aspects of cells or outcomes following administration, for example, improving the persistence, activity and/or proliferation of the cells upon administration to subjects. Provided in some embodiments are methods, cells, compositions, kits, and systems that meet such needs.

SUMMARY

Provided herein are methods of enhancing or modulating proliferation and/or activity of immune cell activity in an immunotherapy, such as a T cell therapy (e.g. CAR-expressing T cells) or a T cell-engaging therapy. In some embodiments, the methods generally involve administrating a combination therapy of an immunotherapy, such as a T cell therapy (e.g. CAR-expressing T cells) or a T cell-engaging therapy, and a tryptophan metabolism and/or kynurenine pathway modulator.

Provided herein are methods of treatment that involve: (a) administering a T cell therapy to a subject having a disease or condition; and (b) administering to the subject a therapeutically effective amount of a tryptophan metabolism and/or kynurenine pathway modulator, wherein administration of the tryptophan metabolism and/or kynurenine pathway modulator is started at a time point greater than 1 day prior to initiation of administration of the T cell therapy.

Provided herein are methods of treatment that involve administering a T cell therapy to a subject having a disease or condition, the subject having been previously administered a therapeutically effective amount of a tryptophan metabolism and/or kynurenine pathway modulator starting at a time point greater than 1 day prior to initiation of the T cell therapy.

In some embodiments of any of the methods provided herein, the administration of the tryptophan metabolism and/or kynurenine pathway modulator is started at a time point that is within or within about 2 days, 3 days, 6 days, 12 days, 15 days, 30 days, 60 days or 90 days or more prior to initiation of the administration of the T cell therapy. In some embodiments, the method further includes continuing administration of the tryptophan metabolism and/or kynurenine pathway modulator with or subsequent to initiation of administration of the T cell therapy. In some embodiments, the method further includes administering the tryptophan metabolism and/or kynurenine pathway modulator subsequent to administering the therapy cell therapy.

Provided herein are methods of treatment that involve: (a) administering a T cell therapy to a subject having a disease or condition; and (b) administering to the subject a therapeutically effective amount of a tryptophan metabolism and/or kynurenine pathway modulator subsequent to initiation of administration of the T cell therapy. Also provided are methods of treatment that involves administering to a subject having cancer a therapeutically effective amount of a tryptophan metabolism and/or kynurenine pathway modulator, the subject having been previously administered a T cell therapy. In some embodiments, the tryptophan metabolism and/or kynurenine pathway modulator is administered within or within about 1 hour, 2 hours, 6 hours, 12 hours, 24 hours or 48 hours subsequent to initiation of the T cell therapy.

In some embodiments, prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator, optionally wherein such prior administration was carried out in combination with an immunomodulatory agent, optionally a checkpoint inhibitor.

Provided herein are methods of treatment that involve: (a) administering a T cell therapy to a subject having a disease or condition; and (b) administering to the subject a therapeutically effective amount of a tryptophan metabolism and/or kynurenine pathway modulator, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

Provided herein are methods of treatment that involve: administering to a subject having a disease or condition a therapeutically effective amount of a tryptophan metabolism and/or kynurenine pathway modulator to a subject having been administered a T cell therapy, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

In some embodiments, the disease or condition is cancer.

In some embodiments, the tryptophan metabolism and/or kynurenine pathway modulator administered in (b) is administered prior to, simultaneously with and/or subsequent to initiation of administration of the T cell therapy. In some embodiments, administration of the tryptophan metabolism and/or kynurenine pathway modulator administered in (b) is started at a time point that is within or within about 2 days, 3 days, 6 days, 12 days, 15 days, 30 days, 60 days or 90 days or more prior to initiation of the administration of the T cell therapy.

In some embodiments, the methods also involve administering the tryptophan metabolism and/or kynurenine pathway modulator administered in (b) subsequent to initiation of administration of the T cell therapy.

In some embodiments, tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; at a time before the number of cells of the T cell therapy detectable in the blood from the subject is decreased compared to in the subject at a preceding time point after initiation of administration of the T cell therapy; at a time before T cells exhibit manifestations of prolonged tryptophan starvation, exhaustion, reduction of effector function, expression of inhibitory receptors and/or loss of proliferative capacity; at a time before a peak or maximum level of the cells of the T cell therapy are detectable in the blood of the subject; and/or the level of interferon-gamma (IFNγ) is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more.

In some embodiments, the tryptophan metabolism and/or kynurenine pathway modulator administered in (b) is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy.

In some embodiments of any of the methods provided herein, the tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; the number of cells of the T cell therapy detectable in the blood from the subject is decreased compared to in the subject at a preceding time point after initiation of administration of the T cell therapy; the number of cells of the T cell therapy detectable in the blood is decreased by more than or more than about 1.5-fold, 2-fold, 3-fold, 4-fold, 5-fold, 10-fold, 50-fold or 100-fold or more, compared to the peak or maximum number of the cells of the T cell therapy detectable in the blood of the subject after initiation of administration of the T cell therapy; and/or at a time after a peak or maximum level of the cells of the T cell therapy are detectable in the blood of the subject, the number of cells of the T cell therapy detectable in the blood from the subject is less than less than 10%, less than 5%, less than 1% or less than 0.1% of total peripheral blood mononuclear cells (PBMCs) in the blood of the subject; the level of IFN-gamma is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more. In some embodiments, the biological sample is a serum or plasma or tumor sample or is a tumor.

In some embodiments of any of the methods provided herein, the tryptophan metabolism and/or kynurenine pathway modulator prevents or reduces the formation, concentration, availability, metabolism and/or effect of an enzyme and/or a metabolite of the kynurenine pathway. In some embodiments, the tryptophan metabolism and/or kynurenine pathway modulator prevents or reduces catabolism of tryptophan or prevents or reduces synthesis or accumulation of a tryptophan metabolite. In some embodiments, the tryptophan metabolite is selected from kynurenine, 3-hydroxykynurenine and 3-hydroxyanthranilic acid (3-HAA). In some embodiments, the tryptophan metabolism and/or kynurenine pathway modulator is a small molecule, peptide, protein, antibody or antigen-binding fragment thereof, an antibody mimetic, an aptamer, or a nucleic acid molecule.

In some embodiments of any of the embodiments herein, the tryptophan metabolism and/or kynurenine pathway modulator is an antagonist of the enzyme kynureninase.

In some embodiments of any of the embodiments herein, the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO). In some embodiments, the tryptophan metabolism and/or kynurenine pathway modulator is a dual-acting IDO/TDO inhibitor. In some embodiments, the tryptophan metabolism and/or kynurenine pathway modulator is an inhibitor of indoleamine-pyrrole 2,3-dioxygenase 1 (IDO1).

In some embodiments of any of the embodiments herein, the tryptophan metabolism and/or kynurenine pathway modulator is an inhibitor of IDO1 and the tryptophan metabolism and/or kynurenine pathway modulator of IDO1 is administered at a time in which there is an increase in the expression or activity of IDO1 in a biological sample from the subject compared to prior to initiation of administration of the T cell therapy or compared to a preceding time point after initiation of administration of the T cell therapy.

In some embodiments, the tryptophan metabolism and/or kynurenine pathway modulator is tryptophan.

In some embodiments of any of the methods provided herein, the cancer contains a tumor negative for IDO1 and/or the subject is not selected for expression of an IDO1 positive tumor; and/or the cancer contains a tumor negative for TDO and/or the subject is not selected for expression of a TDO positive tumor. In some embodiments, the cancer contains a tumor negative for IDO1 and/or the subject is not selected for expression of an IDO1 positive tumor.

In some embodiments of any of the methods provided herein, the cancer comprises a tumor negative for IDO1 prior to initiation of administration of the T cell therapy and/or the subject is not selected for expression of an IDO1 positive tumor prior to initiation of administration of the T cell therapy; and/or the cancer comprises a tumor negative for TDO prior to initiation of administration of the T cell therapy and/or the subject is not selected for expression of a TDO positive tumor prior to initiation of administration of the T cell therapy. In some embodiments, the cancer comprises a tumor negative for IDO1 prior to initiation of administration of the T cell therapy and/or the subject is not selected for expression of an IDO1 positive tumor prior to initiation of administration of the T cell therapy.

Provided herein are methods of treatment that involve (a) administering a T cell therapy to a subject having a disease or condition, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or the subject is not selected for expression of an IDO1 positive tumor or a TDO positive tumor prior to initiation of administration of the T cell therapy; and; and (b) administering to the subject a therapeutically effective amount of a tryptophan metabolism and/or kynurenine pathway modulator that is an inhibitor of IDO1.

Also provided herein are methods of treatment that involve administering to a subject having cancer a therapeutically effective amount of a tryptophan metabolism and/or kynurenine pathway modulator that is an inhibitor of IDO1, the subject having been administered a T cell therapy, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or the subject is not selected for expression of an IDO1 positive tumor or a TDO positive tumor prior to initiation of administration of the T cell therapy.

Also provided herein are methods of treatment that involve administering to a subject having cancer a T cell therapy, the subject having been administered a therapeutically effective amount of a tryptophan metabolism and/or kynurenine pathway modulator that is an inhibitor of IDO1, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or the subject is not selected for expression of an IDO1 positive tumor or a TDO positive tumor prior to initiation of administration of the T cell therapy.

In some embodiments, the disease or condition is cancer.

In some embodiments of any of the methods provided herein, the tryptophan metabolism and/or kynurenine pathway modulator is administered prior to, simultaneously with and/or subsequent to initiation of administration of the T cell therapy.

In some embodiments, prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

In some embodiments, the method also includes administering the tryptophan metabolism and/or kynurenine pathway modulator administered in (b) subsequent to initiation of administration of the T cell therapy.

In some embodiments, tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; at a time before the number of cells of the T cell therapy detectable in the blood from the subject is decreased compared to in the subject at a preceding time point after initiation of administration of the T cell therapy; at a time before T cells exhibit manifestations of prolonged tryptophan starvation, exhaustion, reduction of effector function, expression of inhibitory receptors and/or loss of proliferative capacity; at a time before a peak or maximum level of the cells of the T cell therapy are detectable in the blood of the subject; and/or the level of interferon-gamma (IFNγ) is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more.

In some embodiments, the tryptophan metabolism and/or kynurenine pathway modulator administered in (b) is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy. In some embodiments, the tryptophan metabolism and/or kynurenine pathway modulator administered in (b) is administered within or within about 1 hour, 2 hours, 6 hours, 12 hours, 24 hours or 48 hours subsequent to initiation of the T cell therapy.

In some embodiments, the tryptophan metabolism and/or kynurenine pathway modulator is administered from or from about 0 to 96 hours, 0 to 72 hours, 0 to 48 hours, 0 to 24 hours, 0 to 12 hours or 0 to 6 hours or 0 to 2 hours prior to initiation of the T cell therapy; or the tryptophan metabolism and/or kynurenine pathway modulator is administered no more than 96 hours, 72 hours, 48 hours, 24 hours, 12 hours, 6 hours, 2 hours or 1 hour prior to initiation of the T cell therapy.

In some embodiments of any of the embodiments herein, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino] ethyl}amino)-N-[(4-chloro-2-furyl)methyl]-N'-hydroxy-1, 2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

In some embodiments of any of the embodiments herein, the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat). In some embodiments, the tryptophan metabolism and/or kynurenine pathway modulator is 1-methyl-D-tryptophan (1-MT) (indoximod). In some embodiments, the tryptophan metabolism and/or kynurenine pathway modulator is tryptophan.

Provided herein are methods of treatment that involve: (a) administering a T cell therapy to a subject having a disease or condition; and (b) administering to the subject a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

Also provided herein are methods of treatment that involve administering to a subject having cancer a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), the subject having been administered a T cell therapy.

Also provided herein are methods of treatment that involve administering to a subject having cancer a T cell therapy, the subject having been administered a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

In some embodiments, the disease or condition is cancer.

In some embodiments of any of the embodiments herein, upon administration to the subject the T cell therapy causes an increase or elevation of the level of IFN-gamma in the subject in the local environment of a tumor or in a serum or plasma sample of the subject compared to the level of IFN-gamma in the subject prior to initiation of the T cell therapy.

In some embodiments of any of the embodiments herein, the T cell therapy is or includes tumor infiltrating lymphocytic (TIL) therapy or a T cell therapy that includes genetically engineered cells expressing a recombinant receptor that specifically binds to a ligand. In some embodiments, the T cell therapy is or includes genetically engineered cells expressing a recombinant receptor that specifically binds to a ligand.

In some embodiments of any of the embodiments herein, the genetically engineered cell also includes a modification impacting the expression, presence, or activity of a protein or other factor or molecule associated with one or more activities or outcomes or effects, and/or a nucleic acid encoding such protein or factor. In some aspects, the activities, outcomes, or effects may include those associated with, involved in sensing of, or promoted by tryptophan deficiencies or tryptophan starvation. In some aspects, the activities, outcomes, or effects may include those associated with, involved in sensing of, or promoted by increased amounts or concentrations of kynurenine or one or more kynurenine pathway metabolites and/or kynurenine mediated immunosuppression, and/or decreased tryptophan/kynurenine ratios in the cell or environment. In some embodiments, the protein or factor is or includes a protein involved in or associated with the sensing of tryptophan starvation and/or kynurenine mediated immunosuppressive effects, such as those that may limit T cell function, e.g., in the tumor environment. Such effects may include inhibition or dampening of T cell activity or function and/or promotion of Treg function, levels, or activity. In some embodiments, the protein or factor is involved in IDO-induced immunosuppressive effects in the cell and/or neighboring cells.

Provided herein are methods of treatment that involve administering a genetically engineered T cells to a subject having a disease or condition, wherein the genetically engineered T cell contains (i) a recombinant receptor that specifically binds to a ligand and (ii) modification of expression of a protein involved in or associated with the sensing of tryptophan starvation and/or kynurenine mediated immunosuppressive effects and/or protein associated with IDO-mediated immunosuppressive effects in the cell.

Also provided herein are methods of treatment that involve administering a genetically engineered T cells to a subject having a disease or condition, wherein the genetically engineered T cell comprise (i) a recombinant receptor that specifically binds to a ligand and (ii) a recombinant, engineered and/or ectopically expressed amino acid transporter or chain thereof or a functional and/or catalytically active portion or variant thereof. In some embodiments, the methods also include (b) administering to the subject a therapeutically effective amount of a tryptophan metabolism and/or kynurenine pathway modulator.

Provided herein are methods of treatment that involve: (a) administering a genetically engineered T cells to a subject having a disease or condition, wherein the genetically engineered T cell contains (i) a recombinant receptor that specifically binds to a ligand and (ii) a modification of expression of a protein involved in or associated with the sensing of tryptophan starvation and/or kynurenine mediated immunosuppressive effects and/or a protein associated with IDO-mediated immunosuppressive effects in the cell; and (b) administering to the subject a therapeutically effective amount of a tryptophan metabolism and/or kynurenine pathway modulator.

In some embodiments, the disease or condition is cancer.

In some embodiments, the subject is selected for having a tumor positive for expression of L-type Amino Acid Transporter 1 (LAT1; SLC7A5), LAT2 (SLC7A8), CD98 heavy chain (4F2hc; CD98hc; SLC3A2) and/or proton-assisted amino-acid transporter 4 (PAT4; SLC36A4), or for having cells in the tumor microenvironment that are positive for expression of LAT1, LAT2, CD98hc and/or PAT4.

In some embodiments of any of the embodiments herein, the tryptophan metabolism and/or kynurenine pathway modulator prevents or reduces the formation, concentration, availability, metabolism and/or effect of an enzyme and/or a metabolite of the kynurenine pathway. In some embodiments, the tryptophan metabolism and/or kynurenine pathway modulator prevents or reduces catabolism of tryptophan or prevents or reduces synthesis or accumulation of a tryptophan metabolite. In some embodiments, the tryptophan metabolite is selected from kynurenine, 3-hydroxykynurenine and 3-hydroxyanthranilic acid (3-HAA).

In some embodiments of any of the embodiments herein, the tryptophan metabolism and/or kynurenine pathway modulator is a small molecule, peptide, protein, antibody or antigen-binding fragment thereof, an antibody mimetic, an aptamer, or a nucleic acid molecule.

In some embodiments of any of the embodiments herein, the tryptophan metabolism and/or kynurenine pathway modulator is an antagonist of the enzyme kynureninase.

In some embodiments of any of the embodiments herein, the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO). In some embodiments, the tryptophan metabolism and/or kynurenine pathway modulator is a dual-acting IDO/TDO inhibitor.

In some embodiments of any of the embodiments herein, the tryptophan metabolism and/or kynurenine pathway modulator is an inhibitor of indoleamine-pyrrole 2,3-dioxygenase 1 (IDO1). In some embodiments of any of the embodiments herein, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1, 2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

In some embodiments of any of the embodiments herein, the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat). In some embodiments, the tryptophan metabolism and/or kynurenine pathway modulator is 1-methyl-D-tryptophan (1-MT) (indoximod). In some embodiments, the tryptophan metabolism and/or kynurenine pathway modulator is tryptophan.

In some embodiments of any of the embodiments herein, the tryptophan metabolism and/or kynurenine pathway modulator is administered subsequent to initiation of administration of the T cell therapy.

In some embodiments of any of the embodiments herein, the molecule, protein or factor associated with IDO-mediated immunosuppressive signaling, associated with sensing or responding to tryptophan starvation or insufficiency and/or associated with sensing or responding to kynurenine-mediated immuno-suppression, is mTOR or protein kinase C theta (PKC-Θ).

In some embodiments, prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

In some embodiments, the tryptophan metabolism and/or kynurenine pathway modulator is administered prior to, simultaneously with and/or subsequent to initiation of administration of the T cell therapy. In some embodiments, comprising administering the tryptophan metabolism and/or kynurenine pathway modulator subsequent to initiation of administration of the T cell therapy.

In some embodiments, tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; at a time before the number of cells of the T cell therapy detectable in the blood from the subject is decreased compared to in the subject at a preceding time point after initiation of administration of the T cell therapy; at a time before T cells exhibit manifestations of prolonged tryptophan starvation, exhaustion, reduction of effector function, expression of inhibitory receptors and/or loss of proliferative capacity; at a time before a peak or maximum level of the cells of the T cell therapy are detectable in the blood of the subject; and/or the level of interferon-gamma (IFNγ) is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more.

In some embodiments, the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy. In some embodiments, the tryptophan metabolism and/or kynurenine pathway modulator is administered within or within about 1 hour, 2 hours, 6 hours, 12 hours, 24 hours or 48 hours subsequent to initiation of the T cell therapy.

In some embodiments, the tryptophan metabolism and/or kynurenine pathway modulator is administered from or from about 0 to 96 hours, 0 to 72 hours, 0 to 48 hours, 0 to 24 hours, 0 to 12 hours or 0 to 6 hours or 0 to 2 hours prior to initiation of the T cell therapy; or the tryptophan metabolism and/or kynurenine pathway modulator is administered no more than 96 hours, 72 hours, 48 hours, 24 hours, 12 hours, 6 hours, 2 hours or 1 hour prior to initiation of the T cell therapy.

In some embodiments, the modification comprises recombinant, engineered and/or ectopic expression of the molecule or a functional and/or catalytically active chain, portion or variant thereof. In some embodiments, the molecule is mTOR or protein kinase C theta (PKC-θ).

In some embodiments, the molecule is an amino acid transporter or a chain thereof or a functional and/or catalytically active portion or variant thereof. In some embodiments, the amino acid transporter is a tryptophan transporter. In some embodiments, the amino acid transporter or a chain thereof is selected from among one or more of rBAT (SLC3A1), CD98 heavy chain (4F2hc; SLC3A2), L-type Amino Acid Transporter 1 (LAT1; SLC7A5), LAT2 (SLC7A8), Asc-type amino acid transporter 1 (Asc-1; SLC7A10), Sodium- and chloride-dependent neutral and basic amino acid transporter B(0+)(ATB0,+; SLC6A14), Sodium-dependent neutral amino acid transporter B(0)AT1 (B(0)AT1; SLC6A19), Monocarboxylate transporter 10 (TAT1; SLC16A10), and proton-assisted amino-acid transporter 4 (PAT4; SLC36A4) or a portion thereof. In some embodiments, the amino acid transporter or a chain thereof comprises CD98 heavy chain (4F2hc; SLC3A2) and L-type Amino Acid Transporter 1 (LAT1; SLC7A5) or a portion thereof.

In some embodiments, the amino acid transporter or a chain thereof comprises the amino acid sequence selected from any one of SEQ ID NOs: 36-44 or a portion thereof, or an amino acid sequence having at least 90%, 91%, 92%, 93%, 94%, 95%, 96%, 97%, 98%, or 99% sequence identity to the amino acid sequence selected from any one of SEQ ID NOs: 36-44 or a portion thereof. In some embodiments, the amino acid transporter or a chain thereof is selected from among one or more of CD98 heavy chain (4F2hc; SLC3A2), L-type Amino Acid Transporter 1 (LAT1; SLC7A5), LAT2 (SLC7A8), and proton-assisted amino-acid transporter 4 (PAT4; SLC36A4) or a portion thereof. In some embodiments, the amino acid transporter or a chain thereof comprises CD98 heavy chain (4F2hc; SLC3A2) and L-type Amino Acid Transporter 1 (LAT1; SLC7A5) or a portion thereof.

In some embodiments, the amino acid transporter or a chain thereof comprises the amino acid sequence selected from any one of SEQ ID NOs:37-39 and 44 or a portion thereof, or an amino acid sequence having at least 90%, 91%, 92%, 93%, 94%, 95%, 96%, 97%, 98%, or 99% sequence identity to the amino acid sequence selected from any one of SEQ ID NOs: 37-39 and 44 or a portion thereof.

In some embodiments, expression of the molecule in the cell is under the control of a conditional promoter or enhancer or transactivator.

In some embodiments of any of the embodiments herein, the modification includes recombinant, engineered and/or ectopic expression of the protein or a functional and/or catalytically active portion or variant thereof. In some embodiments, expression of the protein in the cell is under the control of a conditional promoter or enhancer or transactivator.

In some embodiments of any of the embodiments herein, the molecule, protein or factor associated with IDO-mediated immunosuppressive signaling, associated with sensing or responding to tryptophan starvation or insufficiency and/or associated with sensing or responding to kynurenine-mediated immuno-suppression is GCN2 kinase, BLIMP-1, aryl hydrocarbon receptor (AHR) or AHR nuclear transporter (ARNT). In some embodiments, the molecule is selected from among GCN2 kinase, BLIMP-1, aryl hydrocarbon receptor (AHR), AHR nuclear transporter (ARNT), eukaryotic translation initiation factor 2 α (eIF2α), activating transcription factor 4 (ATF4), or CCAAT/enhancer binding protein-homologous protein (CHOP), Gadd45α, Herp, 4E-BP1, eIF4G, JAK1, NFκB-2, FK506-BP8 and IFNγ-R2. In some embodiments, the molecule is GCN2 or CHOP.

In some embodiments of any of the embodiments herein, the modification includes reduced expression of the molecule. In some embodiments, the engineered cell includes an inhibitory nucleic acid or a genetic disruption that reduces expression of the molecule. In some embodiments, expression of the molecule in the cell is reduced by at least 50, 60, 70, 80, 90, or 95% as compared to the expression in the cell in the absence of the agent or gene disruption.

In some embodiments of any of the methods provided herein, the method includes introducing the inhibitory nucleic acid into the cell, thereby effecting reduction in expression of the molecule. In some embodiments, the engineered cell includes an inhibitory nucleic acid and the inhibitory nucleic acid includes an RNA interfering agent. In some embodiments, the inhibitory nucleic acid is or includes or encodes a small interfering RNA (siRNA), a microRNA-adapted shRNA, a short hairpin RNA (shRNA), a hairpin siRNA, a microRNA (miRNA-precursor) or a microRNA (miRNA). In some embodiments, the method includes introducing a nucleic acid encoding or producing the inhibitory nucleic acid into the cell, thereby effecting reduction in expression of the molecule.

In some embodiments of any of the embodiments herein, expression of the inhibitory nucleic acid is under the control of a conditional promoter or enhancer or transactivator.

In some embodiments of any of the embodiments herein, the engineered cell includes a genetic disruption, wherein: the disruption involves disrupting the gene encoding the molecule at the DNA level and/or the disruption is not reversible; and/or the disruption is not transient. In some embodiments, the disruption involves introducing into the cell a DNA binding protein or DNA-binding nucleic acid that specifically binds to or hybridizes the gene encoding the molecule.

In some embodiments of any of the embodiments herein, the disruption involves introducing: (a) a fusion protein that includes a DNA-targeting protein and a nuclease or (b) an RNA-guided nuclease. In some embodiments, the DNA-targeting protein or RNA-guided nuclease that includes a zinc finger protein (ZFP), a TAL protein, or a clustered regularly interspaced short palindromic nucleic acid (CRISPR) specific for the gene. In some embodiments, the disruption includes introducing an agent into the cell, including a zinc finger nuclease (ZFN), a TAL-effector nuclease (TALEN), or a CRISPR-Cas9 combination that specifically binds to, recognizes, or hybridizes to the gene encoding the molecule. In some embodiments, the agent is a CRISPR-Cas9 combination and the CRISPR-Cas9 combination that includes a guide RNA (gRNA) containing a guide sequence that is complementary to, and/or capable of hybridizing to, a target sequence in the gene.

In some embodiments of any of the embodiments herein, the genetic disruption is inducible. In some embodiments, the CRISPR-Cas9 complex is an inducible CRISPR-Cas9 and/or the Cas9 is under the under the control of a conditional promoter or enhancer or transactivator.

In some embodiments of any of the embodiments herein, the disruption contains a deletion of at least a portion of at least one exon of the gene encoding the molecule.

In some embodiments of any of the embodiments herein, the disruption contains a deletion, mutation, and/or insertion in the gene resulting in the presence of a premature stop codon in the gene; and/or the disruption contains a deletion, mutation, and/or insertion within a first or second exon of the gene encoding the molecule.

In some embodiments of any of the embodiments herein, the conditional promoter or enhancer or transactivator is an inducible promoter, enhancer, or transactivator or a repressible promoter, enhancer, or transactivator. In some embodiments, the promoter is selected from among an RNA pol I, pol II or pol II promoter. In some embodiments, the promoter is selected from: a pol III promoter that is a U6 or H1 promoter; or a pol II promoter that is a CMV, SV40 early region or adenovirus major late promoter.

In some embodiments of any of the embodiments herein, the promoter is an inducible promoter. In some embodiments, the promoter contains a Lac operator sequence, a tetracycline operator sequence, a galactose operator sequence or a doxycycline operator sequence, or is an analog thereof.

In some embodiments of any of the embodiments herein, the promoter is a repressible promoter. In some embodiments, the promoter is capable of being bound by a Lac repressor or a tetracycline repressor, or is an analog thereof.

In some embodiments of any of the embodiments herein, the genetically engineered receptor that specifically binds to a ligand is a functional non-T cell receptor. In some embodiments, the genetically engineered receptor that specifically binds to a ligand is a chimeric antigen receptor (CAR). In some embodiments, the CAR contains an extracellular antigen-recognition domain that specifically binds to the antigen and an intracellular signaling region that includes an ITAM. In some embodiments, the intracellular signaling region contains an intracellular domain of a CD3-zeta (CD3) chain.

In some embodiments of any of the embodiments herein, the CAR also contains a costimulatory signaling region. In some embodiments, the costimulatory signaling region contains a signaling domain of CD28 or 4-1BB or an ICOS or a signaling portion thereof. In some embodiments, the costimulatory signaling region is a signaling domain of a CD28.

In some embodiments of any of the embodiments herein, the recombinant receptor is a transgenic T cell receptor (TCR). In some embodiments, the recombinant receptor is a chimeric antigen receptor (CAR).

In some embodiments of any of the embodiments herein, the T cell therapy recognizes or targets an antigen associated with the cancer. In some embodiments, the recombinant receptor binds to, recognizes or targets an antigen associated with the cancer. In some embodiments, the antigen is selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

In some embodiments of any of the embodiments herein, the cancer includes a tumor negative for indoleamine-pyrrole 2,3-dioxygenase 1 (IDO1) and/or the subject is not selected for expression of an IDO1 positive tumor. In some embodiments, the cancer comprises a tumor negative for indoleamine-pyrrole 2,3-dioxygenase 1 (IDO1) prior to initiation of administration of the T cell therapy and/or the subject is not selected for expression of an IDO1 positive tumor prior to initiation of administration of the T cell therapy. In some embodiments, the cancer comprises a tumor positive for expression of L-type Amino Acid Transporter 1 (LAT1; SLC7A5), LAT2 (SLC7A8), CD98 heavy chain (4F2hc; CD98hc; SLC3A2) and/or proton-assisted amino-acid transporter 4 (PAT4; SLC36A4), or the cancer comprises cells in the tumor microenvironment that are positive for expression of LAT1, LAT2, CD98hc and/or PAT4.

In some embodiments of any of the embodiments herein, the cancer is a myeloma, lymphoma, leukemia. In some embodiments, the cancer is non-Hodgkin lymphoma (NHL), an acute lymphoblastic leukemia (ALL), a chronic lymphocytic leukemia (CLL), diffuse large B-Cell lymphoma (DLBCL), and myeloma. In some embodiments, the cancer does not express a B cell antigen or is not a B cell malignancy. In some embodiments, the cancer does not express CD19 and/or the T cell therapy does not include a recombinant receptor that specifically binds CD19 and/or the T cell therapy is a CAR-T cell therapy that does not include an anti-CD19 antigen-binding domain.

In some embodiments of any of the embodiments herein, the cancer is a non-hematological cancer or is a solid tumor.

In some embodiments, the method results in an increase in tryptophan levels and/or a decrease in kynurenine levels in the tumor or in a biological sample from the subject, optionally a serum, plasma or tumor sample, compared to a method involving administration of the T cell therapy but in the absence of the tryptophan metabolism and/or kynurenine pathway modulator or compared to a method in which the cell are administered that do not comprise modification of expression of a molecule associated with IDO-mediated immunosuppressive signaling, associated with sensing or responding to tryptophan starvation or insufficiency and/or associated with sensing or responding to kynurenine-mediated immuno-suppression.

In some embodiments of any of the embodiments herein, the T cell therapy exhibits increased or prolonged expansion and/or persistence in the subject as compared to a method in which the T cell therapy is administered to the subject in the absence of the tryptophan metabolism and/or kynurenine pathway modulator.

In some embodiments of any of the embodiments herein, the tryptophan metabolism and/or kynurenine pathway modulator is administered orally, subcutaneous or intravenously. In some embodiments, the tryptophan metabolism and/or kynurenine pathway modulator is administered orally.

In some embodiments of any of the embodiments herein, the tryptophan metabolism and/or kynurenine pathway modulator is administered in an amount from or from about 2.5 mg to about 5000 mg, 2.5 mg to 2000 mg, 2.5 mg to 1000 mg, 2.5 mg to 500 mg, 2.5 mg to 200 mg, 2.5 mg to 100 mg, 2.5 mg to 50 mg, 2.5 mg to 25 mg, 2.5 mg to 10 mg, 25 mg to 5000 mg, 25 mg to 2000 mg, 25 mg to 1000 mg, 25 mg to 500 mg, 25 mg to 200 mg, 25 mg to 100 mg, 25 mg to 50 mg, 50 mg to 5000 mg, 50 mg to 2000 mg, 50 mg to 1000 mg, 50 mg to 500 mg, 50 mg to 200 mg, 50 mg to 100 mg, 100 mg to 5000 mg, 100 mg to 2000 mg, 100 mg to 1000 mg, 100 mg to 500 mg, 100 mg to 200 mg, 200 mg to 5000 mg, 200 mg to 2000 mg, 200 mg to 1000 mg, 200 mg to 500 mg, 500 mg to 5000 mg, 500 mg to 2000 mg, 500 mg to 1000 mg or 1000 mg to 2000 mg, each inclusive. In some embodiments, the tryptophan metabolism and/or kynurenine pathway modulator is administered six times daily, five times daily, four times daily, three times daily, twice daily or once daily. In some embodiments, the tryptophan metabolism and/or kynurenine pathway modulator is administered at a total daily dosage amount of at least or at least about 5 mg/day, 10 mg/day, 25 mg/day, 50 mg/day, 100 mg/day, 200 mg/day, 400 mg/day, 500 mg/day, 600 mg/day, 800 mg/day, 1000 mg/day, 1200 mg/day, 1600 mg/day, 2000 mg/day, 5000 mg/day or 10000 mg/day.

In some embodiments of any of the embodiments herein, the administration of the tryptophan metabolism and/or kynurenine pathway modulator is continued after initiation of administration of the T cell therapy until: there is an increase in tryptophan levels, a decrease in kynurenine levels and/or an decrease in expression or activity of IDO1, IDO2 or TDO in a biological sample from the subject compared to just prior to administration of the tryptophan metabolism and/or kynurenine pathway modulator or compared to just prior to initiation of administration of the T-cell therapy; the number of cells of the T cell therapy detectable in the blood from the subject is increased compared to in the subject at a preceding time point just prior to administration of the tryptophan metabolism and/or kynurenine pathway modulator or compared to a preceding time point after administration of the T-cell therapy; the number of cells of the T cell therapy detectable in the blood is within 2.0-fold (greater or less) the peak or maximum number of the cells of the T cell therapy detectable in the blood of the subject after initiation of administration of the T cell therapy; and/or the number of cells of the T cell therapy detectable in the blood from the subject is greater than or greater than about 10%, 15%, 20%, 30%, 40%, 50%, or 60% total peripheral blood mononuclear cells (PBMCs) in the blood of the subject.

In some embodiments of any of the embodiments herein, the tryptophan metabolism and/or kynurenine pathway modulator is administered until: the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) the blood contains at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

In some embodiments of any of the embodiments herein, the tryptophan metabolism and/or kynurenine pathway modulator is administered for a time period up to 2 days, up to 7 days, up to 14 days, up to 21 days, up to one month, up to two months, up to three months, up to 6 months or up to 1 year after initiation of the administration of the T cell therapy.

In some embodiments of any of the embodiments herein the T cell therapy includes T cells that are CD4+ or CD8+. In some embodiments, the T cell therapy includes cells that are autologous to the subject. In some embodiments, the T cell therapy includes T cells that are allogeneic to the subject.

In some embodiments of any of the embodiments herein, T cell therapy is administered in an amount to upregulate IDO1 expression in the tumor microenvironment. In some embodiments, IDO1 expression is upregulated in or from myeloid cells, stromal cells or tumor cells. In some embodiments, IDO1 expression is upregulated in or from bone marrow stromal cells.

In some embodiments of any of the methods provided herein, the cell therapy includes administration of a dose that contains a number of cells between or between about $0.5 \times 10^6$ cells/kg body weight of the subject and $5 \times 10^6$ cells/kg, between or between about $0.5 \times 10^6$ cells/kg body weight of the subject and $3 \times 10^6$ cells/kg, between or between about $0.5 \times 10^6$ cells/kg body weight of the subject and $2 \times 10^6$ cells/kg, between or between about $0.5 \times 10^6$ cells/kg body weight of the subject and $1 \times 10^6$ cell/kg, between or between about $1.0 \times 10^6$ cells/kg body weight of the subject and $5 \times 10^6$ cells/kg, between or between about $1.0 \times 10^6$ cells/kg body weight of the subject and $3 \times 10^6$ cells/kg, between or between about $1.0 \times 10^6$ cells/kg body weight of the subject and $2 \times 10^6$ cells/kg, between or between about $2.0 \times 10^6$ cells/kg body weight of the subject and $5 \times 10^6$ cells/kg, between or between about $2.0 \times 10^6$ cells/kg body weight of the subject and $3 \times 10^6$ cells/kg, or between or between about $3.0 \times 10^6$ cells/kg body weight of the subject and $5 \times 10^6$ cells/kg, each inclusive.

In some embodiments of any of the embodiments herein, the dose of cells administered is less than the dose in a method in which the cell therapy is administered without administering the tryptophan metabolism and/or kynurenine pathway modulator or a method in which the cells do not comprise modification of expression of a molecule associated with IDO-mediated immunosuppressive signaling, associated with sensing or responding to tryptophan starvation or insufficiency and/or associated with sensing or responding to kynurenine-mediated immuno-suppression. In some embodiments, the dose is at least 1.5-fold, 2-fold, 3-fold, 4-fold, 5-fold or 10-fold less.

In some embodiments of any of the methods provided herein, the T cell therapy is administered as a single pharmaceutical composition that contains the cells. In some embodiments, the T cell therapy includes a dose of cell that is a split dose, wherein the cells of the dose are administered in a plurality of compositions, which collectively contains the cells of the dose, over a period of no more than three days.

In some embodiments of any of the embodiments herein, the method further involves administering a lymphodepleting chemotherapy prior to administration of the T cell therapy. In some embodiments, the method does not include administering fludarabine to the subject. In some embodiments of any of the embodiments herein, the provided methods do not involve administering a lymphodepleting chemotherapy to the subject prior to administration of the T cell therapy.

In some embodiments, the recombinant receptor is engineered by introduction of a first nucleic acid sequence encoding the recombinant receptor into the cell, and one or more second nucleic acid sequence(s) encoding an agent that is capable of or involved in modification of expression of a molecule associated with IDO-mediated immunosuppressive signaling, associated with sensing or responding to tryptophan starvation or insufficiency and/or associated with sensing or responding to kynurenine-mediated immunosuppression in the cell, into the cell. In some embodiments, the first nucleic acid sequence and the second nucleic acid sequence(s) are comprised in one or more polynucleotides. In some embodiments, the first nucleic acid sequence and the second nucleic acid sequence(s) are comprised in two polynucleotides. In some embodiments, the first nucleic acid and the second nucleic acid(s) are comprised in one or more vector(s), which optionally are viral vector(s).

Provided herein are methods of selecting a subject having a disease or condition for administering a tryptophan metabolism and/or kynurenine pathway modulator, that involve: (a) assessing the level of tryptophan or a tryptophan metabolite, the level of expression or activity of IDO1, IDO2 or TDO, or the level of interferon-gamma (IFNγ) in one or more biological samples from the subject, wherein the biological sample is from a subject that is a candidate for treatment with a T cell therapy; and (b) selecting a subject in which: (i) the level of tryptophan in the sample is below a threshold level; (ii) the level of the tryptophan metabolite is above a threshold level; (iii) the level of expression or activity of IDO1, IDO2 or TDO is above a threshold level; or (iv) the level of the IFNγ is above a threshold level.

In some embodiments, the one or more biological sample is obtained prior to administration of the T cell therapy.

In some embodiments, the methods also involve administering the T cell therapy to the subject. In some embodiments, the methods also involve administering the tryptophan metabolism and/or kynurenine pathway modulator to the selected subject. In some embodiments, the tryptophan metabolism and/or kynurenine pathway modulator is administered to the selected subject prior to or concurrently with initiation of administration of the T cell therapy. In some embodiments, the tryptophan metabolism and/or kynurenine pathway modulator is administered subsequent to initiation of administration of the T cell therapy.

Provided herein are methods of selecting a subject having a disease or condition for administering a tryptophan metabolism and/or kynurenine pathway modulator, that involve: (a) assessing the level of tryptophan or a tryptophan metabolite, the level of expression or activity of IDO1, IDO2 or TDO, or the level of interferon-gamma (IFNγ) in one or more biological samples from the subject, wherein the biological sample is obtained from a subject having been administered a T cell therapy; and (b) selecting a subject in which: (i) the level of tryptophan in the sample is below a threshold level or is decreased compared to the level assessed at a time point prior to initiation of administration of the T cell therapy or a preceding time point after initiation of administration of the T cell therapy; (ii) the level of the tryptophan metabolite is above a threshold level or is increased compared to the level assessed at a time point prior to initiation of administration of the T cell therapy or a preceding time point after initiation of administration of the T cell therapy; (iii) the level of expression or activity of IDO1, IDO2 or TDO is above a threshold level or is increased compared to the level assessed at a time point prior to initiation of administration of the T cell therapy or a preceding time point after initiation of administration of the T cell therapy; or (iv) the level of the IFNγ is above a threshold level or is increased compared to the level assessed at a time point prior to initiation of administration of the T cell therapy or a preceding time point after initiation of administration of the T cell therapy.

In some embodiments, the one or more biological sample is obtained subsequent to administration of the T cell therapy. In some embodiments, the methods also involve, prior to the assessing, administering the cell therapy to the subject. In some embodiments, the methods also involve administering the kynurenine pathway modulator to the subject.

In some embodiments, tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; at a time before the number of cells of the T cell therapy detectable in the blood from the subject is decreased compared to in the subject at a preceding time point after initiation of administration of the T cell therapy; at a time before T cells exhibit manifestations of prolonged tryptophan starvation, exhaustion, reduction of effector function, expression of inhibitory receptors and/or loss of proliferative capacity; at a time before a peak or maximum level of the cells of the T cell therapy are detectable in the blood of the subject; and/or the level of interferon-gamma (IFNγ) is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more.

In some embodiments, the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy. In some embodiments, the tryptophan metabolism and/or kynurenine pathway modulator is administered within or within about 1 hour, 2 hours, 6 hours, 12 hours, 24 hours or 48 hours subsequent to initiation of the T cell therapy.

In some embodiments, the disease or condition is cancer.

In some embodiments, the subject is selected if the level of expression or activity of IDO1, IDO2 or TDO is increased compared to the level assessed at a time point prior to initiation of administration of the T cell therapy. In some embodiments, the subject is selected if the level of tryptophan in the sample is below a threshold level or is decreased compared to the level assessed at a time point prior to initiation of administration of the T cell therapy.

In some embodiments, the threshold level is within 25%, within 20%, within 15%, within 10% or within 5% of the average level, concentration or amount, and/or is within a standard deviation of the average level, concentration or amount in a biological sample from among a plurality of control subjects. In some embodiments, the control subjects are healthy or normal subjects, are subjects who do not have a cancer and/or are subjects prior to receiving administration of the T cell therapy.

In some embodiments, the increase or decrease is by greater than or greater than about 1.2-fold, 1.5-fold, 2-fold, 3-fold, 4-fold, 5-fold, 10-fold or more.

In some embodiments, wherein prior to the assessing, the subject has failed to respond or failed to completely respond to treatment with, relapsed following remission after treatment with, or become refractory to, a prior administration of a tryptophan metabolism and/or kynurenine pathway modulator, optionally wherein such prior administration was carried out in combination with an immunomodulatory agent, optionally a checkpoint inhibitor.

In some embodiments, the biological sample is or is obtained from a serum, plasma or tumor sample.

In some embodiments, the tryptophan metabolite is selected from kynurenine, 3-hydroxykynurenine and 3-hydroxyanthranilic acid (3-HAA).

In some embodiments of any of the embodiments herein, the tryptophan metabolism and/or kynurenine pathway modulator is a small molecule, peptide, protein, antibody or antigen-binding fragment thereof, an antibody mimetic, an aptamer, or a nucleic acid molecule.

In some embodiments of any of the embodiments herein, the tryptophan metabolism and/or kynurenine pathway modulator is an antagonist of the enzyme kynureninase.

In some embodiments of any of the embodiments herein, the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO). In some embodiments, the tryptophan metabolism and/or kynurenine pathway modulator is a dual-acting IDO/TDO inhibitor.

In some embodiments of any of the embodiments herein, the tryptophan metabolism and/or kynurenine pathway modulator is an inhibitor of indoleamine-pyrrole 2,3-dioxygenase 1 (IDO1). In some embodiments of any of the embodiments herein, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

In some embodiments of any of the embodiments herein, the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat). In some embodiments, the tryptophan metabolism and/or kynurenine pathway modulator is 1-methyl-D-tryptophan (1-MT) (indoximod). In some embodiments, the tryptophan metabolism and/or kynurenine pathway modulator is tryptophan.

In some embodiments, the T cell comprises a recombinant receptor that specifically binds to a ligand that is a functional non-T cell receptor.

In some embodiments of any of the embodiments herein, the genetically engineered receptor that specifically binds to a ligand is a functional non-T cell receptor. In some embodiments, the genetically engineered receptor that specifically binds to a ligand is a chimeric antigen receptor (CAR). In some embodiments, the CAR contains an extracellular antigen-recognition domain that specifically binds to the antigen and an intracellular signaling region that includes an ITAM. In some embodiments, the intracellular signaling region contains an intracellular domain of a CD3-zeta (CD3) chain.

In some embodiments of any of the embodiments herein, the CAR also contains a costimulatory signaling region. In some embodiments, the costimulatory signaling region contains a signaling domain of CD28 or 4-1BB or an ICOS or a signaling portion thereof. In some embodiments, the costimulatory signaling region is a signaling domain of a CD28.

In some embodiments of any of the embodiments herein, the recombinant receptor is a transgenic T cell receptor (TCR). In some embodiments, the recombinant receptor is a chimeric antigen receptor (CAR).

In some embodiments of any of the embodiments herein, the T cell therapy recognizes or targets an antigen associated with the cancer. In some embodiments, the recombinant receptor binds to, recognizes or targets an antigen associated with the cancer. In some embodiments, the antigen is selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

Provided herein are engineered cells that contain (a) a genetically engineered receptor that specifically binds to a ligand; and (b) a modification of expression of a molecule associated with IDO-mediated immunosuppressive signaling in the cell, associated with sensing or responding to tryptophan starvation or insufficiency and/or associated with sensing or responding to kynurenine-mediated immunosuppression.

In some embodiments, the molecule is mTOR or protein kinase C theta (PKC-Θ).

Provided are engineered cells that include (a) a recombinant receptor that specifically binds to a ligand; and (b) a modification in expression of a molecule associated with IDO-mediated immunosuppressive signaling, associated with sensing or responding to tryptophan starvation or insufficiency and/or associated with sensing or responding to kynurenine-mediated immuno-suppression in the cell.

In some embodiments, the modification comprises recombinant, engineered and/or ectopic expression in the cell of the molecule or a functional and/or catalytically active portion or variant thereof. In some embodiments, the molecule is mTOR or protein kinase C theta (PKC-Θ).

In some embodiments, the molecule is an amino acid transporter or a chain thereof or a functional and/or catalytically active portion or variant thereof.

Also provided are engineered cells that include (a) a recombinant receptor that specifically binds to a ligand; and (b) a recombinant, engineered and/or ectopically expressed amino acid transporter or chain thereof or a functional and/or catalytically active portion or variant thereof.

In some embodiments, the amino acid transporter is a tryptophan transporter. In some embodiments, T (SLC3A1), CD98 heavy chain (4F2hc; SLC3A2), L-type Amino Acid Transporter 1 (LAT1; SLC7A5), LAT2 (SLC7A8), Asc-type amino acid transporter 1 (Asc-1; SLC7A10), Sodium- and chloride-dependent neutral and basic amino acid transporter B(0+)(ATB0,+; SLC6A14), Sodium-dependent neutral amino acid transporter B(0)AT1 (B(0)AT1; SLC6A19), Monocarboxylate transporter 10 (TAT1; SLC16A10), and proton-assisted amino-acid transporter 4 (PAT4; SLC36A4) or a portion thereof. In some embodiments, the amino acid transporter or a chain thereof comprises CD98 heavy chain (4F2hc; SLC3A2) and L-type Amino Acid Transporter 1 (LAT1; SLC7A5) or a portion thereof.

In some embodiments, the amino acid transporter or a chain thereof comprises the amino acid sequence selected from any one of SEQ ID NOs: 36-115, or an amino acid sequence having at least 90%, 91%, 92%, 93%, 94%, 95%, 96%, 97%, 98%, or 99% sequence identity to the amino acid sequence selected from any one of SEQ ID NOs: 36-115. In some embodiments, the amino acid transporter or a chain thereof is selected from among one or more of CD98 heavy chain (4F2hc; SLC3A2), L-type Amino Acid Transporter 1 (LAT1; SLC7A5), LAT2 (SLC7A8), and proton-assisted amino-acid transporter 4 (PAT4; SLC36A4) or a portion thereof. In some embodiments, the amino acid transporter or a chain thereof comprises CD98 heavy chain (4F2hc; SLC3A2) and L-type Amino Acid Transporter 1 (LAT1; SLC7A5) or a portion thereof.

In some embodiments, the amino acid transporter or a chain thereof comprises the amino acid sequence selected from any one of SEQ ID NOs:37-39 and 115, or an amino acid sequence having at least 90%, 91%, 92%, 93%, 94%, 95%, 96%, 97%, 98%, or 99% sequence identity to the amino acid sequence selected from any one of SEQ ID NOs: 37-39 and 115.

In some embodiments, expression of the molecule or amino acid transporter in the cell is under the control of a conditional promoter or enhancer or transactivator.

In some embodiments, the molecule is selected from among GCN2 kinase, BLIMP-1 aryl hydrocarbon receptor (AHR), AHR nuclear transporter (ARNT), eukaryotic translation initiation factor 2 α (eIF2α), activating transcription factor 4 (ATF4), or CCAAT/enhancer binding protein-homologous protein (CHOP), Gadd45a, Herp, 4E-BP1, eIF4G, JAK1, NFκB-2, FK506-BP8 and IFNγ-R2. In some embodiments, the molecule is GCN2 or CHOP.

In some embodiments, the modification includes recombinant, engineered and/or ectopic expression in the cell of the molecule or a functional and/or catalytically active portion or variant thereof. In some embodiments, the expression of the molecule in the cell is under the control of a conditional promoter or enhancer or transactivator.

In some embodiments, wherein the molecule is GCN2 kinase, aryl hydrocarbon receptor (AHR) or AHR nuclear transporter (ARNT).

In some embodiments, the modification includes reduced expression of the molecule in the cell. In some embodiments, the engineered cell contains an inhibitory nucleic acid or a genetic disruption that reduces expression of the molecule. In some embodiments, the expression of the molecule in the cell is reduced by at least 50, 60, 70, 80, 90, or 95% as compared to the expression in the cell in the absence of the inhibitory nucleic acid or gene disruption.

In some embodiments, the cell contains an inhibitory nucleic acid, thereby effecting reduction in expression of the molecule. In some embodiments, the inhibitory nucleic acid includes an RNA interfering agent. In some embodiments, the inhibitory nucleic acid is or includes or encodes a small interfering RNA (siRNA), a microRNA-adapted shRNA, a short hairpin RNA (shRNA), a hairpin siRNA, a microRNA (miRNA-precursor) or a microRNA (miRNA). In some embodiments, expression of the inhibitory nucleic acid is under the control of a conditional promoter or enhancer or transactivator.

In some embodiments, the engineered cell contains a disrupted gene encoding the molecule, an agent for disruption of a gene encoding the molecule and/or a disruption of a gene encoding the molecule. In some embodiments, the disruption includes disrupting the gene encoding the molecule at the DNA level and/or the disruption is not reversible; and/or the disruption is not transient.

In some embodiments, the disruption is mediated by a DNA binding protein or DNA-binding nucleic acid that specifically binds to or hybridizes the gene encoding the molecule. In some embodiments, the disruption is mediated by (a) a fusion protein including a DNA-targeting protein and a nuclease or (b) an RNA-guided nuclease. In some embodiments, the disruption is mediated by a gene editing nuclease, a zinc finger nuclease (ZFN), a TAL-effector nuclease (TALEN), or a clustered regularly interspaced short palindromic nucleic acid (CRISPR)/Cas9. In some embodiments, the disruption is mediated by a CRISPR/Cas9 and the CRISPR/Cas9 includes a guide RNA (gRNA) containing a guide sequence that is complementary to, and/or capable of hybridizing to, a target sequence in the gene.

In some embodiments, the genetic disruption is conditional or inducible. In some embodiments, the CRISPR-Cas9 complex is an inducible CRISPR-Cas9 and/or the Cas9 is under the under the control of a conditional promoter or enhancer or transactivator.

In some embodiments, the disruption includes a deletion of at least a portion of at least one exon of the gene encoding the molecule. In some embodiments, the disruption includes a deletion, mutation, and/or insertion in the gene resulting in the presence of a premature stop codon in the gene; and/or the disruption includes a deletion, mutation, and/or insertion within a first or second exon of the gene encoding the molecule.

In some embodiments, the conditional promoter or enhancer or transactivator is an inducible promoter, enhancer, or transactivator or a repressible promoter, enhancer, or transactivator, such as an RNA pol I, pol II or pol III promoter. In some embodiments, the promoter is selected from: a pol III promoter that is a U6 or H1 promoter; or a pol II promoter that is a CMV, SV40 early region or adenovirus major late promoter.

In some embodiments, the promoter is an inducible promoter. In some embodiments, the promoter includes a binding site for NFκB or NFAT. In some embodiments, the promoter includes a Lac operator sequence, a tetracycline operator sequence, a galactose operator sequence or a doxycycline operator sequence, or is an analog thereof.

In some embodiments, the promoter is a repressible promoter. In some embodiments, the promoter is capable of being bound by a Lac repressor or a tetracycline repressor, or is an analog thereof.

In some embodiments, the cell is a T cell. In some embodiments, the T cell is a CD8+ T cell. In some embodiments, the T cell is a CD4+ T cell. In some embodiments, the cell is a natural killer (NK) cell. In some embodiments, the cell is an iPS-derived cell.

In some embodiments, the genetically engineered receptor that specifically binds to a ligand is a functional non-T cell receptor. In some embodiments, the genetically engineered receptor that specifically binds to a ligand is a chimeric antigen receptor (CAR).

In some embodiments, the CAR includes an extracellular antigen-recognition domain that specifically binds to the antigen and an intracellular signaling region that includes an ITAM.

In some embodiments, the intracellular signaling region includes an intracellular domain of a CD3-zeta (CD3) chain.

In some embodiments, the CAR also includes a costimulatory signaling region. In some embodiments, the costimulatory signaling region includes a signaling domain of CD28 or 4-1BB or an ICOS or a signaling portion thereof. In some embodiments, costimulatory signaling region is a signaling domain of a CD28.

In some embodiments, the genetically engineered receptor that specifically binds to a ligand is a recombinant receptor.

In some embodiments, the genetically engineered receptor that specifically binds to a ligand is a transgenic T cell receptor (TCR).

In some embodiments, the cell is engineered by introduction of a first nucleic acid sequence encoding the recombinant receptor into the cell, and one or more second nucleic acid sequence(s) encoding an agent that is capable of or involved in modifying expression of a molecule associated with IDO-mediated immunosuppressive signaling, associated with sensing or responding to tryptophan starvation or insufficiency and/or associated with sensing or responding to kynurenine-mediated immuno-suppression in the cell, into the cell. In some embodiments, the first nucleic acid sequence and the second nucleic acid sequence(s) are comprised in one or more polynucleotides. In some embodiments, the first nucleic acid sequence and the second nucleic acid sequence(s) are comprised in two polynucleotides. In some embodiments, the first nucleic acid sequence and the second nucleic acid sequence(s) are comprised in one or more vector(s), which optionally are viral vector(s).

Also provided herein are compositions that include any of the engineered cell described herein. In some embodiments of the compositions, the cells are CD4+ or CD8+ cells. In some embodiments, the compositions also include a pharmaceutically acceptable carrier.

Also provided herein are combinations that include genetically engineered cells expressing a recombinant receptor that binds to a ligand, wherein the recombinant receptor optionally is a T cell receptor (TCR) or a chimeric antigen receptor (CAR); and a tryptophan metabolism and/or kynurenine pathway modulator.

Also provided herein are combinations that include any of the engineered cells described herein or any of the compositions described herein, and a tryptophan metabolism and/or kynurenine pathway modulator.

In some embodiments, the tryptophan metabolism and/or kynurenine pathway modulator prevents or reduces the formation, concentration, availability, metabolism and/or effect of an enzyme and/or a metabolite of the kynurenine pathway, and/or reduces the kynurenine/tryptophan ratio.

In some embodiments, the tryptophan metabolism and/or kynurenine pathway modulator prevents or reduces catabolism of tryptophan or prevents or reduces synthesis or accumulation of a tryptophan metabolite. In some embodiments, the tryptophan metabolite is selected from kynurenine, 3-hydroxykynurenine and 3-hydroxyanthranilic acid (3-HAA).

In some embodiments, the tryptophan metabolism and/or kynurenine pathway modulator is a small molecule, peptide, protein, antibody or antigen-binding fragment thereof, an antibody mimetic, an aptamer, or a nucleic acid molecule.

In some embodiments, the tryptophan metabolism and/or kynurenine pathway modulator is an antagonist of the enzyme kynureninase.

In some embodiments, the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO). In some embodiments, the tryptophan metabolism and/or kynurenine pathway modulator is a dual-acting IDO/TDO inhibitor. In some embodiments, the tryptophan metabolism and/or kynurenine pathway modulator is an inhibitor of indoleamine-pyrrole 2,3-dioxygenase 1 (IDO1).

In some embodiments, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl} amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

In some embodiments, the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat). In some embodiments, the tryptophan metabolism and/or kynurenine pathway modulator is 1-methyl-D-tryptophan (1-MT) (indoximod). In some embodiments, the tryptophan metabolism and/or kynurenine pathway modulator is tryptophan.

In some embodiments, the combination provided herein is packaged as an article of manufacture such as a kit. In some embodiments, article and/or kit further comprises instructions or literature providing for the administration of the engineered cells and/or tryptophan metabolism and/or kynurenine pathway modulator.

Also provided are methods of engineering immune cells expressing a recombinant receptor, that includes contacting a population of cells comprising immune cells with a tryptophan metabolism and/or kynurenine pathway modulator; and introducing a nucleic acid encoding a recombinant receptor into the population of cells under conditions such that the recombinant receptor is expressed.

In some embodiments, the recombinant receptor binds to a ligand, optionally an antigen. In some embodiments, the recombinant receptor is a T cell receptor (TCR) or a chimeric antigen receptor (CAR). In some embodiments, the population of cells is or comprises peripheral blood mononuclear cells. In some embodiments, the population of cells is or comprises T cells. In some embodiments, the T cells are CD4+ and/or CD8+. In some embodiments, the population of cells are isolated from a subject, optionally a human subject.

In some embodiments, the contacting occurs prior to and/or during the introducing.

In some embodiments, the tryptophan metabolism and/or kynurenine pathway modulator prevents or reduces the formation, concentration, availability, metabolism and/or effect of an enzyme and/or a metabolite of the kynurenine pathway. In some embodiments, the tryptophan metabolism and/or kynurenine pathway modulator prevents or reduces catabolism of tryptophan or prevents or reduces synthesis or accumulation of a tryptophan metabolite. In some embodiments, the tryptophan metabolite is selected from kynurenine, 3-hydroxykynurenine and 3-hydroxyanthranilic acid (3-HAA).

In some embodiments, the tryptophan metabolism and/or kynurenine pathway modulator is a small molecule, peptide, protein, antibody or antigen-binding fragment thereof, an antibody mimetic, an aptamer, or a nucleic acid molecule.

In some embodiments, the tryptophan metabolism and/or kynurenine pathway modulator is an antagonist of the enzyme kynureninase.

In some embodiments, the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO). In some embodiments, the tryptophan metabolism and/or kynurenine pathway modulator is a dual-acting IDO/TDO inhibitor. In some embodiments, the tryptophan metabolism and/or kynurenine pathway modulator is an inhibitor of indoleamine-pyrrole 2,3-dioxygenase 1 (IDO1).

In some embodiments, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

In some embodiments, the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat). In some embodiments, the tryptophan metabolism and/or kynurenine pathway modulator is 1-methyl-D-tryptophan (1-MT) (indoximod). In some embodiments, the tryptophan metabolism and/or kynurenine pathway modulator is tryptophan.

Also provided are methods of engineering immune cells expressing a recombinant receptor, that includes introducing a first nucleic acid sequence encoding a recombinant receptor into the population of cells under conditions such that the recombinant receptor is expressed; and introducing one or more second nucleic acid sequence(s) encoding an agent capable of or involved in modification of expression of a molecule associated with IDO-mediated immunosuppressive signaling, associated with sensing or responding to tryptophan starvation or insufficiency and/or associated with sensing or responding to kynurenine-mediated immunosuppression in the cell into the population of cells under conditions such that the agent is expressed.

Also provided are methods of engineering immune cells expressing a recombinant receptor, that includes introducing a first nucleic acid sequence encoding a recombinant receptor into the population of cells under conditions such that the recombinant receptor is expressed; and introducing one or more second nucleic acid sequence(s) encoding a recombinant, engineered and/or ectopically expressed amino acid transporter or chain thereof or a functional and/or catalytically active portion or variant thereof.

In some embodiments, the modification comprises recombinant, engineered and/or ectopic expression of the molecule or a functional and/or catalytically active chain, portion or variant thereof. In some embodiments, the modification comprises reduced expression of the molecule. In some embodiments, the method comprises an inhibitory nucleic acid or a genetic disruption that reduces expression of the molecule.

In some embodiments, the first nucleic acid sequence and the second nucleic acid sequence(s) are comprised in one or more polynucleotides. In some embodiments, the first nucleic acid sequence and the second nucleic acid sequence(s) are comprised in two polynucleotides. In some embodiments, the first nucleic acid sequence and the second nucleic acid sequence(s) are comprised in one or more vector(s), which optionally are viral vector(s).

In some embodiments, the combination provided herein is packaged as a kit. In some embodiments, the kit also includes instructions for administration of the engineered cells and tryptophan metabolism and/or kynurenine pathway modulator. In some embodiments, provided are articles of manufacture and/or kits, such as those comprising the tryptophan metabolism and/or kynurenine pathway modulator, e.g., in a therapeutically effective dose. In some aspects, the articles of manufacture further comprise instructions and/or literature specifying administration of the modulator(s) to a subject having received or that is intended to receive the therapy such as the cell therapy such as an engineered T cell therapy. In some aspects, the instructions or literature further specify the administration to the subject with a disease or condition, where the disease or condition or associated cells or tissues are or have been confirmed to express IDO—optionally following administration of the therapy—and/or one or more amino acid transporters such as LAT-1. In some embodiments, the instructions or literature do not indicate the expression of IDO and/or do not indicate expression of a transporter or other marker, as a prerequisite for administration of the cell therapy.

BRIEF DESCRIPTION OF THE DRAWINGS

FIG. 2A depicts tryptophan concentrations (μM), as measured by ELISA, in the culture supernatant of a co-culture of CD19.A549 cells and anti-CD19 CAR-expressing T cells, at an effector-target (E:T) ratio of 0.3:1, 1:1 or 3:1, in the presence of 0, 0.1, 10 and 1000 nM of IDO1 inhibitor epacadostat, as described in Example 2. The cells were cultured and the tryptophan levels were compared to the tryptophan levels of fresh culture medium.

FIG. 2B depicts kynurenine concentrations (μM), as measured by ELISA, in the culture supernatant of a co-culture of CD19.A549 cells and anti-CD19 CAR-expressing T cells, at a 3:1 E:T, in the presence of 0, 0.1, 10 and 1000 nM epacadostat, as described in Example 2. The cells were cultured and the kynurenine levels were compared to the kynurenine levels of fresh culture medium.

FIG. 2C depicts the tryptophan and kynurenine concentrations (μM) following co-culture of anti-CD19 CAR+ T cells and A549.CD19 IDO target cells in the presence of various epacadostat concentrations for 96 hours.

FIGS. 4A and 4B depict the average number of divisions of anti-CD19 CAR-expressing CD4+ (FIG. 4A) or CD8+ (FIG. 4B) T cells generated from three different healthy donors after a co-culture with CD19-expressing A549 target cells (CD19.A549) in the presence of 0, 10, 100, 250, 500 and 1000 nM epacadostat, as described in Example 3A.

FIGS. 8A and 8B depict the CD25 surface expression levels, as detected by flow cytometry, of anti-CD19 CAR-expressing CD4+ (FIG. 8A) or CD8+ (FIG. 8B) T cells generated from three different healthy donors after a co-culture with CD19-expressing A549 target cells (CD19.A549) in the presence of 0, 10, 100, 250, 500 and 1000 nM epacadostat, as described in Example 3B.

FIGS. 14A and 14B depict T cell proliferation (FIG. 14A) and CAR T-cell count in each well (FIG. 14B), of anti-CD19 CAR-expressing cells, generated from three different donors, after a co-culture with A549.CD19 cells for 96 hours, with 5 μg/mL tryptophan supplementation every 24 hours or in the presence of 250 nM epacadostat. T cell proliferation was measured using dilution of CellTrace™ Violet by flow cytometry.

FIGS. 15A and 15B depicts the mean fluorescence intensity (MFI) of CellTrace™ Violet dye in a co-culture of labeled CD4+ CAR+ T cells (FIG. 15A) or CD8+ CAR+ T cells (FIG. 15B) with K562 human myelogenous leukemia target cells transduced with CD19 (CD19.K562) in tryptophan-depleted media, with or without the addition of various concentrations of supplemental tryptophan. Tryptophan-containing media was used as a control (Trp Control). FIG. 15C depicts the number of CD19.K562 target cells.

Figure 17A:
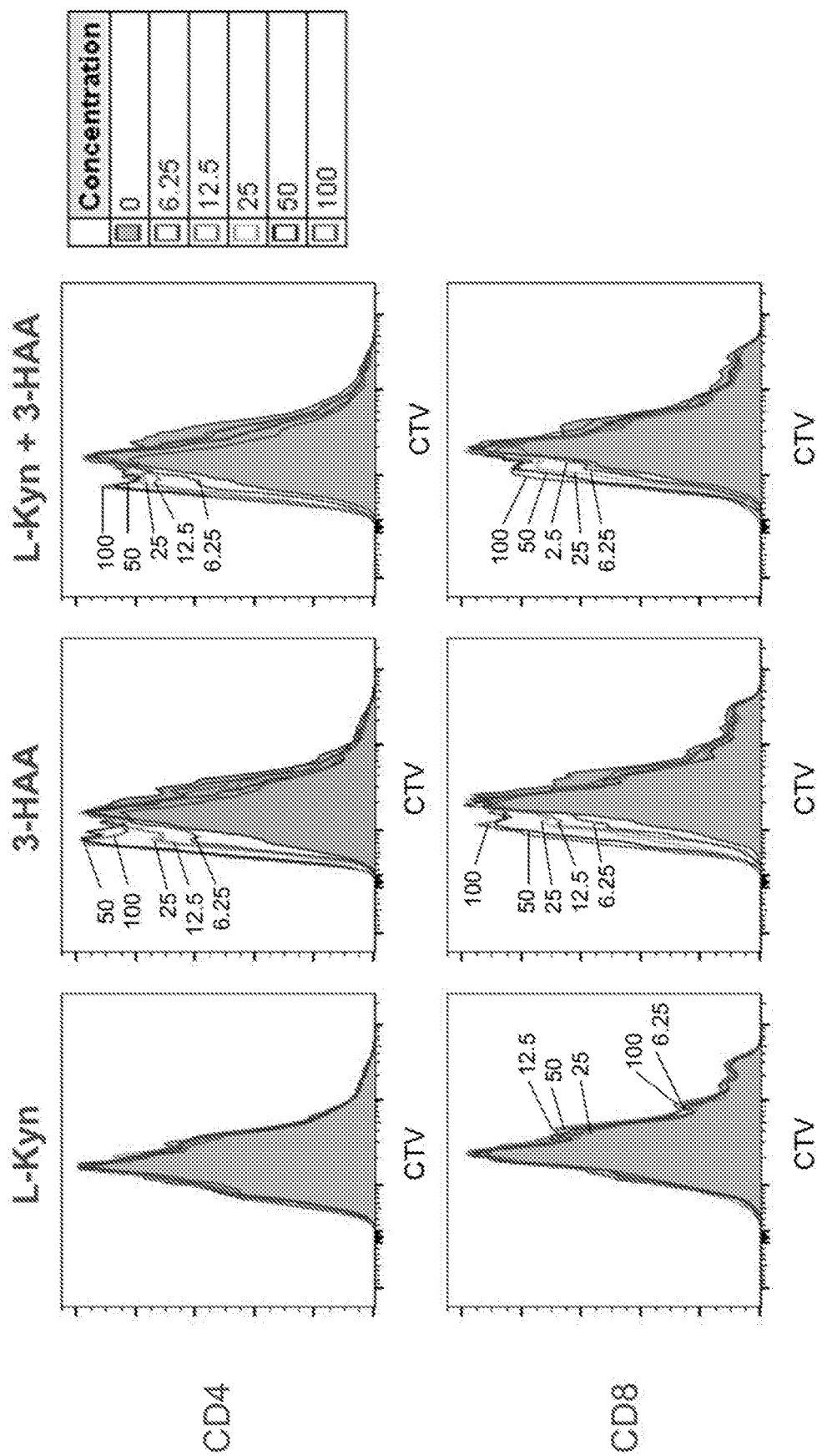
FIG. 17A shows T cell proliferation, of anti-CD19 CAR-expressing T cells after a co-culture with CD19.Daudi target cells (IDO1⁻ target cells that were observed not to induce IDO1 expression) at a 1:1 effector:target (E:T) ratio in the presence of 0, 6.25, 12.5, 25, 50 and 100 μM L-Kynurenine, 3-hydroxyanthranilic acid (3-HAA) or 0, 6.25, 12.5, 25, 50 and 100 μM each of L-Kynurenine and 3-HAA. T cell proliferation was measured using dilution of CellTrace™ Violet by flow cytometry.
Figure 17B:
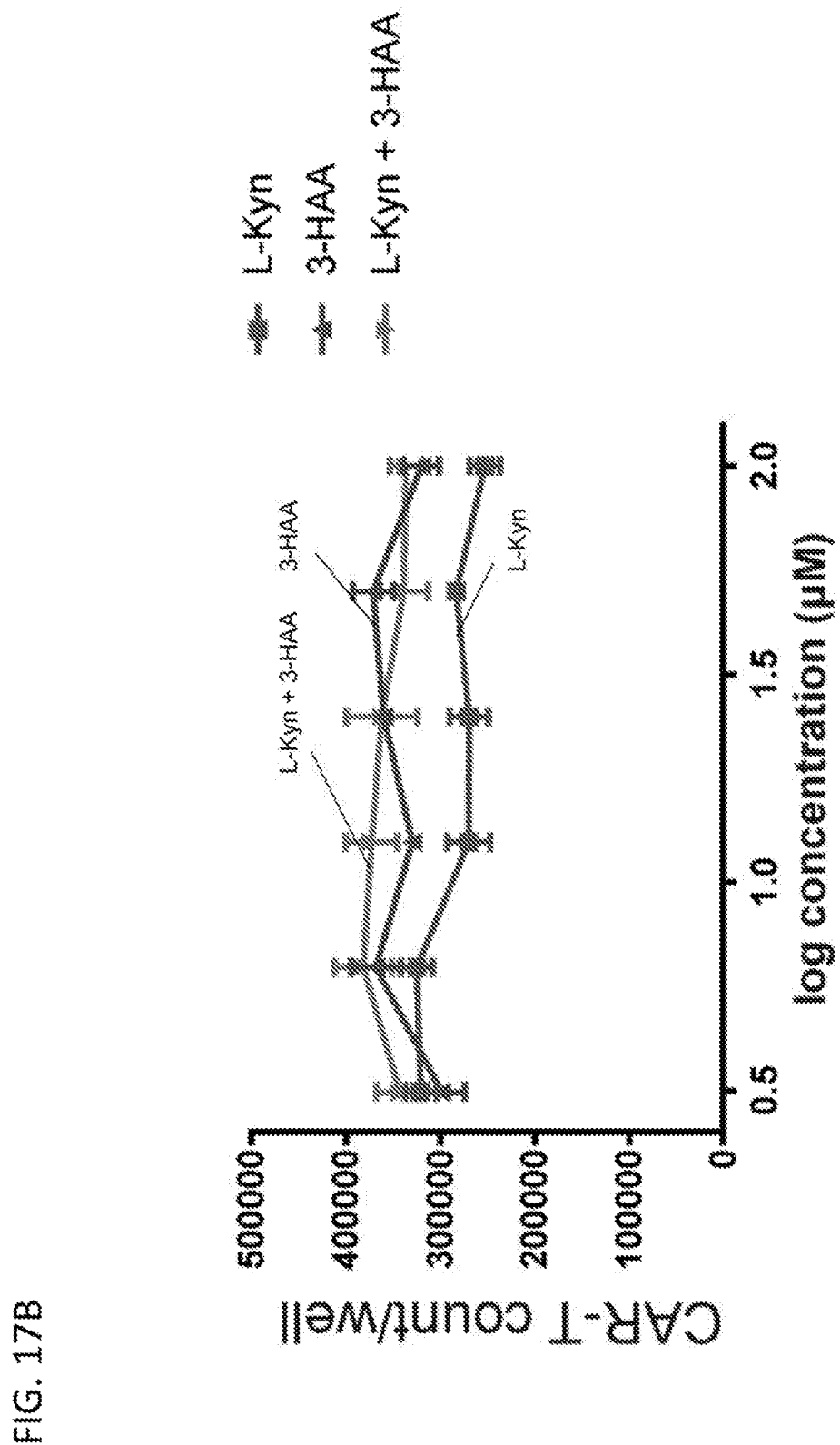

FIG. 17B shows the CAR+ T cell count of anti-CD19 CAR-expressing T cells after a co-culture with IDO1⁻ CD19.K562 cells for 96 hours in the presence of 6.25 to 100 μM L-Kynurenine, 3-hydroxyanthranilic acid (3-HAA) or 6.25 to 100 μM each of L-Kynurenine and 3-HAA.

Figure 18A:
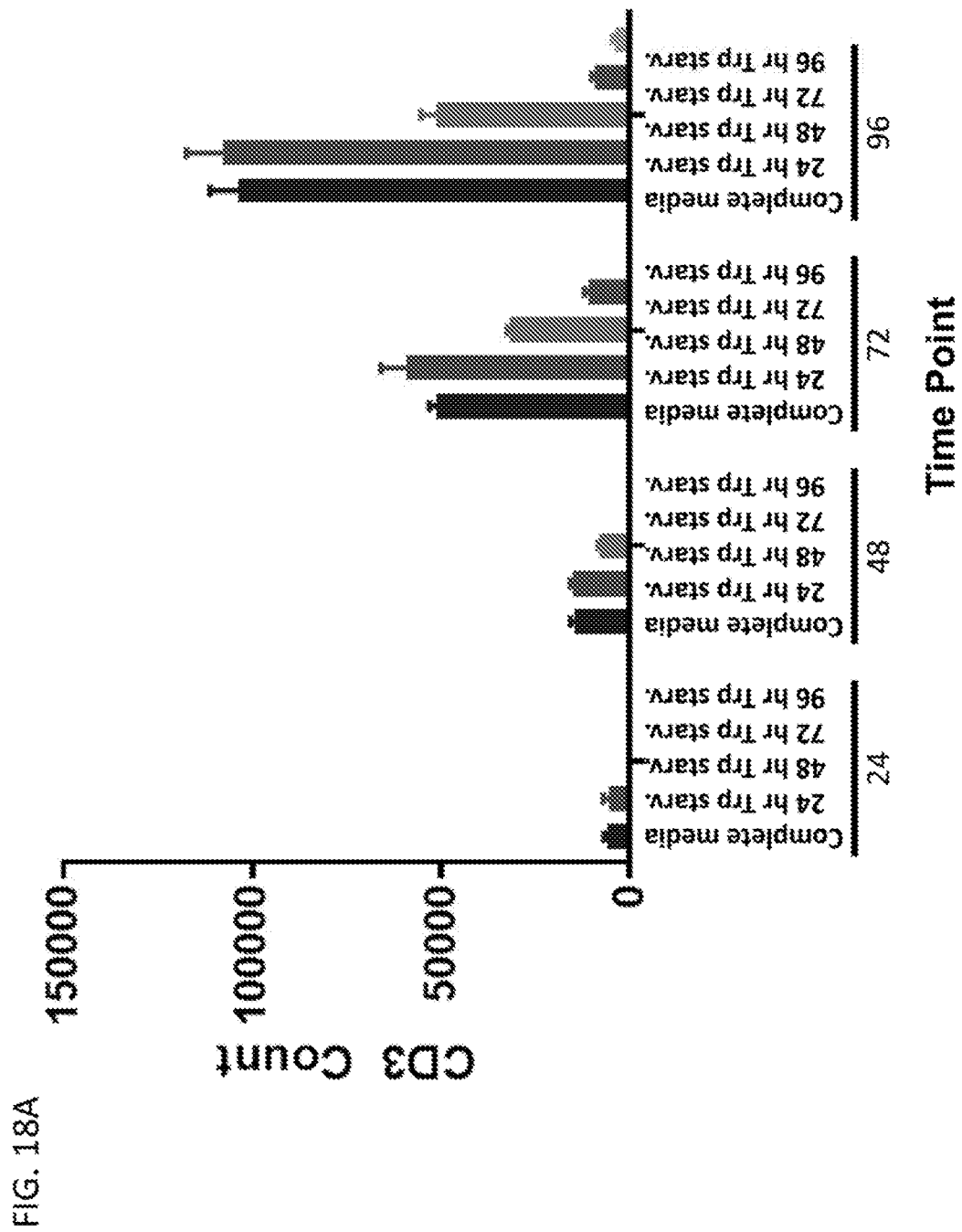
Figure 18C:
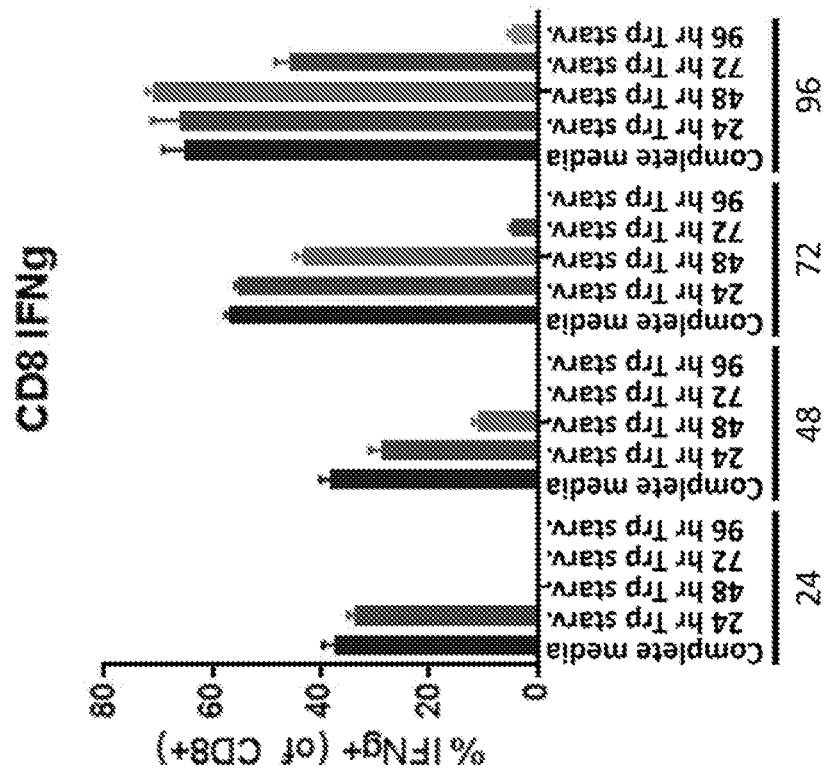
Figure 18B:
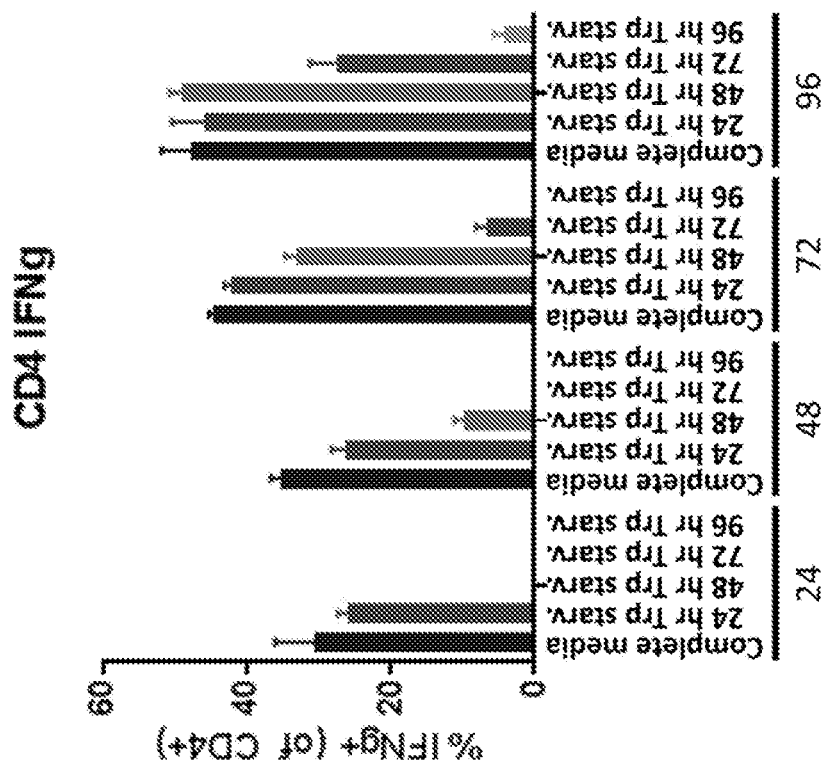
Figures 18D, 18E:
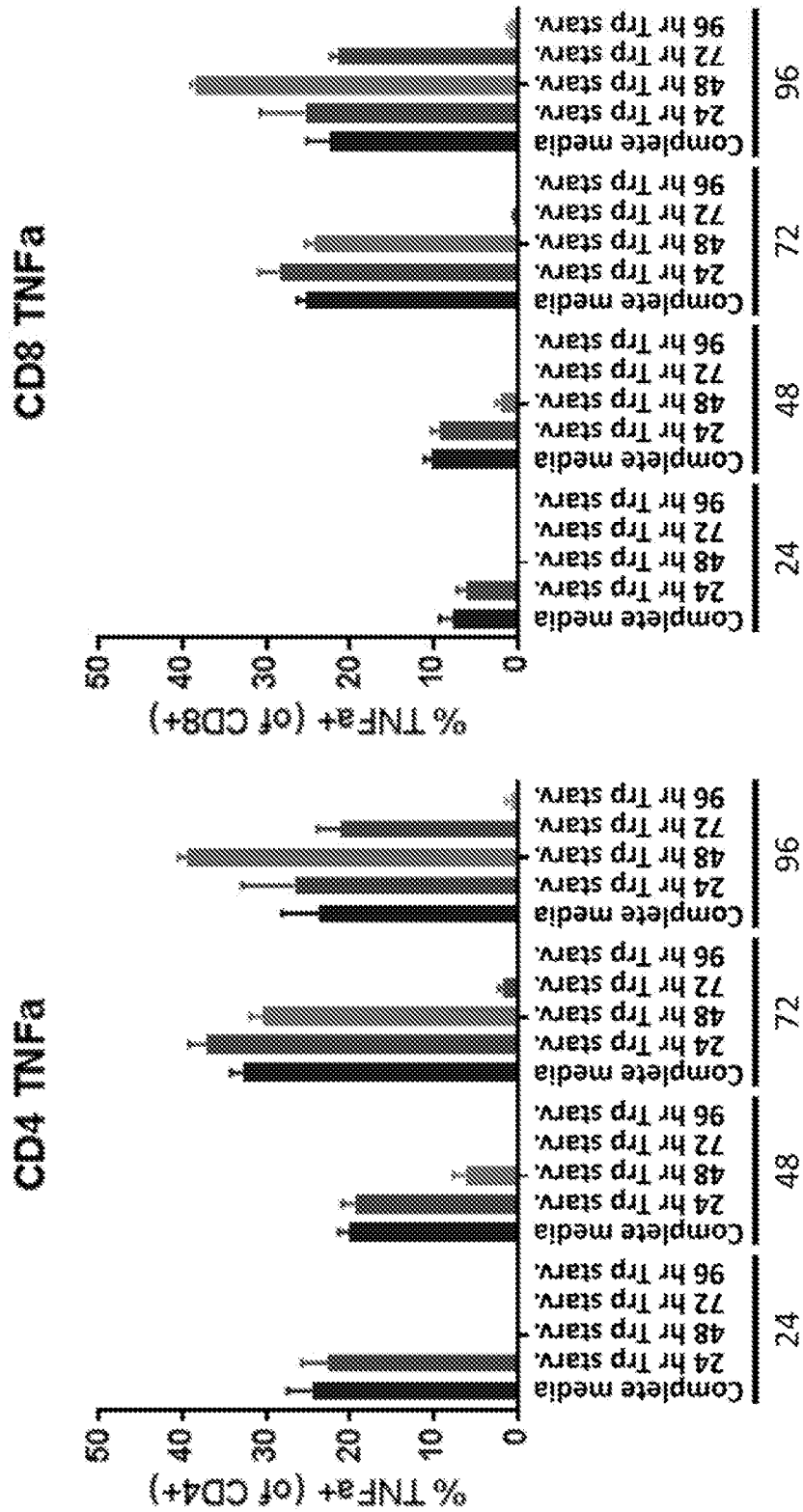

FIG. 18A shows the CD3+ count of anti-CD19 CAR+ cells cultured in tryptophan starvation conditions (chemically defined tryptophan-free media) for 24, 48, 72 or 96 hours (24, 48, 72 or 96 hr Trp starv.); followed by supplemental tryptophan addition, and culturing in the presence of tryptophan until the cells were harvested at 24, 48, 72 or 96 hours. As a control cells were cultured in tryptophan-sufficient media for each respective time period (complete media). Cytokine production of tryptophan starved CD4+ or CD8+ cells are shown in FIG. 18B or 18C, respectively, for IFNγ and FIG. 18D or 18E, respectively, for TNFα.

Figure 19A:
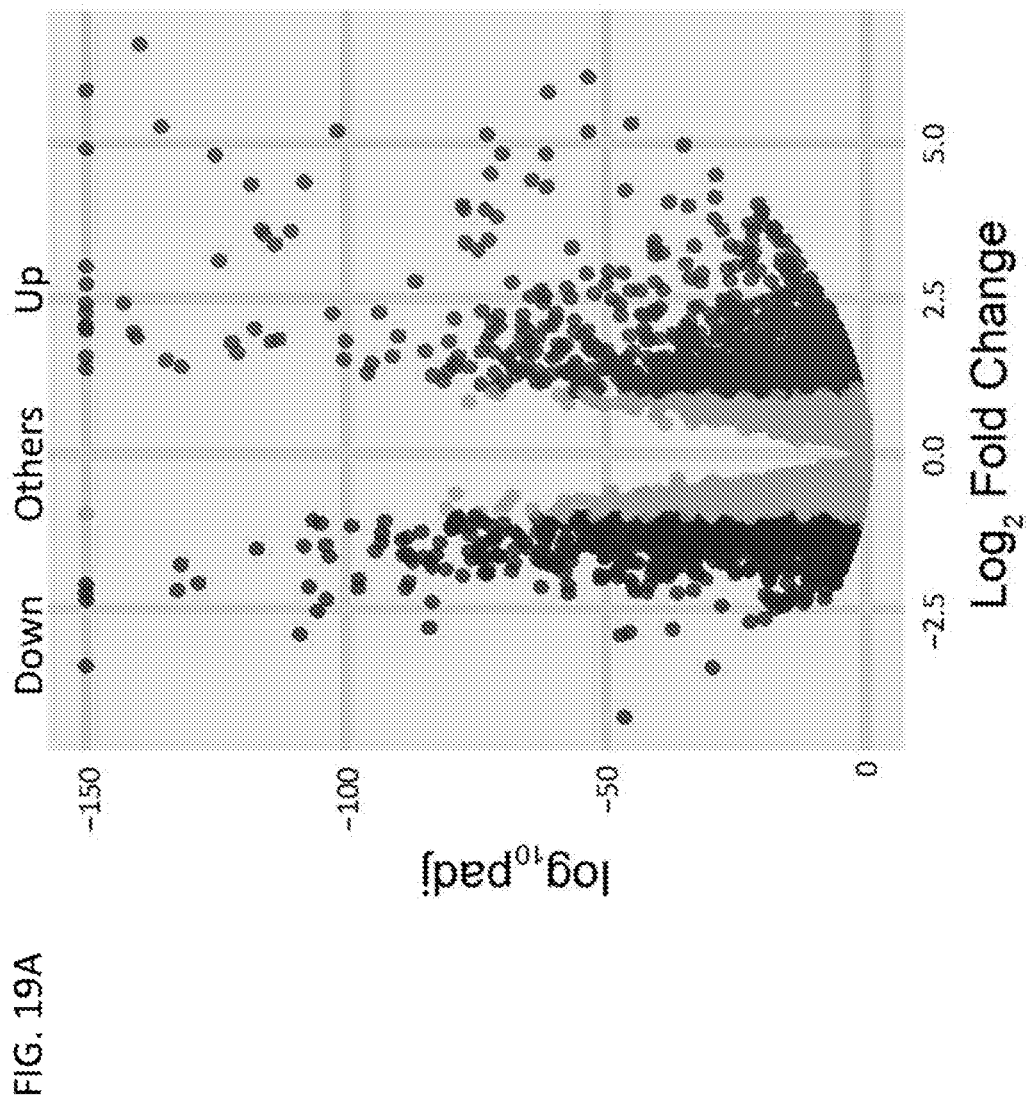

FIG. 19A shows a volcano plot depicting statistical significance of expression ($\log_{10}$ of adjusted p-value) differences of the gene products between CAR+ T cells cultured in tryptophan sufficient and tryptophan starvation conditions, with the $\log_2$ fold-change of expression of each gene product including genes that have been significantly upregulated (right side) or downregulated (left side).

Figure 19B:
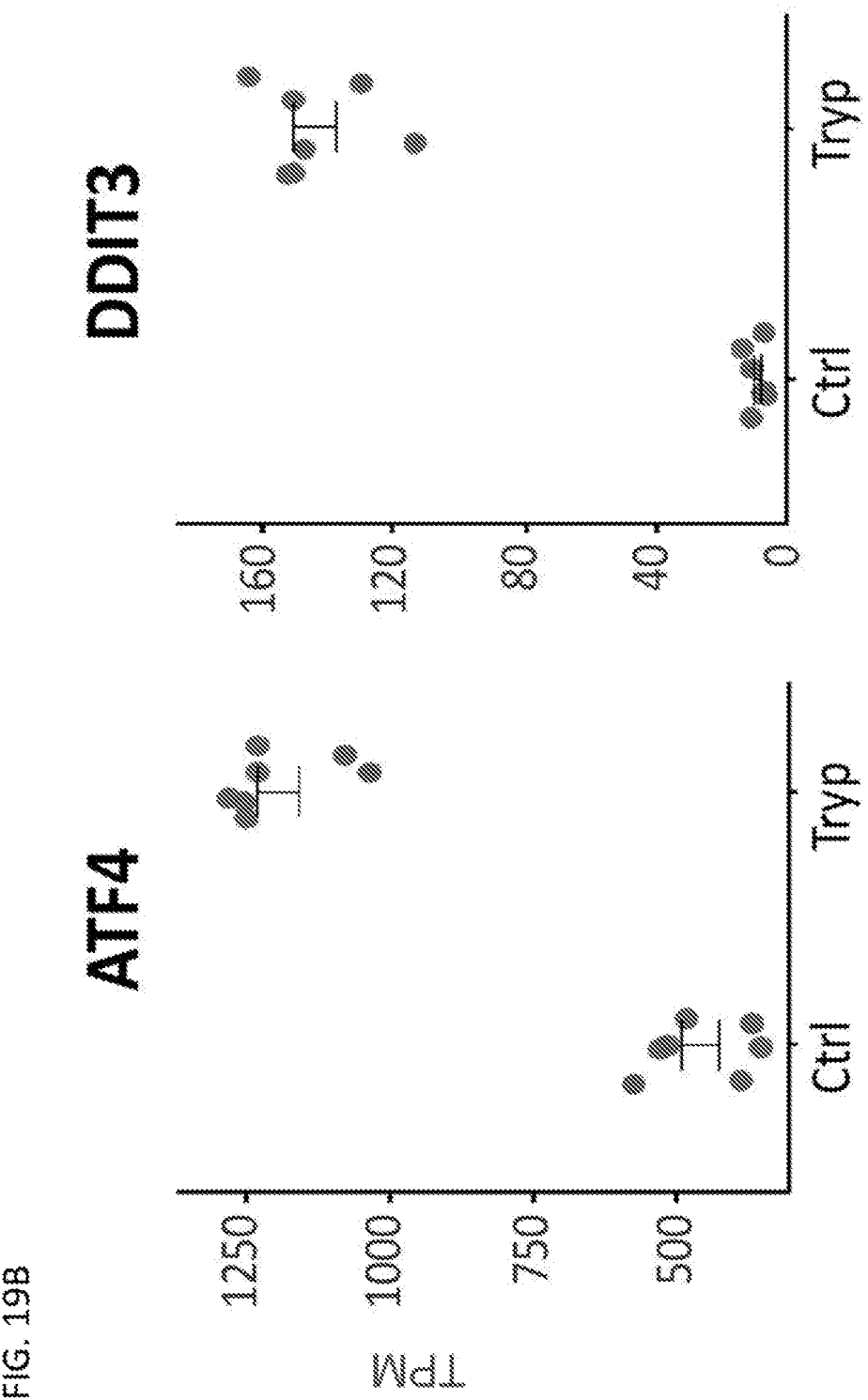

FIG. 19B depicts RNAseq results in CAR+ T cells cultured in tryptophan sufficient (Ctrl) and tryptophan starvation (Tryp) conditions, represented as transcripts per kilobase million (TPM) values, for two exemplary genes encoding members of the eIF2α/ATF4 integrated stress response pathway, ATF4 and DDIT3 (also known as CCAAT/enhancer binding protein-homologous protein (CHOP)).

Figure 19C:
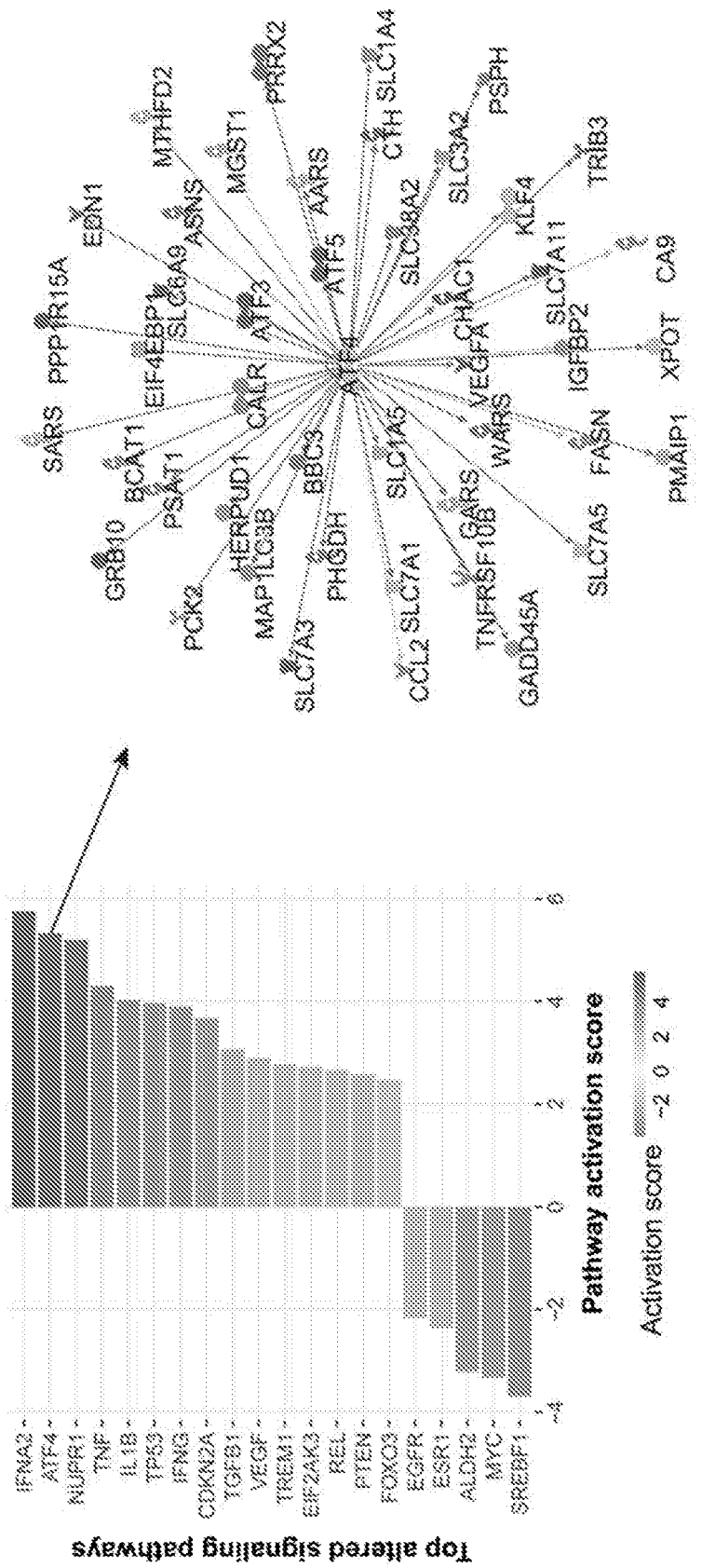

FIG. 19C depicts results based on a gene ontology analysis assessing cellular signaling pathways observed based on expression analyses to be affected in tryptophan starvation conditions, and an exemplary schematic showing genes involved in the ATF4 pathway whose expression was altered.

Figure 20:
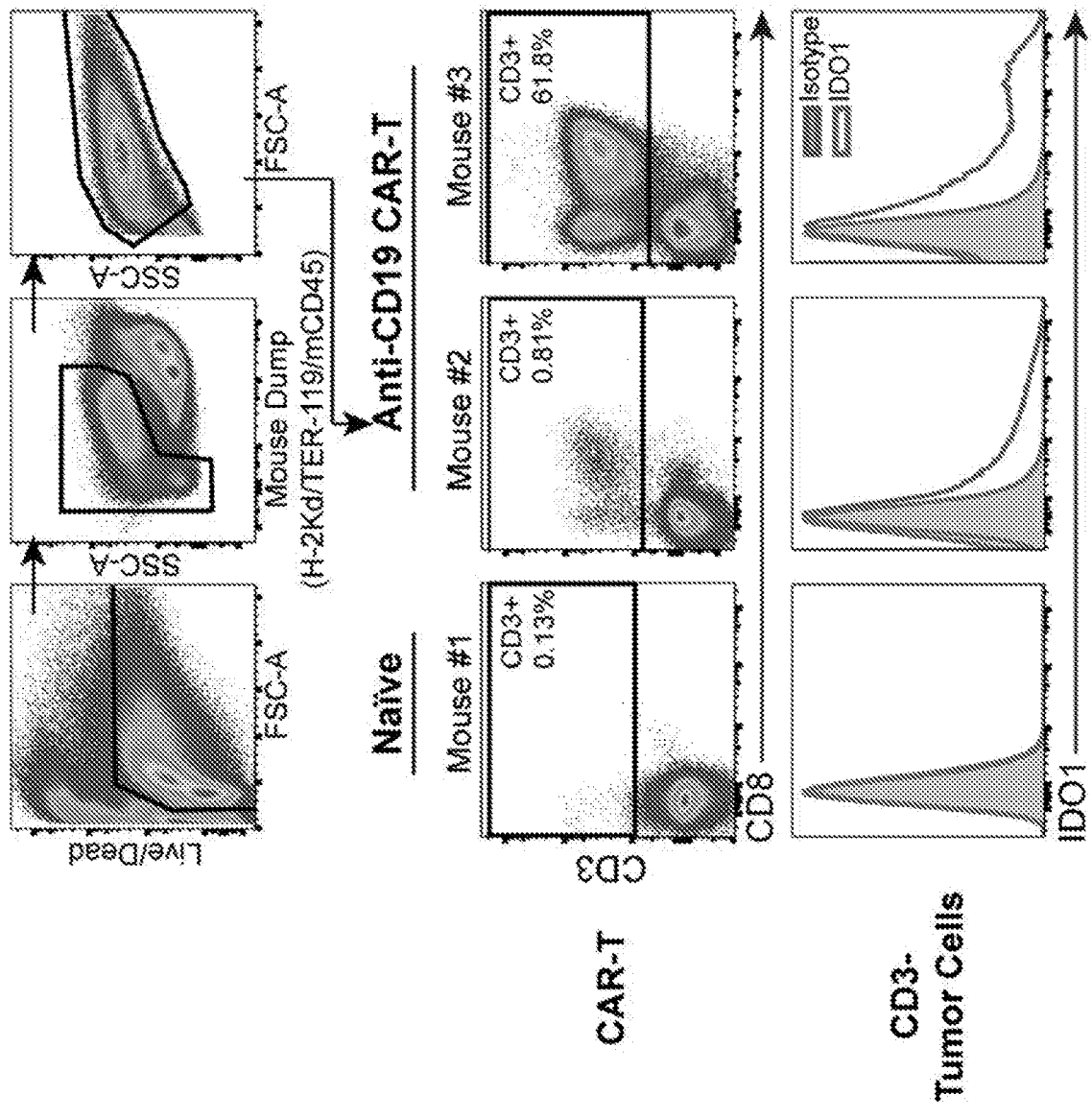

FIG. 20 depicts flow cytometry plots for single cell suspensions isolated from a A549.CD19 cells (IDO⁺) tumor xenograft mouse model with (anti-CD19 CAR-T) or without (naïve) administering anti-CD19 CAR-expressing T cells, showing gating on live, non-mouse cells, and assessing CD3, CD8 and IDO expression.

Figure 21:
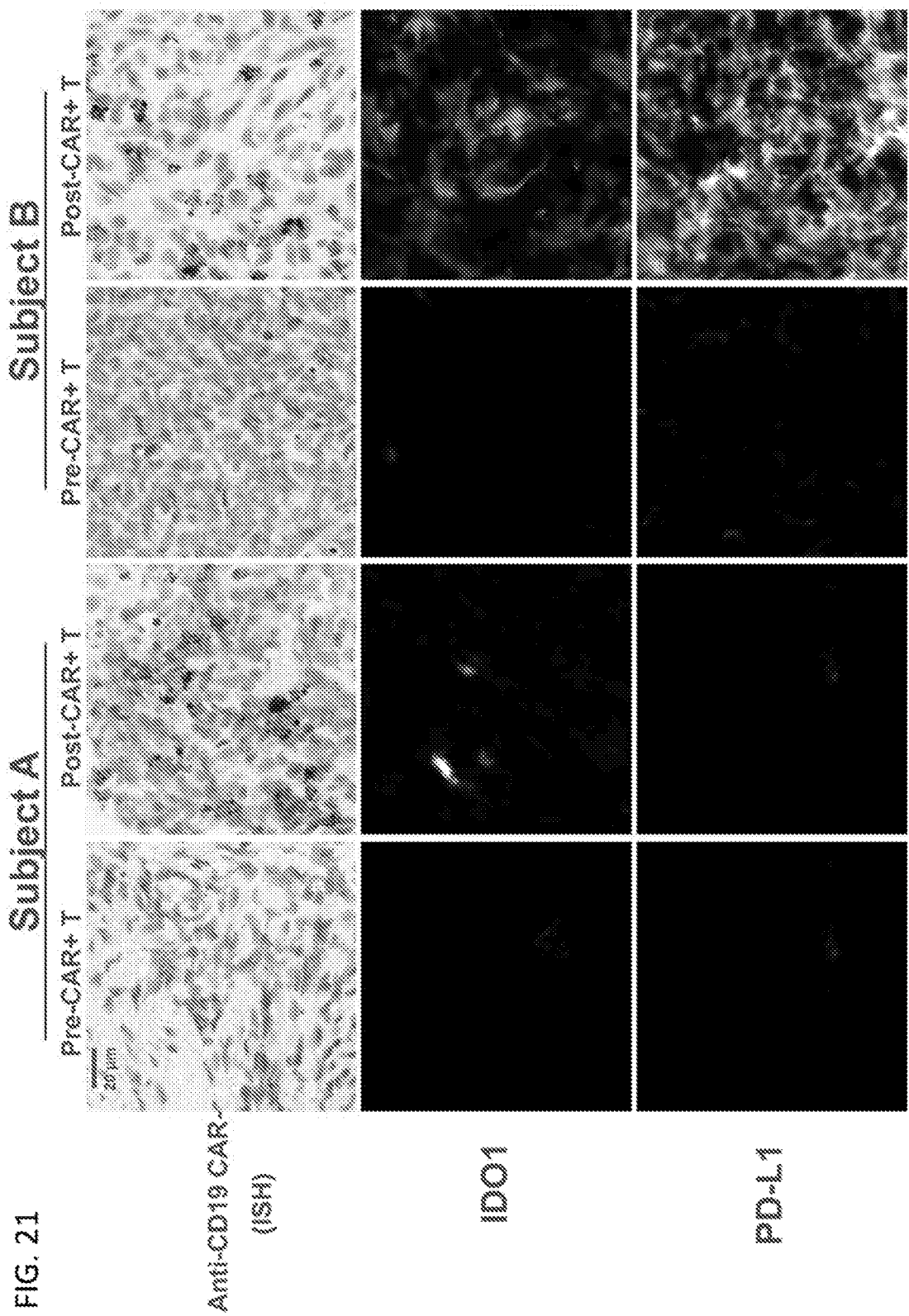

FIG. 21 depicts hematoxylin and eosin (H&E) staining and in situ hybridization (ISH) with probes specific to the mRNA encoding the anti-CD19 CAR, and immunofluorescence staining to assess IDO1 and programmed death-ligand 1 (PD-L1) protein expression, in serial tumor biopsy sections from human subjects with Diffuse Large B-Cell Lymphoma (DLBCL) before and after a single infusion with autologous T cells expressing an anti-CD19 CAR.

DETAILED DESCRIPTION

Provided herein are methods of enhancing or modulating proliferation and/or activity of immune cell activity in connection with an immunotherapy or immunotherapeutic agent, such as a composition including cells for adoptive cell therapy, e.g., such as a T cell therapy (e.g. CAR-expressing T cells) or a T cell-engaging therapeutic agent, such as a bispecific or multispecific agent or antibody, capable of recruiting one or more T cells or other immune cells. In some embodiments, the immunotherapy or immunotherapeutic agent includes one or more checkpoint modulators. In some embodiments, the methods involve administrating a combination therapy of an immunotherapy, such as a T cell therapy (e.g. CAR-expressing T cells) or a T cell-engaging therapy, and a tryptophan metabolic pathway modulator, such as a kynurenine pathway modulator. In some embodiments, the immunotherapy is a T cell therapy and the provided combination therapy with a tryptophan metabolic pathway modulator, such as a kynurenine pathway modulator enhances or modulates proliferation or activity of T cells of the T cell therapy. In some embodiments, the enhancement of proliferation or activity is to a level that is restored or recovered to a baseline or steady state level of such activity, such as to a level or activity that is observed in the absence of effects mediated by immunosuppressive effects due to metabolism, e.g., catabolism, of the essential amino acid tryptophan (TRP).

In some embodiments, the tryptophan metabolism and/or kynurenine pathway modulator is an inhibitor of the enzyme indoleamine-pyrrole 2,3-dioxygenase 1 (IDO1). In some embodiments, the immunotherapy, such as a T cell therapy (e.g. CAR-expressing T cells) or a T cell-engaging therapy is a recombinant-receptor expressing T cell therapy, which optionally is a chimeric antigen receptor (CAR)-expressing cell therapy, a tumor infiltrating lymphocytic (TIL) therapy or a transgenic TCR therapy. In some cases, the recombinant receptor is a chimeric antigen receptor (CAR). In some embodiments, the tryptophan metabolism and/or kynurenine pathway modulator is an inhibitor of the enzyme indoleamine-pyrrole 2,3-dioxygenase 1 (IDO1), an inhibitor of IDO2 and/or an inhibitor of tryptophan 2,3-dioxygenase (TDO). In some embodiments, the modulator is an inhibitor of IDO1, which is optionally epacadostat.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

For clarity of disclosure, and not by way of limitation, the detailed description is divided into the subsections that follow. The section headings used herein are for organizational purposes only and are not to be construed as limiting the subject matter described.

I. MODULATION OF THE KYNEURINE PATHWAY IN THERAPEUTIC METHODS INVOLVING IMMUNOTHERAPY

Provided herein is a combination therapy involving administration of an immunotherapy, such as a cell therapy, and a modulator of tryptophan metabolic pathways such as alternative metabolic pathways, such as modulators of the kynurenine pathway.

In some aspects, in the tumor microenvironment (TME) of many types of cancers, metabolism, e.g., catabolism, of the essential amino acid tryptophan (TRP) is involved in maintaining an immunosuppressive environment. In some aspects, in the TME of many types of cancers, metabolism, e.g., catabolism, of the essential amino acid tryptophan (TRP) is involved in maintaining the immunosuppressive environment. For example, in some aspects, one or more alternative tryptophan metabolism pathway is involved. Among the pathways involved in TRP catabolism is the kynurenine pathway, in which indoleamine-pyrrole 2,3-dioxygenase 1 (IDO1) is involved in TRP degradation by converting L-tryptophan into N-formyl-L-kynurenine, which subsequently is metabolized through a series of steps to form nicotinamide adenine dinucleotide (NAD). Several cell types in the TME, including tumor cells and specific subsets of dendritic cells (DCs), macrophages and immature monocytes, express increased levels of IDO1 in response to inflammatory cues such as interferon γ (IFNγ), tumor necrosis factor alpha (TNFα) or signal transducer and activator of transcription 3 (STAT3)-activator stimuli. In some aspects, "bystander" cells in the tumor microenvironment, e.g., stromal cells such as bone marrow stromal cells, can also express increased levels of IDO1 in response to inflammatory cues such as IFNγ or TNFα.

In some aspects, cancer cells or tumor cells in the TME can promote adaptive immune resistance, a process in which cancer cells or tumor cells change their phenotype in response to a cytotoxic or pro-inflammatory immune response, to limit and evade anti-tumor immune response. In some aspects, specific recognition of cancer cells by immune cells, such as T cells or adoptively transferred T cells, can lead to the production of immune-activating cytokines, e.g., IFNγ or TNFα. Upon production of cytokines, cancer or tumor cells in turn respond by limiting or evading immune responses, e.g., by expression of IDO1, depletion of tryptophan in the microenvironment, or by expression of programmed death ligand 1 (PD-L1) by cancer cells (see, e.g., Ribas, A. (2015) Cancer Discov. 5(9): 915-919). In some cases, the adaptive immune resistance response can limit the activity of T cells in the TME, through the catabolism of tryptophan, resulting in local amino acid deficiency and accumulation of tryptophan catabolites.

In some aspects, certain tumor cells or cancer cells, or other cells in the TME, can exhibit high levels of expression of or upregulate the expression of amino acid transporters, e.g., tryptophan transporters such as LAT1/CD98hc or LAT2/CD98hc, such as in response to tryptophan starvation or exposure to a tryptophan (or other amino acid)-starved environment. In some embodiments, such upregulation and/or expression permits the uptake or increase in uptake of amino acids by the tumor cells, e.g., tryptophan, from the environment. In some aspects, such uptake or increase in uptake by the tumor cell may promote or enhance a tryptophan-depleted or tryptophan-starved environment or condition in the TME (see, e.g., Broer et al. (2011) Biochem. J. 436, 193-211; Wang et al. (2015) Am J Cancer Res 5(4): 1281-1294; Ribas, A. (2015) Cancer Discov. 5(9): 915-919). In some aspects, such expression and uptake or increase in uptake exacerbates the effects of an already starved environment, for example, in which the tumor or tumor-associated cells having upregulated or expressed the transporter take up most or all available tryptophan, such that T cells and/or other immune cells, e.g., engineered T cells of the therapy, are unable to compete for tryptophan and/or experience effects of tryptophan starvation.

In some aspects, as described herein, the generation or exacerbation of tryptophan-depleted or tryptophan-starved conditions, e.g., by the increase in expression and/or activity of IDO1 or by upregulation of expression of tryptophan transporters, e.g., LAT1/CD98hc or LAT2/CD98hc, by diseased cells and/or associated cells or tissues, can inhibit or hinder one or more effects of a cell therapy and/or immune cells, such as the activity, proliferation and/or expansion of anti-tumor immune cells, e.g., T cells. In some aspects, activity of the kynurenine pathway and/or tryptophan metabolism in the tumor microenvironment (TME) can result in one or more immunosuppressive activities. In some aspects, IDO1 expression by tumor cells, myeloid cells and/or stromal cells in the tumor microenvironment (TME) contributes to the immunosuppressive condition in the TME. Expression of high levels of IDO1 in the TME can result in a reduction or depletion of TRP and an increase of kynurenine (KYN), and inhibition of anti-tumor immune responses. In some aspects, expression of IDO1 in the TME can result in depletion of factors or metabolites necessary for the activity, function, proliferation, survival and/or persistence of immune cells, e.g., T cells. In some aspects, IDO1-expressing cells can exert broad and robust immunosuppressive effects, e.g., in the TME, by (1) directing suppression of proliferation and effector of functions of cytotoxic T lymphocytes, NK cells and plasma cells; (2) promoting the conversion of naïve CD4+ T cells into CD4+ CD25+ FOXP3+ Tregs and activating them; and/or (3) triggering immunosuppressive activity in neighboring IDO1-expressing DCs, e.g., by a process known as bystander suppression (Vacchelli et al., (2014) OncoImmunology 3:10, e957994). In some aspects, kynurenine (KYN) and its derivatives can bind to aryl hydrocarbon receptor (AHR). Binding of KYN to AHR results in reprogramming the differentiation of naïve CD4+ T-helper (Th) cells favoring a Treg phenotype while suppressing the differentiation into interleukin-17 (IL-17)-producing Th (Th17) cells. Activation of the AHR also can result in promoting a tolerogenic phenotype on dendritic cells (DC), and can effect suppression of CD8+ T cell responses, immune tolerance to tumor antigen and antigen-induced cell death or anergy. Accumulation of KYN and its derivatives can also be cytotoxic to CD8+ T cells, NK cells and NK T cells.

In some instances, IDO1 is chronically activated in some cancer patients, and increased IDO1 expression can be an independent prognostic variable for reduced survival in some cancer patients, e.g., patients with acute myeloid leukemia (AML), small-cell lung, melanoma, ovarian, colorectal, pancreatic, and endometrial cancers (see, e.g., Moon et al., Journal for ImmunoTherapy of Cancer (2015) 3:51; Platten et al., Front Immunol. 2015 Jan. 12; 5:673; Weinmann, H., ChemMedChem 2016, 11:450-466). Inhibition of IDO1, in some embodiments, can reduce or reverse the immunosuppressive effects and/or other effects of IDO1 in the TME, such as depleting immune effector cells of TRP, promoting the accumulation of KYN and its derivatives, e.g., 3-hydroxykynurenine, kynurenic acid and 3-hydroxyanthranilic acid, some of which can be cytotoxic to CD8+ T cells, NK cells and NK T cells, and also can promote the differentiation of CD4+ T cells to regulatory T cells (Tregs).

In some aspects, T cells can be sensitive to activity of the kynurenine pathway and/or tryptophan metabolism. In some aspects, T cells are sensitive to tryptophan depletion in the environment, e.g., in the TME. In some cases, T cells can sense low tryptophan (TRP) levels via uncharged tRNAs resulting in activation of the kinase general control nonderepressible 2 (GCN2) and initiation of an amino acid starvation response or a stress response resulting in cell cycle arrest, cell death or lack of proliferation. Activation of GCN2 also promotes differentiation of regulatory T cells (Treg) and enhances Treg activity, resulting in further immunosuppression. In some cases, the kynurenine pathway and/or tryptophan metabolism can induce exhaustion, anergy or cell death of effector T cells, suppression of antitumor immune responses or tolerance to tumor antigens, generation and activation of Tregs, and contribute to the immunosuppressive conditions in the TME (see, e.g., Moon et al., Journal for ImmunoTherapy of Cancer (2015) 3:51; Platten et al., Front Immunol. 2015 Jan. 12; 5:673; Weinmann, H., ChemMedChem 2016, 11:450-466). In some aspects, expression of IDO1 in the TME can result in generation of factors or metabolites that contribute to exhaustion, hyporesponsiveness (anergy), lack of proliferation, terminal differentiation and/or differentiation into a suppressive state. In some aspects, the TME can induce exhaustion of T cells, which can lead to a progressive loss of T cell functions and/or in depletion of the cells.

In some aspects, cancer or tumor cells can increase the expression of amino acid transporters, to increase the uptake of amino acids from the TME. For example, expression of components of the L-type amino acid transporters (LATs), which can in some aspects mediate uptake and exchange of amino acids into and out of cells, can be increased in various cancer cells (and/or may be upregulated by tumors and/or cancer cells or tumor-associated cells in response to amino acid starvation or other TME conditions), thereby regulating mTORC1 signaling and protein synthesis. Increased expression of transporters, such as LATs, can result in depletion or further depletion of amino acids, e.g., tryptophan, in the TME, thereby generating a low amino acid environment.

In some aspects, the activity of the immunotherapy, e.g., T cell therapy, may be limited by the immunosuppressive activity or factors present in the local microenvironment of the disease or disorder, e.g., the TME. In some aspects, the TME contains or produces factors or conditions that can suppress the activity, function, proliferation, survival and/or persistence of T cells administered for T cell therapy.

In some aspects, the provided embodiments are based, at least in part, on the observation described herein that T cells, such as CAR T cells, are sensitive to tryptophan starvation. The upregulation of IDO1 in cells in the TME, including tumor cells, can generate a tryptophan starvation environment, which then can inhibit the survival and/or activity of CAR T cells. In some aspects, the suppressive effects of tryptophan starvation may be reduced, overcome and/or reversed by inhibition of factors associated with metabolism, e.g., catabolism, of the essential amino acid tryptophan (TRP), such as IDO1, supplementation of tryptophan and/or augmenting tryptophan uptake by CAR T cells.

In some aspects, prolonged tryptophan starvation in CAR T cells may affect the ability of the CAT T cells to later recover from starvation under conditions in which tryptophan is replenished and/or conditions leading to tryptophan starvation is reversed or attenuated. In some cases, prolonged tryptophan starvation, e.g., prolonged tryptophan depletion in the TME, can result in delay or inability of CAR T cell recovery, e.g., delay or arrest in growth and/or functional activity. In some aspects, the provided embodiments can be used to prevent or reduce prolonged tryptophan starvation and/or facilitate the recovery of CAR T cells from tryptophan starvation. In some aspects, the provided embodiments can be used to prevent or reduce prolonged tryptophan starvation and/or facilitate the recovery of CAR T cells from tryptophan starvation. In some aspects, the provided embodiments permit administered CAR T cells to recover or restore the functional activity and/or growth of the T cells to a baseline or steady state level, e.g., the levels of functional activity and/or growth in normal or steady state condition and/or in conditions that are not tryptophan depleted.

T cell-based therapies, such as adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some contexts, optimal activity or outcome can depend on the ability of the administered cells to recognize and bind to a target, e.g., target antigen, to traffic, localize to and successfully enter appropriate sites within the subject, tumors, and environments thereof. In some contexts, optimal activity or outcome can depend on the ability of the administered cells to become activated, expand, to exert various effector functions, including cytotoxic killing and secretion of various factors such as cytokines, to persist, including long-term, to differentiate, transition or engage in reprogramming into certain phenotypic states (such as long-lived memory, less-differentiated, and effector states), to avoid or reduce immunosuppressive conditions in the local microenvironment of a disease, to provide effective and robust recall responses following clearance and re-exposure to target ligand or antigen, and avoid or reduce exhaustion, anergy, peripheral tolerance, terminal differentiation, and/or differentiation into a suppressive state.

In some aspects, the provided embodiments are based on observations that CAR T cells can induce expression of functional indoleamine-pyrrole 2,3-dioxygenase 1 (IDO1) in cells, such as tumor cells, when stimulated by antigen, and that functional outcomes of the increase (e.g. via kynurenine pathway modulation of tryptophan metabolism) can be modulated by an inhibitor of the enzyme. In addition to tumor cells, IDO1 can be expressed by endothelial cells, mesenchymal stromal cells, such as bone marrow stromal cells, fibroblasts, and various myeloid-derived antigen-presenting cells such as dendritic cells (DCs) and macrophages, which also can be present in the tumor microenvironment. In some aspects, the induction of expression of IDO1 in such cells can be direct or can be indirect, such as via production of interferon-gamma (IFNγ) or tumor necrosis factor alpha (TNFα) in or from CAR-T cells after antigen stimulation.

In some aspects, observations herein indicate tumor cells and other cells in the TME can express increased levels of IDO1 upon administration of CAR T cells in vivo. In some aspects, the increase in IDO1 expression by tumor cells and other cells are in response to inflammatory cues such as interferon γ (IFNγ). In some embodiments, CAR-expressing T cells are capable of inducing IDO1 expression in CAR-targeted antigen-positive cells, and the induction is in part mediated by IFNγ.

Thus, some embodiments provided herein are based on observations herein, indicating that, in some cases, antigen-specific stimulation of T cells, such as recombinant receptor-expressing T cells (e.g. CAR-T cells) can result in an upregulated expression of IDO1 in one or more cells that may be found in or be associated with a tumor or the tumor microenvironment. Such immunosuppressive effects in certain contexts may negatively regulate certain features of, e.g., certain activity, persistence, proliferation, or other function of, a cell therapy such as the recombinant receptor-expressing T cells (e.g. CAR-T cells).

In some embodiments, administration of a tryptophan metabolism or kynurenine pathway modulator, such as an IDO1 inhibitor, in combination with a cell therapy enhances effector function (e.g., cytokine secretion), expansion and/or persistence of cells of the cell therapy. In some embodiments, the enhancement of proliferation or activity is to a level that is restored or recovered to a baseline or steady state level of such activity, such as to a level or activity that is observed in the absence of effects mediated by immunosuppressive effects due to metabolism, e.g., catabolism, of the essential amino acid tryptophan (TRP). In some aspects, the enhancement or increase in effector function (e.g., cytokine secretion), expansion and/or persistence of cells of the cell therapy occurs without an increase in (and/or with a decrease in) one or more markers induced upon activation of the cells, such as T cell activation markers, such as CD25. In some embodiments, the cells exhibit a less-differentiated or less activated surface phenotype, despite exhibiting substantial expansion and/or effector function.

In some embodiments, T cells are sensitive to a tryptophan-depleted or tryptophan-starved environment, e.g., where T cell activity, proliferation and/or expansion may be inhibited in a tryptophan-starved, tryptophan-depleted or tryptophan-insufficient environment. Tumor cells or cancer cells or associated cells, such as associated stromal or myeloid cells, can in some aspects generate, result in, or exacerbate such immunosuppressive environment or conditions by upregulating the activity and/or expression of IDO1, and/or by increasing the activity and/or expression of tryptophan transporters, e.g., LAT1/CD98hc or LAT2/CD98hc. In some aspects, upregulation of transporters may be in response to tryptophan or other amino acid-starved environments. In some aspects, it may cause the tumor or other cells to increase their uptake of tryptophan or other amino acid in the TME, which in some contexts may deplete or diminish the supply or levels of tryptophan available, e.g., in an already-starved environment, for example, available to immune cells such as cells of an adoptive cell therapy. In some cases, cells in the TME, e.g., bystander cells such as stromal cells, can also upregulate the activity and/or expression of IDO1. In some cases, T cell activity, proliferation and/or expansion is affected substantially by the presence of cells that exhibit high expression of tryptophan transporters, such as LAT1/CD98hc.

Results described herein are consistent with the interpretation that T cells expressing a CAR administered for T cell therapy, in embodiments may be particularly sensitive to low TRP levels and/or accumulation of kynurenine and/or may be particularly vulnerable to such effects, e.g., due to their ability to promote pathways leading to tryptophan starvation and/or IDO upregulation, e.g., upon administration and activation. It is observed herein that immunosuppressive effects of the TME, such as those induced by the presence and/or activity of CAR T cells and/or inflammatory signals, may be overcome by administering modulators of tryptophan metabolic pathways such as alternative metabolic pathways, such as modulators of the kynurenine pathway, e.g., inhibitors of IDO1.

In some aspects, immunosuppressive effects of the TME may be and/or may further be overcome by engineering the CAR T cells to compete or survive in a tryptophan-depleted environment, e.g., by overexpression of tryptophan transporters, and/or to be less sensitive to tryptophan depletion, e.g., by reduction of expression of molecules involved in IDO-mediated or IDO-induced or tryptophan starvation-induced immunosuppressive signaling, such as those associated with sensing or responding to tryptophan starvation or insufficiency and/or associated with sensing or responding to kynurenine-mediated immuno-suppression, including molecules that are positively or negatively regulated by IDO-mediated catabolism, e.g. an insufficiency in tryptophan or an accumulation of kynurenine or another tryptophan metabolite. Inhibiting parts of the kynurenine pathway that contributes to the immunosuppressive conditions of the TME, e.g., inhibiting TRP depletion and/or production of KYN and its derivatives, or engineering cells to be more resistant to tryptophan-starved or tryptophan-depleted immunosuppressive environment, can increase one or more post-administration parameters or outcomes following administration of an immunotherapy, such as a T cell therapy (e.g. CAR-expressing T cells) or a T cell-engaging therapy.

Accordingly, a combination therapy using an immunotherapy, such as a T cell therapy (e.g. CAR-expressing T cells) or a T cell-engaging therapy, and a tryptophan metabolism and/or kynurenine pathway modulator can reduce or reverse some of the immunosuppressive effects of the TME and tryptophan depleted conditions, as well as restore and/or increase the activity, outcome, response to, and/or persistence of the immunotherapy, e.g. cell therapy.

II. COMBINATION THERAPY

Provided are methods for combination therapy that include administering to a subject 1) a modulator such as a tryptophan or tryptophan metabolism modulator, such as a modulator of an alternative tryptophan metabolic pathway, e.g., a kynurenine pathway modulator, e.g., an inhibitor of IDO1, and 2) an immunotherapy or immunotherapeutic agent, such as an adoptive immune cell therapy, e.g., T cell therapy (e.g. CAR-expressing cell, e.g., T cells) or a T cell-engaging or immune modulatory therapy, e.g., a multi-specific T cell recruiting antibody and/or checkpoint inhibitor. Also provided are combinations and articles of manufacture, such as kits, that contain a composition comprising the immunotherapeutic agent, such as the cells, and a composition comprising the kynurenine pathway modulator, and uses of such compositions and combinations to treat or prevent diseases, conditions, and disorders, including cancers. In some embodiments, the immunotherapy is a cell therapy, e.g., immune cell therapy, e.g., cell therapy involving cells containing one or more recombinant immune receptor, e.g., T cell therapy (e.g. administrating CAR-expressing T cells). Such methods can include administration of the modulator, e.g., kynurenine pathway modulator, prior to, simultaneously with, during, during the course of (including once and/or periodically during the course of), and/or subsequently to, the administration (e.g., initiation of administration) of the immunotherapeutic agent or immunotherapy, such as the T cell therapy (e.g. CAR-expressing T cells) or other therapy such as the T cell-engaging therapy. In some embodiments, the administrations can involve sequential or intermittent administrations of the modulator, e.g., kynurenine pathway modulator, and/or the immunotherapy or immunotherapeutic agent, e.g. T cell therapy. In some embodiments, the kynurenine pathway modulator is administered prior to, simultaneously with and/or subsequent to initiation of administration of the T cell therapy.

In some embodiments, the immunotherapy, such as a T cell therapy (e.g. CAR-expressing T cells) or a T cell-engaging therapy, and tryptophan metabolism and/or kynurenine pathway modulator are provided as pharmaceutical compositions for administration to the subject. In some embodiments, the pharmaceutical compositions contain therapeutically effective amounts of one or both of the agents for combination therapy, e.g., T cells for adoptive cell therapy and an IDO1 inhibitor. In some embodiments, the agents are formulated for administration in separate pharmaceutical compositions. In some embodiments, any of the pharmaceutical compositions provided herein can be formulated in dosage forms appropriate for each route of administration.

In some embodiments, the combination therapy, which includes administering the immunotherapy (e.g. T cell therapy, including engineered cells, such as CAR-T cell therapy) and the tryptophan metabolism and/or kynurenine pathway modulator or compositions thereof, are administered to a subject or patient having a disease or condition to be treated (e.g. cancer) or at risk for having the disease or condition (e.g. cancer). In some aspects, the methods treat, e.g., ameliorate one or more symptom of, the disease or condition, such as by lessening tumor burden in a cancer expressing an antigen recognized by an engineered T cell.

In some embodiments, the immunotherapy for use in connection with the provided methods include T cell therapy using engineered T cells, including cells engineered with a recombinant receptor (e.g. CAR-T cells). In some cases, the T cells can be sensitive to activity of the kynurenine pathway and/or tryptophan metabolism. In some aspects, the T cells can be sensitive to tryptophan starvation depletion in the environment, e.g., in the TME. In some cases, tumor cells and/or other cells in the TME can increase the expression of IDO1 and/or amino acid transporters such as tryptophan transporters, e.g., LAT1/CD98hc or LAT2/CD98hc, which can reduce the amount of tryptophan available to the CAR T cells in the TME by metabolizing tryptophan and/or transporting extracellular tryptophan into the tumor cells and/or other cells. In some cases, tryptophan starvation or depletion can lead to exhaustion, anergy or cell death of effector T cells, suppression of antitumor immune responses or tolerance to tumor antigens, generation and activation of Tregs, and contribute to the immunosuppressive conditions in the TME (see, e.g., Moon et al., Journal for Immuno-Therapy of Cancer (2015) 3:51; Platten et al., Front Immunol. 2015 Jan. 12; 5:673; Weinmann, H., ChemMedChem 2016, 11:450-466). In some aspects, tryptophan starvation or depletion can reduce or inhibit the functional activity and/or survival of CAR T cells.

In some aspects, prolonged tryptophan starvation or depletion in CAR T cells may affect its ability to recover from starvation or depletion and/or reverse the effect of starvation or depletion. In some cases, prolonged tryptophan starvation or depletion, e.g., prolonged exposure to tryptophan depleted conditions in the TME, can result in delay or inability of CAR T cell recovery, e.g., delay or arrest in growth and/or functional activity. In some cases, prolonged tryptophan starvation or depletion, e.g., tryptophan starvation or depletion for about 48 hours, 72 hours, 96 hours, 5 days, 6 days, 7 days, 14 days, 21 days, 28 days or more, can reduce or abolish the T cell's ability to recover from or reverse the effect of starvation or depletion.

In some aspects, the provided embodiments can be used to prevent or reduce prolonged tryptophan starvation or depletion and/or facilitate the recovery of CAR T cells from tryptophan starvation or depletion, and/or prevent, reduce or reverse the immunosuppressive effects and/or other effects of IDO1 upregulation in the TME. In some aspects, the provided embodiments can be used to reduce or prevent tryptophan starvation or depletion and/or to recover the functional activity and/or growth of the T cells, e.g., engineered T cells for cell therapy, to a baseline or steady state level, e.g., the levels of functional activity and/or growth in normal or steady state conditions, e.g., conditions where tryptophan is sufficient. In some embodiments, the prevention and/or recovery is achieved by inhibiting the activity of IDO1, preventing the depletion of tryptophan in the TME, and/or increasing the ability of the T cells to uptake available tryptophan from the environment. In some embodiments, a combination therapy, such as any described herein, can be used to prevent or reduce from tryptophan starvation or depletion, or facilitate the recovery of CAR-T cells from tryptophan starvation or depletion. In some cases, the provided embodiments, the prevention of tryptophan starvation or depletion and/or facilitating recovery from tryptophan starvation or depletion, e.g., to recover or maintain baseline or steady state T cell activity, is performed prior to the establishment of prolonged tryptophan starvation or depletion, e.g., before T cells become incapable of reversing or recovering from the starvation or depletion.

In some aspects, the provided embodiments, e.g., a combination therapy of T cell therapy, such as CAR-T and/or a tryptophan metabolism and/or kynurenine pathway modulator can be given to a subject that has failed, is no longer responsive, and/or have relapsed following administration other therapies. In some embodiments, the provided embodiments can be used to treat subjects that have failed another therapy, become resistant to another therapy and/or that have relapsed following administration other therapies, such as a prior treatment with a tryptophan metabolism and/or kynurenine pathway modulator, e.g., IDO1 inhibitor. In some aspects, the provided embodiments, e.g., a combination therapy of T cell therapy, such as CAR-T and/or a tryptophan metabolism and/or kynurenine pathway modulator can be given to a subject that has failed, is no longer responsive, and/or have relapsed following administration of an IDO inhibitor, such as epacadostat.

The provided embodiments of administering a tryptophan metabolism and/or kynurenine pathway modulator can improve responses to freshly administered cell therapy. Because a fresh source of T cells (e.g. CAR-T cells, generated by obtaining T cells from the subject, engineering to express the recombinant receptor, activating and/or expanding) is introduced into the subject, the tryptophan metabolism and/or kynurenine pathway modulator, e.g., IDO1 inhibitor can exert its effect on the administered T cells, even though T cells from the subject that have not been engineered has failed or is no longer responsive to treatment to a prior administration of a tryptophan metabolism and/or kynurenine pathway modulator, e.g., IDO1 inhibitor, such as epacadostat. In some embodiments, the fresh source of cells, e.g., engineered T cells, may not have been subject to tryptophan starvation. Thus, even though the subject may have failed or is no longer responsive to a prior treatment with a tryptophan metabolism and/or kynurenine pathway modulator, the administered tryptophan metabolism and/or kynurenine pathway modulator can facilitate the prevention of tryptophan starvation or depletion and/or facilitating recovery from tryptophan starvation or depletion, e.g., to recover or maintain baseline or steady state T cell activity, of the fresh source of cells, e.g., engineered T cells.

In some embodiments, the combination therapy can be administered to subjects that have failed, become resistant to and/or have relapsed following administration of other prior therapies, such as a prior administration of a combination therapy of a tryptophan metabolism and/or kynurenine pathway modulator therapy, and immunomodulatory therapy, e.g., an immune checkpoint inhibitor therapy. In some embodiments, the prior immunomodulatory therapy is not a prior T cell therapy. In some embodiments, the subjects have not been administered a prior T cell therapy.

In some embodiments, the subject, prior to administration of the CAR-T cells, has been administered a combination of the tryptophan pathway modulator and a checkpoint inhibitor or other immunotherapy. In some aspects, the subject did not exhibit a benefit of the tryptophan pathway modulator over administration of the immunotherapy or checkpoint inhibitor alone.

In some embodiments, the subject is identified or selected for administration of one or more steps of the embodiments provided herein if the subject has failed, become resistant to and/or relapsed following a prior treatment such as a prior administration of a tryptophan metabolism and/or kynurenine pathway modulator, e.g., IDO1 inhibitor, such as epacadostat, optionally wherein such prior administration was carried out in combination with an immunomodulatory therapy that is not a T cell therapy, e.g., an immune checkpoint inhibitor therapy. In some embodiments, the combination therapy can be administered to subjects that have failed, become resistant to and/or having relapsed following other prior treatments, such as a prior administration of a combination therapy of a tryptophan metabolism and/or kynurenine pathway modulator, e.g., IDO1 inhibitor, such as epacadostat, and an immune modulator, e.g., an immune checkpoint inhibitor. In some embodiments, the prior immunomodulatory therapy is not a prior T cell therapy. In some embodiments, the subjects have not been administered a prior T cell therapy.

In some embodiments, the disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by bacterial, viral or other pathogens. Exemplary antigens, which include antigens associated with various diseases and conditions that can be treated, include any of antigens described herein. In particular embodiments, the recombinant receptor expressed on engineered cells of a combination therapy, including a chimeric antigen receptor or transgenic TCR, specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. In some embodiments, the antigen associated with the disease or disorder is selected from the group consisting of orphan tyrosine kinase receptor ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the methods can be used to treat a myeloma, a lymphoma or a leukemia. In some embodiments, the methods can be used to treat a non-Hodgkin lymphoma (NHL), an acute lymphoblastic leukemia (ALL), a chronic lymphocytic leukemia (CLL), a diffuse large B-cell lymphoma (DLBCL), acute myeloid leukemia (AML), or a myeloma, e.g., a multiple myeloma (MM). In some embodiments, the methods can be used to treat a MM or a DBCBL.

In some embodiments, the methods can be used to treat a cancer that is not a B cell malignancy and/or does not express a B cell antigen. In some embodiments, the methods can be used to treat a cancer that does not express CD19. In some embodiments, the provided methods employ a recombinant receptor-expressing T cell (e.g. CAR-T cell) that does not target or specifically bind CD19.

In some embodiments, the methods can be used to treat a non-hematologic cancer, such as a solid tumor. In some embodiments, the methods can be used to treat a bladder, lung, brain, melanoma (e.g. small-cell lung, melanoma), breast, cervical, ovarian, colorectal, pancreatic, endometrial, esophageal, kidney, liver, prostate, skin, thyroid, or uterine cancers.

In some embodiments, the disease or disorder is associated with an immunosuppressive local environment. In some embodiments, the disease or disorder is associated with tryptophan metabolism and/or kynurenine pathway activation in the local environment of the disease. For example, in some embodiments, the disease or disorder is associated with reduced tryptophan levels and/or increased levels of kynurenine (KYN) or its derivatives in the local microenvironment of the disease or disorder, e.g., tumor microenvironment (TME). In some embodiments, the disease or disorder is associated with increased expression of enzymes or factors involved in the kynurenine pathway, e.g., indoleamine-pyrrole 2,3-dioxygenase 1 (IDO1), in the cells in the TME, or the cells in the TME are induced to express enzymes or factors involved in the kynurenine pathway, e.g., indoleamine-pyrrole 2,3-dioxygenase 1 (IDO1).

In some embodiments, the disease or disorder is not associated with increased expression of enzymes or factors involved in the kynurenine pathway, e.g., indoleamine-pyrrole 2,3-dioxygenase 1 (IDO1). In some embodiments, the disease or disorder, e.g. cancer, comprises a tumor negative for IDO1, IDO2 or TDO and/or the subject is not selected for expression of an IDO1, IDO2 or TDO positive tumor.

For the prevention or treatment of disease, the appropriate dosage of tryptophan metabolism and/or kynurenine pathway modulators (e.g. IDO1 inhibitor) and/or immunotherapy, such as a T cell therapy (e.g. CAR-expressing T cells) or a T cell-engaging therapy, may depend on the type of disease to be treated, the type of tryptophan metabolism and/or kynurenine pathway modulator, cells and/or recombinant receptors expressed on the cells, the severity and course of the disease, route of administration, whether the tryptophan metabolism and/or kynurenine pathway modulator, e.g., IDO1 inhibitor, and/or the immunotherapy, e.g., T cell therapy, are administered for preventive or therapeutic purposes, previous therapy, frequency of administration, the subject's clinical history and response to the cells, and the discretion of the attending physician. The compositions and cells are in some embodiments suitably administered to the subject at one time or over a series of treatments. Exemplary dosage regimens and schedules for the provided combination therapy are described.

In some embodiments, the immunotherapy, e.g. T cell therapy, and the tryptophan metabolism and/or kynurenine pathway modulator are administered as part of a further combination treatment, which can be administered simultaneously with or sequentially to, in any order, another therapeutic intervention. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the methods further include a lymphodepleting therapy, such as administration of a chemotherapeutic agent. In some embodiments, the methods do not include a lymphodepleting therapy.

Prior to, during or following administration of the immunotherapy (e.g. T cell therapy, such as CAR-T cell therapy) and/or a tryptophan metabolism and/or kynurenine pathway modulator, the biological activity of the immunotherapy, e.g. the biological activity of the engineered cell populations, in some embodiments is measured, e.g., by any of a number of known methods. Parameters to assess include the ability of the engineered cells to destroy target cells, measured using any suitable method known in the art, such as assays described further below in Section III below. In some embodiments, the biological activity of the cells, e.g., T cells administered for the T cell based therapy, is measured by assaying expression and/or secretion of one or more cytokines. In some aspects the biological activity is measured by assessing the disease burden and/or clinical outcome, such as reduction in tumor burden or load. In some embodiments, the levels of, and/or changes or alterations in the levels of, factors or effectors, e.g., enzymes and/or metabolites of the kynurenine pathway are measured. In some embodiments, administration of one or both agents of the combination therapy and/or any repeated administration of the therapy, can be determined based on the results of the assays before, during, during the course of or after administration of one or both agents of the combination therapy. In some embodiments, results of such assays can be used to identify, select, screen and/or exclude subjects, before and/or after administration of one or more step of the combination therapy, e.g., immunotherapy (e.g. T cell therapy, such as CAR-T cell therapy) and/or a tryptophan metabolism and/or kynurenine pathway modulator. In some embodiments, certain subjects are identified or selected for treatment with immunotherapy (e.g. T cell therapy, such as CAR-T cell therapy) and/or a tryptophan metabolism and/or kynurenine pathway modulator based on the results of the assay.

A. Administration of Immunotherapy (e.g. T Cell Therapy or T Cell-Engaging Therapy)

In some embodiments of the methods, compositions, combinations, kits and uses provided herein, the combination therapy includes administering to a subject an immunotherapy, such as a T cell therapy (e.g. CAR-expressing T cells) or a T cell-engaging therapy. Such therapies can be administered prior to, subsequent to, simultaneously with administration of one or more tryptophan metabolism and/or kynurenine pathway modulators (e.g. IDO1 inhibitors) as described.

In some embodiments, the immunotherapy is a cell-based therapy that is or comprises administration of cells, such as immune cells, for example T cell or NK cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject. Exemplary of such cell therapies, e.g. T cell therapies, for use in the provided methods are described below.

In some embodiments, the immunotherapy is or comprises a T cell-engaging therapy that is or comprises a binding molecule capable of binding to a surface molecule expressed on a T cell. In some embodiments, the surface molecule is an activating component of a T cell, such as a component of the T cell receptor complex. In some embodiments, the surface molecule is CD3 or is CD2. In some embodiments, the T cell-engaging therapy is or comprises an antibody or antigen-binding fragment. In some embodiments, the T cell-engaging therapy is a bispecific antibody containing at least one antigen-binding domain binding to an activating component of the T cell (e.g. a T cell surface molecule, e.g. CD3 or CD2) and at least one antigen-binding domain binding to a surface antigen on a target cell, such as a surface antigen on a tumor or cancer cell, for example any of the listed antigens as described herein, e.g. CD19. In some embodiments, the simultaneous or near simultaneous binding of such an antibody to both of its targets can result in a temporary interaction between the target cell and T cell, thereby resulting in activation, e.g. cytotoxic activity, of the T cell and subsequent lysis of the target cell. Among such exemplary bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). In some embodiments, the T-cell engaging therapy is blinatumomab (CD3xCD19 BiTE) or AMG 330. Any of such T cell-engagers can be used in used in the provided methods.

1. T Cell Therapy

In some aspects, the T cell therapy is or comprises a tumor infiltrating lymphocytic (TIL) therapy, a transgenic TCR therapy or a T cell therapy comprising genetically engineered cells, such as a recombinant-receptor expressing cell therapy. In some embodiments, the recombinant receptor specifically binds to a ligand, such as one associated with a disease or condition, e.g. associated with or expressed on a cell of a tumor or cancer. In some embodiments, the T cell therapy includes administering T cells engineered to express a chimeric antigen receptor (CAR).

In some embodiments, the provided cells express and/or are engineered to express receptors, such as recombinant receptors, including those containing ligand-binding domains or binding fragments thereof, and T cell receptors (TCRs) and components thereof, and/or functional non-TCR antigen receptors, such as chimeric antigen receptors (CARs). In some embodiments, the recombinant receptor contains an extracellular ligand-binding domain that specifically binds to an antigen. In some embodiments, the recombinant receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Among the engineered cells, including engineered cells containing recombinant receptors, are described in Section IV below. Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

In some embodiments, the T cell therapy for use in connection with the provided methods include engineered T cells, including cells engineered with a recombinant receptor (e.g. CAR-T cells), that are modified in expression, such as a reduction in or an increase in expression, of one or more molecules associated with IDO-mediated immunosuppressive signaling, associated with sensing or responding to tryptophan starvation, insufficiency or shortage and/or associated with sensing or responding to kynurenine-mediated immuno-suppression (e.g. due to accumulation of a tryptophan metabolite) in the cell compared to the expression of such proteins induced during normal processes of IDO-mediated signaling and/or in response to or associated with sensing tryptophan starvation or insufficiency and/or in response to, or associated with sensing, kynurenine-mediated immuno-suppression. Included among such proteins are proteins whose expression, when altered in T cells in response to tryptophan metabolism, e.g. catabolism, such as occurs as a result of IDO activity, contributes to, causes or is associated with immunosuppression of T cells, leading to, in some cases, immune tolerance and tumor escape from immune surveillance. Such proteins can include those that are responsive to a decrease, depletion or deficiency of certain amino acids, e.g. tryptophan, and/or are responsive to an increase or accumulation of certain amino acid metabolites, e.g. kynurenine. Exemplary of such proteins include, but are not limited to, GCN2 kinase, BLIMP-1/PRDM1, aryl hydrocarbon receptor (AHR), AHR nuclear translocator (ARNT), mTOR, protein kinase C theta (PKC-θ). Upregulation of expression or translocated expression of GCN2, CHOP, BLIMP-1, AHR or AHR nuclear translocator (ARNT) and/or downregulation or reduced expression of mTOR or PKC-theta is, in some cases, associated with autophagy, T cell anergy, reduced T cell activation and/or decreased T cell proliferation (see e.g. Metz et al. (2012) Oncoimmunology, 1:1460-1468; Moon et al. (2015) J Immunother Cancer, 3:51; Platten et al. (2015) Frontiers in Immunology, 5:1).

In some embodiments, the provided engineered cells are modified by recombinant, engineered and/or ectopic expression of one or more protein the expression of which is normally or in a natural setting decreased or reduced in a T cell upon IDO-mediated signaling and/or in response to tryptophan shortage or accumulation of a tryptophan metabolite (e.g. kynurenine). In some embodiments, the one or more protein is mTOR or PKC-theta. In some embodiments, the provided engineered cells are modified by recombinant, engineered and/or ectopic expression of one or more molecules that can promote uptake by cells expressing such molecules of tryptophan or other amino acid in a tryptophan starvation or tryptophan insufficiency condition, e.g., one or more chains of an amino acid transporter or one or more amino acid transporters, such as CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4).

In some embodiments, the provided engineered cells comprise recombinant, engineered, or ectopic expression of mTOR, PKC-theta, CD98hc, LAT1, LAT2 or PAT4, or a functional portion or variant thereof, such as via introduction of a nucleic acid construct encoding mTOR, PKC-theta, CD98hc, LAT1, LAT2 or PAT4. In some embodiments, expression of mTOR, PKC-theta, CD98hc, LAT1, LAT2 or PAT4 is under the control of a heterologous promoter or enhancer, such as is under the control of an inducible promoter. In some embodiments, following IDO-mediating signaling and/or in response to tryptophan shortage or expression of the protein, such engineered cells are capable of a higher or increased expression of mTOR, PKC-theta, CD98hc, LAT1, LAT2 or PAT4 in the cell than expression of the protein in a similar cell but that is not so modified by the recombinant, engineered and/or ectopic expression. In some embodiments, expression of such a protein, e.g. mTOR, PKC-theta, CD98hc, LAT1, LAT2 or PAT4, is increased by at least or at least about 1.2-fold, 1.5-fold, 2.0-fold, 3.0-fold, 5.0-fold, 6.0-fold, 7.0-fold, 8.0-fold, 9.0-fold, 10.0-fold or more under certain conditions associated with IDO-mediated signaling, tryptophan shortage and/or accumulation of a tryptophan metabolite compared to expression of the protein under the same conditions in a cell that is not so modified by the recombinant, engineered or ectopic expression.

In some embodiments, the provided engineered cells are modified by reduced expression of one or more protein whose expression is normally increased and/or translocated in a T cell upon IDO-mediated signaling and/or in response to tryptophan shortage or accumulation of a tryptophan metabolite (e.g. kynurenine). In some embodiments, the one or more protein is GCN2 kinase, BLIMP-1/PRDM1, AHR or AHR nuclear translocator (ARNT). In some embodiments, such cells have reduced expression of GCN2, CHOP, BLIMP-1/PRDM1, AHR or ARNT. In some embodiments, reduced expression is carried out via an agent, such as an inhibitory nucleic acid molecule or an agent capable of mediating genetic disruption of the gene encoding the protein. In some embodiments, expression of the agent is under the control of a conditional promoter or enhancer, such as an inducible promoter, thereby conditionally regulating the reduction in expression of such protein. Exemplary systems and agents for effecting reduced expression and/or genetic disruption are described below. In some embodiments, expression of the one or more protein (e.g. GCN2, CHOP, BLIMP-1/PRDM1 and/or AHR) in the cell is reduced by at least 50, 60, 70, 80, 90, or 95% as compared to the expression in a similar cell in the absence of the agent or gene disruption under the same conditions.

In some embodiments, the engineered cell comprises recombinant, engineered, or ectopic expression of one or more of mTOR, PKC-theta, CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4), or a functional portion or variant thereof, and comprises reduced expression of one or more of GCN2, CHOP, BLIMP-1/PRDM1 or AHR.

In some embodiments, the provided engineered cells that are modified in expression of a protein associated with IDO-mediated signaling, such as in response to tryptophan shortage or accumulation of a tryptophan metabolite, can be used in combination with a tryptophan metabolism and/or kynurenine pathway modulator (e.g. IDO1 inhibitor) to provide certain additional advantages compared to a method in which the engineered cells are not so modified. In some aspects, certain tryptophan metabolism and/or kynurenine pathway modulators may not target, e.g. inhibit, all downstream activities associated with tryptophan catabolism, in which case the provided engineered cells can provide additional resistance of the engineered T cell therapy to the immunosuppressive effects of the kynurenine pathway and/or signaling of IDO1 or other pathway enzyme. In some cases, combining such modified engineered cells with a combination therapy involving a tryptophan metabolism and/or kynurenine pathway modulator (e.g. IDO1 inhibitor) can reduce the amount or frequency of administration of the tryptophan metabolism and/or kynurenine pathway modulator (e.g. IDO1 inhibitor). In certain aspects, the modification of the protein in the provided engineered cells is conditional, e.g. inducible, whereby modification of protein expression (e.g. of one or more of GCN2, CHOP, BLIMP-1, ARH, ARNT, mTOR, PKC-theta, CD98hc, LAT1, LAT2 or PAT4) can be controlled under certain conditions, such as at a time where the tryptophan metabolism and/or kynurenine pathway modulator may not be available or active.

In some embodiments, induction of the modified expression (e.g. reduced or increased expression) is at a time in which there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy. In some embodiments, induction of the modified expression (e.g. reduced or increased expression) is at a time in which there is evidence of increased T cell anergy or exhaustion of the T cell therapy, a decrease in T cell proliferation and/or a decrease in T cell activation. In any of such embodiments, such increase or decrease can be greater than or greater than about 1.5-fold, 2.0-fold, 3.0-fold, 4-fold, 5-fold, 6-fold, 7-fold, 8-fold, 9-fold, 10-fold or more compared to the level or activity prior to initiation of administration of the T cell therapy or compared to a preceding time point after initiation of the T cell therapy. In some embodiments, induction of the modified expression (e.g. reduced or increased expression) is at a time in which the number of cell of the T cell therapy detectable in the blood is: decreased (e.g. decrease by 1.5-fold, 2-fold, 3-fold, 4-fold, 5-fold, 10-fold or more decreased) compared to the number of T cells at a preceding time point after initiation of the T cell therapy; less than 1.5-fold 2-fold, 3-fold, 4-fold, 5-fold, 10-fold, 50-fold, 100-fold or more less than the peak or maximum number of cells of the T cell therapy detectable in the blood of the subject after initiation of the T cell therapy; less than or about less than 10%, 9%, 8%, 7%, 6%, 5%, 4%, 3%, 2%, 1%, 0.5%, 0.2% or 0.1% of the cells of the T cell therapy are detectable in the blood at a time after a peak of maximum level of such cells has been detected in the blood.

In some embodiments, the provided methods comprise administering an inducible agent to induce modification of expression (e.g. reduced or increased expression) of such a protein in the engineered cell. In some embodiments, the inducible agent is allolactose or IPTG, tetracycline or a tetracycline derivative or doxycycline or a doxycycline derivative. The choice of inducing agent depends, for example, on the particular inducible system, such as the particular promoter, for controlling expression of the protein or for controlling expression of an agent that mediates disrupted or reduced expression of the protein (e.g. inhibitory nucleic acid, nuclease or nuclease system or complex). In some embodiments, the inducing agent is rapamycin or other inducing agent capable of facilitating chemically induced dimerization of two subunits required for activity, e.g. inducible split-Cas9 (Zetche et al. (2015) Nat. Biotechnol., 33:139-142). Exemplary conditional, such as inducible systems, are described below.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means. The cells are administered in a dosing regimen to achieve a therapeutic effect, such as a reduction in tumor burden. Dosing and administration may depend in part on the schedule of administration of the tryptophan metabolism and/or kynurenine pathway modulator, which can be administered prior to, subsequent to and/or simultaneously with initiation of administration of the T cell therapy. Various dosing schedules of the T cell therapy include but are not limited to single or multiple administrations over various time-points, bolus administration, and pulse infusion.

a. Compositions and Formulations

In some embodiments, the dose of cells of the T cell therapy, such a T cell therapy comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders.

In some embodiments, the T cell therapy, such as engineered T cells (e.g. CAR T cells), are formulated with a pharmaceutically acceptable carrier. In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the agent or host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235, 871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains agents or cells in amounts effective to treat or prevent the disease or condition, such as a therapeutically effective or prophylactically effective amount. Therapeutic or prophylactic outcome(s) and/or efficacy in some embodiments is monitored by periodic assessment of treated subjects. For repeated administrations over several days or longer, depending on the condition, the treatment is repeated until a desired suppression or amelioration or prevention of disease or condition sign or symptoms occurs or is deemed likely to have occurred or to occur. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some cases, the cell therapy is administered as a single pharmaceutical composition comprising the cells. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

b. Dosage Schedule and Administration

In some embodiments, a dose of cells is administered to subjects in accord with the provided methods. In some embodiments, the size or timing of the doses is determined as a function of the particular disease or condition in the subject. It is within the level of a skilled artisan to empirically determine the size or timing of the doses for a particular disease in view of the provided description.

In certain embodiments, the cells, or individual populations of sub-types of cells, are administered to the subject at a range of about 0.1 million to about 100 billion cells and/or that amount of cells per kilogram of body weight of the subject, such as, e.g., 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values. In some embodiments, where the subject is a human, the dose includes between about $1 \times 10^6$ and $3 \times 10^8$ total recombinant receptor (e.g., CAR)-expressing cells, e.g., in the range of about $1 \times 10^7$ to $2 \times 10^8$ such cells, such as $1 \times 10^7$, $5 \times 10^7$, $1 \times 10^8$ or $1.5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^5$ to $5 \times 10^8$ total recombinant receptor-expressing T cells or total T cells, $1 \times 10^5$ to $1 \times 10^8$ total recombinant receptor-expressing T cells or total T cells, from or from about $5 \times 10^5$ to $1 \times 10^7$ total recombinant receptor-expressing T cells or total T cells, or from or from about $1 \times 10^6$ to $1 \times 10^7$ total recombinant receptor-expressing T cells or total T cells, each inclusive.

In some embodiments, the cell therapy comprises administration of a dose comprising a number of cells that is at least or at least about or is or is about $0.1 \times 10^6$ cells/kg body weight of the subject, $0.2 \times 10^6$ cells/kg, $0.3 \times 10^6$ cells/kg, $0.4 \times 10^6$ cells/kg, $0.5 \times 10^6$ cells/kg, $1 \times 10^6$ cell/kg, $2.0 \times 10^6$ cells/kg, $3 \times 10^6$ cells/kg or $5 \times 10^6$ cells/kg.

In some embodiments, the cell therapy comprises administration of a dose comprising a number of cells is between or between about $0.1 \times 10^6$ cells/kg body weight of the subject and $1.0 \times 10^7$ cells/kg, between or between about $0.5 \times 10^6$ cells/kg and $5 \times 10^6$ cells/kg, between or between about $0.5 \times 10^6$ cells/kg and $3 \times 10^6$ cells/kg, between or between about $0.5 \times 10^6$ cells/kg and $2 \times 10^6$ cells/kg, between or between about $0.5 \times 10^6$ cells/kg and $1 \times 10^6$ cell/kg, between or between about $1.0 \times 10^6$ cells/kg body weight of the subject and $5 \times 10^6$ cells/kg, between or between about $1.0 \times 10^6$ cells/kg and $3 \times 10^6$ cells/kg, between or between about $1.0 \times 10^6$ cells/kg and $2 \times 10^6$ cells/kg, between or between about $2.0 \times 10^6$ cells/kg body weight of the subject and $5 \times 10^6$ cells/kg, between or between about $2.0 \times 10^6$ cells/kg and $3 \times 10^6$ cells/kg, or between or between about $3.0 \times 10^6$ cells/kg body weight of the subject and $5 \times 10^6$ cells/kg, each inclusive.

In some embodiments, the dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, nor more than at or about $9 \times 10^5$ cells/kg, no more than at or about $1 \times 10^6$ cells/kg, or no more than at or about $2 \times 10^6$ cells/kg. In some embodiments, the dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In the context of adoptive cell therapy, administration of a given "dose" of cells encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

The term "split dose" refers to a dose that is split so that it is administered over more than one day. This type of dosing is encompassed by the present methods and is considered to be a single dose. In some embodiments, the cells of a split dose are administered in a plurality of compositions, collectively comprising the cells of the dose, over a period of no more than three days.

Thus, the dose of cells may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+CD8+ ratio, e.g., 1:1) involves the administration of a cell composition containing one of the populations and then administration of a separate cell composition comprising the other of the populations, where the administration is at or approximately at the target or desired ratio.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4+ to CD8+ cells, and/or is based on a desired fixed or minimum dose of CD4+ and/or CD8+ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4+ to CD8+ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some cases, the provided methods allow a lower dose of such cells to be administered, to achieve the same or better efficacy or other outcome of treatment as the dose in a method in which the cell therapy is administered without administering the tryptophan metabolism and/or kynurenine pathway modulator (e.g. IDO1 inhibitor) or a method in which the cells do not comprise modification of expression of a protein associated with IDO-mediated immunosuppressive signaling, associated with sensing or in response to tryptophan starvation or insufficiency and/or associated with sensing or in response to kynurenine-mediated immunosuppression. In some embodiments, the dose of cells administered is less than the dose in a method in which the cell therapy is administered without administering the tryptophan metabolism and/or kynurenine pathway modulator (e.g. IDO1 inhibitor) or a method in which the cells do not comprise modification of expression of a protein associated with IDO-mediated immunosuppressive signaling, that is induced or activated in response to or associated with sensing of starvation or insufficiency and/or associated with sensing or responding to kynurenine-mediated immunosuppression, such as at least 1.5-fold, 2-fold, 3-fold, 4-fold, 5-fold or 10-fold less than the dose in a method in which the cell therapy is administered without administering the tryptophan metabolism and/or kynurenine pathway modulator (e.g. IDO1 inhibitor) or a method in which the cells do not comprise modification of expression of a protein associated with IDO-mediated immunosuppressive signaling, associated with sensing or responding to tryptophan starvation or insufficiency and/or associated with sensing or responding to kynurenine-mediated immuno-suppression. In some embodiments, for example, the lower dose contains less than about $5 \times 10^6$ cells, recombinant receptor (e.g. CAR)-expressing cells, T cells, and/or PBMCs per kilogram body weight of the subject, such as about or less than about $4 \times 10^6$, $3 \times 10^6$, $2 \times 10^6$, $1 \times 10^6$, $0.5 \times 10^6$ or $0.1 \times 10^6$ such cells per kilogram body weight of the subject.

In some embodiments, one or more subsequent dose of cells can be administered to the subject. In some embodiments, the subsequent dose of cells is administered greater than or greater than about 7 days, 14 days, 21 days, 28 days or 35 days after initiation of administration of the first dose of cells. The subsequent dose of cells can be more than, approximately the same as, or less than the first dose. In some embodiments, administration of the T cell therapy, such as administration of the first and/or second dose of cells, can be repeated.

In some embodiments, initiation of administration of the cell therapy, e.g. the dose of cells or a first dose of a split dose of cells, is administered before (prior to), concurrently with or after (subsequently or subsequent to) the administration of the tryptophan metabolism and/or kynurenine pathway modulator, e.g., IDO1 inhibitor.

In some embodiments, the dose of cells, or the subsequent dose of cells, is administered 0 to 90 days, such as 0 to 30 days, 0 to 15 days, 0 to 6 days, 0 to 96 hours, 0 to 24 hours, 0 to 12 hours, 0 to 6 hours, or 0 to 2 hours, 2 hours to 30 days, 2 hours to 15 days, 2 hours to 6 days, 2 hours to 96 hours, 2 hours to 24 hours, 2 hours to 12 hours, 2 hours to 6 hours, 6 hours to 90 days, 6 hours to 30 days, 6 hours to 15 days, 6 hours to 6 days, 6 hours to 96 hours, 6 hours to 24 hours, 6 hours to 12 hours, 12 hours to 90 days, 12 hours to 30 days, 12 hours to 15 days, 12 hours to 6 days, 12 hours to 96 hours, 12 hours to 24 hours, 24 hours to 90 days, 24 hours to 30 days, 24 hours to 15 days, 24 hours to 6 days, 24 hours to 96 hours, 96 hours to 90 days, 96 hours to 30 days, 96 hours to 15 days, 96 hours to 6 days, 6 days to 90 days, 6 days to 30 days, 6 days to 15 days, 15 days to 90 days, 15 days to 30 days or 30 days to 90 days after starting or initiating administration of the tryptophan metabolism and/or kynurenine pathway modulator. In some embodiments, the dose of cells, or the subsequent dose of cells, is administered after starting or initiating administration of the tryptophan metabolism and/or kynurenine pathway modulator. In some embodiments, the dose of cells is administered at least or about at least or about 1 hour, 2 hours, 6 hours, 12 hours, 24 hours, 2 days, 3 days, 6 days, 12 days, 15 days, 30 days, 60 days or 90 days after starting or initiating administration of the tryptophan metabolism and/or kynurenine pathway modulator.

In some embodiments, the dose of cells is administered at a time when one or more effects of the tryptophan metabolism and/or kynurenine pathway modulator, e.g., IDO1 inhibitor, are achieved. In some embodiments, the method involves, subsequent to administering the tryptophan metabolism and/or kynurenine pathway modulator, e.g., IDO1 inhibitor, but prior to administering the T cell therapy, e.g., adoptive T cell therapy, assessing a sample from the subject for alteration in the level of metabolites in the kynurenine pathway, e.g., TRP, KYN or derivatives of KYN, and/or expression levels of factors or effectors, e.g., enzymes, involved in the kynurenine pathway, e.g., IDO1, or other phenotypes or desired outcomes as described herein, e.g., such as those described in Section III. In some embodiments, the dose of cells is administered at a time in which the tryptophan metabolism and/or kynurenine pathway modulatory (e.g. IDO1 inhibitor) has, or is likely to have, resulted in an alteration in the level of metabolites in the kynurenine pathway, such as increase in the levels of TRP or a decrease in the levels of KYN or a KYN derivative (e.g. increase or decrease by at least or about at least 1.2-fold, 1.5-fold, 2-fold, 3-fold, 4-fold, 5-fold, 6-fold, 7-fold, 8-fold, 10-fold or more) compared to the level at a time just prior to administration of the tryptophan metabolism and/or kynurenine pathway modulator. Such parameters and other parameters, and exemplary for determining or assessing such, are described in Section III.

In some embodiments, the initiation of administration of the dose of cells of the T cell therapy, e.g., adoptive T cell therapy, is administered prior to administration of the tryptophan metabolism and/or kynurenine pathway modulator, e.g., IDO1 inhibitor. In some embodiments, the dose of cells is administered at least or at least about 1 hour, at least or at least about 2 hours, at least or at least about 3 hours, at least or at least about 6 hours, at least or at least about 12 hours, at least or at least about 1 day, at least or at least about 2 days, at least or at least about 3 days, at least or about at least 4 days, at least or at least about 5 days, at least or about at least 6 days, at least or at least about 7 days, at least or about at least 12 days, at least or at least about 14 days, at least or about at least 15 days, at least or at least about 21 days, at least or at least about 28 days, at least or about at least 30 days, at least or at least about 35 days, at least or at least about 42 days, at least or about at least 60 days or at least or about at least 90 days prior to administering the tryptophan metabolism and/or kynurenine pathway modulator (e.g. IDO1 inhibitor).

In some embodiments, the method involves, subsequent to administering the dose of cells of the T cell therapy, e.g., adoptive T cell therapy, but prior to administering the tryptophan metabolism and/or kynurenine pathway modulator, e.g., IDO1 inhibitor, assessing a sample from the subject for alteration in the level of metabolites in the kynurenine pathway, e.g., TRP, KYN or derivatives of KYN, and/or expression levels of factors or effectors, e.g., enzymes, involved in the kynurenine pathway, e.g., IDO1, or other phenotypes or desired outcomes as described herein, e.g., such as those described in Section III. In some embodiments, the administration of the tryptophan metabolism and/or kynurenine pathway modulatory is at a time in which the prior administration of the immunotherapy (e.g. T cell therapy, such as CAR-T cell therapy) has, or is likely to have, caused or induced, directly or indirectly, an alteration in the level of metabolites in the kynurenine pathway, such as a decrease in the levels of TRP or an increase in the levels of KYN or a KYN derivate (e.g. increase or decrease by at least or about at least 1.2-fold, 1.5-fold, 2-fold, 3-fold, 4-fold, 5-fold, 6-fold, 7-fold, 8-fold, 10-fold or more) compared to the level at a time just prior to initiation of the immunotherapy (e.g. T cell therapy, such as CAR-T cell therapy) or at a preceding time point after initiation of the immunotherapy. Various parameters for determining or assessing the regimen of the combination therapy are described in Section III.

B. Administration of Tryptophan Metabolism and/or Kynurenine Pathway Modulators

The provided methods, compositions, combinations, kits and uses involve administration of a modulator of the kynurenine pathway, e.g., an inhibitor of the enzyme indoleamine-pyrrole 2,3-dioxygenase 1 (IDO1). In some embodiments, the tryptophan metabolism and/or kynurenine pathway modulator, e.g., IDO1 inhibitor, is administered prior to, subsequently to, during, simultaneously or near simultaneously, sequentially and/or intermittently with administration of the immunotherapy, e.g., T cell therapy, e.g., administration of T cells expressing a chimeric antigen receptor (CAR).

1. Tryptophan Metabolism and/or Kynurenine Pathway Modulators

In some embodiments, the tryptophan metabolism and/or kynurenine pathway modulator is an inhibitor and/or an antagonist that inhibits the activity of a factor and/or an enzyme in the kynurenine pathway. In some embodiments, the tryptophan metabolism and/or kynurenine pathway modulator affects the levels of the metabolites in the kynurenine pathway, e.g., results in an increase or a decrease of a particular metabolite of the kynurenine pathway.

In some embodiments, the tryptophan metabolism and/or kynurenine pathway modulator modulates, e.g., regulates, inhibits, induces or activates, one or more factors or effectors, e.g., enzymes, involved in the pathway. In some embodiments, the tryptophan metabolism and/or kynurenine pathway modulator modulates, e.g., regulates, inhibits or activates, indoleamine-pyrrole 2,3-dioxygenase 1 (IDO1), IDO2, tryptophan 2,3-dioxygenase (TDO), kynurenine formamidase, kynureninase, L-kynurenine hydrolase, kynurenine-3-monooxygenase, kynurenine 3-hydroxylase, 3-hydroxyanthranilic acid oxygenase, 3-hydroxyanthranilate 3,4-dioxygenase, kynurenine amino-transferase, and/or quinolinic acid phosphoribosyl transferase.

In some embodiments, the tryptophan metabolism and/or kynurenine pathway modulator modulates or regulates, e.g., increases or decreases, the level, availability, concentration, effect, activity, metabolism, synthesis and/or degradation of one or more metabolites in the kynurenine pathway. In some embodiments, the metabolite of the kynurenine pathway is L-tryptophan, n-formylkynurenine, DL-kynurenine, L-kynurenine, 3-hydroxy-DL-kynurenine, kynurenic acid, quinaldic acid, kynuramine, 3-hydroxy-L-kynurenine, 3-hydroxy-D-kynurenine, 3-hydroxy-anthranilic acid, xanthommatin, anthranilic acid, xanthurenic acid, picolinioc acid, quinolinic acid and/or cinnabarinic acid as well as all substantially homologous analogs and variations.

In some embodiments, the tryptophan metabolism and/or kynurenine pathway modulator modulates, e.g., regulates, inhibits or activates, the catabolism of tryptophan and/or the synthesis of N-formyl-L-kynurenine, kynurenine and/or its derivatives, e.g., 3-hydroxykynurenine, kynurenic acid and 3-hydroxyanthranilic acid, which contribute to the immunosuppressive conditions in the TME. In some embodiments, the tryptophan metabolism and/or kynurenine pathway modulator causes, mediates or results in an increase of the level of tryptophan (TRP) and/or a decrease of the level of kynurenine (KYN). In some embodiments, the tryptophan metabolism and/or kynurenine pathway modulator is an inhibitor of indoleamine-pyrrole 2,3-dioxygenase 1 (IDO1). In some embodiments, the tryptophan metabolism and/or kynurenine pathway modulator is an inhibitor of IDO2 and/or tryptophan 2,3-dioxygenase (TDO).

In some embodiments, the tryptophan metabolism and/or kynurenine pathway modulator modulates, e.g., regulates, inhibits or activates, upstream and/or downstream factors or effectors, e.g., enzymes, in tryptophan catabolism, e.g., components of signaling, transcription and/or transport of tryptophan and/or tryptophan catabolism or catabolism component(s), by virtue of modulation of the kynurenine pathway. In some embodiments, the tryptophan metabolism and/or kynurenine pathway modulator modulates factors or effectors involved in tryptophan catabolism, e.g., general control non-derepressible 2 (GCN2), inflammatory cues such as interferon γ (IFNγ), tumor necrosis factor alpha (TNFα), signal transducer and activator of transcription 3 (STAT3), mammalian target of rapamycin (mTOR), aryl hydrocarbon receptor (AHR), AHR nuclear translocator (ARNT), dioxin responsive element (DRE), transporters of amino acids such as TRP (tryptophan) transporters (e.g., CD98 and/or associated chains, such as one or more of a CD98/LAT-1 transporter complex, e.g., CD98 heavy chain (4F2hc; SLC3A2) and/or a L-type Amino Acid Transporter 1 (LAT1; SLC7A5), LAT2 (SLC7A8), proton-assisted amino-acid transporter 4 (PAT4; SLC36A4), Asc-1, Asc-2, ATB0, B0AT1, TAT1), PR domain zinc finger protein 1 (PRDM1, also known as BLIMP-1), eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8 and/or IFNγ-R2.

In some embodiments, the tryptophan metabolism and/or kynurenine pathway modulator is a small molecule, a peptide, a polypeptide, an antibody or antigen-binding fragment thereof, an antibody mimetic, an aptamer or a nucleic acid molecule (e.g. siRNA), a lipid, a polysaccharide or any combination thereof. In some embodiments, the tryptophan metabolism and/or kynurenine pathway modulator is an inhibitor or an activator of a particular factor and/or enzyme of the kynurenine pathway. In some embodiments, the tryptophan metabolism and/or kynurenine pathway modulator is an agonist or an antagonist of a particular factor and/or enzyme of the kynurenine pathway. In some embodiments, the kynurenine inhibitor is an analog or derivative of one or more metabolites of the kynurenine pathway. In some embodiments, the tryptophan metabolism and/or kynurenine pathway modulator is an inhibitor that is a small molecule. In some embodiments, the tryptophan metabolism and/or kynurenine pathway modulator is a protein or polypeptide.

The agent, e.g., the metabolic pathway modulator, e.g., the tryptophan metabolic pathway modulator, e.g., alternative tryptophan pathway modulator, e.g., kynurenine pathway modulator, is administered by any of a number of suitable means, for example, by oral administration, injection, bolus infusion, parenterally, intrapulmonary administration, intranasal administration, and/or intralesional administration. In some aspects, the agent is administered locally and/or systemically. In some aspects, the agent is added or used to treat one or more other therapeutic agents or products, or precursors thereto. In one example, it is added during the process of generating cells for administration in adoptive cell therapy, such as cells expressing one or more engineered immunoreceptors, such as CARs, e.g., CAR-expressing T cells.

In some embodiments, the tryptophan metabolism and/or kynurenine pathway modulator is tryptophan, e.g., supplemental tryptophan.

a. IDO1 Inhibitors

In some embodiments, the inhibitor in the combination therapy is an inhibitor of IDO1. IDO1 belongs to a family of three heme-dependent dioxygenases that generally play a role in catalyzing a first rate-limiting step of the metabolism of L-tryptophan in the kynurenine pathway, which includes IDO1, IDO2 and TDO. The three enzymes convert L-tryptophan into N-formyl-L-kynurenine, which subsequently is metabolized through a series of steps to form nicotinamide adenine dinucleotide (NAD).

In some embodiments, the IDO1 inhibitor is any of those described and/or summarized in International PCT publication Nos. WO 2011/056652; WO 2012/142237; WO 2014/159248; WO 2008/058178; WO 2010/005958; WO 2014/150646; WO 2014/150677; WO 2015/002918; WO 2015/006520; WO 2016/024233; WO 2016/026772; WO 2015/082499; WO 2016/012615; WO 2011/045341; WO 2015/119944; WO 2006/005185; WO 2016/051181; WO 2014/186035; WO 2008/052352; WO 2009/073620; U.S. Patent Pub. No. US 2005/186289; US 2007/0105907; US 2016/0060266; US 2016/0046596; U.S. Pat. No. 7,098,209; Chinese Patent Pub. No. CN 105567690; CN 103070868; CN 102579452; Zádori et al., Expert Opinion on Therapeutic Patents (2016), DOI:10.1080/13543776.2016.1189531; Rohrig et al., J. Med. Chem. 2012, 55:5270-5290; Rohrig et al., J. Med. Chem. 2015, 58:9421-9437; Meininger et al., Biochim. Biophys. Acta Proteins Proteomics 2011, 1814: 1947-1954; Tojo et al., ACS Med. Chem. Lett. 2014, 5:1119-1123; Vacchelli et al., (2014) OncoImmunology 3:10, e957994; Moon et al., Journal for ImmunoTherapy of Cancer (2015) 3:51; Platten et al., Front Immunol. 2015 Jan. 12; 5:673; Weinmann, H., ChemMedChem 2016, 11:450-466; Liu et al., Blood. 2010 Apr. 29; 115(17):3520-30; Ninomiya et al., Blood. 2015 Jun. 18; 125(25):3905-16; Sheridan, C. Nature Biotechnology 33, 321-322 (2015); Carvalho et al., Org. Biomol. Chem. 2014, 12:2663-2674; Eguchi et al., Arch. Biochem. Biophys. 1984, 232:602-609; Peterson et al., Med. Chem. Res. 1993, 3:473-482; Sono et al., Biochemistry 1989, 28:5392-5399; Opitz et al., PLoS One. 2011; 6(5): e19823; and Saito et al., Biochem. J. 1993, 291:11-14. Exemplary IDO1 inhibitors include: epacadostat (INCB024360), indoximod (1-methyl-D-tryptophan), an IDO peptide vaccine, and NLG919.

In some embodiments, IDO1 inhibitors include those that can increases the antitumor activities of various chemotherapeutic (e.g., platinum compounds, taxane derivatives, cyclophosphamide) without increased toxicity.

In some embodiments, the IDO1 inhibitor is a small molecule, peptide, protein, antibody or antigen-binding fragment thereof, an antibody mimetic, an aptamer, or a nucleic acid molecule (e.g. siRNA).

In some embodiments, the IDO1 inhibitor is a small molecule. In some embodiments, the IDO1 inhibitor is a hydroxyamidine derivative, a tryptophan analog or derivative, an indole derivative or analog, a compound with a quinone or iminoquinone scaffold, an imidazole derivative, such as a phenylimidazole (PIM) or a phenylimidazole derivative, a 1,2,3-triazole derivative, a compound based on a thiazolotriazole scaffold, an imidazothiazole derivative, a 2,3-Diamino-furo[2,3-c]pyridine and 2,3-diaminobenzo[b]thiophene derivative, a natural product inhibitor or derivative or a single aromatic ring compound or derivative.

In some embodiments, the IDO1 inhibitor is a hydroxyamidine derivative.

In some embodiments, the IDO1 inhibitor is a compound of Formula I:

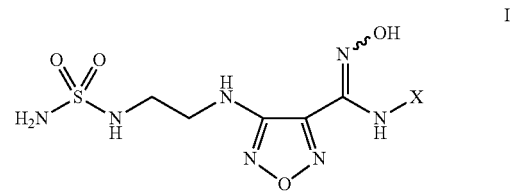

or a pharmaceutically acceptable salt thereof; wherein: X is

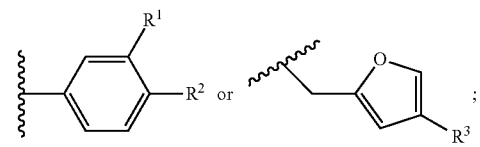

$R^1$ is Cl, Br, CF3, or CN; $R^2$ is H or F; and $R^3$ is Cl or Br.

In some embodiments, the IDO1 inhibitor is a compound of Formula Ia:

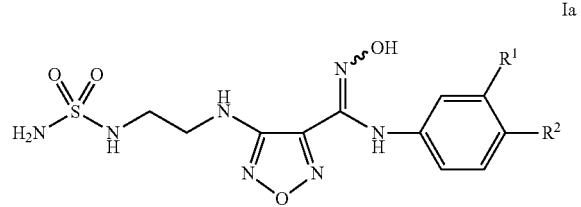

or a pharmaceutically acceptable salt thereof.

In some embodiments, the IDO inhibitor is a compound of Formula Ib:

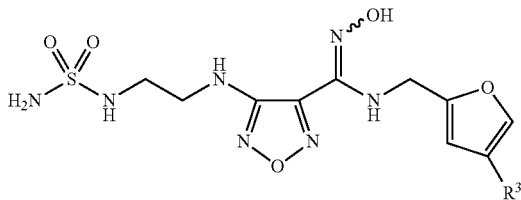

or a pharmaceutically acceptable salt thereof.

In some embodiments, the IDO1 inhibitor is 4-({2-[(aminosulfonyl)amino]ethyl}amino)-N-(3-bromo-4-fluorophenyl)-N'-hydroxy-1,2,5-oxadiazole-3-carboximidamide (epacadostat, also known as INCB024360) or a pharmaceutically acceptable salt thereof or derivatives thereof. In some embodiments, the IDO1 inhibitor is 4-({2-[(aminosulfonyl)amino]ethyl}amino)-N-(3-chloro-4-fluorophenyl)-N'-hydroxy-1,2,5-oxadiazole-3-carboximidamide or a pharmaceutically acceptable salt thereof. In some embodiments, the IDO1 inhibitor is 4-({2-[(aminosulfonyl)amino]ethyl}amino)-N-[4-fluoro-3-(trifluoromethyl)phenyl]-N'-hydroxy-1,2,5-oxadiazole-3-carboximidamide or a pharmaceutically acceptable salt thereof. In some embodiments, the IDO1 inhibitor is 4-({2-[(aminosulfonyl)amino]ethyl}amino)-N'-hydroxy-N-[3-(trifluoromethyl)phenyl]-1,2,5-oxadiazole-3-carboximidamide or a pharmaceutically acceptable salt thereof. In some embodiments, the IDO1 inhibitor is 4-({2-[(aminosulfonyl)amino]ethyl}amino)-N-(3-cyano-4-fluorophenyl)-N'-hydroxy-1,2,5-oxadiazole-3-carboximidamide or a pharmaceutically acceptable salt thereof. In some embodiments, the IDO1 inhibitor is 4-({2-[(aminosulfonyl)amino]ethyl}amino)-N-[(4-bromo-2-furyl)methyl]-N'-hydroxy-1,2,5-oxadiazole-3-carboximidamide or a pharmaceutically acceptable salt thereof. In some embodiments, the IDO1 inhibitor is 4-({2-[(aminosulfonyl)amino]ethyl}amino)-N-[(4-chloro-2-furyl)methyl]-N'-hydroxy-1,2,5-oxadiazole-3-carboximidamide or a pharmaceutically acceptable salt thereof. In some embodiments, the IDO1 inhibitor is any of the inhibitors described in International PCT Pub. No. WO 2008/058178, WO 2010/005958 and WO 2015/119944.

In some embodiments, the IDO1 inhibitor is 4-({2-[(aminosulfonyl)amino]ethyl}amino)-N-(3-bromo-4-fluorophenyl)-N'-hydroxy-1,2,5-oxadiazole-3-carboximidamide (epacadostat, also known as INCB024360) or a pharmaceutically acceptable salt thereof or derivatives thereof.

In some embodiments, the IDO inhibitor is the following compound:

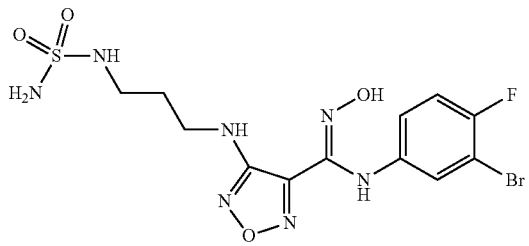 [SMILES: NS(=O)(=O)NCCCNc1nonc1/C(=N/O)Nc1ccc(F)c(Br)c1]

or a pharmaceutically acceptable salt thereof.

In some embodiments, the IDO1 inhibitor is a tryptophan analog or derivative, or indole derivative or analog. In some embodiments, the IDO1 inhibitor is a 1-methyltryptophan (1-MT), e.g., 1-methyl-D-tryptophan or 1-methyl-L-tryptophan, 2,5-dihydro-L-phenylalanine, or methylthiohydantoin-D,L-tryptophan (MTH-trp or necrostatin 1). In some embodiments the IDO1 inhibitor is a brassinin and derivative, e.g., S-allyl-brassinin, S-benzyl-brassinin, 5-Bromobrassinin, bras sinin-derived dithiocarbamate, a 1-methyl-tryptophantirapazamine compound, a tryptoline derivative or a tryptamine derivative. In some embodiments, the IDO1 inhibitor is a 1-methyltryptophan, a competitive inhibitor of IDO1 (and IDO2) that exists as a mixture of chiral isoforms (i.e., 1-methyl-D-tryptophan and 1-methyl-L-tryptophan). In some embodiments, IDO1 inhibitor is 1-methyl-D-tryptophan (1-D-MT; also known as indoximod or NLG8189). In some embodiments, the IDO1 inhibitor is such as any of those described in US 2005/186289 and U.S. Pat. No. 7,098,209. In some embodiments, the IDO1 inhibitor is 1-methyl-L-tryptophan (1-L-MT).

In some embodiments, the IDO1 inhibitor is a compound with a quinone or iminoquinone scaffold. In some embodiments, the IDO1 inhibitor is a catechol, hydroquinone, p-quinone, L-dihydroxyphenylalanine, L-epinephrine, menadione, benzofuranoquinone, β-lapachone or a naphthoquinone-based compound, Exiguamine A, annulin B, pyranonaphthoquinone, indolequinone, pyranonaphthoquinone, pyrroloiminoquinone, β-lapachone, cinnabarinic acid, benzofuranquinone, xestosaprol O analog, 4-iminonaphthalen-1-one derivative, NSC111041, mitomycin C or derivatives thereof. In some embodiments, the IDO1 inhibitor is such as any of those described in WO 2008/052352; WO 2006/005185; and Carvalho et al., Org. Biomol. Chem. 2014, 12:2663-2674, or derivatives thereof.

In some embodiments, the IDO1 inhibitor is an imidazole derivative, such as a phenylimidazole (PIM) or a phenylimidazole derivative. In some embodiments, the IDO1 inhibitor is 2-hydroxyphenylimidazole or 4-phenylimidazole, or derivatives thereof, such as those described in International PCT Pub. No. WO 2011/056652. In some embodiments, the IDO1 inhibitor is a tricyclic compound based on PIM, such as those described in International PCT Pub. No. WO 2012/142237 and WO 2014/159248. In some embodiments, the IDO1 inhibitor is 1-cyclohexyl-2-(5H-imidazo[5,1-a]isoindol-5-yl)ethanol (NLG919; also known as GDC-0919 or GTPL9019), econazole or derivatives thereof.

In some embodiments, the IDO inhibitor is a 1,2,3-triazole derivative, such as a derivative of 4-phenyl-1,2,3-triazole, such as those described in Rohrig et al., J. Med. Chem. 2012, 55:5270-5290.

In some embodiments, the IDO1 inhibitor is a compound based on a thiazolotriazole scaffold, such as those described in Meininger et al., Biochim. Biophys. Acta Proteins Proteomics 2011, 1814:1947-1954. In some embodiments, the IDO1 inhibitor is N-(1,3-benzodioxol-5-yl)-2-{[5-(4-methylphenyl)[1,3]thiazolo[2,3-c][1,2,4]triazol-3-yl]sulfanyl}acetamide (AMG-1), or derivatives thereof.

In some embodiments, the IDO inhibitor is an imidazothiazole derivative, such as those described in Tojo et al., ACS Med. Chem. Lett. 2014, 5:1119-1123. In some embodiments, the IDO inhibitor is miconazole. In some embodiments, the IDO1 inhibitor is a compound based on a 2-aminophenylurea scaffold, such as those described in WO 2014/150646, WO 2014/150677, WO 2015/002918 and WO 2015/006520.

In some embodiments, the IDO1 inhibitor is a natural product inhibitor or derivative thereof. In some embodiments, the IDO1 inhibitor is norharman/β-carboline, benzomalvin, halicloic acid, thielavin, tryptanthrin or galanal, such as those described in Eguchi et al., Arch. Biochem.

Biophys. 1984, 232:602-609; Peterson et al., Med. Chem. Res. 1993, 3:473-482; Sono et al., Biochemistry 1989, 28:5392-5399; and Saito et al., Biochem. J. 1993, 291:11-14.

In some embodiments, the IDO1 inhibitor is a single aromatic ring compound or derivative thereof, such as O-benzylhydroxylamine, phenylhydrazine, benzyl mercaptan, S-benzylisothiourea derivative, thiosemicarbazide derivative, dithiocarbamate derivative or AC12308, or derivatives thereof, and any of those described in WO 2009/073620.

In some embodiments, the IDO1 inhibitor is a 2,3-Diamino-furo[2,3-c]pyridine and 2,3-diaminobenzo[b]thiophene derivative, such as ($N^3$-(3-chloro-4-fluorophenyl)furo[2,3-c]pyridine-2,3-diamine or $N^3$-(3-chloro-4-fluorophenyl)benzo[b]thiophene-2,3-diamine, and any of those described in WO 2014/186035.

In some embodiments, the IDO1 inhibitor is an agent that can reduce expression of, delete, eliminate, knockout, knock down, or disrupt the expression of the IDO1 gene. In some embodiments, the IDO1 inhibitor is a negative regulator of transcription factors that control IDO1 expression. In some embodiments, the IDO1 inhibitor is a negative regulator of Bin1 or KIT signaling. In some embodiments, the inhibitor is an inhibitory nucleic acid that can reduce or control the expression of the endogenous IDO1 gene. In some embodiments, the inhibitory nucleic acid is or contains or encodes a small interfering RNA (siRNA), a microRNA-adapted shRNA, a short hairpin RNA (shRNA), a hairpin siRNA, a microRNA precursor (pre-miRNA or pri-miRNA), a microRNA (miRNA), antisense RNA, or ribozymes, see, e.g., inhibitory nucleic acids described in CN105567690, or variants thereof, or those described in Opitz et al., PLoS One. 2011; 6(5): e19823.

In some embodiments, the IDO1 inhibitor is selected from among 1-methyl-D-tryptophan (also known as indoximod and NLG8189), 1-methyl-L-tryptophan, 4-({2-[(aminosulfonyl)amino]ethyl}amino)-N-(3-bromo-4-fluorophenyl)-N'-hydroxy-1,2,5-oxadiazole-3-carboximidamide (epacadostat; INCB024360), methylthiohydantoin-D,L-tryptophan, 4-phenylimidazole, NSC401366, NLG919, F001287, PF-06840003, INCB023843, 2-hydroxyphenylimidazole, 4-phenyl-1,2,3-triazole, hydroxyamidine, compounds with a thiazolotriazole scaffold, imidazothiazole, compounds with a 2-aminophenylurea scaffold, IDO1-targeting vaccines and IDO-1 targeting inhibitory nucleic acids.

In some embodiments, the IDO1 inhibitor is MTH-Trp, a β-carboline, a naphthoquinone-based compound, S-allylbrassinin, S-benzyl-brassinin, 5-Bromo-brassinin, a phenylimidazole-based compound, 4-phenylimidazole, Exiguamine A or NSC401366, or any of those described in Moon et al., Journal for ImmunoTherapy of Cancer (2015) 3:51.

In some embodiments, the IDO1 inhibitors include those that have been under clinical development as single-agent therapy or for combination therapy with other anti-cancer agents, e.g., nab-paclitaxel, gemcitabine, docetaxel, ipilimumab, a PDCD1-targeting monoclonal antibody, a dendritic cell-based p53 vaccine and a multipeptide-based vaccine. In some embodiments, the IDO1 inhibitor is selected from among IDO1 inhibitors under clinical development, such as epacadostat (INCB024360; developer: Incyte), indoximod (1-D-MT; developer: NewLink Genetics), an IDO peptide vaccine (developer: Copenhagen University), F001287, PF-06840003 (developer Pfizer/iTeos) and NLG919 (developer: NewLink Genetics). Exemplary IDO1 inhibitors that are being developed for clinical studies, the types of therapies and their indications include those described in Moon et al., Journal for ImmunoTherapy of Cancer (2015) 3:51.

b. Other Tryptophan Metabolism and/or Kynurenine Pathway Modulators

In some embodiments, the tryptophan metabolism and/or kynurenine pathway modulator is an inhibitor of IDO2 or TDO, which also can catalyze the first rate-limiting step of the kynurenine pathway. In some embodiments, the IDO1 inhibitor is a broad inhibitor that can also inhibit IDO2 and/or TDO. In some embodiments, the inhibitor is specific to IDOL IDO2 or TDO. In some embodiments, the tryptophan metabolism and/or kynurenine pathway modulator is a dual-acting IDO/TDO inhibitor.

In some embodiments, the tryptophan metabolism and/or kynurenine pathway modulator is a TDO inhibitor, such as fluorinated indole derivatives 680C91 or LM10, and/or any of those described in Dolusic et al., J Med Chem. 2011 Aug. 11; 54(15):5320-34. In some embodiments, the tryptophan metabolism and/or kynurenine pathway modulator is a specific inhibitor of IDO2, such as tenatoprazole, and/or any of those described in Bakmiwewa et al., Bioorg Med Chem Lett. 2012; 22(24):7641-7646. In some embodiments, the IDO1 inhibitor can inhibit both IDO1 and IDO2, such as indoximod (1-D-MT). In some embodiments, the IDO1 inhibitors can also inhibit IDO2 and/or TDO.

In some embodiments, the tryptophan metabolism and/or kynurenine pathway modulator modulates subsequent steps of the kynurenine pathway, such as reactions catalyzed by kynurenine aminotransferase, kynurenine 3-monooxygenase, kynureninase and/or 3-hydroxyanthranilate 3,4-dioxygenase. In some embodiments, the tryptophan metabolism and/or kynurenine pathway modulator is an inhibitor of kynurenine aminotransferase, kynurenine 3-monooxygenase, kynureninase and/or 3-hydroxyanthranilate 3,4-dioxygenase. In some embodiments, the tryptophan metabolism and/or kynurenine pathway modulator includes any of those described in EP 2331095; EP 2420494; EP 2736337; EP 2750677; EP 2751086; EP 2833879; US 2012/0046324; US 2012/0329812; US 2013/0029988; US 2013/0331370; US 2014/0329795; US 2014/0329816; US 2015/0057238; U.S. Pat. No. 8,710,237; WO 2008/022286; WO 2010/017132; WO 2010/017179; WO 2011/091153; WO 2013/016488; WO 2013/033068; WO 2013/033085; WO 2013/033085; WO 2013/151707; WO 2015/047978 and Zádori et al., Expert Opinion on Therapeutic Patents (2016), DOI: 10.1080/13543776.2016.1189531.

In some embodiments, the tryptophan metabolism and/or kynurenine pathway modulator modulates or regulates the level, availability, concentration, effect, activity, metabolism, synthesis and/or degradation of 3-hydroxy anthranilic acid (3-HAA), L-kynurenine, quinolinic acid and/or cinnabarinic acid.

In some embodiments, the tryptophan metabolism and/or kynurenine pathway modulator prevents or reduces the synthesis or accumulation kynurenine, 3-hydroxykynurenine or 3-hydroxyanthranilic acid (3-HAA). In some embodiments, the tryptophan metabolism and/or kynurenine pathway modulator is an inhibitor or an antagonist of kynureninase. Kynureninase catalyzes the conversion of 3-hydroxykynurenine to 3-hydroxy anthranilic acid (3-HAA) and the conversion of kynurenine to anthranilic acid. Inhibition of kynureninase reduce the levels of 3-HAA. Exemplary kynureninase inhibitors include O-methoxybenzoylalanine 2-amino-4-[3'-hydroxyphenyl]-4-hydroxybutanoic acid and those described in US 2015/0175712.

In some embodiments, the tryptophan metabolism and/or kynurenine pathway modulator is an enzyme, e.g., an enzyme involved in a kynurenine pathway or derivatives or modified forms thereof. In some embodiments, the tryptophan metabolism and/or kynurenine pathway modulator is a kynureninase enzyme, which reduces kynurenine levels by catalyzing the catabolism of L-kynurenine and 3-hydroxy-L-kynurenine. In some embodiments, the tryptophan metabolism and/or kynurenine pathway modulator is a modified kynureninase, such as those described in US 2015/0064154.

In some embodiments, the tryptophan metabolism and/or kynurenine pathway modulator is a modulator of other components of the kynurenine pathway or upstream or downstream effectors, e.g., components involved in tryptophan metabolism and/or signaling, e.g., general control non-derepressible 2 (GCN2), inflammatory cues such as interferon γ (IFNγ), signal transducer and activator of transcription 3 (STAT3), aryl hydrocarbon receptor (AHR), AHR nuclear translocator (ARNT), dioxin responsive element (DRE), transporters of amino acids such as TRP (tryptophan) transporters (e.g., CD98 and/or associated chains, such as one or more of a CD98/LAT-1 transporter complex, e.g., CD98 heavy chain (4F2hc; SLC3A2) and/or a L-type Amino Acid Transporter 1 (LAT1; SLC7A5), LAT2 (SLC7A8), proton-assisted amino-acid transporter 4 (PAT4; SLC36A4), Asc-1, Asc-2, ATB0, B0AT1, TAT1), PR domain zinc finger protein 1 (PRDM1, also known as BLIMP-1), eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8 and/or IFNγ-R2 (see, e.g., McGaha et al. (2012) Immunol. Rev. 249(1): 135-157; Munn et al. (2005) Immunity 22; 633-642; Broer et al. (2011) Biochem. J. 436:193-211).

2 Compositions and Formulations

In some embodiments of the methods, compositions, combinations, kits and uses provided herein, the combination therapy can be administered in one or more compositions, e.g., a pharmaceutical composition containing a tryptophan metabolism and/or kynurenine pathway modulator, e.g. an IDO1 inhibitor, and/or the immunotherapy, e.g., T cell therapy.

In some embodiments, the composition, e.g., a pharmaceutical composition containing a tryptophan metabolism and/or kynurenine pathway modulator, e.g. an IDO1 inhibitor, can include carriers such as a diluent, adjuvant, excipient, or vehicle with which the tryptophan metabolism and/or kynurenine pathway modulator, e.g., an IDO1 inhibitor, and/or the cells are administered. Examples of suitable pharmaceutical carriers are described in "Remington's Pharmaceutical Sciences" by E. W. Martin. Such compositions will contain a therapeutically effective amount of the tryptophan metabolism and/or kynurenine pathway modulator, e.g., an IDO1 inhibitor, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Saline solutions and aqueous dextrose and glycerol solutions also can be employed as liquid carriers, particularly for injectable solutions. The pharmaceutical compositions can contain any one or more of a diluents(s), adjuvant(s), antiadherent(s), binder(s), coating(s), filler(s), flavor(s), color(s), lubricant(s), glidant(s), preservative(s), detergent(s), sorbent(s), emulsifying agent(s), pharmaceutical excipient(s), pH buffering agent(s), or sweetener(s) and a combination thereof. In some embodiments, the pharmaceutical composition can be liquid, solid, a lyophilized powder, in gel form, and/or combination thereof. In some aspects, the choice of carrier is determined in part by the particular inhibitor and/or by the method of administration.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), stabilizers and/or preservatives. The compositions containing the tryptophan metabolism and/or kynurenine pathway modulator, e.g., IDO1 inhibitor can also be lyophilized.

In some embodiments, the pharmaceutical compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. In some embodiments, other modes of administration also are contemplated. In some embodiments, the administration is by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, administration is by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration. In some embodiments, it is administered by multiple bolus administrations, for example, over a period of no more than 3 days, or by continuous infusion administration.

In some embodiments, the administration can be local, topical or systemic depending upon the locus of treatment. In some embodiments local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. In some embodiments, compositions also can be administered with other biologically active agents, either sequentially, intermittently or in the same composition. In some embodiments, administration also can include controlled release systems including controlled release formulations and device controlled release, such as by means of a pump. In some embodiments, the administration is oral.

In some embodiments, pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. In some embodiments, unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. In some embodiments, a multiple dose form is a plurality of identical unit dosage forms packaged in a single container to be administered in segregated unit dose form. Examples of multiple dose forms include vials, bottles of tablets or capsules or bottles of pints or gallons.

3. Tryptophan Metabolism and/or Kynurenine Pathway Modulators Dosage and Schedule In some embodiments, the method involves administering to the subject a therapeutically effective amount of a tryptophan metabolism and/or kynurenine pathway modulator, e.g., an inhibitor of IDO1, and the immunotherapy, such as a T cell therapy (e.g. CAR-expressing T cells) or a T cell-engaging therapy. In some embodiments, the tryptophan metabolism and/or kynurenine pathway modulator, e.g., an inhibitor of IDO1, is administered prior to, subsequently to, during, during the course of, simultaneously, near simultaneously, sequentially and/or intermittently with the administration of the immunotherapy, such as a T cell therapy (e.g. CAR-expressing T cells) or a T cell-engaging therapy. In some embodiments, the method involves administering the tryptophan metabolism and/or kynurenine pathway modulator, e.g., an inhibitor of IDO1, prior to administration of the T cell therapy. In other embodiments, the method involves administering the tryptophan metabolism and/or kynurenine pathway modulator, e.g., an inhibitor of IDO1, after administration of the T cell therapy. In some embodiments, the tryptophan metabolism and/or kynurenine pathway modulator, e.g., an inhibitor of IDO1, is not further administered after initiation of the T cell therapy. In some embodiments, the dosage schedule comprises administering the tryptophan metabolism and/or kynurenine pathway modulator, e.g., an inhibitor of IDO1, prior to and after initiation of the T cell therapy. In some embodiments, the dosage schedule comprises administering the tryptophan metabolism and/or kynurenine pathway modulator, e.g., an inhibitor of IDO1, simultaneously with the administration of the T cell therapy.

In some embodiments, the tryptophan metabolism and/or kynurenine pathway modulator, e.g., IDO1 inhibitor, is administered multiple times in multiple doses. In some embodiments, the tryptophan metabolism and/or kynurenine pathway modulator, e.g., IDO1 inhibitor, is administered once. In some embodiments, the tryptophan metabolism and/or kynurenine pathway modulator, e.g., IDO1 inhibitor, is administered six times daily, five times daily, four times daily, three times daily, twice daily, once daily, every other day, every three days, twice weekly, once weekly or only one time prior to or subsequently to initiation of administration of the immunotherapy (e.g. T cell therapy, such as CAR-T cell therapy). In some aspects, the frequency of administration of the tryptophan metabolism and/or kynurenine pathway modulator, e.g., IDO1 inhibitor, is twice weekly, once weekly, once every 14 days, once every 21 days or once every month. In some embodiments, the tryptophan metabolism and/or kynurenine pathway modulator, e.g., IDO1 inhibitor is administered in multiple doses in regular intervals prior to, during, during the course of, and/or after the period of administration of the immunotherapy (e.g. T cell therapy, such as CAR-T cell therapy). In some embodiments, the tryptophan metabolism and/or kynurenine pathway modulator, e.g., IDO1 inhibitor, is administered in one or more doses in regular intervals prior to the administration of the immunotherapy (e.g. T cell therapy, such as CAR-T cell therapy). In some embodiments, the tryptophan metabolism and/or kynurenine pathway modulator, e.g., IDO1 inhibitor, is administered in one or more doses in regular intervals after the administration of the immunotherapy (e.g. T cell therapy, such as CAR-T cell therapy). In some embodiments, one or more of the doses of the tryptophan metabolism and/or kynurenine pathway modulator, e.g., IDO1 inhibitor, can occur simultaneously with the administration of a dose of the immunotherapy (e.g. T cell therapy, such as CAR-T cell therapy).

In some embodiments, the dose, frequency, duration, timing and/or order of administration of the tryptophan metabolism and/or kynurenine pathway modulator, e.g., IDO1 inhibitor, is determined, based on particular thresholds or criteria of results of the screening step and/or assessment of treatment outcomes described herein, e.g., those described in Section III herein.

In some embodiments, the tryptophan metabolism and/or kynurenine pathway modulator, e.g., IDO1 inhibitor is administered prior to the administration of the immunotherapy (e.g. T cell therapy, such as CAR-T cell therapy). In some aspects, the timing of administration of the tryptophan metabolism and/or kynurenine pathway modulator is such that there is sufficient time to increase the tryptophan (TRP) levels or reduce the kynurenine (KYN) levels in a biological sample of the subject, such as in the tumor microenvironment (TME) of the tumor to be treated. In some embodiments, the administration of the tryptophan metabolism and/or kynurenine pathway modulatory is at a time in which the modulator (e.g. IDO1 inhibitor) has, or is likely to have, resulted in an alteration in the level of metabolites in the kynurenine pathway, such as increase in the levels of TRP or a decrease in the levels of KYN or a KYN derivative (e.g. increase or decrease by at least or about at least 1.2-fold, 1.5-fold, 2-fold, 3-fold, 4-fold, 5-fold, 6-fold, 7-fold, 8-fold, 10-fold or more) compared to the level at a time just prior to administration of the tryptophan metabolism and/or kynurenine pathway modulator. Exemplary methods to assess or determine parameters associated with an alteration in the level of such metabolites in the kynurenine pathway are described in Section III.

In some embodiments, the tryptophan metabolism and/or kynurenine pathway modulator, e.g., IDO1 inhibitor is administered from or from about 0 to 90 days, such as 0 to 30 days, 0 to 15 days, 0 to 6 days, 0 to 96 hours, 0 to 24 hours, 0 to 12 hours, 0 to 6 hours, or 0 to 2 hours, 2 hours to 30 days, 2 hours to 15 days, 2 hours to 6 days, 2 hours to 96 hours, 2 hours to 24 hours, 2 hours to 12 hours, 2 hours to 6 hours, 6 hours to 90 days, 6 hours to 30 days, 6 hours to 15 days, 6 hours to 6 days, 6 hours to 96 hours, 6 hours to 24 hours, 6 hours to 12 hours, 12 hours to 90 days, 12 hours to 30 days, 12 hours to 15 days, 12 hours to 6 days, 12 hours to 96 hours, 12 hours to 24 hours, 24 hours to 90 days, 24 hours to 30 days, 24 hours to 15 days, 24 hours to 6 days, 24 hours to 96 hours, 96 hours to 90 days, 96 hours to 30 days, 96 hours to 15 days, 96 hours to 6 days, 6 days to 90 days, 6 days to 30 days, 6 days to 15 days, 15 days to 90 days, 15 days to 30 days or 30 days to 90 days prior to initiation of the immunotherapy (e.g. T cell therapy, such as CAR-T cell therapy). In some aspects, the tryptophan metabolism and/or kynurenine pathway modulator, e.g., IDO1 inhibitor, is administered no more than about 96 hours, 72 hours, 48 hours, 24 hours, 12 hours, 6 hours, 2 hours or 1 hour prior to initiation of the immunotherapy (e.g. T cell therapy, such as CAR-T cell therapy).

In some embodiments, the tryptophan metabolism and/or kynurenine pathway modulator, e.g., IDO1 inhibitor, is administered at least or about at least 1 hour, at least or about at least 2 hours, at least or about at least 6 hours, at least or about at least 12 hours, at least or about at least 1 day, at least or about at least 2 days, at least or about at least 3 days, at least or about at least 4 days, at least or about at least 5 days, at least or about at least 6 days, at least or about at least 7 days, at least or at least about 12 days, at least or about at least 14 days, at least or at least about 15 days, at least or about at least 21 days, at least or at least about 24 days, at least or about at least 28 days, at least or about at least 30 days, at least or about at least 35 days or at least or about at least 42 days, at least or about at least 60 days, or at least or about at least 90 days prior to initiation of the administration of the immunotherapy (e.g. T cell therapy, such as a CAR-T cell therapy). In some embodiments, the tryptophan metabolism and/or kynurenine pathway modulator, e.g. IDO1 inhibitor, is administered up to 2 days, up to 3 days, up to 4 days, up to 5 days, up to 6 days, up to 7 days, up to 8 days, up to 12 days, up to 14 days, up to 15 days, up to 21 days, up to 24 days, up to 28 days, up to 30 days, up to 35 days, up to 42 days, up to 60 days or up to 90 days prior to initiation of administration of the immunotherapy (e.g. T cell therapy, such as CAR-T cell therapy). In some embodiments, administration of the tryptophan metabolism and/or kynurenine pathway modulator, e.g., IDO1 inhibitor starts at a time point greater than 1 day prior to initiation of administration of the immunotherapy (e.g. T cell therapy, such as CAR-T cell therapy).

In some embodiments, the tryptophan metabolism and/or kynurenine pathway modulator, e.g., IDO1 inhibitor, is administered after administration of the T cell therapy, such as CAR-T cell therapy (e.g., initiation of administration), but prior to the time that some of the T cells reach peak or maximum expansion, the state of prolonged tryptophan starvation, exhaustion, anergy, cell death, retraction, suppression of antitumor immune responses or tolerance to tumor antigens and/or is incapable of recovering from starvation, e.g., tryptophan starvation, and/or reverse the effect of starvation. In some cases, the tryptophan metabolism and/or kynurenine pathway modulator, e.g., IDO1 inhibitor, is administered prior to the time when the T cells exhibit a delay or an arrest in growth and/or functional activity due to tryptophan depletion. In some embodiments, the tryptophan metabolism and/or kynurenine pathway modulator, e.g., IDO1 inhibitor, is administered less than about less than or less than about 1 hour, less than or less than about 2 hours, less than or less than about 6 hours, less than or less than about 12 hours, less than or less than about 1 day, less than or less than about 2 days, less than or less than about 3 days, less than or less than about 4 days, less than or less than about 5 days, less than or less than about 6 days, less than or less than about 7 days after administration (e.g., initiation of administration) of the T cell therapy. In some embodiments, the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy. In some embodiments, the tryptophan metabolism and/or kynurenine pathway modulator is administered within or within about 1 hour, 2 hours, 6 hours, 12 hours, 24 hours, 48 hours, 72 hours, 96 hours, 5 days, 6 days or 7 days subsequent to initiation of the T cell therapy. In some embodiments, the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 8 days, 9 days, 10 days, 11 days, 12 days, 13 days or 14 days subsequent to initiation of the T cell therapy. In some embodiments, the tryptophan metabolism and/or kynurenine pathway modulator is administered within or within about 1 hour, 2 hours, 6 hours, 12 hours, 24 hours or 48 hours subsequent to initiation of the T cell therapy.

In some embodiments, the tryptophan metabolism and/or kynurenine pathway modulator, e.g., IDO1 inhibitor, is administered after administration of the T cell therapy, such as CAR-T cell therapy (e.g., initiation of administration), at or after a time that the subject receiving the T cell therapy exhibits increased IDO1 expression and/or expression of amino acid transporters such as tryptophan transporters, e.g., LAT1, LAT2, CD98hc and/or PAT4, in a tumor sample from the subject, compared to a sample obtained prior to administration of the T cell therapy, a reference point and/or a sample from a different subject. In some embodiments, the subject is identified or selected for administration of the tryptophan metabolism and/or kynurenine pathway modulator, e.g., IDO1 inhibitor, if a tumor sample from the subject exhibits increased IDO1 expression and/or expression of amino acid transporters such as tryptophan transporters, e.g., LAT1, LAT2, CD98hc and/or PAT4, compared to a sample obtained prior to administration of the T cell therapy, a reference point and/or a sample from a different subject.

In some embodiments, the tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; at a time before the number of cells of the T cell therapy detectable in the blood from the subject is decreased compared to in the subject at a preceding time point after initiation of administration of the T cell therapy; at a time before T cells exhibit manifestations of prolonged tryptophan starvation, exhaustion, reduction of effector function, expression of inhibitory receptors and/or loss of proliferative capacity; at a time before a peak or maximum level of the cells of the T cell therapy are detectable in the blood of the subject; and/or the level of interferon-gamma (IFNγ) is increased in a biological sample from the subject compared to prior to initiation of administration of the T cell therapy or compared to a preceding time point after initiation of administration of the T cell therapy. In some embodiments, the increase or decrease is by greater than or greater than about 1.2-fold, 1.5-fold, 2-fold, 3-fold, 4-fold, 5-fold, 10-fold or more.

In some of any such embodiments in which the tryptophan metabolism and/or kynurenine pathway modulatory is given prior to the immunotherapy (e.g. T cell therapy, such as CAR-T cell therapy), the administration of the tryptophan metabolism and/or kynurenine pathway modulator, e.g., IDO1 inhibitor, continues at regular intervals until the initiation of the immunotherapy and/or for a time after the initiation of the immunotherapy.

In some embodiments, the tryptophan metabolism and/or kynurenine pathway modulator, e.g., IDO1 inhibitor is administered after administration of the immunotherapy (e.g. T cell therapy, such as CAR-T cell therapy). In some embodiments, the administration of the tryptophan metabolism and/or kynurenine pathway modulatory is at a time in which the prior administration of the immunotherapy (e.g. T cell therapy, such as CAR-T cell therapy) has, or is likely to have, caused or induced, directly or indirectly, an alteration in the level of metabolites in the kynurenine pathway, such as a decrease in the levels of TRP or an increase in the levels of KYN or a KYN derivate (e.g. increase or decrease by at least or about at least 1.2-fold, 1.5-fold, 2-fold, 3-fold, 4-fold, 5-fold, 6-fold, 7-fold, 8-fold, 10-fold or more) compared to the level at a time just prior to initiation of the immunotherapy (e.g. T cell therapy, such as CAR-T cell therapy) or at a preceding time point after initiation of the immunotherapy. Exemplary methods to assess or determine parameters associated with an alteration in the level of such metabolites in the kynurenine pathway are described in Section III.

In some embodiments, the tryptophan metabolism and/or kynurenine pathway modulator is administered within or within about 1 hours, 2 hours, 6 hours, 12 hours, 24 hours, 48 hours, 96 hours, 4 days, 5 days, 6 days or 7 days, 14 days, 15 days, 21 days, 24 days, 28 days, 30 days, 36 days, 42 days, 60 days, 72 days or 90 days after initiation of administration of the immunotherapy (e.g. T cell therapy). In some embodiments, the provided methods involve continued administration, such as at regular intervals, of the tryptophan metabolism and/or kynurenine pathway modulator after initiation of administration of the immunotherapy.

In some embodiments, the tryptophan metabolism and/or kynurenine pathway modulator, e.g. an IDO1 inhibitor, is administered up to or up to about 1 day, up to or up to about 2 days, up to or up to about 3 days, up to or up to about 4 days, up to or up to about 5 days, up to or up to about 6 days, up to or up to about 7 days, up to or up to about 12 days, up to or up to about 14 days, up to or up to about 21 days, up to or up to about 24 days, up to or up to about 28 days, up to or up to about 30 days, up to or up to about 35 days, up to or up to about 42 days, up to or up to about 60 days or up to or up to about 90 days, up to or up to about 120 days, up to or up to about 180 days, up to or up to about 240 days or up to or up about 360 days or more after the administration of the immunotherapy (e.g. T cell therapy, such as CAR-T cell therapy).

In some of any such above embodiments, the tryptophan metabolism and/or kynurenine pathway modulator, e.g. an IDO1 inhibitor, is administered prior to and after initiation of administration of the immunotherapy (e.g. T cell therapy, such as CAR-T cell therapy).

In some embodiments of the methods provided herein, the tryptophan metabolism and/or kynurenine pathway modulator, e.g., IDO1 inhibitor, and the immunotherapy (e.g. T cell therapy, such as CAR-T cell therapy) are administered simultaneously or near simultaneously.

In some embodiments, the tryptophan metabolism and/or kynurenine pathway modulator (e.g. IDO1 inhibitor) is administered twice a day.

In some embodiments, the tryptophan metabolism and/or kynurenine pathway modulator, e.g., IDO1 inhibitor, is independently administered in a dosage amount of from or from about 0.02 mg per kg body weight of the subject (mg/kg) to about 200 mg/kg body weight, such as 0.02 mg/kg to 100 mg/kg, 0.02 mg/kg to 100 mg/kg, 0.02 mg/kg to 50 mg/kg, 0.02 mg/kg to 10 mg/kg, 0.02 mg/kg to 1.0 mg/kg, 0.02 mg/kg to 0.2 mg/kg, 0.2 mg/kg to 100 mg/kg, 0.2 mg/kg to 50 mg/kg, 0.2 mg/kg to 10 mg/kg, 0.2 mg/kg to 1.0 mg/kg, 1.0 mg/kg to 200 mg/kg, 1.0 mg/kg to 100 mg/kg, 1.0 mg/kg to 50 mg/kg, 1.0 mg/kg to 10 mg/kg, 10 mg/kg to 200 mg/kg, 10 mg/kg to 100 mg/kg, 10 mg/kg to 50 mg/kg, 50 mg/kg to 200 mg/kg, 50 mg/kg to 100 mg/kg or 100 mg/kg to 200 mg/kg. In some embodiments, the tryptophan metabolism and/or kynurenine pathway modulator, e.g., IDO1 inhibitor is administered at a dosage at or about 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.5 mg/kg, 0.55 mg·kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 1.1 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 50 mg/kg, 75 mg/kg, 100 mg/kg, or 250 mg/kg or more.

In some embodiments, the tryptophan metabolism and/or kynurenine pathway modulator, e.g., IDO1 inhibitor, is administered, or each administration of the tryptophan metabolism and/or kynurenine pathway modulator is independently administered, in a dosage amount of from or from about 2.5 mg to about 5000 mg, such as 2.5 mg to 2000 mg, 2.5 mg to 1000 mg, 2.5 mg to 500 mg, 2.5 mg to 200 mg, 2.5 mg to 100 mg, 2.5 mg to 50 mg, 2.5 mg to 25 mg, 2.5 mg to 10 mg, 25 mg to 5000 mg, 25 mg to 2000 mg, 25 mg to 1000 mg, 25 mg to 500 mg, 25 mg to 200 mg, 25 mg to 100 mg, 25 mg to 50 mg, 50 mg to 5000 mg, 50 mg to 2000 mg, 50 mg to 1000 mg, 50 mg to 500 mg, 50 mg to 200 mg, 50 mg to 100 mg, 100 mg to 5000 mg, 100 mg to 2000 mg, 100 mg to 1000 mg, 100 mg to 500 mg, 100 mg to 200 mg, 200 mg to 5000 mg, 200 mg to 2000 mg, 200 mg to 1000 mg, 200 mg to 500 mg, 500 mg to 5000 mg, 500 mg to 2000 mg, 500 mg to 1000 mg or 1000 mg to 2000 mg, each inclusive.

In some embodiments, the tryptophan metabolism and/or kynurenine pathway modulator, e.g., IDO1 inhibitor, is administered, or each administration of the tryptophan metabolism and/or kynurenine pathway modulator is independently administered orally, in a dosage amount dosage amount of from or from about 2.5 mg to about 5000 mg, such as 2.5 mg to 2000 mg, 2.5 mg to 1000 mg, 2.5 mg to 500 mg, 2.5 mg to 200 mg, 2.5 mg to 100 mg, 2.5 mg to 50 mg, 2.5 mg to 25 mg, 2.5 mg to 10 mg, 25 mg to 5000 mg, 25 mg to 2000 mg, 25 mg to 1000 mg, 25 mg to 500 mg, 25 mg to 200 mg, 25 mg to 100 mg, 25 mg to 50 mg, 50 mg to 5000 mg, 50 mg to 2000 mg, 50 mg to 1000 mg, 50 mg to 500 mg, 50 mg to 200 mg, 50 mg to 100 mg, 100 mg to 5000 mg, 100 mg to 2000 mg, 100 mg to 1000 mg, 100 mg to 500 mg, 100 mg to 200 mg, 200 mg to 5000 mg, 200 mg to 2000 mg, 200 mg to 1000 mg, 200 mg to 500 mg, 500 mg to 5000 mg, 500 mg to 2000 mg, 500 mg to 1000 mg or 1000 mg to 2000 mg, each inclusive.

In some embodiments, the tryptophan metabolism and/or kynurenine pathway modulator, e.g., IDO1 inhibitor, is administered, or each administration of the tryptophan metabolism and/or kynurenine pathway modulator is independently administered, orally, at a frequency of six times daily, five times daily, four times daily, three times daily, twice daily, once daily, every other day, every three days, twice weekly or once weekly. In some embodiments, the tryptophan metabolism and/or kynurenine pathway modulator, e.g., IDO1 inhibitor, is administered, or each administration of the tryptophan metabolism and/or kynurenine pathway modulator is independently administered, six times daily, five times daily, four times daily, three times daily, twice daily or once daily.

In some embodiments, the tryptophan metabolism and/or kynurenine pathway modulator, e.g., IDO1 inhibitor, is administered, or each administration of the tryptophan metabolism and/or kynurenine pathway modulator is independently administered, in a total daily dosage amount of at least or at least about 5 mg/day, 10 mg/day, 25 mg/day, 50 mg/day, 100 mg/day, 200 mg/day, 400 mg/day, 500 mg/day, 600 mg/day, 800 mg/day, 1000 mg/day, 1200 mg/day, 1600 mg/day, 2000 mg/day, 5000 mg/day or 10000 mg/day.

In some aspects, the tryptophan metabolism and/or kynurenine pathway modulator, e.g., IDO1 inhibitor, is administered, or each administration of the tryptophan metabolism and/or kynurenine pathway modulator is independently administered, in a dosage amount of at least or at least about or about 0.02 mg per kg body weight of the subject (mg/kg), 0.2 mg/kg, 1 mg/kg, 3 mg/kg, 6 mg/kg, 10 mg/kg, 20 mg/kg, 30 mg/kg, 50 mg/kg, 100 mg/kg or 200 mg/kg; or in a dosage amount of at least or at least about 2.5 mg, 25 mg, 50 mg, 100 mg, 200 mg, 400 mg, 500 mg, 600 mg, 800 mg, 1000 mg, 1200 mg, 1600 mg, 2000 mg or 5000 mg.

In some embodiments, the tryptophan metabolism and/or kynurenine pathway modulator is a protein or a polypeptide or a derivative thereof, and the tryptophan metabolism and/or kynurenine pathway modulator is administered in a dosage amount of about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any ranges between the doses.

In some embodiments, the tryptophan metabolism and/or kynurenine pathway modulator, e.g., IDO1 inhibitor, is administered, or each administration of the tryptophan metabolism and/or kynurenine pathway modulator is independently administered, by intravenous administration, e.g., intravenous injection. In some embodiments, In some embodiments, the tryptophan metabolism and/or kynurenine pathway modulator is a protein or a polypeptide or a derivative thereof, and the tryptophan metabolism and/or kynurenine pathway modulator is administered in a dosage amount of about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any ranges between the doses.

C. Lymphodepleting Treatments

In some aspects, the provided methods can further include administering one or more lymphodepleting therapies, such as prior to or simultaneous with initiation of administration of the immunotherapy, such as a T cell therapy (e.g. CAR-expressing T cells) or a T cell-engaging therapy. In some embodiments, the lymphodepleting therapy comprises administration of a phosphamide, such as cyclophosphamide. In some embodiments, the lymphodepleting therapy can include administration of fludarabine. In some embodiments, fludarabine is excluded in the lymphodepleting therapy. In some embodiments, a lymphodepleting therapy is not administered.

In some embodiments, preconditioning subjects with immunodepleting (e.g., lymphodepleting) therapies can improve the effects of adoptive cell therapy (ACT). Preconditioning with lymphodepleting agents, including combinations of cyclosporine and fludarabine, have been effective in improving the outcome of transferred tumor infiltrating lymphocyte (TIL) cells in cell therapy, including to improve response and/or persistence of the administered cells. See, e.g., Dudley et al., Science, 298, 850-54 (2002); Rosenberg et al., Clin Cancer Res, 17(13):4550-4557 (2011). Likewise, in the context of CAR$^+$ T cells, several studies have incorporated lymphodepleting agents, most commonly cyclophosphamide, fludarabine, bendamustine, or combinations thereof, sometimes accompanied by low-dose irradiation. See Han et al., Journal of Hematology & Oncology, 6:47 (2013); Kochenderfer et al., Blood, 119: 2709-2720 (2012); Kalos et al., Sci Transl Med, 3(95):95ra73 (2011); Clinical Trial Study Record Nos. NCT02315612; NCT01822652.

Such preconditioning can be carried out with the goal of reducing the risk of one or more of various outcomes that could dampen activity or outcome or response of or to the therapy. These include the phenomenon known as "cytokine sink," by which T cells, B cells, NK cells compete with TILs for homeostatic and activating cytokines, such as IL-2, IL-7, and/or IL-15; suppression of TILs by regulatory T cells, NK cells, or other cells of the immune system; impact of negative regulators in the tumor microenvironment. Muranski et al., Nat Clin Pract Oncol. December; 3(12): 668-681 (2006).

In some embodiments, the provided method further involves administering a lymphodepleting therapy to the subject. In some embodiments, the method involves administering the lymphodepleting therapy to the subject prior to the administration of the dose of cells for T cell based therapy. In some embodiments, the lymphodepleting therapy contains a chemotherapeutic agent such as fludarabine and/or cyclophosphamide. In some embodiments, the lymphodepleting therapy does not contain fludarabine. In some embodiments, the lymphodepleting therapy only contains cyclophosphamide. In some embodiments, the administration of the cells and/or the lymphodepleting therapy is carried out via outpatient delivery.

In some embodiments, the methods further include administering a preconditioning agent, such as a lymphodepleting or chemotherapeutic agent, such as cyclophosphamide, fludarabine, or combinations thereof, to a subject prior to the administration of the dose of cells. For example, the subject may be administered a preconditioning agent at least 2 days prior, such as at least 3, 4, 5, 6, or 7 days prior, to the first or subsequent doses of the immunotherapy, such as a T cell therapy (e.g. CAR-expressing T cells) or a T cell-engaging therapy. In some embodiments, the subject is administered a preconditioning agent no more than 7 days prior, such as no more than 6, 5, 4, 3, or 2 days prior, to the administration of the dose of cells.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 30 mg/m$^2$, or 24 mg/m$^2$ and 26 mg/m$^2$. In some instances, the subject is administered 25 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the dose of cells.

In some embodiments, prior to receiving the T cells, e.g., CAR-expressing T cells, subjects receive a tryptophan metabolism and/or kynurenine pathway modulator, at least 1 day, 2 days, 3, days, 4 days, 5 days, 6 days, 7 days, 14 days, 21 days, 28 days or 30 days before the administration of cells and a lymphodepleting preconditioning chemotherapy of cyclophosphamide administered at least two days before the T cells, e.g., CAR-expressing T cells and generally no more than 7 days before administration of cells. In some cases, for example, cyclophosphamide is given at least 1 day, 2 days, 3, days, 4 days, 5 days, 6 days, 7 days, 14 days, 21 days, 28 days or 30 days after the administration of the tryptophan metabolism and/or kynurenine pathway modulator, e.g., IDO1 inhibitor. After preconditioning treatment, subjects are administered the dose of CAR-expressing T cells as described herein.

In some embodiments, the administration of the preconditioning agent, e.g., for lymphodepleting therapy, prior to infusion of the dose of cells improves an outcome of the treatment. For example, in some aspects, preconditioning improves the efficacy, outcome or activity of treatment with the dose or increases the persistence of the recombinant receptor-expressing cells (e.g., CAR-expressing cells, such as CAR-expressing T cells) in the subject. In some embodiments, preconditioning treatment increases disease-free survival, such as the percent of subjects that are alive and exhibit no minimal residual or molecularly detectable disease after a given period of time following the dose of cells. In some embodiments, the time to median disease-free survival is increased.

Once the cells are administered to the subject (e.g., human), the biological activity of the engineered cell populations in some aspects is measured by any of a number of known methods or any assessment methods or assays described herein, e.g., in Section III. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy*, 32(7): 689-702 (2009), and Herman et al., *J. Immunological Methods*, 285(1): 25-40 (2004). In certain embodiments, the biological activity of the cells also can be measured by assaying expression and/or secretion of certain cytokines. In some aspects the biological activity is measured by assessing clinical outcome, such as reduction in tumor burden or load. In some aspects, toxic outcomes, persistence and/or expansion of the cells, and/or presence or absence of a host immune response, are assessed.

In some embodiments, the administration of the preconditioning agent, e.g., lymphodepleting therapy, prior to infusion of the dose of cells improves an outcome of the treatment such as by improving the efficacy outcome or activity of treatment with the dose or increases the persistence of the recombinant receptor-expressing cells (e.g., CAR-expressing cells, such as CAR-expressing T cells) in the subject. In some embodiments, the lymphodepleting therapy is not given prior to administration of the immunotherapy, e.g., T cell therapy, and/or the tryptophan metabolism and/or kynurenine pathway modulator, e.g., IDO1 inhibitor.

III. SCREENING, ASSESSING OR SELECTING SUBJECTS AND ASSESSING TREATMENT OUTCOMES

In some embodiments of the methods, compositions, combinations, kits and uses provided herein, the combination therapy can further include one or more screening and/or assessment steps to determine suitability for the combination therapy, to identify or select subjects for treatment with the combination therapy and/or continuing the combination therapy, and/or a step for assessment of treatment outcomes and/or monitoring treatment outcomes. In some embodiments, the screening step can include step to identify subjects for treatment, such as assessment or evaluation of certain parameters, such as any described herein. In some embodiments, the step for assessment of treatment outcomes can include steps to evaluate and/or to monitor treatment and/or to identify subjects for administration of further or remaining steps of the therapy and/or for repeat therapy. In some embodiments, the screening step and/or assessment of treatment outcomes can be used to determine the dose, frequency, duration, timing and/or order of the combination therapy provided herein.

In some embodiments, the provided combination therapy results in any one or more of the treatment outcomes, such as a feature associated with any one or more of the parameters associated with the therapy or treatment, as described below.

In some embodiments, the combination therapy can be used to overcome immunosuppressive conditions of the TME and increase the activity of the immunotherapy, such as a T cell therapy (e.g. CAR-expressing T cells) or a T cell-engaging therapy. In some embodiments, modulation of the kynurenine pathway, e.g., inhibiting tryptophan (TRP) depletion and/or production of kynurenine (KYN) and its derivatives, results in enhanced proliferation and/or activity of the T cells, thereby effecting increased activity of the immunotherapy, such as a T cell therapy (e.g. CAR-expressing T cells) or a T cell-engaging therapy, compared to the activity of the immunotherapy alone. In some embodiments, the screening steps and/or assessment of treatment of outcomes can be used to determine and/or monitor the activity of the combination therapy.

In some aspects, screening or assessing certain parameters as described can be used to identify subjects that are suitable for, susceptible to and/or responsive to a particular treatment, e.g., combination therapy methods provided herein, or to monitor treatment and/or to identify an effective dosage for a subject or sub-group or other group of subjects. In some embodiments, such screening or assessments can be used to select or identify patients predicted to be responsive to treatment. In some embodiments, the screening step is used to determine the dose, frequency, duration, timing and/or order of the combination therapy provided herein.

In some embodiments, any of the screening steps and/or assessment of treatment of outcomes described herein can be used prior to, during, during the course of, or subsequent to administration of one or more steps of the provided combination therapy, e.g., administration of the immunotherapy, such as a T cell therapy (e.g. CAR-expressing T cells) or a T cell-engaging therapy, and/or a tryptophan metabolism and/or kynurenine pathway modulator. In some embodiments, assessment is made prior to, during, during the course of, or after performing any of the methods provided herein. In some embodiments, the assessment is made prior to performing the methods provided herein. In some embodiments, assessment is made after performing one or more steps of the methods provided herein. In some embodiments, the assessment is performed prior to administration of administration of one or more steps of the provided combination therapy, for example, to screen and identify patients suitable and/or susceptible to receive the combination therapy. In some embodiments, the assessment is performed during, during the course of, or subsequent to administration of one or more steps of the provided combination therapy, for example, to assess the intermediate or final treatment outcome, e.g., to determine the activity of the treatment and/or to determine whether to continue or repeat the treatments and/or to determine whether to administer the remaining steps of the combination therapy.

In some embodiments, the screening step and/or assessment of treatment outcomes includes assessment of the levels and changes, e.g., alterations, of levels of factors, e.g., enzymes, and/or metabolites of the kynurenine pathway. In some embodiments, the screening step and/or assessment of treatment of outcomes includes assessing immune functions, e.g., immune functions of the T cells administered for cell based therapy and/or of the endogenous T cells in the body. In some embodiments, the screening step and/or assessment of treatment of outcomes includes assessing the survival and/or function of the T cells administered for cell based therapy. In some embodiments, the screening step and/or assessment of treatment of outcomes includes assessing the levels of cytokines or growth factors. In some embodiments, the screening step and/or assessment of treatment of outcomes includes assessing disease burden and/or improvements, e.g., assessing tumor burden and/or clinical outcomes. In some embodiments, either of the screening step and/or assessment of treatment of outcomes can include any of the assessment methods and/or assays described herein and/or known in the art, and can be performed one or more times, e.g., prior to, during, during the course of, or subsequently to administration of one or more steps of the combination therapy.

In some embodiments, particular parameters can be assessed to select patients for combination therapy, determine the order, dose or regimen of the combination therapy, determine the treatment outcomes and/or to determine activity of combination therapy. In some embodiments, such parameters include, for example, levels of metabolites in the kynurenine pathway, e.g., TRP, KYN or derivatives of KYN, expression levels of factors or effectors, e.g., enzymes, involved in the kynurenine pathway, e.g., IDO1, T cell proliferation, T cell activity, cell phenotype assessment, e.g., T cell surface marker expression, and/or activity of treatment. Assessments can be made in vivo, ex vivo or in vitro, and particular parameter can be determined from a biological sample, e.g., a serum sample, a plasma sample, a tumor biopsy or via in vivo imaging. Biological samples include, but are not limited to, body fluids, such as blood, plasma, serum, cerebrospinal fluid, synovial fluid, urine and sweat, tissue and organ samples or tumor samples including processed samples derived therefrom, such as isolated cells and/or tissue sections from a tumor biopsy.

Exemplary sets of parameters associated with a treatment outcome, which can be assessed in some embodiments of the methods provided herein, include plasma kynurenine/tryptophan ratio, peripheral blood immune cell population profile, tumor burden and expression levels of plasma tumor markers and markers of immune modulation and IDO1$^+$ expression.

A. Screening, Identification and/or Selection of Subjects and Determination of Dosage and Scheduling In some embodiments, the subject can be screened prior to the administration of one or more steps of the combination therapy. For example, the subject can be screened for level, availability, concentration, effect, activity, metabolism, synthesis and/or degradation of factors, e.g., enzymes, and/or metabolites of the kynurenine pathway, and/or characteristics of the disease and/or disease burden, e.g., tumor burden, prior to or after administration of one or more steps of the combination therapy, and/or characteristics or history of prior treatment and/or response to prior treatment, to determine suitability, responsiveness and/or susceptibility to administering one or more steps of the combination therapy.

In some embodiments, the subject can be screened for level, availability, concentration, effect, activity, metabolism, synthesis and/or degradation of factors or effectors, e.g., enzymes, and/or metabolites of the kynurenine pathway, e.g., levels of metabolites in the kynurenine pathway, e.g., TRP, KYN or derivatives of KYN, expression levels of factors or effectors, e.g., enzymes, involved in the kynurenine pathway, e.g., IDO1, and/or amino acid transporters, e.g., LAT1, LAT2, CD98hc and/or PAT4, from a biological sample from the subject, e.g., tumor, blood and/or serum samples. In some embodiments, any of the parameters associated with therapy, screening, identification or treatment outcomes described herein, such as those described in Section III.C. below, can be used as relevant parameters to determine suitability, responsiveness and/or susceptibility of treatment and/or to screen, identify and/or select subjects for treatment, e.g., with some of the embodiments provided herein, e.g., one or more steps of the combination therapy.

In some embodiments, the subject can be screened after administration of one of the steps of the combination therapy, to determine and identify subjects to receive the remaining steps of the combination therapy. For example, in some embodiments, the tryptophan metabolism and/or kynurenine pathway modulator is administered prior to administration of the immunotherapy, such as a T cell therapy (e.g. CAR-expressing T cells) or a T cell-engaging therapy, and the level of factors, e.g., enzymes, and/or metabolites of the kynurenine pathway is assessed prior to administration of the immunotherapy. In some embodiments, the immunotherapy, such as a T cell therapy (e.g. CAR-expressing T cells) or a T cell-engaging therapy, is administered prior to the administration of the tryptophan metabolism and/or kynurenine pathway modulator, and the proliferation and/or activity of the administered T cells and/or the level of factors, e.g., enzymes, and/or metabolites of the kynurenine pathway is assessed prior to administration of the tryptophan metabolism and/or kynurenine pathway modulator. In some embodiments, the subject can be screened for particular characteristics of the disease, e.g., tumor or tumor microenvironment (TME) and/or disease burden, e.g., tumor burden, prior to administration of the combination therapy. For example, in some embodiments, the subject who has received a T cell therapy, e.g., a CAR T cell therapy, is assessed for increased IDO1 expression in the tumor sample and/or circulating metabolite levels, such as circulating tryptophan or kynurenine levels, to select and/or identify the subject for administration with the tryptophan metabolism and/or kynurenine pathway modulator. Any of the assessment methods and/or assays described herein and/or known in the art, and can be performed as a step for screening subjects for the combination therapy.

In some embodiments, provided are methods of selecting subjects having a disease or condition for treatment. In some embodiments, provided are methods of assessing parameters, e.g., any parameters described herein, to screen and/or identify subjects for treatment. In some embodiments, the treatment is administering a tryptophan metabolism and/or kynurenine pathway modulator, in particular, in combination with a T cell therapy.

In some embodiments, the methods for screening, identifying and/or selecting includes methods for assessment of parameters, such as levels and/or amount of factors, molecules and/or agents, that are indicative of or associated with induction or generation of factors, molecules and/or agents involved in or indicative of adaptive immune resistance, activation of the tryptophan metabolism/kynurenine pathway, IDO1 expression and/or tryptophan depletion. In some embodiments, such assessment involves determining the levels and/or amount of parameters, such as factors, molecules and/or agents, and/or determining a change in the parameters. In some embodiments, such levels and/or amount of parameters and/or changes in levels and/or amount of parameters are directly or inversely correlated with activation of the tryptophan metabolism/kynurenine pathway, IDO1 expression and/or tryptophan depletion in the subject.

In some embodiments, the methods involve identifying and/or selecting subjects having a disease or condition, for treatment, based on the results of the screening and/or assessment. In some embodiments, the subject is selected or identified, in which the levels and/or amount of parameters and/or changes in levels and/or amount of parameters, indicates, e.g., is directly or inversely correlated with, activation of the tryptophan metabolism/kynurenine pathway, IDO1 expression and/or tryptophan depletion. In some embodiments, such subjects are identified and/or selected for administration of a tryptophan metabolism and/or kynurenine pathway modulator, and/or a T cell therapy.

In some embodiments, the parameter, such as levels and/or amount of factors, molecules and/or agents, that are indicative of or associated with adaptive immune resistance, activation of the tryptophan metabolism/kynurenine pathway, IDO1 expression and/or tryptophan depletion, includes the level of tryptophan or a tryptophan metabolite, the level of expression or activity of IDO1, IDO2 or TDO, or the level of interferon-gamma (IFNγ).

In some embodiments, a high level of the parameter, such as a level above a threshold level, or an increase in the parameter, compared to a preceding time point, is associated with or indicative of adaptive immune resistance, activation of the tryptophan metabolism/kynurenine pathway, IDO1 expression and/or tryptophan depletion. In some embodiments, low level of the parameter, such as a level below a threshold level, or a decrease in the parameter, compared to a preceding time point, is associated with or indicative of adaptive immune resistance, activation of the tryptophan metabolism/kynurenine pathway, IDO1 expression and/or tryptophan depletion. In some embodiments, subjects are selected for administration of a tryptophan metabolism and/or kynurenine pathway modulator if the results of assessment are associated with or indicative of adaptive immune resistance, activation of the tryptophan metabolism/kynurenine pathway, IDO1 expression and/or tryptophan depletion.

In some embodiments, the parameter can be assessed to in vivo, ex vivo or in vitro, and the parameter can be determined from a biological sample, e.g., a serum sample, a plasma sample, a tumor biopsy or via in vivo imaging. Biological samples include, but are not limited to, body fluids, such as blood, plasma, serum, cerebrospinal fluid, synovial fluid, urine and sweat, tissue and organ samples or tumor samples including processed samples derived therefrom, such as isolated cells and/or tissue sections from a tumor biopsy.

In some embodiments, one or more biological sample is obtained prior to administration of the T cell therapy. In some embodiments, one or more biological sample is obtained subsequent to administration of the T cell therapy. In some embodiments, one or more biological sample is obtained subsequent to administration of the T cell therapy and the tryptophan metabolism and/or kynurenine pathway modulator.

In some embodiments, assessment is performed prior to administration of the T cell therapy. In some embodiments, assessment is performed subsequent to administration of the T cell therapy. In some embodiments, assessment is performed prior to administration of the tryptophan metabolism and/or kynurenine pathway modulator. In some embodiments, assessment is performed subsequent to administration of the tryptophan metabolism and/or kynurenine pathway modulator. In some embodiments, assessment is performed subsequent to administration of the T cell therapy and the tryptophan metabolism and/or kynurenine pathway modulator.

In some embodiments, the parameter is the level of tryptophan, and the level of tryptophan in the sample is below a threshold level or is decreased compared to the level assessed at a time point prior to initiation of administration of the T cell therapy or a preceding time point after initiation of administration of the T cell therapy. In some embodiments, the level of tryptophan can be inversely related to adaptive immune resistance, activation of the tryptophan metabolism/kynurenine pathway, IDO1 expression and/or tryptophan depletion.

In some embodiments, the parameter is the level of expression or activity of IDO1, IDO2 or TDO, and the level of expression or activity of IDO1, IDO2 or TDO, is above a threshold level or is increased compared to the level assessed at a time point prior to initiation of administration of the T cell therapy or a preceding time point after initiation of administration of the T cell therapy. In some embodiments, the level of expression or activity of IDO1, IDO2 or TDO can be directly related to adaptive immune resistance, activation of the tryptophan metabolism/kynurenine pathway, IDO1 expression and/or tryptophan depletion.

In some embodiments, the parameter is the level of the IFNγ, and the level of the IFNγ, is above a threshold level or is increased compared to the level assessed at a time point prior to initiation of administration of the T cell therapy or a preceding time point after initiation of administration of the T cell therapy. In some embodiments, the level of expression or activity of IDO1, IDO2 or TDO can be directly related to adaptive immune resistance, activation of the tryptophan metabolism/kynurenine pathway, IDO1 expression and/or tryptophan depletion.

In some embodiments, the subject is identified or selected, if the level of tryptophan in the sample is below a threshold level or is decreased compared to the level assessed at a time point prior to initiation of administration of the T cell therapy or a preceding time point after initiation of administration of the T cell therapy; the level of the tryptophan metabolite is above a threshold level or is increased compared to the level assessed at a time point prior to initiation of administration of the T cell therapy or a preceding time point after initiation of administration of the T cell therapy; the level of expression or activity of IDO1, IDO2 or TDO is above a threshold level or is increased compared to the level assessed at a time point prior to initiation of administration of the T cell therapy or a preceding time point after initiation of administration of the T cell therapy; or the level of the IFNγ is above a threshold level or is increased compared to the level assessed at a time point prior to initiation of administration of the T cell therapy or a preceding time point after initiation of administration of the T cell therapy.

In some embodiments, the subject is selected if the level of expression or activity of IDO1, IDO2 or TDO is increased compared to the level assessed at a time point prior to initiation of administration of the T cell therapy. In some embodiments, the subject is selected if the level of tryptophan in the sample is below a threshold level or is decreased compared to the level assessed at a time point prior to initiation of administration of the T cell therapy.

In some embodiments, the threshold level is within 25%, within 20%, within 15%, within 10% or within 5% of the average level, concentration or amount, and/or is within a standard deviation of the average level, concentration or amount in a biological sample from among a plurality of control subjects. In some embodiments, the control subjects are healthy or normal subjects, are subjects who do not have a cancer and/or are subjects prior to receiving administration of the T cell therapy. In some embodiments, the increase or decrease is by greater than or greater than about 1.2-fold, 1.5-fold, 2-fold, 3-fold, 4-fold, 5-fold, 10-fold or more.

In some embodiments, the screening and/or assessment involves assessment of the number, function, state and/or phenotype of the administered T cells. For example, in some embodiments, the screening and/or assessment involves assessment of the peak or maximum level of the cells of the T cell therapy is detectable in the blood of the subject. In some embodiments, the screening and/or assessment involves assessment of T cell function, state and/or phenotype, including state of prolonged tryptophan starvation, exhaustion, anergy, cell death, retraction, suppression of antitumor immune responses or tolerance to tumor antigens and/or capacity or ability to recover from starvation, e.g., tryptophan starvation, and/or reverse the effect of starvation.

In some embodiments, the screening and/or assessment involves assessment of the cells present in or near the tumor, e.g., CAR T cells, tumor cells and/or bystander cells, and/or characterizing the cells present in or near the tumor, e.g., CAR T cells, tumor cells and/or bystander cells. In some embodiments, the screening and/or assessment involves assessment of IDO1 expression and/or expression of amino acid transporters such as tryptophan transporters, e.g., LAT1, LAT2, CD98hc and/or PAT4, in a sample from the subject, e.g., a tumor sample from the subject, such as a biopsy and/or isolated cells. In some embodiments, the subject is identified or selected for administration of the tryptophan metabolism and/or kynurenine pathway modulator, e.g., IDO1 inhibitor, if a tumor sample from the subject exhibits increased IDO1 expression and/or expression of amino acid transporters such as tryptophan transporters, e.g., LAT1, LAT2, CD98hc and/or PAT4, compared to a sample obtained prior to administration of the T cell therapy, a reference point and/or a sample from a different subject.

In some embodiments, the screening and/or assessment involves assessment of the levels of kynurenine pathway metabolites, e.g., tryptophan or kynurenine and/or their derivatives. In some embodiments, the screening and/or assessment involves assessment of levels of kynurenine pathway metabolites in a biological sample, e.g., a blood, serum, plasma or tumor sample, from a subject. In some embodiments, the subject is identified or selected for administration of the tryptophan metabolism and/or kynurenine pathway modulator, e.g., IDO1 inhibitor, if the kynurenine pathway metabolites in a biological sample, e.g., serum or plasma sample, from a subject is altered, e.g., increased or decreased, compared to a sample obtained prior to administration of the T cell therapy, a reference point and/or a sample from a different subject.

In some embodiments, the screening and/or assessment involves assessment of any prior therapies and/or outcomes. In some embodiments, the screening and/or assessment involves assessing responsiveness or failure of a prior treatment, resistance to a prior treatment and/or relapse following a prior treatment. In some aspects, the screening and/or assessment involves assessment of response of the subject to prior treatment, e.g. chemotherapy or immunotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered. In some embodiments, the prior treatment can be any therapy, e.g., any conventional cancer therapy, such as chemotherapy. In some embodiments, the prior treatment is administration of a tryptophan metabolism and/or kynurenine pathway modulator therapy, e.g., IDO1 inhibitor therapy and/or an immunomodulatory therapy that is not a T cell therapy, e.g., an immune checkpoint inhibitor therapy. In some embodiments, the prior treatment is a combination therapy of a tryptophan metabolism and/or kynurenine pathway modulator, e.g., IDO1 inhibitor and an immune modulator, e.g., an immune checkpoint inhibitor.

In some embodiments, the subject is identified or selected for administration of one or more steps of the embodiments provided herein if the subject has failed, become resistant to and/or relapsed following a prior treatment such as a prior administration of a tryptophan metabolism and/or kynurenine pathway modulator therapy, e.g., IDO1 inhibitor therapy, optionally wherein such prior administration was carried out in combination with an immunomodulatory therapy that is not a T cell therapy, e.g., an immune checkpoint inhibitor therapy. In some embodiments, the combination therapy can be administered to subjects that have failed, become resistant to and/or having relapsed following other prior treatments, such as a prior administration of a combination therapy of a tryptophan metabolism and/or kynurenine pathway modulator, e.g., IDO1 inhibitor and an immune modulator, e.g., an immune checkpoint inhibitor. In some embodiments, the prior immunomodulatory therapy is not a prior T cell therapy. In some embodiments, the subjects have not been administered a prior T cell therapy. In some embodiments, the screening step and/or assessment of treatment outcomes can be used to determine the dose, frequency, duration, timing and/or order of the combination therapy provided herein. In some embodiments, the tryptophan metabolism and/or kynurenine pathway modulator is administered after initiation of administration of the recombinant receptor-expressing cells at a time in which: there is a decrease in tryptophan levels, an increase in kynurenine levels and/or an increase in IDO1 expression or activity in serum or plasma sample from the subject compared to prior to initiation of administration of the engineered cells or compared to a preceding time point after initiation of administration of the engineered cells; and/or the number of engineered cells detectable in the blood from the subject is decreased compared to in the subject at a preceding time point after administration of the engineered cells.

In some embodiments, the tryptophan metabolism and/or kynurenine pathway modulator is administered at a time in which: there is a decrease in tryptophan levels, an increase in kynurenine levels and/or an increase in expression or activity of IDO1, IDO2 or TDO in a biological sample from the subject compared to prior to initiation of administration of the T cell therapy or compared to a preceding time point after initiation of administration of the T cell therapy; the number of cells of the T cell therapy detectable in the blood from the subject is decreased compared to in the subject at a preceding time point after initiation of administration of the T cell therapy; the number of cells of the T cell therapy detectable in the blood is less than or less than about 1.5-fold, 2-fold, 3-fold, 4-fold, 5-fold, 10-fold, 50-fold or 100-fold or less the peak or maximum number of the cells of the T cell therapy detectable in the blood of the subject after initiation of administration of the T cell therapy; and/or at a time after a peak or maximum level of the cells of the T cell therapy are detectable in the blood of the subject, the number of cells of the T cell therapy detectable in the blood from the subject is less than less than 10%, less than 5%, less than 1% or less than 0.1% of total peripheral blood mononuclear cells (PBMCs) in the blood of the subject; the level of IFNγ or TNFα is increased in a biological sample from the subject compared to prior to initiation of administration of the T cell therapy or compared to a preceding time point after initiation of administration of the T cell therapy.

In some embodiments, the tryptophan metabolism and/or kynurenine pathway modulator is administered at a time prior to the peak or maximum level of the cells of the T cell therapy is detectable in the blood of the subject. In some embodiments, the tryptophan metabolism and/or kynurenine pathway modulator is administered at a time prior to retraction from peak or maximum level of the cells in the T cell therapy, such as prior to the point in which the number of cells of the T cell therapy detectable in the blood from the subject is decreased compared to in the subject at a preceding time point after initiation of administration of the T cell therapy.

In some embodiments, the tryptophan metabolism and/or kynurenine pathway modulator, e.g., an IDO1 inhibitor, is administered at a time in which there is an increase in the expression or activity of IDO1 in a biological sample from the subject compared to prior to initiation of administration of the T cell therapy or compared to a preceding time point after initiation of administration of the T cell therapy.

In some embodiments, the administration of the tryptophan metabolism and/or kynurenine pathway modulator, e.g., an IDO1 inhibitor, is continued after initiation of administration of the immunotherapy, e.g., T cell therapy, until there is a sustained maximum increase in tryptophan levels, a sustained maximum decrease in kynurenine levels or a sustained maximum decrease in IDO1 expression or activity, in a biological sample from the subject, optionally a serum or plasma sample, compared to just prior to administration of the tryptophan metabolism and/or kynurenine pathway modulator, e.g., IDO1 inhibitor or compared to just prior to initiation of the immunotherapy, e.g., T cell therapy. In some embodiments, the tryptophan metabolism and/or kynurenine pathway modulator, e.g., an IDO1 inhibitor, is administered until there is a sustained maximum increase in the number of engineered cells detectable in the blood from the subject compared to in the subject just prior to administration of the tryptophan metabolism and/or kynurenine pathway modulator, e.g., IDO1 inhibitor. For example, in some embodiments, the tryptophan metabolism and/or kynurenine pathway modulator, e.g., an IDO1 inhibitor, is administered for a time period up to 2 days, up to 7 days, up to 14 days, up to 21 days, up to 28 days, up to 35 days or up to 42 days, up to one month, up to two months, up to three months, up to 6 months or up to 1 year after initiation of the administration of the immunotherapy, e.g., T cell therapy.

In some embodiments, the tryptophan metabolism and/or kynurenine pathway modulator, e.g., an IDO1 inhibitor, is administered until the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

In some embodiments, the method is administered to subjects with a cancer comprising a tumor negative for IDO1 and/or the subject is not selected for expression of an IDO1 positive tumor; and/or the method is administered to subjects with a cancer comprising a tumor negative for TDO and/or the subject is not selected for expression of a TDO positive tumor.

In some embodiments, the subject (e.g., to which the provided therapeutic agents are administered) is a subject with or suspected of having a cancer or tumor-associated tissue or cell that is or has been deemed to be positive for expression of an amino acid transporter capable of taking up or exchanging tryptophan, such as an L-type Amino Acid Transporter 1 (LAT1; SLC7A5) or one or more chains of a complex thereof, LAT2 (SLC7A8), CD98 heavy chain (4F2hc; CD98hc; SLC3A2) and/or proton-assisted amino-acid transporter 4 (PAT4; SLC36A4), or subjects with a cancer that contains cells, e.g., bystander cells in the tumor microenvironment, that express high levels of or are positive for expression of LAT1, LAT2, CD98hc and/or PAT4. In embodiments, the articles of manufacture comprise one or more of the agents and literature and/or instructions that indicate administration of the therapy to such a subject and/or indicate that subjects are to be assessed for such tumor, tumor-associated tissue or cell, or marker, prior to treatment.

In some embodiments of any of the methods for assessment, screening, identification and/or selection of subjects further comprises administration of a tryptophan metabolism and/or kynurenine pathway modulator and/or a T cell therapy. In some embodiments, the method further comprises administering the T cell therapy to the subject. In some embodiments, the method further comprises administering the tryptophan metabolism and/or kynurenine pathway modulator to the selected subject. In some embodiments of any of the methods for assessment, screening, identification and/or selection of subjects further comprises, prior to the assessing, administering the cell therapy to the subject. In some embodiments of any of the methods for assessment, screening, identification and/or selection of subjects further comprises administering the kynurenine pathway modulator to the subject.

In some embodiments, the tryptophan metabolism and/or kynurenine pathway modulator is administered to the selected subject prior to or concurrently with initiation of administration of the T cell therapy. In some embodiments, the tryptophan metabolism and/or kynurenine pathway modulator is administered subsequent to initiation of administration of the T cell therapy. In some embodiments, the one or more biological sample is obtained subsequent to administration of the T cell therapy.

B. Assessment of Treatment Outcomes and/or Monitoring Treatment Outcomes

In some embodiments of the methods, compositions, combinations, kits and uses provided herein, the combination therapy can include a step for assessment of treatment outcome and/or for monitoring treatment outcomes. In some embodiments, the step for assessment of treatment outcomes and/or monitoring treatment outcomes includes assessment methods and/or assays to monitor treatment and evaluate an outcome such as activity or efficacy of treatment. In some embodiments, the step for assessment of treatment outcomes can include steps to evaluate and/or to monitor treatment and/or to identify subjects for further or remaining steps of the therapy and/or to repeat therapy. In some embodiments, the step for assessment of treatment outcome and/or for monitoring treatment outcomes is used to determine the dose, frequency, duration, timing and/or order of the combination therapy provided herein.

In some embodiments, the assessment of treatment of outcomes described herein can be used during, during the course of, or subsequent to administration of one or more steps of the provided combination therapy, e.g., administration of the immunotherapy, such as a T cell therapy (e.g. CAR-expressing T cells) or a T cell-engaging therapy, and a tryptophan metabolism and/or kynurenine pathway modulator, for example, to assess the intermediate or final treatment outcome, e.g., to determine or monitor the activity of the treatment, to determine to continue or repeat the treatments, to determine whether to administer the remaining steps of the combination therapy, and/or to determine particular dose, frequency, duration, timing and/or order of the combination therapy. In some embodiments, the assessment of treatment of outcomes described herein is used after the administration of both the administration of the immunotherapy, such as a T cell therapy (e.g. CAR-expressing T cells) or a T cell-engaging therapy, and administration of a tryptophan metabolism and/or kynurenine pathway modulator.

In some embodiments, the assessment of treatment outcome and/or for monitoring treatment outcomes includes assessment methods and/or assays described herein, e.g., assessment of the levels and/or change in levels of factors or effectors, e.g., enzymes, and/or metabolites of the kynurenine pathway, immune functions, e.g., immune functions of the T cells administered for cell based therapy and/or of the endogenous T cells in the body, survival and/or function of the T cells administered for cell based therapy, cytokines or growth factors, disease burden and/or improvements, e.g., assessing tumor burden and/or clinical outcomes. Any of the assessment methods and/or assays described herein and/or known in the art, and can be performed as a step for assessment of treatment outcome and/or for monitoring treatment outcomes.

In some embodiments, any of the assessment methods and/or assays can be performed once or more than once, or repeatedly. In some embodiments, administration of one or both agents of the combination therapy and/or any repeated administration of the therapy, can be determined based on the results of the assays before, during or after administration of one or both agents of the combination therapy.

In some embodiments, exemplary treatment outcome of the methods provide herein include alterations in the levels of kynurenine pathway metabolites, e.g., increased TRP levels or reversal of tryptophan depletion, decrease in production of KYN and its derivatives, enhanced T cell proliferation, enhanced T cell functional activity, changes in immune cell phenotypic marker expression, decreased disease burden, e.g., tumor burden, improved clinical outcomes and/or enhanced activity of therapy. In some embodiments, the methods provided herein result in an increase in tryptophan levels and/or a decrease in kynurenine levels in a biological sample, e.g., a serum or plasma sample, from a subject, compared to a method involving administration of the but in the absence of the tryptophan metabolism and/or kynurenine pathway modulator.

In some embodiments of the immunotherapy methods provided herein, such as a T cell therapy (e.g. CAR-expressing T cells) or a T cell-engaging therapy, assessment of the parameter includes assessing the expansion and/or persistence in the subject of the administered T cells for the immunotherapy, e.g., T cell therapy, as compared to a method in which the immunotherapy is administered to the subject in the absence of the tryptophan metabolism and/or kynurenine pathway modulator, e.g. IDO1 inhibitor. In some embodiments, the methods result in the administered T cells exhibiting increased or prolonged expansion and/or persistence in the subject as compared to a method in which the T cell therapy is administered to the subject in the absence of the tryptophan metabolism and/or kynurenine pathway modulator.

In some embodiments, the methods also affect activity of the cell therapy in the subject. In some embodiments, the persistence, expansion, and/or presence of recombinant receptor-expressing, e.g., CAR-expressing, cells in the subject following administration of the dose of cells in the method with the tryptophan metabolism and/or kynurenine pathway modulator, e.g., IDO1 inhibitor, is greater as compared to that achieved via a method without the tryptophan metabolism and/or kynurenine pathway modulator. In some embodiments, the administration of the tryptophan metabolism and/or kynurenine pathway modulator, e.g., IDO1 inhibitor decreases disease burden, e.g., tumor burden, in the subject as compared to a method in which the dose of cells expressing the recombinant receptor is administered to the subject in the absence of the tryptophan metabolism and/or kynurenine pathway modulator, e.g., IDO1 inhibitor. In some embodiments, the administration of the tryptophan metabolism and/or kynurenine pathway modulator, e.g., IDO1 inhibitor, decreases blast marrow in the subject as compared to a method in which the dose of cells expressing the recombinant receptor is administered to the subject in the absence of the tryptophan metabolism and/or kynurenine pathway modulator, e.g., IDO1 inhibitor. In some embodiments, the administration of the tryptophan metabolism and/or kynurenine pathway modulator, e.g., IDO1 inhibitor, results in improved clinical outcomes, e.g., objective response rate (ORR), progression-free survival (PFS) and overall survival (OS), compared to a method in which the dose of cells expressing the recombinant receptor is administered to the subject in the absence of the tryptophan metabolism and/or kynurenine pathway modulator.

In some embodiments, a change and/or an alteration, e.g., an increase, an elevation, a decrease or a reduction, in levels, values or measurements of a parameter compared to the levels, values or measurements of the same parameter in a different time point of assessment, a different condition, a reference point and/or a different subject is determined or assessed. For example, in some embodiments, a fold change, e.g., an increase or decrease, in particular parameters, e.g., number of engineered T cells in a sample, compared to the same parameter in a different condition, e.g., before or after administration of the tryptophan metabolism and/or kynurenine pathway modulator, can be determined. In some embodiments, the levels, values or measurements of two or more parameters are determined, and relative levels are compared. In some embodiments, the determined levels, values or measurements of parameters are compared to the levels, values or measurements from a control sample or an untreated sample. In some embodiments, the determined levels, values or measurements of parameters are compared to the levels from a sample from the same subject but at a different time point. The values obtained in the quantification of individual parameter can be combined for the purpose of disease assessment, e.g., by forming an arithmetical or logical operation on the levels, values or measurements of parameters by using multi-parametric analysis. In some embodiments, a ratio of two or more specific parameters can be calculated.

C. Parameters Associated with Therapy, Screening, Identification or Treatment Outcomes 1. Tryptophan and Kynurenine Metabolite and Enzyme Levels In some embodiments, parameters associated with therapy or a treatment outcome, which include parameters that can be assessed for the screening steps and/or assessment of treatment of outcomes and/or monitoring treatment outcomes, include levels of metabolites of the kynurenine pathway, e.g., tryptophan and/or kynurenine, or factors or effectors, e.g., enzymes, receptors or signaling molecules, involved in the kynurenine pathway. As discussed above in Section II.B.1, the kynurenine pathway is a key pathway in tryptophan metabolism, and involves numerous steps and involves various metabolites, some of which contribute to the immunosuppressive TME. In some embodiments, assessment of kynurenine pathway metabolite levels, can be performed to select patients for combination therapy, determine the order, dose or regimen of the combination therapy, determine the treatment outcomes and/or to determine activity of combination therapy.

In some embodiments, the parameter assessed is the level, changes, e.g., alterations, in the levels and/or expression levels of one or more enzyme in the kynurenine pathway. In some embodiments, an enzyme of the kynurenine pathway is indoleamine-pyrrole 2,3-dioxygenase 1 (IDO1), IDO2, tryptophan 2,3-dioxygenase (TDO), kynurenine formamidase, kynureninase, L-kynurenine hydrolase, kynurenine-3-monooxygenase, kynurenine 3-hydroxylase, 3-hydroxyanthranilic acid oxygenase, 3-hydroxyanthranilate 3,4-dioxygenase, kynurenine amino-transferase, and/or quinolinic acid phosphoribosyl transferase. In some embodiments, the levels of one or more enzymes in a biological sample is determined using any of the conventional methods for detecting expression of a gene and/or gene product, e.g., methods for detecting nucleic acids and/or proteins, e.g., intracellular enzymes.

In some embodiments, the parameter assessed is the expression level and/or activation status of factors, e.g., effectors, involved in the kynurenine pathway and/or components involved in tryptophan metabolism, signaling and/or transport such as expression levels of a tryptophan transporter or transporter complex such as LAT-1 or related transporters. In some embodiments, exemplary parameters assessed include expression level or activation state, e.g., phosphorylation state or cellular localization, of components involved in tryptophan metabolism, transport, and/or signaling, e.g., general control non-derepressible 2 (GCN2), interferon γ (IFNγ), tumor necrosis factor alpha (TNFα), signal transducer and activator of transcription 3 (STAT3), mammalian target of rapamycin (mTOR), aryl hydrocarbon receptor (AHR), AHR nuclear translocator (ARNT), dioxin responsive element (DRE), transporters of amino acids such as TRP (tryptophan) transporters (e.g., CD98 and/or associated chains, such as one or more of a CD98/LAT-1 transporter complex, e.g., CD98 heavy chain (4F2hc; SLC3A2) and/or a L-type Amino Acid Transporter 1 (LAT1; SLC7A5), LAT2 (SLC7A8), proton-assisted amino-acid transporter 4 (PAT4; SLC36A4), Asc-1, Asc-2, ATB0, B0AT1, TAT1), PR domain zinc finger protein 1 (PRDM1, also known as BLIMP-1), eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8 and/or IFNγ-R2.

In some embodiments, the parameter assessed is the levels or changes, e.g., alterations, in the levels, availability, concentration, effect, activity, metabolism, synthesis and/or degradation of one or more metabolite in the kynurenine pathway. In some embodiments, a metabolite of the kynurenine pathway is L-tryptophan, n-formylkynurenine, D and/or L-kynurenine, kynurenic acid, quinaldic acid, kynuramine, 3-hydroxy-L-kynurenine, 3-hydroxy-D-kynurenine, xanthommatin, anthranilic acid, xanthurenic acid, 3-hydroxy anthranilic acid, picolinioc acid, quinolinic acid and/or cinnabarinic acid.

In some embodiments, methods or assays to detect or determine the level, availability, concentration, effect, activity, metabolism, synthesis and/or degradation of metabolites or factors or effectors, e.g., enzymes, receptors or signaling molecules, involved in the kynurenine pathway includes any of the methods known in the art for detecting levels of metabolites, proteins, nucleic acids or other biomolecules in a biological sample. For example, the methods for detection include immunohistochemistry, ELISA, EIA, immunofluorescence, polymerase chain reaction (PCR), reverse transcriptase PCR (RT-PCR), in situ PCR, quantitative PCR, flow cytometry, fluorescence-activated cell sorting (FACS), enzymatic activity assays, gas chromatography/mass spectroscopy (GC/MS), high performance liquid chromatography (HPLC), liquid chromatography-dual mass spectrometry (LC-MS/MS), liquid chromatography-electrospray ionization-tandem mass spectrometry (LC-ESI-MS), nuclear magnetic resonance (NMR), in situ hybridization, Western blot, Northern blot, Southern blot, in vivo imaging, microarrays, transcriptome sequencing, and/or any high throughput methods known in the art.

In some embodiments, the metabolite levels can be determined using any techniques known in the art. For example, levels of TRP, KYN and/or KYN derivative from a biological sample can be determined using biosensors, optical devices coupled to enzymatic assays, biochips, analytical devices such as mass-spectrometers, NMR-analyzers, enzyme-linked immunosorbent assay (ELISA), radioimmunoassay or chromatography techniques such as high performance liquid chromatography (HPLC), liquid chromatography-dual mass spectrometry (LC-MS/MS), liquid chromatography-electrospray ionization-tandem mass spectrometry (LC-ESI-MS), fluorescence detection and/or spectrophotometric methods, including measuring spectroscopic absorbance after reacting with Ehrlich reagent (2% p-dimethylaminobenzaldehyde in glacial acetic acid). In some embodiments, the metabolite levels can be determined using HPLC. For example, in some embodiments, tryptophan and kynurenine levels can be determined by HPLC by comparing to an amino acid standard and/or an amino acid standard+kynurenine.

In some embodiments, the biological sample is a serum sample, plasma sample, tissue sample and/or a tumor sample, e.g., a tumor biopsy. In some embodiments, biological samples include, but are not limited to, body fluids, such as blood, plasma, serum, cerebrospinal fluid, synovial fluid, urine and sweat, tissue and organ samples or tumor samples including processed samples derived therefrom. In some embodiments, the biological sample includes isolated cells and/or tissue sections from a tumor biopsy. In some embodiments, assessments can be made in vivo, ex vivo or in vitro, and particular parameter can be determined from a biological sample or via in vivo imaging.

In some embodiments, tryptophan uptake by cells and intracellular tryptophan levels can be determined using a tryptophan-sensing fluorescence indicator protein (FLIP). In some embodiments, the FLIP includes a tryptophan sensing molecule based on tryptophan operon repressor derived from *Escherichia coli*, and includes a fluorescence resonance energy transfer (FRET) fluorophore pair. Binding of tryptophan to the FLIP results in a change in conformation and FRET ratio (see, e.g., Kaper et al. (2007) PLoS Biol 5(10): e257), thereby allowing detection of intracellular tryptophan levels.

In some aspects, detecting the expression levels includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more factors, effectors, enzymes and/or surface markers are detected by an enzyme linked immunosorbent assay (ELISA), immunoblotting, immunoprecipitation, radioimmunoassay (RIA), immuno staining, flow cytometry assay, surface plasmon resonance (SPR), chemiluminescence assay, lateral flow immunoassay, inhibition assay or avidity assay.

In some embodiments, the parameter for at least one of the one or more factors, effectors, enzymes and/or surface markers is determined using a binding reagent that specifically binds to at least one biomarker. In some cases, the binding reagent is an antibody or antigen-binding fragment thereof, an aptamer or a nucleic acid probe.

In some embodiments, enzymatic assays can be used to detect the levels of IDO1 in the biological a biological sample, e.g., a serum sample, plasma sample, tissue sample or a tumor sample. Exemplary enzymatic assays for IDO1 include 2,2-diphenyl-1-picrylhydrazyl (DPPH) antioxidant assay, menadione (2-methyl-1,4-naphthoquinone) redox assay or heme-based redox assays.

In some embodiments, the level of two or more factors or effectors, e.g., enzymes, and/or metabolites is determined, and relative levels are compared. In some embodiments, the determined level of enzyme, factor and/or metabolite is compared to the levels from a control sample or an untreated sample. In some embodiments, the determined level of enzyme, factor and/or metabolite is compared to the levels from a sample from the same subject but at a different time point. The values obtained in the quantification of individual enzymes or metabolites of the kynurenine pathways can be combined for the purpose of disease assessment, e.g., by forming an arithmetical or logical operation on the determine concentrations or by using multi-parametric analysis. In some embodiments, the parameter assessed is the plasma kynurenine/tryptophan ratio.

In some embodiments, the parameter assessed is a change and/or an alteration, e.g., an increase or a decrease relative to a different time point of assessment, in different conditions and/or compared to a reference point, of levels of metabolites of the kynurenine pathway, e.g., tryptophan and/or kynurenine, or factors or effectors, e.g., enzymes, receptors or signaling molecules, involved in the kynurenine pathway. For example, in some embodiments, the parameter assessed is a change in tryptophan levels, kynurenine levels and/or expression levels of IDO1, IDO2 and/or TDO. In some embodiments, the fold change in the increase or decrease is determined. In some embodiments, the change, e.g., an increase or decrease, in the levels of factors or effectors, e.g., enzymes, or metabolites in the kynurenine pathway is greater than or greater than about 1.2-fold, 1.5-fold, 2-fold, 3-fold, 4-fold, 5-fold, 10-fold or more. In some embodiments, any of the described parameters, e.g., expression level of IDO1, IDO2 and/or TDO or other biomarkers related to tryptophan, can be used among other parameters or biomarkers to assess or characterize the activity, phenotypes, proliferation and/or function of the T cells used for therapy, before, during or after engineering, correlate with treatment outcomes or toxicity outcomes, to identify or select patients for treatment, and/or to determine dosing or other treatment regimes.

In some embodiments, the parameters assessed include the expression and/or activity of amino acid transporters, e.g., tryptophan transporters, in the cancer, tumor or cells in the tumor microenvironment (TME). In some embodiments, the expression and/or activity of one or more amino acid transporters or chains thereof, e.g., L-type Amino Acid Transporter 1 (LAT1; SLC7A5), LAT2 (SLC7A8), CD98 heavy chain (4F2hc; CD98hc; SLC3A2) and/or proton-assisted amino-acid transporter 4 (PAT4; SLC36A4), are assessed. In some embodiments, the tumor cells or cancer cells in a biological sample obtained from the subject, express high levels of LAT1, LAT2, CD98hc and/or PAT4, or are positive for expression of LAT1, LAT2, CD98hc and/or PAT4. In some embodiments, other cells in the tumor microenvironment, e.g., bystander cells such as stromal cells or myeloid cells, also express high levels of LAT1, LAT2, CD98hc and/or PAT4. In some embodiments, bone marrow stromal cells, dendritic cells and/or macrophages can express high levels of LAT1, LAT2, CD98hc and/or PAT4.

In some embodiments, subjects for treatment with the methods, cells, compositions and/or kits described herein, such as with recombinant receptor-expressing cells (e.g. CAR T cells) that are modified in expression of a molecule (e.g. protein) involved in IDO-mediated immunosuppressive signaling, associated with sensing or responding to tryptophan starvation or insufficiency and/or associated with sensing or responding to kynurenine-mediated immuno-suppression, including molecules that are positively or negatively regulated by IDO-mediated catabolism, e.g. an insufficiency in tryptophan or an accumulation of kynurenine or another tryptophan metabolite, can be identified or selected based on such parameters. For example, in some embodiments, subjects that tumor cells or cancer cells expressing high levels of LAT1, LAT2, CD98hc and/or PAT4, or are positive for expression of LAT1, LAT2, CD98hc and/or PAT4, can be administered recombinant receptor-expressing cells that are also modified to recombinantly express a molecule (e.g., a protein) involved in tryptophan uptake, transport and/or metabolism, e.g., LAT1, LAT2, CD98hc and/or PAT4.

2 T Cell Exposure, Persistence and Proliferation

In some embodiments, the parameter associated with therapy or a treatment outcome, which include parameters that can be assessed for the screening steps and/or assessment of treatment of outcomes and/or monitoring treatment outcomes, is or includes assessment of the exposure, persistence and proliferation of the T cells, e.g., T cells administered for the T cell based therapy. In some embodiments, the increased exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells used for the immunotherapy, e.g. T cell therapy, before or after administering one or more steps of the combination therapy provided herein.

In some embodiments, the administration of the tryptophan metabolism and/or kynurenine pathway modulator, e.g. IDO1 inhibitor, are designed to promote exposure of the subject to the cells, e.g., T cells administered for T cell based therapy, such as by promoting their expansion and/or persistence over time, e.g. by overcoming the immunosuppressive effects or conditions in the tumor microenvironment (TME).

In some embodiments, the T cell therapy exhibits increased or prolonged expansion and/or persistence in the subject as compared to a method in which the T cell therapy is administered to the subject in the absence of the tryptophan metabolism and/or kynurenine pathway modulator, e.g., IDO1 inhibitor.

In some embodiments, the provided methods increase exposure of the subject to the administered cells (e.g., increased number of cells or duration over time) and/or improve activity and therapeutic outcomes of the immunotherapy, e.g. T cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the administration of the tryptophan metabolism and/or kynurenine pathway modulator, e.g., IDO1 inhibitor, can increase the maximum, total, and/or duration of exposure to the cells, e.g. T cells administered for the T cell based therapy, in the subject as compared to administration of the T cells alone in the absence of the tryptophan metabolism and/or kynurenine pathway modulator. In some aspects, administration of the tryptophan metabolism and/or kynurenine pathway modulator, e.g., IDO1 inhibitor, in the context of high disease burden (and thus higher amounts of antigen) enhances activity as compared with administration of the T cells alone in the absence of the tryptophan metabolism and/or kynurenine pathway modulator in the same context, which may result in immunosuppression, anergy and/or exhaustion which may prevent expansion and/or persistence of the cells. In some embodiments, administering the tryptophan metabolism and/or kynurenine pathway modulator, e.g. IDO1 inhibitor, in the context of high disease burden reduces exhaustion of the administered cells, thereby increasing clinical activity as compared to other methods, such as those where a higher initial dose is administered.

In some embodiments, the presence and/or amount of cells expressing the recombinant receptor (e.g., CAR-expressing cells administered for T cell based therapy) in the subject following the administration of the T cells and before, during and/or after the administration of the tryptophan metabolism and/or kynurenine pathway modulator, is detected. In some aspects, quantitative PCR (qPCR) is used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the T cells, e.g., CAR-expressing T cells. In some aspects, the cells are detected at or at least at 2, 4, or 6 weeks following, or 3, 6, or 12, 18, or 24, or 30 or 36 months, or 1, 2, 3, 4, 5, or more years, following the administration of the T cells, e.g., CAR-expressing T cells and/or the tryptophan metabolism and/or kynurenine pathway modulator.

In some embodiments, the persistence of receptor-expressing cells (e.g. CAR-expressing cells) in the subject by the methods, following the administration of the T cells, e.g., CAR-expressing T cells and/or the tryptophan metabolism and/or kynurenine pathway modulator, is greater as compared to that which would be achieved by alternative methods such as those involving the administration of the immunotherapy alone, e.g., administration the T cells, e.g., CAR-expressing T cells, in the absence of the kynurenine modulator The exposure, e.g., number of cells, e.g. T cells administered for T cell therapy, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some embodiments, the assessment of the presence and/or amount of T cells administered in the T cell therapy includes assessment of the presence and/or amount of T cells in or near the tumor site, e.g., in the tumor microenvironment (TME). In some embodiments, the assessment involves determining the presence and/or amount of the administered T cells that infiltrate the tumor, e.g., a solid tumor. In some embodiments, the presence and/or amount of the administered T cells is assessed from a biological sample from a subject, e.g., body fluids, such as blood, plasma, serum, cerebrospinal fluid, synovial fluid, urine and sweat, tissue and organ samples or tumor samples including processed samples derived therefrom. In some embodiments, the biological sample includes isolated cells and/or tissue sections from a tumor biopsy. In some embodiments, the assessment of the presence and/or amount of T cells administered in the T cell therapy includes assessment of the presence and/or amount of administered T cells that infiltrate the tumor, in a sample of isolated cells and/or tissue sections from a tumor biopsy.

In some aspects, increased exposure of the subject to the cells includes increased expansion of the cells. In some embodiments, the receptor expressing cells, e.g. CAR-expressing cells, expand in the subject following administration of the T cells, e.g., CAR-expressing T cells, and/or following administration of tryptophan metabolism and/or kynurenine pathway modulator, e.g., IDO1 inhibitor. In some aspects, the methods result in greater expansion of the cells compared with other methods, such as those involving the administration of the T cells, e.g., CAR-expressing T cells, in the absence of administering the tryptophan metabolism and/or kynurenine pathway modulator, e.g., IDO1 inhibitor.

In some aspects, the method results in high in vivo proliferation of the administered cells, for example, as measured by flow cytometry. In some aspects, high peak proportions of the cells are detected. For example, in some embodiments, at a peak or maximum level following the administration of the T cells, e.g., CAR-expressing T cells and/or the tryptophan metabolism and/or kynurenine pathway modulator, in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR, per microgram of DNA, or at least 0.1, 0.2, 0.3, 0.4, 0.5, 0.6, 0.7, 0.8, or 0.9 receptor-expressing, e.g., CAR-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the T cells, e.g., CAR-expressing T cells and/or the tryptophan metabolism and/or kynurenine pathway modulator or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject.

In some embodiments, cells expressing the receptor are detectable in the serum, plasma, blood or tissue, e.g., tumor sample, of the subject, e.g., by a specified method, such as qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the T cells, e.g., CAR-expressing T cells, or after administration of the tryptophan metabolism and/or kynurenine pathway modulator, e.g., IDO1 inhibitor, for at least at or about 2, 3, 4, 5, 6, 7, 8, 9, 10, 11, 12, 13, 14, 15, 16, 17, 18, 19, 20, 21, 22, 23, or 24 or more weeks following the administration of the T cells, e.g., CAR-expressing T cells, and/or the tryptophan metabolism and/or kynurenine pathway modulator, e.g., IDO1 inhibitor.

In some aspects, at least about $1 \times 10^2$, at least about $1 \times 10^3$, at least about $1 \times 10^4$, at least about $1 \times 10^5$, or at least about $1 \times 10^6$ or at least about $5 \times 10^6$ or at least about $1 \times 10^7$ or at least about $5 \times 10^7$ or at least about $1 \times 10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, plasma, serum, tissue, or compartment thereof, such as in the blood, e.g., peripheral blood, or disease site, e.g., tumor, thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the T cells, e.g., CAR-expressing T cells, and/or following the administration of the tryptophan metabolism and/or kynurenine pathway modulator, e.g., IDO1 inhibitor. Such cell numbers may be as detected by flow cytometry-based or quantitative PCR-based methods and extrapolation to total cell numbers using known methods. See, e.g., Brentjens et al., *Sci Transl Med.* 2013 5 (177), Park et al, Molecular Therapy 15(4):825-833 (2007), Savoldo et al., *JCI* 121(5): 1822-1826 (2011), Davila et al., (2013) *PLoS ONE* 8(4): e61338, Davila et al., *Oncoimmunology* 1(9):1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8. 9, 10, 11, or 12 months or at least 2 or 3 years following administration of the cells, e.g., CAR-expressing T cells, and/or the tryptophan metabolism and/or kynurenine pathway modulator, e.g., IDO1 inhibitor. In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the T cells, e.g., CAR-expressing T cells, or tryptophan metabolism and/or kynurenine pathway modulator, e.g., IDO1 inhibitor, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, plasma, serum, blood, tissue and/or disease site thereof, e.g., tumor site, at a time that is at least about 3 months, at least about 6 months, at least about 12 months, at least about 1 year, at least about 2 years, at least about 3 years, or more than 3 years, following the administration of the cells, e.g., following the initiation of the administration of the T cells, e.g., CAR-expressing T cells, and/or the tryptophan metabolism and/or kynurenine pathway modulator, e.g., IDO1 inhibitor.

In some embodiments, the area under the curve (AUC) for concentration of receptor- (e.g., CAR-) expressing cells in a fluid, plasma, serum, blood, tissue, organ and/or disease site, e.g. tumor site, of the subject over time following the administration of the T cells, e.g., CAR-expressing T cells and/or following the administration of the tryptophan metabolism and/or kynurenine pathway modulator, e.g., IDO1 inhibitor, is greater as compared to that achieved via an alternative dosing regimen where the subject is administered the T cells, e.g., CAR-expressing T cells, in the absence of administering tryptophan metabolism and/or kynurenine pathway modulator, e.g., IDO1 inhibitor.

In some aspects, the method results in high in vivo proliferation of the administered cells, for example, as measured by flow cytometry. In some aspects, high peak proportions of the cells are detected. For example, in some embodiments, at a peak or maximum level following the T cells, e.g., CAR-expressing T cells and/or tryptophan metabolism and/or kynurenine pathway modulator, e.g., IDO1 inhibitor, in the blood, plasma, serum, tissue or disease site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

3. T Cell Functional Activity

In some embodiments, parameters associated with therapy or a treatment outcome, which include parameters that can be assessed for the screening steps and/or assessment of treatment of outcomes and/or monitoring treatment outcomes, includes one or more of activity, phenotype, proliferation or function of T cells. In some embodiments, any of the known assays in the art for assessing the activity, phenotypes, proliferation and/or function of the T cells, e.g., T cells administered for T cell therapy, can be used. Prior to and/or subsequent to administration of the cells and/or a tryptophan metabolism and/or kynurenine pathway modulator, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al., J. Immunological Methods, 285(1): 25-40 (2004). In certain embodiments, the biological activity of the cells is measured by assaying expression and/or secretion of one or more cytokines, such as CD107a, IFNγ, IL-2, GM-CSF and TNFα, and/or by assessing cytolytic activity.

In some embodiments, assays for the activity, phenotypes, proliferation and/or function of the T cells, e.g., T cells administered for T cell therapy include, but are not limited to, ELISPOT, ELISA, cellular proliferation, cytotoxic lymphocyte (CTL) assay, binding to the T cell epitope, antigen or ligand, or intracellular cytokine staining, proliferation assays, lymphokine secretion assays, direct cytotoxicity assays, and limiting dilution assays. In some embodiments, proliferative responses of the T cells can be measured, e.g. by incorporation of $^3$H-thymidine, BrdU (5-Bromo-2'-Deoxyuridine) or 2'-deoxy-5-ethynyluridine (EdU) into their DNA or dye dilution assays, using dyes such as carboxyfluorescein diacetate succinimidyl ester (CFSE), CellTrace Violet, or membrane dye PKH26.

In some embodiments, assessing the activity, phenotypes, proliferation and/or function of the T cells, e.g., T cells administered for T cell therapy, include measuring cytokine production from T cells, and/or measuring cytokine production in a biological sample from the subject, e.g., plasma, serum, blood, and/or tissue samples, e.g., tumor samples. In some cases, such measured cytokines can include, without limitation, interlekukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample.

In some embodiments, assessing the activity, phenotypes, proliferation and/or function of the T cells, e.g., T cells administered for T cell therapy, include assessing cell phenotypes, e.g., expression of particular cell surface markers. In some embodiments, the T cells, e.g., T cells administered for T cell therapy, are assessed for expression of T cell activation markers, T cell exhaustion markers, and/or T cell differentiation markers. In some embodiments, the cell phenotype is assessed before administration. In some embodiments, the cell phenotype is assessed after administration. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, CD62L$^{low}$, CCR7$^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some aspects, detecting the expression levels includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more factors, effectors, enzymes and/or surface markers are detected by an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, detection of cytokines and/or surface markers is determined using a binding reagent that specifically binds to at least one biomarker. In some cases, the binding reagent is an antibody or antigen-binding fragment thereof, an aptamer or a nucleic acid probe.

In some embodiments, the activity, phenotypes, proliferation and/or function of the engineered cells, e.g., in combination therapy and/or cells engineered to comprise a modification of expression of a protein associated with IDO-mediated immunosuppressive signaling, associated with sensing or responding to tryptophan starvation or insufficiency and/or associated with sensing or responding to kynurenine-mediated immuno-suppression in the cells, such as in response to a shortage or insufficiency of tryptophan or an accumulation of kynurenine or other tryptophan metabolite, and/or is involved in tryptophan uptake or transport into the cells, can also be assessed using similar assays, e.g., functional assays and/or in vitro assays, described above. In some embodiments, the activity, phenotypes, proliferation and/or function of the engineered cells can be tested after culturing in tryptophan-containing media, with or without addition of supplemental tryptophan, or in tryptophan-free media, with or without addition of supplemental tryptophan. In some embodiments, the assays can be performed after culturing in low tryptophan conditions or tryptophan starvation conditions, or in tryptophan-free media.

In some embodiments, assessment of one or more of activity, phenotype, proliferation or function of T cells includes assessment of the response to amino acid starvation, e.g., tryptophan depletion or tryptophan starvation. In some embodiments, assessment of the activity, phenotype, proliferation or function of T cells includes assessment of exhaustion, anergy or cell death of effector T cells, suppression of antitumor immune responses or tolerance to tumor antigens, functional activity and/or survival, in response to tryptophan depletion and/or tryptophan starvation. In some embodiments, assessment of the activity, phenotype, proliferation or function of T cells includes assessment of the T cell under prolonged tryptophan starvation, such as under tryptophan starvation conditions that may affect the T cell's ability to recover from starvation and/or reverse the effect of starvation, e.g., delay or arrest in growth and/or functional activity. In some embodiments, assessment of one or more of activity, phenotype, proliferation or function of T cells includes assessment of recovery from, or reversal of, the effect of tryptophan starvation, e.g., prolonged tryptophan starvation. In some embodiments, recovery from tryptophan starvation includes recovery of baseline or steady state T cell activity, e.g., as assessed by any T cell functional assays described herein.

4. Disease Burden

In some embodiments, parameters associated with therapy or a treatment outcome, which include parameters that can be assessed for the screening steps and/or assessment of treatment of outcomes and/or monitoring treatment outcomes, includes tumor or disease burden. The administration of the immunotherapy, such as a T cell therapy (e.g. CAR-expressing T cells) or a T cell-engaging therapy and/or the tryptophan metabolism and/or kynurenine pathway modulator, can reduce or prevent the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden. In some embodiments, administration of the tryptophan metabolism and/or kynurenine pathway modulator, e.g., IDO1 inhibitor, is timed with respect to a decrease in burden and/or relapse following the administration of the immunotherapy, such as a T cell therapy (e.g. CAR-expressing T cells) or a T cell-engaging therapy.

In some embodiments, the tryptophan metabolism and/or kynurenine pathway modulator, e.g., IDO1 inhibitor, is administered to the subject at a time after the administration of the immunotherapy, such as a T cell therapy (e.g. CAR-expressing T cells) or a T cell-engaging therapy, in which it is likely that tumor burden of the subject has been reduced by the administration of the immunotherapy, e.g. T cell therapy. In some embodiments, the immunotherapy, such as a T cell therapy (e.g. CAR-expressing T cells) or a T cell-engaging therapy is administered to the subject at a time after the administration of the tryptophan metabolism and/or kynurenine pathway modulator, e.g., IDO1 inhibitor, in which it is likely that tumor burden of the subject has been reduced by the administration of the tryptophan metabolism and/or kynurenine pathway modulator, e.g., IDO1 inhibitor. In some embodiments, it is not necessary that the tumor burden actually be reduced in all subjects prior to administration of the immunotherapy, such as a T cell therapy (e.g. CAR-expressing T cells) or a T cell-engaging therapy and/or tryptophan metabolism and/or kynurenine pathway modulator, e.g., IDO1 inhibitor, but that tumor burden is reduced on average in subjects treated, such as based on clinical data, in which a majority of subjects treated with such a combination therapy exhibit a reduced tumor burden, such as at least 50%, 60%, 70%, 80%, 90%, 95% or more of subjects treated with the combination therapy, exhibit a reduced tumor burden.

In some embodiments, at a point in time after disease burden has been reduced by the immunotherapy, e.g. T cell therapy, or is likely to have been reduced by the immunotherapy, e.g. T cell therapy, a tryptophan metabolism and/or kynurenine pathway modulator, e.g., IDO1 inhibitor, is administered to the subject, thereby further reducing and/or eliminating disease or a symptom or outcome thereof or preventing expansion or progression thereof, by virtue of enhancing survival, proliferation and/or expansion of the administered T cells. In some embodiments, at a point in time after disease burden has been reduced by administration of the tryptophan metabolism and/or kynurenine pathway modulator, e.g., IDO1 inhibitor, or is likely to have been reduced by the administration of the tryptophan metabolism and/or kynurenine pathway modulator, e.g., IDO1 inhibitor, a tryptophan metabolism and/or kynurenine pathway modulator, e.g., IDO1 inhibitor, the immunotherapy, such as a T cell therapy (e.g. CAR-expressing T cells) or a T cell-engaging therapy, is administered to the subject, thereby further reducing and/or eliminating disease or a symptom or outcome thereof or preventing expansion or progression thereof, by virtue of enhancing survival, proliferation and/or expansion of the administered T cells. The context of reduced disease burden at the time of the administration of the immunotherapy, such as a T cell therapy (e.g. CAR-expressing T cells) or a T cell-engaging therapy and/or the tryptophan metabolism and/or kynurenine pathway modulator, e.g., IDO1 inhibitor, in some aspects reduces the likelihood of exhaustion of the administered cells, e.g., CAR-expressing T cells, thereby improving activity.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood, lymph or bone marrow in the context of certain hematological malignancies. Disease burden can include, in some embodiments, the mass of a tumor, the number or extent of metastases and/or the percentage of blast cells present in the bone marrow.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. In some embodiments, the subject has a myeloma, a lymphoma or a leukemia. In some embodiments, the subject has a non-Hodgkin lymphoma (NHL), an acute lymphoblastic leukemia (ALL), a chronic lymphocytic leukemia (CLL), a diffuse large B-cell lymphoma (DLBCL) or a myeloma, e.g., a multiple myeloma (MM). In some embodiments, the subject has a MM or a DBCBL. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM).

In some embodiments, the subject has a solid tumor.

In the case of MM, exemplary parameters to assess the extent of disease burden include such parameters as number of clonal plasma cells (e.g., >10% on bone marrow biopsy or in any quantity in a biopsy from other tissues; plasmacytoma), presence of monoclonal protein (paraprotein) in either serum or urine, evidence of end-organ damage felt related to the plasma cell disorder (e.g., hypercalcemia (corrected calcium >2.75 mmol/1); renal insufficiency attributable to myeloma; anemia (hemoglobin <10 g/dl); and/or bone lesions (lytic lesions or osteoporosis with compression fractures)).

In the case of DLBCL, exemplary parameters to assess the extent of disease burden include such parameters as cellular morphology (e.g., centroblastic, immunoblastic, and anaplastic cells), gene expression, miRNA expression and protein expression (e.g., expression of BCL2, BCL6, MUM1, LMO2, MYC, and p21).

In the case of leukemia, the extent of disease burden can be determined by assessment of residual leukemia in blood or bone marrow. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, for leukemia, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD$^-$, such that, in some cases, no leukemia cells are able to be detected in the subject using PCR or flow cytometry techniques.

In some embodiments, the methods and/or administration of an immunotherapy, such as a T cell therapy (e.g. CAR-expressing T cells) or a T cell-engaging therapy and/or tryptophan metabolism and/or kynurenine pathway modulator, e.g., IDO1 inhibitor, decrease(s) disease burden as compared with disease burden at a time immediately prior to the administration of the immunotherapy, e.g., T cell therapy and/or tryptophan metabolism and/or kynurenine pathway modulator, e.g., IDO1 inhibitor. In some aspects, administration of the immunotherapy, e.g. T cell therapy, reduces disease burden, e.g. tumor burden. In some embodiments, the tryptophan metabolism and/or kynurenine pathway modulator, e.g., IDO1 inhibitor, effects a reduction, e.g., a further reduction, in disease burden.

In some aspects, administration of the tryptophan metabolism and/or kynurenine pathway modulator, e.g., IDO1 inhibitor, reduces disease burden, e.g. tumor burden. In some embodiments, administration of the immunotherapy, e.g. T cell therapy, the effects a reduction, e.g., a further reduction, in disease burden.

In some aspects, administration of the immunotherapy, e.g. T cell therapy and/or tryptophan metabolism and/or kynurenine pathway modulator, e.g., IDO1 inhibitor, may prevent an increase in disease burden, and this may be evidenced by no change in disease burden.

In some aspects, the disease or condition persists following administration of the immunotherapy, e.g. T cell therapy and/or administration of the immunotherapy, e.g. T cell therapy, is not sufficient to eradicate the disease or condition in the subject.

In some aspects, administration of the immunotherapy, e.g. T cell therapy and/or tryptophan metabolism and/or kynurenine pathway modulator, e.g., IDO1 inhibitor, reduces disease burden as compared to disease burden at a time immediately prior to the administration of immunotherapy, e.g. T cell therapy, or at a time immediately prior to the tryptophan metabolism and/or kynurenine pathway modulator, e.g., IDO1 inhibitor. In some aspects, for example in the context of relapse, administration of the tryptophan metabolism and/or kynurenine pathway modulator, e.g., IDO1 inhibitor, effects a reduction in disease burden as compared to the peak level of disease burden following administration of the immunotherapy, e.g. T cell therapy.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative therapy, such as one in which the subject receives immunotherapy, e.g. T cell therapy alone, in the absence of administration of the tryptophan metabolism and/or kynurenine pathway modulator, e.g., IDO1 inhibitor. In some embodiments, disease burden is reduced to a greater extent or for a greater duration following the combination therapy of administration of the immunotherapy, e.g., T cell therapy, and the tryptophan metabolism and/or kynurenine pathway modulator, e.g., IDO1 inhibitor, compared to the reduction that would be effected by administering each of the agent alone, e.g., administering the tryptophan metabolism and/or kynurenine pathway modulator, e.g., IDO1 inhibitor, to a subject having not received the immunotherapy, e.g. T cell therapy; or administering the immunotherapy, e.g. T cell therapy, to a subject having not received the tryptophan metabolism and/or kynurenine pathway modulator, e.g., IDO1 inhibitor.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified. In some embodiments, exemplary parameters for determination include particular clinical outcomes indicative of amelioration or improvement in the disease or condition, e.g., tumor. Such parameters include: duration of disease control, including complete response (CR), partial response (PR) or stable disease (SD) (see, e.g., Response Evaluation Criteria In Solid Tumors (RECIST) guidelines), objective response rate (ORR), progression-free survival (PFS) and overall survival (OS). Specific thresholds for the parameters can be set to determine the activity of the method of combination therapy provided herein.

In some aspects, disease burden is measured or detected prior to administration of the immunotherapy, e.g. T cell therapy, following the administration of the immunotherapy, e.g. T cell therapy but prior to administration of the tryptophan metabolism and/or kynurenine pathway modulator, e.g., IDO1 inhibitor, following administration of the tryptophan metabolism and/or kynurenine pathway modulator, e.g., IDO1 inhibitor but prior to the administration of the immunotherapy, e.g., T cell therapy, and/or following the administration of both the immunotherapy, e.g. T cell therapy and the tryptophan metabolism and/or kynurenine pathway modulator, e.g., IDO1 inhibitor. In the context of multiple administration of one or more steps of the combination therapy, disease burden in some embodiments may be measured prior to or following administration of any of the steps, doses and/or cycles of administration, or at a time between administration of any of the steps, doses and/or cycles of administration.

In some embodiments, the burden is decreased by or by at least at or about 10, 20, 30, 40, 50, 60, 70, 80, 90, or 100 percent after administration of the immunotherapy, e.g. T cell therapy. In some aspects, administration of the tryptophan metabolism and/or kynurenine pathway modulator, e.g., IDO1 inhibitor, effects a further reduction in disease burden, e.g. tumor burden, such as at or about 10, 20, 30, 40, 50, 60, 70, 80, 90, or 100 percent decrease in burden compared to immediately prior to the administration of the tryptophan metabolism and/or kynurenine pathway modulator, e.g., IDO1 inhibitor, or overall compared to immediately prior to the immunotherapy, e.g. T cell therapy. In some embodiments, the burden is decreased by or by at least at or about 10, 20, 30, 40, 50, 60, 70, 80, 90, or 100 percent after administration of the tryptophan metabolism and/or kynurenine pathway modulator, e.g., IDO1 inhibitor. In some aspects, administration of the immunotherapy, e.g. T cell therapy, effects a further reduction in disease burden, e.g. tumor burden, such as at or about 10, 20, 30, 40, 50, 60, 70, 80, 90, or 100 percent decrease in burden compared to immediately prior to the administration of the immunotherapy, e.g. T cell therapy, or overall compared to immediately prior to the tryptophan metabolism and/or kynurenine pathway modulator, e.g., IDO1 inhibitor.

In some embodiments, disease burden, tumor size, tumor volume, tumor mass, and/or tumor load or bulk is reduced following the immunotherapy, e.g. T cell therapy and/or the tryptophan metabolism and/or kynurenine pathway modulator, e.g., IDO1 inhibitor, by at least at or about 10, 20, 30, 40, 50, 60, 70, 80, 90% or more compared to that immediately prior to the administration of the immunotherapy, e.g. T cell therapy, or the tryptophan metabolism and/or kynurenine pathway modulator, e.g., IDO1 inhibitor.

In some embodiments, reduction of disease burden by the method comprises an induction in morphologic complete remission, for example, as assessed at 1 month, 2 months, 3 months, or more than 3 months, after administration of, e.g., initiation of, the combination therapy.

In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the method of combination therapy provided herein, is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the method of combination therapy, is less than about 80%, less than about 70%, less than about 60%, less than about 50%, less than about 40%, less than about 30%, less than about 20%, or less than about 10%.

In some aspects, reduction of disease burden, e.g. debulking of the tumor, following the administration of the combination therapy, reduces toxicity or toxic outcomes following the administration. Toxic outcomes following a reduction in tumor burden can be assessed using any of the methods known in the art.

In some aspects, reduction of disease burden, e.g. debulking of the tumor, resulting from the present methods improves the persistence of the cells, e.g. T cells administered for immunotherapy, e.g. T cell therapy, in the subject. For example, in some aspects, administration of the combination therapy, e.g., administration of the immunotherapy, such as a T cell therapy (e.g. CAR-expressing T cells) or a T cell-engaging therapy and the tryptophan metabolism and/or kynurenine pathway modulator, e.g., IDO1 inhibitor, reduces disease burden, e.g. tumor burden, such that the cells administered in the combination therapy, persist for longer than cells treated using other methods of therapy, such as administering the immunotherapy, such as a T cell therapy (e.g. CAR-expressing T cells) or a T cell-engaging therapy alone, in the absence of administering the tryptophan metabolism and/or kynurenine pathway modulator.

In some aspects, the increased or prolonged expansion and/or persistence of the dose of cells in the subject administered with the tryptophan metabolism and/or kynurenine pathway modulator, e.g., IDO1 inhibitor, is associated with a benefit in tumor related outcomes in the subject. In some embodiments, the tumor related outcome includes a decrease in tumor burden or a decrease in blast marrow in the subject. In some embodiments, the tumor burden is decreased by or by at least at or about 10, 20, 30, 40, 50, 60, 70, 80, 90, or 100 percent after administration of the method. In some embodiments, disease burden, tumor size, tumor volume, tumor mass, and/or tumor load or bulk is reduced following the dose of cells by at least at or about 50%, 60%, 70%, 80%, 90% or more compared a subject that has been treated with a method that does not involve the administration of a tryptophan metabolism and/or kynurenine pathway modulator, e.g., IDO1 inhibitor.

IV. T CELL THERAPY AND ENGINEERING CELLS

In some embodiments, the T cell therapy for use in accord with the provided combination therapy methods includes administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or $CD8^+$ or $CD4^+$ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments as described, the cells are further engineered to comprise a modification of expression of a protein associated with IDO-mediated immunosuppressive signaling, associated with sensing or responding to tryptophan starvation or insufficiency and/or associated with sensing or responding to kynurenine-mediated immuno-suppression in the cells, such as in response to a shortage or insufficiency of tryptophan or an accumulation of kynurenine or other tryptophan metabolite, and/or is involved in tryptophan uptake or transport into the cells. In some embodiments, the modification comprises recombinant, engineered and/or ectopic expression of a molecule or a functional or catalytically active portion or variant thereof involved in IDO-mediated immunosuppressive signaling, associated with sensing or responding to tryptophan starvation or insufficiency and/or associated with sensing or responding to kynurenine-mediated immuno-suppression, such as recombinant, engineered and/or ectopic expression of mTOR or protein kinase C theta (PKC-Θ) or a functional or catalytically active portion or variant thereof. In some embodiments, the modification comprises recombinant, engineered and/or ectopic expression of a molecule or a functional or catalytically active portion or variant thereof involved in tryptophan uptake or transport into the cells, e.g., one or more amino acid transporters.

In some embodiments, the modifications comprises reduced expression of a molecule or a functional or catalytically active portion or variant thereof involved in IDO-mediated immunosuppressive signaling, associated with sensing or responding to tryptophan starvation or insufficiency and/or associated with sensing or responding to kynurenine-mediated immuno-suppression in the engineered cells, such as reduced expression of GCN2 kinase, Blimp-1 (PRDM1), aryl hydrocarbon receptor (AHR) or AHR nuclear transporter (ARNT) or a functional or catalytically active portion or variant thereof. In some cases, reduced expression is due to or a result of disrupted gene expression of the protein. In some aspects, expression is reduced by at least 50, 60, 70, 80, 90, or 95% as compared to the expression in the cell in the absence of the modification.

A. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors. In some embodiments, other chimeric receptors include chimeric autoantibody receptors (CAARs), such as any described in U.S. Patent Application Pub. No. US 2017/0051035.

1. Chimeric Antigen Receptors (CARS)

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov., 3(4): 388-398 (2013); Davila et al., PLoS ONE 8(4): e61338 (2013); Turtle et al., Curr. Opin. Immunol., 24(5): 633-39 (2012); Wu et al., Cancer, 18(2): 160-75 (2012). In some aspects, the antigen receptors include a CAR as described in U.S. Pat. No. 7,446,190, and those described in International Patent Application Publication No. WO/2014055668 A1. Examples of the CARs include CARs as disclosed in any of the aforementioned publications, such as WO2014031687, U.S. Pat. Nos. 8,339, 645, 7,446,179, US 2013/0149337, U.S. Pat. Nos. 7,446, 190, 8,389,282, Kochenderfer et al., Nature Reviews Clinical Oncology, 10, 267-276 (2013); Wang et al., J. Immunother. 35(9): 689-701 (2012); and Brentjens et al., Sci Transl Med. 5(177) (2013). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a $C_H1/C_L$ and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to $C_H2$ and $C_H3$ domains, or IgG4 hinge linked to the CH3 domain. Exemplary spacers include, but are not limited to, those described in Hudecek et al., Clin. Cancer Res., 19:3153 (2013), international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD 134, CD137, or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25 or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker and/or cells expressing the CAR or other antigen receptor further includes a surrogate marker, such as a cell surface marker, which may be used to confirm transduction or engineering of the cell to express the receptor, such as a truncated version of a cell surface receptor, such as truncated EGFR (tEGFR). In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7. An exemplary T2A linker sequence comprises the sequence of amino acids set forth in SEQ ID NO: 6 or 45 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 45.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant or a portion thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant or a portion thereof, and an intracellular signaling domain containing a signaling portion of CD28 or functional variant or a portion thereof and a signaling portion of CD3 zeta or functional variant or a portion thereof. In some embodiments, the CAR contains an antibody, e.g., antibody fragment, a transmembrane domain that is or contains a transmembrane portion of CD28 or a functional variant or a portion thereof, and an intracellular signaling domain containing a signaling portion of a 4-1BB or functional variant or a portion thereof and a signaling portion of CD3 zeta or functional variant or a portion thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or a portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant or a portion thereof, such as an 112 AA cytoplasmic domain of isoform 3 of human CD3ζ (Accession No. P20963.2) or a CD3 zeta signaling domain as described in U.S. Pat. No. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 45, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 45. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

2. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al., (2003) *Nat Immunol*, 4, 55-62; Holler et al., (2000) *Proc Natl Acad Sci USA,* 97, 5387-92), phage display (Li et al., (2005) *Nat Biotechnol*, 23, 349-54), or T cell display (Chervin et al., (2008) *J Immunol Methods,* 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models known to those of skill in the art. In some embodiments, for predicting MHC class I binding sites, such models include, but are not limited to, ProPred1 (Singh and Raghava (2001) *Bioinformatics* 17(12):1236-1237, and SYFPEITHI (see Schuler et al., (2007) *Immunoinformatics Methods in Molecular Biology,* 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class I binding sites, such models include, but are not limited to, ProPred1 (described in more detail in Singh and Raghava, ProPred: prediction of HLA-DR binding sites. *BIOINFORMATICS* 17(12):1236-1237 2001), and SYFPEITHI (see Schuler et al., SYFPEITHI, Database for Searching and T-Cell Epitope Prediction. in *Immunoinformatics Methods in Molecular Biology*, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, See e.g., Soo Hoo, W. F. et al., *PNAS (USA)* 89, 4759 (1992); Wülfing, C. and Plückthun, A., *J. Mol. Biol.* 242, 655 (1994); Kurucz, I. et al., *PNAS (USA)* 90 3830 (1993); International published PCT Nos. WO 96/13593, WO 96/18105, WO99/60120, WO99/18129, WO 03/020763, WO2011/044186; and Schlueter, C. J. et al., *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO: 16). In some embodiments, the linker has the sequence GSADDAKKDAAKKDGKS (SEQ ID NO: 17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about $10^{-5}$ and $10^{-12}$ M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in PCT Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptors include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or activity may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or activity is achieved.

B. Cells and Preparation of Cells for Genetic Engineering

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of $CD4^+$ and/or of $CD8^+$ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MALT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase one or more post-administration parameters or outcomes, such as to improve long-term survival, expansion, and/or engraftment following administration, which in some aspects is particularly robust in such sub-populations. See Terakura et al., *Blood.* 1:72-82 (2012); Wang et al., *J Immunother.* 35(9):689-701 (2012). In some embodiments, combining TCM-enriched CD8+ T cells and CD4+ T cells further enhances one or more post-administration parameters or outcomes.

In embodiments, memory T cells are present in both CD62L+ and CD62L- subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L- and CD45RO-.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in PCT Pub. Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al., *J Immunother.* 35(9): 651-660 (2012), Terakura et al., *Blood.* 1:72-82 (2012), and Wang et al., *J Immunother.* 35(9):689-701 (2012).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al., *Lab Chip* 10, 1567-1573 (2010); and Godin et al., *J Bio-* photon. 1(5):355-376 (2008). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al., *J Immunother.* 35(9): 651-660 (2012), Terakura et al., *Blood.* 1:72-82 (2012), and/or Wang et al., *J Immunother.* 35(9):689-701 (2012).

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4$^+$ and/or CD8$^+$ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Modified Expression of Molecules Associated with Immunosuppressive Signaling

In some aspects, provided are genetically engineered cells, including recombinant receptor-expressing cells (e.g. CAR T cells) that are modified in expression of a molecule (e.g. protein) involved in IDO-mediated immunosuppressive signaling, associated with sensing or responding to tryptophan starvation or insufficiency and/or associated with sensing or responding to kynurenine-mediated immuno-suppression, including molecules that are positively or negatively regulated by IDO-mediated catabolism, e.g. an insufficiency in tryptophan or an accumulation of kynurenine or another tryptophan metabolite. In some aspects, modification involves expression of a molecule (e.g., a protein) involved in tryptophan uptake, transport and/or metabolism.

In some embodiments, the molecule is a molecule that is negatively regulated by IDO-mediated catabolism, such as a molecule whose expression or activity is reduced or inhibited in response to IDO-mediated immunosuppressive signaling, to tryptophan starvation or insufficiency and/or to kynurenine-mediated immuno-suppression, which reduced expression or activity leads to, is involved or associated with or facilitates immunosuppressive activity of the cell. Exemplary of such proteins include, but are not limited to, mTOR and PKC theta, which are proteins that are inhibited in response to IDO-mediated catabolism (see e.g. Metz et al. (2012) Oncoimmunology, 1:1460-1468). Other examples include amino acid transporters, such as L-type amino acid transporters (LATs), which are involved in uptake of amino acid nutrients from the environment (Wang et al. (2015) Am J Cancer Res 5(4):1281-1294). In some embodiments, the provided genetically engineered cells are modified by recombinant, engineered or ectopic expression of a protein that is negatively regulated by IDO-mediated catabolism, such as by introducing into a cell an exogenous nucleic acid encoding the protein, e.g. encoding mTOR or PKC-theta. In some embodiments, the provided genetically engineered cells are modified by recombinant, engineered or ectopic expression of a molecule that can increase the uptake of amino acids, such as tryptophan, from the microenvironment that can contain low levels of amino acids, such as amino acid transporters, e.g., CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4).

In some embodiments, the molecule is a molecule that is positively regulated by IDO-mediated immunosuppressive signaling, tryptophan starvation or insufficiency and/or in response to kynurenine-mediated immuno-suppression, such as a molecule whose expression, activity, or transport in the cell is increased or promoted in response to IDO-mediated immunosuppressive signaling, tryptophan starvation or insufficiency and/or in response to kynurenine-mediated immune-suppression, which increased or promoted expression, activity or transport is leads to, is involved in or associated with or facilitates the immunosuppressive activity of the cell. Exemplary of such proteins include, but are not limited to, GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2. For example, GCN2 is involved in a stress kinase pathway that becomes activated upon IDO-mediated tryptophan degradation (Sucher et al. (2010) Int. J. Tryptophan Res., 3:113-120). In some embodiments, the provided genetically engineered cells are modified by reduced or disrupted expression of a gene encoding such proteins, such as modified by reduced or disrupted expression of a gene encoding GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2.

In some aspects, tumor cells or cancer cells can exhibit high levels of expression of or upregulate the expression of amino acid transporters, e.g., tryptophan transporters such as LAT1/CD98hc or LAT2/CD98hc, to increase the uptake of amino acids, e.g., tryptophan, from the environment and create a tryptophan-depleted condition, hindering the proliferation of immune cells, e.g., T cells (see, e.g., Broer et al. (2011) Biochem. J. 436, 193-211; Wang et al. (2015) Am J Cancer Res 5(4):1281-1294; Ribas, A. (2015) Cancer Discov. 5(9): 915-919), as a mechanism to evade anti-tumor immune response. In some embodiments, cells administered for cell therapy, e.g., adoptive cell therapy, can be engineered to survive, compete or proliferate in such environments, e.g., by the recombinant expression or overexpression of amino acid transporter(s) and/or by reducing expression of a molecule involved in IDO-mediated immunosuppressive signaling, associated with sensing or responding to tryptophan starvation or insufficiency and/or associated with sensing or responding to kynurenine-mediated immuno-suppression, for example, GCN2, CCAAT/enhancer binding protein-homologous protein (CHOP), Blimp-1, AHR or ARNT. In some embodiments, subjects that have tumors or cancers with elevated levels of LAT1, LAT2, CD98hc and/or PAT4, can be identified or selected for treatment with any of the methods, cells, compositions and/or kits described herein.

In some embodiments, the modification of expression of a molecule (e.g. protein) involved in IDO-mediated immunosuppressive signaling, associated with sensing or responding to tryptophan starvation or insufficiency and/or associated with sensing or responding to kynurenine-mediated immuno-suppression, including molecules that are positively or negatively regulated by IDO-mediated catabolism, e.g. an insufficiency in tryptophan or an accumulation of kynurenine or another tryptophan metabolite, is carried out by introducing nucleic acids for ectopic or recombinant expression of a molecule, or nucleic acids that can repress, reduce the expression of, or disrupt a gene encoding the molecule, into the cell to be engineered, together with nucleic acids encoding a recombinant receptor, e.g., CAR. For example, in some embodiments, a first nucleic acid encoding the recombinant receptor and a second nucleic acid encoding the molecule or portion thereof or an agent that is capable of modifying the expression of the molecule (e.g., an agent that an agent that reduces or is capable of reducing expression of the molecule or an agent that is capable of disrupting the gene encoding the molecule) are introduced into the cell.

In some embodiments, the nucleic acid encoding the recombinant receptor and the nucleic acid encoding the molecule or portion thereof or an agent that is capable of modifying the expression of the molecule can be contained in one, two, three or more polynucleotides and/or vectors, in any combination or arrangements. The vectors can be any of the vectors described herein, including viral vectors and expression vectors. For example, in some embodiments, a first polynucleotide, vector or construct contains nucleic acid encoding the recombinant receptor, and a second polynucleotide, vector or construct contains the nucleic acid encoding the recombinant receptor and the nucleic acid encoding the molecule or portion thereof or an agent that is capable of modifying the expression of the molecule. In some embodiments, one or more components of the molecule or the agent that is capable of modifying the expression of a molecule, can be encoded in one or more polynucleotides. The nucleic acid encoding the recombinant receptor and the nucleic acid encoding the molecule or portion thereof or an agent that is capable of modifying the expression of the molecule can each be operably linked to a promoter for expression, or can be operably linked to one promoter, in one polynucleotide. Each of the polynucleotides can be multicistronic. Each of the polynucleotides can also encode one or more marker, such as a surface marker, e.g., truncated EGFR (tEGFR) or Thy1.1. In some embodiments, where two or more polynucleotides are introduced, the two or more polynucleotides can encode the same or different surface markers.

Also provided are compositions containing one or more of the polynucleotides, vectors or constructs, such as any described above. In some embodiments, the polynucleotides, vectors, constructs or compositions can be used to engineer cells, such as T cells, to express any of the recombinant receptors, molecules involved in IDO-mediated immunosuppressive signaling, associated with sensing or responding to tryptophan starvation or insufficiency and/or or associated with sensing or responding to kynurenine-mediated immuno-suppression, including molecules that are positively or negatively regulated by IDO-mediated catabolism, e.g. an insufficiency in tryptophan or an accumulation of kynurenine or another tryptophan metabolite, and/or an agent that is capable of modifying the expression of such molecules.

1. Recombinant, Engineered and/or Ectopic Expression

In some embodiments, methods of preparing genetically engineered cells include recombinantly or ectopically expressing in a cell a molecule, e.g., a protein, involved in IDO-mediated immunosuppressive signaling, associated with sensing or responding to tryptophan starvation or insufficiency and/or associated with sensing or responding to kynurenine-mediated immuno-suppression, such as a molecule negatively regulated by IDO-mediated immunosuppressive signaling, tryptophan starvation or insufficiency and/or kynurenine-mediated immuno-suppression, for example, mTOR or PKC-theta, or amino acid transporters, such as L-type Amino Acid Transporters (LATs). In some embodiments, a nucleic acid molecule, e.g. vector, encoding the molecule negatively regulated by IDO-mediated catabolism (e.g. mTOR or PKC-theta), or encoding one or more chains of an amino acid transporters (e.g. CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4)) is introduced into the cell, which introduction can occur simultaneously or sequentially with introduction of the nucleic acid encoding the transgenic receptor, such as the CAR.

In some embodiments, the molecule, e.g., protein, involved in IDO-mediated immunosuppressive signaling, IDO-mediated immunosuppressive signaling, associated with sensing or responding to tryptophan starvation or insufficiency and/or associated with sensing or responding to kynurenine-mediated immuno-suppression, such as negatively regulated by IDO-mediated immunosuppressive signaling, tryptophan starvation or insufficiency and/or kynurenine-mediated immuno-suppression, is or comprises mTOR or a functional fragment or functional variant or a portion thereof, such as a functional fragment or functional variant or a portion that is catalytically active and/or whose expression or activity is negatively regulated (e.g. decreased) by IDO-mediated immunosuppressive signaling, tryptophan starvation or insufficiency and/or kynurenine-mediated immuno-suppression. Plasmids or vectors encoding for ectopic expression of mTOR are known and can be generated by standard recombinant DNA technology methods or can be purchased commercially (see e.g. Zhao et al. (2016) Nature Communications, 7:11309; Dressen et al. (2010) Biotechnology and Bioengineering, 108:853-866). In some embodiments, mTOR comprises the sequence of amino acids set forth in SEQ ID NO: 20, or a functional variant or a portion thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 20, or is a functional fragment thereof. In some embodiments, mTOR is encoded by a sequence of nucleotides that comprises the sequence of nucleotides set forth in SEQ ID NO: 21, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 21, and that encodes a functional protein, variant, or fragment thereof. In some embodiments, mTOR is a human protein.

In some embodiments, the molecule, e.g., protein, involved in IDO-mediated immunosuppressive signaling, associated with sensing or responding to tryptophan starvation or insufficiency and/or associated with sensing or responding to kynurenine-mediated immuno-suppression, such as negatively regulated by IDO-mediated immunosuppressive signaling, tryptophan starvation or insufficiency and/or kynurenine-mediated immuno-suppression, is or comprises PKC-theta or a functional fragment or functional variant or a portion thereof, such as a functional fragment or functional variant or a portion that is catalytically active and/or whose expression or activity is negatively regulated (e.g. decreased) by IDO-mediated immunosuppressive signaling, tryptophan starvation or insufficiency and/or kynurenine-mediated immuno-suppression. Plasmids or vectors encoding for ectopic expression of PKC-theta are known and can be generated by standard recombinant DNA technology methods or can be purchased commercially (see e.g. Belguise et al. (2012) Oncogene, 31:4889-4897; Wing-yiu et al. (2010) J Biol. Chem., 285:23889-98). In some embodiments, PKC-theta comprises the sequence of amino acids set forth in SEQ ID NO: 22, or a functional variant or a portion thereof comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 22, or is a functional fragment thereof. In some embodiments, PKC-theta is encoded by a sequence of nucleotides that comprises the sequence of nucleotides set forth in SEQ ID NO: 23, or a sequence of nucleotides that exhibits at least 85%, 86%, 87%, 88%, 89%, 90%, 91%, 92%, 93%, 94%, 95%, 96%, 97%, 98%, 99% or more sequence identity to SEQ ID NO: 23, and that encodes a functional protein, variant, or fragment thereof. In some embodiments, PKC-theta is a human protein.

In some embodiments, the molecule, e.g., protein, involved in IDO-mediated immunosuppressive signaling, IDO-mediated immunosuppressive signaling, associated with sensing or responding to tryptophan starvation or insufficiency and/or associated with sensing or responding to kynurenine-mediated immuno-suppression, such as negatively regulated by IDO-mediated immunosuppressive signaling, tryptophan starvation or insufficiency and/or kynurenine-mediated immuno-suppression, is or comprises an amino acid transporter, e.g., a tryptophan transporter. In the TME, upregulation of IDO1 and/or amino acid transporters by the cancer or tumor cells or "bystander" cells, can result in an amino acid starvation condition, e.g., tryptophan starvation condition. Thus, the proliferation and/or function of the immune cells, e.g., engineered T cells, may be suppressed due to the lack of sufficient tryptophan in the microenvironment. Recombinantly or ectopically expressing molecules, e.g., amino acid transporters, in the immune cell can allow the immune cells to respond to tryptophan starvation or insufficiency, e.g., by more efficient uptake of tryptophan or other amino acids in an amino acid starvation environment created by the activity of IDO1 and/or upregulation of amino acid transporters by tumor or cancer cells and/or bystander cells. In some embodiments, the engineered T cells are also engineered to recombinantly or ectopically express one or more chain of amino acid transporters or one or more amino acid transporter(s) selected from CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4).

In some embodiments, the molecule, e.g., protein, associated with sensing or responding to tryptophan starvation or insufficiency is an amino acid transporter. In some embodiments, the amino acid transporter is a SLC (solute carrier) family transporter. In some embodiments, the amino acid transporter is a tryptophan transporter. In some embodiments, the amino acid transporter is an arginine transporter.

In some embodiments, the amino acid transporter is a heteromeric amino acid transporter (HAT). HATs are amino acid antiporters (exchangers) with a 1:1 stoichiometry. In some embodiments, HATs are composed of a heavy chain (SLC3 family) and a light chain (SLC7 family), which are linked by a conserved disulfide bridge. In general, the heavy chain is essential for trafficking of the holotransporter to the membrane, and whereas the light chain catalyzes the transporter function. Typically, humans have two heavy chains: rBAT (related to broad specificity neutral or cationic amino acid transport, also called SLC3A1; exemplary sequence set forth in SEQ ID NO:36) and 4F2hc (4F2 cell-surface-antigen heavy chain; also named CD98 heavy chain or SLC3A2; exemplary sequence set forth in SEQ ID NO:37), in the human SLC3 family. The heavy chain (SLC3) members are type II membrane N-glycoproteins with a single transmembrane domain segment, an intracellular N-terminus and a large extracellular C terminus. Typically, in humans, six SLC7 members (LAT1 (SLC7A5; exemplary sequence set forth in SEQ ID NO:38), LAT2 (SLC7A8; exemplary sequence set forth in SEQ ID NO:39), y+LAT1 (SLC7A7), y+LAT2 (SLC7A6), Asc-1 (SLC7A10; exemplary sequence set forth in SEQ ID NO:40) and xCT (SLC7A11)) heterodimerize with 4F2hc. The light chain (SLC7) members have a 12-transmembrane domain topology, and have homology to bacterial amino acid transporters (see, e.g., Broer et al. (2011) Biochem. J. 436, 193-211; Wang et al. (2015) Am J Cancer Res 5(4):1281-1294). See also Lin et al., Neoplasia. 2004 January; 6(1): 74-84; Barollo et al., PLoS One. 2016; 11(5): e0156044.

In some embodiments, the amino acid transporter is an L-type amino acid transporter (LAT). In some embodiments, the amino acid transporter comprises 4F2hc (CD98hc)/LAT1 heterodimer, or 4F2hc (CD98hc)/LAT2 heterodimer, which form the L-type transport system (transports large neutral amino acids, e.g., leucine). In some embodiments, the amino acid transporter comprises a 4F2hc (CD98hc)/Asc-1 heterodimer or a heterodimer that comprises Asc-2, which can form the ASC transporter (transporters with a preference for alanine, serine and cysteine).

In some embodiments, the amino acid transporter is an SLC6 family transporter. In some embodiments, the amino acid transporter is SLC6A14 (ATB$^{0,+}$; exemplary sequence set forth in SEQ ID NO:41), a transporter for neutral and cationic amino acids (system B0,+), or SLC6A19 (B$^{0}$AT1, broad neutral (0) amino acid transporter 1; exemplary sequence set forth in SEQ ID NO:42), which transports all 16 neutral amino acids in co-transport with 1 Na$^{+}$. In some embodiments, the amino acid transporter is a T-type transporter (transporter for aromatic amino acids), such as TAT1 (also known as monocarboxylate transporter 10 or SLC16A10; exemplary sequence set forth in SEQ ID NO:43). In some embodiments, the amino acid transporter is an SLC36 family transporter. In some embodiments, the amino acid transporter is proton-assisted amino-acid transporter 4 (PAT4; also known as SLC36A4; exemplary sequence set forth in SEQ ID NO:44), an equilibrative transporter for proline and tryptophan which is not coupled to proton co-transport.

In some embodiments, the molecule, e.g., protein, involved in IDO-mediated immunosuppressive signaling, IDO-mediated immunosuppressive signaling, associated with sensing or responding to tryptophan starvation or insufficiency and/or associated with sensing or responding to kynurenine-mediated immuno-suppression, such as negatively regulated by IDO-mediated immunosuppressive signaling, tryptophan starvation or insufficiency and/or kynurenine-mediated immuno-suppression, is or comprises an amino acid transporter, e.g., an amino acid transporter that comprises the sequence of amino acids set forth in SEQ ID NOs: 36-44, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NOs: 36-44. In some embodiments, the amino acid transporter(s) is encoded by a sequence of nucleotides that comprises the sequence of nucleotides that encode a sequence of amino acids set forth in set forth in SEQ ID NOs: 36-44, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NOs: 36-44, and that encodes a functional protein, variant, or fragment thereof. In some embodiments, the amino acid transporter is a human protein or a variant thereof.

In some embodiments, the amino acid transporter is a heterodimer, comprising a heavy chain (e.g., 4F2hc) comprising the sequence of amino acids set forth in SEQ ID NO:36 or 37, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 36 or 37, and a light chain (e.g., LAT1, LAT2 or Asc-1) comprising any one of the sequence of amino acids set forth in SEQ ID NOs:38-40, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to any one of SEQ ID NO:38-40. In some embodiments, the amino acid transporter(s) is encoded by a sequence of nucleotides that comprises the sequence of nucleotides that encode a heavy chain (e.g., 4F2hc) comprising the sequence of amino acids set forth in SEQ ID NO:36 or 37, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 36 or 37, and a light chain (e.g., LAT1, LAT2 or Asc-1) comprising any one of the sequence of amino acids set forth in SEQ ID NOs:38-40, or a functional variant or a portion thereof, e.g., comprising a sequence of amino acids that exhibits at least 85%, 86%, 87%, 88%, 89%, 90%, 91%, 92%, 93%, 94%, 95%, 96%, 97%, 98%, 99% or more sequence identity to any one of SEQ ID NO:38-40. In some embodiments, the amino acid transporter is a human protein or a variant thereof.

In some embodiments, a nucleic acid encoding a genetically engineered receptor that specifically binds to a ligand, such as a recombinant, e.g., chimeric, receptor, and a molecule negatively regulated by IDO-mediated immunosuppressive signaling, tryptophan starvation or insufficiency and/or kynurenine-mediated immuno-suppression, such as mTOR or PKC-theta, or functional portion thereof, are introduced into a cell for expression. In some embodiments, a first nucleic acid encodes the genetically engineered receptor that specifically binds to a ligand and a second nucleic acid encodes the molecule negatively regulated by IDO-mediated immunosuppressive signaling, tryptophan starvation or insufficiency and/or kynurenine-mediated immuno-suppression, such as mTOR or PKC-theta, or one or more chain of amino acid transporters or one or more amino acid transporter(s) selected from CD98 heavy chain (4F2hc; SLC3A2), L-type Amino Acid Transporter 1 (LAT1;

SLC7A5), LAT2 (SLC7A8) and/or proton-assisted amino-acid transporter 4 (PAT4; SLC36A4). In some embodiments, the first and second nucleic acids In some embodiments, a nucleic acid encoding a genetically engineered receptor that specifically binds to a ligand, such as a recombinant, e.g., chimeric, receptor, and a molecule involved in and/or associated with sensing or responding to tryptophan starvation or insufficiency, e.g., an amino acid transporter, such as one or more chains of an amino acid transporter, e.g., a SLC (solute carrier) family transporter, or functional portion thereof, are introduced into a cell for expression. In some embodiments, one or more nucleic acid molecules that encode one or more chains or components of the amino acid transporter, and one or more components of the genetically engineered receptor, are introduced into the cell. For example, in some embodiments, a first nucleic acid encodes the genetically engineered receptor that specifically binds to a ligand and a second nucleic acid encoding one or more chains of an amino acid transporter, such as one or more chains of CD98hc and/or LAT1 or LAT2. In some embodiments, the one or more chains of the L-type amino acid transporter is recombinantly or ectopically expressing in the cell, e.g., via introduction of one or more polynucleotides containing nucleic acids encoding one or more chains of the amino acid transporter and/or one or more amino acid transporters.

In some embodiments, the nucleic acid is multicistronic, such as bicistronic or otherwise permits the coexpression of multiple, separate peptide chains, such as two or more, from the same promoter. The transcript in some embodiments has the potential to code for more than one final product, such as two final products. In some embodiments, at least one of the nucleic acids contains an internal ribosome binding site (IRES) separating the encoded molecules such that the genetically engineered receptor and the molecule involved in a metabolic pathway are expressed under the control of the same promoter. As used herein, an "internal ribosome entry site" (IRES) refers to a nucleotide sequence that allows for translation initiation in the middle of a messenger RNA (mRNA) sequence as part of protein synthesis.

In some embodiments, the nucleic acid includes one or more ribosomal skip sequences, such as picornavirus 2A ribosomal skip peptide, so that the two or more peptide chains or other products may be expressed in operable linkage with the same promoter, but produced as separate chains. For example, in some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 49), equine rhinitis A virus (E2A, e.g., SEQ ID NO: 48), Thosea asigna virus (T2A, e.g., SEQ ID NO: 6 or 45), and porcine teschovirus-1 (P2A, e.g., SEQ ID NO: 46 or 47) as described in U.S. Patent Publication No. 20070116690.

In some embodiments, the nucleic acid or acids encoding the genetically engineered receptor that specifically binds to a ligand and the molecule negatively regulated by IDO-mediated catabolism, such as mTOR or PKC-theta, or the molecule associated with sensing or responding to tryptophan starvation or insufficiency, such as one or more chains of amino acid transporter(s) or one or more amino acid transporter(s), such as one or more of CD98 heavy chain (4F2hc; SLC3A2), L-type Amino Acid Transporter 1 (LAT1; SLC7A5), LAT2 (SLC7A8) and/or proton-assisted amino-acid transporter 4 (PAT4; SLC36A4), are expressed in the same or different nucleic acid molecule(s) and/or vectors. In some embodiments, a nucleic acid molecule can contain a first nucleic acid encodes the genetically engineered receptor that specifically binds to a ligand and a second nucleic acid encoding one or more chains of an amino acid transporter, such as one or more chains of CD98hc and/or LAT1 or LAT2. In some embodiments, a nucleic acid molecule and/or vector can contain a first nucleic acid encodes the genetically engineered receptor that specifically binds to a ligand and a second nucleic acid encoding one chains of an amino acid transporter, such as CD98hc, and a third nucleic acid encoding another chains of an amino acid transporter, such as LAT1 or LAT2. In some embodiments, the first, second and/or third nucleic acids can be contained in two or more separate polynucleotides and/or vectors. The vectors can be any of the vectors described herein, including viral vectors and expression vectors.

2 Repressing, Reducing or Disrupting Gene Expression

In some embodiments, methods of preparing genetically engineered cells include introducing an agent that reduces or is capable of reducing expression of a molecule involved in IDO-mediated immunosuppressive signaling, associated with sensing or responding to tryptophan starvation or insufficiency and/or associated with sensing or responding to kynurenine-mediated immuno-suppression, such as a protein positively regulated by IDO-mediated immunosuppressive signaling, tryptophan starvation or insufficiency and/or kynurenine-mediated immuno-suppression, for example, GCN2, CCAAT/enhancer binding protein-homologous protein (CHOP), Blimp-1, AHR, ARNT, eukaryotic translation initiation factor 2 α (eIF2α), activating transcription factor 4 (ATF4), Gadd45α, Herp, 4E-BP1, eIF4G, JAK1, NFκB-2, FK506-BP8, IFNγ-R2, in the cell, which introduction can occur simultaneously or sequentially with introduction of the nucleic acid encoding the transgenic receptor, such as the CAR. In some embodiments, a nucleic acid molecule that includes, is encompassed within, or encodes the agent is introduced into the cells. Also provided are cells comprising a genetically engineered (recombinant) cell surface receptors and that have reduced expression of, or are disrupted in a gene encoding, a protein positively regulated by IDO-mediated immunosuppressive signaling, tryptophan starvation or insufficiency and/or kynurenine-mediated immuno-suppression, such as GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2. In some embodiments, the cells comprise an agent, such as an inhibitory nucleic acid molecule, that reduces or represses expression of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, expression, activity, and/or function is reduced by effecting repression of one or more genes encoding the one or more protein in the cell.

In some embodiments, the gene repression is carried out by effecting a disruption in the gene, such as a knock-out, insertion, missense or frameshift mutation, such as a biallelic frameshift mutation, deletion of all or part of the gene, e.g., one or more exon or portion thereof, and/or knock-in. Such disruptions in some embodiments can be effected by an agent that includes sequence-specific or targeted nucleases, including DNA-binding targeted nucleases and gene editing nucleases such as zinc finger nucleases (ZFN) and transcription activator-like effector nucleases (TALENs), and RNA-guided nucleases such as a CRISPR-associated nuclease (Cas), specifically designed to be targeted to the sequence of a gene or a portion thereof. In some embodiments, such sequence-specific or targeted nucleases are encoding by an inhibitory nucleic acid molecule. In some embodiments, such nucleases can be guided or targeted by DNA-binding nucleic acid molecules, such as a guide RNA (gRNA).

In some embodiments, gene repression is carried out by effecting a reduction in expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, such gene repression is achieved using an inhibitory nucleic acid molecule, such as by RNA interference (RNAi), short interfering RNA (siRNA), short hairpin (shRNA), micro RNA (miRNA), antisense RNA, and/or ribozymes, which can be used to selectively suppress or repress expression of the gene. siRNA technology includes that based on RNAi utilizing a double-stranded RNA molecule having a sequence homologous with the nucleotide sequence of mRNA which is transcribed from the gene, and a sequence complementary with the nucleotide sequence. siRNA generally is homologous/complementary to one region of mRNA which is transcribed from the gene, or may be siRNA including a plurality of RNA molecules which are homologous/complementary to different regions. In some embodiments, gene repression is achieved using a DNA-binding nucleic acid molecule, such as a guide RNA (gRNA), and a variant of an RNA-guided nuclease, such as an enzymatically inactive Cas9 (eiCas9) protein or a fusion protein containing eiCas9. In some embodiments, gene repression is achieved by DNA-binding targeted proteins, such as zinc finger proteins (ZFP) or fusion proteins containing ZFP.

a. Reducing Protein Expression

In some embodiments, the provided methods and cells result in knockdown, such as a reduction or repression, of expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8, IFNγ-R2) in the cells. In some embodiments, the knockdown can be transient, such as is conditional. In some embodiments, the knockdown is non-transient or permanent.

In some embodiments, knocking down, repressing or reducing expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8, IFNγ-R2) can be achieved by RNA interference (RNAi). In some embodiments, RNAi can be mediated by double stranded RNA (dsRNA) molecules that have sequence-specific homology to their target nucleic acid sequences (Caplen, N. J., et al., Proc. Natl. Acad. Sci. USA 98:9742-9747 (2001)). Biochemical studies in Drosophila cell-free lysates indicate that, in some embodiments, the mediators of RNA-dependent gene silencing are 21-25 nucleotide "small interfering" RNA duplexes (siRNAs). The siRNAs can be derived from the processing of dsRNA by an RNase enzyme known as Dicer (Bernstein, E., et al., Nature 409:363-366 (2001)). siRNA duplex products can be recruited into a multi-protein siRNA complex termed RNA Induced Silencing Complex (RISC). In some embodiments, a RISC can then be guided to a target nucleic acid (suitably mRNA), where the siRNA duplex interacts in a sequence-specific way to mediate cleavage in a catalytic fashion (Bernstein, E., et al., Nature 409: 363-366 (2001); Boutla, A., et al., Curr. Biol. 11:1776-1780 (2001)). Small interfering RNAs can be synthesized and used according to procedures that are well known in the art and that will be familiar to the ordinarily skilled artisan. Small interfering RNAs comprise between about 0 to about 50 nucleotides (nt). In examples of nonlimiting embodiments, siRNAs can comprise about 5 to about 40 nt, about 5 to about 30 nt, about 10 to about 30 nt, about 15 to about 25 nt, or about 20-25 nucleotides.

In some embodiments, an RNA interfering agent is at least partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA comprises complementary regions that hybridize with each other, the RNA will be said to self-hybridize. In some embodiments, an inhibitory nucleic acid, such as an RNA interfering agent, includes a portion that is substantially complementary to a target gene. In some embodiments, an RNA interfering agent optionally includes one or more nucleotide analogs or modifications. One of ordinary skill in the art will recognize that RNAi agents can include ribonucleotides, deoxyribonucleotides, nucleotide analogs, modified nucleotides or backbones, etc. In some embodiments, RNA interfering agents may be modified following transcription. In some embodiments, RNA interfering agents comprise one or more strands that hybridize or self-hybridize to form a structure that comprises a duplex portion between about 15-29 nucleotides in length, optionally having one or more mismatched or unpaired nucleotides within the duplex. In some embodiments, RNA interfering agents include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA.

In some embodiments, the term "short, interfering RNA" (siRNA) refers to a nucleic acid that includes a double-stranded portion between about 15-29 nucleotides in length and optionally further comprises a single-stranded overhang (e.g., 1-6 nucleotides in length) on either or both strands. In some embodiments, the double-stranded portion can be between 17-21 nucleotides in length, e.g., 19 nucleotides in length. In some embodiments, the overhangs are present on the 3' end of each strand, can be 2 nucleotides long, and can be composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. One of ordinary skill in the art will appreciate that one or more mismatches or unpaired nucleotides can be present in the duplex formed by the two siRNA strands. In some embodiments, one strand of an siRNA (the "antisense" or "guide" strand) includes a portion that hybridizes with a target nucleic acid, e.g., an mRNA transcript. In some embodiments, the antisense strand is perfectly complementary to the target over about 15-29 nucleotides, sometimes between 17-21 nucleotides, e.g., 19 nucleotides, meaning that the siRNA hybridizes to the target transcript without a single mismatch over this length. However, one of ordinary skill in the art will appreciate that one or more mismatches or unpaired nucleotides may be present in a duplex formed between the siRNA strand and the target transcript.

In some embodiments, expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) is reduced or repressed using small-hairpin RNAs (shRNAs) that target nucleic acids encoding the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, a short hairpin RNA (shRNA) is a nucleic acid molecule comprising at least two complementary portions hybridized or capable of hybridizing to form a duplex structure sufficiently long to mediate RNAi (typically between 15-29 nucleotides in length), and at least one single-stranded portion, typically between approximately 1 and 10 nucleotides in length that forms a loop connecting the ends of the two sequences that form the duplex. In some embodiments, the structure may further comprise an overhang. Suitable shRNA sequences for the knock down of a given target gene are well known in the art or can readily be determined by a person skilled in the art.

In some embodiments, the duplex formed by hybridization of self-complementary portions of the shRNA may have similar properties to those of siRNAs and, as described below, shRNAs can be processed into siRNAs by the conserved cellular RNAi machinery. Thus shRNAs can be precursors of siRNAs and can be similarly capable of inhibiting expression of a target transcript. In some embodiments, an shRNA includes a portion that hybridizes with a target nucleic acid, e.g., an mRNA transcript, and can be perfectly complementary to the target over about 15-29 nucleotides, sometimes between 17-21 nucleotides, e.g., 19 nucleotides. However, one of ordinary skill in the art will appreciate that one or more mismatches or unpaired nucleotides may be present in a duplex formed between the shRNA strand and the target transcript.

In some embodiments, the shRNA comprises a nucleotide (e.g. DNA) sequence of the structure A-B-C or C-B-A. In some embodiments, the cassette comprises at least two DNA segments A and C or C and A, wherein each of said at least two segments is under the control of a separate promoter as defined above (such as the Pol III promoter including inducible U6, H1 or the like). In the above segments: A can be a 15 to 35 bp or a 19 to 29 bp DNA sequence being at least 90%, or 100% complementary to the gene to be knocked down (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2); B can be a spacer DNA sequence having 5 to 9 bp forming the loop of the expressed RNA hairpin molecule, and C can be a 15 to 35 or a 19 to 29 bp DNA sequence being at least 85% complementary to the sequence A.

In some embodiments, an RNA interfering agent is considered to be "targeted" to a transcript and to the gene that encodes the transcript if (1) the RNAi agent comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi agent and a 15 nucleotide portion of the transcript, under conditions (excluding temperature) typically found within the cytoplasm or nucleus of mammalian cells is no more than approximately 15° C. lower or no more than approximately 10° C. lower, than the Tm of a duplex that would be formed by the same 15 nucleotides of the RNA interfering agent and its exact complement; and/or (3) the stability of the transcript is reduced in the presence of the RNA interfering agent as compared with its absence. In some embodiments, an RNA interfering agent targeted to a transcript can also considered targeted to the gene that encodes and directs synthesis of the transcript. In some embodiments, a target region can be a region of a target transcript that hybridizes with an antisense strand of an RNA interfering agent. In some embodiments, a target transcript can be any RNA that is a target for inhibition by RNA interference.

In some embodiments, siRNA selectively suppresses the expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In addition, all of the nucleotide sequences of siRNA may be derived from the nucleotide sequence of the mRNA of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), or a part thereof may be derived from the nucleotide sequence.

In some embodiments, the siRNA can be comprised of ribonucleotides, and a part thereof may include nucleotides other than ribonucleotides, for example, deoxyribonucleotides, a derivative of deoxyribonucleotides, a derivative of ribonucleotides, etc. The siRNA can be synthesized by a known chemical synthesis method, but the method is not particularly limited. In some embodiments, it may be enzymatically (e.g., using an RNA polymerase) prepared using a suitable template nucleic acid. In some embodiments, the siRNA may be in the form of single-stranded RNA which can form a duplex in the molecule, and single-stranded RNA with a stem-loop structure (short hairpin structure: sh structure) having the siRNA part as a stem and an arbitrary sequence as a loop (shRNA). In some embodiments, a sequence of 1 to 30 nucleotides, 1 to 25 nucleotides, or 5 to 22 nucleotides can be used as the arbitrary sequence.

The sequence of the siRNA can be appropriately designed based on a gene sequence whose expression is desired to be suppressed. Many siRNA design algorithms have been reported (see, e.g., WO 2004/0455543, and WO 2004/048566), and a commercially available software can also be used. In addition, there are many companies which design siRNA from information of a gene sequence whose expression is desired to be suppressed, and synthesize and provide the siRNA. Therefore, a person skilled in the art can easily obtain the siRNA based on the gene sequence whose expression is desired to be suppressed. In some embodiments, any siRNA which selectively suppresses expression of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) can be generated or commercially obtained. Exemplary siRNA for targeting GCN2 include those described in Barnes et al. (2009) J. Biol. Chem., 183:5768-5777; Malmberg and Adams (2008) J. Biol. Chem., 283:19229-19234 or commercially available, for example, from Dharmacon (Lafayette, CO; e.g. catalog number D-044353-02). Exemplary siRNA for targeting BLIMP-1 include those described in Yu et al. (2012) PLoS One, e33287; Yan et al. (2007) PNAS, 104:1841-1846) or commercially available, for example, from Santa Cruz Biotechnology (CA; e.g. catalog number sc-37714). Exemplary siRNA for targeting CCAAT/enhancer-binding protein-homologous protein (CHOP) include those described in Kim et al. (2012) Horm Metab Res 45 (1):9-14, Ryder et al., Biochem Biophys Res Commun. (2013) 430(4): 1283-1288, or commercially available, for example, from ThermoFisher Scientific (e.g. catalog number AM16708). Exemplary siRNA for targeting AHR or ARNT include those as described in Adelrahim et al. (2003) Mol. Pharmacol., 63:1373-81; Overvik et al. (2014) Cell Communication and Signaling, 12:48; Ishida et al. (2010) Carcinogenesis, 31:287-295) or commercially available, for example, from Applied Biological Materials (Richmond, BC, Canada; Catalog. No. iV000726). Exemplary siRNA for targeting ATF4 include those described in Armstrong et al., (2010) J. Biol. Chem. 285:6091:6100, or commercially available, for example, from ThermoFisher Scientific (e.g. catalog number AM16708). Exemplary siRNA for targeting eIF2α include those described in Fan et al. (2016) Scientific Reports 6:21145, Wang et al. (2015) PLoS ONE 10(6): e0130806, or commercially available, for example, from Santa Cruz Biotechnology (e.g. catalog number sc-35272).

In some embodiments, shRNA and siRNA segments may further comprise stop and/or polyadenylation sequences.

In some embodiments, an antisense nucleotide can be used for suppressing the expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, the antisense nucleotide can be used for suppressing the expression of a protein, for example, by directly interfering with translation of the mRNA molecule of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), by degradation of mRNA by an RNA degradation enzyme H, by interfering with the 5' capping of mRNA, by masking the 5' cap, by preventing binding of a translation factor with mRNA, or by inhibiting polyadenylation of mRNA. In some embodiments, the suppression of the expression of a protein can occur by hybridization between an antisense nucleotide and the mRNA of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, a specific targeting site on the mRNA is selected as a target of the antisense nucleotide in order to reduce stability of, or degrade mRNA. In some embodiments, when one or more target sites are identified, a nucleotide having a nucleotide sequence sufficiently complementary with the target site (that is, which hybridizes sufficiently and with sufficient specificity under the physiological conditions) can be designed. In some embodiments, the antisense nucleotide can have, for example, a chain length of 8 to 100 nucleotides, 10 to 80 nucleotides, or 14 to 35 nucleotides.

In some embodiments, methods of introduction or delivery into a cell can be the same or similar to methods as described above for introduction of a nucleic acid encoding a genetically engineered antigen receptor into a cell. In some embodiments, expression of an inhibitory nucleic acid, such as an shRNA or siRNA, in cells, e.g. T cells, can be achieved using any conventional expression system, e.g., a lentiviral expression system. In some embodiments, the RNA can be a component of a viral vector. In some embodiments, the viral vector comprises an oligonucleotide that inhibits expression of the protein positively regulated by IDO-mediated immunosuppressive signaling, tryptophan starvation or insufficiency and/or kynurenine-mediated immunosuppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), or encodes a shRNA or other inhibitory nucleic acid having such capability. In some embodiments, the viral vector is a lentivirus vector. In some embodiments, the lentivirus vector is an integrating lentivirus vector.

In some embodiments, suitable promoters include, for example, RNA polymerase (pol) III promoters including, but not limited to, the (human and murine) U6 promoters, the (human and murine) H1 promoters, and the (human and murine) 7SK promoters. In some embodiments, a hybrid promoter also can be prepared that contains elements derived from, for example, distinct types of RNA polymerase (pol) III promoters. In some embodiments, modified promoters that contain sequence elements derived from two or more naturally occurring promoter sequences can be combined by the skilled person to effect transcription under a desired set of conditions or in a specific context. For example, the human and murine U6 RNA polymerase (pol) III and H1 RNA pol III promoters are well characterized. One skilled in the art will be able to select and/or modify the promoter that is most effective for the desired application and cell type so as to optimize modulation of the expression of one or more genes. In some embodiments, the promoter sequence can be one that does not occur in nature, so long as it functions in a eukaryotic cell, such as, for example, a mammalian cell.

In some embodiments, an exemplary delivery vehicle is a nanoparticle, e.g., a liposome or other suitable sub-micron sized delivery system. In some embodiments, the use of lipid formulations is contemplated for the introduction of the nucleic acids into a cell. The lipid particle may be a nucleic acid-lipid particle, which may be formed from a cationic lipid, a non-cationic lipid, and optionally a conjugated lipid that prevents aggregation of the particle. The nucleic acid may be encapsulated in the lipid portion of the particle, thereby protecting it from enzymatic degradation. A stable nucleic acid-lipid particle can be a particle made from lipids (e.g., a cationic lipid, a non-cationic lipid, and optionally a conjugated lipid that prevents aggregation of the particle), wherein the nucleic acid is fully encapsulated within the lipid.

In some embodiments, the lipid particles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the lipid particles are substantially non-toxic. In some embodiments, nucleic acids, when present in the lipid particles of the present invention, can be resistant in aqueous solution to degradation with a nuclease.

In some embodiments, a lipid particle provides a nucleic acid with full encapsulation, partial encapsulation, or both. In some embodiments, the nucleic acid is fully encapsulated in the lipid particle to form a nucleic acid-lipid particle.

In some embodiments, a conjugated lipid inhibits aggregation of lipid particles, including, polyethylene glycol (PEG)-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates (e.g., POZ-DAA conjugates; polyamide oligomers (e.g., ATTA-lipid conjugates), and mixtures thereof. In some embodiments, PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In some embodiments, non-ester containing linker moieties, such as amides or carbamates, are used.

In some embodiments, an amphipathic lipid can have a hydrophobic portion that orients into a hydrophobic phase, and a hydrophilic portion orients toward the aqueous phase. In some embodiments, hydrophilic characteristics derive from the presence of polar or charged groups such as carbohydrates, phosphate, carboxylic, sulfato, amino, sulfhydryl, nitro, hydroxyl, and other like groups. In some embodiments, hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and (3-acyloxyacids, are also within the group designated as amphipathic lipids. Additionally, the amphipathic lipids described above can be mixed with other lipids including triglycerides and sterols.

In some embodiments, a neutral lipid exists either in an uncharged or neutral zwitterionic form at a selected pH. In some embodiments, at physiological pH, such lipids include, for example, diacylphosphatidylcholine, diacylphosphatidylethanolamine, ceramide, sphingomyelin, cephalin, cholesterol, cerebrosides, and diacylglycerols.

In some embodiments, a non-cationic lipid may be any amphipathic lipid as well as any other neutral lipid or anionic lipid.

In some embodiments, an anionic lipid is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

In some embodiments, a hydrophobic lipid has apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane. In some embodiments, the nucleic acid-lipid particle comprises: (a) a nucleic acid (e.g., an interfering RNA); (b) a cationic lipid comprising from about 50 mol % to about 65 mol % of the total lipid present in the particle; (c) a non-cationic lipid comprising from about 25 mol % to about 45 mol % of the total lipid present in the particle; and (d) a conjugated lipid that inhibits aggregation of particles comprising from about 5 mol % to about 10 mol % of the total lipid present in the particle.

In some embodiments, the nucleic acid-lipid particle comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle.

In some embodiments, the nucleic acid-lipid particle comprises: (a) a nucleic acid (e.g., an interfering RNA); (b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. In some embodiments, a CRISPR/Cas system can be used for knocking down, such as reducing or suppressing, the expression of a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), e.g. using methods similar to those as described in WO2015/161276. Exemplary features of CRISPR/Cas systems are described below and can be adapted for use in reducing or suppressing expression of a molecule, rather than disrupting or deleting a gene encoding the molecule, by using an enzymatically inactive nuclease. In some embodiments, a guide RNA (gRNA) targeting a gene encoding the protein positively regulated by IDO-mediated immunosuppressive signaling, tryptophan starvation or insufficiency and/or kynurenine-mediated immunosuppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), or the promoter, enhancer or other cis- or trans-acting regulatory regions, can be introduced in combination with a modified Cas9 protein or a fusion protein containing the modified Cas9 protein, to suppress the expression of, e.g., knock-down, of the gene(s). In some embodiments, the Cas9 molecule is an enzymatically inactive Cas9 (eiCas9) molecule, which comprises a mutation, e.g., a point mutation, that causes the Cas9 molecule to be inactive, e.g., a mutation that eliminates or substantially reduces the Cas9 molecule cleavage activity. In some embodiments the eiCas9 molecule is fused, directly or indirectly to, a transcription activator or repressor protein.

In some embodiments, the promoter region of the gene is targeted to knockdown expression of the protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). A targeted knockdown approach reduces or eliminates expression of the functional gene product. In some embodiments, targeted knockdown is mediated by targeting an enzymatically inactive Cas9 (eiCas9) or an eiCas9 fused to a transcription repressor domain or chromatin modifying protein to alter transcription, e.g., to block, reduce, interfere with, or decrease transcription, of the gene. gRNA targeting a target sequence in or near the gene, if targeted by an eiCas9 or an eiCas9 fusion protein, results in reduction or elimination of expression of functional gene product, such as the protein positively regulated by IDO-mediated catabolism (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, transcription is reduced or eliminated.

In some embodiments, a targeting domain of the gRNA molecule is configured to target an enzymatically inactive Cas9 (eiCas9) or an eiCas9 fusion protein (e.g., an eiCas9 fused to a transcription repressor domain), sufficiently close to a target sequence in the genome to reduce, decrease or repress expression of the gene. In some embodiments, an eiCas9 is fused to a transcription repressor domain or chromatin modifying protein to alter transcription, e.g., to block, reduce, interfere with or decrease transcription, of the gene. In some embodiments, one or more eiCas9s may be used to block binding of one or more endogenous transcription factors. In another embodiment, an eiCas9 can be fused to a chromatin modifying protein. Altering chromatin status can result in decreased expression of the target gene. One or more eiCas9s fused to one or more chromatin modifying proteins may be used to alter chromatin status.

In some embodiments, the targeting domain is configured to target the promoter region of the gene to block transcription initiation, binding of one or more transcription enhancers or activators, and/or RNA polymerase. One or more gRNA can be used to target an eiCas9 to the promoter region of the gene.

In some embodiments, a complex of the targeting CRISPR gRNA and the enzymatically inactive nuclease, e.g. iCas9 or eiCas9 fusion protein, can be introduced into a cell by methods known to a skilled artisan, including those described below in connection with CRISPR/Cas systems. In some embodiments, the CRISPR gRNA and enzymatically inactive nuclease, e.g. iCas9 or eiCas9 fusion protein, is transiently introduced to the cell, e.g., by transient introduction of the ribonucleoprotein complex (RNP) complex. In some embodiments, nucleic acid molecules encoding the gRNA and/or eiCas9 are introduced to the cell using any conventional expression system, e.g., a lentiviral expression system. In some embodiments, methods of introduction or delivery into a cell can be the same or similar to the methods as described below for introduction of a nucleic acid-protein complex, such as a ribonucleoprotein (RNP) complex into a cell.

In some embodiments, gene knockdown is achieved by DNA-binding targeted proteins, such as zinc finger proteins (ZFP) or fusion proteins containing ZFP, that target genes encoding the protein involved in IDO-mediated immuno-suppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, a DNA-binding proteins, such as a ZFP, can effect target gene repression by interfering with or inhibiting the expression of the target gene. Exemplary features of DNA-binding proteins, including ZFPs, are described below and can be adapted for use in reducing or suppressing expression of a molecule, rather than disrupting or deleting a gene encoding the molecule, by introduction without the effector protein (e.g. endonuclease, such as a zinc finger nuclease (ZFN)).

b. Knockout of Expression

In some aspects, the knockout, such as disruption of, genes encoding a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a gene editing nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, gene editing results in a genomic disruption or knock-out of genes encoding a protein positively regulated by IDO-mediated catabolism (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2).

In some embodiments, the repression is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease.

Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073 and US20140120622.

In some embodiments, the DNA-targeting molecule, complex, or combination contains a DNA-binding molecule and one or more additional domain, such as an effector domain to facilitate the repression or disruption of the gene. For example, in some embodiments, the gene disruption or repression is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 20050064474; 20060188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as gene editing nucleases and gene editing nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone non-homologous end joining (NHEJ) and homology-directed repair (HDR). In some embodiments the nuclease is an endonuclease, such as a zinc finger nuclease (ZFN), TALE nuclease (TALEN), an RNA-guided endonuclease (RGEN), such as a CRISPR-associated (Cas) protein, or a meganuclease.

In some embodiments, a donor nucleic acid, e.g., a donor plasmid or nucleic acid encoding the genetically engineered antigen receptor, is provided and is inserted by HDR at the site of gene editing following the introduction of the DSBs. Thus, in some embodiments, the disruption of the gene and the introduction of the antigen receptor, e.g., CAR, are carried out simultaneously, whereby the gene is disrupted in part by knock-in or insertion of the CAR-encoding nucleic acid.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

1) ZFPs and ZFNs; TALs, TALEs, and TALENs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al., Frontiers in Immunology, 4(221), 1-7 (2013).

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP.

Among the ZFPs are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In some aspects, repression of the gene is carried out by contacting a first target site in the gene with a first ZFP, thereby repressing the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains. In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type IIS restriction enzyme and one or more zinc finger binding domains, which may or may not be engineered. In some embodiments, the cleavage domain is from the Type IIS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.

In some embodiments, ZFNs target a gene encoding a protein positively regulated by IDO-mediated catabolism (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some aspects, the ZFNs efficiently generate a double strand break (DSB), for example at a predetermined site in the coding region of the gene. Typical regions targeted include exons, regions encoding N-terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of proteins. Gaj et al., Trends in Biotechnology, 2013, 31(7), 397-405. In some embodiments, commercially available zinc fingers are used or are custom designed. (See, for example, Sigma-Aldrich catalog numbers CSTZFND, CSTZFN, CTI1-1KT, and PZD0020).

2) TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 20110301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known. See, U.S. Patent Publication No. 20110301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE-nuclease (TALEN). In some aspects the TALEN is a fusion protein comprising a DNA-binding domain derived from a TALE and a nuclease catalytic domain to cleave a nucleic acid target sequence. In some embodiments, the TALE DNA-binding domain has been engineered to bind a target sequence within genes that encode the target antigen and/or the immunosuppressive molecule. For example, in some aspects, the TALE DNA-binding domain may target a gene encoding a protein involved in IDO-mediated immunosuppressive signaling, associated with sensing or responding to tryptophan starvation or insufficiency and/or associated with sensing or responding to kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2).

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, Trends Biochem Sci. 1998 October; 23(10):394-8) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., Trends in Biotechnology, 2013, 31(7), 397-405). A library of TALENs targeting 18,740 human protein-coding genes has been constructed (Kim et al., Nature Biotechnology. 31, 251-258 (2013)). Custom-designed TALE arrays are commercially available through Cellectis Bioresearch (Paris, France), Transposagen Biopharmaceuticals (Lexington, KY, USA), and Life Technologies (Grand Island, NY, USA). TALE-nucleases targeting GCN2 or BLIMP-1 are known (see e.g. published WO2015155341).

In some embodiments the TALENs are introduced as transgenes encoded by one or more plasmid vectors. In some aspects, the plasmid vector can contain a selection marker which provides for identification and/or selection of cells which received said vector.

3) RGENs (CRISPR/Cas Systems)

In some embodiments, the repression is carried out using one or more DNA-binding nucleic acids, such as disruption via an RNA-guided endonuclease (RGEN), or other form of repression by another RNA-guided effector molecule. For example, in some embodiments, the repression is carried out using clustered regularly interspaced short palindromic repeats (CRISPR) and CRISPR-associated (Cas) proteins. See Sander and Joung, Nature Biotechnology, 32(4): 347-355.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system, or a "targeting sequence"), and/or other sequences and transcripts from a CRISPR locus.

In some embodiments, the CRISPR/Cas nuclease or CRISPR/Cas nuclease system includes a non-coding RNA molecule (guide) RNA (gRNA), whose sequence-specifically binds to DNA, and a Cas protein (e.g., Cas9), with nuclease functionality (e.g., two nuclease domains), or a variant thereof.

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes* or *Staphylococcus aureus*. In some embodiments, Cas9 nuclease (e.g., that encoded by mRNA from *Staphylococcus aureus* or from *Streptococcus pyogenes*, e.g. pCW-Cas9, Addgene #50661, Wang et al. (2014) Science, 3:343-80-4; or nuclease or nickase lentiviral vectors available from Applied Biological Materials (ABM; Canada) as Cat. No. K002, K003, K005 or K006) and a guide RNA specific to the target gene (e.g. a gene which encodes a protein involved in IDO-mediated immunosuppressive signaling, such as GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) are introduced into cells.

In general, a CRISPR system is characterized by elements that promote the formation of a CRISPR complex at the site of a target sequence. In some embodiments, the target sequence or target site is a gene encoding a protein involved in IDO-mediated immunosuppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). For example, the target sequence is in or near the gene, which encodes GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2. Typically, in the context of formation of a CRISPR complex, "target sequence" generally refers to a sequence, e.g., a gene or a genomic sequence, to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex. In some embodiments, a guide sequence is selected to reduce the degree of secondary structure within the guide sequence. Secondary structure may be determined by any suitable polynucleotide folding algorithm.

In general, a guide sequence includes a targeting domain comprising a polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some examples, the targeting domain of the gRNA is complementary, e.g., at least 80, 85, 90, 95, 98 or 99% complementary, e.g., fully complementary, to the target sequence on the target nucleic acid, such as the target sequence in the gene encoding the protein positively regulated by IDO-mediated catabolism (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2).

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of the CRISPR/Cas complex to a target sequence may be assessed by any suitable assay. For example, the components of the CRISPR/Cas system sufficient to form the CRISPR/Cas complex, including the guide sequence to be tested, may be provided to the cell having the corresponding target sequence, such as by transfection with vectors encoding the components of the CRISPR/Cas complex, followed by an assessment of preferential cleavage within the target sequence, such as by Surveyor assay as described herein. Similarly, cleavage of a target polynucleotide sequence may be evaluated in a test tube by providing the target sequence, components of the CRISPR/Cas complex, including the guide sequence to be tested and a control guide sequence different from the test guide sequence, and comparing binding or rate of cleavage at the target sequence between the test and control guide sequence reactions.

In some embodiments, a Cas nuclease and gRNA (e.g. including a fusion of crRNA specific for the target sequence and fixed tracrRNA) are introduced into the cell. In general, target sites at the 5' end of the gRNA target the Cas nuclease to the target site, e.g., the gene, using complementary base pairing. In some embodiments, the target site is selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the target nucleic acid complementary to the targeting domain is located at an early coding region of a gene of interest. Targeting of the early coding region can be used to knockout (i.e., eliminate expression of) the gene of interest. In some embodiments, the early coding region of a gene of interest includes sequence immediately following a start codon (e.g., AUG), or within 500 bp of the start codon (e.g., less than 500, 450, 400, 350, 300, 250, 200, 150, 100 or 50 bp). In some embodiments, the target sequence is within 200, 150 or 100 bp of the start codon of the gene. Targeting of the promoter region or regions near the transcription start site can be used to knockdown (i.e., reduce the expression of) the gene of interest. For example, regions near the transcription start site can include regions within 500 bp upstream of the transcription start site (e.g., less than 500, 450, 400, 350, 300, 250, 200, 150, 100 or 50 bp). In some embodiments, the target sequence can be within the promoter, enhancer or other cis- or trans-acting regulatory regions.

It is within the level of a skilled artisan to design or identify a gRNA sequence that is or comprises a sequence targeting a gene encoding a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), including the exon sequence and sequences of regulatory regions, including promoters and activators. A genome-wide gRNA database for CRISPR genome editing is publicly available, which contains exemplary single guide RNA (sgRNA) target sequences in constitutive exons of genes in the human genome or mouse genome (see e.g., http://genescript.com/gRNA-database.html; see also, Sanjana et al. (2014) Nat. Methods, 11:783-4; http://www.e-crisp.org/E-CRISP/; http://crispr.mit.edu/; https://www.dna20.com/eCommerce/cas9/input). In some embodiments, the gRNA sequence is or comprises a sequence with minimal off-target binding to a non-target gene.

Exemplary target sequences in a gene encoding a protein positively regulated by IDO-mediated immunosuppressive signaling, tryptophan starvation or insufficiency and/or kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) that are complementary to gRNA targeting domain sequences are known or can be designed. Exemplary target sequences to the gene encoding AHR that are complementary to gRNA targeting domain sequences are set forth in SEQ ID NOS: 24-29. Exemplary target sequences to the gene encoding ARNT that are complementary to gRNA targeting domain sequences are set forth in SEQ ID NOS: 30-35. Exemplary target sequences to the gene encoding GCN2 that are complementary to gRNA targeting domain sequences are set forth in SEQ ID NOS: 50-55. Exemplary target sequences to the gene encoding CHOP that are complementary to gRNA targeting domain sequences are set forth in SEQ ID NOS: 56-61. Exemplary target sequences to the gene encoding ATF4 that are complementary to gRNA targeting domain sequences are set forth in SEQ ID NOS: 62-67. Exemplary target sequences to the gene encoding eIF2α that are complementary to gRNA targeting domain sequences are set forth in SEQ ID NOS: 68-73.

In some embodiments, the CRISPR system induces double stranded breaks (DSBs) at the target site, followed by disruptions as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

In some embodiments, disruption includes insertion of a sequence into the gene. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence.

In some embodiments, a tracr sequence also may be included, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of the CRISPR complex. As with the target sequence, in some embodiments, complete complementarity is not necessarily needed. In some embodiments, the tracr sequence has at least 50%, 60%, 70%, 80%, 90%, 95% or 99% of sequence complementarity along the length of the tracr mate sequence when optimally aligned.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences.

Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In some aspects, loop forming sequences for use in hairpin structures are four nucleotides in length, and have the sequence GAAA. However, longer or shorter loop sequences may be used, as may alternative sequences. In some embodiments, the sequences include a nucleotide triplet (for example, AAA), and an additional nucleotide (for example C or G). Examples of loop forming sequences include CAAA and AAAG. In some embodiments, the transcript or transcribed polynucleotide sequence has at least two or more hairpins. In some embodiments, the transcript has two, three, four or five hairpins. In a further embodiment, the transcript has at most five hairpins. In some embodiments, the single transcript further includes a transcription termination sequence, such as a polyT sequence, for example six T nucleotides.

In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of the CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to the cell.

In some embodiments, a vector comprises a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from S. Pyogenes, S. aureus or S. pneumonia. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A; SEQ ID NO:19) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ.

In some embodiments, Cas9 or split Cas9 lacks endonuclease activity. In some embodiments, the resulting Cas9 or split Cas9 is co-expressed with guide RNA designed to comprise a complementary sequence of the target nucleic acid sequence, for example, a gene encoding a protein involved in IDO-mediated immunosuppressive signaling, associated with sensing or responding to tryptophan starvation or insufficiency and/or associated with sensing or responding to kynurenine-mediated immuno-suppression (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2). In some embodiments, expression of Cas9 lacking endonuclease activity yields specific silencing or reduction of the gene of interest. This system is named CRISPR interference (CRISPRi) (Qi, Larson et al. 2013). In some embodiments, the silencing may occur at the transcriptional or the translational step. In some embodiments, the silencing may occur by directly blocking transcription, for example by blocking transcription elongation or by targeting key cis-acting motifs within any promoter, sterically blocking the association of their cognate trans-acting transcription factors. In some embodiments, the Cas9 lacking endonuclease activity comprises both non-functional HNH and RuvC domains. In some embodiments, the Cas9 or split Cas9 polypeptide comprises inactivating mutations in the catalytic residues of both the RuvC-like and HNH domains. For example, the catalytic residues required for cleavage Cas9 activity can be D10, D31, H840, H865, H868, N882 and N891 of Cas9 of *S. pyogenes* (COG3513-SEQ ID NO:18) or aligned positions using CLUSTALW method on homologues of Cas Family members. In some embodiments, the residues comprised in HNH or RuvC motifs can be those described in the above paragraph. In some embodiments, any of these residues can be replaced by any one of the other amino acids, for example by an alanine residue. In some embodiments, mutation in the catalytic residues means either substitution by another amino acids, or deletion or addition of amino acids that cause the inactivation of at least one of the catalytic domain of Cas9.

Non-limiting examples of mutations in a Cas9 protein are known in the art (see e.g. WO2015/161276), any of which can be included in a CRISPR/Cas9 system in accord with the provided methods.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. In some embodiments, one or more codons (e.g. 1, 2, 3, 4, 5, 10, 15, 20, 25, 50, or more, or all codons) in a sequence encoding the CRISPR enzyme correspond to the most frequently used codon for a particular amino acid.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme in combination with (and optionally complexed with) a guide sequence is delivered to the cell. In some embodiments, methods for introducing a protein component into a cell according to the present disclosure (e.g. Cas9/gRNA RNPs) may be via physical delivery methods (e.g. electroporation, particle gun, Calcium Phosphate transfection, cell compression or squeezing), liposomes or nanoparticles.

Commercially available kits, gRNA vectors and donor vectors, for knockout of a protein involved in IDO-mediated immunosuppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) via CRISPR are available, for example, from Santa Cruz Biotechnology (e.g. GCN2 CRISPR/Cas9 KO plasmid, Cat. No. sc-402313; Blimp-1 CRISPR/Cas9 KO plasmid Cat. No. sc-400585; ARNT CRISPR/Cas9 KO plasmid, Cat. No. sc-401039); Origene (e.g. AHR knockout kit and gRNA vector, Cat. No. KN209832; Blimp-1 (PRDM1) knockout kit and gRNA vector, Cat. No. KN217363, CHOP (DDIT3) knockout kit and gRNA vector, Cat. No. KN201301, ATF4 knockout kit and gRNA vector, Cat. No. 202233 and EIF2S1 knockout kit and gRNA vector, Cat. No. KN200368).

In some aspects, target polynucleotides, such as genes encoding a protein involved in IDO-mediated immunosuppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), are modified in the cell in which the CRISPR complex is introduced. In some embodiments, the method comprises allowing the CRISPR complex to bind to the target polynucleotide to effect cleavage of said target polynucleotide thereby modifying the target polynucleotide, wherein the CRISPR complex comprises the CRISPR enzyme complexed with a guide sequence that hybridizes to a target sequence within said target polynucleotide, wherein said guide sequence is linked to a tracr mate sequence which in turn hybridizes to a tracr sequence.

In some embodiments, the method comprises allowing the CRISPR complex to bind to the polynucleotide such that said binding results in increased or decreased expression of said polynucleotide; wherein the CRISPR complex comprises a CRISPR enzyme complexed with a guide sequence that hybridizes to a target sequence within said polynucleotide, wherein said guide sequence is linked to a tracr mate sequence which in turn hybridizes to a tracr sequence.

c. Delivery of Agents, Nucleic Acids Encoding the Gene Disrupting Molecules and Complexes In some aspects, a nucleic acid encoding a nucleic acid molecule that is, includes or encodes a nucleic acid inhibitory molecule, such as an RNA interfering molecule, DNA-targeting molecule, complex thereof (e.g. Cas9/gRNA RNPs), or combination, is administered or introduced to the cell. In some embodiments, such nucleic acid molecule or complex thereof can be introduced into cells, such as T cells, by methods well known in the art. Such methods include, but are not limited to, introduction in the form of recombinant viral vectors (e.g. retroviruses, lentiviruses, adenoviruses), liposomes or nanoparticles. In some embodiments, methods can include microinjection, electroporation, particle bombardment, Calcium Phosphate transfection, cell compression, squeezing. In some embodiments, the polynucleotides may be included in vectors, more particularly plasmids or virus, in view of being expressed in the cells.

In some embodiments, viral and non-viral based gene transfer methods can be used to introduce nucleic acids into cells, such as T cells. Such methods can be used to administer nucleic acids encoding components to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). Other delivery vehicles include polymeric carriers, chemical carriers, lipoplexes, polyplexes, dendrimers, nanoparticles, emulsion and/or agents that trigger natural endocytosis or phagocytosis pathways.

In some embodiments, delivery is via the use of RNA or DNA viral based systems for the delivery of nucleic acids. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994). Viral-based systems in some embodiments include retroviral, lentivirus, adenoviral, adeno-associated and herpes simplex virus vectors for gene transfer.

In some embodiments, the nucleic acid is administered in the form of an expression vector, such as a viral expression vector. In some aspects, the expression vector is a retroviral expression vector, an adenoviral expression vector, a DNA plasmid expression vector, or an AAV expression vector. In some embodiments, the introduced vector, such as a viral vector, also includes nucleic acid encoding the genetically engineered antigen receptor, such as CAR. In some embodiments, the nucleic acids can be provided on separate expression cassettes operably linked to a promoter for control of separate expression therefrom.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase. In a further embodiment, the expression of the gene product is decreased.

In some embodiments, an agent capable of inducing a genetic disruption, such as a knockdown or a knockout of genes encoding a protein involved in IDO-mediated immunosuppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), is introduced as a complex, such as a ribonucleoprotein (RNP) complex. RNP complexes include a sequence of ribonucleotides, such as an RNA or a gRNA molecule, and a polypeptide, such as a Cas9 protein or variant thereof. In some embodiments, the Cas9 protein is delivered as an RNP complex that comprises a Cas9 protein and a gRNA molecule, e.g., a gRNA targeted for the specific gene. In some embodiments, the RNP that includes one or more gRNA molecules targeted for the gene, and a Cas9 enzyme or variant thereof, is directly introduced into the cell via physical delivery (e.g., electroporation, particle gun, Calcium Phosphate transfection, cell compression or squeezing), liposomes or nanoparticles. In particular embodiments, the RNP includes one or more gRNA molecules targeted for a gene encoding GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2 and a Cas9 enzyme or variant thereof is introduced via electroporation.

In some embodiments, the degree of knockout of a gene, encoding a protein involved in IDO-mediated immunosuppressive signaling (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2), at various time points, e.g., 24 to 72 hours after introduction of agent, can be assessed using any of a number of well-known assays for assessing gene disruption in cells. Such assays can include determining the level of transcription or protein expression or cell surface expression.

3. Conditional Systems

In some embodiments, the provided engineered cells include cells modified to result in conditional, such as inducible, expression of a protein involved in IDO-mediated immunosuppressive signaling, including those that are positively or negatively regulated by IDO-mediated catabolism. In some embodiments, expression of the gene encoding a recombinant, engineered or ectopic expression of a protein involved in IDO-mediated immunosuppressive signaling that is negatively regulated by IDO-mediated catabolism (e.g. mTOR or PKC theta) or an amino acid transporter (e.g., CD98hc, LAT1, LAT2 or PAT4) is conditional. In some embodiments, the deletion, knockout, disruption, reduction of expression, disruption of expression, inhibition of upregulation and/or inhibition of function of genes encoding a protein positively regulated by IDO-mediated catabolism (e.g. GCN2, CHOP, Blimp-1, AHR, ARNT, eIF2α, ATF4, Gadd45α, Herp, 4E-BP1, eIF4G, JAK1, NFκB-2, FK506-BP8, IFNγ-R2) is conditional. In some embodiments, conditional suppression of genes may be initiated or induced upon signaling induced by the antigen receptor (e.g. CAR), a decrease or reduction in detectable antigen receptor-expressing cells (e.g. CAR-T cells) in the blood, an increase in IFN-gamma or TNFα in a biological sample, a decrease in tryptophan and/or an increase in kynurenine or another tryptophan metabolite in a biological sample, a decline in persistence of administered cells engineered with an antigen receptor (e.g. CAR) and/or upon such cells exhibiting an exhaustive phenotype, such as any of the parameters described herein. In some embodiments, conditional suppression may facilitate therapeutic applications by resulting in cells that exhibit an increased duration of exposure and/or by allowing time and/or dosage control of the treatment.

In some embodiments, expression or activity of the protein involved in IDO-mediated immunosuppressive signaling is constitutive; in some embodiments, one or more of such expression or activity is engineered to be conditional, for example, induced or repressed by one or more natural or non-natural events or molecules.

In some embodiments, the protein involved in IDO-mediated immunosuppressive signaling is operably linked an inducing or repressing element, such as one or more enhancer(s), and/or transactivator(s) or repressors or other sequences or molecules for control of expression, e.g., via control of transcription or translation. As used herein, "operably linked" or "operably associated" includes reference to a functional linkage of at least two sequences. For example, operably linked includes linkage between a promoter and a second sequence, wherein the promoter sequence initiates and mediates transcription of the DNA sequence corresponding to the second sequence. Operably associated includes linkage between an inducing or repressing element and a promoter, wherein the inducing or repressing element acts as a transcriptional activator of the promoter.

In some embodiments, expression of the protein involved in IDO-mediated immunosuppressive signaling is under the control of a constitutive promoter, enhancer, or transactivator. In some embodiments, the expression is under the control of a conditional promoter, enhancer or transactivator. In some embodiments, the conditional promoter, enhancer or transactivator is an inducible promoter, enhancer or transactivator, a repressible promoter, enhancer or transactivator, or a tissue-specific promoter, enhancer or transactivator.

Exemplary tissue specific promoters include, but are not limited to, those that are active in heart, lung, esophagus, muscle, intestine, breast, prostate, stomach, bladder, liver, spleen, pancreas, kidney, neurons, myocytes, leukocytes, immortalized cells, neoplastic cells, tumor cells, cancer cells, duodenum, jejunum, ileum, cecum, colon, rectum, salivary glands, gall bladder, urinary bladder, trachea, larynx, pharynx, aorta, arteries capillaries, veins, thymus, mandibular lymph nodes, mesenteric lymph node, bone marrow, pituitary gland, thyroid gland, parathyroid glands, adrenal glands, brain, cerebrum, cerebellum, medulla, pons, spinal cord, sciatic nerve, skeletal muscle, smooth muscle, bone, testes, epididymis, prostate, seminal vesicles, penis, ovaries, uterus, mammary glands, vagina, skin, eyes or optic nerve.

Exemplary cell specific promoters include T cells, such as the CD4 mini-promoter/enhancer described in Zhao-Emonet, et al. (2000) *J. Gene. Med.*, 2: 416-425.

In some embodiments, the expression of the protein involved in IDO-mediated immunosuppressive signaling is conditional upon (e.g., is induced or repressed by, such as via an inducible promoter or other element) by one or more specific conditions, events, or molecules found or found at relatively higher levels in particular, regions of the body, disease, activation state, or tissues. For example, the in some embodiments the promoter can be inducible or suppressible by hypoxia, glucose-poor or other nutrient-poor conditions, deficiencies in metabolites such as amino acids (e.g. tryptophan) or nucleic acids or lipids, elements of the tumor microenvironment, or other elements of metabolic pathways or metabolites or levels thereof. See, e.g. Cao, et al. (2001) *Gene Ther.*, 8: 1357-1362 and Dachs, et al. (2000) *Eur. J. Cancer*, 36:1649-1660, and Greco et al., (2002) *Gene Ther.*, 9:1403-1411. In some embodiments, expression is conditioned upon activation signals or pathways, or signaling via a particular receptor, such as a cytokine or antigen receptor (e.g. CAR or TCR). In some embodiments, expression is regulated by activation or proliferative events. Exemplary inducible systems are those activatable by NFκB, NFAT or Nur77.

In some embodiments, expression of any of the nucleic acids described herein may be externally controlled by treating the cell with a modulating factor, such as doxycycline, tetracycline or analogues thereof. Analogues of tetracycline are for example chlortetracycline, oxytetracycline, demethylchloro-tetracycline, methacycline, doxycycline and minocycline.

In some embodiments, inducible transcription and/or expression may be implemented using a transactivator induced promoter together with said transactivator. In some embodiments, such a transactivator induced promoter comprises control elements for the enhancement or repression of transcription of the transgene or nucleic acid of interest. Control elements include, without limitation, operators, enhancers and promoters. In some embodiments, a transactivator inducible promoter is transcriptionally active when bound to a transactivator, which in turn is activated under a specific set of conditions, for example, in the presence or in the absence of a particular combination of chemical signals, for example, by a modulating factor selected for example from the previous list.

The transactivator induced promoter may be any promoter herein mentioned which has been modified to incorporate transactivator binding sequences, such as several tet-operator sequences, for example 3, 4, 5, 6, 7, 8, 9, or 10 tet-operator sequences. In some embodiments, the tet-operator sequences are in tandem. In some embodiments, the promoter is a tetracycline response element (TRE). Such sequences can for example replace the functional recognition sites for Staf and Oct-1 in the distal sequence element (DSE) of the U6 promoter, including the human U6 promoter.

Specific examples of transcription modulator domains that induce expression in the presence of modulating factor include, but are not limited to, the transcription modulator domains found in the following transcription modulators: the Tet-On transcription modulator; and the Tet-On Advanced transcription modulator and the Tet-On 3G transcription modulator; all of which are available from Clontech Laboratories, Mountain View, CA Specific examples of transcription modulator domains that induce expression in the absence of modulating factor include, but are not limited to, the transcription modulator domains found in the following transcription modulators: the Tet-off transcription modulator and the Tet-Off Advanced transcription modulator, both of which are available from Clontech Laboratories, Mountain View, CA These systems can be adapted and used according to procedures that are well known in the art and that will be familiar to the ordinarily skilled artisan.

In some embodiments, the transactivator induced promoter comprises a plurality of transactivator binding sequences operatively linked to the inhibitory nucleic acid molecule.

The transactivator may be provided by a nucleic acid sequence, in the same expression vector or in a different expression vector, comprising a modulating factor-dependent promoter operatively linked to a sequence encoding the transactivator. The term "different expression vector" is intended to include any vehicle for delivery of a nucleic acid, for example, a virus, plasmid, cosmid or transposon. Suitable promoters for use in said nucleic acid sequence include, for example, constitutive, regulated, tissue-specific or ubiquitous promoters, which may be of cellular, viral or synthetic origin, such as CMV, RSV, PGK, EF1α, NSE, synapsin, β-actin, GFAP.

An exemplary transactivator according to some embodiments is the rtTA-Oct2 transactivator composed of the DNA binding domain of rtTA2-M2 and of the Oct-2Q(Q→A) activation domain. Another exemplary transactivator according to some embodiments is the rtTA-Oct3 transactivator composed of the DNA binding domain of the Tet-repressor protein (E. coli) and of the Oct-2Q(Q→A) activation domain. Both are described in patent application WO 2007/004062.

Some embodiments include an isolated nucleotide sequence encoding a regulatory fusion protein (RPR), wherein the fusion protein contains (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized.

In some embodiments, the transcription blocking domain may be derived from a bacterial, bacteriophage, eukaryotic, or yeast repressor protein. In some embodiments, the transcription blocking domain is derived from a bacterial or bacteriophage repressor protein, such as, for example, TetR, LexA, LacI, TrpR, Arc, and LambdaCI. In some embodiments, the transcription blocking domain is derived from a eukaryotic repressor protein, such as, for example, GAL4. In some embodiments, the transcription blocking domain is a mutated restriction enzyme capable of binding but not cleaving DNA, and the operator is a recognition site for the restriction enzyme. In some embodiments, for example, the transcription blocking domain is a mutated NotI.

In some embodiments, the ligand-binding domain is derived from a steroid, thyroid, or retinoid receptor. In some embodiments, the ligand-binding domain is derived from an estrogen receptor, and the cognate ligand is an estrogen. In some embodiments, the estrogen receptor contains one or more mutations, for example, the T2 mutations, and the cognate ligand is tamoxifen. These systems can be adapted and used according to procedures that are well known in the art and that will be familiar to the ordinarily skilled artisan.

In some embodiments, the RheoSwitch system can be used to modulate transcription. In some embodiments, the RheoSwitch system includes a Rheoreceptor and Rheoactivator proteins, which can be activated by the presence of RSL1 ligand. In some embodiments, the receptor and activator stably dimerize and bind to the response element and turn on transcription in the presence of the RSL1 ligand (see, for example, the Instruction Manual for "RheoSwitch® Mammalian Inducible Expression System," New England BioLabs® Inc., Version 1.3, November 2007; Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. and Christopoulos, T. K., Annal. Chem. 74:4378-4385 (2002); Katalam, A. K., et al., Molecular Therapy 13:S103 (2006); and Karzenowski, D. et al., Molecular Therapy 13:S194 (2006)).

In some embodiments, electromagnetic energy can be used to modulate transcription, including, for example, the systems and methods described in WO 2014/018423, incorporated herein by reference.

In some embodiments, controllable regulation of RNA transcription can be achieved by including a repressor binding region, such as, for example, from the lac repressor/operator system as modified for mammals. See Hu and Davidson, 1987, and Kozak, 1986.

In some embodiments, an introduced nucleic acid, such as one that is or encodes an inhibitory agent, can be removed at a time subsequent to its integration in a host genome, such as by using site-specific recombination methods. In some embodiments, an inhibitory agent, such as a nucleic acid that is or encodes CRISPR, gRNA, Cas, ZFP, ZFN, TALE, TALEN, RNAi, siRNA, shRNA, miRNA, antisense RNA and/or ribozymes, is placed between recombination site sequences, such as loxP. In some embodiments, the nucleic acid includes at least one (typically two) site(s) for recombination mediated by a site-specific recombinase. In some embodiments, site-specific recombinases catalyze introduction or excision of DNA fragments from a longer DNA molecule. In some embodiments, these enzymes recognize a relatively short, unique nucleic acid sequence, which serves for both recognition and recombination. In some embodiments, a recombination site contains short inverted repeats (6, 7, or 8 base pairs in length) and the length of the DNA-binding element can be approximately 11 to approximately 13 bp in length.

In some embodiments, the vectors may comprise one or more recombination sites for any of a wide variety of site-specific recombinases. It is to be understood that the target site for a site-specific recombinase is in addition to any site(s) required for integration of a viral, e.g. lentiviral, genome. In some embodiments, a nucleic acid includes one or more sites for a recombinase enzyme selected from the group consisting of Cre, XerD, HP1 and Flp. These enzymes and their recombination sites are well known in the art (see, for example, Sauer et al., 1989, Nucleic Acids Res., 17:147; Gorman et al., 2000, Curr. Op. Biotechnol, 11:455; O'Gorman et al., 1991, Science, 251: 1351; Kolb, 2002, Cloning Stem Cells, 4:65; Kuhn et al., 2002, Methods Mol. Biol, 180:175).

In some embodiments, these recombinases catalyze a conservative DNA recombination event between two 34-bp recognition sites (loxP and FRT, respectively). In some embodiments, placing a heterologous nucleic acid sequence operably linked to a promoter element between two loxP sites (in which case the sequence is "floxed") allows for controlled expression of the introduced nucleic acid encoding an inhibitory agent, such as any of those described herein, following transfer into a cell. By inducing expression of Cre within the cell, the heterologous nucleic acid sequence is excised, thus preventing further transcription and/or effectively eliminating expression of the sequence. Some embodiments comprise Cre-mediated gene activation, in which either heterologous or endogenous genes may be activated, e.g., by removal of an inhibitory element or a polyadenylation site.

As described above, positioning a heterologous nucleic acid sequence between loxP sites allows for controlled expression of the heterologous sequence following transfer into a cell. By inducing Cre expression within the cell, the heterologous nucleic acid sequence can be excised, thus preventing further transcription and/or effectively eliminating expression of the sequence. Cre expression may be induced in any of a variety of ways. For example, Cre may be present in the cells under control of an inducible promoter, and Cre expression may be induced by activating the promoter. Alternatively or additionally, Cre expression may be induced by introducing an expression vector that directs expression of Cre into the cell. Any suitable expression vector can be used, including, but not limited to, viral vectors such as lentiviral or adenoviral vectors. The phrase "inducing Cre expression" as used herein refers to any process that results in an increased level of Cre within a cell.

Lentiviral transfer plasmids comprising two loxP sites are useful in any applications for which standard vectors comprising two loxP sites can be used. For example, selectable markers may be placed between the loxP sites. This allows for sequential and repeated targeting of multiple genes to a single cell (or its progeny). After introduction of a transfer plasmid comprising a floxed selectable marker into a cell, stable transfectants may be selected. After isolation of a stable transfectant, the marker can be excised by induction of Cre. The marker may then be used to target a second gene to the cell or its progeny. Lentiviral particles comprising a lentiviral genome derived from the transfer plasmids may be used in the same manner.

In some embodiments, transfer plasmids and lentiviral particles may be used to achieve constitutive, conditional, reversible, or tissue-specific expression in cells, tissues, or organisms. Some embodiments include a method of reversibly expressing a transcript in a cell comprising: (i) delivering a lentiviral vector to the cell, wherein the lentiviral vector comprises a heterologous nucleic acid, and wherein the heterologous nucleic acid is located between sites for a site-specific recombinase; and (ii) inducing expression of the site-specific recombinase within the cell, thereby preventing synthesis of the transcript within those cells. According to some embodiments, a nucleic acid encoding the site-specific recombinase is operably linked to an inducible promoter, and the inducing step comprises inducing the promoter as described above.

D. Vectors and Methods for Genetic Engineering

Introduction of the nucleic acid molecules encoding the recombinant receptor and/or encoding a protein involved in IDO-mediated immunosuppressive signaling, associated with sensing or responding to tryptophan starvation or insufficiency and/or associated with sensing or responding to kynurenine-mediated immuno-suppression in the cell or encoding an agent regulating expression of a protein involved in IDO-mediated immunosuppressive signaling, associated with sensing or responding to tryptophan starvation or insufficiency and/or associated with sensing or responding to kynurenine-mediated immuno-suppression in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, prior to or during gene transfer, the cells are incubated or cultured in the presence of a modulator of a tryptophan metabolic pathway, such as a kynurenine pathway modulator, including any as described herein. In some embodiments, a tryptophan metabolism and/or kynurenine modulator (e.g. an IDO1 inhibitor) is added during the cell manufacturing process, for example, during the process of engineering CAR-T cells. In some aspects, the presence of the modulator can improve the quality of the population of cells produced. In some aspects, the modulator (e.g. IDO1 inhibitor) may increase the proliferation or expansion of cells or may alter one or more signaling pathways thereby resulting in cells with a less-differentiated or less activated surface phenotype, despite exhibiting substantial expansion and/or effector function.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the ant-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the activity or outcome of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991) and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

V. ARTICLES OF MANUFACTURE AND KITS

Also provided are kits and articles of manufacture containing the provided tryptophan metabolism and/or kynurenine pathway modulators, e.g., IDO1 inhibitors, and components for the immunotherapy, e.g., antibody or antigen binding fragment thereof or T cell therapy, e.g. engineered cells, and/or compositions thereof. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may include (a) a first container with a composition contained therein, wherein the composition includes the antibody or engineered cells used for the immunotherapy, e.g. T cell therapy; and (b) a second container with a composition contained therein, wherein the composition includes the second agent, such as a tryptophan metabolism and/or kynurenine pathway modulator, e.g., IDO1 inhibitor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

In some embodiments, the kit or article of manufacture includes any of the engineered cells, tryptophan metabolism and/or kynurenine pathway modulators, combinations, compositions, polynucleotides, set of polynucleotides, composition containing set of polynucleotides, vectors, set of vectors, composition containing set of vectors, kits, additional therapeutic agents, agents used for diagnosis and/or assessment and/or agents used for engineering cells for the immunotherapy.

In some embodiments, the kit or article of manufacture further contains instructions for administering the combination therapy, e.g., immunotherapy (e.g. T cell therapy, such as CAR-T cell therapy) and/or a tryptophan metabolism and/or kynurenine pathway modulator. In some embodiments, the kit or article of manufacture further contains instructions for screening and/or assessment steps to determine suitability for the combination therapy, to identify subjects for treatment with the combination therapy and/or continuing the combination therapy, and/or a step for assessment of treatment outcomes and/or monitoring treatment outcomes.

VI. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The term "pharmaceutical formulation" refers to a preparation which is in such form as to permit the biological activity of an active ingredient contained therein to be effective, and which contains no additional components which are unacceptably toxic to a subject to which the formulation would be administered.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a "subject" is a mammal, such as a human or other animal, and typically is human. In some embodiments, the subject, e.g., patient, to whom the tryptophan metabolism and/or kynurenine pathway modulators, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the tryptophan metabolism and/or kynurenine pathway modulator, e.g. IDO1 inhibitor or engineered cells administered. In some embodiments, the provided methods involve administering the tryptophan metabolism and/or kynurenine pathway modulator, e.g. IDO1 inhibitor, engineered cells, or compositions at effective amounts, e.g., therapeutically effective amounts.

VII. EXEMPLARY EMBODIMENTS

Among the provided embodiments are:
1. A method of treatment, comprising:
   (a) administering a T cell therapy to a subject having a disease or condition, which optionally is a cancer; and
   (b) administering to the subject a therapeutically effective amount of a tryptophan metabolism and/or kynurenine pathway modulator, wherein administration of the tryptophan metabolism and/or kynurenine pathway modulator is started at a time point greater than 1 day prior to initiation of administration of the T cell therapy and/or administering the T cell therapy.
2. A method of treatment, comprising administering a T cell therapy to a subject having a disease or condition, which optionally is a cancer, the subject having been previously administered a therapeutically effective amount of a tryptophan metabolism and/or kynurenine pathway modulator starting at a time point greater than 1 day prior to initiation of the T cell therapy.
3. The method of embodiment 1 or embodiment 2, wherein administration of the tryptophan metabolism and/or kynurenine pathway modulator is started at a time point that is within or within about 2 days, 3 days, 6 days, 12 days, 15 days, 30 days, 60 days or 90 days or more prior to initiation of the administration of the T cell therapy.
4. The method of any of embodiments 1-3, further comprising continuing administration of the tryptophan metabolism and/or kynurenine pathway modulator with or subsequent to initiation of administration of the T cell therapy and/or administering the T cell therapy.
5. The method of any of embodiments 1-4, further comprising administering the tryptophan metabolism and/or kynurenine pathway modulator subsequent to initiation of administration of the T cell therapy and/or administering the T cell therapy.
6. A method of treatment, comprising:
   (a) administering a T cell therapy to a subject having a disease or condition, which optionally is a cancer; and
   (b) administering to the subject a therapeutically effective amount of a tryptophan metabolism and/or kynurenine pathway modulator subsequent to initiation of administration of the T cell therapy and/or administering the T cell therapy.
7. A method of treatment, comprising administering to a subject having a disease or condition, which optionally is a cancer a therapeutically effective amount of a tryptophan metabolism and/or kynurenine pathway modulator, the subject having been previously administered a T cell therapy.
8. The method of any of embodiments 1-7, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator, optionally wherein such prior administration was carried out in combination with an immunomodulatory agent, optionally a checkpoint inhibitor.
9. A method of treatment, comprising:
   (a) administering a T cell therapy to a subject having a disease or condition, which optionally is a cancer; and
   (b) administering to the subject a therapeutically effective amount of a tryptophan metabolism and/or kynurenine pathway modulator, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

10. A method of treatment, comprising administering to a subject having a disease or condition, which optionally is a cancer a therapeutically effective amount of a tryptophan metabolism and/or kynurenine pathway modulator to a subject having been administered a T cell therapy, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

11. The method of any of embodiments 1-10, wherein the disease or condition is cancer.

12. The method of embodiment 9 or embodiment 11, wherein the tryptophan metabolism and/or kynurenine pathway modulator administered in (b) is administered prior to, simultaneously with and/or subsequent to initiation of administration of the T cell therapy and/or administering the T cell therapy.

13. The method of any of embodiments 9, 11 or 12, wherein administration of the tryptophan metabolism and/or kynurenine pathway modulator administered in (b) is started at a time point that is within or within about 2 days, 3 days, 6 days, 12 days, 15 days, 30 days, 60 days or 90 days or more prior to initiation of the administration of the T cell therapy.

14. The method of any of embodiments 9-12, comprising administering the tryptophan metabolism and/or kynurenine pathway modulator administered in (b) subsequent to initiation of administration of the T cell therapy and/or administering the T cell therapy.

15. The method of any of embodiments 5-12, and 14, wherein the tryptophan metabolism and/or kynurenine pathway modulator is administered at a time in which:
 there is a decrease in tryptophan levels, an increase in kynurenine levels and/or an increase in expression or activity of IDO1, IDO2 or TDO in a biological sample from the subject compared to prior to initiation of administration of the T cell therapy and/or administering the T cell therapy or compared to a preceding time point after initiation of administration of the T cell therapy and/or administering the T cell therapy;
 at a time before the number of cells of the T cell therapy detectable in the blood from the subject is decreased compared to in the subject at a preceding time point after initiation of administration of the T cell therapy and/or administering the T cell therapy;
 at a time before T cells exhibit manifestations of prolonged tryptophan starvation, exhaustion, reduction of effector function, expression of inhibitory receptors and/or loss of proliferative capacity;
 at a time before a peak or maximum level of the cells of the T cell therapy are detectable in the blood of the subject;
 the level of interferon-gamma (IFNγ) is increased in a biological sample from the subject compared to prior to initiation of administration of the T cell therapy and/or administering the T cell therapy or compared to a preceding time point after initiation of administration of the T cell therapy and/or administering the T cell therapy;
 the number of cells of the T cell therapy detectable in the blood from the subject is decreased compared to in the subject at a preceding time point after initiation of administration of the T cell therapy and/or administering the T cell therapy;
 the number of cells of the T cell therapy detectable in the blood is decreased by more than or more than about 1.5-fold, 2-fold, 3-fold, 4-fold, 5-fold, 10-fold, 50-fold or 100-fold or more, compared to the peak or maximum number of the cells of the T cell therapy detectable in the blood of the subject after initiation of administration of the T cell therapy and/or administering the T cell therapy; and/or
 at a time after a peak or maximum level of the cells of the T cell therapy are detectable in the blood of the subject, the number of cells of the T cell therapy detectable in the blood from the subject is less than 10%, less than 5%, less than 1% or less than 0.1% of total peripheral blood mononuclear cells (PBMCs) in the blood of the subject.

16. The method of embodiment 15, wherein the increase or decrease is by greater than or greater than about 1.2-fold, 1.5-fold, 2-fold, 3-fold, 4-fold, 5-fold, 10-fold or more.

17. The method of any of embodiments 5-12 and 14-16, wherein the tryptophan metabolism and/or kynurenine pathway modulator administered in (b) is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy.

18. The method of any of embodiments 5-12 and 14-17, wherein the tryptophan metabolism and/or kynurenine pathway modulator administered in (b) is administered within or within about 1 hour, 2 hours, 6 hours, 12 hours, 24 hours or 48 hours subsequent to initiation of the T cell therapy.

19. The method of embodiment 15 or embodiment 16, wherein the biological sample is a serum or plasma or tumor sample or is a tumor.

20. The method of any of embodiments 1-19, wherein the tryptophan metabolism and/or kynurenine pathway modulator prevents or reduces the formation, concentration, availability, metabolism and/or effect of an enzyme and/or a metabolite of the kynurenine pathway.

21. The method of any of embodiments 1-20, wherein the tryptophan metabolism and/or kynurenine pathway modulator prevents or reduces catabolism of tryptophan, prevents or reduces synthesis or accumulation of a tryptophan metabolite or decreases the kynurenine to tryptophan ratio.

22. The method of embodiment 21, wherein the tryptophan metabolite is selected from kynurenine, 3-hydroxykynurenine and 3-hydroxyanthranilic acid (3-HAA).

23. The method of any of embodiments 1-22, wherein the tryptophan metabolism and/or kynurenine pathway modulator is a small molecule, peptide, protein, antibody or antigen-binding fragment thereof, an antibody mimetic, an aptamer, or a nucleic acid molecule.

24. The method of any of embodiments 1-23, wherein the tryptophan metabolism and/or kynurenine pathway modulator is an antagonist of the enzyme kynureninase.

25. The method of any of embodiments 1-23, wherein the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO).

26. The method of any of embodiments 1-23 and 25, wherein the tryptophan metabolism and/or kynurenine pathway modulator is a dual-acting IDO/TDO inhibitor.

27. The method of any of embodiments 1-23 and 25, wherein the tryptophan metabolism and/or kynurenine pathway modulator is an inhibitor of indoleamine-pyrrole 2,3-dioxygenase 1 (IDO1).

28. The method of any of embodiments 6-23, 25 and 27, wherein the tryptophan metabolism and/or kynurenine pathway modulator is an inhibitor of IDO1 and the inhibitor of IDO1 is administered at a time in which there is an increase in the expression or activity of IDO1 in a biological sample from the subject compared to prior to initiation of administration of the T cell therapy and/or administering the T cell therapy or compared to a preceding time point after initiation of administration of the T cell therapy and/or administering the T cell therapy.

29. The method of any of embodiments 1-23, wherein the tryptophan metabolism and/or kynurenine pathway modulator is tryptophan.

30. The method of any one of embodiments 1-29, wherein:
the cancer comprises a tumor negative for IDO1 prior to initiation of administration of the T cell therapy and/or administering the T cell therapy and/or the subject is not selected for expression of an IDO1 positive tumor prior to initiation of administration of the T cell therapy and/or administering the T cell therapy; and/or
the cancer comprises a tumor negative for TDO prior to initiation of administration of the T cell therapy and/or administering the T cell therapy and/or the subject is not selected for expression of a TDO positive tumor prior to initiation of administration of the T cell therapy and/or administering the T cell therapy.

31. The method of embodiment 30, wherein the cancer comprises a tumor negative for IDO1 prior to initiation of administration of the T cell therapy and/or administering the T cell therapy and/or the subject is not selected for expression of an IDO1 positive tumor prior to initiation of administration of the T cell therapy and/or administering the T cell therapy.

32. A method of treatment, comprising:
(a) administering a T cell therapy to a subject having a disease or condition, which optionally is a cancer, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or administering the T cell therapy and/or the subject is not selected for expression of an IDO1 positive tumor or a TDO positive tumor prior to initiation of administration of the T cell therapy and/or administering the T cell therapy; and
(b) administering to the subject a therapeutically effective amount of a tryptophan metabolism and/or kynurenine pathway modulator that is an inhibitor of IDO1.

33. The method of embodiment 32, wherein the tryptophan metabolism and/or kynurenine pathway modulator administered in (b) is administered prior to, simultaneously with and/or subsequent to initiation of administration of the T cell therapy and/or administering the T cell therapy.

34. A method of treatment, comprising administering to a subject having a disease or condition, which optionally is a cancer a therapeutically effective amount of a tryptophan metabolism and/or kynurenine pathway modulator that is an inhibitor of IDO1, the subject having been administered a T cell therapy, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or administering the T cell therapy and/or the subject is not selected for expression of an IDO1 positive tumor or a TDO positive tumor prior to initiation of administration of the T cell therapy and/or administering the T cell therapy.

35. A method of treatment, comprising administering to a subject having a disease or condition, which optionally is a cancer a T cell therapy, the subject having been administered a therapeutically effective amount of a tryptophan metabolism and/or kynurenine pathway modulator that is an inhibitor of IDO1, wherein the cancer comprises a tumor negative for indoleamine-pyrrole 2,3-dioxygenase 1 (IDO1) or tryptophan 2,3-dioxygenase (TDO) prior to initiation of administration of the T cell therapy and/or administering the T cell therapy and/or the subject is not selected for expression of an IDO1 positive tumor or a TDO positive tumor prior to initiation of administration of the T cell therapy and/or administering the T cell therapy.

36. The method of any of embodiments 32-35, wherein the disease or condition is cancer.

37. The method of any of embodiments 32-35, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

38. The method of any of embodiments 35-37, comprising administering the tryptophan metabolism and/or kynurenine pathway modulator administered in (b) subsequent to initiation of administration of the T cell therapy and/or administering the T cell therapy.

39. The method of any of embodiments 32-34 and 36-38, wherein tryptophan metabolism and/or kynurenine pathway modulator is administered at a time in which:
there is a decrease in tryptophan levels, an increase in kynurenine levels and/or an increase in expression or activity of IDO1, IDO2 or TDO in a biological sample from the subject compared to prior to initiation of administration of the T cell therapy and/or administering the T cell therapy or compared to a preceding time point after initiation of administration of the T cell therapy and/or administering the T cell therapy;
at a time before the number of cells of the T cell therapy detectable in the blood from the subject is decreased compared to in the subject at a preceding time point after initiation of administration of the T cell therapy and/or administering the T cell therapy;
at a time before T cells exhibit manifestations of prolonged tryptophan starvation, exhaustion, reduction of effector function, expression of inhibitory receptors and/or loss of proliferative capacity;
at a time before a peak or maximum level of the cells of the T cell therapy are detectable in the blood of the subject;
the level of interferon-gamma (IFNγ) is increased in a biological sample from the subject compared to prior to initiation of administration of the T cell therapy and/or administering the T cell therapy or compared to a preceding time point after initiation of administration of the T cell therapy and/or administering the T cell therapy;

the number of cells of the T cell therapy detectable in the blood from the subject is decreased compared to in the subject at a preceding time point after initiation of administration of the T cell therapy and/or administering the T cell therapy;

the number of cells of the T cell therapy detectable in the blood is decreased by more than or more than about 1.5-fold, 2-fold, 3-fold, 4-fold, 5-fold, 10-fold, 50-fold or 100-fold or more, compared to the peak or maximum number of the cells of the T cell therapy detectable in the blood of the subject after initiation of administration of the T cell therapy and/or administering the T cell therapy; and/or at a time after a peak or maximum level of the cells of the T cell therapy are detectable in the blood of the subject, the number of cells of the T cell therapy detectable in the blood from the subject is less than 10%, less than 5%, less than 1% or less than 0.1% of total peripheral blood mononuclear cells (PBMCs) in the blood of the subject.

40. The method of embodiment 39, wherein the increase or decrease is by greater than or greater than about 1.2-fold, 1.5-fold, 2-fold, 3-fold, 4-fold, 5-fold, 10-fold or more.

41. The method of any of embodiments 32-34 and 36-40, wherein the tryptophan metabolism and/or kynurenine pathway modulator administered in (b) is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy.

42. The method of any of embodiments 32-34 and 36-41, wherein the tryptophan metabolism and/or kynurenine pathway modulator administered in (b) is administered within or within about 1 hour, 2 hours, 6 hours, 12 hours, 24 hours or 48 hours subsequent to initiation of the T cell therapy.

43. The method of any of embodiments 32, 33 and 35-37, wherein:

the tryptophan metabolism and/or kynurenine pathway modulator administered in (b) is administered from or from about 0 to 96 hours, 0 to 72 hours, 0 to 48 hours, 0 to 24 hours, 0 to 12 hours or 0 to 6 hours or 0 to 2 hours prior to initiation of the T cell therapy; or the tryptophan metabolism and/or kynurenine pathway modulator administered in (b) is administered no more than 96 hours, 72 hours, 48 hours, 24 hours, 12 hours, 6 hours, 2 hours or 1 hour prior to initiation of the T cell therapy.

44. The method of any of embodiments 1-23 and 25-43, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

45. The method of embodiment 44, wherein the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

46. The method of embodiment 44, wherein the tryptophan metabolism and/or kynurenine pathway modulator is 1-methyl-D-tryptophan (1-MT) (indoximod).

47. The method of any of embodiments 32-43, wherein the tryptophan metabolism and/or kynurenine pathway modulator is tryptophan.

48. A method of treatment, comprising:
    (a) administering a T cell therapy to a subject having a disease or condition, which optionally is a cancer; and
    (b) administering to the subject a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), which optionally is epacadostat.

49. A method of treatment, comprising administering to a subject having a disease or condition, which optionally is a cancer a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), which optionally is epacadostat, the subject having been administered a T cell therapy.

50. A method of treatment, comprising administering to a subject having a disease or condition, which optionally is a cancer a T cell therapy, the subject having been administered a therapeutically effective amount of a tryptophan metabolism and/or kynurenine pathway modulator, wherein the tryptophan metabolism and/or kynurenine pathway modulator is or comprises 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), which optionally is epacadostat.

51. The method of any of embodiments 48-50, wherein the disease or condition is cancer.

52. The method of any of embodiments 1-51, wherein upon administration to the subject the T cell therapy causes an increase or elevation of the level of interferon-gamma (IFNγ) in the subject in the local environment of a tumor or in a serum or plasma sample of the subject compared to the level of IFN-gamma in the subject prior to initiation of the T cell therapy.

53. The method of any of embodiments 1-52, wherein the T cell therapy is or comprises tumor infiltrating lymphocytic (TIL) therapy or a T cell therapy comprising genetically engineered cells expressing a recombinant receptor that specifically binds to a ligand.

54. The method of embodiment 53, wherein the T cell therapy is or comprises genetically engineered cells expressing a recombinant receptor that specifically binds to a ligand.

55. The method of embodiment 54, wherein the genetically engineered cell further comprises a modification of expression of a molecule associated with IDO-mediated immunosuppressive signaling, associated with sensing or responding to tryptophan starvation or insufficiency and/or associated with sensing or responding to kynurenine-mediated immuno-suppression in the cell.

56. A method of treatment, comprising administering a genetically engineered T cells to a subject having a disease or condition, which optionally is a cancer, wherein the genetically engineered T cell comprise (i) a recombinant receptor that specifically binds to a ligand and (ii) modification of expression of a molecule associated with IDO-mediated immunosuppressive signaling, associated with sensing or responding to tryptophan starvation or insufficiency and/or associated with sensing or responding to kynurenine-mediated immuno-suppression in the cell.

57. A method of treatment, comprising administering a genetically engineered T cells to a subject having a disease or condition, which optionally is a cancer, wherein the genetically engineered T cell comprise (i) a recombinant receptor that specifically binds to a ligand and (ii) a recombinant, engineered and/or ectopically expressed amino acid transporter or chain thereof or a functional and/or catalytically active portion or variant thereof.

58. The method of embodiment 57, further comprising (b) administering to the subject a therapeutically effective amount of a tryptophan metabolism and/or kynurenine pathway modulator.

59. A method of treatment, comprising:
  (a) administering a genetically engineered T cells to a subject having a disease or condition, which optionally is a cancer, wherein the genetically engineered T cell comprises (i) a recombinant receptor that specifically binds to a ligand and (ii) a modification of expression of a molecule associated with IDO-mediated immunosuppressive signaling, associated with sensing or responding to tryptophan starvation or insufficiency and/or associated with sensing or responding to kynurenine-mediated immuno-suppression in the cell; and
  (b) administering to the subject a therapeutically effective amount of a tryptophan metabolism and/or kynurenine pathway modulator.

60. The method of any of embodiments 56-59, wherein the disease or condition is cancer.

61. The method of any of embodiments 55-60, wherein the subject is selected for having a tumor positive for expression of L-type Amino Acid Transporter 1 (LAT1; SLC7A5), LAT2 (SLC7A8), CD98 heavy chain (4F2hc; CD98hc; SLC3A2) and/or proton-assisted amino-acid transporter 4 (PAT4; SLC36A4), or for having cells in the tumor microenvironment that are positive for expression of LAT1, LAT2, CD98hc and/or PAT4.

62. The method of any of embodiments 58-60, wherein the tryptophan metabolism and/or kynurenine pathway modulator prevents or reduces the formation, concentration, availability, metabolism and/or effect of an enzyme and/or a metabolite of the kynurenine pathway.

63. The method of any of embodiments 59-62, wherein the tryptophan metabolism and/or kynurenine pathway modulator prevents or reduces catabolism of tryptophan or prevents or reduces synthesis or accumulation of a tryptophan metabolite.

64. The method of embodiment 63, wherein the tryptophan metabolite is selected from kynurenine, 3-hydroxykynurenine and 3-hydroxyanthranilic acid (3-HAA).

65. The method of any of embodiments 59-64, wherein the tryptophan metabolism and/or kynurenine pathway modulator is a small molecule, peptide, protein, antibody or antigen-binding fragment thereof, an antibody mimetic, an aptamer, or a nucleic acid molecule.

66. The method of any of embodiments 59-65, wherein the tryptophan metabolism and/or kynurenine pathway modulator is an antagonist of the enzyme kynureninase.

67. The method of any of embodiments 59-66, wherein the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO).

68. The method of any of embodiments 59-65 and 67, wherein the tryptophan metabolism and/or kynurenine pathway modulator is a dual-acting IDO/TDO inhibitor.

69. The method of any of embodiments 59-65 and 67, wherein the tryptophan metabolism and/or kynurenine pathway modulator is an inhibitor of indoleamine-pyrrole 2,3-dioxygenase 1 (IDO1).

70. The method of any of embodiments 59-65 and 50-52, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

71. The method of embodiment 70, wherein the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

72. The method of embodiment 70, wherein the tryptophan metabolism and/or kynurenine pathway modulator is 1-methyl-D-tryptophan (1-MT) (indoximod).

73. The method of any of embodiments 59-65, wherein the tryptophan metabolism and/or kynurenine pathway modulator is tryptophan.

74. The method of any of embodiments 48-73, wherein prior to initiation of administration of the composition comprising T cells, the subject has failed to respond or failed to completely respond to treatment with, relapsed following remission after treatment with, or become refractory to, a prior administration of a tryptophan metabolism and/or kynurenine pathway modulator optionally wherein such prior administration was carried out in combination with an immunomodulatory agent, optionally a checkpoint inhibitor.

75. The method of any of embodiments 48-55 and 57-74, wherein the tryptophan metabolism and/or kynurenine pathway modulator administered in (b) is administered prior to, simultaneously with and/or subsequent to initiation of administration of the T cell therapy and/or administering the T cell therapy.

76. The method of any of embodiments 48-55 and 57-75, comprising administering the tryptophan metabolism and/or kynurenine pathway modulator administered in (b) subsequent to initiation of administration of the T cell therapy and/or administering the T cell therapy.

77. The method of any of embodiments 48-55 and 57-76, wherein tryptophan metabolism and/or kynurenine pathway modulator is administered at a time in which:
there is a decrease in tryptophan levels, an increase in kynurenine levels and/or an increase in expression or activity of IDO1, IDO2 or TDO in a biological sample from the subject compared to prior to initiation of administration of the T cell therapy and/or administering the T cell therapy or compared to a preceding time point after initiation of administration of the T cell therapy and/or administering the T cell therapy;
at a time before the number of cells of the T cell therapy detectable in the blood from the subject is decreased compared to in the subject at a preceding time point after initiation of administration of the T cell therapy and/or administering the T cell therapy;
at a time before T cells exhibit manifestations of prolonged tryptophan starvation, exhaustion, reduction of effector function, expression of inhibitory receptors and/or loss of proliferative capacity;
at a time before a peak or maximum level of the cells of the T cell therapy are detectable in the blood of the subject;
the level of interferon-gamma (IFNγ) is increased in a biological sample from the subject compared to prior to initiation of administration of the T cell therapy and/or administering the T cell therapy or compared to a preceding time point after initiation of administration of the T cell therapy and/or administering the T cell therapy;
the number of cells of the T cell therapy detectable in the blood from the subject is decreased compared to in the subject at a preceding time point after initiation of administration of the T cell therapy and/or administering the T cell therapy;
the number of cells of the T cell therapy detectable in the blood is decreased by more than or more than about 1.5-fold, 2-fold, 3-fold, 4-fold, 5-fold, 10-fold, 50-fold or 100-fold or more, compared to the peak or maximum number of the cells of the T cell therapy detectable in the blood of the subject after initiation of administration of the T cell therapy and/or administering the T cell therapy; and/or
at a time after a peak or maximum level of the cells of the T cell therapy are detectable in the blood of the subject, the number of cells of the T cell therapy detectable in the blood from the subject is less than 10%, less than 5%, less than 1% or less than 0.1% of total peripheral blood mononuclear cells (PBMCs) in the blood of the subject.

78. The method of embodiment 77, wherein the increase or decrease is by greater than or greater than about 1.2-fold, 1.5-fold, 2-fold, 3-fold, 4-fold, 5-fold, 10-fold or more.

79. The method of any of embodiments 48-55 and 57-78, wherein the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy.

80. The method of any of embodiments 48-55 and 57-79, wherein the tryptophan metabolism and/or kynurenine pathway modulator is administered within or within about 1 hour, 2 hours, 6 hours, 12 hours, 24 hours or 48 hours subsequent to initiation of the T cell therapy.

81. The method of any of embodiments 48-55 and 57-75, wherein:
the tryptophan metabolism and/or kynurenine pathway modulator is administered from or from about 0 to 96 hours, 0 to 72 hours, 0 to 48 hours, 0 to 24 hours, 0 to 12 hours or 0 to 6 hours or 0 to 2 hours prior to initiation of the T cell therapy; or
the tryptophan metabolism and/or kynurenine pathway modulator is administered no more than 96 hours, 72 hours, 48 hours, 24 hours, 12 hours, 6 hours, 2 hours or 1 hour prior to initiation of the T cell therapy.

82. The method of any of embodiments 55-81, wherein the modification comprises recombinant, engineered and/or ectopic expression of the molecule or a functional and/or catalytically active chain, portion or variant thereof.

83. The method of any of embodiments 55-82, wherein the molecule is mTOR or protein kinase C theta (PKC-Θ).

84. The method of any of embodiments 55-82, wherein the molecule is an amino acid transporter or a chain thereof or a functional and/or catalytically active portion or variant thereof.

85. The method of embodiment 84, wherein the amino acid transporter is a tryptophan transporter.

86. The method of embodiment 84 or embodiment 85, wherein the amino acid transporter or a chain thereof is selected from among one or more of rBAT (SLC3A1), CD98 heavy chain (4F2hc; SLC3A2), L-type Amino Acid Transporter 1 (LAT1; SLC7A5), LAT2 (SLC7A8), Asc-type amino acid transporter 1 (Asc-1; SLC7A10), Sodium- and chloride-dependent neutral and basic amino acid transporter B(0+)(ATB0,+; SLC6A14), Sodium-dependent neutral amino acid transporter B(0)AT1 (B(0)AT1; SLC6A19), Monocarboxylate transporter 10 (TAT1; SLC16A10), and proton-assisted amino-acid transporter 4 (PAT4; SLC36A4) or a portion thereof.

87. The method of any of embodiments 84-86, wherein the amino acid transporter or a chain thereof comprises the amino acid sequence selected from any one of SEQ ID NOs: 36-44 or a portion thereof, or an amino acid sequence having at least 90%, 91%, 92%, 93%, 94%, 95%, 96%, 97%, 98%, or 99% sequence identity to the amino acid sequence selected from any one of SEQ ID NOs: 36-44 or a portion thereof.

88. The method of any of embodiments 84-87, wherein the amino acid transporter or a chain thereof is selected from among one or more of CD98 heavy chain (4F2hc; SLC3A2), L-type Amino Acid Transporter 1 (LAT1; SLC7A5), LAT2 (SLC7A8), and proton-assisted amino-acid transporter 4 (PAT4; SLC36A4) or a portion thereof.

89. The method of any of embodiments 84-87, wherein the amino acid transporter or a chain thereof comprises CD98 heavy chain (4F2hc; SLC3A2) and L-type Amino Acid Transporter 1 (LAT1; SLC7A5) or a portion thereof.

90. The method of any of embodiments 84-88, wherein the amino acid transporter or a chain thereof comprises the amino acid sequence selected from any one of SEQ ID NOs:37-39 and 44 or a portion thereof, or an amino acid sequence having at least 90%, 91%, 92%, 93%, 94%, 95%, 96%, 97%, 98%, or 99% sequence identity to the amino acid sequence selected from any one of SEQ ID NOs: 37-39 and 44 or a portion thereof.

91. The method of any of embodiments 82-90, wherein expression of the molecule in the cell is under the control of a conditional promoter or enhancer or transactivator.

92. The method of any of embodiments 55-91, wherein the molecule is selected from among GCN2 kinase, BLIMP-1, aryl hydrocarbon receptor (AHR), AHR nuclear transporter (ARNT), eukaryotic translation initiation factor 2 α (eIF2α), activating transcription factor 4 (ATF4), or CCAAT/enhancer binding protein-homologous protein (CHOP), Gadd45α, Herp, 4E-BP1, eIF4G, JAK1, NFκB-2, FK506-BP8 and IFNγ-R2.

93. The method of embodiment 92, wherein the molecule is GCN2 or CHOP.

94. The method of 55-81, 92 and 93, wherein the modification comprises reduced expression of the molecule.

95. The method of embodiment 94, wherein the engineered cell comprises an inhibitory nucleic acid or a genetic disruption that reduces expression of the molecule.

96. The method of embodiment 94 or embodiment 95, wherein expression of the molecule in the cell is reduced by at least 50, 60, 70, 80, 90, or 95% as compared to the expression in the cell in the absence of the inhibitory nucleic acid or gene disruption.

97. The method of embodiment 95 or embodiment 96, comprising introducing the inhibitory nucleic acid into the cell, thereby effecting reduction in expression of the molecule.

98. The method of embodiment 96 or embodiment 97, comprising introducing a nucleic acid encoding or producing the inhibitory nucleic acid into the cell, thereby effecting reduction in expression of the molecule.

99. The method of any of embodiments 95-98, wherein the engineered cell comprises an inhibitory nucleic acid and the inhibitory nucleic acid comprises an RNA interfering agent.

100. The method of any of embodiments 95-99, wherein the inhibitory nucleic acid is or comprises or encodes a small interfering RNA (siRNA), a microRNA-adapted shRNA, a short hairpin RNA (shRNA), a hairpin siRNA, a microRNA (miRNA-precursor) or a microRNA (miRNA).

101. The method of any of embodiments 95-100, wherein expression of the inhibitory nucleic acid is under the control of a conditional promoter or enhancer or transactivator.

102. The method of embodiment 95 or embodiment 96, wherein the engineered cell comprises a genetic disruption, wherein:
the disruption comprises disrupting the gene encoding the molecule at the DNA level and/or
the disruption is not reversible; and/or
the disruption is not transient.

103. The method of any of embodiments 95, 96 and 102, wherein the disruption comprises introducing into the cell a DNA binding protein or DNA-binding nucleic acid that specifically binds to or hybridizes the gene encoding the molecule.

104. The method of any of embodiments 95, 96, 102 and 103, wherein the disruption comprises introducing: (a) a fusion protein comprising a DNA-targeting protein and a nuclease or (b) an RNA-guided nuclease.

105. The method of embodiment 104, wherein the DNA-targeting protein or RNA-guided nuclease comprises a zinc finger protein (ZFP), a TAL protein, or a clustered regularly interspaced short palindromic nucleic acid (CRISPR) specific for the gene.

106. The method of any of embodiments 95, 96 and 102-105, wherein the disruption comprises introducing an agent into the cell comprising a zinc finger nuclease (ZFN), a TAL-effector nuclease (TALEN), or a CRISPR-Cas9 combination that specifically binds to, recognizes, or hybridizes to the gene encoding the molecule.

107. The method of embodiment 106, wherein the agent is a CRISPR-Cas9 combination and the CRISPR-Cas9 combination comprises a guide RNA (gRNA) comprising a guide sequence that is complementary to, and/or capable of hybridizing to, a target sequence in the gene.

108. The method of any of embodiments 95, 96 and 102-107, wherein the genetic disruption is inducible.

109. The method of embodiment 108, wherein the CRISPR-Cas9 complex is an inducible CRISPR-Cas9 and/or the Cas9 is under the under the control of a conditional promoter or enhancer or transactivator.

110. The method of any of embodiments 95, 96 and 102-109, wherein the disruption comprises a deletion of at least a portion of at least one exon of the gene encoding the molecule.

111. The method of any of embodiments 95, 96 and 102-110, wherein:
the disruption comprises a deletion, mutation, and/or insertion in the gene resulting in the presence of a premature stop codon in the gene; and/or
the disruption comprises a deletion, mutation, and/or insertion within a first or second exon of the gene encoding the molecule.

112. The method of any of embodiments 91, 101 or 109, wherein the conditional promoter or enhancer or transactivator is an inducible promoter, enhancer, or transactivator or a repressible promoter, enhancer, or transactivator.

113. The method of embodiment 112, wherein the promoter is selected from among an RNA pol I promoter; a pol II promoter, optionally CMV, SV40 early region or adenovirus major late promoter; or pol III promoter, optionally a U6 or H1 promoter.

114. The method of embodiment 112 or embodiment 113, wherein the promoter is an inducible promoter.

115. The method of embodiment 114, wherein the promoter comprises a binding site for NFκB or NFAT.

116. The method of embodiment 114, wherein the promoter comprises a Lac operator sequence, a tetracycline operator sequence, a galactose operator sequence or a doxycycline operator sequence, or is an analog thereof.

117. The method of embodiment 112 or embodiment 113, wherein the promoter is a repressible promoter.

118. The method of embodiment 117, wherein the promoter is capable of being bound by or recognized by a Lac repressor or a tetracycline repressor, or an analog thereof.

119. The method of any of embodiments 1-118, wherein the T cell comprises a recombinant receptor that specifically binds to a ligand that is a functional non-T cell receptor.

120. The method of any of embodiments 1-119, wherein the T cell comprises a recombinant receptor that specifically binds to a ligand that is a chimeric antigen receptor (CAR).

121. The method of embodiment 120, wherein the CAR comprises an extracellular antigen-recognition domain that specifically binds to the antigen and an intracellular signaling region comprising an ITAM.

122. The method of embodiment 121, wherein the intracellular signaling region comprises an intracellular domain of a CD3-zeta (CD3ζ) chain.

123. The method of embodiment 121 or embodiment 122, wherein the CAR further comprises a costimulatory signaling region.

124. The method of embodiment 123, wherein the costimulatory signaling region comprises a signaling domain of a CD28, a 4-1BB or an ICOS or a signaling portion thereof.

125. The method of embodiment 123 or embodiment 124, wherein the costimulatory signaling region is a signaling domain of a CD28.

126. The method of any of embodiments 53-125, wherein the recombinant receptor is a transgenic T cell receptor (TCR).

127. The method of any of embodiments 53-125, wherein the recombinant receptor is a chimeric antigen receptor (CAR).

128. The method of any of embodiments 1-127, wherein the T cell therapy recognizes or targets an antigen associated with the cancer.

129. The method of any of embodiments 53-128, wherein the recombinant receptor binds to, recognizes or targets an antigen associated with the cancer.

130. The method of embodiment 129, wherein the antigen is selected from ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

131. The method of any of embodiments 48-130, wherein the cancer comprises a tumor negative for indoleamine-pyrrole 2,3-dioxygenase 1 (IDO1) prior to initiation of administration of the T cell therapy and/or administering the T cell therapy and/or the subject is not selected for expression of an IDO1 positive tumor prior to initiation of administration of the T cell therapy and/or administering the T cell therapy.

132. The method of any of embodiments 48-131, wherein the cancer comprises a tumor positive for expression of L-type Amino Acid Transporter 1 (LAT1; SLC7A5), LAT2 (SLC7A8), CD98 heavy chain (4F2hc; CD98hc; SLC3A2) and/or proton-assisted amino-acid transporter 4 (PAT4; SLC36A4), or the cancer comprises cells in the tumor microenvironment that are positive for expression of LAT1, LAT2, CD98hc and/or PAT4.

133. The method of any of embodiments 1-132, wherein the cancer is a myeloma, lymphoma, leukemia.

134. The method of any of embodiments 1-133, wherein the cancer is non-Hodgkin lymphoma (NHL), an acute lymphoblastic leukemia (ALL), a chronic lymphocytic leukemia (CLL), diffuse large B-Cell lymphoma (DLBCL), or myeloma.

135. The method of any of embodiments 1-133, wherein the cancer does not express a B cell antigen or is not a B cell malignancy.

136. The method of any of embodiments 1-133 and 135, wherein the cancer does not express CD19 and/or the T cell therapy does not comprise a recombinant receptor that specifically binds CD19 and/or the T cell therapy is a CAR-T cell therapy that does not comprise an anti-CD19 antigen-binding domain.

137. The method of any of embodiments 1-133, 135 and 136, wherein the cancer is a non-hematological cancer or is a solid tumor.

138. The method of any of embodiments 1-137, wherein the method results in an increase in tryptophan levels and/or a decrease in kynurenine levels in the tumor or in a biological sample from the subject, optionally a serum, plasma or tumor sample, compared to a method involving administration of the T cell therapy but in the absence of the tryptophan metabolism and/or kynurenine pathway modulator.

139. The method of any of embodiments 1-138, wherein the T cell therapy exhibits increased or prolonged expansion and/or persistence in the subject as compared to a method in which the T cell therapy is administered to the subject in the absence of the tryptophan metabolism and/or kynurenine pathway modulatory or a method in which a similar T cell is administered but in which the T cells do not comprise modification of expression of a molecule associated with IDO-mediated immunosuppressive signaling, associated with sensing or responding to tryptophan starvation or insufficiency and/or associated with sensing or responding to kynurenine-mediated immuno-suppression.

140. The method of any of embodiments 1-139, wherein the tryptophan metabolism and/or kynurenine pathway modulator is administered orally, subcutaneously or intravenously.

141. The method of embodiment 140, wherein the tryptophan metabolism and/or kynurenine pathway modulator is administered orally.

142. The method of any of embodiments 1-141, wherein the tryptophan metabolism and/or kynurenine pathway modulator is administered in an amount from or from about 2.5 mg to about 5000 mg, 2.5 mg to 2000 mg, 2.5 mg to 1000 mg, 2.5 mg to 500 mg, 2.5 mg to 200 mg, 2.5 mg to 100 mg, 2.5 mg to 50 mg, 2.5 mg to 25 mg, 2.5 mg to 10 mg, 25 mg to 5000 mg, 25 mg to 2000 mg, 25 mg to 1000 mg, 25 mg to 500 mg, 25 mg to 200 mg, 25 mg to 100 mg, 25 mg to 50 mg, 50 mg to 5000 mg, 50 mg to 2000 mg, 50 mg to 1000 mg, 50 mg to 500 mg, 50 mg to 200 mg, 50 mg to 100 mg, 100 mg to 5000 mg, 100 mg to 2000 mg, 100 mg to 1000 mg, 100 mg to 500 mg, 100 mg to 200 mg, 200 mg to 5000 mg, 200 mg to 2000 mg, 200 mg to 1000 mg, 200 mg to 500 mg, 500 mg to 5000 mg, 500 mg to 2000 mg, 500 mg to 1000 mg or 1000 mg to 2000 mg, each inclusive.

143. The method of any of embodiments 1-142, wherein the tryptophan metabolism and/or kynurenine pathway modulator is administered six times daily, five times daily, four times daily, three times daily, twice daily or once daily.

144. The method of any of embodiments 1-143, wherein the tryptophan metabolism and/or kynurenine pathway modulator is administered at a total daily dosage amount of at least or at least about 5 mg/day, 10 mg/day, 25 mg/day, 50 mg/day, 100 mg/day, 200 mg/day, 400 mg/day, 500 mg/day, 600 mg/day, 800 mg/day, 1000 mg/day, 1200 mg/day, 1600 mg/day, 2000 mg/day, 5000 mg/day or 10000 mg/day.

145. The method of any of embodiments 1-144, wherein the administration of the tryptophan metabolism and/or kynurenine pathway modulator is continued after initiation of administration of the T cell therapy and/or administering the T cell therapy until:
  there is an increase in tryptophan levels, a decrease in kynurenine levels and/or an decrease in expression or activity of IDO1, IDO2 or TDO in a biological sample from the subject compared to compared to just prior to administration of the tryptophan metabolism and/or kynurenine pathway modulator or compared to just prior to initiation of administration of the T-cell therapy;
  the number of cells of the T cell therapy detectable in the blood from the subject is increased compared to in the subject at a preceding time point just prior to administration of the tryptophan metabolism and/or kynurenine pathway modulator or compared to a preceding time point after administration of the T-cell therapy;

the number of cells of the T cell therapy detectable in the blood is within 2.0-fold (greater or less) of the peak or maximum number of the cells of the T cell therapy detectable in the blood of the subject after initiation of administration of the T cell therapy and/or administering the T cell therapy; and/or the number of cells of the T cell therapy detectable in the blood from the subject is greater than or greater than about 10%, 15%, 20%, 30%, 40%, 50%, or 60% of total peripheral blood mononuclear cells (PBMCs) in the blood of the subject.

146. The method of any of embodiments 1-145, wherein the tryptophan metabolism and/or kynurenine pathway modulator is administered until:

the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) the blood of the subject contains at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

147. The method of any of embodiments 1-146, wherein the expression or level of CD25 on the surface of the cells of the T cell therapy is reduced following said administration to the subject as compared to the expression or level in a method in which the T cell therapy is administered to the subject in the absence of the tryptophan metabolism and/or kynurenine pathway modulator or a method in which a similar T cell therapy is administered but in which the T cells do not comprise modification of expression of a molecule associated with IDO-mediated immunosuppressive signaling, associated with sensing or responding to tryptophan starvation or insufficiency and/or associated with sensing or responding to kynurenine-mediated immuno-suppression.

148. The method of embodiment 147, wherein the expression is reduced by at least or at least about 1.2-fold, 1.5-fold, 2.0-fold, 3.0-fold, 4.0-fold, 5-fold, 6-fold, 7-fold, 8-fold, 9-fold, 10-fold or more.

149. The method of any of embodiments 1-148, wherein the tryptophan metabolism and/or kynurenine pathway modulator is administered for a time period up to 2 days, up to 7 days, up to 14 days, up to 21 days, up to one month, up to two months, up to three months, up to 6 months or up to 1 year after initiation of the administration of the T cell therapy.

150. The method of any of embodiments 1-149, wherein the T cell therapy comprises T cells that are CD4+ or CD8+.

151. The method of any of embodiments 1-150, wherein the T cell therapy comprises cells that are autologous to the subject.

152. The method of any of embodiments 1-150, wherein the T cell therapy comprises T cells that are allogeneic to the subject.

153. The method of any of embodiments 1-152, wherein the T cell therapy is administered in an amount to upregulate IDO1 expression in the tumor microenvironment.

154. The method of embodiment 153, wherein IDO1 expression is upregulated in or from myeloid cells, stromal cells or tumor cells.

155. The method of embodiment 154, wherein IDO1 expression is upregulated in or from bone marrow stromal cells.

156. The method of any of embodiments 1-155, wherein the cell therapy comprises administration of a dose comprising a number of cells between or between about $0.5 \times 10^6$ cells/kg body weight of the subject and $5 \times 10^6$ cells/kg, between or between about $0.5 \times 10^6$ cells/kg and $3 \times 10^6$ cells/kg, between or between about $0.5 \times 10^6$ cells/kg and $2 \times 10^6$ cells/kg, between or between about $0.5 \times 10^6$ cells/kg and $1 \times 10^6$ cell/kg, between or between about $1.0 \times 10^6$ cells/kg body weight of the subject and $5 \times 10^6$ cells/kg, between or between about $1.0 \times 10^6$ cells/kg and $3 \times 10^6$ cells/kg, between or between about $1.0 \times 10^6$ cells/kg and $2 \times 10^6$ cells/kg, between or between about $2.0 \times 10^6$ cells/kg body weight of the subject and $5 \times 10^6$ cells/kg, between or between about $2.0 \times 10^6$ cells/kg and $3 \times 10^6$ cells/kg, or between or between about $3.0 \times 10^6$ cells/kg body weight of the subject and $5 \times 10^6$ cells/kg, each inclusive.

157. The method of any of embodiments 1-156, wherein the dose of cells administered is less than the dose in a method in which the cell therapy is administered without administering the tryptophan metabolism and/or kynurenine pathway modulator or a method in which the cells do not comprise modification of expression of a molecule associated with IDO-mediated immunosuppressive signaling, associated with sensing or responding to tryptophan starvation or insufficiency and/or associated with sensing or responding to kynurenine-mediated immuno-suppression.

158. The method of embodiment 157, wherein the dose is at least 1.5-fold, 2-fold, 3-fold, 4-fold, 5-fold or 10-fold less.

159. The method of any of embodiments 1-158, wherein the T cell therapy is administered as a single pharmaceutical composition comprising the cells.

160. The method of any of embodiments 1-159, wherein the T cell therapy comprises a dose of cell that is a split dose, wherein the cells of the dose are administered in a plurality of compositions, collectively comprising the cells of the dose, over a period of no more than three days.

161. The method of any of embodiments 1-160, wherein the method further comprises administering a lymphodepleting chemotherapy prior to administration of the T cell therapy.

162. The method of embodiment 161, wherein the method does not comprise administering fludarabine to the subject.

163. The method of any of embodiments 1-160, does not comprise administering a lymphodepleting chemotherapy to the subject prior to administration of the T cell therapy.

164. The method of any of embodiments 55-163, wherein the recombinant receptor is engineered by introduction of a first nucleic acid sequence encoding the recombinant receptor into the cell, and one or more second nucleic acid sequence(s) encoding an agent that is capable of or involved in modification of expression of a molecule associated with IDO-mediated immunosuppressive signaling, associated with sensing or responding to tryptophan starvation or insufficiency and/or associated with sensing or responding to kynurenine-mediated immuno-suppression in the cell, into the cell.

165. The method of embodiment 164, wherein the first nucleic acid sequence and the second nucleic acid sequence(s) are comprised in one or more polynucleotides.

166. The method of embodiment 164, wherein the first nucleic acid sequence and the second nucleic acid sequence(s) are comprised in two polynucleotides.

167. The method of any of embodiments 164-166, wherein the first nucleic acid and the second nucleic acid(s) are comprised in one or more vector(s), which optionally are viral vector(s).

168. A method of selecting a subject having a disease or condition, which optionally is a cancer for administering a tryptophan metabolism and/or kynurenine pathway modulator, the method comprising:
(a) assessing the level of tryptophan or a tryptophan metabolite, the level of expression or activity of IDO1, IDO2 or TDO, or the level of interferon-gamma (IFNγ) in one or more biological samples from the subject, wherein the biological sample is from a subject that is a candidate for treatment with a T cell therapy; and
(b) selecting a subject in which:
 (i) the level of tryptophan in the sample is below a threshold level;
 (ii) the level of the tryptophan metabolite is above a threshold level;
 (iii) the level of expression or activity of IDO1, IDO2 or TDO is above a threshold level; or
 (iv) the level of the IFNγ is above a threshold level.

169. The method of embodiment 168, wherein the one or more biological sample is obtained prior to administration of the T cell therapy.

170. The method of embodiment 168 or embodiment 169, further comprising administering the T cell therapy to the subject.

171. The method of any of embodiments 168-170, further comprising administering the tryptophan metabolism and/or kynurenine pathway modulator to the selected subject.

172. The method of embodiment 171, wherein the tryptophan metabolism and/or kynurenine pathway modulator is administered to the selected subject prior to or concurrently with initiation of administration of the T cell therapy and/or administering the T cell therapy.

173. The method of embodiment 171, wherein the tryptophan metabolism and/or kynurenine pathway modulator is administered subsequent to initiation of administration of the T cell therapy and/or administering the T cell therapy.

174. A method of selecting a subject having a disease or condition, which optionally is a cancer for administering a tryptophan metabolism and/or kynurenine pathway modulator, the method comprising:
(a) assessing the level of tryptophan or a tryptophan metabolite, the level of expression or activity of IDO1, IDO2 or TDO, or the level of interferon-gamma (IFNγ) in one or more biological samples from the subject, wherein the biological sample is obtained from a subject having been administered a T cell therapy; and
(b) selecting a subject in which:
 (i) the level of tryptophan in the sample is below a threshold level or is decreased compared to the level assessed at a time point prior to initiation of administration of the T cell therapy and/or administering the T cell therapy or a preceding time point after initiation of administration of the T cell therapy and/or administering the T cell therapy;
 (ii) the level of the tryptophan metabolite is above a threshold level or is increased compared to the level assessed at a time point prior to initiation of administration of the T cell therapy and/or administering the T cell therapy or a preceding time point after initiation of administration of the T cell therapy and/or administering the T cell therapy;
 (iii) the level of expression or activity of IDO1, IDO2 or TDO is above a threshold level or is increased compared to the level assessed at a time point prior to initiation of administration of the T cell therapy and/or administering the T cell therapy or a preceding time point after initiation of administration of the T cell therapy and/or administering the T cell therapy; or
 (iv) the level of the IFNγ is above a threshold level or is increased compared to the level assessed at a time point prior to initiation of administration of the T cell therapy and/or administering the T cell therapy or a preceding time point after initiation of administration of the T cell therapy and/or administering the T cell therapy.

175. The method of embodiment 174, wherein the one or more biological sample is obtained subsequent to administration of the T cell therapy.

176. The method of embodiment 174 or embodiment 175, further comprising, prior to the assessing, administering the cell therapy to the subject.

177. The method of any of embodiments 174-176, further comprising administering the kynurenine pathway modulator to the subject.

178. The method of any of embodiments 173-177, wherein tryptophan metabolism and/or kynurenine pathway modulator is administered at a time in which:
there is a decrease in tryptophan levels, an increase in kynurenine levels and/or an increase in expression or activity of IDO1, IDO2 or TDO in a biological sample from the subject compared to prior to initiation of administration of the T cell therapy and/or administering the T cell therapy or compared to a preceding time point after initiation of administration of the T cell therapy and/or administering the T cell therapy;
at a time before the number of cells of the T cell therapy detectable in the blood from the subject is decreased compared to in the subject at a preceding time point after initiation of administration of the T cell therapy and/or administering the T cell therapy;
at a time before T cells exhibit manifestations of prolonged tryptophan starvation, exhaustion, reduction of effector function, expression of inhibitory receptors and/or loss of proliferative capacity;
at a time before a peak or maximum level of the cells of the T cell therapy are detectable in the blood of the subject; and/or
the level of interferon-gamma (IFNγ) is increased in a biological sample from the subject compared to prior to initiation of administration of the T cell therapy and/or administering the T cell therapy or compared to a preceding time point after initiation of administration of the T cell therapy and/or administering the T cell therapy.

179. The method of embodiment 178, wherein the increase or decrease is by greater than or greater than about 1.2-fold, 1.5-fold, 2-fold, 3-fold, 4-fold, 5-fold, 10-fold or more.

180. The method of any of embodiments 173-179, wherein the tryptophan metabolism and/or kynurenine pathway modulator is administered within or within about 1 hour, 2 hours, 6 hours, 12 hours, 24 hours, 48 hours, 72 hours, 96 hours, 5 days, 6 days, 7 days, 14 days, 21 days, 28 days subsequent to initiation of the T cell therapy.

181. The method of any of embodiments 173-180, wherein the tryptophan metabolism and/or kynurenine pathway modulator is administered within or within about 1 hour, 2 hours, 6 hours, 12 hours, 24 hours or 48 hours subsequent to initiation of the T cell therapy.

182. The method of any of embodiments 168-171, wherein the disease or condition is cancer.

183. The method of embodiment 168-172, wherein the subject is selected if the level of expression or activity of IDO1, IDO2 or TDO is increased compared to the level assessed at a time point prior to initiation of administration of the T cell therapy and/or administering the T cell therapy.

184. The method of embodiment 168-183, wherein the subject is selected if the level of tryptophan in the sample is below a threshold level or is decreased compared to the level assessed at a time point prior to initiation of administration of the T cell therapy and/or administering the T cell therapy.

185. The method of any of embodiments 168-184, wherein the threshold level is within 25%, within 20%, within 15%, within 10% or within 5% of the average level, concentration or amount, and/or is within a standard deviation of the average level, concentration or amount in a biological sample from among a plurality of control subjects.

186. The method of embodiment 185, wherein the control subjects are healthy or normal subjects, are subjects who do not have a cancer and/or are subjects prior to receiving administration of the T cell therapy.

187. The method of any of embodiments 168-184, wherein the increase or decrease is by greater than or greater than about 1.2-fold, 1.5-fold, 2-fold, 3-fold, 4-fold, 5-fold, 10-fold or more.

188. The method of any of embodiments 168-187, wherein prior to the assessing, the subject has failed to respond or failed to completely respond to treatment with, relapsed following remission after treatment with, or become refractory to, a prior administration of a tryptophan metabolism and/or kynurenine pathway modulator, optionally wherein such prior administration was carried out in combination with an immunomodulatory agent, optionally a checkpoint inhibitor.

189. The method of any of embodiments 168-184, wherein the biological sample is or is obtained from a serum, plasma or tumor sample.

190. The method of any of embodiments 168-170, wherein the tryptophan metabolite is selected from kynurenine, 3-hydroxykynurenine and 3-hydroxyanthranilic acid (3-HAA).

191. The method of any of embodiments 168-190, wherein the tryptophan metabolism and/or kynurenine pathway modulator is a small molecule, peptide, protein, antibody or antigen-binding fragment thereof, an antibody mimetic, an aptamer, or a nucleic acid molecule.

192. The method of any of embodiments 168-191, wherein the tryptophan metabolism and/or kynurenine pathway modulator is an antagonist of the enzyme kynureninase.

193. The method of any of embodiments 168-192, wherein the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO).

194. The method of any of embodiments 168-191 and 193, wherein the tryptophan metabolism and/or kynurenine pathway modulator is a dual-acting IDO/TDO inhibitor.

195. The method of any of embodiments 168-191 and 193, wherein the tryptophan metabolism and/or kynurenine pathway modulator is an inhibitor of indoleamine-pyrrole 2,3-dioxygenase 1 (IDO1).

196. The method of any of embodiments 168-191 and 193-195, wherein the tryptophan metabolism and/or kynurenine pathway modulator is selected from 1-methyl-D-tryptophan (1-MT) (indoximod), 14-({2-[(aminosulfonyl)amino]ethyl}amino)-N-(3-bromo-14-fluorophenyl)-N'-hydroxy-1,2,5-oxadiazole-3-carboximidamide (INCB024360, epacadostat), 14-({2-[(aminosulfonyl)amino]ethyl}amino)-N-(3-chloro-14-fluorophenyl)-N'-hydroxy-1,2,5-oxadiazole-3-carboximidamide, 14-({2-[(aminosulfonyl)amino]ethyl}amino)-N-[4-fluoro-3-(trifluoromethyl)phenyl]-N'-hydroxy-1,2,5-oxadiazole-3-carboximidamide, 14-({2-[(aminosulfonyl)amino]ethyl}amino)-N'-hydroxy-N-[3-(trifluoromethyl)phenyl]-1,2,5-oxadiazole-3-carboximidamide, 14-({2-[(aminosulfonyl)amino]ethyl}amino)-N-(3-cyano-14-fluorophenyl)-N'-hydroxy-1,2,5-oxadiazole-3-carboximidamide, 14-({2-[(aminosulfonyl)amino]ethyl}amino)-N-[(4-bromo-2-furyl)methyl]-N'-hydroxy-1,2,5-oxadiazole-3-carboximidamide, 14-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

197. The method of embodiment 196, wherein the tryptophan metabolism and/or kynurenine pathway modulator is 14-({2-[(aminosulfonyl)amino]ethyl}amino)-N-(3-bromo-14-fluorophenyl)-N'-hydroxy-1,2,5-oxadiazole-3-carboximidamide (INCB024360, epacadostat).

198. The method of embodiment 196, wherein the tryptophan metabolism and/or kynurenine pathway modulator is 1-methyl-D-tryptophan (1-MT) (indoximod).

199. The method of any of embodiments 168-191, wherein the tryptophan metabolism and/or kynurenine pathway modulator is tryptophan.

200. The method of any of embodiments 168-199, wherein the T cell comprises a recombinant receptor that specifically binds to a ligand that is a functional non-T cell receptor.

201. The method of any of embodiments 168-200, wherein the T cell comprises a recombinant receptor that specifically binds to a ligand that is a chimeric antigen receptor (CAR).

202. The method of embodiment 201, wherein the CAR comprises an extracellular antigen-recognition domain that specifically binds to the antigen and an intracellular signaling region comprising an ITAM.

203. The method of embodiment 202, wherein the intracellular signaling region comprises an intracellular domain of a CD3-zeta (CD3) chain.

204. The method of embodiment 202 or embodiment 203, wherein the CAR further comprises a costimulatory signaling region.

205. The method of embodiment 204, wherein the costimulatory signaling region comprises a signaling domain of a CD28, a 4-1BB or an ICOS or a signaling portion thereof.

206. The method of embodiment 204 or embodiment 205, wherein the costimulatory signaling region is a signaling domain of a CD28.

207. The method of any of embodiments 53-206, wherein the recombinant receptor is a transgenic T cell receptor (TCR).

208. The method of any of embodiments 53-206, wherein the recombinant receptor is a chimeric antigen receptor (CAR).

209. The method of any of embodiments 1-208, wherein the T cell therapy recognizes or targets an antigen associated with the cancer.

210. The method of any of embodiments 53-209, wherein the recombinant receptor binds to, recognizes or targets an antigen associated with the cancer.

211. The method of embodiment 210, wherein the antigen is selected from ROR1, Her2, L1-CAM, CD19, CD20, CD22, mesothelin, CEA, hepatitis B surface antigen, antifolate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

212. An engineered cell, comprising:
(a) a recombinant receptor that specifically binds to a ligand; and
(b) a modification in expression of a molecule associated with IDO-mediated immunosuppressive signaling, associated with sensing or responding to tryptophan starvation or insufficiency and/or associated with sensing or responding to kynurenine-mediated immunosuppression in the cell.

213. The engineered cell of embodiment 212, wherein the modification comprises recombinant, engineered and/or ectopic expression in the cell of the molecule or a functional and/or catalytically active portion or variant thereof.

214. The engineered cell of embodiment 212 or embodiment 213, wherein the molecule is mTOR or protein kinase C theta (PKC-Θ).

215. The engineered cell of embodiment 212 or embodiment 213, wherein the molecule is an amino acid transporter or a chain thereof or a functional and/or catalytically active portion or variant thereof.

216. An engineered cell, comprising:
(a) a recombinant receptor that specifically binds to a ligand; and
(b) a recombinant, engineered and/or ectopically expressed amino acid transporter or chain thereof or a functional and/or catalytically active portion or variant thereof.

217. The engineered cell of embodiment 215 or embodiment 216, wherein the amino acid transporter is a tryptophan transporter.

218. The engineered cell of any of embodiments 215-217, wherein the amino acid transporter or a chain thereof is selected from among one or more of rBAT (SLC3A1), CD98 heavy chain (4F2hc; SLC3A2), L-type Amino Acid Transporter 1 (LAT1; SLC7A5), LAT2 (SLC7A8), Asc-type amino acid transporter 1 (Asc-1; SLC7A10), Sodium- and chloride-dependent neutral and basic amino acid transporter B(0+)(ATB0,+; SLC6A14), Sodium-dependent neutral amino acid transporter B(0)AT1 (B(0)AT1; SLC6A19), Monocarboxylate transporter 10 (TAT1; SLC16A10), and proton-assisted amino-acid transporter 4 (PAT4; SLC36A4) or a portion thereof.

219. The engineered cell of any of embodiments 215-218, wherein the amino acid transporter or a chain thereof comprises the amino acid sequence selected from any one of SEQ ID NOs: 36-115, or an amino acid sequence having at least 90%, 91%, 92%, 93%, 94%, 95%, 96%, 97%, 98%, or 99% sequence identity to the amino acid sequence selected from any one of SEQ ID NOs: 36-115.

220. The engineered cell of any of embodiments 215-219, wherein the amino acid transporter or a chain thereof is selected from among one or more of CD98 heavy chain (4F2hc; SLC3A2), L-type Amino Acid Transporter 1 (LAT1; SLC7A5), LAT2 (SLC7A8), and proton-assisted amino-acid transporter 4 (PAT4; SLC36A4) or a portion thereof.

221. The engineered cell of any of embodiments 215-219, wherein the amino acid transporter or a chain thereof comprises CD98 heavy chain (4F2hc; SLC3A2) and L-type Amino Acid Transporter 1 (LAT1; SLC7A5) or a portion thereof.

222. The engineered cell of any of embodiments 215-220, wherein the amino acid transporter or a chain thereof comprises the amino acid sequence selected from any one of SEQ ID NOs:37-39 and 115, or an amino acid sequence having at least 90%, 91%, 92%, 93%, 94%, 95%, 96%, 97%, 98%, or 99% sequence identity to the amino acid sequence selected from any one of SEQ ID NOs: 37-39 and 115.

223. The engineered cell of any of embodiments 212-222, wherein expression of the molecule or amino acid transporter in the cell is under the control of a conditional promoter or enhancer or transactivator.

224. The engineered cell of embodiment 212, wherein the molecule is selected from among GCN2 kinase, BLIMP-1 aryl hydrocarbon receptor (AHR), AHR nuclear transporter (ARNT), eukaryotic translation initiation factor 2 α (eIF2α), activating transcription factor 4 (ATF4), or CCAAT/enhancer binding protein-homologous protein (CHOP), Gadd45α, Herp, 4E-BP1, eIF4G, JAK1, NFκB-2, FK506-BP8 and IFNγ-R2.

225. The engineered cell of embodiment 224, wherein the molecule is GCN2 or CHOP.

226. The engineered cell of embodiment 224 or embodiment 225, wherein the modification comprises reduced expression of the molecule in the cell.

227. The engineered cell of any of embodiments 224-226, wherein the engineered cell comprises an inhibitory nucleic acid or a genetic disruption that reduces expression of the molecule.

228. The engineered cell of embodiment 226 or embodiment 227, wherein expression of the molecule in the cell is reduced by at least 50, 60, 70, 80, 90, or 95% as compared to the expression in the cell in the absence of the inhibitory nucleic acid or gene disruption.

229. The engineered cell of any of embodiments 226-228, wherein the cell comprises an inhibitory nucleic acid, thereby effecting reduction in expression of the molecule.

230. The engineered cell of embodiment 229, wherein the inhibitory nucleic acid comprises an RNA interfering agent.

231. The engineered cell of embodiment 229 or embodiment 230, wherein the inhibitory nucleic acid is or comprises or encodes a small interfering RNA (siRNA), a microRNA-adapted shRNA, a short hairpin RNA (shRNA), a hairpin siRNA, a microRNA (miRNA-precursor) or a microRNA (miRNA).

232. The engineered cell of any of embodiments 229-231, wherein expression of the inhibitory nucleic acid is under the control of a conditional promoter or enhancer or transactivator.

233. The engineered cell of embodiment 227 or embodiment 228, wherein the engineered cell comprises a disrupted gene encoding the molecule, an agent for disruption of a gene encoding the molecule and/or a disruption of a gene encoding the molecule.

234. The engineered cell of embodiment 233, wherein:
the disruption comprises disrupting the gene encoding the molecule at the DNA level and/or the disruption is not reversible; and/or
the disruption is not transient.

235. The engineered cell of embodiment 233 or embodiment 234, wherein the disruption is mediated by a DNA binding protein or DNA-binding nucleic acid that specifically binds to or hybridizes the gene encoding the molecule.

236. The engineered cell of any of embodiments 233-235, wherein the disruption is mediated by (a) a fusion protein comprising a DNA-targeting protein and a nuclease or (b) an RNA-guided nuclease.

237. The engineered cell of any of embodiments 233-236, wherein the disruption is mediated by a gene editing nuclease, a zinc finger nuclease (ZFN), a TAL-effector nuclease (TALEN), or a clustered regularly interspaced short palindromic nucleic acid (CRISPR)/Cas9.

238. The engineered cell of embodiment 237, wherein the disruption is mediated by a CRISPR/Cas9 and the CRISPR/Cas9 comprises a guide RNA (gRNA) comprising a guide sequence that is complementary to, and/or capable of hybridizing to, a target sequence in the gene.

239. The engineered cell of any of embodiments 233-238, wherein the genetic disruption is conditional or inducible.

240. The engineered cell of embodiment 239, wherein the CRISPR-Cas9 complex is an inducible CRISPR-Cas9 and/or the Cas9 is under the under the control of a conditional promoter or enhancer or transactivator.

241. The engineered cell of any of embodiments 233-240, wherein the disruption comprises a deletion of at least a portion of at least one exon of the gene encoding the molecule.

242. The engineered cell of any of embodiments 233-241, wherein:
the disruption comprises a deletion, mutation, and/or insertion in the gene resulting in the presence of a premature stop codon in the gene; and/or
the disruption comprises a deletion, mutation, and/or insertion within a first or second exon of the gene encoding the molecule.

243. The engineered cell of any of embodiments 196, 232, 239 and 240, wherein the conditional promoter or enhancer or transactivator is an inducible promoter, enhancer, or transactivator or a repressible promoter, enhancer, or transactivator.

244. The engineered cell of embodiment 243, wherein the promoter is selected from among an RNA pol I, pol II or pol III promoter.

245. The engineered cell of embodiment 244, wherein the promoter is selected from:
a pol III promoter that is a U6 or H1 promoter; or
a pol II promoter that is a CMV, SV40 early region or adenovirus major late promoter.

246. The engineered cell of any of embodiments 243-245, wherein the promoter is an inducible promoter.

247. The engineered cell of embodiment 246, wherein the promoter comprises a binding site for NFκB or NFAT.

248. The engineered cell of embodiment 246, wherein the promoter comprises a Lac operator sequence, a tetracycline operator sequence, a galactose operator sequence or a doxycycline operator sequence, or is an analog thereof.

249. The engineered cell of any of embodiments 243-245, wherein the promoter is a repressible promoter.

250. The engineered cell of embodiment 249, wherein the promoter is capable of being bound by or recognized by a Lac repressor or a tetracycline repressor, or an analog thereof 251. The engineered cell of any of embodiments 212-250, wherein the cell is a T cell.

252. The engineered cell of embodiment 251, wherein the T cell is a CD8+ T cell.

253. The engineered cell of embodiment 251, wherein the T cell is a CD4+ T cell.

254. The engineered cell of any of embodiments 212-250, wherein the cell is a natural killer (NK) cell.

255. The engineered cell of any of embodiments 212-250, wherein the cell is an iPS-derived cell.

256. The engineered cell of any of embodiments 212-255, wherein the recombinant receptor that specifically binds to a ligand is a functional non-T cell receptor.

257. The engineered cell of any of embodiments 212-256, wherein the recombinant receptor that specifically binds to a ligand is a chimeric antigen receptor (CAR).

258. The engineered cell of embodiment 257, wherein the CAR comprises an extracellular antigen-recognition domain that specifically binds to the antigen and an intracellular signaling region comprising an ITAM.

259. The engineered cell of embodiment 258, wherein the intracellular signaling region comprises an intracellular domain of a CD3-zeta (CD3) chain.

260. The engineered cell of embodiment 258 or embodiment 259, wherein the CAR further comprises a costimulatory signaling region.

261. The engineered cell of embodiment 260, wherein the costimulatory signaling region comprises a signaling domain of a CD28, a 4-1BB or an ICOS or a signaling portion thereof.

262. The engineered cell of embodiment 260 or embodiment 261, wherein the costimulatory signaling region is a signaling domain of a CD28.

263. The engineered cell of any of embodiments 212-262, wherein the recombinant receptor that specifically binds to a ligand is a functional non-T cell receptor 264. The engineered cell of any of embodiments 212-262, wherein the recombinant receptor that specifically binds to a ligand is a transgenic T cell receptor (TCR).

265. The engineered cell of any of embodiments 212-264, wherein the cell is engineered by introduction of a first nucleic acid sequence encoding the recombinant receptor into the cell, and one or more second nucleic acid sequence (s) encoding an agent that is capable of or involved in modifying expression of a molecule associated with IDO-mediated immunosuppressive signaling, associated with sensing or responding to tryptophan starvation or insufficiency and/or associated with sensing or responding to kynurenine-mediated immuno-suppression in the cell, into the cell.

266. The engineered cell of embodiment 265, wherein the first nucleic acid sequence and the second nucleic acid sequence(s) are comprised in one or more polynucleotides.

267. The engineered cell of embodiment 265, wherein the first nucleic acid sequence and the second nucleic acid sequence(s) are comprised in two polynucleotides.

268. The engineered cell of any of embodiments 265-267, wherein the first nucleic acid sequence and the second nucleic acid sequence(s) are comprised in one or more vector(s), which optionally are viral vector(s).

269. A composition comprising the engineered cell of any of embodiments 212-268.

270. The composition of embodiment 269, wherein the cells are CD4+ or CD8+ cells.

271. The composition of embodiment 270, further comprising a pharmaceutically acceptable carrier.

272. A combination, comprising:
genetically engineered cells expressing a recombinant receptor that binds to a ligand, wherein the recombinant receptor optionally is a T cell receptor (TCR) or a chimeric antigen receptor (CAR); and
a tryptophan metabolism and/or kynurenine pathway modulator.

273. A combination, comprising:
the engineered cells of any of embodiments 212-268 or the composition of any of embodiments 199-201; and
a tryptophan metabolism and/or kynurenine pathway modulator.

274. The combination of embodiment 272 or embodiment 273, wherein the tryptophan metabolism and/or kynurenine pathway modulator prevents or reduces the formation, concentration, availability, metabolism and/or effect of an enzyme and/or a metabolite of the kynurenine pathway.

275. The combination of any of embodiments 272-274, wherein the tryptophan metabolism and/or kynurenine pathway modulator prevents or reduces catabolism of tryptophan or prevents or reduces synthesis or accumulation of a tryptophan metabolite.

276. The combination of embodiment 275, wherein the tryptophan metabolite is selected from kynurenine, 3-hydroxykynurenine and 3-hydroxyanthranilic acid (3-HAA).

277. The combination of any of embodiments 272-276, wherein the tryptophan metabolism and/or kynurenine pathway modulator is a small molecule, peptide, protein, antibody or antigen-binding fragment thereof, an antibody mimetic, an aptamer, or a nucleic acid molecule.

278. The combination of any of embodiments 272-277, wherein the tryptophan metabolism and/or kynurenine pathway modulator is an antagonist of the enzyme kynureninase.

279. The combination of any of embodiments 272-277, wherein the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO).

280. The combination of any of embodiments 272-277 and 279, wherein the tryptophan metabolism and/or kynurenine pathway modulator is a dual-acting IDO/TDO inhibitor.

281. The combination of any of embodiments 272-277, 279 and 280, wherein the tryptophan metabolism and/or kynurenine pathway modulator is an inhibitor of indoleamine-pyrrole 2,3-dioxygenase 1 (IDO1).

282. The combination of any of embodiments 272-277 and 279-281, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-([amino-sulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

283. The combination of embodiment 282, wherein the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

284. The combination of embodiment 282, wherein the tryptophan metabolism and/or kynurenine pathway modulator is 1-methyl-D-tryptophan (1-MT) (indoximod).

285. The combination of embodiment 272-277, wherein the tryptophan metabolism and/or kynurenine pathway modulator is tryptophan.

286. The combination of any of embodiments 272-285 that is packaged as an article of manufacture such as a kit.

287. The combination of embodiment 286, wherein the article and/or kit further comprises instructions or literature providing for the administration of the engineered cells and/or tryptophan metabolism and/or kynurenine pathway modulator.

288. A method of engineering immune cells expressing a recombinant receptor, comprising:
contacting a population of cells comprising immune cells with a tryptophan metabolism and/or kynurenine pathway modulator; and
introducing a nucleic acid encoding a recombinant receptor into the population of cells under conditions such that the recombinant receptor is expressed.

289. The method of embodiment 288, wherein the recombinant receptor binds to a ligand, optionally an antigen.

290. The method of embodiment 288 or embodiment 289, wherein the recombinant receptor is a T cell receptor (TCR) or a chimeric antigen receptor (CAR).

291. The method any of embodiments 288-290, wherein the population of cells is or comprises peripheral blood mononuclear cells.

292. The method of any of embodiments 288-290, wherein the population of cells is or comprises T cells.

293. The method of embodiment 292, wherein the T cells are CD4+ and/or CD8+.

294. The method of any of embodiments 288-293, wherein the population of cells are isolated from a subject, optionally a human subject.

295. The method of any of embodiments 288-294, wherein the contacting occurs prior to and/or during the introducing.

296. The method of any of embodiments 288-295, wherein the tryptophan metabolism and/or kynurenine pathway modulator prevents or reduces the formation, concentration, availability, metabolism and/or effect of an enzyme and/or a metabolite of the kynurenine pathway.

297. The method of any of embodiments 288-296, wherein the tryptophan metabolism and/or kynurenine pathway modulator prevents or reduces catabolism of tryptophan or prevents or reduces synthesis or accumulation of a tryptophan metabolite.

298. The method of embodiment 297, wherein the tryptophan metabolite is selected from kynurenine, 3-hydroxykynurenine and 3-hydroxyanthranilic acid (3-HAA).

299. The method of any of embodiments 288-298, wherein the tryptophan metabolism and/or kynurenine pathway modulator is a small molecule, peptide, protein, antibody or antigen-binding fragment thereof, an antibody mimetic, an aptamer, or a nucleic acid molecule.

300. The method of any of embodiments 288-299, wherein the tryptophan metabolism and/or kynurenine pathway modulator is an antagonist of the enzyme kynureninase.

301. The method of any of embodiments 288-299, wherein the tryptophan metabolism and/or kynurenine pathway modulator is an inhibitor of one or more enzymes selected from the group consisting of indoleamine-pyrrole 2,3-dioxygenase 1 (IDO1), an inhibitor of IDO2 and an inhibitor of tryptophan 2,3-dioxygenase (TDO).

302. The method of any of embodiments 288-299 and 301, wherein the tryptophan metabolism and/or kynurenine pathway modulator is a dual-acting IDO/TDO inhibitor.

303. The method of any of embodiments 288-299, 301 and 302, wherein the tryptophan metabolism and/or kynurenine pathway modulator is an inhibitor of indoleamine-pyrrole 2,3-dioxygenase 1 (IDO1).

304. The method of any of embodiments 288-299 and 301-303, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-([aminosulfonyl)amino]ethyl} amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F001287, PF-06840003 or pharmaceutically acceptable salt or prodrug thereof or a combination thereof.

305. The method of embodiment 304, wherein the tryptophan metabolism and/or kynurenine pathway modulator is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

306. The method of embodiment 304, wherein the tryptophan metabolism and/or kynurenine pathway modulator is 1-methyl-D-tryptophan (1-MT) (indoximod).

307. The method of any of embodiments 288-299, wherein the tryptophan metabolism and/or kynurenine pathway modulator is tryptophan.

308. A method of engineering immune cells expressing a recombinant receptor, comprising:
introducing a first nucleic acid sequence encoding a recombinant receptor into the population of cells under conditions such that the recombinant receptor is expressed; and
introducing one or more second nucleic acid sequence(s) encoding an agent capable of or involved in modification of expression of a molecule associated with IDO-mediated immunosuppressive signaling, associated with sensing or responding to tryptophan starvation or insufficiency and/or associated with sensing or responding to kynurenine-mediated immuno-suppression in the cell into the population of cells under conditions such that the agent is expressed.

309. A method of engineering immune cells expressing a recombinant receptor, comprising:
introducing a first nucleic acid sequence encoding a recombinant receptor into the population of cells under conditions such that the recombinant receptor is expressed; and
introducing one or more second nucleic acid sequence(s) encoding a recombinant, engineered and/or ectopically expressed amino acid transporter or chain thereof or a functional and/or catalytically active portion or variant thereof.

310. The method of embodiment 308, wherein the modification comprises recombinant, engineered and/or ectopic expression of the molecule or a functional and/or catalytically active chain, portion or variant thereof.

311. The method of embodiment 308, wherein the modification comprises reduced expression of the molecule.

312. The method of embodiment 311, wherein the method comprises an inhibitory nucleic acid or a genetic disruption that reduces expression of the molecule.

313. The method of any of embodiments 308-312, wherein the first nucleic acid sequence and the second nucleic acid sequence(s) are comprised in one or more polynucleotides.

314. The method of any of embodiments 308-312, wherein the first nucleic acid sequence and the second nucleic acid sequence(s) are comprised in two polynucleotides.

315. The method of any of embodiments 308-314, wherein the first nucleic acid sequence and the second nucleic acid sequence(s) are comprised in one or more vector(s), which optionally are viral vector(s).

VIII. EXAMPLES

The following examples are included for illustrative purposes only and are not intended to limit the scope of the invention.

Example 1: Assessment of Indoleamine-Pyrrole 2,3-Dioxygenase (IDO1) Expression Following Incubation of Tumor Cells in the Presence of Interferon-Gamma (IFNγ) or Chimeric Antigen Receptor (CAR)-Expressing T Cells Expression of indoleamine-pyrrole 2,3-dioxygenase 1 (IDO1) in various tumor cells was assessed following incubation with interferon-gamma (IFNγ) or chimeric antigen receptor (CAR)-expressing T cells specific for an antigen expressed by the tumor cells.

A. Interferon-Gamma (IFNγ) Stimulation

Figure 1A:
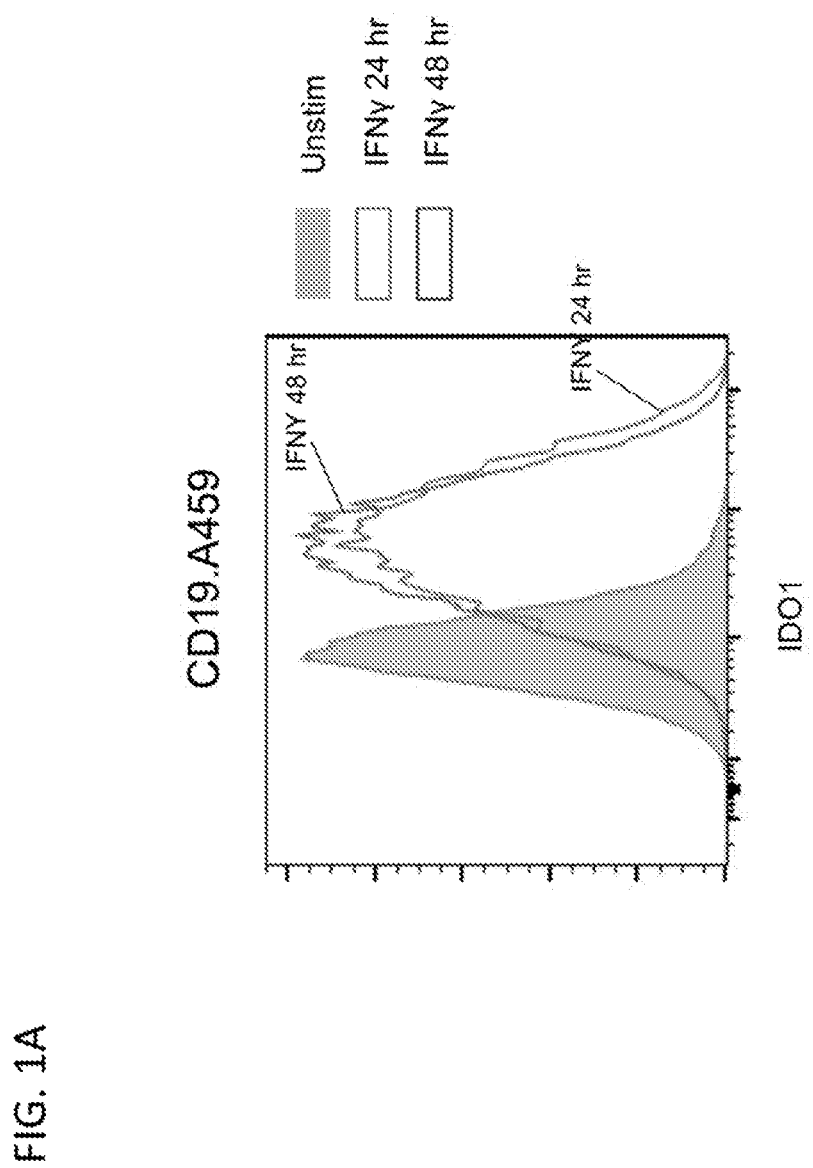
FIG. 1A depicts the expression level of indoleamine-pyrrole 2,3-dioxygenase (IDO1), as detected by flow cytometry, in A549 adenocarcinoma cells expressing CD19 (CD19.A549), following stimulation with interferon gamma (IFNγ) for 24 or 48 hours, and in unstimulated CD19.A549 cells, as described in Example 1.

A549 adenocarcinoma human alveolar basal epithelial cells transduced with human CD19 (CD19.A549 cells, which may also referred to as A549.CD19 cells) were assessed for expression of indoleamine-pyrrole 2,3-dioxygenase 1 (IDO1) following stimulation with interferon-gamma (IFNγ). CD19.A549 cells were stimulated with IFNγ for 24 or 48 hours and IDO1 levels were assessed by flow cytometry using an anti-IDO antibody. As shown in FIG. 1A, following IFNγ stimulation for 24 and 48 hours, the cells were observed to have increased expression of endogenous IDO1 as compared to unstimulated cells. Increased IDO1 expression was not detected in other CD19$^+$ tumor cell lines in this assay, including JeKo-1, Daudi, Raji and Nalm-6 cells, following incubation with IFNγ under similar conditions.

Figure 1B:
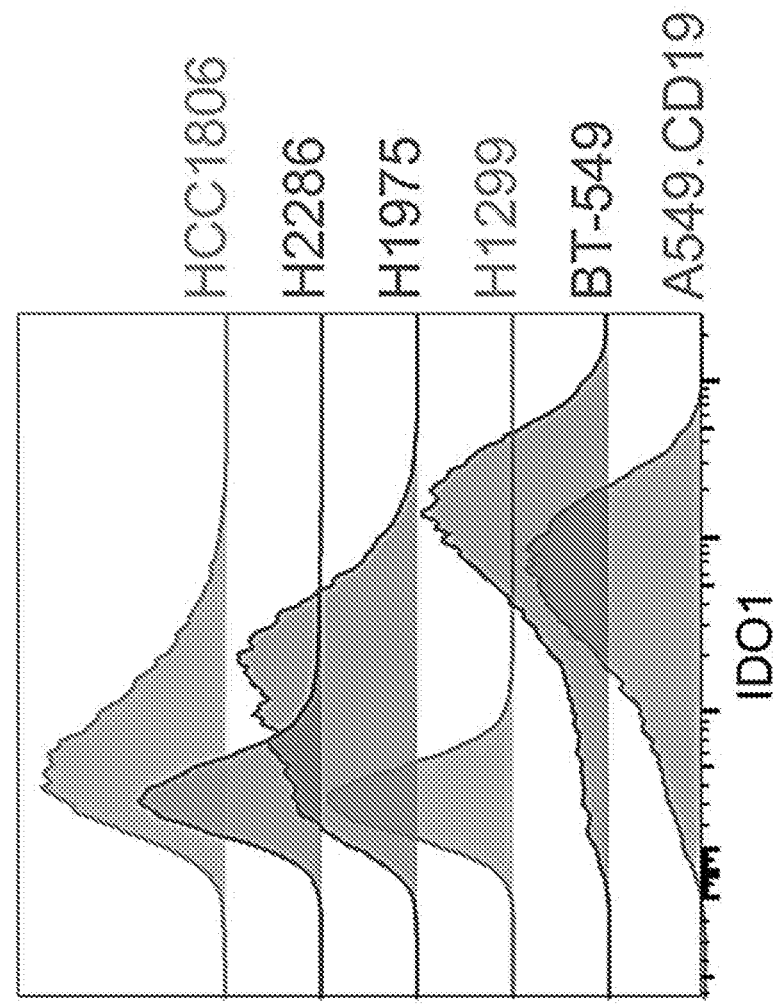
FIG. 1B depicts the IDO1 expression level, as detected by flow cytometry, in HCC1806 human breast cancer cell line; H2286 human small cell lung cancer cell line; H1975 human non-small cell lung cancer cell line; H1299 human non-small cell lung cancer lymph node metastasis cell line; BT-549 human breast cancer cell line; and A549 adenocarcinoma cells expressing CD19 (A549.CD19), following stimulation with interferon gamma (IFNγ).

Additionally, IDO1 expression was assessed following in various cell lines that express the receptor tyrosine kinase-like orphan receptor 1 (ROR1) antigen following incubation of the cells with interferon-gamma (IFNγ). HCC1806 (ATCC® CRL-2335™) human breast cancer cell line; H2286 (ATCC® CRL-5938™) human small cell lung cancer cell line; H1975 (ATCC® CRL-5908™) human non-small cell lung cancer cell line; H1299 (ATCC® CRL-5803™) human non-small cell lung cancer lymph node metastasis cell line; BT-549 (ATCC® HTB-122™) human breast cancer cell line; and CD19.A549 cells described above, which express endogenous ROR1, were incubated in the presence of 20 ng/mL recombinant human IFNγ overnight. IDO1 expression was assessed using flow cytometry as described above. Results are shown in FIG. 1B.

Figure 1C:
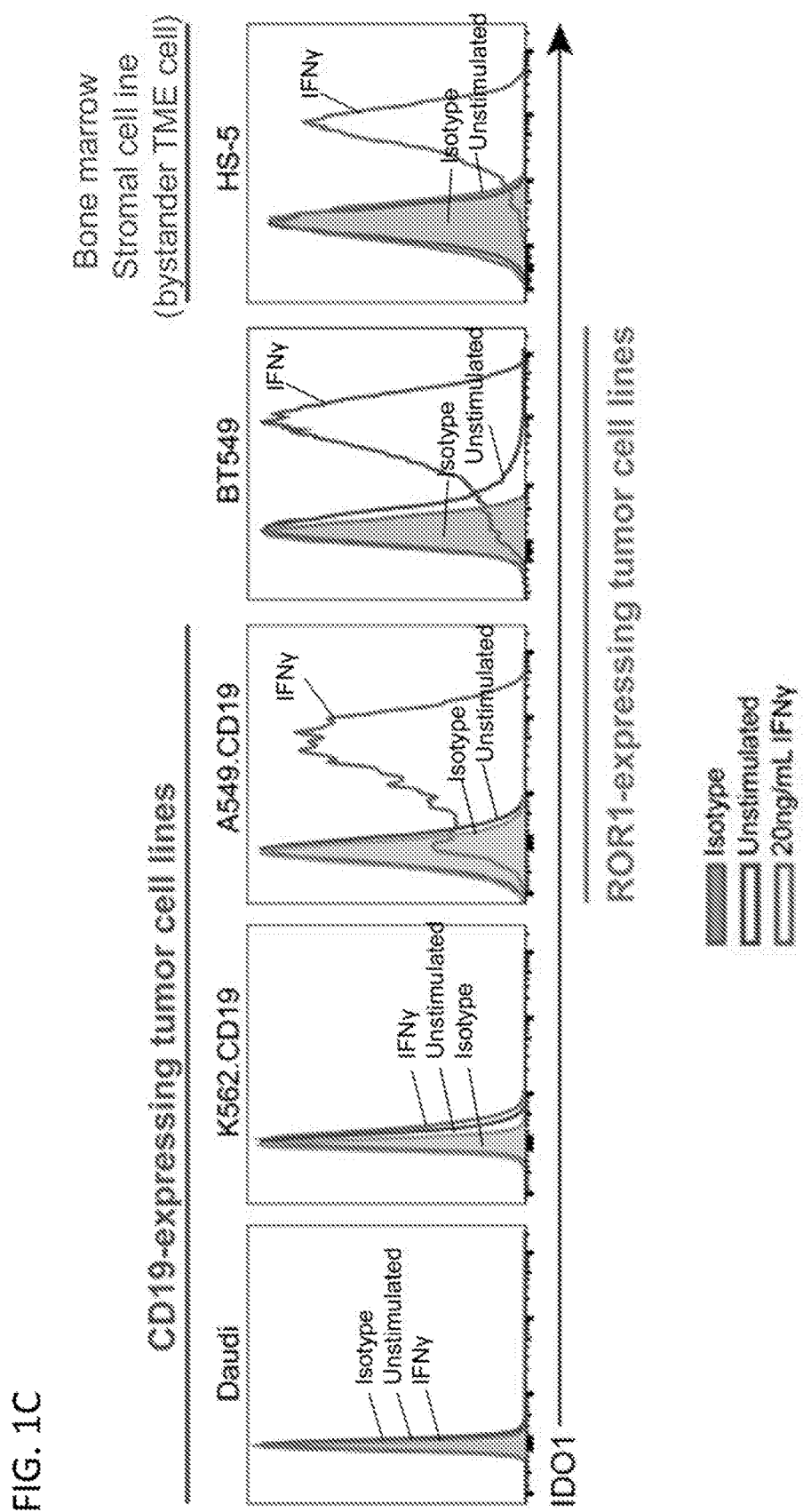
FIG. 1C depicts the IDO1 expression level, as detected by flow cytometry, in Daudi, K562 cells expressing CD19 (K562.CD19), A549 cells expressing CD19 (A549.CD19), BT-549 human breast cancer cell line and HS-5 human bone marrow stromal cells, following stimulation with interferon gamma (IFNγ).

Levels of IDO1 expression in various CD19-expressing tumor cell lines (Daudi, K562.CD19 or A549.CD19), ROR1-expressing tumor cells lines (A549.CD19 or BT-549) and a HS-5 human bone marrow stromal cell line were assessed following incubation overnight with 20 ng/mL recombinant human IFNγ. Results are shown in FIG. 1C.

B. Co-Culture with Chimeric Antigen Receptor (CAR)-Expressing T Cells

To assess whether incubation in the presence of chimeric antigen receptor (CAR)-expressing T cells modulated IDO1 expression, anti-CD19 CAR-expressing cells were co-cultured with CD19.A549 cells. The CAR included an anti-CD19 scFv, an Ig-derived spacer, a human CD28-derived transmembrane domain, a human 4-1BB-derived intracellular domain and a human CD3 zeta-derived signaling domain. A lentiviral vector containing a nucleic acid molecule encoding the CAR was used to transduce primary human T cells isolated from the blood of healthy donors by apheresis.

Figure 1E:
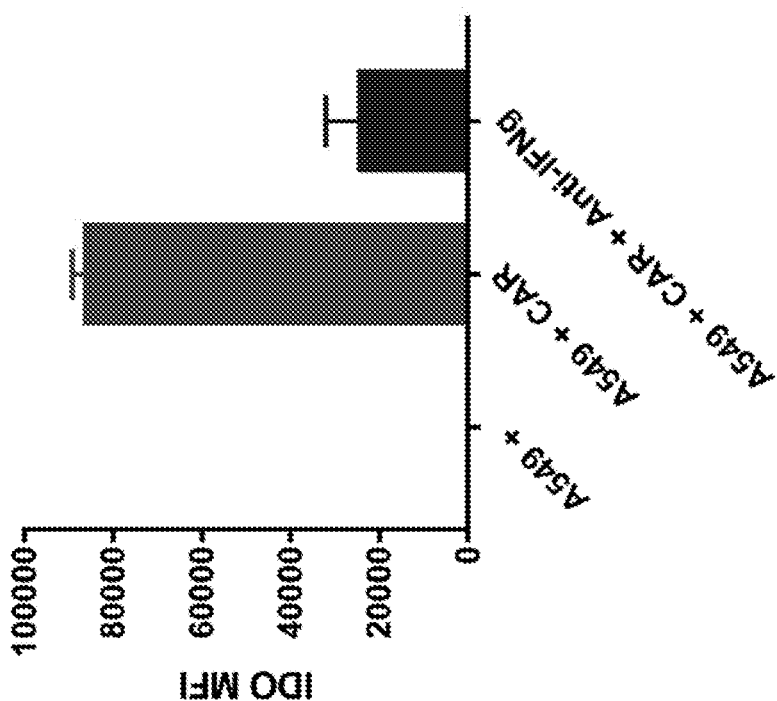
FIG. 1E is a bar graph representing the mean fluorescence intensity (MFI) of IDO1, of the co-culture with anti-CD19 chimeric antigen receptor (CAR)-expressing T cells or anti-CD19 chimeric antigen receptor (CAR)-expressing T cells together with and 10 μg/mL anti-IFNγ antibody, compared to CD19.A549 cells cultured alone.
Figure 1D:
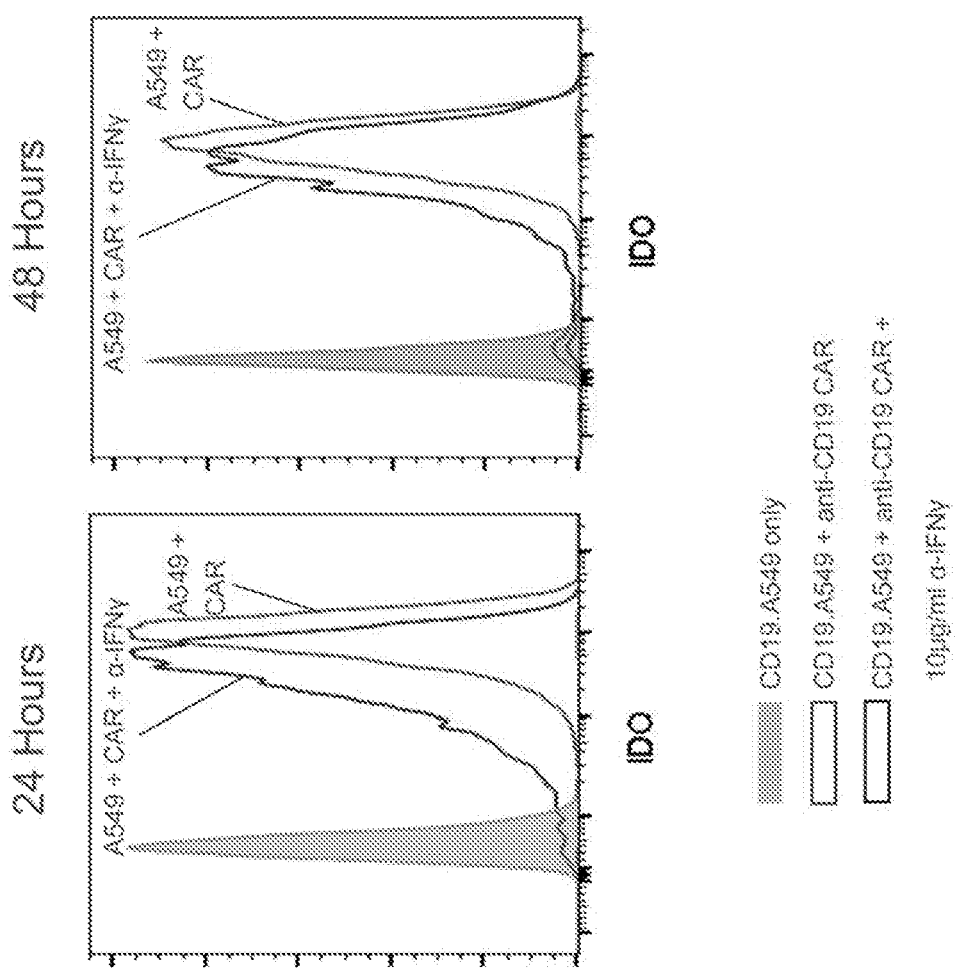
FIG. 1D depicts the IDO1 expression level, as detected by flow cytometry, in A549 adenocarcinoma cells expressing CD19 (CD19.A549), following co-culture with anti-CD19 chimeric antigen receptor (CAR)-expressing T cells or anti-CD19 chimeric antigen receptor (CAR)-expressing T cells together with and 10 μg/mL anti-IFNγ antibody for either 24 hours or 48 hours, compared to CD19.A549 cells cultured alone, as described in Example 1.

The genetically engineered anti-CD19 CAR-expressing T cells were co-cultured with the CD19.A549 cells at a 1:1 effector:target (E:T) cell ratio for 24 hours or 48 hours and IDO1 expression was assessed by intracellular staining via flow cytometry. Cultures were performed in the presence or absence of a blocking anti-IFN-gamma antibody (at a concentration of 10 μg/mL). As shown in FIGS. 1D and 1E, increased IDO1 expression levels were observed in the CD19.A549 cells cultured in the presence of CAR-expressing cells, as compared to the levels in CD19.A549 cells cultured alone. The results were consistent with the ability of CAR-expressing T cells to induce IDO1 expression in CAR-targeted antigen-positive cells. The addition of the anti-IFN-gamma blocking antibody was observed to reduce the increased levels of IDO1 expression (FIGS. 1D and 1E). Increased IDO1 expression levels in these cells also were observed at 96 hours following initiation of co-cultures with CD19-targeting CAR-expressing T cells.

Figure 1F:
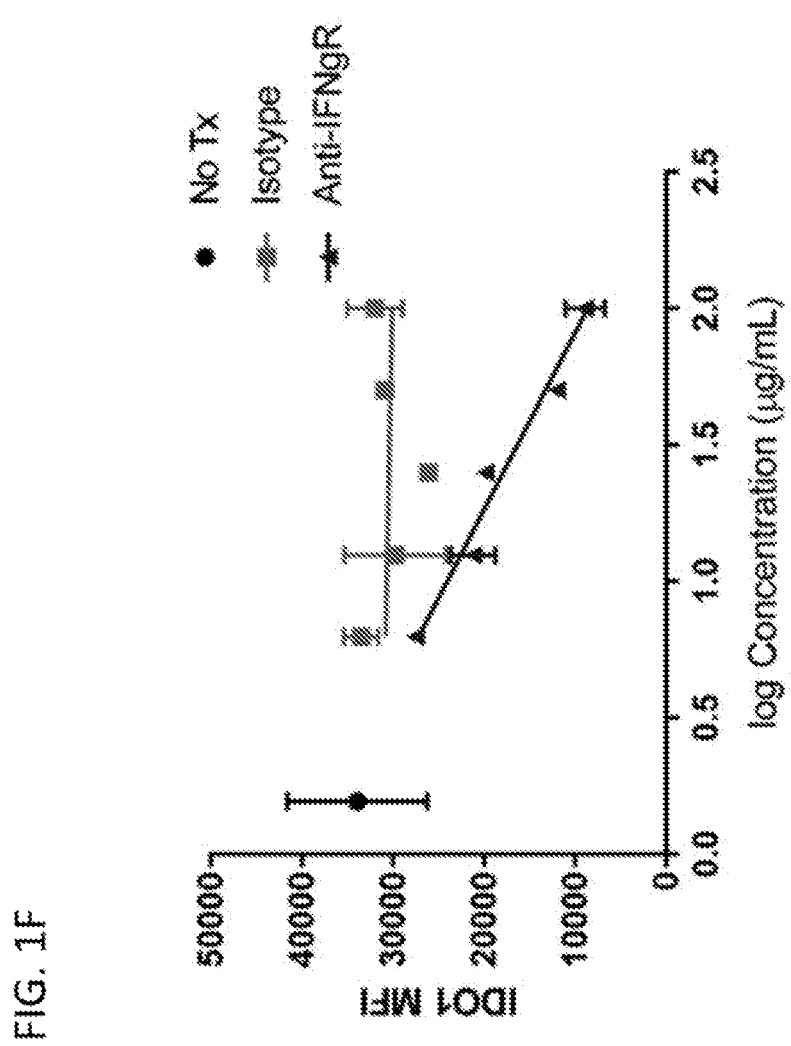
FIG. 1F depicts the mean fluorescence intensity (MFI) of IDO1 as assessed by flow cytometry, in A549.CD19 target cells following co-culture with anti-CD19 chimeric antigen receptor (CAR)-expressing T cells or anti-CD19 CAR T cells together in the absence (no treatment, no Tx) or presence of increasing concentrations (from 0.75 to 2.0 μm/mL) of an anti-interferon-gamma receptor (IFNγR) antibody, or an isotype control.

In another study, IDO$^+$ A549.CD19 target cells were co-cultured for 24 hours with anti-CD19 CAR T cells (or non-transduced control T cells) at an effector:target (E:T) ratio of 1:1, in the presence of increasing concentrations (from 0.75 to 2.0 μg/mL) of an anti-interferon-gamma receptor (IFNγR) antibody, or an isotype control. IDO1 expression on target cells was measured by flow cytometry. As shown in FIG. 1F (mfi=mean fluorescence intensity), a dose-dependent reduction in increased IDO expression levels in the presence of CAR-T cells (as compared to non-transduced control cells) was observed, in the presence of increasing concentrations of the anti-IFNγR blocking antibody In another study, CD19.A549 cells, which also express endogenous ROR1, or parental A549 (CD19−) cells were cultured for 24 hours, alone (untreated) or with primary human T cells engineered to express either the anti-CD19 CAR or an anti-ROR1 CAR (including an anti-ROR1 scFv, an Ig-derived spacer, a human 4-1BB-derived intracellular domain and a human CD3 zeta-derived signaling domain). Cell supernatants were harvested to assess interferon gamma (IFNγ), and target cells were assessed for IDO1 expression by flow cytometry.

Figure 1G:
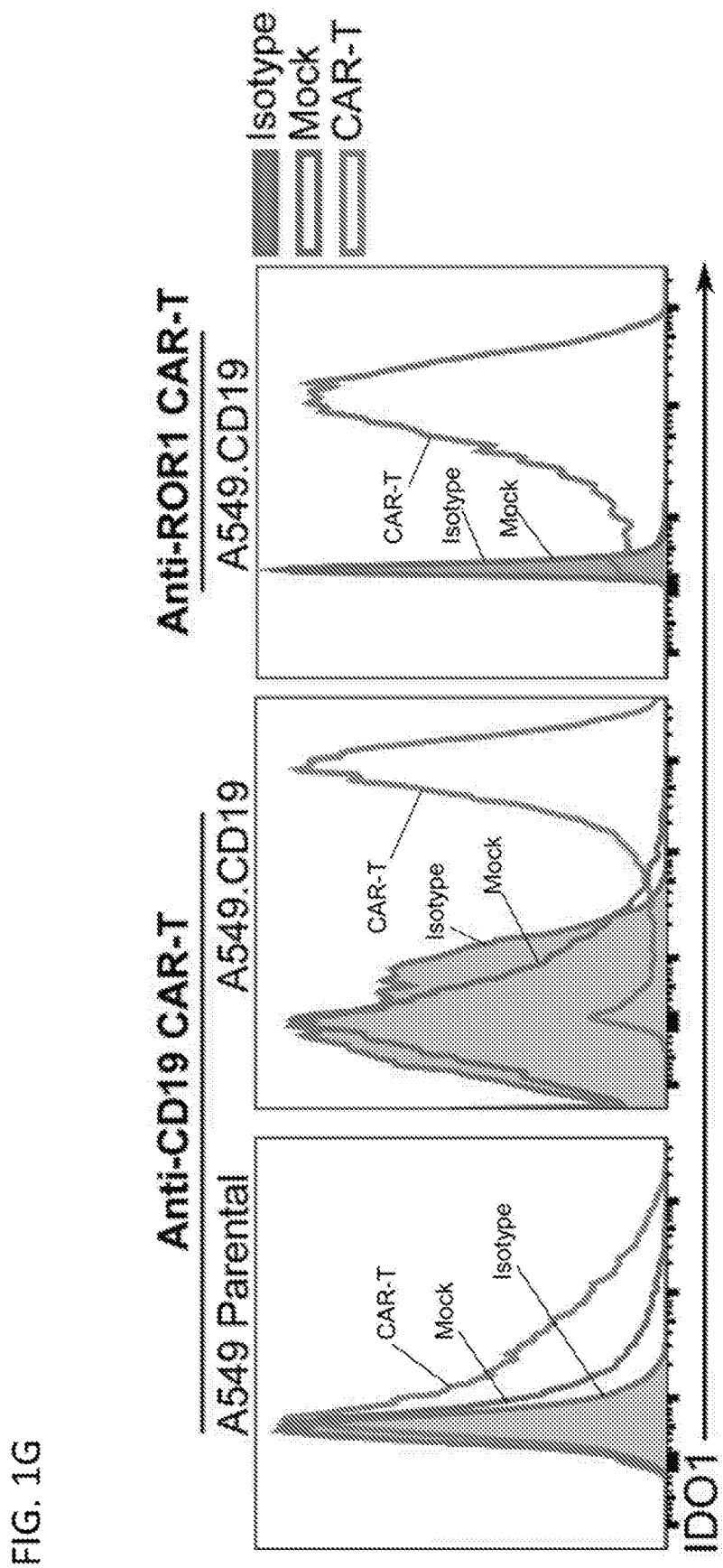
FIG. 1G depicts the IDO1 expression level, as detected by flow cytometry, in A549 adenocarcinoma cells expressing CD19 (A549.CD19) or parental A549 cells, following co-culture with anti-CD19 chimeric antigen receptor (CAR)-expressing T cells, anti-ROR1 chimeric antigen receptor (CAR)-expressing T cells, or mock transduced cells, for 24 hours.
Figure 1H:
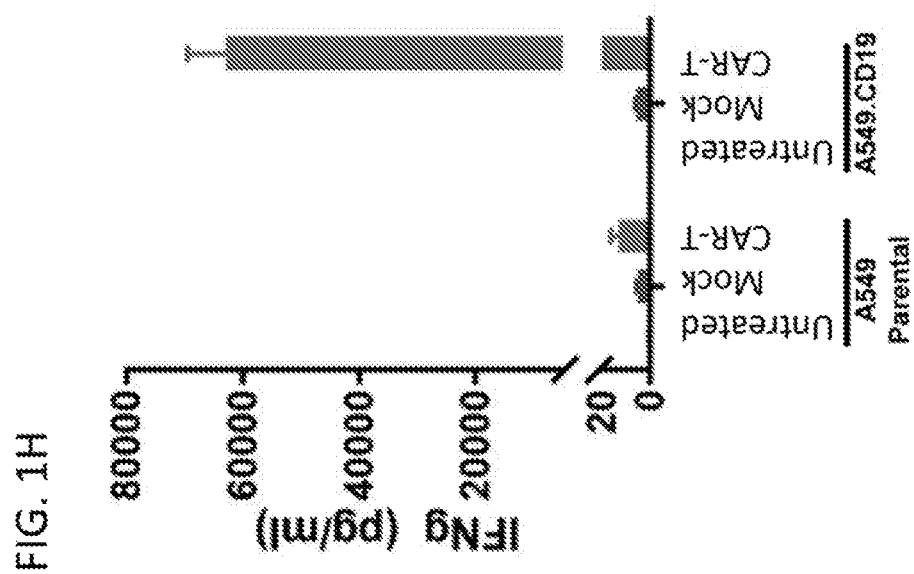
FIG. 1H depicts IFNγ production in culture supernatants following co-culture of anti-CD19 CAR+ T cells or mock transduced cells with A549 adenocarcinoma cells expressing CD19 (A549.CD19) or parental A549 cells.

Representative histograms are shown in FIGS. 1G and 1H. As shown in FIG. 1G, an increase in IDO1 expression was observed following culture with anti-CD19 or anti-ROR1 CAR T cells in CD19.A549 cells but was not observed in A549 parental (CD19−) cells following culture with anti-CD19 CAR T cells upon co-culture with anti-CD19 CAR cells. Likewise, as shown in FIG. 1H, increased IFNγ concentrations were observed in supernatants following co-culture of anti-CD19 CAR+ T cells with CD19.A549 cells (expressing CAR target antigen CD19), as compared to with A549 parental control.

C. IFNγ Production and IDO1 Expression

Target cells engineered to express various levels of the CD19 antigen were co-cultured with anti-CD19 CAR T cells and production of IFNγ by CAR-T cells and induction of IDO1 by antigen-expressing cells was assessed.

Figure 1J:
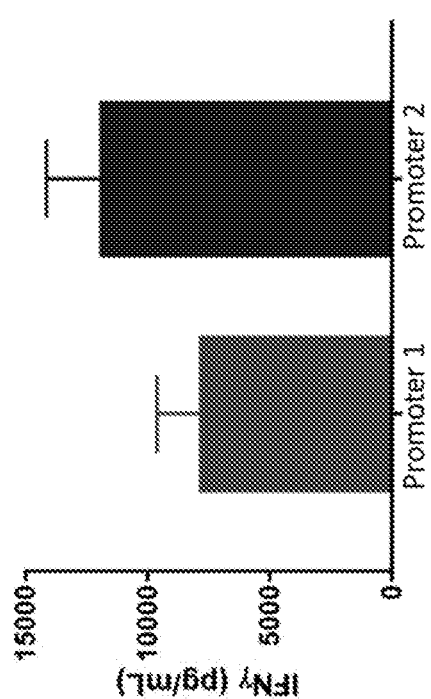
FIG. 1J depicts the IFNγ production from a co-culture of the A549 target cells expressing endogenous CD19 under the control of one of two different promoters and anti-CD19 CAR-T cells or no CAR-T cell control.
Figure 1I:
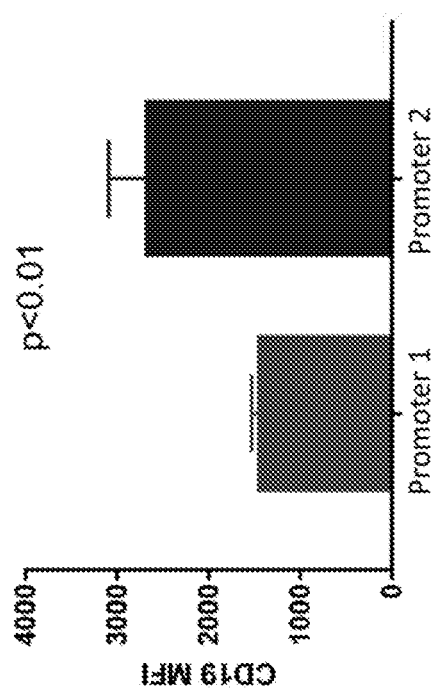
FIG. 1I shows the level of CD19 expression in A549 target cells expressing endogenous CD19 under the control of one of two different promoters.
Figure 1L:
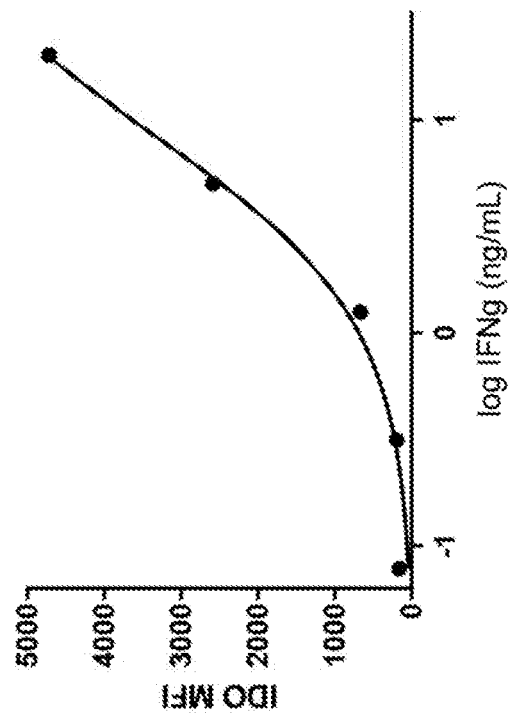
FIG. 1L depicts IDO1 expression in CD19.A549 cells cultured with various concentrations of recombinant human IFNγ
Figure 1K:
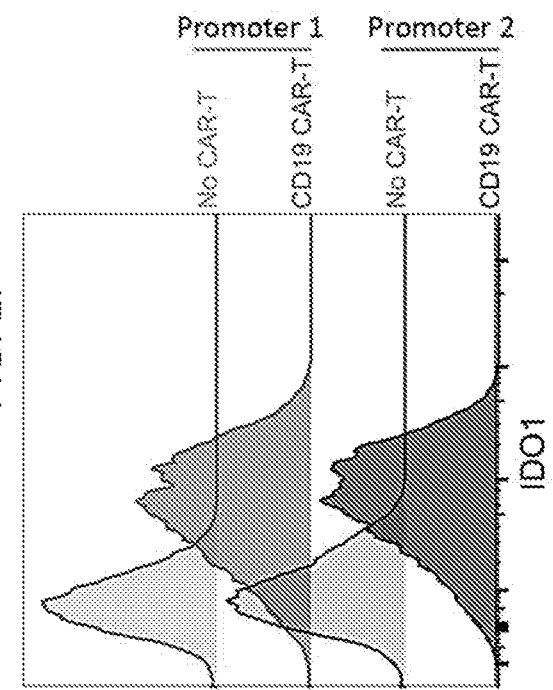
FIG. 1K depicts IDO expression, as determined by flow cytometry, in the co-cultures described in FIG. 1J.

Anti-CD19 CAR-T cells were co-cultured with A549 target cells expressing endogenous CD19 under the control of one of two different promoters, driving different levels of CD19 expression (see FIG. 1I). IDO1 expression and IFNγ production were determined as described above. Results are shown in FIGS. 1J-1K.

CD19.A549 cells were cultured with various concentrations of recombinant human IFNγ. As shown in FIG. 1L, a dose-responsive increase in IDO1 expression, as determined by mean fluorescence intensity (MFI) by flow cytometry, was observed with increasing IFNγ concentrations Example 2: Tryptophan and Tryptophan Metabolite Levels Following Co-Culture of Tumor Cells with Chimeric Antigen Receptor (CAR)-Expressing T Cells IDO1 is involved in the oxidation of tryptophan into kynurenine. Tryptophan metabolite levels were assessed following co-culture of antigen-expressing cells with antigen specific-CAR T cells in the presence or absence of an IDO1 inhibitor, epacadostat.

A. Tryptophan and Kynurenine Levels in the Presence of an IDO1 Inhibitor

Anti-CD19 CAR-expressing T cells generated substantially as described in Example 1 were co-cultured with CD19.A549 cells for 96 hours at an effector-target (E:T) ratio of 0.3:1, 1:1 or 3:1, in the presence of 0, 0.1, 10 or 1000 nM epacadostat. Amounts of tryptophan (and of kynurenine, for 3:1 E:T ratio samples) in co-culture supernatants were measured by ELISA, and compared to those observed in fresh culture medium.

As shown in FIG. 2A, amounts of tryptophan measured in supernatant from co-cultures at all E:T ratios were lower than those observed in medium alone. This result was consistent with an ability of CAR-expressing T cells to promote increased IDO1 expression and/or function in CAR target-expressing CD19.A549 cells. Co-culture in the presence of epacadostat (e.g., at 1000 nM) was observed to restore levels of tryptophan. FIG. 2B also shows that kynurenine amounts observed in supernatants from co-cultures of CAR-expressing T cells and antigen-expressing CD19.A549 cells were higher than those observed in culture in medium alone. This result was also consistent with the ability of CAR-expressing T cells to induce or enhance IDO1 in target-expressing CD19.A549 cells. Epacadostat at 1000 nM was observed to reduce kynurenine levels in the co-culture supernatants. These results were consistent with a finding that CAR-expressing T cells can induce expression of functional IDO1, and that functional outcomes of this increase (e.g., kynurenine pathway modulation) can be modulated by an inhibitor of the enzyme.

In another study, anti-CD19 CAR$^+$ T cells and A549.CD19 IDO$^+$ target cells were co-cultured in the presence of increasing concentrations of epacadostat, for 96 hours. Results are shown in FIG. 2C.

B. Tryptophan and Kynurenine Levels in Co-Culture with IDO1$^+$ or IDO1$^-$ Target Cells Tryptophan and Kynurenine levels in culture supernatant were measured, following co-culture of anti-CD19 CAR-expressing T cells generated substantially as described in Example 1, with CD19-expressing target cells that were either CD19.A549 cells (IDO1$^+$ target cells that were capable of induced IDO1 expression) or CD19.Daudi cells (IDO1$^-$ target cells that were not observed to express IDO or to induce IDO1 expression in response to stimuli) at a 1:1 effector:target (E:T) ratio. Amounts of tryptophan and kynurenine in the supernatants were measured by ELISA.

Figure 2E:
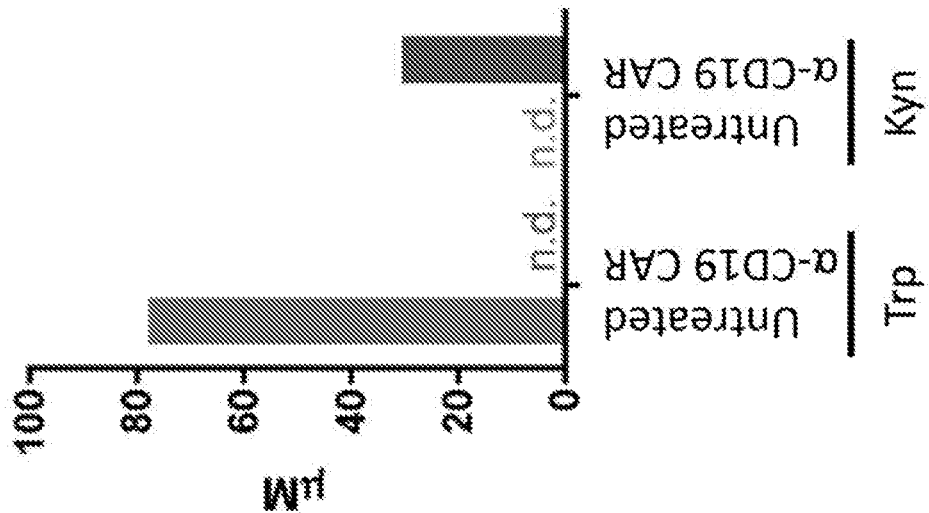
FIG. 2E depicts the tryptophan and kynurenine concentrations (μM), in the culture supernatant of A549.CD19 cells (IDO$^+$ target cells) cultured alone (untreated) or with anti-CD19 CAR-expressing T cells (α-CD19 CAR), for 24 hours.
Figure 2D:
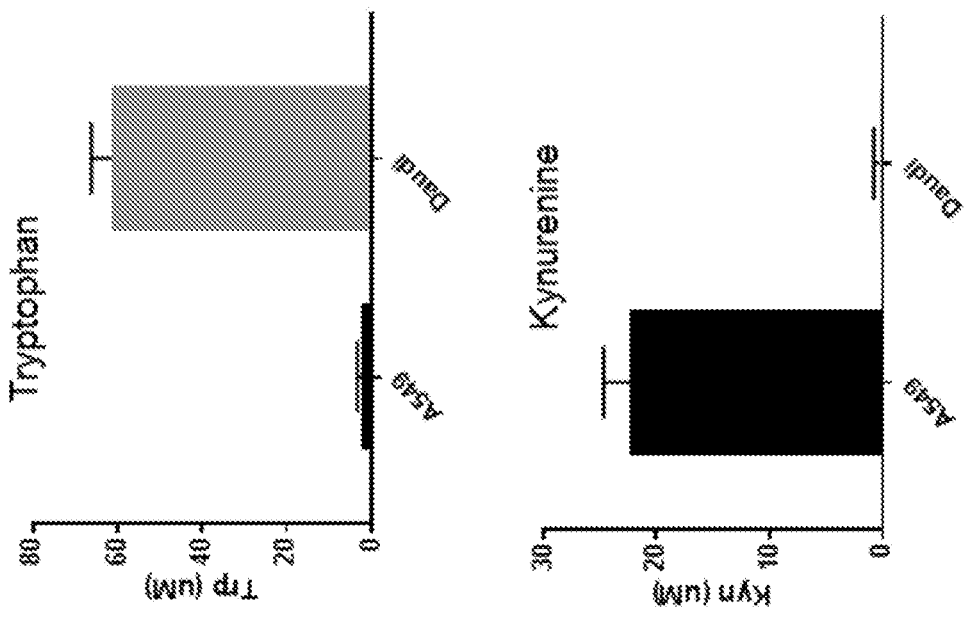
FIG. 2D depicts the tryptophan and kynurenine concentrations (μM), as measured by ELISA, in the culture supernatant of co-culture of CD19.A549 (IDO1+) or CD19.Daudi cells (IDO1−) and anti-CD19 CAR-expressing T cells, at a 1:1 effector:target (E:T) ratio.

As shown in FIG. 2D, levels of tryptophan detected were higher in co-cultures containing Daudi cells as compared to co-cultures containing A549 cells. Conversely, the amount of kynurenine was observed to be higher in a co-culture containing A549 cells compared to in a co-culture containing Daudi cells. This result was consistent with a conclusion that CAR-expressing T cells can, e.g., upon activation in response to encounter with CAR antigen, promote increased IDO1 expression on certain cells such as certain tumor cell lines or other cells, such as A549 target cells. The increased IDO1 expression in some contexts can metabolize tryptophan, e.g., into kynurenine, which may result in the depletion of tryptophan and/or accumulation of kynurenine or other tryptophan metabolites in the environment, such as in the tumor microenvironment (TME).

C. Tryptophan and Kynurenine Levels in Co-Culture of Target Cells With CAR$^+$ T Cells Tryptophan and Kynurenine levels in culture supernatant were measured using high performance liquid chromatography (HPLC), from A549.CD19 cells (IDO$^+$ target cells) cultured alone (untreated) or with anti-CD19 CAR-expressing T cells (α-CD19 CAR), for 24 hours. Results are shown in FIG. 2E (n.d.: not detectable), the supernatant from A549.CD19 cells cultured alone had high tryptophan but undetectable levels of kynurenine, but the supernatant from the co-culture of anti-CD19 CAR+ T cells and the IDO$^+$ A549.CD19 target cells contained undetectable levels of tryptophan but increased levels of kynurenine.

Example 3: Effect of IDO1 Inhibitor Epacadostat on Functional Responses of Anti-CD19 CAR-Expressing T Cells Cultured with CD19-Expressing Tumor Cells Studies were conducted to assess effects of IDO1 inhibition on CAR-T cell functional responses following co-culture with antigen-expressing tumor cells. Proliferation, cytokine production, and cell surface marker expression in anti-CD19 CAR-expressing T cells were assessed after co-culture with target (CD19)-expressing tumor cell lines. The CAR-expressing T cells were generated substantially as described in Example 1.

Figure 3:
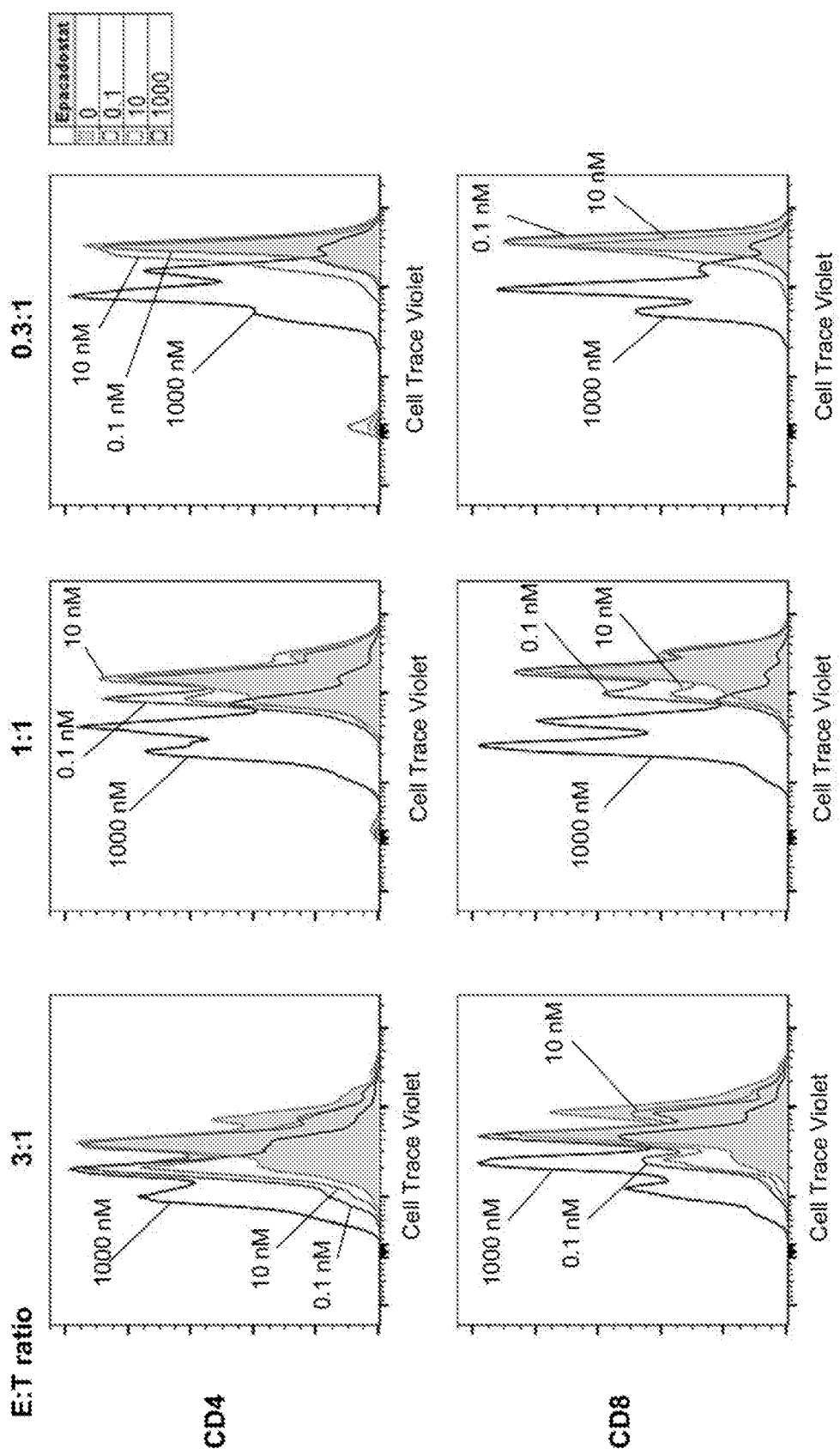
FIG. 3 depicts T cell proliferation, of anti-CD19 CAR-expressing CD4+ and CD8+ T cells after a co-culture with CD19-expressing A549 target cells (CD19.A549) at a 0.3:1, 1:1 or 3:1 E:T ratio, in the presence of 0, 0.1, 10 and 1000 nM epacadostat, as described in Example 3A. T cell proliferation was measured using dilution of CellTrace™ Violet by flow cytometry.

A. Assessment of Proliferation of Anti-CD19 CAR T Cells in the Presence of IDO1 Inhibitor and/or IDO+ Target Cells Anti-CD19 CAR-expressing T cells were labeled with CellTrace™ violet (ThermoFisher) cell proliferation assay dye, washed and incubated for 96 hours with CD19-expressing A549 target cells (CD19.A549) at a 0.3:1, 1:1 or 3:1 effector:target (E:T) ratio in the presence of 0, 0.1, 10 and 1000 nM epacadostat. Cells were stained for expression of CD4 and CD8 and proliferation of T cell populations determined by flow cytometry, based on the extent of dilution of the CellTrace™ Violet dye. As shown in FIG. 3, an IDO1 inhibitor dose-dependent increase in proliferation was observed in both CD4$^+$ and CD8$^+$ CAR-expressing T cells.

Similar methods were used to assess proliferation of anti-CD19 CAR-expressing T cells generated from three different healthy donors following co-culture with CD19-expressing A549 target cells (CD19.A549). Labeled anti-CD19 CAR-expressing T cells from each donor were co-cultured with CD19.A549 for 96 hours, in the presence of various concentrations of the IDO inhibitor epacadostat and proliferation was assessed as described above. As shown in FIGS. 4A and 4B, the presence of the inhibitor was observed to increase proliferation of CD4$^+$ and CD8$^+$ CAR-expressing T cells derived from all three donors, in a dose-dependent manner.

Figure 4C:
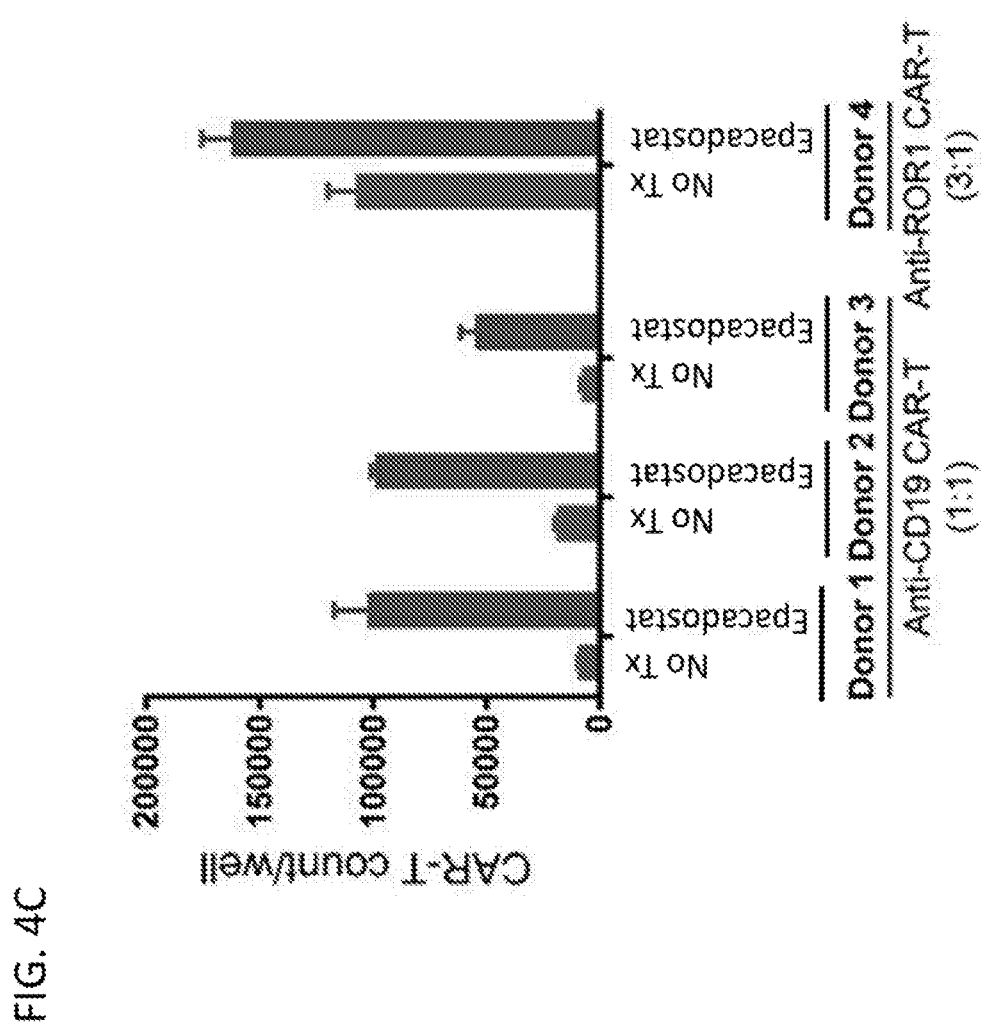
FIG. 4C depicts the number of CAR-T cells per well in co-cultures of anti-CD19 CAR-expressing T cells generated from one of three different healthy donors, at an E:T ratio of 1:1, or anti-ROR1 CAR-expressing T cells generated from a different donor, at an E:T ratio of 3:1, with CD19.A549 cells for 96 hours in the presence of 250 nM epacadostat.

A similar experiment was performed by co-culturing anti-CD19 CAR-expressing T cells generated from one of three different healthy donors with CD19.A549 cells for 96 hours in the presence of 250 nM epacadostat. The number of CAR T cells in each well was determined using CountBright Absolute Counting beads. As shown in FIG. 4C, the presence of the IDO1 inhibitor resulted in higher number CAR T cells compared to the absence of the inhibitor, for CAR T cells from all three donors. Staining for T cells subsets, CD3, CD4 and CD8, by flow cytometry indicated a similar fold increase in number of each CAR T cell subset following incubation in the presence of epacadostat compared to the absence of inhibitor. The results were consistent with a finding that an IDO1 inhibitor can counter the inhibitory effect of IDO1 expression to lead to increased proliferation of CAR T cells.

B. Proliferation of Anti-ROR1 CAR T Cells in the Presence of IDO1 Inhibitor and IDO+ Target Cells Similar methods were used to assess the effect of the IDO1 inhibitor on proliferation of anti-ROR1 CAR-expressing T cells cultured in the presence of antigen-expressing target cells. Anti-ROR1 CAR-expressing cells, described in Example 1, were co-cultured with CD19.A549 cells, which express endogenous ROR1, at an E:T ratio of 3:1, for 96 hours in the presence of 250 nM epacadostat. As shown in FIG. 4C, the presence of the IDO1 inhibitor resulted in a higher number of CAR T cells compared to cells incubated in the absence of the inhibitor.

Figure 5A:
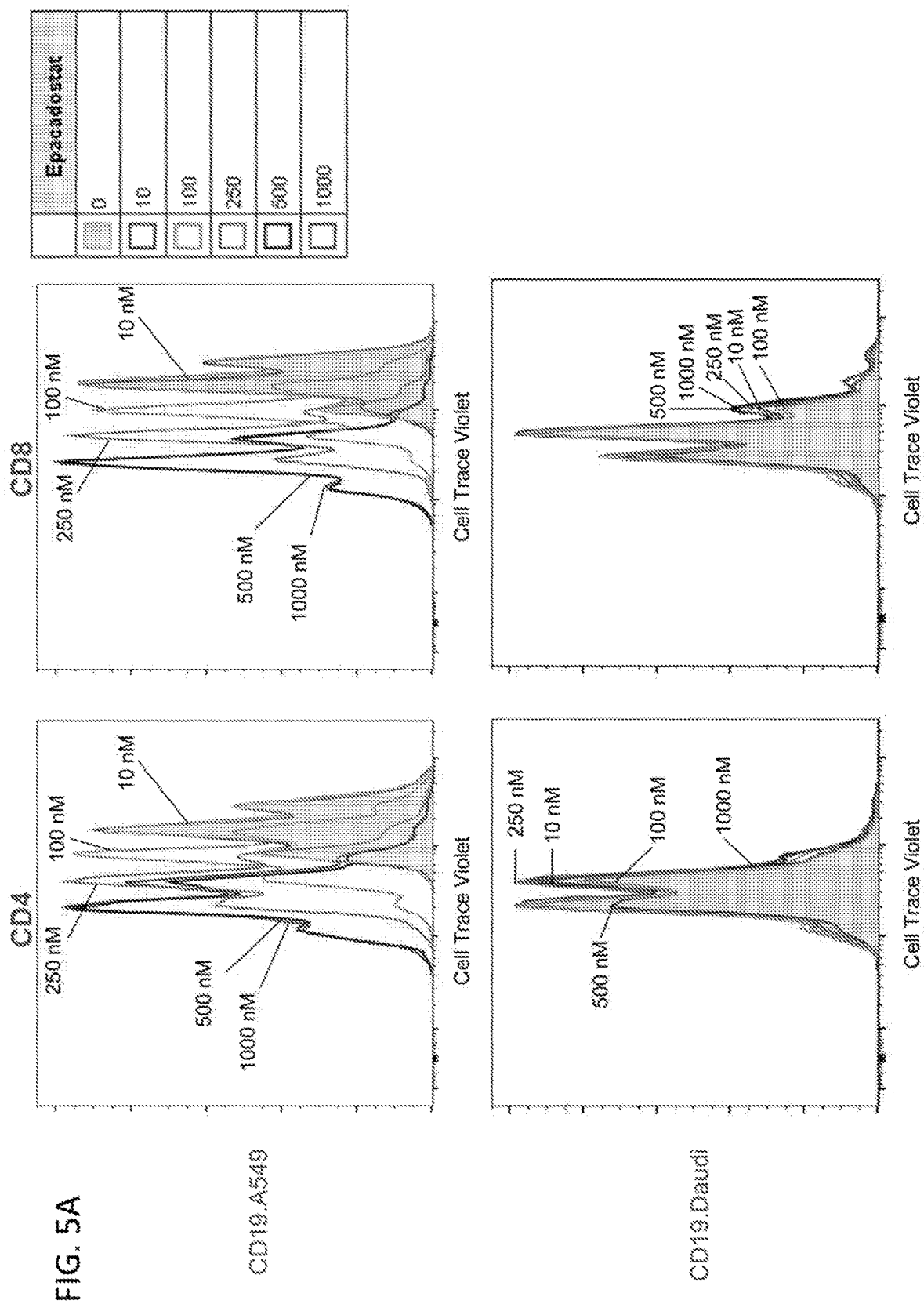
FIG. 5A depicts T cell proliferation, of anti-CD19 CAR-expressing CD4+ and CD8+ T cells after a co-culture with IDO1+A549 target cells (CD19.A549) or IDO1− Daudi target cells (CD19.Daudi) at a 1:1 E:T ratio, in the presence of 0, 10, 100, 250, 500 and 1000 nM epacadostat, as described in Example 3A. T cell proliferation was measured using dilution of CellTrace™ Violet by flow cytometry.
Figure 5B:
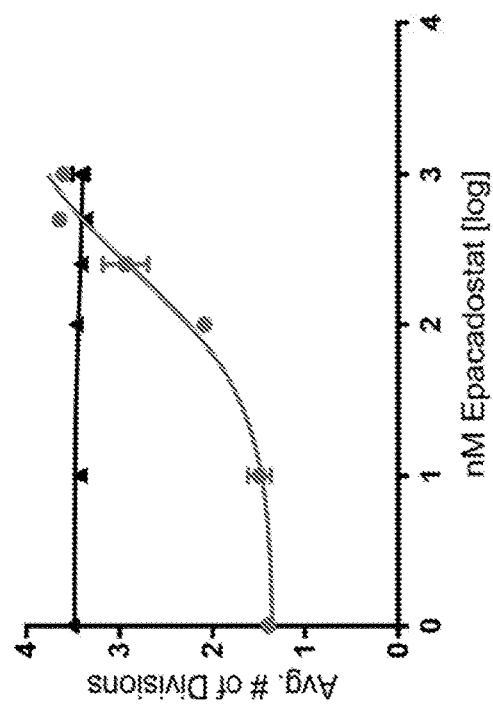
FIGS. 5B and 5C depict the average number of divisions of anti-CD19 CAR-expressing CD4+(FIG. 5B) or CD8+ (FIG. 5C) T cells after a co-culture with IDO1+A549 target cells or IDO1− Daudi target cells in the presence of 0, 10, 100, 250, 500 and 1000 nM epacadostat, as described in Example 3A.
Figure 5C:
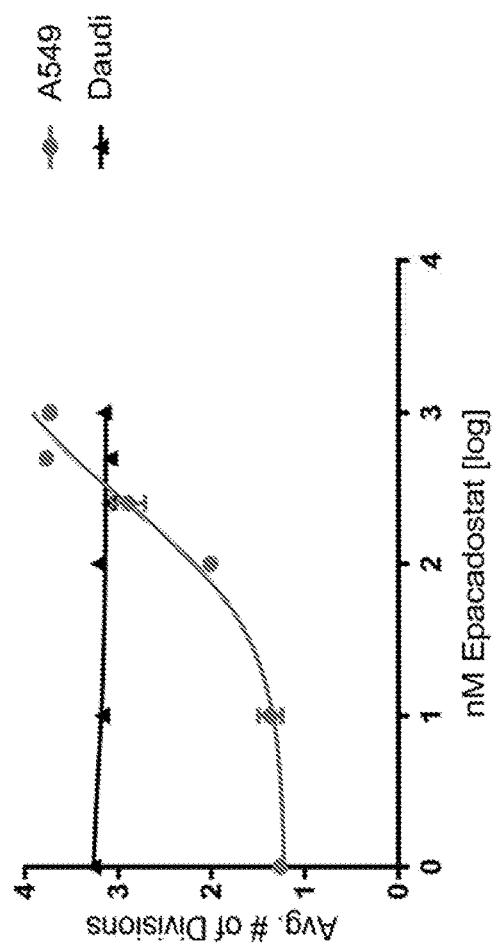

C. Proliferation of Anti-CD19 CAR T Cells in the Presence of IDO1 Inhibitor and IDO+ and IDO– Target Cells The effect of epacadostat on proliferation of CAR-expressing T cells was compared following co-culture of anti-CD19 CAR-expressing cells with either IDO1$^+$ cells (CD19.A549) or IDO1$^-$ cells (CD19.Daudi) at a 1:1 E:T ratio. Proliferation was assessed as described above in the absence or presence of various concentrations of epacadostat. As shown in FIGS. 5A, 5B and 5C, the presence of the inhibitor in the co-cultures was observed to lead to increased proliferation of CD4$^+$ and CD8$^+$ CAR-expressing T cells in a dose-dependent manner when co-cultured with IDO1$^+$ cells (A549), but not when co-cultured with IDO1$^-$ cells (Daudi). The estimated EC$_{50}$ for epacadostat in A549 cells was approximately 223 nM.

Similar methods were used to assess the effect of the IDO1 inhibitor on proliferation of CAR-expressing T cells following co-culture of anti-CD19 CAR-expressing cells with either IDO1⁺ cells (A549.CD19) or IDO1⁻ cells (K562.CD19). Proliferation was assessed as described above in the absence or presence of various concentrations of epacadostat (at 0, 15.6, 62.5, 250 or 1000 nM), at an E:T ratio of 1:1 for A549.CD19 cells or 5:1 for K562.CD19 cells. The average number of CAR T cell divisions was calculated based on peaks in dye dilution, and proliferation of CD4⁺ and CD8⁺ subsets was compared. The presence of the inhibitor in the co-cultures was observed to lead to a dose-dependent increase in proliferation of CAR-expressing T cells, including CD4+ and CD8+ populations, when such cells were co-cultured with IDO1⁺ cells, but not when co-cultured with IDO1⁻ cells.

The observed dose-dependent effect of the inhibitor on proliferation and expansion of CAR T cells in culture was also visualized by microscopy following co-culture of labeled CD19-A549 target cells with unlabeled CAR-expressing T cells at a 1:1 effector:target ratio in the presence of either 1 µM epacadostat or no inhibitor. Cells were visualized at 72 hours and 120 hours. At 120 hours, a large increase in CAR-expressing T cells (unlabeled) was observed, associated with a relatively lower number of labeled effector cells, following incubation in the presence of the inhibitor, as compared to control cells incubated in the absence of the inhibitor. These results were consistent with the ability of IDO1, observed herein to be induced by exposure to CAR-expressing T cells, to in turn reduce the expansion and/or survival of CAR-expressing T cells, in a manner dependent upon IDO1 function (as evidenced by reversal of this effect in the presence of the IDO1 inhibitor).

D. Sustained Proliferation of Anti-CD19 CAR T Cells in the Presence of IDO1 Inhibitor Expansion of anti-CD19 expressing CAR cells following co-culture with A549 adenocarcinoma human alveolar basal epithelial cells transduced with human CD19 (CD19.A549 cells) was assessed for over 10 days. Anti-CD19 CAR-expressing T cells from each donor were co-cultured with CD19.A549 for up to approximately 340 hours in the presence of 0, 3.9, 15.6, 62.5, 250 and 1000 nM epacadostat, at a 1:1, 0.5:1 or 0.25:1 E:T ratio. Expansion was assessed based on % confluency in the culture as determined over time. A dose-dependent effect of the inhibitor was observed, with increasing expansion of CAR-expressing T cells, which became more apparent at later timepoints and extended expansion beyond 5 days in culture. The IDO1 inhibitor-promoted increase in expansion was sustained for more than 10 days in culture. The results were consistent with a conclusion that IDO-upregulation and/or IDO-dependent signaling can occur or be promoted following CAR-T antigen-specific activation and result in dampening of proliferation of the CAR-T cells, e.g., over a 5- or 10-day period, and that inhibition of IDO can in some contexts rescue such inhibition.

E. Cytokine Release

Figure 6:
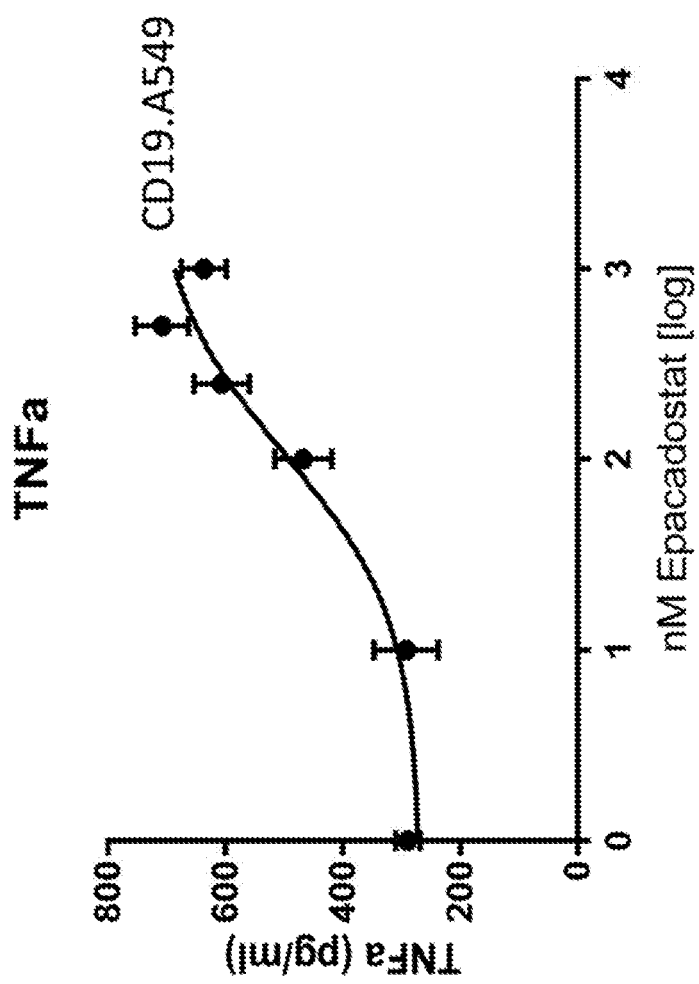
FIG. 6 depicts the level of tumor necrosis factor alpha (TNFα) (pg/ml), as measured by a TNFα Assay kit, in the culture supernatant of a co-culture of CD19.A549 cells and anti-CD19 CAR-expressing T cells, at a 1:1 E:T ratio in the presence of 0, 10, 100, 250, 500 and 1000 nM epacadostat, as described in Example 3B.

Amounts of tumor necrosis factor alpha (TNFα) were assessed from the supernatant of anti-CD19 CAR-expressing T cells co-cultured for 48 hours at a 1:1 E:T ratio with CD19.A549 cells in the presence of various concentrations of epacadostat. As shown in FIG. 6, the presence of the inhibitor in the co-cultures was observed to result in increased TNFα production in a dose-dependent manner. TNFα levels were below those observed for cultures in the presence of IDO1⁻CD19.Daudi cells, which were above the detection limits in this assay for all conditions tested.

F. Cell Phenotype Marker Expression

Cell surface expression of CD25 was assessed by flow cytometry on CD4⁺ and CD8⁺ CAR-expressing T cells after co-culture of T cells at a 1:1 E:T ratio with either IDO1⁺ CD19.A549 cells or IDO1⁻CD19.Daudi cells for 96 hours in the presence of various concentrations of epacadostat.

Figures 7A, 7B:
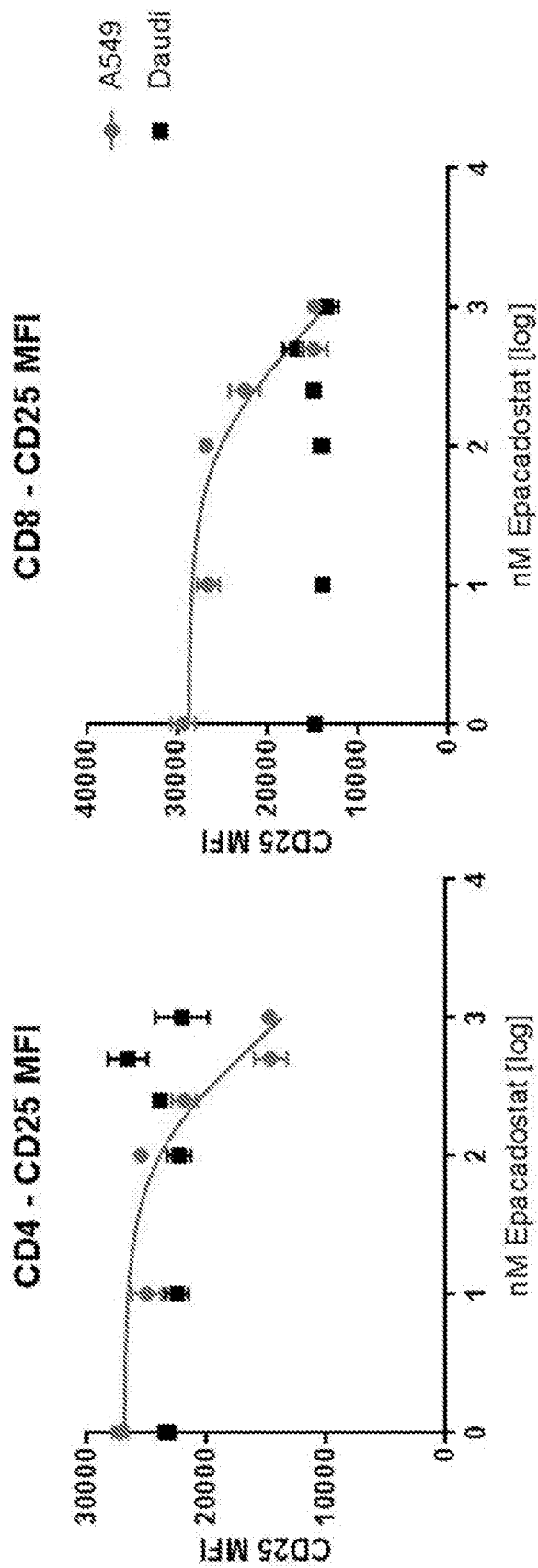
FIGS. 7A and 7B depict the CD25 surface expression levels, as detected by flow cytometry, of anti-CD19 CAR-expressing CD4+ (FIG. 7A) or CD8+ (FIG. 7B) T cells after a co-culture with IDO1+A549 target cells or IDO1− Daudi target cells in the presence of 0, 10, 100, 250, 500 and 1000 nM epacadostat, as described in Example 3B.

As shown in FIGS. 7A and 7B, the observed surface expression levels (mean fluorescence intensity (MFI)) of CD25, on both CD4⁺ and CD8⁺ CAR-expressing T cell populations, at 96 hours following co-culture of T cells with IDO1⁺ CD19.A549 cells was reduced by the presence of epacadostat in the cultures, in a dose-dependent manner. In contrast, the CD25 surface expression levels observed at 96 hours were not affected by the presence of epacadostat in co-cultures of CAR-expressing cells with IDO1⁻ target cells (CD19.Daudi cells).

As shown in FIGS. 8A and 8B, similar impacts on CD25 expression also were observed on CD4⁺ and CD8⁺ anti-CD19 CAR-expressing T cells generated from three different healthy donors following co-culture with CD19.A549 cells.

G. Cytolytic Activity

Cytolytic activity of anti-CD19 CAR-expressing T cells in the presence of various concentrations of epacadostat was determined. Anti-CD19 CAR-expressing T cells individually produced from T cells from each donor were co-cultured with CD19.A549, labeled with NucRed dye, for up to approximately 340 hours in the presence of 0, 3.9, 15.6, 62.5, 250 and 1000 nM epacadostat, at a 0.25:1 E:T ratio. Lysis of target cells was measured over time using the Incucyte quantitative cell analysis system (Essen BioScience) by assessing the staining intensity of cells for the NucRed dye. Cells in which lysis occurred exhibited reduced staining intensity for the dye. The area under the curve (AUC) for the NucRed dye⁺ cells was determined for up to approximately 340 hours, for each epacadostat concentration.

Figure 8C:
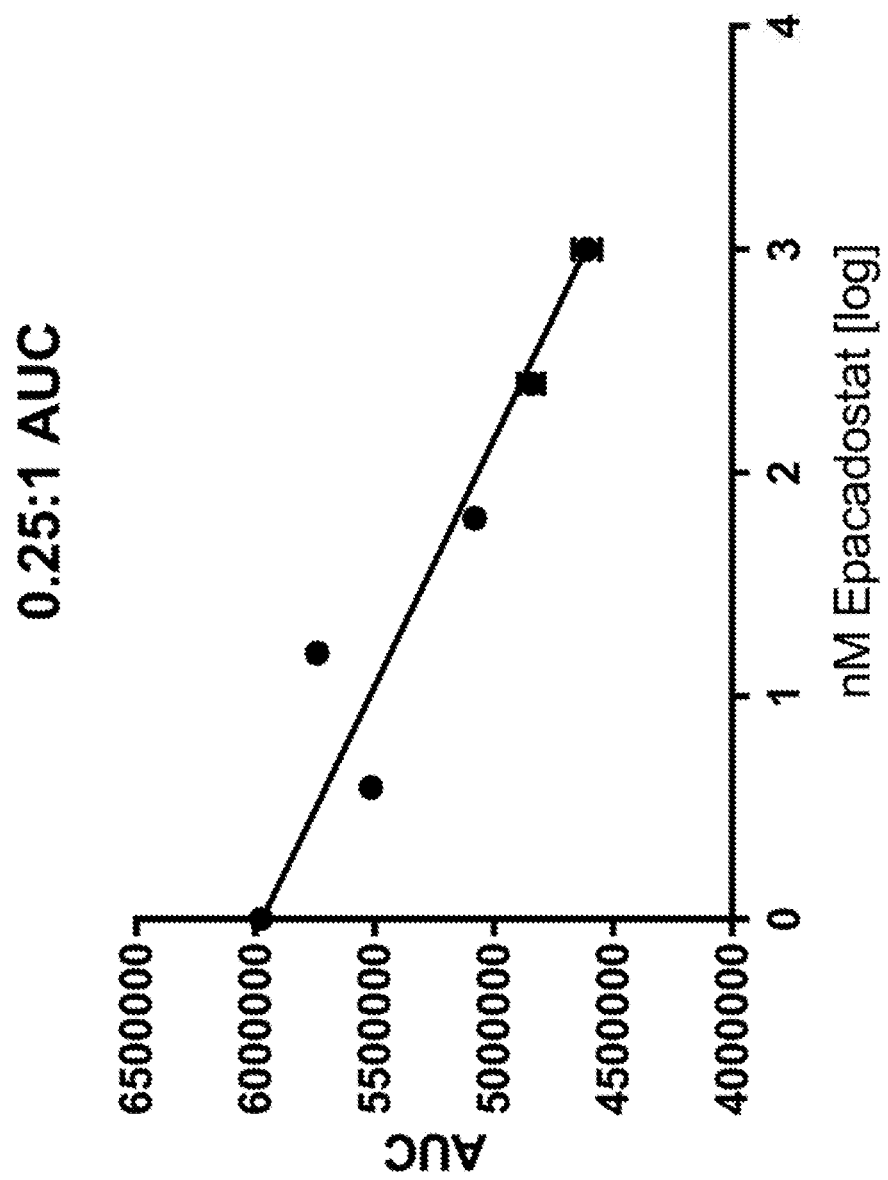
FIG. 8C depicts the area under the curve (AUC) from a plot of NucRed-labeled CD19.A549 cells, co-cultured with anti-CD19 CAR-expressing T cells, incubated for approximately 340 hours, in the presence of 0, 3.9, 15.6, 62.5, 250 and 1000 nM epacadostat, at a 0.25:1 E:T ratio.

As shown in FIG. 8C, cultures incubated with epacadostat showed a dose-dependent reduction of NucRed dye intensity, as observed by a decrease in AUC. The results were consistent with an interpretation that the presence of epacadostat enhanced the function and/or proliferation and/or survival of the anti-CD19 CAR+ cells in cultures with CD19.A549 (IDO⁺) cells, in a dose-dependent manner.

Example 4: Assessing the Effect of Fludarabine on IDO1 Expression and Cell Viability in Tumor Cell Lines Effects of fludarabine, a purine analog used in chemotherapy and/or adoptive T cell therapy (e.g., in lymphodepleting preconditioning in connection therewith), on the expression of IDO1 and cell viability of tumor cells were assessed. CD19.A549 cells were incubated, with or without IFNγ, for 48 hours. After 24 hours, increasing concentrations of fludarabine were added to the culture. IDO1 expression levels were determined by flow cytometry as described in Example 1A, and mean fluorescence intensity (MFI) was calculated. Cell viability also was assessed.

Figure 9A:
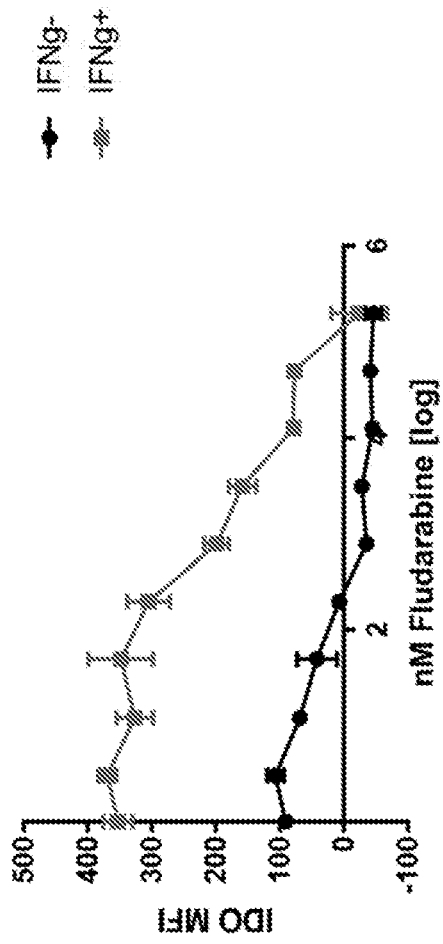
FIG. 9A depicts the IDO1 expression level, as detected by flow cytometry, in A549 adenocarcinoma cells expressing CD19 (CD19.A549), with or without stimulation with interferon gamma (IFNγ) for 48 hours, in the presence of increasing concentration of purine analog fludarabine.
Figure 9B:
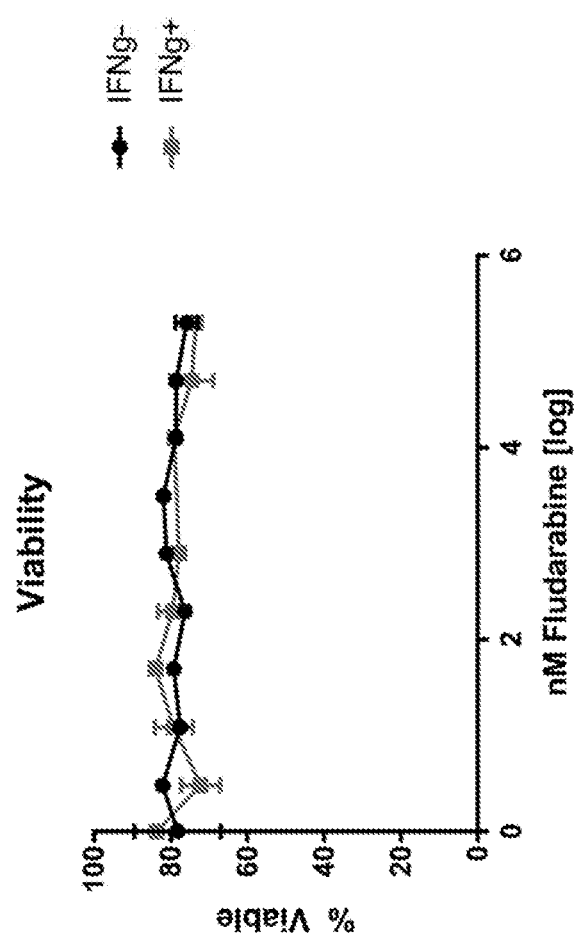
FIG. 9B depicts the percentage of viable cells in the culture of A549 adenocarcinoma cells expressing CD19 (CD19.A549), with or without stimulation with interferon gamma (IFNγ) for 48 hours, in the presence of increasing concentration of purine analog fludarabine.

As shown in FIG. 9A, addition of fludarabine reduced IDO1 levels in a dose-dependent manner. The effect of fludarabine resulted in a decrease in the basal level of IDO1 in unstimulated CD19.A549 cells as well a decrease in IFNγ-mediated upregulation of IDO1 levels to levels below the basal level of IDO1 in unstimulated CD19.A549 cells. As shown in FIG. 9B, 24 hours of fludarabine treatment did not substantially affect the viability of CD19.A549 cells.

Figure 9C:
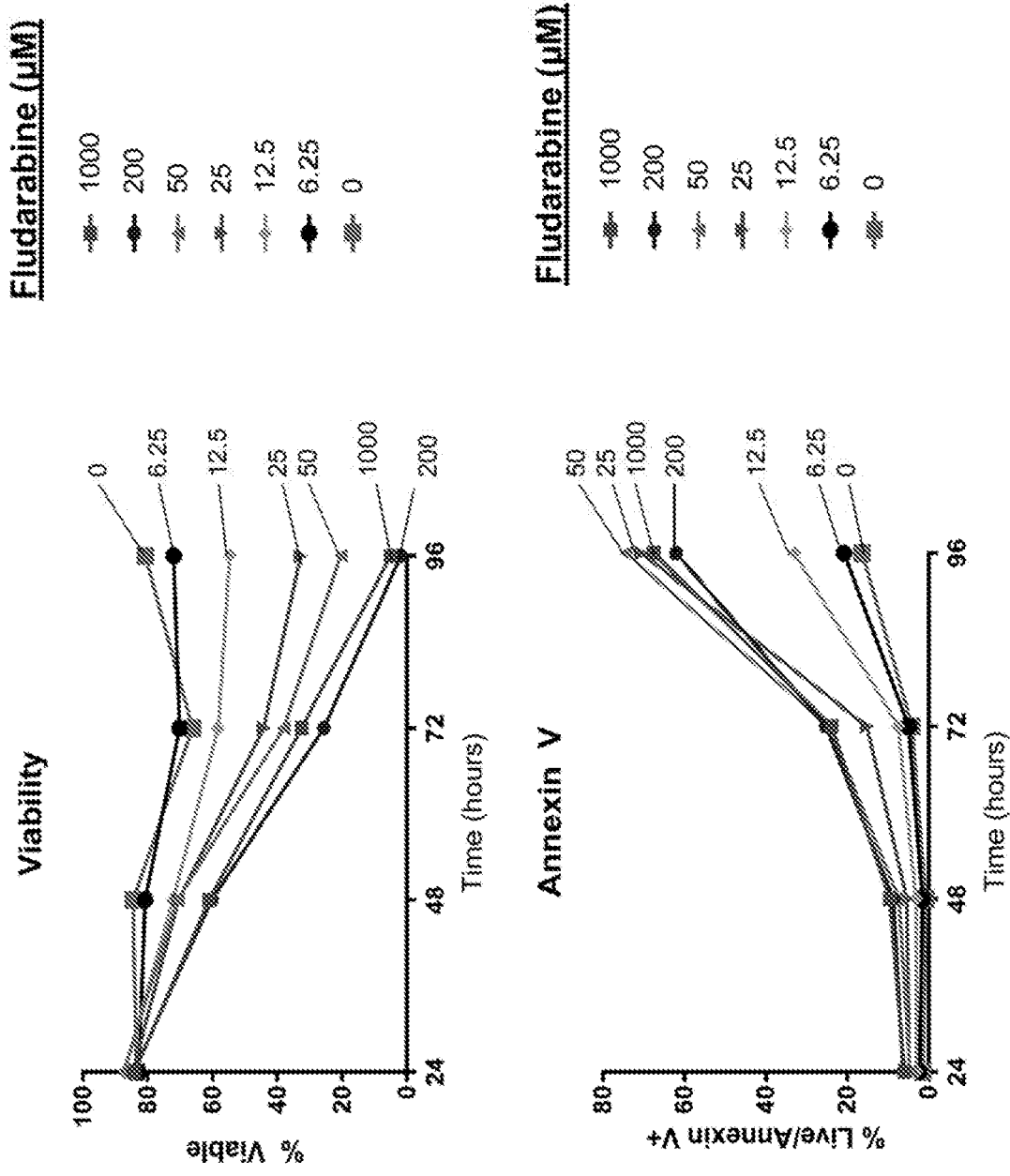
FIG. 9C depicts the % viable cells and annexin V staining results over 96 hours, in CD19.A549 cells cultured with or without IFNγ, in the presence of 0, 6.25, 12.5, 25, 50, 200 or 1000 μM fludarabine, which was added at 48 hours.
Figure 9D:
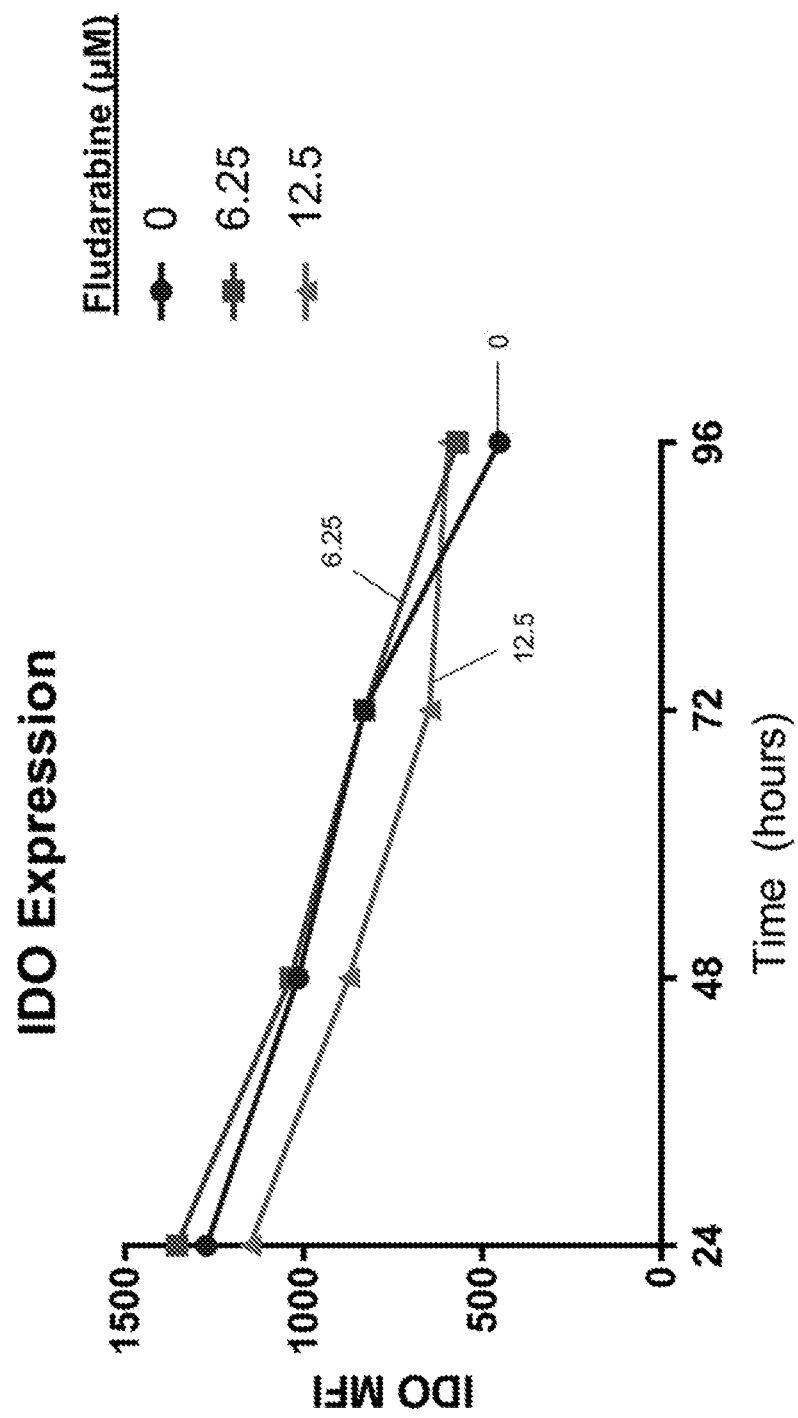
FIG. 9D depicts the mean fluorescence intensity (MFI) of IDO1 expression over 96 hours in CD19.A549 cells cultured with or without IFNγ, in the presence of 0, 6.25 or 12.5 μM fludarabine

The effect of high doses of fludarabine on the viability and apoptosis of CD19.A549 cells over time was also assessed. CD19.A549 cells were incubated, with or without IFNγ, for 48 hours. After 48 hours, a dose of 0, 6.25, 12.5, 25, 50, 200 or 1000 μM of fludarabine was added. IDO1 expression and % viability were measured as described above, and apoptosis was measured using Annexin V staining, every 24 hours, for 96 hours. Higher doses of fludarabine were observed to result in decreased cell viability and increased apoptosis after 24 or more hours in culture (FIG. 9C), and lower doses of fludarabine were observed not to affect IDO1 expression levels over time in IFNγ-stimulated CD19.A549 cells (FIG. 9D).

Example 5: Tryptophan Supplementation in Co-Cultures of Anti-CD19 CAR-Expressing T Cells and CD19-Expressing Tumor Cells Capable of Inducing IDO Expression in Response to CAR-T Activity CAR T cells were co-cultured with target cells and either the IDO1 inhibitor epacadostat or supplemental tryptophan. The CAR-expressing T cells were generated substantially as described in Example 1.

A. Proliferation of CAR T Cells in the Presence of IDO1 Inhibitor or Tryptophan

Anti-CD19 CAR-expressing T cells were incubated for 96 hours with CD19-expressing A549 target cells (CD19.A549) at a 1:1 effector:target (E:T) ratio in the presence of 0, 10, 100 and 1000 nM epacadostat, added at the beginning of the co-culture, or 5 μg/mL tryptophan, added to the culture every 24 hours.

Figure 10A:
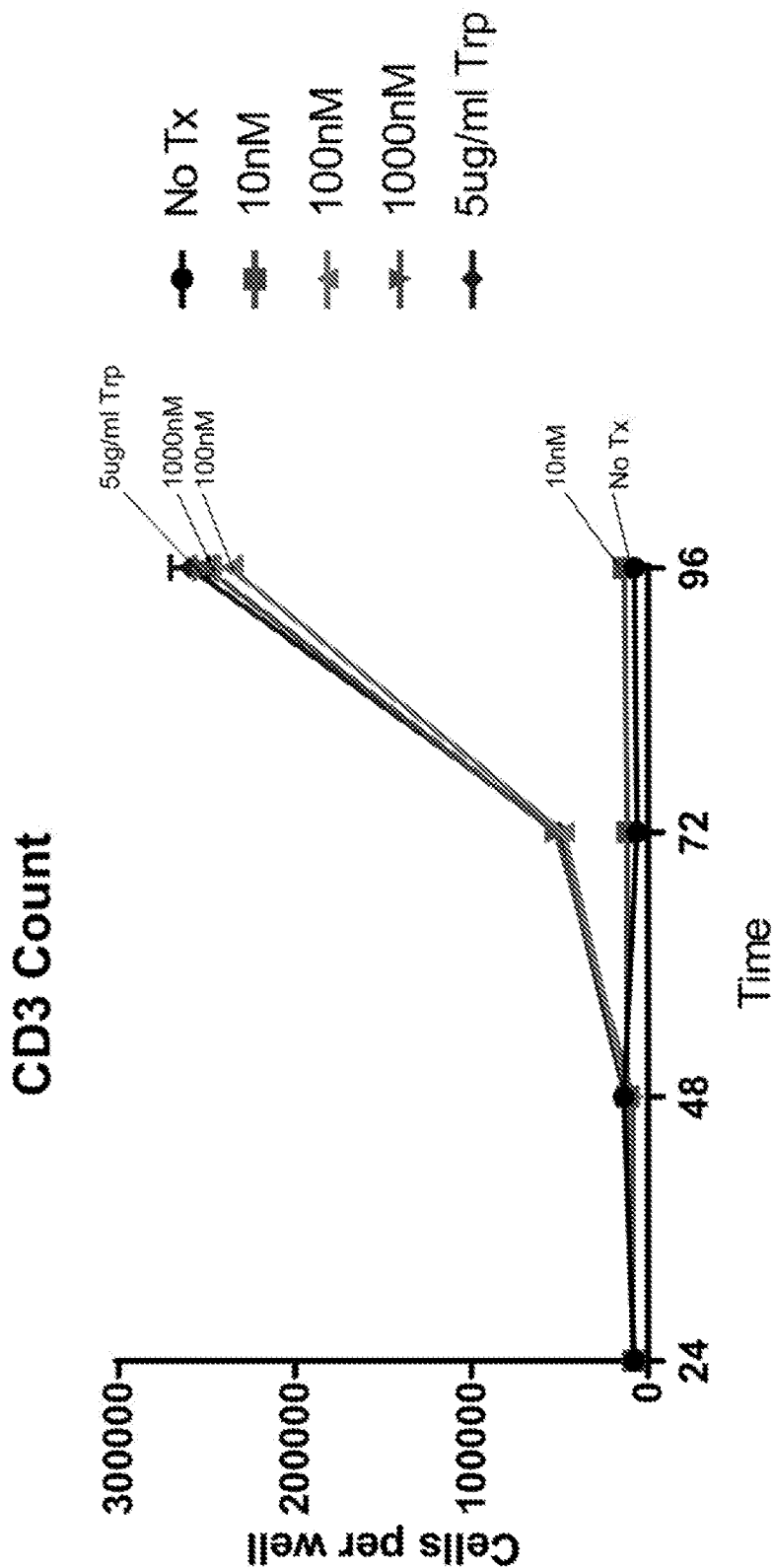
FIG. 10A depicts the total number of CD3+ cells per well, in a co-culture of anti-CD19 CAR-expressing T cells, incubated for 96 hours with CD19.A549 at a 1:1 E:T ratio in the presence of 0, 10, 100 and 1000 nM epacadostat added at the beginning of the co-culture, or 5 μg/mL supplemental tryptophan, added to the culture every 24 hours.

FIG. 10A depicts the total number of CD3$^+$ cell counts observed for individual wells. As shown in FIG. 10A, similar T cell counts, over time, were observed following culture of the cells with supplemented tryptophan or 100 nM or 1000 nM epacadostat. The results were consistent with a finding that supplemental tryptophan can restore CAR T cell proliferation and/or survival in a tryptophan-starved environment and/or environment in which IDO expression has been induced on cells in the environment, such as in response to CAR activity, and that tryptophan starvation may account for suppressive effects of induction of IDO in tumor or associated cells such as in the TME. In some aspects, restoration via tryptophan and/or IDO inhibitor or other tryptophan metabolism or pathway modulator may be used to counteract suppression of CAR T cell function(s) and/or activity, e.g., in an environment in which IDO is induced, such as in response to CAR-T cell induced activities.

B. Cytokine Release

Amounts of granulocyte-macrophage colony-stimulating factor (GM-CSF), interferon-gamma (IFNγ), interlekukin-2 (IL-2) and tumor necrosis factor-alpha (TNFα) were assessed in supernatants of the co-cultures described in Example 5.A above.

Figure 10B:
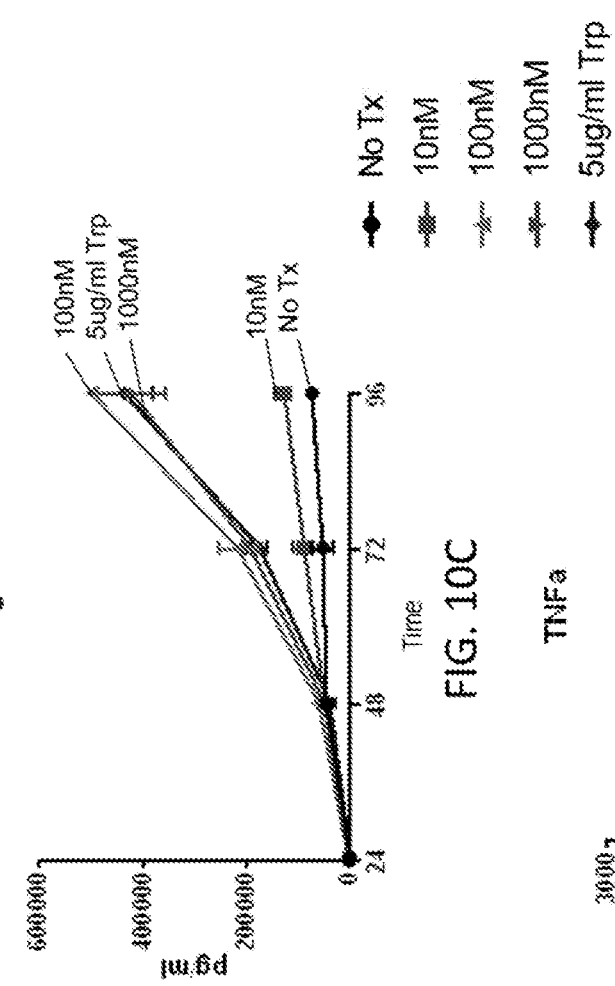
FIGS. 10B-10E depict the amount of cytokines GM-CSF (FIG. 10B), IFNγ (FIG. 10C), IL-2 (FIG. 10D), and TNFα (FIG. 10E), from the co-culture.
Figure 10C:
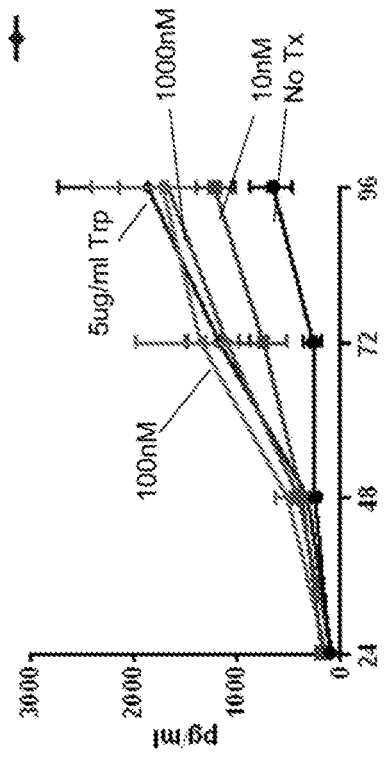
Figure 10D:
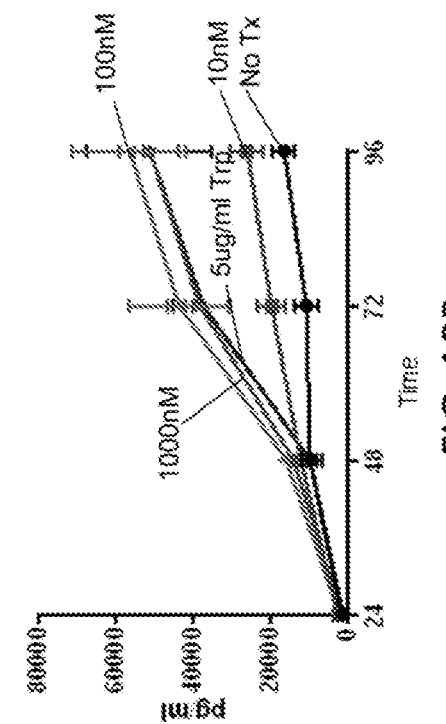
Figure 10E:
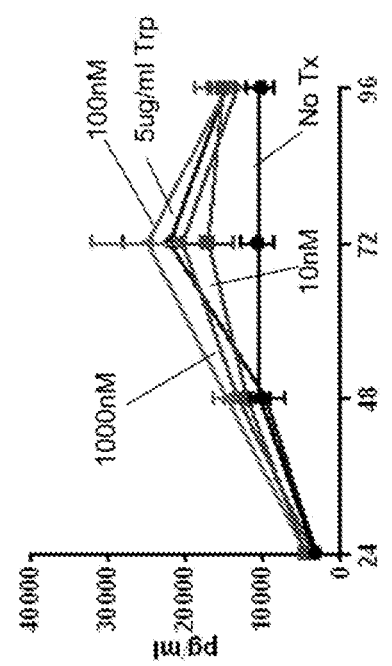

As shown in FIGS. 10B, 10C and 10E, the presence of epacadostat (10, 100 or 1000 nM) or supplemental tryptophan in the co-culture resulted in increased level of GM-CSF, IFNγ and TNFα, respectively, compared to the co-culture in the absence of added epacadostat or supplemental tryptophan. As shown in FIG. 10D, IL-2 levels were increased in the co-cultures containing epacadostat (10, 100 or 1000 nM) or supplemental tryptophan for up to 72 hours, and the levels decreased at 96 hours. The results were consistent with a finding that supplemental tryptophan can restore CAR T cell proliferation and/or survival in a tryptophan-starved environment and/or environment in which IDO expression has been induced on cells in the environment, such as in response to CAR activity, and that tryptophan starvation may account for suppressive effects of induction of IDO in tumor or associated cells such as in the TME.

C. Cell Phenotype Marker Expression

Cell surface expression of CD25 were assessed by flow cytometry on CD4$^+$ and CD8$^+$ CAR-expressing T cells from the co-cultures described in Example 5.A above.

Figure 10G:
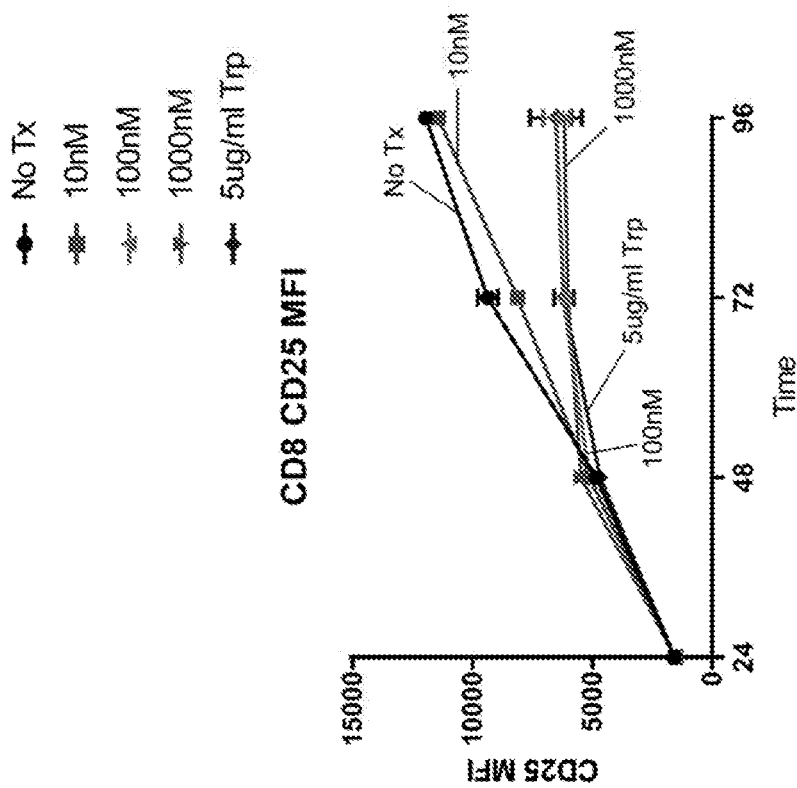
FIGS. 10F and 10G depict the mean fluorescence intensity (MFI) of CD25 expression in CD4+ (FIG. 10F) and CD8+ (FIG. 10G) T cells in the co-culture.
Figure 10F:
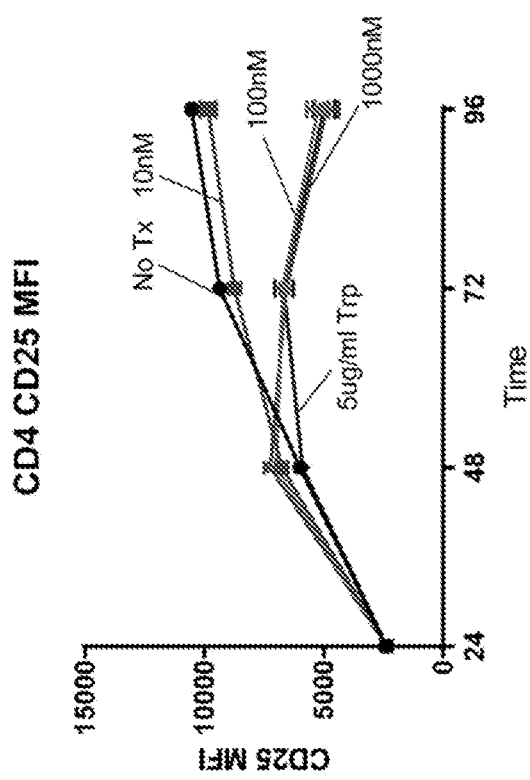

As shown in FIGS. 10F and 10G, following co-culture of CD4$^+$ or CD8$^+$ T cells with CD19.A549 cells (IDO1$^+$ target cells that are capable of induced IDO1 expression), the observed surface expression levels (mean fluorescence intensity (MFI)) of CD25 was reduced in the presence of supplemental tryptophan or 100 nM or 1000 nM epacadostat in the cultures. The results were consistent with a finding that supplemental tryptophan can restore CAR T cell proliferation and/or survival in a tryptophan-starved environment and/or environment in which IDO expression has been induced on cells in the environment, such as in response to CAR activity, and that tryptophan starvation may account for suppressive effects of induction of IDO in tumor or associated cells such as in the TME.

Example 6: Assessment of Indoleamine-Pyrrole 2,3-Dioxygenase (IDO1) Expression in Various Cells A. Expression of IDO1 in Bone Marrow Stromal Cells in the Presence of Interferon Gamma (IFNγ) or CAR T Cells Expression level of Indoleamine-Pyrrole 2,3-Dioxygenase 1 (IDO1) was determined in bone marrow stromal cells upon stimulation by interferon-gamma (IFNγ) or with co-incubation with CAR-expressing T cells. Bone marrow stromal cells are exemplary of bystander cells, e.g., non-tumor cells, present in the TME.

HS-5 human bone marrow stromal cells were stimulated with 20 ng/mL recombinant human IFNγ for 24 hours.

Figures 11A, 11B:
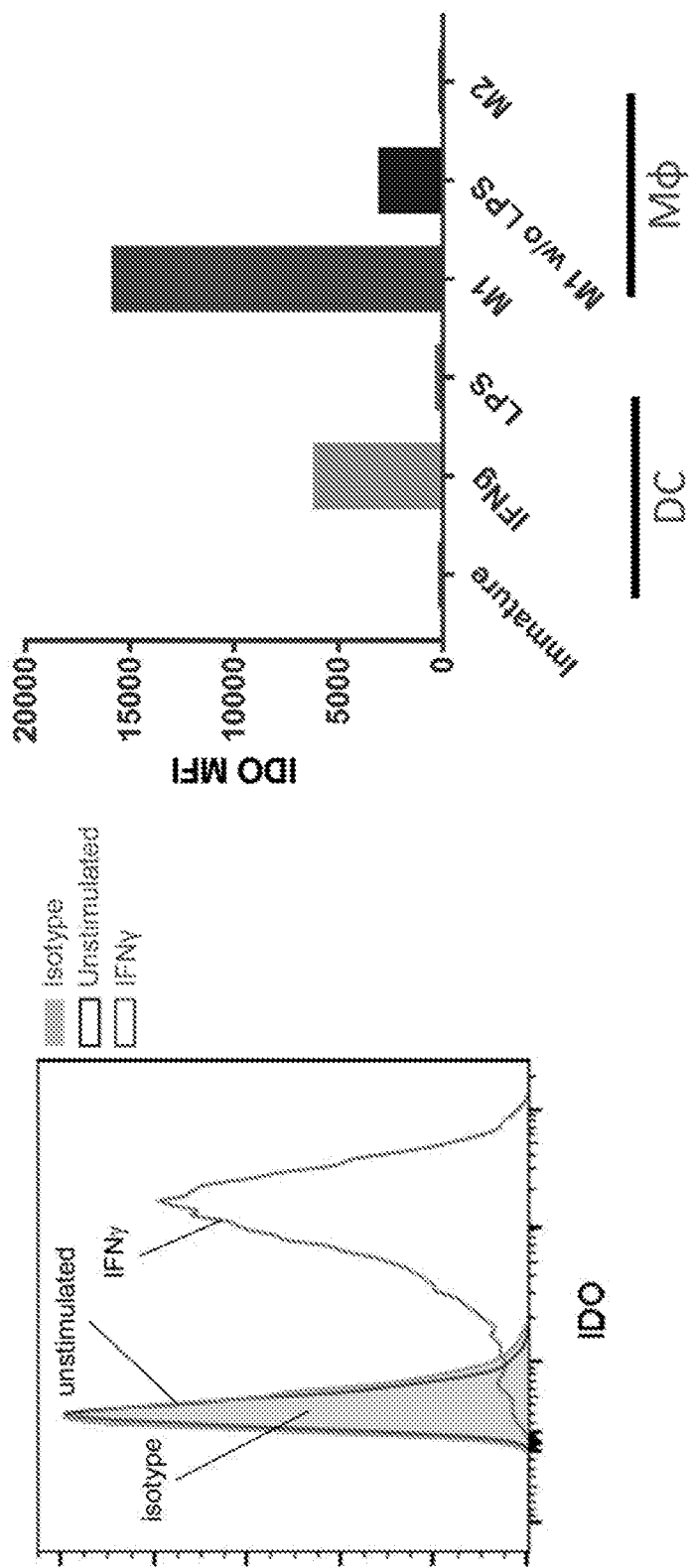
FIG. 11A depicts the expression level of indoleamine-pyrrole 2,3-dioxygenase (IDO1), as detected by flow cytometry, in HS-5 human bone marrow stromal cells, stimulated with 20 ng/mL recombinant human IFNγ for 24 hours.
FIG. 11B depicts the mean fluorescence intensity (MFI) of IDO1, in dendritic cells (DC) and macrophages (MΦ) upon stimulation by interferon-gamma (IFNγ) or lipopolysaccharide (LPS) was determined by flow cytometry.

As shown in FIG. 11A, incubation of HS-5 bone marrow stromal cells with IFNγ resulted in an increase of IDO1 expression in the cells. Co-culture of HS-5 cells with target cancer cells and CAR+ T cells also resulted in an increase of IDO1 expression in the HS-5 cells. The results were consistent with the finding that incubation of non-tumor bystander cells with IFNγ or target cells and CAR+ T cells can promote IDO1 expression by the bystander cells.

B. Expression of IDO1 in Dendritic Cells and Macrophages in the Presence of Interferon Gamma (IFNγ)

To assess whether myeloid cells present in the TME, including tumor-associated macrophages and dendritic cells, can be induced to express IDO1, the expression level of IDO1 in dendritic cells and macrophages upon stimulation by interferon-gamma (IFNγ) or lipopolysaccharide (LPS) was determined by flow cytometry. Dendritic cells were subject to monoculture with GM-CSF and interleukin-4 (IL-4), and macrophages were subject to monoculture with M-CSF, for 6 days. After monoculture, the cells were stimulated with IFNγ and/or LPS for 24 hours, and IDO1 expression was determined by flow cytometry. As shown in FIG. 11B, dendritic cells (DC) induced IDO1 expression upon stimulation by IFNγ, and M1 macrophages (MΦ) induced IDO1 expression in the absence of LPS stimulation.

C. Proliferation of CAR T Cells in the Presence of IDO$^+$ Bone Marrow Stromal Cells Proliferation of CAR T cells in the presence of IDO1-expressing bone marrow stromal cells or an IDO1 inhibitor was determined. CAR T cells and target cancer cells expressing an antigen recognized by the CAR were co-cultured, in the presence or absence of HS-5 cells (IDO1$^+$ bystander cells that are capable of induced IDO1 expression), for 96 hours, in the presence of various concentration of epacadostat. Proliferation of the CAR T cells was not substantially affected by the presence of IDO1$^+$ bone marrow stem cells, in the presence or absence of IDO1 inhibitor epacadostat.

Example 7: Assessment of L-Type Amino Acid Transporter (LAT) Expression on Target Cells, Primary Human T cells, Chimeric Antigen Receptor (CAR)-Expressing T Cells, Dendritic Cells and Macrophages A. Expression Levels of LAT1

Levels of expression of L-type Amino Acid Transporter 1 (LAT1, encoded by the SLC7A5 gene in humans) by various cells were assessed.

Figure 12A:
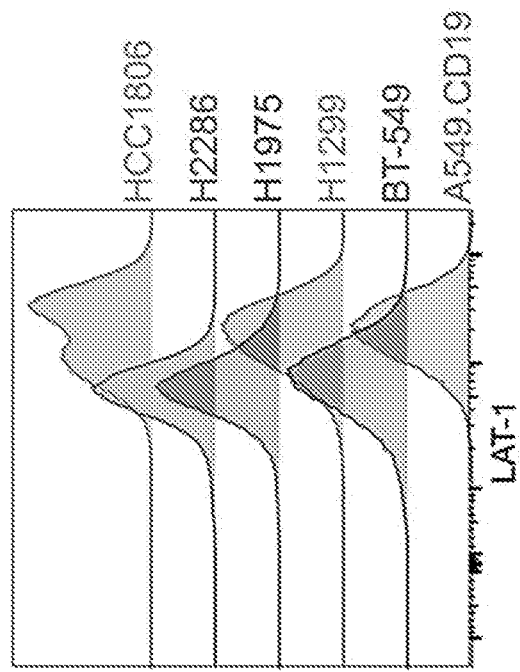
FIG. 12A depicts the mean fluorescence intensity (MFI) of L-type Amino Acid Transporter 1 (LAT1, encoded by the SLC7A5 gene in humans), as detected by flow cytometry, in Daudi, K562, HS-5 and A549 cells.

LAT1 expression on Daudi, K562, HS-5 (human bone marrow stromal cells) and A549 cells was measured by flow cytometry using an anti-LAT1 antibody. The results are shown in FIG. 12A. Exemplary mRNA expression levels are set forth in Table 1 below (see Cancer Cell Line Encyclopedia (CCLE) database).

TABLE 1

| SLC7A Expression Levels in Cancer Cell Lines (from Cancer Cell Line Encyclopedia (CCLE)) | |
|---|---|
| Cell_Line_ID | SLC7A5 (FPKM) |
| A549_LUNG | 602.5735 |
| DAUDI_HAEMATOPOIETIC_AND_LYMPHOID_TISSUE | 44.94462 |
| GRANTA519_HAEMATOPOIETIC_AND_LYMPHOID_TISSUE | 159.1588 |
| JURKAT_HAEMATOPOIETIC_AND_LYMPHOID_TISSUE | 180.9491 |
| K562_HAEMATOPOIETIC_AND_LYMPHOID_TISSUE | 122.664 |
| MM1S_HAEMATOPOIETIC_AND_LYMPHOID_TISSUE | 73.09056 |
| NALM6_HAEMATOPOIETIC_AND_LYMPHOID_TISSUE | 106.7949 |
| OPM2_HAEMATOPOIETIC_AND_LYMPHOID_TISSUE | 173.9881 |
| RAJI_HAEMATOPOIETIC_AND_LYMPHOID_TISSUE | 127.4476 |
| RPMI8226_HAEMATOPOIETIC_AND_LYMPHOID_TISSUE | 82.51015 |
| SKMEL28_SKIN | 137.2393 |

Figure 12B:
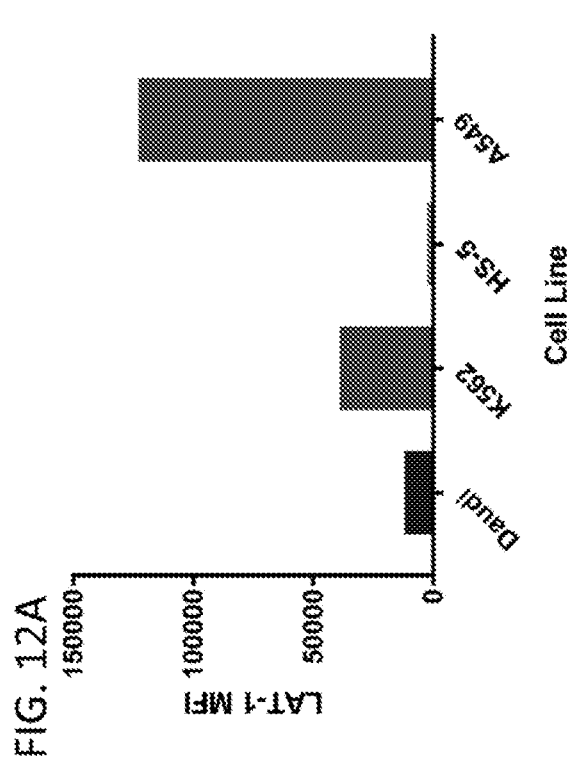
FIG. 12B depicts LAT1 expression levels, as detected by flow cytometry, in HCC1806 human breast cancer cell line; H2286 human small cell lung cancer cell line; H1975 human non-small cell lung cancer cell line; H1299 human non-small cell lung cancer lymph node metastasis cell line; BT-549 human breast cancer cell line; and A549 adenocarcinoma cells expressing CD19 (A549.CD19), following stimulation with interferon gamma (IFNγ).

LAT1 expression levels in cell lines expressing receptor tyrosine kinase-like orphan receptor 1 (ROR1) were measured by flow cytometry using an anti-LAT1 antibody, following stimulation with interferon-gamma (IFNγ). HCC1806, H2286, H1975, H1299, BT-549 and CD19.A549, described in Example 1C above, were stimulated with 20 ng/mL recombinant human IFNγ overnight and assessed for LAT1 expression. Results are shown in FIG. 12B.

B. Expression Level of LAT1 on Dendritic Cells and Macrophages

Figure 12C:
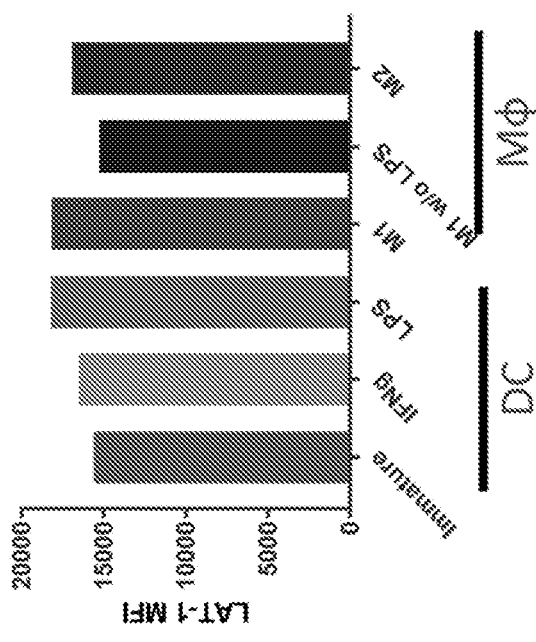
FIG. 12C depicts the MFI of LAT1 in dendritic cells (DC) and macrophages (MΦ) upon stimulation by interferon-gamma (IFNγ) or lipopolysaccharide (LPS) was determined by flow cytometry.

Levels of LAT1 expression in dendritic cells and macrophages, following cultures stimulated with interferon-gamma (IFNγ) or lipopolysaccharide (LPS) as described in Example 6B, were determined by flow cytometry. Results are shown in FIG. 12C. LAT1 expression also was observed to increase in T cells following activation, including in CAR-expressing T cells.

C. Expression Level of LAT1 and CD98hc on CAR T Cells

Expression of SLC7A5 (encoding for LAT1) mRNA levels were assessed using RNAseq in various primary human T cell populations, including various anti-CD19 CAR-expressing T cell populations. Specifically, CD4+ and CD8+ cell populations, separately, for each of three different anti-CD19 CAR+ T cell compositions were assessed. For each population, cells were assessed following engineering of primary human T cells to express the CAR (generally via selection, viral transduction, expansion and cryopreservation) and thaw, or following subsequent stimulation in the presence of target cells expressing the CD19 antigen. SLC7A5 mRNA levels also were assessed in CD4+ and CD8+ cells from starting primary human PBMC samples that had been engineered to generate one of the different CD19-targeted CAR+ cell compositions. The results showed expression of LAT1 mRNA in each sample with increased LAT1 mRNA in CAR-expressing cells, as compared to human PBMC sample cells, and increased levels following stimulation of CAR-T cells in the presence of cells expressing the CAR-targeted antigen. Similar results were observed for Additionally, SLC7A5 (encoding for LAT1, light chain) mRNA and SLC3A2 (encoding for CD98 heavy chain) mRNA were observed at similar levels in one of the exemplary anti-CD19 CAR+ T cell compositions.

LAT1 protein expression levels were compared in cells expressing two different CARs, CD4+ and CD8+ populations of human peripheral blood mononuclear cell (PBMC) samples, and A549 tumor cell line cells, by flow cytometry using an anti-LAT1 antibody. The results showed higher LAT1 expression in CAR T cells as compared to PBMC samples, and a substantial increase in LAT1 expression in tumor cells (A549 cells) as compared to both PBMC and CAR+ populations.

Example 8: Proliferation of Chimeric Antigen Receptor (CAR)-Expressing T Cells Co-Cultured with IDO1$^+$ LAT1$^-$ Bone Marrow Stromal Cells Proliferation of CAR-expressing T cells cultured with IDO1$^+$ cells that did not express high levels of LAT1 was assessed.

CAR-expressing CD4$^+$ and CD8$^+$ T cells were labeled with CellTrace™ violet (ThermoFisher) dye, and co-cultured for 96 hours with target cells that express the antigen recognized by the CAR (1:1 E:T ratio), HS-5 human bone marrow stromal cells (IDO1$^+$ bystander cells that are capable of induced IDO1 expression; at 1:1 CAR+:bystander cell ratio), or both the target cells and HS-5 cells (1:1:1 CAR+:target:bystander cell ratio). HS-5 bystander cells express high IDO1 and low LAT1. The proliferation of CD4$^+$ and CD8$^+$ CAR-expressing T cells were determined by dilution of the CellTrace™ violet dye.

Figure 13:
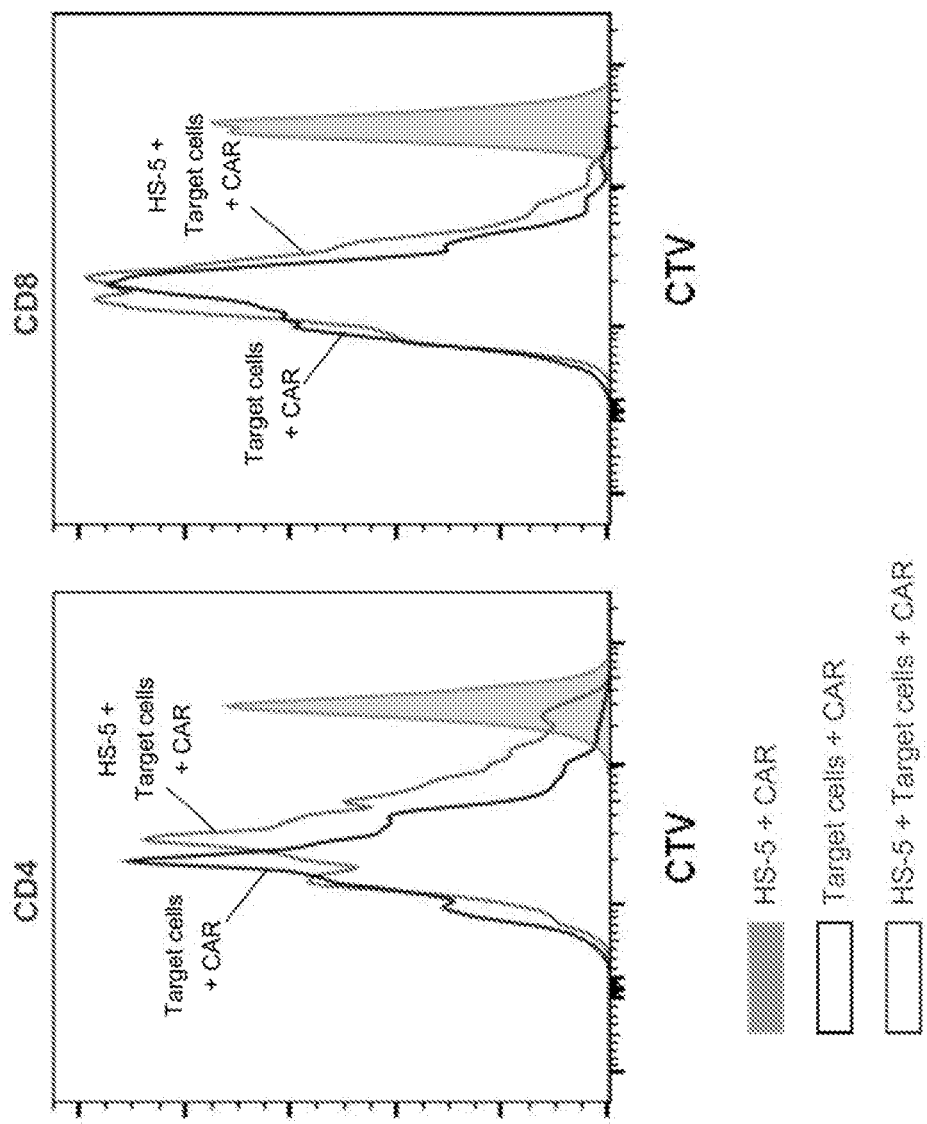
FIG. 13 depicts T cell proliferation, of CAR-expressing T cells after a co-culture with HS-5 human bone marrow stromal cells or target cells, at a 1:1 E:T ratio, or with HS-5 cells and target cells, at a 1:1:1 ratio. T cell proliferation was measured using dilution of CellTrace™ Violet by flow cytometry.

The results showed that co-culture of target cells and CAR T cells induced the proliferation of CAR T cells, whereas co-culture of HS-5 bystander cells alone and CAR T cells did not induce proliferation of the CAR T cells, as depicted in FIG. 13. The co-culture with both target cells and HS-5 cells showed similar proliferation as the co-culture with target cells. The results were consistent with the finding that the presence of HS-5 cells, which can be induced to express IDO1 upon stimulation with interferon-gamma (IFNγ) but do not express high LAT1, does not affect the proliferation of CAR T cells upon stimulation.

Example 9: Tryptophan Starvation and Supplementation

A. Addition of Supplemental Tryptophan to CAR T Cells Following Inhibition by IDO1-Expressing Target Cells Anti-CD19 CAR-expressing cells generated substantially as described in Example 1 were labeled with CellTrace™ Violet dye and cultured with IDO1$^+$ A549.CD19 cells for 96 hours, alone or in the presence of 5 μg/mL supplemental tryptophan (added every 24 hours) or 250 nM IDO inhibitor, epacadostat. Proliferation was assessed by flow cytometry, and CAR+ T cell count in each well was determined.

Results are shown in FIGS. 14A and 14B. It was observed that tryptophan supplementation of CAR-T cells co-cultured in the presence of target cells (observed to upregulate IDO1 and inhibit proliferation in this context) restored proliferation of the CAR-T cells, to a similar degree as that observed by addition of the IDO-inhibitor, as compared to no treatment (no Tx). The results are consistent with a conclusion that tryptophan starvation mediates inhibitory effects of IDO1-expressing target cells following CAR-T cell-induced upregulation of IDO.

B. Impact of Tryptophan Starvation on CAR-T Antigen-Specific Function

Effects of tryptophan starvation on antigen-induced function of CAR-T cells were assessed. CAR-expressing T cells labeled with CellTrace™ violet were co-cultured with target cells (K562 human myelogenous leukemia target cells transduced with CD19 (CD19.K562)) that had been observed not to induce IDO1-expression, in tryptophan-depleted media, with or without the addition of various concentrations of supplemental tryptophan. Tryptophan-containing media was used as a control (Trp Control). Target cell count and proliferation (assessed by flow cytometry via CTV dye dilution; MFI=mean fluorescence intensity).

Results are shown in FIGS. 15A, 15B and 15C, The results were consistent with an inhibitory effect of tryptophan starvation on antigen-specific function of CAR T cells, which was similar to that observed in the presence of upregulated IDO1, which could be reversed by the addition of supplemental tryptophan during culture.

Figure 15E:
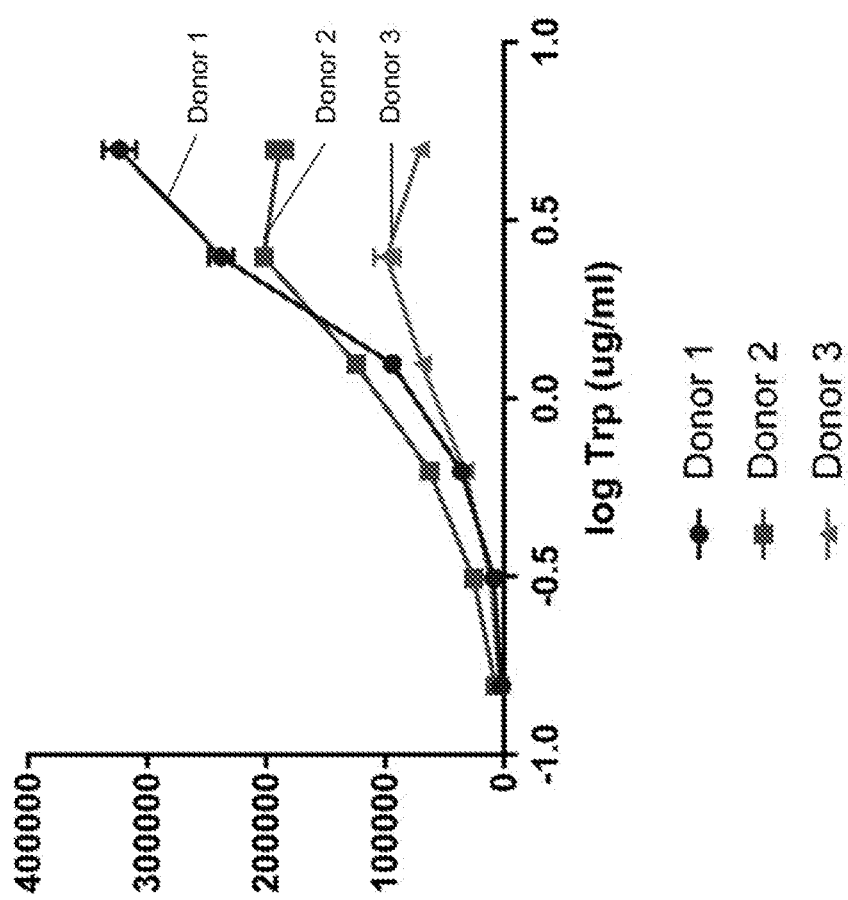
FIG. 15E depicts the CAR+ T cell counts (y-axis) from a similar study, with anti-CD19 CAR-expressing T cells generated from three different donors
Figure 15D:
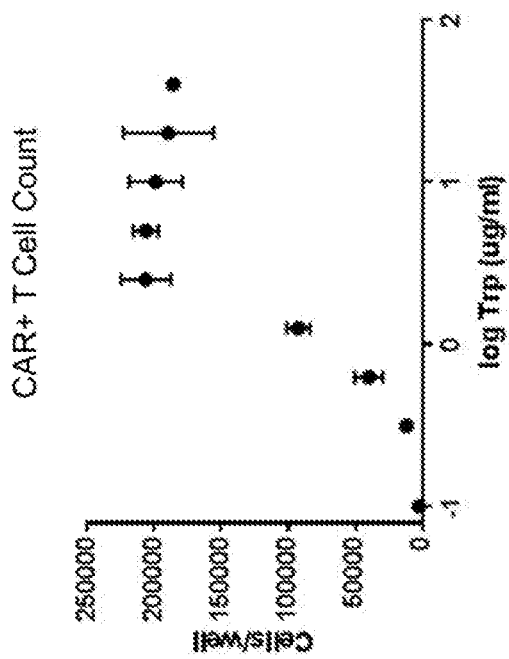
FIG. 15D depicts the CAR+ T cell count, from a culture of anti-CD19 CAR-expressing cells, incubated with plate-bound anti-idiotypic agonistic antibody, in tryptophan-depleted media, alone or supplemented with various concentrations of tryptophan.

A similar study was carried out to assess effects of tryptophan-starvation, but in which CAR-mediated function was induced using an agonistic anti-idiotype antibody specific for the CAR as opposed to antigen-expressing target cells. Anti-CD19 CAR-expressing cells, generated substantially as described in Example 1, were stimulated for 96 hours using plate-bound anti-idiotypic agonistic antibody, in tryptophan-depleted media, alone or supplemented with various concentrations of tryptophan. The number of CD3$^+$ cells per well was determined. Representative results from exemplary studies are shown in FIG. 15D and FIG. 15E (results from three different donors). A similar result was observed in similar experiments using T cells that express a CAR directed to a different antigen. The results were consistent with an inhibition of CAR-mediated function by tryptophan starvation, which could be restored by supplemental tryptophan.

C. Impact of Tryptophan-Starved Conditions on CAR-T Function Following Re-Exposure to Antigen under Tryptophan-Starved or Tryptophan-Sufficient Conditions Anti-CD19 CAR-expressing cells, generated substantially as described in Example 1, were incubated for 96 hours with CD19-expressing A549 target cells (CD19.A549) (which as described were observed to exhibit IDO1 expression following CAR-T co-culture). Co-culture was carried out for 96 hours in the presence of 0, 15.6, 62.5, 250 or 1000 nM of the IDO inhibitor, epacadostat. Results are shown in FIG. 16A.

Cells that had been incubated without epacadostat (0 nM) were subsequently cultured for an additional 96 hours, with or without supplemental tryptophan, added to the culture every 24 hours, without adding fresh target cells or other additional stimulatory agent. Results are shown in FIG. 16B.

Figures 16A, 16B:
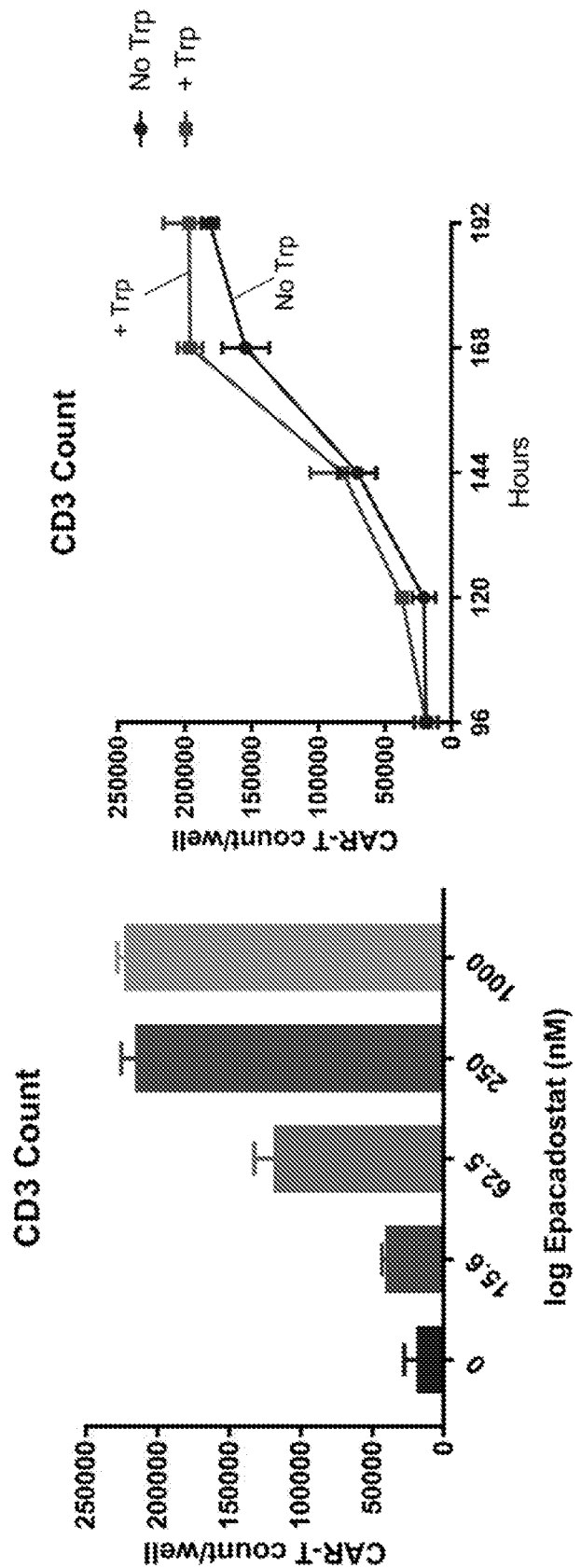
FIG. 16A depicts the CAR-T cell count in each well, in a co-culture of anti-CD19 CAR+ T cells and CD19-expressing A549 target cells (CD19.A549) incubated for 96 hours in the presence of 0, 15.6, 62.5, 250 and 1000 nM epacadostat.
FIG. 16B depicts the CAR-T cell count in each well from the co-culture without epacadostat, that was subsequently cultured for another 96 hours with or without supplemental tryptophan added every 24 hours.

As shown in FIG. 16B, following IDO-mediated inhibition, proliferation of tryptophan supplementation CAR$^+$ T cells incubated without epacadostat, a similar increase in the T cell count was observed over time following the subsequent 96 hour incubation, with or without supplemental tryptophan.

Effect of tryptophan starvation on CAR-T function (proliferation, cytokine production) following subsequent re-exposure to antigen was assessed. Anti-CD19 CAR-expressing cells, generated using T cells from two different donors substantially as described in Example 1, were co-cultured with CD19-expressing A549 target cells (CD19.A549) which were observed to be capable of IDO1 induction, for 96 hours in cell media in the absence of epacadostat (no treatment (no Tx)) or with 250 nM epacadostat (epacadostat). The cells were harvested, counted and re-cultured with fresh CD19-expressing A549 target cells (CD19.A549) in tryptophan-depleted media (media from the "no tx" cultures at 96 hours) with or without supplemented tryptophan. Intracellular levels of interferon-gamma (IFNγ) and interlekukin-2 (IL-2) were assessed by intracellular cytokine staining, and the percentage of CD4+ or CD8+ cells deemed positive for the given intracellular cytokine production was determined.

Figure 16C:
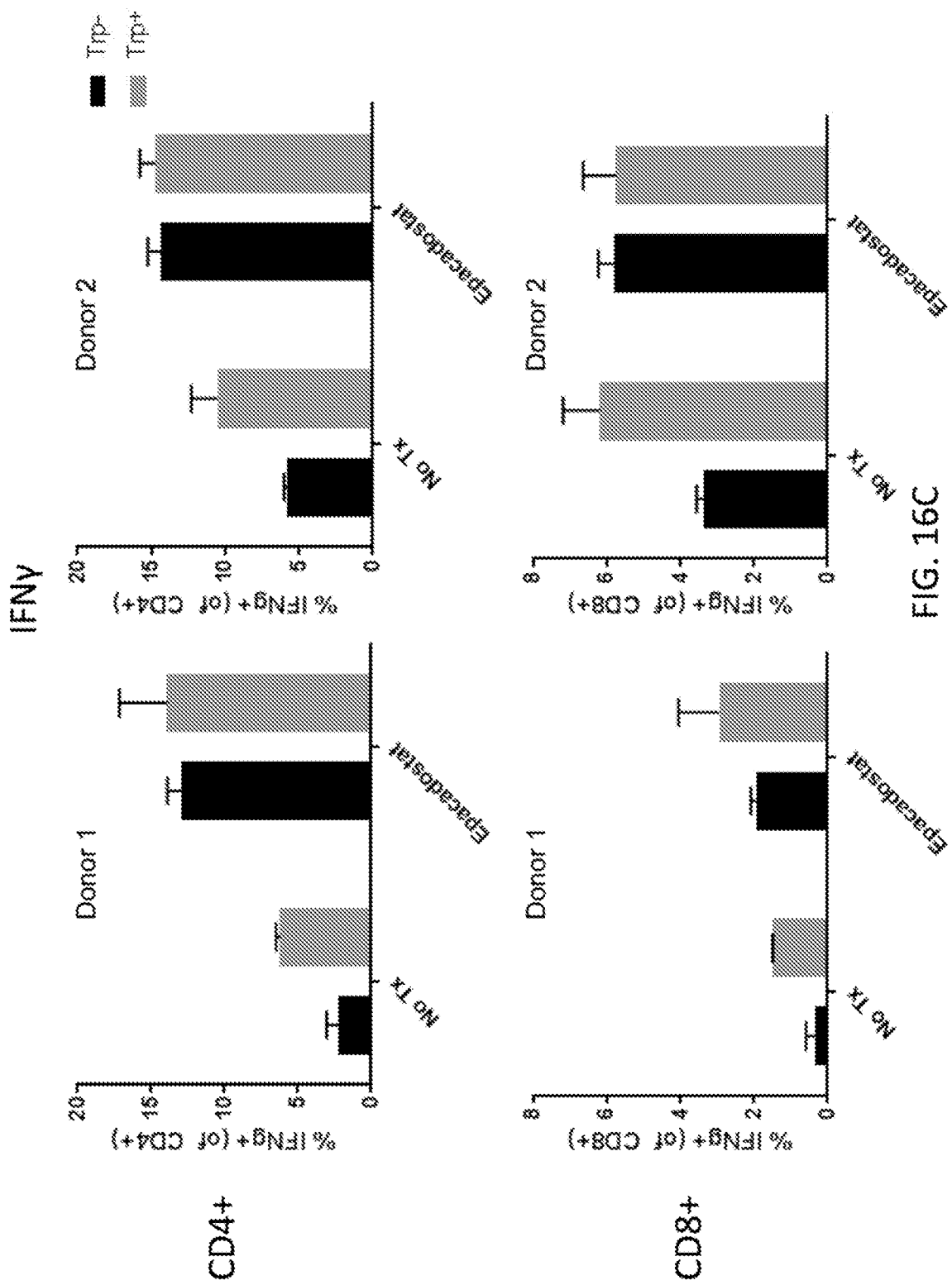
FIGS. 16C and 16D depict the percentage of IFNγ+ cells (FIG. 16C) and IL-2+ cells (FIG. 16D) among CD4+ or CD8+ anti-CD19 CAR-expressing cells, generated using T cells from two different donors, co-cultured with CD19-expressing A549 target cells (CD19.A549), for 96 hours in cell media in the absence of epacadostat (no treatment (no Tx)) or with 250 nM epacadostat (epacadostat); followed by re-culture with fresh CD19-expressing A549 target cells (CD19.A549) in tryptophan-depleted media (media from the "no tx" cultures at 96 hours) with or without supplemented tryptophan.
Figure 16D:
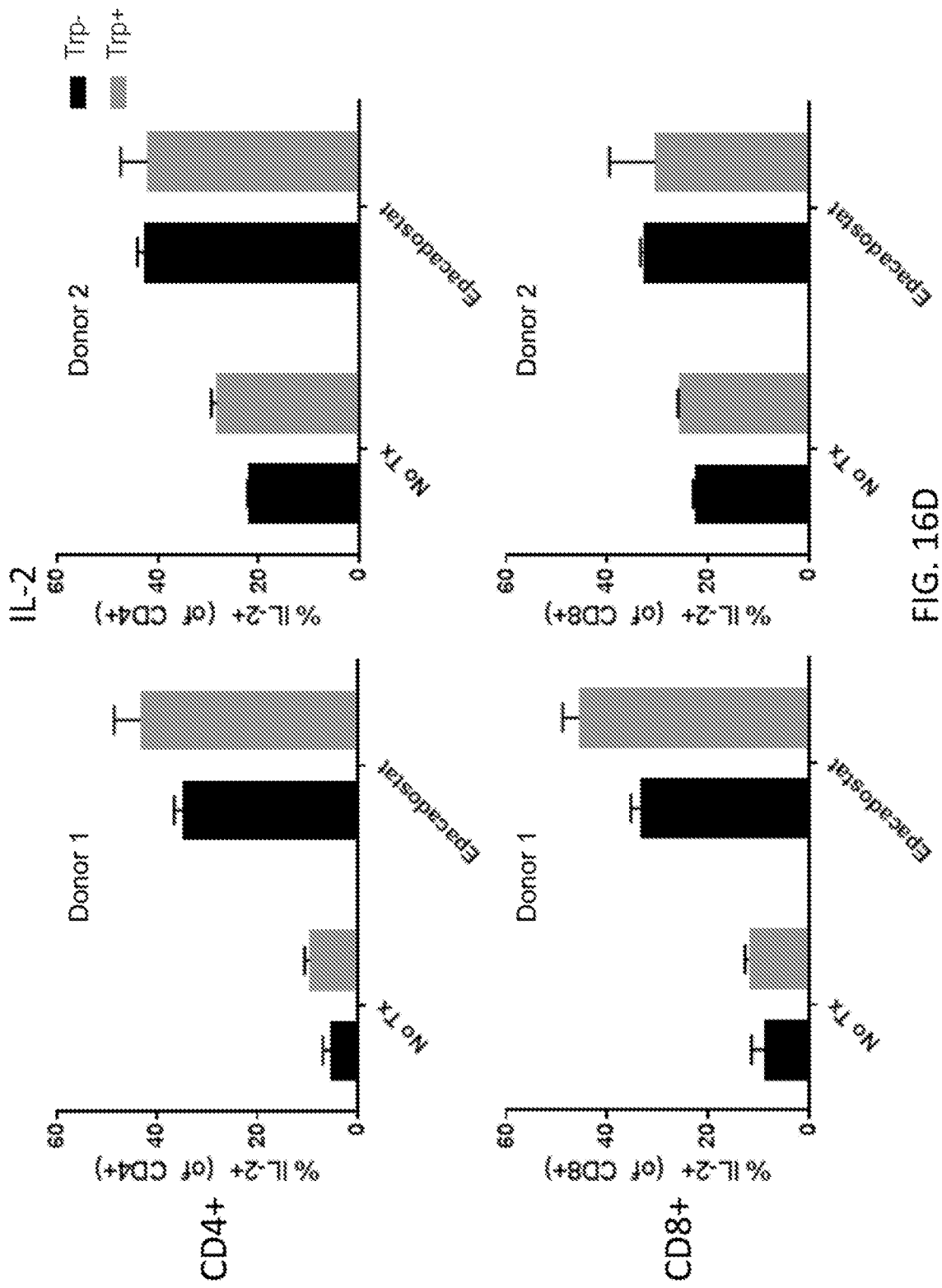

Results are shown in FIGS. 16C and 16D. As shown, CAR-T cells considered to be tryptophan-starved (those that had been incubated with target cells seen to induce IDO-1 expression under incubation conditions, without the IDO inhibitor (no Tx)), exhibited a reduction in cytokine production (as compared to those that had been incubated in the presence of the IDO1 inhibitor), following re-encounter of the cells with target cells. The observed reduction was partially restored with tryptophan supplementation in the subsequent culture, consistent with an observation that the addition of tryptophan following tryptophan starvation of CAR-T cells may be able to restore some but not necessarily all functionality.

Example 10: Effect of Increased Tryptophan Metabolite on Proliferation of CAR-Expressing T Cells Cultured with CD19-Expressing Tumor Cells Tryptophan metabolites were added to co-culture of CAR+ T cells and IDO-target cells to determine whether the presence of tryptophan metabolites affects proliferation of CAR T cells.

Anti-CD19 CAR-expressing T cells, generated substantially as described in Example 1, were labeled with Cell- Trace™ violet (ThermoFisher) dye, washed and co-cultured for 96 hours with CD19.Daudi target cells (IDO1⁻ target cells that were observed not to induce IDO1 expression) at a 1:1 effector:target (E:T) ratio in the presence of 0, 6.25, 12.5, 25, 50 and 100 μM L-Kynurenine, 3-hydroxyanthranilic acid (3-HAA) or 0, 6.25, 12.5, 25, 50 and 100 μM each of L-Kynurenine and 3-HAA. L-kynurenine and 3-HAA are metabolites produced as a result of IDO1-mediated oxidation of tryptophan. Cells were stained for surface expression of CD4 and CD8. Proliferation of T cell populations was determined by flow cytometry, based on the extent of dilution of the CellTrace™ violet dye.

As shown in FIG. 17A, the presence of tryptophan metabolites L-kynurenine and 3-HAA did not inhibit CAR T cell proliferation when co-cultured with CD19.Daudi target cells.

A similar study was performed by co-culturing anti-CD19 CAR-expressing cells with IDO1⁻ CD19.K562 cells for 96 hours in the presence of 6.25 to 100 μM L-Kynurenine, 3-hydroxyanthranilic acid (3-HAA) or 6.25 to 100 μM each of L-Kynurenine and 3-HAA. The number of CD3⁺ cells per well was determined using CountBright beads. As shown in FIG. 17B, the presence of tryptophan metabolites L-kynurenine and 3-HAA did not substantially affect CAR T cell numbers when co-cultured with CD19.K562 target cells.

Example 11: Assessment of Recovery from Tryptophan Starvation

CAR-expressing T cells were starved for tryptophan for varying periods of time, and recovery of cell proliferation and cytokine production after tryptophan starvation was assessed.

Anti-CD19 CAR-expressing T cells, generated as described in Example 1, were cultured in tryptophan starvation conditions (chemically defined tryptophan-free media) for 24, 48, 72 or 96 hours (24, 48, 72 or 96 hr Trp starv.). After tryptophan starvation for the indicated time, supplemental tryptophan was added to the cultures. The cells then were cultured in the presence of tryptophan until the cells were harvested at 24, 48, 72 or 96 hours. As a control, reflecting tryptophan sufficient conditions, cells were cultured in tryptophan-sufficient media for each respective time period (complete media). The number of CD3⁺ cells per well was assessed. Intracellular production of interferon-gamma (IFNγ) and tumor necrosis factor alpha (TNFα) was assessed by intracellular cytokine staining, and the percentage of CD4+ or CD8+ cells positive for cytokine accumulation was determined.

Results are shown in FIG. 18A. The results were consistent with an observation that tryptophan starvation, at least for 48 hours or greater reduced the ability of cells to proliferate. It was observed that addition of supplemental tryptophan did not completely restore proliferative capacity, out to 96 hours. Similar results were observed when assessing cytokine production of tryptophan starved CD4+ or CD8+ cells (IFNγ (FIG. 18B or 18C, respectively) or TNFα (FIG. 18D or 18E, respectively)). The results were consistent with the finding that tryptophan starvation of CAR-T cells for greater than 24 hours, e.g., 48 hours or greater, may result in impaired function that may not necessarily be restored by restoration of normal or sufficient tryptophan levels.

Example 12: Gene Expression Analysis for Chimeric Antigen Receptor (CAR)-Expressing T Cells in Tryptophan Starvation Conditions CAR-expressing T cells were analyzed by RNASeq to assess changes in gene expression and signaling pathway alterations in tryptophan starved conditions in the presence of CAR target antigen.

CAR-expressing T cells, generated using T cells from seven (7) different donors substantially as described in Example 1 above, were stimulated with plate bound anti-idiotypic antibody for 2 days in tryptophan-free media, supplemented with optimal (5 μg/mL; tryptophan sufficient) or suboptimal (0.625 μg/mL; tryptophan starvation) concentrations of tryptophan. RNA from harvested cells was isolated. Strand-specific, barcoded cDNA libraries were prepared. Samples were sequenced to yield 75-base, single end RNAseq reads.

RNASeq reads were mapped to the human genome and aligned. Gene level differential expression analysis were performed, taking donor and treatment into account. Prior to differential expression analysis, the gene set was filtered for protein-coding genes. Differentially expressed genes were identified by imposing a $\log_2$ fold change cutoff of ±1 and a Benjamini-Hochberg adjusted false discovery rate (FDR) cutoff of 0.01.

A volcano plot depicting statistical significance of expression ($\log_{10}$ of adjusted p-value) differences of the gene products between tryptophan sufficient (Ctrl) and tryptophan starvation (Tryp) conditions, with the $\log_e$ fold-change of expression of each gene product including genes that have been significantly upregulated (right side) or downregulated (left side), is shown in FIG. 19A. RNAseq results, represented as transcripts per kilobase million (TPM) values, for two exemplary genes encoding members of the eIF2α/ATF4 integrated stress response pathway, ATF4 and DDIT3 (also known as CCAAT/enhancer binding protein-homologous protein (CHOP)) are shown in FIG. 19B. As shown, these genes were significantly upregulated in low tryptophan conditions. Protein expression of DDIT3 (CHOP) was confirmed by Western blot.

FIG. 19C shows results based on a gene ontology analysis assessing cellular signaling pathways observed based on expression analyses to be affected in tryptophan starvation conditions, and an exemplary schematic showing genes involved in the ATF4 pathway whose expression was altered.

The results were consistent with a finding that tryptophan starvation leads to gene expression changes in various genes, including genes involved in stress response pathways and other pathways.

Example 13: Assessment of Indoleamine-Pyrrole 2,3-Dioxygenase (IDO1) Expression in a Tumor Xenograft Mouse Model Following Administration of Chimeric Antigen Receptor (CAR)-Expressing T Cells Expression of IDO1 in tumors following treatment with CAR-expressing T cells targeting an antigen expressed by the tumor (or no treatment (naïve)) was assessed in a mouse xenograft model.

The tumor xenograft mouse model was generated by subcutaneously implanting $5 \times 10^6$ A549.CD19 cells (IDO⁺). Nineteen (19) days after tumor implantation, to animals in the treatment group, anti-CD19 CAR-expressing T cells were administered. On day 9 after CAR+ T cell administration, tumors were harvested. Tumor samples were processed into single cell suspensions, which were assessed by flow cytometry. Gating on live, non-mouse cells, CD3, CD8 and IDO expression was assessed. Results are shown in FIG. 20. The results indicated the presence of both CD8+ and CD8-negative CAR+ T cells (non-mouse CD3+ cells) in animals that had been treated with CAR+ T cells, but not non-treated animals. Expression of IDO1 was observed in non-CD3+ non-mouse cell populations (presumed to contain A549.CD19+ tumor cells) in treated but not non-treated animals. The results are consistent with the upregulation of IDO in tumors with intratumoral tumor-specific CAR-T cells.

Formalin-fixed sections of tumor tissues were stained and assessed by immunofluorescence microscopy for CD3, CD19 and IDO1. Robust staining of CD19 was observed in the tumor, surrounded and infiltrated by human CD3-expressing cells (consistent with the presence of anti-CD19 CAR+ T cells surrounding and infiltrating the tumor). Additionally, IDO1 staining was observed at the interface of the CD19+ tumor and CD3+ population. The results were consistent with upregulation of IDO1-expression in a mouse xenograft tumor model following administration of tumor-targeting CAR+ T cells.

Example 14: Assessment of Indoleamine-Pyrrole 2,3-Dioxygenase (IDO1) Expression and Adaptive Immune Resistance in Human Subject Biopsies Following Administration of Chimeric Antigen Receptor (CAR)-Expressing T Cells Expression of IDO1 was assessed in tumor biopsy samples obtained from human subjects with Diffuse Large B-Cell Lymphoma (DLBCL) before and after a single infusion with autologous T cells expressing an anti-CD19 CAR containing 41BB and CD3zeta cytoplasmic signaling domains.

Tumor biopsies were assessed that had been obtained from subjects prior, and at 7 to 20 days post-CAR+ T cell administration. Tumor biopsy sections were stained with hematoxylin and eosin (H&E) and assessed for tissue quality and tumor identification. CAR+ cell infiltration in the biopsy was assessed using an in situ hybridization (ISH) probe specific to the mRNA encoding the anti-CD19 CAR. Immunofluorescence staining was used to assess IDO1 and programmed death-ligand 1 (PD-L1) protein expression.

As shown in FIG. 21, increased IDO1 and PD-L1 expression in tumors of some DLBCL subjects following CAR+ T cell administration and localization of CAR+ T cells to tumors.

Example 15: Engineering of CAR T cells to Overexpress Amino Acid Transporters

In an exemplary method, T cells isolated from a human subject, are engineered to express a chimeric antigen receptor (CAR), such as an anti-CD19 CAR, and to overexpress an amino acid transporter or one or more chains thereof, e.g., a transporter that includes L-type Amino Acid Transporter 1 (LAT1; SLC7A5) as the light chain and optionally CD98 heavy chain (CD98hc; 4F2hc; SLC3A2) as the heavy chain. $CD4^+$ and $CD8^+$ T cells are selected from an apheresis product sample from the subject. In some examples, one or more nucleic acid sequences encoding the CAR is also introduced into the cell. In some examples, the nucleic acid sequences encoding the CAR can be linked to a surface marker (e.g., EGFRt) to confirm transduction. In some cases, one or more nucleic acids, e.g., nucleic acids contained in one or more viral vectors encoding one or more chain of the amino acid transporter or one or more amino acid transporters, is introduced into the cell. In some cases the encoded amino acid transporter is a monomer. In some cases the encoded amino acid transporter is a dimer, such as a heterodimer. In some examples, a chain of the amino acid transporter can be LAT1 (SLC7A5), LAT2 (SLC7A8) or proton-assisted amino-acid transporter 4 (PAT4; SLC36A4). In some examples, the nucleic acid sequences encoding an amino acid transporter also includes nucleic acid sequences encoding the CD98 heavy chain (CD98hc; 4F2hc; SLC3A2). In some examples, the nucleic acid sequences encoding the amino acid transporter(s) or chain(s) is linked to a nucleic acid sequence encoding a different surface marker (e.g., Thy1.1) to confirm transduction with nucleic acid sequences encoding the amino acid transporter.

The one or more viral vectors containing nucleic acid sequences encoding a CAR and/or the amino acid transporter(s) or chain(s) are introduced into the $CD4^+$ and $CD8^+$ cells by viral transduction. In some examples, following the introduction, cells are further incubated, generally at 37° C., for example, to allow for cell expansion. The resulting T cells express a chimeric antigen receptor and overexpress an amino acid transporter.

In some examples, the function of the engineered cells, e.g., CAR LAT1/CD98hc+ cells, are assessed in tryptophan starvation conditions (e.g., Tryptophan-free media supplemented with limiting amounts of tryptophan and/or in the presence of $IDO1^+$ and/or $LAT1^+$ cells).

Example 16: Engineering of CAR+ T Cells to Reduce the Expression of Amino Acid Starvation Regulators In an exemplary method, T cells isolated from a human subject, are engineered to express a chimeric antigen receptor (CAR), such as an anti-CD19 CAR, and to reduce or abolish the expression of amino acid starvation regulators. In some examples, the T cells are engineered to abolish or reduce the expression of amino acid starvation regulators, such as general control nonderepressible 2 (GCN2), eukaryotic translation initiation factor 2 α (eIF2α), activating transcription factor 4 (ATF4), or CCAAT/enhancer binding protein-homologous protein (CHOP). In some examples, T cells are engineered to abolish or reduce the expression of components of pathway regulated by GCN2, for example, CHOP, Gadd45α, Herp 4E-BP1, eIF4G, JAK1, NFκB-2, FK506-BP8 or IFNγ-R2. In some examples, expression of GCN2, eIF2α, ATF4 or CHOP is abolished or reduced by inhibitory nucleic acids, such as an RNA interfering agent, e.g., short hairpin RNA (shRNA) or short interfering RNA (siRNA). In some examples, inhibitory nucleic acids or nucleic acid molecules encoding the inhibitory nucleic acids are introduced into the CAR-expressing cells. In some examples, GCN2, eIF2α, ATF4 or CHOP is abolished or reduced via a disruption of the gene encoding the proteins. In some examples, the disruption is achieved by gene editing. For example, the disruption of GCN2, eIF2α, ATF4 or CHOP is achieved by introduction of a gene editing nuclease, a zinc finger nuclease (ZFN), a clustered regularly interspaced short palindromic nucleic acid (CRISPR)/Cas9, and/or a TAL-effector nuclease (TALEN). In some examples, nucleic acids that target the genes, e.g., guide RNAs, are also introduced into the engineered T cell. In some cases, a ribonucleoprotein complex (RNP) comprising a gene editing nuclease and a targeting nucleic acid, e.g., guide RNAs, are introduced into the cell.

In some examples, the function of the engineered cells, e.g., CAR-expressing GCN2-cells, are assessed in tryptophan starvation conditions (e.g., Tryptophan-free media supplemented with limiting amounts of tryptophan and/or in the presence of IDO1+ and/or LAT1+ cells).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) Homo sapiens |
| 3 | ESKYGPPCPPCPGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPVL DSDGSFFLYSRLTVDKSRWQEGNVFSCSVMHEALHNHYTQKSLSLSLGK | Hinge-CH2-CH3 spacer Homo sapiens |
| 5 | RWPESPKAQASSVPTAQPQAEGSLAKATTAPATTRNTGRGGEEKKKEKEKEEQEERETKT PECPSHTQPLGVYLLTPAVQDLWLRDKATFTCFVVGSDLKDAHLTWEVAGKVPTGGVEEG LLERHSNGSQSQHSRLTLPRSLWNAGTSVTCTLNHPSLPPQRLMALREPAAQAPVKLSLN LLASSDPPEAASWLLCEVSGFSPPNILLMWLEDQREVNTSGFAPARPPPQPGSTTFWAWS VLRVPAPPSPQPATYTCVVSHEDSRTLLNASRSLEVSYVTDH | IgD-hinge-Fc Homo sapiens |
| 6 | LEGGGEGRGSLLTCGDVEENPGPR | T2A artificial |
| 7 | RKVCNGIGIGEFKDSLSINATNIKHFKNCTSISGDLHILPVAFRGDSFTHTPPLDPQELD ILKTVKEITGFLLIQAWPENRTDLHAFENLEIIRGRTKQHGQFSLAVVSLNITSLGLRSL KEISDGDVIISGNKNLCYANTINWKKLFGTSGQKTKIISNRGENSCKATGQVCHALCSPE GCWGPEPRDCVSCRNVSRGRECVDKCNLLEGEPREFVENSECIQCHPECLPQAMNITCTG RGPONCIQCARYIDGPHCVKTCPAGVMGENNTLVWKYADAGHVCHLCHPNCTYGCTGPGL EGCPTNGPKIPSIATGMVGALLLLLVVALGIGLFM | tEGFR artificial |
| 8 | FWVLVVVGGVLACYSLLVTVAFIIFWV | CD28 (amino acids 153-179 of Accession No. P10747) Homo sapiens |
| 9 | IEVMYPPPYLDNEKSNGTIIHVKGKHLCPSPLFPGPSKPFWVLVVVGGVLACYSLLVTVA FIIFWV | CD28 (amino acids 114-179 of Accession No. P10747) Homo sapiens |
| 10 | RSKRSRLLHSDYMNMTPRRPGPTRKHYQPYAPPRDFAAYRS | CD28 (amino acids 180-220 of P10747) Homo sapiens |
| 11 | RSKRSRGGHSDYMNMTPRRPGPTRKHYQPYAPPRDFAAYRS | CD28 (LL to GG) Homo sapiens |
| 12 | KRGRKKLLYIFKQPFMRPVQTTQEEDGCSCRFPEEEEGGCEL | 4-1BB (amino acids 214-255 of Q07011.1) Homo sapiens |
| 13 | RVKFSRSADAPAYQQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPPR | CD3 zeta Homo sapiens |
| 14 | RVKFSRSAEPPAYQQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPPR | CD3 zeta Homo sapiens |
| 15 | RVKFSRSADAPAYKQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPPR | CD3 zeta Homo sapiens |

| SEQ ID NO. | SEQUENCE | DESCRIPTION |
|---|---|---|
| 16 | PGGG-(SGGGG)5-P- wherein P is proline, G is glycine and S is serine | linker |
| 17 | GSADDAKKDAAKKDGKS | Linker |
| 18 | MDKKYSIGLDIGTNSVGWAVITDEYKVPSKKFKVLGNTDRHSIKKNLIGALLFDSGETAE<br>ATRLKRTARRRYTRRKNRICYLQEIFSNEMAKVDDSFFHRLEESFLVEEDKKHERHPIFG<br>NIVDEVAYHEKYPTIYHLRKKLVDSTDKADLRLIYLALAHMIKFRGHFLIEGDLNPDNSD<br>VDKLFIQLVQTYNQLFEENPINASGVDAKAILSARLSKSRRLENLIAQLPGEKKNGLFGN<br>LIALSLGLTPNFKSNFDLAEDAKLQLSKDTYDDDLDNLLAQIGDQYADLFLAAKNLSDAI<br>LLSDILRVNTEITKAPLSASMIKRYDEHHQDLTLLKALVRQQLPEKYKEIFFDQSKNGYA<br>GYIDGGASQEEFYKFIKPILEKMDGTEELLVKLNREDLLRKQRTFDNGSIPHQIHLGELH<br>AILRRQEDFYPFLKDNREKIEKILTFRIPYYVGPLARGNSRFAWMTRKSEETITPWNFEE<br>VVDKGASAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRFNASLGTYHDLLKI<br>IKDKDFLDNEENEDILEDIVLTLTLFEDREMIEERLKTYAHLFDDKVMKQLKRRRYTGWG<br>RLSRKLINGIRDKQSGKTILDFLKSDGFANRNFMQLIHDDSLTFKEDIQKAQVSGQGDSL<br>HEHIANLAGSPAIKKGILQTVKVVDELVKVMGRHKPENIVIEMARENQTTQKGQKNSRER<br>MKRIEEGIKELGSQILKEHPVENTQLQNEKLYLYYLQNGRDMYVDQELDINRLSDYDVDH<br>IVPQSFLKDDSIDNKVLTRSDKNRGKSDNVPSEEVVKKMKNYWRQLLNAKLITQRKFDNL<br>TKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKLPK<br>YSLFELENGRKRMLASAGELQKGNELALPSKYVNFLYLASHYEKLKGSPEDNEQKQLFVE<br>QHKHYLDEIIEQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD | S. Pyogenes Cas9 Q99ZW2 |
| 19 | MDKKYSIGLAIGTNSVGWAVITDEYKVPSKKFKVLGNTDRHSIKKNLIGALLFDSGETAE<br>ATRLKRTARRRYTRRKNRICYLQEIFSNEMAKVDDSFFHRLEESFLVEEDKKHERHPIFG<br>NIVDEVAYHEKYPTIYHLRKKLVDSTDKADLRLIYLALAHMIKFRGHFLIEGDLNPDNSD<br>VDKLFIQLVQTYNQLFEENPINASGVDAKAILSARLSKSRRLENLIAQLPGEKKNGLFGN<br>LIALSLGLTPNFKSNFDLAEDAKLQLSKDTYDDDLDNLLAQIGDQYADLFLAAKNLSDAI<br>LLSDILRVNTEITKAPLSASMIKRYDEHHQDLTLLKALVRQQLPEKYKEIFFDQSKNGYA<br>GYIDGGASQEEFYKFIKPILEKMDGTEELLVKLNREDLLRKQRTFDNGSIPHQIHLGELH<br>AILRRQEDFYPFLKDNREKIEKILTFRIPYYVGPLARGNSRFAWMTRKSEETITPWNFEE<br>VVDKGASAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRFNASLGTYHDLLKI<br>IKDKDFLDNEENEDILEDIVLTLTLFEDREMIEERLKTYAHLFDDKVMKQLKRRRYTGWG<br>RLSRKLINGIRDKQSGKTILDFLKSDGFANRNFMQLIHDDSLTFKEDIQKAQVSGQGDSL<br>HEHIANLAGSPAIKKGILQTVKVVDELVKVMGRHKPENIVIEMARENQTTQKGQKNSRER<br>MKRIEEGIKELGSQILKEHPVENTQLQNEKLYLYYLQNGRDMYVDQELDINRLSDYDVDH<br>IVPQSFLKDDSIDNKVLTRSDKNRGKSDNVPSEEVVKKMKNYWRQLLNAKLITQRKFDNL<br>TKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKLPK<br>YSLFELENGRKRMLASAGELQKGNELALPSKYVNFLYLASHYEKLKGSPEDNEQKQLFVE<br>QHKHYLDEIIEQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD | S. Pyogenes Cas9 D10A |
| 20 | MLGTGPAAATTAATTSSNVSVLQQFASGLKSRNEETRAKAAKELQHYVTMELREMSQEES<br>TRFYDQLNHHIFELVSSSDANERKGGILAIASLIGVEGGNATRIGRFANYLRNLLPSNDP<br>VVMEMASKAIGRLAMAGDTFTAEYVEFEVKRALEWLGADRNEGRRHAAVLVLRELAISVP<br>TFFFQQVQPFFDNIFVAVWDPKQAIREGAVAALRACLILTTQREPKEMQKPQWYRHTFEE<br>AEKGFDETLAKEKGMNRDDRIHGALLILNELVRISSMEGERLREEMEEITQQQLVHDKYC<br>KDLMGFGTKPRHITPFTSFQAVQPQQSNALVGLLGYSSHQGLMGFGTSPSPAKSTLVESR<br>CCRDLMEEKFDQVCQWVLKCRNSKNSLIQMTILNLLPRLAAFRPSAFTDTQYLQDTMNHV<br>LSCVKKEKERTAAFQALGLLSVAVRSEFKVYLPRVLDIIRAALPPKDFAHKRQKAMQVDA<br>TVFTCISMLARAMGPGIQQDIKELLEPMLAVGLSPALTAVLYDLSRQIPQLKKDIQDGLL<br>KMLSLVLMHKPLRHPGMPKGLAHQLASPGLTTLPEASDVGSITLALRTLGSFEFEGHSLT<br>QFVRHCADHFLNSEHKEIRMEAARTCSRLLTPSIHLISGHAHVVSQTAVQVVADVLSKLL<br>VVGITDPDPDIRYCVLASLDERFDAHLAQAENLQALFVALNDQVFEIRELAICTVGRLSS<br>MNPAFVMPFLRKMLIQILTELEHSGIGRIKEQSARMLGHLVSNAPRLIRPYMEPILKALI<br>LKLKDPDPDPNPGVINNVLATIGELAQVSGLEMRKWVDELFIIIMDMLQDSSLLAKRQVA<br>LWTLGQLVASTGYVVEPYRKYPTLLEVLLNFLKTEQNQGTRREAIRVLGLLGALDPYKHK<br>VNIGMIDQSRDASAVSLSESKSSQDSSDYSTSEMLVNMGNLPLDEFYPAVSMVALMRIFR<br>DQSLSHHHTMVVQAITFIFKSLGLKCVQFLPQVMPTFLNVIRVCDGAIREFLFQQLGMLV<br>SFVKSHIRPYMDEIVTLMREFWVMNTSIQSTIILLIEQIVVALGGEFKLYLPQLIPHMLR<br>VFMHDNSPGRIVSIKLLAAIQLFGANLDDYLHLLLPPIVKLFDAPEAPLPSRKAALETVD<br>RLTESLDFTDYASRIIHPIVRTLDQSPELRSTAMDTLSSLVFQLGKKYQIFIPMVNKVLV<br>RHRINHQRYDVLICRIVKGYTLADEEEDPLIYQHRMLRSGQGDALASGPVETGPMKKLHV<br>STINLQKAWGAARRVSKDDWLEWLRRLSELLLKDSSSPSLRSCWALAQAYNPMARDLFNA<br>AFVSCWSELNEDQQDELIRSIELALTSQDIAEVTQTLLNLAEFMEHSDKGPLPLRDDNGI | MTOR_HUMAN Serine/threonine-protein kinase mTOR; UniProt No. P42345 |

| SEQ ID NO. | SEQUENCE | DESCRIPTION |
|---|---|---|
| | VLLGERAAKCRAYAKALHYKELEFQKGPTPAILESLISINNKLQQPEAAAGVLEYAMKHF GELEIQATWYEKLHEWEDALVAYDKKMDTNKDDPELMLGRMRCLEALGEWGQLHQQCCEK WTLVNDETQAKMARMAAAAAWGLGQWDSMEEYTCMIPRDTHDGAFYRAVLALHQDLFSLA QQCIDKARDLLDAELTAMAGESYSRAYGAMVSCHMLSELEEVIQYKLVPERREIIRQIWW ERLQGCQRIVEDWQKILMVRSLVVSPHEDMRTWLKYASLCGKSGRLALAHKTLVLLLGVD PSRQLDHPLPTVHPQVTYAYMKNMWKSARKIDAFQHMQHFVQTMQQQAQHAIATEDQQHK QELHKLMARCFLKLGEWQLNLQGINESTIPKVLQYYSAATEHDRSWYKAWHAWAVMNFEA VLHYKHQNQARDEKKKLRHASGANITNATTAATTAATATTTASTEGSNSESEAESTENSP TPSPLQKKVTEDLSKTLLMYTVPAVQGFFRSISLSRGNNLQDTLRVLTLWFDYGHWPDVN EALVEGVKAIQIDTWLQVIPQLIARIDTPRPLVGRLIHQLLTDIGRYHPQALIYPLTVAS KSTTTARHNAANKILKNMCEHSNTLVQQAMMVSEELIRVAILWHEMWHEGLEEASRLYFG ERNVKGMFEVLEPLHAMMERGPQTLKETSFNQAYGRDLMEAQEWCRKYMKSGNVKDLTQA WDLYYHVFRRISKQLPQLTSLELQYVSPKLLMCRDLELAVPGTYDPNQPIIRIQSIAPSL QVITSKQRPRKLTLMGSNGHEFVFLLKGHEDLRQDERVMQLFGLVNTLLANDPTSLRKNL SIQRYAVIPLSTNSGLIGWVPHCDTLHALIRDYREKKKILLNIEHRIMLRMAPDYDHLTL MQKVEVFEHAVNNTAGDDLAKLLWLKSPSSEVWFDRRTNYTRSLAVMSMVGYILGLGDRH PSNLMLDRLSGKILHIDFGDCFEVAMTREKFPEKIPFRLTRMLTNAMEVTGLDGNYRITC HTVMEVLREHKDSVMAVLEAFVYDPLLNWRLMDTNTKGNKRSRTRTDSYSAGQSVEILOG VELGEPAHKKTGTTVPESIHSFIGDGLVKPEALNKKAIQIINRVRDKLTGRDFSHODTLD VPTQVELLIKQATSHENLCQCYIGWCPFW | |
| 21 | GCTCCCGGCTTAGAGGACAGCGGGGAAGGCGGGCGGTGGGGCAGGGGGCCTGAAGCGGCG GTACCGGTGCTGGCGGCGGCAGCTGAGGGCTTGGCCGAAGCCGCGCGAACCTCAGGGCAA GATGCTTGGAACCGGACCTGCCGCCGCCACCACCGCTGCCACCACATCTAGCAATGTGAG CGTCCTGCAGCAGTTTGCCAGTGGCCTAAAGAGCCGGAATGAGGAAACCAGGGCCAAAGC CGCCAAGGAGCTCCAGCACTATGTCACCATGGAACTCCGAGAGATGAGTCAAGAGGAGTC TACTCGGCTTCTATGACCAACTGAACCATCACATTTTTGAATTGGTTTCCAGCTCAGATGC CAATGAGAGGAAAGGTGGCATCTTGGCCATAGCTAGCCTCATAGGAGTGGAAGGTGGGAA TGCCACCCGAATTGGCAGATTTGCCAACTATCTTCGGAACCTCCTCCCCTCCAATGACCC AGTTGTCATGGAAATGGCATCCAAGGCCATTGGCCGTCTTGCCATGGCAGGGGACACTTT TACCGCTGAGTACGTGGAATTTGAGGTGAAGCGAGCCCTGGAATGGCTGGGTGCTGACCG CAATGAGGGCCGGAGACATGCAGCTGTCCTGGTTCTCCGTGAGCTGGCCATCAGCGTCCC TACCTTCTTCTTCCAGCAAGTGCAACCCTTCTTTGACAACATTTTTGTGGCCGTGTGGGA CCCCAAACAGGCCATCCGTGAGGGAGCTGTAGCCGCCCTTCGTGCCTGTCTGATTCTCAC AACCCAGCGTGAGCCGAAGGAGATGCAGAAGCCTCAGTGGTACAGGCACACATTTGAAGA AGCAGAGAAGGGATTTGATGAGACCTTGGCCAAAGAGAAGGGCATGAATCGGGATGATCG GATCCATGGAGCCTTGTTGATCCTTAACGAGCTGGTCCGAATCAGCAGCATGGAGGGAGA GCGTCTGAGAGAAGAAATGGAAGAAATCACACAGCAGCAGCTGGTACACGACAAGTACTG CAAAGATCTCATGGGCTTCGGAACAAAACCTCGTCACATTACCCCCTTCACCAGTTTCCA GGCTGTACAGCCCCAGCAGTCAAATGCCTTGGTGGGGCTGCTGGGGTACAGCTCTCACCA AGGCCTCATGGGATTTGGGACCTCCCCCAGTCCAGCTAAGTCCACCCTGGTGGAGAGCCG GTGTTGCAGAGACTTGATGGAGGAGAAATTTGATCAGGTGTGCCAGTGGGTGCTGAAATG CAGGAATAGCAAGAACTCGCTGATCCAAATGACAATCCTTAATTTGTTGCCCCGCTTGGC TGCATTCCGACCTTCTGCCTTCACAGATACCCAGTATCTCCAAGATACCATGAACCATGT CCTAAGCTGTGTCAAGAAGGAGAAGGAACGTACAGCGGCCTTCCAAGCCCTGGGGCTACT TTCTGTGGCTGTGAGGTCTGAGTTTAAGGTCTATTTGCCTCGCGTGCTGGACATCATCCG AGCGGCCCTGCCCCCAAAGGACTTCGCCCATAAGAGGCAGAAGGCAATGCAGGTGGATGC CACAGTCTTCACTTGCATCAGCATGCTGGCTCGAGCAATGGGGCCAGGCATCCAGCAGGA TATCAAGGAGCTGCTGGAGCCCATGCTGGCAGTGGGACTAAGCCCTGCCCTCACTGCAGT GCTCTACGACCTGAGCCGTCAGATTCCACAGCTAAAGAAGGACATTCAAGATGGGCTACT GAAAATGCTGTCCCTGGTCCTTATGCACAAACCCCTTCGCCACCCAGGCATGCCCAAGGG CCTGGCCCATCAGCTGGCCTCTCCTGGCCTCACGACCCCTCCCTGAGGCCAGCGATGTGGG CAGCATCACTCTTGCCCTCCGAACGCTTGGCAGCTTTGAATTTGAAGGCCACTCTCTGAC CCAATTTGTTCGCCACTGTGCGGATCATTTCCTGAACAGTGAGCACAAGGAGATCCGCAT GGAGGCTGCCCGCACCTGCTCCCGCCTGCTCACACCCTCCATCCACCTCATCAGTGGCCA TGCTCATGTGGTTAGCCAGACCGCAGTGCAAGTGGTGGCAGATGTGCTTAGCAAACTGCT CGTAGTTGGGATAACAGATCCTGACCCTGACATTCGCTACTGTGTCTTGGCGTCCCTGGA CGAGCGCTTTGATGCACACCTGGCCCAGGCGGAGAACTTGCAGGCCTTGTTTGTGGCTCT GAATGACCAGGTGTTTGAGATCCGGGAGCTGGCCATCTGCACTGTGGGCCGACTCAGTAG CATGAACCCTGCCTTTGTCATGCCTTTCCTGCGCAAGATGCTCATCCAGATTTTGACAGA GTTGGAGCACAGTGGGATTGGAAGAATCAAAGAGCAGAGTGCCCGCATGCTGGGGCACCT GGTCTCCAATGCCCCCGACTCATCCGCCCTACATGGAGCCTATTCTGAAGGCATTAAT TTTGAAACTGAAAGATCCAGACCCTGATCCAAACCCAGGTGTGATCAATAATGTCCTGGC AACAATAGGAGAATTGGCACAGGTTAGTGGCCTGGAAATGAGGAAATGGGTTGATGAACT TTTTATTATCATCATGGACATGCTCCAGGATTCCTCTTTGTTGGCCAAAAGGCAGGTGGC TCTGTGGACCCTGGGACAGTTGGTGGCCAGCACTGGCTATGTAGTAGAGCCCTACAGGAA GTACCCTACTTTGCTTGAGGTGCTACTGAATTTTCTGAAGACTGAGCAGAACCAGGGTAC ACGCAGAGAGGCCATCCGTGTGTTAGGGCTTTTAGGGGCTTTGGATCCTTACAAGCACAA AGTGAACATTGGCATGATAGACCAGTCCCGGGATGCCTCTGCTGTCAGCCTGTCAGAATC CAAGTCAAGTCAGGATTCCTCTGACTATAGCACTAGTGAAATGCTGGTCAACATGGGAAA CTTGCCTCTGGATGAGTTCTACCCAGCTGTGTCCATGGTGGCCCTGATGCGGATCTTCCG AGACCAGTCACTCTCTCATCATCACACCATGGTTGTCCAGGCCATCACCTTCATCTTCAA GTCCCTGGGACTCAAATGTGTGCAGTTCCTGCCCCAGGTCATGCCCACGTTCCTTAACGT CATTCGAGTCTGTGATGGGGCCATCCGGGAATTTTGTTCCAGCAGCTGGGAATGTTGGT GTCACCTTTGTGAAGAGCCACATCAGACCTTATATGGATGAAATAGTCACCCTCATGAGAGA ATTCTGGGTCATGAACACCTCAATTCAGAGCACGATCATTCTTCTCATTGAGCAAATTGT | Homo sapiens mechanistic target of rapamycin (MTOR), mRNA; Acc. No. NM_004958.3 |

-continued

| SEQ ID NO. | SEQUENCE | DESCRIPTION |
|---|---|---|
| | GGTAGCTCTTGGGGGTGAATTTAAGCTCTACCTGCCCCAGCTGATCCCACACATGCTGCG<br>TGTCTTCATGCATGACAACAGCCCAGGCCGCATTGTCTCTATCAAGTTACTGGCTGCAAT<br>CCAGCTGTTTGGCGCCAACCTGGATGACTACCTGCATTTACTGCTGCCTCCTATTGTTAA<br>GTTGTTTGATGCCCTGAAGCTCCACTGCCATCTCGAAAGGCAGCGCTAGAGACTGTGGA<br>CCGCCTGACGGAGTCCCTGGATTTCACTGACTATGCCTCCCGGATCATTCACCCTATTGT<br>TCGAACACTGGACCAGAGCCCAGAACTGCGCTCCACAGCCATGGACACGCTGTCTTCACT<br>TGTTTTTCAGCTGGGGAAGAAGTACCAAATTTTCATTCCAATGGTGAATAAAGTTCTGGT<br>GCGACACCGAATCAATCATCAGCGCTATGATGTGCTCATCTGCAGAATTGTCAAGGGATA<br>CACACTTGCTGATGAAGAGGAGGATCCTTTGATTTACCAGCATCGGATGCTTAGGAGTGG<br>CCAAGGGGATGCATTGGCTAGTGGACCAGTGGAAACAGGACCCATGAAGAAACTGCACGT<br>CAGCACCATCAACCTCCAAAAGGCCTGGGGCGCTGCCAGGAGGGTCTCCAAAGATGACTG<br>GCTGGAATGCTGAGACGGCTGAGCCTGGAGCTGCTGAAGGACTCATCATCGCCCTCCCT<br>GCGCTCCTGCTGGGCCCTGGCACAGGCCTACAACCCGATGGCCAGGGATCTCTTCAATGC<br>TGCATTTGTGTCCTGCTGGTCTGAACTGAATGAAGATCAACAGGATGAGCTCATCAGAAG<br>CATCGAGTTGGCCCTCACCTCACAAGACATCGCTGAAGTCACACAGACCCTCTTAAACTT<br>GGCTGAATTCATGGAACACAGTGACAAGGGCCCCCTGCCACTGAGAGATGACAATGGCAT<br>TGTTCTGCTGGGTGAGAGAGCTGCCAAGTGCCGAGCATATGCCAAAGCACTACACTACAA<br>AGAACTGGAGTTCCAGAAAGGCCCCACCCCTGCCATTCTAGAATCTCTCATCAGCATTAA<br>TAATAAGCTACAGCAGCCGGAGGCAGCGGCCGGAGTGTTAGAATATGCCATGAAACACTTT<br>TGGAGAGCTGGAGATCCAGGCTACCTGGTATGAGAAACTGCACGAGTGGGAGGATGCCCT<br>TGTGGCCTATGACAAGAAAATGGACACCAACAAGGACGACCCAGAGCTGATGCTGGGCCG<br>CATGCGCTGCCTCGAGGCCTTGGGGAATGGGGTCAACTCCACCAGCAGTGCTGTGAAAA<br>GTGGACCCTGGTTAATGATGAGACCCAAGCCAAGATGGCCCGGATGGCTGCTGCAGCTGC<br>ATGGGGTTTAGGTCAGTGGGACAGCATGGAAGAATACACCTGTATGATCCCTCGGGACAC<br>CCATGATGGGGCATTTTATAGAGCTGTGCTGGCACTGCATCAGGACCTCTTCTCCTTGGC<br>ACAACAGTGCATTGACAAGGCCAGGGACCTGCTGGATGCTGAATTAACTGCGATGGCAGG<br>AGAGAGTTACAGTCGGGCATATGGGGCCATGGTTTCTTGCCACATGCTGTCCGAGCTGGA<br>GGAGGTTATCCAGTACAAACTTGTCCCCGAGCGACGAGAGATCATCCGCCAGATCTGGTG<br>GGAGAGACTGCAGGGCTGCCAGCGTATCGTAGAGGACTGGCAGAAAATCCTTATGGTGCG<br>GTCCCTTGTGGTCAGCCCTCATGAAGACATGAGAACCTGGCTCAAGTATGCAAGCCTGTG<br>CGGCAAGAGTGGCAGGCTGGCTCTTGCTCATAAAACTTTAGTGTTGCTCCTGGGAGTTGA<br>TCCGTCTCGGCAACTTGACCATCCTCTGCCAACAGTTCACCCTCAGGTGACCTATGCCTA<br>CATGAAAAACATGTGGAAGAGTGCCCGCAAGATCGATGCCTTCCAGCACATGCAGCATTT<br>TGTCCAGACCATGCAGCAACAGGCCCAGCATGCCATCGCTACTGAGGACCAGCAGCATAA<br>GCAGGAACTGCACAAGCTCATGGCCCGATGCTTCCTGAAACTTGGAGAGTGGCAGCTGAA<br>TCTACAGGGCATCAATGAGAGCACAATCCCCAAAGTGCTGCAGTACTACAGCGCCGCCAC<br>AGAGCACGACCGCAGCTGGTACAAGGCCTGGCATGCGTGGGCAGTGATGAACTTCGAAGC<br>TGTGCTACACTACAAACATCAGAACCAAGCCCGCGATGAGAAGAAGAAACTGCGTCATGC<br>CAGCGGGGCCAACATCACCAACGCCACCACTGCCGCCACCACGGCCGCCACTGCCACCAC<br>CACTGCCAGCACCAGGGCAGCAACAGTGAGAGCGAGGCCGAGAGCACCGAGAACAGCCC<br>CACCCCATCGCCGCTGCAGAAGAAGGTCACTGAGGATCTGTCCAAAACCCTCCTGATGTA<br>CACGGTGCCTGCCGTCCAGGGCTTCTTCCGTTCCATCTCCTTGTCACGAGGCAACAACCT<br>CCAGGATACACTCAGAGTTCTCACCTTATGGTTTGATTATGGTCACTGGCCAGATGTCAA<br>TGAGGCCTTAGTGGAGGGGTGAAAGCCATCCAGATTGATACCTGGCTACAGGTTATACC<br>TCAGCTCATTGCAAGAATTGATACGCCCAGACCCTTGGTGGGACGTCTCATTCACCAGCT<br>TCTCACAGACATTGGTCGGTACCACCCCAGGCCCTCATCTACCCACTGACAGTGGCTTC<br>TAAGTCTACCACGACAGCCCGGCACAATGCAGCCAACAAGATTCTGAAGAACATGTGTGA<br>GCACAGCAACACCCTGGTCCAGCAGGCCATGATGGTGAGCGAGGAGCTGATCCGAGTGGC<br>CATCCTCTGGCATGAGATGTGGCATGAAGGCCTGGAAGAGGCATCTCGTTTGTACTTTGG<br>GGAAAGGAACGTGAAAGGCATGTTTGAGGTGCTGGAGCCCTTGCATGCTATGATGGAACG<br>GGGCCCCCAGACTCTGAAGGAAACATCCTTTAATCAGGCCTATGGTCGAGATTTAATGGA<br>GGCCCAAGAGTGGTGCAGGAAGTACATGAAATCAGGGAATGTCAAGGACCTCACCCAAGC<br>CTGGGACCTCTATTATCATGTGTTCCGACGAATCTCAAAGCAGCTGCCTCAGCTCACATC<br>CTTAGAGCTGCAATATGTTTCCCCAAAACTTCTGATGTGCCGGGACCTTGAATTGGCTGT<br>GCCAGGAACATATGACCCCAACCAGCCAATCATTCGCATTCAGTCCATAGCACCGTCTTT<br>GCAAGTCATCACATCCAAGCAGAGGCCCGGAAATTGACACTTATGGGCAGCAACGGACA<br>TGAGTTTGTTTTCCTTCTAAAAGGCCATGAAGATCTGCGCCAGGATGAGCGTGTGATGCA<br>GCTCTTCGGCCTGGTTAACACCCTTCTGGCCAATGACCCAACATCTCTTCGGAAAAACCT<br>CAGCATCCAGAGATACGCTGTCATCCCTTTATCGACCAACTCGGGCCTCATTGGCTGGGT<br>TCCCCACTGTGACACACTGCACGCCCTCATCCGGGACTACAGGGAGAAGAAGAAGATCCT<br>TCTCAACATCGAGCATCGCATCATGTTGCGGATGGCTCCGGACTATGACCACTTGACTCT<br>GATGCAGAAGGTGGAGGTGTTTGAGCATGCCGTCAATAATACAGCTGGGGACGACCTGGC<br>CAAGCTGCTGTGGCTGAAAAGCCCCAGCTCCGAGGTGTGGTTTGACCGAAGAACCAATTA<br>TACCCGTTCTTTAGCGGTCATGTCAATGGTTGGGTATATTTTAGGCCTGGGAGATAGACA<br>CCCATCCAACCTGATGCTGGACCGTCTGAGTGGGAAGATCTGCACATTGACTTTGGGGA<br>CTGCTTTGAGGTTGCTATGACCCGAGAGAAGTTTCCAGAGAAGATTCCATTTAGACTAAC<br>AAGAATGTTGACCAATGCTATGGAGGTTACAGGCCTGGATGGCAACTACAGAATCACATG<br>CCACACAGTGATGGAGGTGCTGCGAGAGCACAAGGACAGTGTCATGGCCGTGCTGGAAGC<br>CTTTGTCTATGACCCCTTGCTGAACTGGAGGCTGATGGACACAAATACCAAAGGCAACAA<br>GCGATCCCGAACGAGGACGGATTCCTACTCTGCTGGCCAGTCAGTCGAAATTTTGGACGG<br>TGTGGAACTTGGAGAGCCAGCCCATAAGAAAACGGGGACCACAGTGCCAGAATCTATTCA<br>TTCTTTTCATTGGAGACGGTTTGGTGAAACCAGAGGCCCTAAATAAGAAAGCTATCCAGAT<br>TATTAACAGGGTTCGAGATAAGCTCACTGGTCGGGACTTCTCTCATGATGACACTTTGGA<br>TGTTCCAACGCAAGTTGAGCTGCTCATCAAACAAGCGACATCCCATGAAAACCTCTGCCA<br>GTGCTATATTGGCTGGTGCCCTTTCTGGTAACTGGAGGCCCAGATGTGCCCATCACGTTT<br>TTTCTGAGGCTTTTGTACTTTAGTAAATGCTTCCACTAAACTGAAACCATGGTGAGAAAG | |

| SEQ ID NO. | SEQUENCE | DESCRIPTION |
|---|---|---|
| | TTTGACTTTGTTAAATATTTTGAAATGTAAATGAAAAGAACTACTGTATATTAAAAGTTG<br>GTTTGAACCAACTTTCTAGCTGCTGTTGAAGAATATATTGTCAGAAACACAAGGCTTGAT<br>TTGGTTCCCAGGACAGTGAAACATAGTAATACCACGTAAATCAAGCCATTCATTTTGGGG<br>AACAGAAGATCCATAACTTTAGAAATACGGGTTTTGACTTAACTCACAAGAGAACTCATC<br>ATAAGTACTTGCTGATGGAAGAATGACCTAGTTGCTCCTCTCAACATGGGTACAGCAAAC<br>TCAGCACAGCCAAGAAGCCTCAGGTCGTGGAGAACATGGATTAGGATCCTAGACTGTAAA<br>GACACAGAAGATGCTGACCTCACCCCTGCCACCTATCCCAAGACCTCACTGGTCTGTGGA<br>CAGCAGCAGAAATGTTTGCAAGATAGGCCAAATGAGTACAAAAGGTCTGTCTTCCATCA<br>GACCCAGTGATGCTGCGACTCACACGCTTCAATTCAAGACCTGACCGCTAGTAGGGAGGT<br>TTATTCAGATCGCTGGCAGCCTCGGCTGAGCAGATGCACAGAGGGGATCACTGTGCAGTG<br>GGACCACCCTCACTGGCCTTCTGCAGCAGGGTTCTGGGATGTTTTCAGTGGTCAAAATAC<br>TCTGTTTAGAGCAAGGGCTCAGAAAACAGAAATACTGTCATGGAGGTGCTGAACACAGGG<br>AAGGTCTGGTACATATTGGAAATTATGAGCAGAACAAATACTCAACTAAATGCACAAAGT<br>ATAAAGTGTAGCCATGTCTAGACACCATGTTGTATCAGAATAATTTTTGTGCCAATAAAT<br>GACATCAGAATTTTAAACATATGTAAAAAAAA | |
| 22 | MSPFLRIGLSNFDCGSCQSCQGEAVNPYCAVLVKEYVESENGQMYIQKKPTMYPPWDSTF<br>DAHINKGRVMQIIVKGKNVDLISETTVELYSLAERCRKNNGKTEIWLELKPQGRMLMNAR<br>YFLEMSDTKDMNEFETEGFFALHQRRGAIKQAKVHHVKCHEFTATFFPQPTFCSVCHEFV<br>WGLNKQGYQCRQCNAAIHKKCIDKVIAKCTGSAINSRETMFHKERFKIDMPHRFKVYNYK<br>SPTFCEHCGTLLWGLARQGLKCDACGMNVHHRCQTKVANLCGINQKLMAEALAMIESTQQ<br>ARCLRDTEQIFREGPVEIGLPCSIKNEARPPCLPTPGKREPQGISWESPLDEVDKMCHLP<br>EPELNKERPSLQIKLKIEDPFILHKMLGKGSFGKVFLAEFKKTNQFFAIKALKKDVVLMDD<br>DVECTMVEKRVLSLAWEHPFLTHMFCTFQTKENLFFVMEYLNGGDLMYHIQSCHKFDLSR<br>ATFYAAEIILGLQPFLHSKGIVYRDLKLDNILLDKDGHIKIADFGMCKENMLGDAKTNTFC<br>GTPDYIAPEILLGQKYNHSVDWWSFGVLLYEMLIGQSPFHGQDEEELFHSIRMDNPFYPR<br>WLEKEAKDLLVKLFVREPEKRLGVRGDIRQHPLFREINWEELERKEIDPPFRPKVKSPFD<br>CSNFDKEFLNEKPRLSFADRALINSMDQNMFRNFSFMNPGMERLIS | HUMAN Protein kinase C theta UniProt No. Q04759 |
| 23 | CCGCCAGCCCCGCCAGTCCCCGCGCAGTCCCCGCGCAGTCCCCGCGCAGTCCCAGCGCCA<br>CCGGGCAGCAGCGGCGCCGTGCTCGCTCCAGGGCGCAACCATGTCGCCATTTCTTCGGAT<br>TGGCTTGTCCAACTTTGACTGCGGGTCCTGCCAGTCTTGTCAGGGCGAGGCTGTTAACCC<br>TTACTGTGCTGTGCTCGTCAAAGAGTATGTCGAATCAGAGAACGGGCAGATGTATATCCA<br>GAAAAAGCCTACCATGTACCCACCCTGGGACAGCACTTTTGATGCCCATATCAACAAGGG<br>AAGAGTCATGCAGATCATTGTGAAAGGCAAAAACGTGGACCTCATCTCTGAAACCACCGT<br>GGAGCTCTACTCGCTGGCTGAGAGGTGCAGGAAGAACAACGGGAAGACAGAAATATGGTT<br>AGAGCTGAAACCTCAAGGCCGAATGCTAATGAATGCAAGATACTTTCTGGAAATGAGTGA<br>CACAAAGGACATGAATGAATTTGAGACGGAAGGCTTCTTTGCTTTGCATCAGCGCCGGGG<br>TGCCATCAAGCAGGCAAAGGTCCACCACGTCAAGTGCCACGAGTTCACTGCCACCTTCTT<br>CCCACAGCCCACATTTTGCTCTGTCTGCCACGAGTTTGTCTGGGGCCTGAACAAACAGGG<br>CTACCAGTGCCGACAATGCAATGCAGCAATTCACAAGAAGTGTATTGATAAAGTTATAGC<br>AAAGTGCACAGGATCAGCTATCAATAGCCGAGAAACCATGTTCCACAAGGAGAGATTCAA<br>AATTGACATGCCACACAGATTTAAAGTCTACAATTACAAGAGCCCGACCTTCTGTGAACA<br>CTGTGGGACCCTGCTGTGGGGACTGGCACGGCAAGGACTCAAGTGTGATGCATGTGGCAT<br>GAATGTGCATCATAGATGCCAGACAAAGGTGGCCAACCTTTGTGGCATAAACCAGAAGCT<br>AATGGCTGAAGCGCTGGCCATGATTGAGAGCACTCAACAGGCTCGCTGCTTAAGAGATAC<br>TGAACAGATCTTCAGAGAAGGTCCGGTTGAAATTGGTCTCCCATGCTCCATCAAAAATGA<br>AGCAAGGCCGCCATGTTTACCGACACCGGGAAAAAGAGAGCCTCAGGGCATTTCCTGGGA<br>GTCTCCGTTGGATGAGGTGGATAAAATGTGCCATCTTCCAGAACCTGAACTGAACAAAGA<br>AAGACCATCTCTGCAGATTAAACTAAAAATTGAGGATTTTATCTTGCACAAAATGTTGGG<br>GAAAGGAAGTTTTGGCAAGGTCTTCCTGGCAGAATTCAAGAAAACCAATCAATTTTTCGC<br>AATAAAGGCTTAAAGAAAGATGTGGTCTTGATGGACGATGATGTTGAGTGCACGATGGT<br>AGAGAAGAGAGTTCTTTCCTTGGCCTGGGAGCATCCGTTTCTGACGCACATGTTTTGTAC<br>ATTCCAGACCAAGGAAAACCTCTTTTTTGTGATGGAGTACCTCAACGGAGGGGACTTAAT<br>GTACCACATCCAAAGCTGCCACAAGTTCGACCTTTCCAGAGCGACGTTTTATGCTGCTGA<br>AATCATTCTTGGTCTGCAGTTCCTTCATTCCAAAGGAATAGTCTACAGGGACCTGAAGCT<br>AGATAACATCCTGTTAGACAAAGATGGACATATCAAGATCGCGGATTTTGGAATGTGCAA<br>GGAGAACATGTTAGGAGATGCCAAGACGAATACCTTCTGTGGGACACCTGACTACATCGC<br>CCCAGAGATCTTGCTGGGTCAGAAATACAACCACTCTGTGGACTGGTGGTCCTTCGGGGT<br>TCTCCTTTATGAAATGCTGATTGGTCAGTCGCCTTTCCACGGGCAGGATGAGGAGGAGCT<br>CTTCCACTCCATCCGCATGGACAATCCCTTTTACCCACGGTGGCTGGAGAAGGAAGCAAA<br>GGACCTTCTGGTGAAGCTCTTCGTGCGAGAACCTGAGAAGAGGCTGGGCGTGAGGGGAGA<br>CATCCGCCAGCACCCTTTGTTTCGGGAGATCAACTGGGAGGAACTTGAACGGAAGGAGAT<br>TGACCCACCGTTCCGGCCGAAAGTGAAATCACCATTTGACTGCAGCAATTTCGACAAAGA<br>ATTCTTAAACGAGAAGCCCCGGCTGTCATTTGCCGACAGAGCACTGATCAACAGCATGGA<br>CCAGAATATGTTCAGGAACTTTTCCTTCATGAACCCCGGGATGGAGCGGCTGATATCCTG<br>AATCTTGCCCCTCAGAGACAGGAAAGAATTTGCCTTCTCCCTGGGAACTGGTTCAAGAG<br>ACACTGCTTGGGTTCCTTTTTCAACTTGGAAAAAGAAAGAAACACTCAACAATAAAGACT<br>GAGACCCGTTCGCCCCCATGTGACTTTTATCTGTAGCAGAAACCAAGTCTACTTCACTAA<br>TGACGATGCCGTGTGTCTCGTCTCCTGACATGTCTCACAGACGTCCTGAAGTTAGGTCA<br>TTACTAACCATAGTTATTTACTTGAAAGATGGGTCTCCGCACTTGGAAAGGTTTCAAGAC<br>TTGATACTGCAATAAATTATGGCTCTTCACCTGGGCGCCAACTGCTGATCAATGAAATGC<br>TTGTTGAATCAGGGGCAAACGGAGTACAGACGTCTCAAGACTGAAACGGCCCCATTGCCT<br>GGTCTAGTAGCGGATCTCACTCAGCCGCAGACAAGTAATCACTAACCCGTTTTATTCTAT<br>TCCTATCTGTGGATGTGTAAATGGCTGGGGGGCCAGCCCTGGATAGGTTTTTATGGGAAT<br>TCTTTACAATAAACATAGCTTGTAACTTGAGATCTACAAATCCATTCATCCTGATTGGGC | Homo sapiens protein kinase C theta (PRKCQ, mRNA; Acc. No. NM_006257.4 |

| SEQ ID NO. | SEQUENCE | DESCRIPTION |
|---|---|---|
| | ATGAAATCCATGGTCAAGAGGACAAGTGGAAAGTGAGAGGGAAGGTTTGCTAGACACCTT<br>CGCTTGTTATCTTGTCAAGATAGAAAAGATAGTATCATTTCACCCTTGCCAGTAAAAACC<br>TTTCCATCCACCCATTCTCAGCAGACTCCAGTATTGGCACAGTCACTCACTGCCATTCTC<br>ACACTATAACAAGAAAGAAATGAAGTGCATAAGTCTCCTGGGAAAAGAACCTTAACCCC<br>TTCTCGTGCCATGACTGGTGATTTCATGACTCATAAGCCCCTCCGTAGGCATCATTCAAG<br>ATCAATGGCCATGCATGCTGTTTGCAGCAGTCAATTGAGTTGAATTAGAATTCCAACCA<br>TACATTTTAAAGGTATTTGTGCTGTGTGTATATTTTGATAAAATGTTTGTGACTTCATGGC<br>AAACAGGTGGATGTGTAAAAATGGAATAAAAAAAAAAAAAGAGTCAAAAAAAAA | |
| 24 | AAGTCGGTCTCTATGCCGCT | AHR CRISPR gRNA target sequence |
| 25 | TTGCTGCTCTACAGTTATCC | AHR CRISPR gRNA target sequence |
| 26 | AATTTCAGCGTCAGCTACAC | AHR CRISPR gRNA target sequence |
| 27 | AGACCGACTTAATACAGAGT | AHR CRISPR gRNA target sequence |
| 28 | TCCGTTTCTTTCAGTAGGGG | AHR CRISPR gRNA target sequence |
| 29 | AGTTGTCACTACAGATGCTT | AHR CRISPR gRNA target sequence |
| 30 | GTCGCCGCTTAATAGCCCTC | ARNT CRISPR gRNA target sequence |
| 31 | TGATCAGATGTCTAACGATA | ARNT CRISPR gRNA target sequence |
| 32 | GACATCAGATGTACCATCAC | ARNT CRISPR gRNA target sequence |
| 33 | CTCAGCCTATTCACAGAAAC | ARNT CRISPR gRNA target sequence |
| 34 | TGAATAGGCTGAGCTTTGTG | ARNT CRISPR gRNA target sequence |
| 35 | GTGGAGGAGCCATTGTCCAG | ARNT CRISPR gRNA target sequence |
| 36 | MAEDKSKRDSIEMSMKGCQTNNGFVHNEDILEQTPDPGSSTDNLKHSTRGILGSQEPDFK<br>GVQPYAGMPKEVLFQFSGQARYRIPREILFWLTVASVLVLIAATIAIIALSPKCLDWWQE<br>GPMYQIYPRSFKDSNKDGNGDLKGIQDKLDYITALNIKTVWITSFYKSSLKDFRYGVEDF<br>REVDPIFGTMEDFENLVAAIHDKGLKLIIDFIPNHTSDKHIWFQLSRTRTGKYTDYYIWH<br>DCTHENGKTIPPNNWLSVYGNSSWHPDEVRNQCYFHQFMKEQPDLNFRNPDVQEEIKEIL<br>RFWLTKGVDGFSLDAVKFLLEAKHLRDEIQVNKTQIPDTVTQYSELYHDFTTTQVGMHDI<br>VRSFRQTMDQYSTEPGRYRFMGTEAYAESIDRTVMYYGLPFIQEADFPFNNYLSMLDTVS<br>GNSVYEVITSWMENMPEGKWPNWMIGGPDSSRLTSRLGNQYVNVMNMLLFTLPGTPITYY<br>GEEIGMGNIVAANLNESYDINTLRSKSPMQWDNSSNAGFSEASNTWLPTNSDYHTVNVDV<br>QKTQPRSALKLYQDLSLLHANELLLNRGWFCHLRNDSHYVVYTRELDGIDRIFIVVLNFG<br>ESTLLNLHNMISGLPAKMRIRLSTNSADKGSKVDTSGIFLDKGEGLIFEHNTKNLLHRQT<br>AFRDRCFVSNRACYSSVLNILYTSC | human Neutral and basic amino acid transport protein rBAT (SLC3A1) isoform 1 Uniprot Q07837 |
| 37 | MELQPPEASIAVVSIPRQLPGSHSEAGVQGLSAGDDSELGSHCVAQTGLELLASGDPLPS<br>ASQNAEMIETGSDCVTQAGLQLLASSDPPALASKNAEVTGTMSQDTEVDMKEVELNELEP<br>EKQPMNAASGAAMSLAGAEKNGLVKIKVAEDEAEAAAAAKFTGLSKEELLKVAGSPGWVR<br>TRWALLLLFWLGWLGMLAGAVVIIVRAPRCRELPAQKWWHTGALYRIGDLQAFQGHGAGN<br>LAGLKGRLDYLSSLKVKGLVLGPIHKNQKDDVAQTDLLQIDPNFGSKEDFDSLLQSAKKK<br>SIRVILDLTPNYRGENSWFSTQVDTVATKVKDALEFWLQAGVDGFQVRDIENLKDASSFL | human 4F2 cell-surface antigen heavy chain (CD98hc; SLC3A2) isoform 1 |

| SEQ ID NO. | SEQUENCE | DESCRIPTION |
|---|---|---|
| | AEWQNITKGFSEDRLLIAGTNSSDLQQILSLLESNKDLLLTSSYLSDSGSTGEHTKSLVT QYLNATGNRWCSWSLSQARLLTSFLPAQLLRLYQLMLFTLPGTPVFSYGDEIGLDAAALP GQPMEAPVMLWDESSFPDIPGAVSANMTVKGQSEDPGSLLSLFRRLSDQRSKERSLLHGD FHAFSAGPGLFSYIRHWDQNERFLVVLNFGDVGLSAGLQASDLPASASLPAKADLLLSTQ PGREEGSPLELERLKLEPHEGLLLRFPYAA | Uniprot P08195 |
| 38 | MAGAGPKRRALAAPAAEEKEEAREKMLAAKSADGSAPAGEGEGVTLQRNITLLNGVAIIV GTIIGSGIFVTPTGVLKEAGSPGLALVVWAACGVFSIVGALCYAELGTTISKSGGDYAYM LEVYGSLPAFLKLWIELLIIRPSSQYIVALVFATYLLKPLFPTCPVPEEAAKLVACLCVL LLTAVNCYSVKAATRVQDAFAAAKLLALALIILLGFVQIGKGDVSNLDPNFSFEGTKLDV GNIVLALYSGLFAYGGWNYLNFVTEEMINPYRNLPLAIIISLPIVTLVYVLTNLAYFTTL STEQMLSSEAVAVDFGNYHLGVMSWIIPVFVGLSCFGSVNGSLFTSSRLFFVGSREGHLP SILSMIHPQLLTPVPSLVFTCVMTLLYAFSKDIFSVINFFSFFNWLCVALAIIGMIWLRH RKPELERPIKVNLALPVFFILACLFLIAVSFWKTPVECGIGFTIILSGLPVYFFGVWWKN KPKWLLQGIFSTTVLCQKLMQVVPQET | human Large neutral amino acids transporter small subunit 1 (LAT1; SLC7A5) isoform 1 Uniprot Q01650 |
| 39 | MEEGARHRNNTEKKHPGGGESDASPEAGSGGGGVALKKEIGLVSACGIIVGNIIGSGIFV SPKGVLENAGSVGLALIVWIVTGFITVVGALCYAELGVTIPKSGGDYSYVKDIFGGLAGF LRLWIAVLVIYPTNQAVIALTFSNYVLQPLFPTCFPPESGLRLLAAICLLLLTWVNCSSV RWATRVQDIFTAGKLLALALIIIMGIVQICKGEYFWLEPKNAFENFQEPDIGLVALAFLQ GSFAYGGWNFLNYVTEELVDPYKNLPRAIFISIPLVTFVYVFANVAYVTAMSPQELLASN AVAVTFGEKLLGVMAWIMPISVALSTFGGVNGSLFTSSRLFFAGAREGHLPSVLAMIHVK RCTPIPALLFTCISTLLMLVTSDMYTLINYVGFINYLFYGVTVAGLPILVLRWKKPDIPRPI KINLLFPIIYLLFWAFLLVFSLWSEPVVCGIGLAIMLTGVPVYFLGVYWQHKPKCFSDFI ELLTLVSQKMCVVVYPEVERGSGTEEANEDMEEQQQPMYQPTPTKDKDVAGQPQP | human Large neutral amino acids transporter small subunit 2 (LAT2; SLC7A8) isoform 1 Uniprot Q9UHI5 |
| 40 | MAGHTQQPSGRGNPRPAPSPSPVPGTVPGASERVALKKEIGLLSACTIIIGNIIGSGIFI SPKGVLEHSGSVGLALFVWVLGGGVTALGSLCYAELGVAIPKSGGDYAYVTEIFGGLAGF LLLWSAVLIMYPTSLAVISMTFSNYVLQPVFPNCIPPTTASRVLSMACLMLLTWVNSSSV RWATRIQDMFTGGKLLALSLIIGVGLLQIFQGHFEELRPSNAFAFWMTPSVGHLALAFLQ GSFAFSGWNFLNYVTEEMVDARKNLPRAIFISIPLVTFVYTFTNIAYFTAMSPQELLSSN AVAVTFGEKLLGYFSWVMPVSVALSTFGGINGYLFTYSRLCFSGAREGHLPSLLAMIHVR HCTPIPALLVCCGATAVIMLVGDTYTLINYVSFINYLCYGVTILGLLLLRWRRPALHRPI KVNLLIPVAYLVFWAFLLVFSFISEPMVCGVGVIIILTGVPIFFLGVFWRSKPKCVHRLT ESMTHWGQELCFVVYPQDAPEEEENGPCPPSLLPATDKPSKPQ | human Asc-type amino acid transporter 1 (Asc-1; SLC7A10) isoform 1 Uniprot Q9NS82 |
| 41 | MDKLKCPSFFKCREKEKVSASSENFHVGENDENQDRGNWSKKSDYLLSMIGYAVGLGNVW RFPYLTYSNGGGAFLIPYAIMLALAGLPLFFLECSLGQFASLGPVSVWRILPLFQGVGIT MVLISIFVTIYYNVIIAYSLYYMFASFQSELPWKNCSSWSDKNCSRSPIVTHCNVSTVNK GIQEIIQMNKSWVDINNFTCINGSEIYQPGQLPSEQYWNKVALQRSSGMNETGVIVWYLA LCLLLAWLIVGAALFKGIKSSGKVVYFTALFPVVLLILLVRGATLEGASKGISYYIGAQ SNFTKLKEAEVWKDAATQIFYSLSVAWGGLVALSSYNKFKNNCFSDAIVVCLTNCLTSVF AGFAIFSILGHMAHISGKEVSQVVKSGFDLAFIAYPEALAQLPGGPFWSILFFFMLLTLG LDSQFASIETITTTIQDLFPKVMKKMRVPITLGCCLVLFLGLCVTQAGIYVVHLIDHF CAGWGILIAAILELVGIIWIYGGNRFIEDTEMMIGAKRWIFWLWWRACWFVITPLLIAI FIWSLVQFHRPNYGAIPYPDWGVALGWCMIVFCIIWIPIMAAIKIIQAKGNIFQRLISCC RPASNWGPYLEQHRGERYKDMVDPKKEADHEIPTVSGSRKPE | human Sodium- and chloride- dependent neutral and basic amino acid transporter B(0+)(ATB0, +; SLC6A14) isoform 1 Uniprot Q9UN76 |
| 42 | MVRLVLPNPGLDARIPSLAELETIEQEEASSRPKWDNKAQYMLTCLGFCVGLGNVWRFPY LCQSHGGGAFMIPFLILLVLEGIPLLYLEFAIGQRLRRGSLGVWSSIHPALKGLGLASML TSFMVGLYYNTIISWIMWYLFNSFQEPLPWSDCPLNENQTGYVDECARSSPVDYFWYRET LNISTSISDSGSIQWWMLLCLACAWSVLYMCTIRGIETTGKAVYITSLTPYVVLTIFLIR GLTLKGATNGIVFLFTPNVTELAQPDTWLDAGAQVFFSFSLAFGGLISFSSYNSVHNNCE KDSVIVSIINGFTSVYVAIVVYSVIGFRATQRYDDCFSTNILTLINGFDLPEGNVTQENF VDMQQRCNASDPAAYAQLVFQTCDINAFLSEAVEGTGLAFIVFTEAITKMPLSPLWSVLF FIMLFCLGLSSMFGNMEGVVVPLQDLRVIPPKWPKEVLTGLICLCGTFLIGFIFTLNSGQY WLSLLDSYAGSIPLLIIAFCEMFSVVYVYGVDRFNKDIEFMIGHKPNIFWQTWRVVSPL LMLIIFLFFFVVEVSQELTYSIWDPGYEEFPKSQKISYPNWVYVVVVIVAGVPSLTIPGY AIYKLIRNHCQKPGDHQGLVSTLSTASMNGDLKY | human Sodium- dependent neutral amino acid transporter B(0)AT1 (B(0)AT1; SLC6A19) isoform 1 Uniprot Q69517 |
| 43 | MVLSQEEPDSARGTSEAQPLGPAPTGAAPPPGPGPSDSPEAAVEKVEVELAGPATAEPHE PPEPPEGGWGWLVMLAAMWCNGSVFGIQNACGVLFVSMLETFGSKDDDKMVFKTAWVGSL SMGMIFFCCPIVSVFTDLFGCRKTAVVGAAVGFVGLMSSSFVSSIEPLYLTYGIIFACGC SFAYQPSLVILGHYFKKRLGLVNGIVTAGSSVFTILLPLLLRVLIDSVGLFYTLRVLCIF MFVLFLAGFTYRPLATSTKDKESGGSGSSLFSRKKFSPPKKIFKVTAYAVWAVGI PLALFGYFVPYVHLMKHVNERFQDEKNKEVVLMCIGVTSGVGRLLFGRIADYVPGVKKVY LQVLSFFFIGLMSSMMIPLCSIFGALIAVCLIMGLFDGCFISIMAPIAFELVGAQDVSQAI GFLLGFMSIPMTVGPPIAGLLRDKLGSYDVAFYLAGVPPLIGGAVLCFIPWIHSKKQREI SKTTGKEKMEKMLENQNSLLSSSSGMFKKESDSII | human Monocarboxylate transporter 10 (TAT1; SLC16A10) isoform 1 Uniprot Q8TF71 |
| 44 | MEAAATPAAAGAARREELDMDVMRPLINEQNFDGTSDEEHEQELLPVQKHYQLDDQEGIS FVQTLMHLLKGNIGTGLLGLPLAIKNAGIVLGPISLVFIGIISVHCMHILVRCSHFLCLR FKKSTLGYSDTVSFAMEVSPWSCLQKQAAWGRSVVDFFLVITQLGFCSVYIVFLAENVKQ VHEGFLESKVFISNSTNSSNPCERRSVDLRIYMLCFLPFIILLVFIRELKNLFVLSFLAN VSMAVSLVIIYQYVVRNMPDPHNLPIVAGWKKYPLFFGTAVFAFEGIGVVLPLENQMKES KRFPQALNIGMGIVTTLYVTLATLGYMCFHDEIKGSITLNLPQDVWLYQSVKILYSFGIF | human Proton- coupled amino acid transporter 4 (PAT4; SLC36A4) isoform 1 Uniprot Q6YBV0 |

-continued

| SEQ ID NO. | SEQUENCE | DESCRIPTION |
|---|---|---|
|  | VTYSIQFYVPAEIIIPGITSKFHTKWKQICEFGIRSFLVSITCAGAILIPRLDIVISFVG AVSSSTLALILPPLVEILTFSKEHYNIWMVLKNISIAFTGVVGFLLGTYITVEEIIYPTP KVVAGTPQSPFLNLNSTCLTSGLK |  |
| 45 | EGRGSLLTCGDVEENPGP | T2A |
| 46 | GSGATNFSLLKQAGDVEENPGP | P2A |
| 47 | ATNFSLLKQAGDVEENPGP | P2A |
| 48 | QCTNYALLKLAGDVESNPGP | E2A |
| 49 | VKQTLNFDLLKLAGDVESNPGP | F2A |
| 50 | CGCTGAGAAATGACTGCACG | GCN2 CRISPR gRNA target sequence |
| 51 | CATATACTTCTTCACCAGTT | GCN2 CRISPR gRNA target sequence |
| 52 | ATGTACTCACACATCTGGAT | GCN2 CRISPR gRNA target sequence |
| 53 | TTAGGTGATGATCTTTGAAC | GCN2 CRISPR gRNA target sequence |
| 54 | TACCTCCCCACAGTGTTTCT | GCN2 CRISPR gRNA target sequence |
| 55 | AAAATCTCGCCTAGAAGAAC | GCN2 CRISPR gRNA target sequence |
| 56 | CCGAGCTCTGATTGACCGAA | CHOP CRISPR gRNA target sequence |
| 57 | AGGAAATCGAGCGCCTGACC | CHOP CRISPR gRNA target sequence |
| 58 | CCAGCTGGACAGTGTCCCGA | CHOP CRISPR gRNA target sequence |
| 59 | CTCTTGCAGGTCCTCATACC | CHOP CRISPR gRNA target sequence |
| 60 | GCGAGTCGCCTCTACTTCCC | CHOP CRISPR gRNA target sequence |
| 61 | GGCTGGAAAGCAGCGCATGA | CHOP CRISPR gRNA target sequence |
| 62 | AGGATCGTAAGGTTTGGGAC | ATF4 CRISPR gRNA target sequence |
| 63 | TAATAAGCAGCCCCCCCAGA | ATF4 CRISPR gRNA target sequence |
| 64 | CCACTCACCCTTGCTGTTGT | ATF4 CRISPR gRNA target sequence |

| SEQ ID NO. | SEQUENCE | DESCRIPTION |
| --- | --- | --- |
| 65 | TCTCTTAGATGATTACCTGG | ATF4 CRISPR gRNA target sequence |
| 66 | GCAACGTAAGCAGTGTAGTC | ATF4 CRISPR gRNA target sequence |
| 67 | TTTGCAGAGGATGCCTTCTC | ATF4 CRISPR gRNA target sequence |
| 68 | CAGGCTGTCAAAATTCGAGC | eIF2alpha CRISPR gRNA target sequence |
| 69 | CATTCTTCGTCATGTTGCTG | eIF2alpha CRISPR gRNA target sequence |
| 70 | GTACTTGTCATCAAAGACCC | eIF2alpha CRISPR gRNA target sequence |
| 71 | GTAAAGAAGCCCTAAGAGC | eIF2alpha CRISPR gRNA target sequence |
| 72 | GACCAGAGACCCATCTATTT | eIF2alpha CRISPR gRNA target sequence |
| 73 | TACAGAAAACATGCCCATTA | eIF2alpha CRISPR gRNA target sequence |

What is claimed:

1. A method of treatment of cancer in a subject in need thereof, comprising:
   (a) administering a T cell therapy to the subject having cancer; and
   (b) administering to the subject a therapeutically effective amount of an inhibitor of indoleamine-pyrrole 2,3-dioxygenase 1 (IDO1) subsequent to the initiation of administration of the T cell therapy,
   wherein the T cell therapy comprises an engineered T cell comprising a recombinant receptor that specifically binds to an antigen, wherein the recombinant receptor is a chimeric antigen receptor (CAR) or a transgenic T cell receptor (TCR),
   wherein the inhibitor of IDO1 is administered within 14 days subsequent to the initiation of the T cell therapy,
   wherein, prior to the administration of the T cell therapy, the subject has not been administered an IDO inhibitor for treatment of cancer, and
   wherein the cancer comprises a tumor comprising cells negative for IDO1 prior to the initiation of administration of the T cell therapy.

2. The method of claim 1, wherein the inhibitor of IDO1 is administered within 7 days subsequent to the initiation of the T cell therapy.

3. The method of claim 1, wherein the inhibitor of IDO1 is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl amino)-N'-hydroxy-N-[3-(trifluoromethyl)phenyl]-1,2,5-oxadiazole-3-carboximidamide, 4412-[(aminosulfonyl)amino]ethyl}amino)-N-(3-cyano-4-fluorophenyl)-N'-hydroxy-1,2,5-oxadiazole-3-carboximidamide, 4-(12-[(aminosulfonyl)amino]ethyl amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), F001287, PF-06840003 or pharmaceutically acceptable salt or prodrug thereof or a combination thereof.

4. The method of claim 3, wherein the inhibitor of IDO1 is 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat).

5. The method of claim 1, wherein upon administration to the subject the T cell therapy causes an increase or elevation of the level of interferon-gamma (IFNγ) in the subject in the local environment of the tumor or in a serum or plasma sample of the subject compared to the level of IFN-gamma in the subject prior to the initiation of the T cell therapy, wherein the increase or elevation of the level of IFNγ in the subject results in an increase or elevation of expression of IDO1 in cells present in the local environment of the tumor.

6. The method of claim 1, wherein inhibitor of IDO1 is administered at a time in which:
   there is a decrease in tryptophan levels, an increase in kynurenine levels, or an increase in expression or activity of IDO1 in a biological sample from the subject compared to prior to the initiation of administration of the T cell therapy or compared to a preceding time point after the initiation of administration of the T cell therapy;
   at a time before the number of cells of the T cell therapy detectable in the blood from the subject is decreased compared to in the subject at a preceding time point after the initiation of administration of the T cell therapy;
   at a time before T cells exhibit manifestations of prolonged tryptophan starvation, exhaustion, reduction of effector function, expression of inhibitory receptors, or loss of proliferative capacity;
   at a time before a peak or maximum level of the cells of the T cell therapy are detectable in the blood of the subject; or
   the level of interferon-gamma (IFNγ) is increased in a biological sample from the subject compared to prior to the initiation of administration of the T cell therapy or compared to a preceding time point after the initiation of administration of the T cell therapy.

7. The method of claim 1, wherein the recombinant receptor is a CAR and the CAR comprises an extracellular antigen-binding domain that specifically binds to the antigen and an intracellular signaling region comprising an ITAM.

8. The method of claim 7, wherein the intracellular signaling region comprises an intracellular domain of a CD3-zeta (CD3ζ) chain.

9. The method of claim 7, wherein the CAR further comprises a costimulatory signaling region.

10. The method of claim 9, wherein the costimulatory signaling region comprises a signaling domain of a CD28, a 4-1BB or an ICOS or a signaling portion thereof.

11. The method of claim 1, wherein the antigen is selected from the group consisting of ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

12. The method of claim 1, wherein the cancer is a myeloma, a lymphoma, a leukemia, a non-hematological cancer or a solid tumor.

13. The method of claim 12, wherein the cancer is a non-Hodgkin lymphoma (NHL), an acute lymphoblastic leukemia (ALL), a chronic lymphocytic leukemia (CLL), a diffuse large B-Cell lymphoma (DLBCL), or a multiple myeloma.

14. The method of claim 1, wherein the method results in:
   an increase in tryptophan levels or a decrease in kynurenine levels in the tumor or in a biological sample from the subject, compared to a method involving administration of the T cell therapy but in the absence of the inhibitor of IDO1;
   increased or prolonged expansion or persistence of T cells of the T cell therapy in the subject as compared to a method in which the T cell therapy is administered to the subject in the absence of the inhibitor of IDOL or a method in which a similar T cell is administered but in which the T cells do not comprise modification of expression of a molecule associated with DO-mediated immunosuppressive signaling, associated with sensing or responding to tryptophan starvation or insufficiency or associated with sensing or responding to kynurenine-mediated immuno-suppression;
   reduced expression or level of CD25 on the surface of the cells of the T cell therapy following said administration to the subject as compared to the expression or level in a method in which the T cell therapy is administered to the subject in the absence of the inhibitor of IDOL or a method in which a similar T cell therapy is administered but in which the T cells do not comprise modification of expression of a molecule associated with IDO-mediated immunosuppressive signaling, associated with sensing or responding to tryptophan starvation or insufficiency or associated with sensing or responding to kynurenine-mediated immuno-suppression;
   an increase in tryptophan levels, a decrease in kynurenine levels or a decrease in expression or activity of IDO1 in a biological sample from the subject compared to compared to just prior to administration of the inhibitor of IDO1 or compared to just prior to the initiation of administration of the T cell therapy;

an increase in the number of cells of the T cell therapy detectable in the blood from the subject compared to in the subject at a preceding time point just prior to administration of the inhibitor of IDO1 or compared to a preceding time point after administration of the T cell therapy;

the number of cells of the T cell therapy detectable in the blood being within 2.0-fold (greater or less) of the peak or maximum number of the cells of the T cell therapy detectable in the blood of the subject after the initiation of administration of the T cell therapy;

the number of cells of the T cell therapy detectable in the blood from the subject being greater than or greater than about 10%, 15%, 20%, 30%, 40%, 50%, or 60% of total peripheral blood mononuclear cells (PBMCs) in the blood of the subject;

the concentration or number of engineered cells in the blood of the subject being (i) at least at or about 10 engineered cells per microliter, (ii) at least 20%, 30%, 40% or 50% of the total number of peripheral blood mononuclear cells (PBMCs), (iii) at least or at least about $1\times10^5$ engineered cells; or (iv) the blood of the subject contains at least 5,000 copies of recombinant receptor-encoding DNA per micrograms DNA;

at day 90 following the initiation of the T cells, CAR-expressing cells are detectable in the blood or serum of the subject; or at day 90 following the initiation of the T cells, the blood of the subject contains at least 20% CAR-expressing cells, at least 10 CAR-expressing cells per microliter or at least $1\times10^4$ CAR-expressing cells.

15. The method of claim 1, wherein the T cell therapy comprises CD4+ T cells or CD8+ T cells.

16. The method of claim 1, wherein the T cell therapy comprises CD4+ T cells or CD8+ T cells.

17. The method of claim 1, wherein the T cell therapy comprises administration of a dose of T cells comprising between at or about $1\times10^7$ and at or about $2\times10^8$ total T cells comprising the recombinant receptor.

18. The method of claim 1, wherein the engineered cell further comprises a modification of expression of a molecule associated with IDO-mediated immunosuppressive signaling, associated with sensing or responding to tryptophan starvation or insufficiency, or associated with sensing or responding to kynurenine-mediated immuno-suppression in the cell, wherein the molecule is selected from the group consisting of:

mTOR, protein kinase C theta (PKC-Θ);

rBAT (SLC3A1), CD98 heavy chain (4F2hc; SLC3A2), L-type Amino Acid Transporter 1 (LAT1; SLC7A5), LAT2 (SLC7A8), Asc-type amino acid transporter 1 (Asc-1; SLC7A10), Sodium- and chloride-dependent neutral and basic amino acid transporter B(0+) (ATB0,+; SLC6A14), Sodium-dependent neutral amino acid transporter B(0)AT1 (B(0)AT1; SLC6A19), Monocarboxylate transporter 10 (TAT1; SLC16A10), proton-assisted amino-acid transporter 4 (PAT4; SLC36A4) or a portion thereof;

GCN2 kinase, BLIMP-1, aryl hydrocarbon receptor (AHR), AHR nuclear transporter (ARNT), eukaryotic translation initiation factor 2 α (eIF2α), activating transcription factor 4 (ATF4), CCAAT/enhancer binding protein-homologous protein (CHOP), Gadd45α, Herp, 4E-BP1, eIF4G, JAK1, NFκB-2, FK506-BP8, and IFNγ-R2.

19. The method of claim 18, wherein:

the modification comprises recombinant, engineered, or ectopic expression of the molecule or a functional or catalytically active chain, portion, or variant thereof;

the modification comprises introducing an inhibitory nucleic acid; or the modification comprises introducing a genetic disruption in the gene encoding the molecule that reduces expression of the molecule.

20. The method of claim 1, wherein the recombinant receptor is a CAR.

21. The method of claim 1, wherein the inhibitor of IDO1 is administered within 5 days subsequent to the initiation of the T cell therapy.

22. The method of claim 1, wherein the inhibitor of IDO1 is administered at least 2 days subsequent to the initiation of the T cell therapy.

* * * * *

SEQUENCE LISTING

<160> NUMBER OF SEQ ID NOS: 73

<210> SEQ ID NO 1
<211> LENGTH: 12
<212> TYPE: PRT
<213> ORGANISM: Artificial Sequence
<220> FEATURE:
<223> OTHER INFORMATION: spacer derived from homo sapiens igG4 hinge

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Artificial Sequence
<220> FEATURE:
<223> OTHER INFORMATION: spacer derived from IgG4 hinge of Homo sapiens

<400> SEQUENCE: 2
gaatctaagt acggaccgcc ctgcccccct tgccct                                 36

<210> SEQ ID NO 3
<211> LENGTH: 119
<212> TYPE: PRT
<213> ORGANISM: Artificial Sequence
<220> FEATURE:
<223> OTHER INFORMATION: Hinge-CH3 spacer derived from Homo sapiens

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Artificial Sequence
<220> FEATURE:
<223> OTHER INFORMATION: spacer derived from Hinge-CH2-CH3 Homo sapiens

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Artificial Sequence
<220> FEATURE:
<223> OTHER INFORMATION: IgD-hinge-Fc Homo sapiens

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 6
<211> LENGTH: 24
<212> TYPE: PRT
<213> ORGANISM: Artificial Sequence
<220> FEATURE:
<223> OTHER INFORMATION: T2A sequence artificial

<400> SEQUENCE: 6

Leu Glu Gly Gly Gly Glu Gly Arg Gly Ser Leu Leu Thr Cys Gly Asp

```
1               5                   10                  15
Val Glu Glu Asn Pro Gly Pro Arg
                20
```

<210> SEQ ID NO 7
<211> LENGTH: 335
<212> TYPE: PRT
<213> ORGANISM: Artificial Sequence
<220> FEATURE:
<223> OTHER INFORMATION: tEGFR artificial

<400> SEQUENCE: 7

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
        130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
                260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
        290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

-continued

```
<210> SEQ ID NO 8
<211> LENGTH: 27
<212> TYPE: PRT
<213> ORGANISM: Homo sapiens
<220> FEATURE:
<221> NAME/KEY: MISC_FEATURE
<223> OTHER INFORMATION: CD28 (amino acids 153-179 of Accession No.
      P10747) Homo sapiens

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<221> NAME/KEY: MISC_FEATURE
<223> OTHER INFORMATION: CD28 (amino acids 114-179 of Accession No.
      P10747) Homo sapiens

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<221> NAME/KEY: MISC_FEATURE
<223> OTHER INFORMATION: CD28 (amino acids 180-220 of P10747)
      Homo sapiens

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Artificial Sequence
<220> FEATURE:
<223> OTHER INFORMATION: CD28 (LL to GG) Homo sapiens

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
```

```
                        20                  25                  30

Pro Arg Asp Phe Ala Ala Tyr Arg Ser
            35                  40

<210> SEQ ID NO 12
<211> LENGTH: 42
<212> TYPE: PRT
<213> ORGANISM: Homo sapiens
<220> FEATURE:
<221> NAME/KEY: MISC_FEATURE
<223> OTHER INFORMATION: 4-1BB (amino acids 214-255 of Q07011.1) Homo
      sapiens

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 13
<211> LENGTH: 112
<212> TYPE: PRT
<213> ORGANISM: Homo sapiens
<220> FEATURE:
<221> NAME/KEY: MISC_FEATURE
<223> OTHER INFORMATION: CD3 zeta Homo sapiens

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<221> NAME/KEY: MISC_FEATURE
<223> OTHER INFORMATION: CD3 zeta Homo sapiens

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
```

```
                50               55                60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

```
<210> SEQ ID NO 15
<211> LENGTH: 112
<212> TYPE: PRT
<213> ORGANISM: Homo sapiens
<220> FEATURE:
<221> NAME/KEY: MISC_FEATURE
<223> OTHER INFORMATION: CD3 zeta Homo sapiens

<400> SEQUENCE: 15

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

```
<210> SEQ ID NO 16
<211> LENGTH: 30
<212> TYPE: PRT
<213> ORGANISM: Artificial Sequence
<220> FEATURE:
<223> OTHER INFORMATION: linker sequence

<400> SEQUENCE: 16

Pro Gly Gly Gly Ser Gly Gly Gly Ser Gly Gly Gly Ser
 1               5                  10                  15

Gly Gly Gly Ser Gly Gly Gly Ser Gly Gly Gly Pro
                20                  25                  30
```

```
<210> SEQ ID NO 17
<211> LENGTH: 17
<212> TYPE: PRT
<213> ORGANISM: Artificial Sequence
<220> FEATURE:
<223> OTHER INFORMATION: Linker

<400> SEQUENCE: 17

Gly Ser Ala Asp Asp Ala Lys Lys Asp Ala Ala Lys Lys Asp Gly Lys
 1               5                  10                  15

Ser
```

```
<210> SEQ ID NO 18
<211> LENGTH: 1368
<212> TYPE: PRT
<213> ORGANISM: Streptococcus pyogenes
```

```
<220> FEATURE:
<221> NAME/KEY: MISC_FEATURE
<223> OTHER INFORMATION: S. Pyogenes Cas9 Q99ZW2

<400> SEQUENCE: 18

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
```

```
           385                 390                 395                 400
Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

```
Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215
```

| Glu | Leu | Gln | Lys | Gly | Asn | Glu | Leu | Ala | Leu | Pro | Ser | Lys | Tyr | Val |
|-----|-----|-----|-----|-----|-----|-----|-----|-----|-----|-----|-----|-----|-----|-----|
| 1220 | | | | | 1225 | | | | | 1230 | | | | |

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
 1250                1255                1260

His Tyr Leu Asp Glu Ile Ile Glu Gln Ile Ser Glu Phe Ser Lys
 1265                1270                1275

Arg Val Ile Leu Ala Asp Ala Asn Leu Asp Lys Val Leu Ser Ala
 1280                1285                1290

Tyr Asn Lys His Arg Asp Lys Pro Ile Arg Glu Gln Ala Glu Asn
 1295                1300                1305

Ile Ile His Leu Phe Thr Leu Thr Asn Leu Gly Ala Pro Ala Ala
 1310                1315                1320

Phe Lys Tyr Phe Asp Thr Thr Ile Asp Arg Lys Arg Tyr Thr Ser
 1325                1330                1335

Thr Lys Glu Val Leu Asp Ala Thr Leu Ile His Gln Ser Ile Thr
 1340                1345                1350

Gly Leu Tyr Glu Thr Arg Ile Asp Leu Ser Gln Leu Gly Gly Asp
 1355                1360                1365

<210> SEQ ID NO 19
<211> LENGTH: 1368
<212> TYPE: PRT
<213> ORGANISM: Streptococcus pyogenes
<220> FEATURE:
<221> NAME/KEY: MISC_FEATURE
<223> OTHER INFORMATION: S. Pyogenes Cas9 D10A

<400> SEQUENCE: 19

Met Asp Lys Lys Tyr Ser Ile Gly Leu Ala Ile Gly Thr Asn Ser Val
 1               5                  10                  15

Gly Trp Ala Val Ile Thr Asp Glu Tyr Lys Val Pro Ser Lys Lys Phe
        20                  25                  30

Lys Val Leu Gly Asn Thr Asp Arg His Ser Ile Lys Lys Asn Leu Ile
    35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

```
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
```

```
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
```

1040                1045                1050

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 20
<211> LENGTH: 2549
<212> TYPE: PRT
<213> ORGANISM: Homo sapiens
<220> FEATURE:
<221> NAME/KEY: MISC_FEATURE
<223> OTHER INFORMATION: MTOR_HUMAN Serine/threonine-protein kinase
      mTOR; UniProt No. P42345

<400> SEQUENCE: 20

Met Leu Gly Thr Gly Pro Ala Ala Ala Thr Thr Ala Ala Thr Thr Ser
1               5                   10                  15

```
Ser Asn Val Ser Val Leu Gln Gln Phe Ala Ser Gly Leu Lys Ser Arg
             20                  25                  30

Asn Glu Glu Thr Arg Ala Lys Ala Lys Glu Leu Gln His Tyr Val
         35                  40                  45

Thr Met Glu Leu Arg Glu Met Ser Gln Glu Ser Thr Arg Phe Tyr
 50                  55                  60

Asp Gln Leu Asn His His Ile Phe Glu Leu Val Ser Ser Ser Asp Ala
 65                  70                  75                  80

Asn Glu Arg Lys Gly Gly Ile Leu Ala Ile Ala Ser Leu Ile Gly Val
                 85                  90                  95

Glu Gly Gly Asn Ala Thr Arg Ile Gly Arg Phe Ala Asn Tyr Leu Arg
             100                 105                 110

Asn Leu Leu Pro Ser Asn Asp Pro Val Val Met Glu Met Ala Ser Lys
         115                 120                 125

Ala Ile Gly Arg Leu Ala Met Ala Gly Asp Thr Phe Thr Ala Glu Tyr
130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                 165                 170                 175

Ile Ser Val Pro Thr Phe Phe Phe Gln Gln Val Gln Pro Phe Phe Asp
             180                 185                 190

Asn Ile Phe Val Ala Val Trp Asp Pro Lys Gln Ala Ile Arg Glu Gly
         195                 200                 205

Ala Val Ala Ala Leu Arg Ala Cys Leu Ile Leu Thr Thr Gln Arg Glu
210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                 245                 250                 255

Arg Asp Asp Arg Ile His Gly Ala Leu Leu Ile Leu Asn Glu Leu Val
             260                 265                 270

Arg Ile Ser Ser Met Glu Gly Glu Arg Leu Arg Glu Glu Met Glu Glu
         275                 280                 285

Ile Thr Gln Gln Gln Leu Val His Asp Lys Tyr Cys Lys Asp Leu Met
290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                 325                 330                 335

Ser Ser His Gln Gly Leu Met Gly Phe Gly Thr Ser Pro Ser Pro Ala
             340                 345                 350

Lys Ser Thr Leu Val Glu Ser Arg Cys Cys Arg Asp Leu Met Glu Glu
         355                 360                 365

Lys Phe Asp Gln Val Cys Gln Trp Val Leu Lys Cys Arg Asn Ser Lys
370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                 405                 410                 415

Met Asn His Val Leu Ser Cys Val Lys Lys Glu Lys Glu Arg Thr Ala
             420                 425                 430
```

```
Ala Phe Gln Ala Leu Gly Leu Leu Ser Val Ala Val Arg Ser Glu Phe
            435                 440                 445

Lys Val Tyr Leu Pro Arg Val Leu Asp Ile Ile Arg Ala Ala Leu Pro
450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
        530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
```

```
            850                 855                 860
Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                    885                 890                 895

Tyr Lys His Lys Val Asn Ile Gly Met Ile Asp Gln Ser Arg Asp Ala
                900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
            930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                    965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
            995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260
```

```
Asn Leu Gln Lys Ala Trp Gly Ala Ala Arg Val Ser Lys Asp
1265                1270                1275

Asp Trp Leu Glu Trp Leu Arg Arg Leu Ser Leu Glu Leu Leu Lys
1280                1285                1290

Asp Ser Ser Pro Ser Leu Arg Ser Cys Trp Ala Leu Ala Gln
1295                1300                1305

Ala Tyr Asn Pro Met Ala Arg Asp Leu Phe Asn Ala Ala Phe Val
1310                1315                1320

Ser Cys Trp Ser Glu Leu Asn Glu Asp Gln Gln Asp Glu Leu Ile
1325                1330                1335

Arg Ser Ile Glu Leu Ala Leu Thr Ser Gln Asp Ile Ala Glu Val
1340                1345                1350

Thr Gln Thr Leu Leu Asn Leu Ala Glu Phe Met Glu His Ser Asp
1355                1360                1365

Lys Gly Pro Leu Pro Leu Arg Asp Asp Asn Gly Ile Val Leu Leu
1370                1375                1380

Gly Glu Arg Ala Ala Lys Cys Arg Ala Tyr Ala Lys Ala Leu His
1385                1390                1395

Tyr Lys Glu Leu Glu Phe Gln Lys Gly Pro Thr Pro Ala Ile Leu
1400                1405                1410

Glu Ser Leu Ile Ser Ile Asn Asn Lys Leu Gln Gln Pro Glu Ala
1415                1420                1425

Ala Ala Gly Val Leu Glu Tyr Ala Met Lys His Phe Gly Glu Leu
1430                1435                1440

Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650
```

```
Leu Lys Tyr Ala Ser Leu Cys Gly Lys Ser Gly Arg Leu Ala Leu
    1655             1660             1665

Ala His Lys Thr Leu Val Leu Leu Leu Gly Val Asp Pro Ser Arg
    1670             1675             1680

Gln Leu Asp His Pro Leu Pro Thr Val His Pro Gln Val Thr Tyr
    1685             1690             1695

Ala Tyr Met Lys Asn Met Trp Lys Ser Ala Arg Lys Ile Asp Ala
    1700             1705             1710

Phe Gln His Met Gln His Phe Val Gln Thr Met Gln Gln Gln Ala
    1715             1720             1725

Gln His Ala Ile Ala Thr Glu Asp Gln Gln His Lys Gln Glu Leu
    1730             1735             1740

His Lys Leu Met Ala Arg Cys Phe Leu Lys Leu Gly Glu Trp Gln
    1745             1750             1755

Leu Asn Leu Gln Gly Ile Asn Glu Ser Thr Ile Pro Lys Val Leu
    1760             1765             1770

Gln Tyr Tyr Ser Ala Ala Thr Glu His Asp Arg Ser Trp Tyr Lys
    1775             1780             1785

Ala Trp His Ala Trp Ala Val Met Asn Phe Glu Ala Val Leu His
    1790             1795             1800

Tyr Lys His Gln Asn Gln Ala Arg Asp Glu Lys Lys Lys Leu Arg
    1805             1810             1815

His Ala Ser Gly Ala Asn Ile Thr Asn Ala Thr Thr Ala Ala Thr
    1820             1825             1830

Thr Ala Ala Thr Ala Thr Thr Thr Ala Ser Thr Glu Gly Ser Asn
    1835             1840             1845

Ser Glu Ser Glu Ala Glu Ser Thr Glu Asn Ser Pro Thr Pro Ser
    1850             1855             1860

Pro Leu Gln Lys Lys Val Thr Glu Asp Leu Ser Lys Thr Leu Leu
    1865             1870             1875

Met Tyr Thr Val Pro Ala Val Gln Gly Phe Phe Arg Ser Ile Ser
    1880             1885             1890

Leu Ser Arg Gly Asn Asn Leu Gln Asp Thr Leu Arg Val Leu Thr
    1895             1900             1905

Leu Trp Phe Asp Tyr Gly His Trp Pro Asp Val Asn Glu Ala Leu
    1910             1915             1920

Val Glu Gly Val Lys Ala Ile Gln Ile Asp Thr Trp Leu Gln Val
    1925             1930             1935

Ile Pro Gln Leu Ile Ala Arg Ile Asp Thr Pro Arg Pro Leu Val
    1940             1945             1950

Gly Arg Leu Ile His Gln Leu Leu Thr Asp Ile Gly Arg Tyr His
    1955             1960             1965

Pro Gln Ala Leu Ile Tyr Pro Leu Thr Val Ala Ser Lys Ser Thr
    1970             1975             1980

Thr Thr Ala Arg His Asn Ala Ala Asn Lys Ile Leu Lys Asn Met
    1985             1990             1995

Cys Glu His Ser Asn Thr Leu Val Gln Gln Ala Met Met Val Ser
    2000             2005             2010

Glu Glu Leu Ile Arg Val Ala Ile Leu Trp His Glu Met Trp His
    2015             2020             2025

Glu Gly Leu Glu Glu Ala Ser Arg Leu Tyr Phe Gly Glu Arg Asn
    2030             2035             2040

Val Lys Gly Met Phe Glu Val Leu Glu Pro Leu His Ala Met Met
```

```
                2045                2050                2055
Glu Arg Gly Pro Gln Thr Leu Lys Glu Thr Ser Phe Asn Gln Ala
        2060                2065                2070

Tyr Gly Arg Asp Leu Met Glu Ala Gln Glu Trp Cys Arg Lys Tyr
        2075                2080                2085

Met Lys Ser Gly Asn Val Lys Asp Leu Thr Gln Ala Trp Asp Leu
        2090                2095                2100

Tyr Tyr His Val Phe Arg Arg Ile Ser Lys Gln Leu Pro Gln Leu
        2105                2110                2115

Thr Ser Leu Glu Leu Gln Tyr Val Ser Pro Lys Leu Leu Met Cys
        2120                2125                2130

Arg Asp Leu Glu Leu Ala Val Pro Gly Thr Tyr Asp Pro Asn Gln
        2135                2140                2145

Pro Ile Ile Arg Ile Gln Ser Ile Ala Pro Ser Leu Gln Val Ile
        2150                2155                2160

Thr Ser Lys Gln Arg Pro Arg Lys Leu Thr Leu Met Gly Ser Asn
        2165                2170                2175

Gly His Glu Phe Val Phe Leu Leu Lys Gly His Glu Asp Leu Arg
        2180                2185                2190

Gln Asp Glu Arg Val Met Gln Leu Phe Gly Leu Val Asn Thr Leu
        2195                2200                2205

Leu Ala Asn Asp Pro Thr Ser Leu Arg Lys Asn Leu Ser Ile Gln
        2210                2215                2220

Arg Tyr Ala Val Ile Pro Leu Ser Thr Asn Ser Gly Leu Ile Gly
        2225                2230                2235

Trp Val Pro His Cys Asp Thr Leu His Ala Leu Ile Arg Asp Tyr
        2240                2245                2250

Arg Glu Lys Lys Lys Ile Leu Leu Asn Ile Glu His Arg Ile Met
        2255                2260                2265

Leu Arg Met Ala Pro Asp Tyr Asp His Leu Thr Leu Met Gln Lys
        2270                2275                2280

Val Glu Val Phe Glu His Ala Val Asn Asn Thr Ala Gly Asp Asp
        2285                2290                2295

Leu Ala Lys Leu Leu Trp Leu Lys Ser Pro Ser Ser Glu Val Trp
        2300                2305                2310

Phe Asp Arg Arg Thr Asn Tyr Thr Arg Ser Leu Ala Val Met Ser
        2315                2320                2325

Met Val Gly Tyr Ile Leu Gly Leu Gly Asp Arg His Pro Ser Asn
        2330                2335                2340

Leu Met Leu Asp Arg Leu Ser Gly Lys Ile Leu His Ile Asp Phe
        2345                2350                2355

Gly Asp Cys Phe Glu Val Ala Met Thr Arg Glu Lys Phe Pro Glu
        2360                2365                2370

Lys Ile Pro Phe Arg Leu Thr Arg Met Leu Thr Asn Ala Met Glu
        2375                2380                2385

Val Thr Gly Leu Asp Gly Asn Tyr Arg Ile Thr Cys His Thr Val
        2390                2395                2400

Met Glu Val Leu Arg Glu His Lys Asp Ser Val Met Ala Val Leu
        2405                2410                2415

Glu Ala Phe Val Tyr Asp Pro Leu Leu Asn Trp Arg Leu Met Asp
        2420                2425                2430

Thr Asn Thr Lys Gly Asn Lys Arg Ser Arg Thr Arg Thr Asp Ser
        2435                2440                2445
```

| | | | | | | | | | | |
|---|---|---|---|---|---|---|---|---|---|---|
| Tyr | Ser | Ala | Gly | Gln | Ser | Val | Glu | Ile | Leu | Asp | Gly | Val | Glu | Leu |
| | | | 2450 | | | | 2455 | | | | 2460 | | | |
| Gly | Glu | Pro | Ala | His | Lys | Lys | Thr | Gly | Thr | Thr | Val | Pro | Glu | Ser |
| 2465 | | | | | 2470 | | | | | 2475 | | | | |
| Ile | His | Ser | Phe | Ile | Gly | Asp | Gly | Leu | Val | Lys | Pro | Glu | Ala | Leu |
| | 2480 | | | | | 2485 | | | | | 2490 | | | |
| Asn | Lys | Lys | Ala | Ile | Gln | Ile | Ile | Asn | Arg | Val | Arg | Asp | Lys | Leu |
| | | 2495 | | | | | 2500 | | | | | 2505 | | |
| Thr | Gly | Arg | Asp | Phe | Ser | His | Asp | Asp | Thr | Leu | Asp | Val | Pro | Thr |
| | | | 2510 | | | | | 2515 | | | | 2520 | | |
| Gln | Val | Glu | Leu | Leu | Ile | Lys | Gln | Ala | Thr | Ser | His | Glu | Asn | Leu |
| | 2525 | | | | | 2530 | | | | | 2535 | | | |
| Cys | Gln | Cys | Tyr | Ile | Gly | Trp | Cys | Pro | Phe | Trp |
| 2540 | | | | | 2545 | | | | | |

<210> SEQ ID NO 21
<211> LENGTH: 8733
<212> TYPE: DNA
<213> ORGANISM: Homo sapiens
<220> FEATURE:
<221> NAME/KEY: misc_feature
<223> OTHER INFORMATION: Homo sapiens mechanistic target of rapamycin
      (MTOR), mRNA; Acc. No. NM_004958.3

<400> SEQUENCE: 21

```
gctcccggct tagaggacag cggggaaggc gggcggtggg gcaggggggcc tgaagcggcg      60
gtaccggtgc tggcggcggc agctgaggcc ttggccgaag ccgcgcgaac ctcagggcaa     120
gatgcttgga accggacctg ccgccgccac caccgctgcc accacatcta gcaatgtgag     180
cgtcctgcag cagtttgcca gtggcctaaa gagccggaat gaggaaacca gggccaaagc     240
cgccaaggag ctccagcact atgtcaccat ggaactccga gagatgagtc aagaggagtc     300
tactcgcttc tatgaccaac tgaaccatca cattttttgaa ttggtttcca gctcagatgc     360
caatgagagg aaaggtggca tcttggccat agctagcctc ataggagtgg aaggtgggaa     420
tgccacccga attggcagat tgccaactat tcttcggaac ctcctcccct ccaatgaccc     480
agttgtcatg gaaatggcat ccaaggccat ggccgtcctt gccatggcag ggacacttttt     540
taccgctgag tacgtggaat tgaggtgaa gcgagccctg gaatggctgg gtgctgaccg     600
caatgagggc cggagacatg cagctgtcct ggttctccgt gagctggcca tcagcgtccc     660
taccttcttc ttccagcaag tgcaacccctt ctttgacaac attttttgtgg ccgtgtggga     720
ccccaaacag gccatccgtg agggagctgt agccgcccctt cgtgcctgtc tgattctcac     780
aacccagcgt gagccgaagg agatgcagaa gcctcagtgg tacaggcaca catttgaaga     840
agcagagaag ggatttgatg agaccttggc caaagagaag ggcatgaatc gggatgatcg     900
gatccatgga gccttgttga tccttaacga gctggtccga atcagcagca tggagggaga     960
gcgtctgaga gaagaaatgg aagaaatcac acagcagcag ctggtacacg acaagtactg    1020
caaagatctc atgggcttcg gaacaaaacc tcgtcacatt ccccccttca ccagtttcca    1080
ggctgtacag cccagcagt caaatgcctt ggtggggctg ctggggtaca gctctccacca    1140
aggcctcatg ggatttggga cctcccccag tccagctaag tccaccctgg tggagagccg    1200
gtgttgcaga gacttgatgg aggagaaatt tgatcaggtg tgccagtggg tgctgaaatg    1260
caggaatagc aagaactcgc tgatccaaat gacaatcctt aatttgttgc cccgcttggc    1320
tgcattccga ccttctgcct tcacagatac ccagtatctc caagatacca tgaaccatgt    1380
```

```
cctaagctgt gtcaagaagg agaaggaacg tacagcggcc ttccaagccc tggggctact    1440
ttctgtggct gtgaggtctg agtttaaggt ctatttgcct cgcgtgctgg acatcatccg    1500
agcggccctg cccccaaagg acttcgccca taagaggcag aaggcaatgc aggtggatgc    1560
cacagtcttc acttgcatca gcatgctggc tcgagcaatg gggccaggca tccagcagga    1620
tatcaaggag ctgctggagc ccatgctggc agtgggacta agccctgccc tcactgcagt    1680
gctctacgac ctgagccgtc agattccaca gctaaagaag acattcaag atgggctact     1740 gaaaatgctg tccctggtcc ttatgcacaa acccttcgc cacccaggca tgcccaaggg     1800 cctgcccat cagctggcct ctcctggcct cacgacctc cctgaggcca gcgatgtggg      1860
cagcatcact cttgccctcc gaacgcttgg cagctttgaa tttgaaggcc actctctgac    1920
ccaatttgtt cgccactgtg cggatcattt cctgaacagt gagcacaagg agatccgcat    1980
ggaggctgcc cgcacctgct cccgcctgct cacaccctcc atccacctca tcagtggcca    2040
tgctcatgtg gttagccaga ccgcagtgca agtggtggca gatgtgctta gcaaactgct    2100
cgtagttggg ataacagatc ctgaccctga cattcgctac tgtgtcttgg cgtccctgga    2160
cgagcgcttt gatgcacacc tggcccaggc ggagaacttg caggccttgt tgtggctct    2220 gaatgaccag gtgtttgaga tccgggagct ggccatctgc actgtgggcc gactcagtag    2280
catgaaccct gcctttgtca tgcctttcct gcgcaagatg ctcatccaga ttttgacaga    2340
gttggagcac agtgggattg aagaatcaa agagcagagt gcccgcatgc tggggcacct     2400
ggtctccaat gcccccgac tcatccgccc tacatggag cctattctga aggcattaat      2460
tttgaaactg aaagatccag accctgatcc aaacccaggt gtgatcaata atgtcctggc    2520
aacaatagga gaattggcac aggttagtgg cctggaaatg aggaaatggg ttgatgaact    2580
ttttattatc atcatggaca tgctccagga ttcctctttg ttggccaaaa ggcaggtggc    2640
tctgtggacc ctgggacagt tggtggccag cactggctat gtagtagagc cctacaggaa    2700
gtaccctact ttgcttgagg tgctactgaa ttttctgaag actgagcaga accagggtac    2760
acgcagagag gccatccgtg tgttagggct tttaggggct ttggatcctt acaagcacaa    2820
agtgaacatt ggcatgatag accagtcccg ggatgcctct gctgtcagcc tgtcagaatc    2880
caagtcaagt caggattcct ctgactatag cactagtgaa atgctggtca acatgggaaa    2940
cttgcctctg gatgagttct acccagctgt gtccatggtg gccctgatgc ggatcttccg    3000
agaccagtca ctctctcatc atcacaccat ggttgtccag gccatcacct tcatcttcaa    3060
gtccctggga ctcaaatgtg tgcagttcct gccccaggtc atgcccacgt tccttaacgt    3120
cattcgagtc tgtgatgggg ccatccggga attttttgttc cagcagctgg gaatgttggt   3180
gtcctttgtg aagagccaca tcagaccctta tatggatgaa atagtcaccc tcatgagaga    3240
attctgggtc atgaacacct caattcagag cacgatcatt cttctcattg agcaaattgt    3300
ggtagctctt gggggtgaat ttaagctcta cctgccccag ctgatcccac acatgctgcg    3360
tgtcttcatg catgacaaca gcccaggccg cattgtctct atcaagttac tggctgcaat    3420
ccagctgttt ggcgccaacc tggatgacta cctgcattta ctgctgcctc ctattgttaa    3480
gttgtttgat gcccctgaag ctccactgcc atctcgaaag gcagcgctag agactgtgga    3540
ccgcctgacg gagtccctgg atttcactga ctatgcctcc cggatcattc accctattgt    3600
tcgaacactg gaccagagcc cagaactgcg ctccacagcc atggacacgc tgtcttcact    3660 tgttttttcag ctggggaaga agtaccaaat tttcattcca atggtgaata agttctctgg    3720
```

```
gcgacaccga atcaatcatc agcgctatga tgtgctcatc tgcagaattg tcaagggata    3780
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg     3960
gctggaatgg ctgagacggc tgagcctgga gctgctgaag gactcatcat cgccctccct    4020
gcgctcctgc tgggccctgg cacaggccta aacccgatg gccagggatc tcttcaatgc     4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtc ccgagcatat gccaaagcac tacactacaa    4320
agaactggag ttccagaaag gccccacccc tgccattcta gaatctctca tcagcattaa    4380
taataagcta cagcagccgg aggcagcggc cggagtgtta aatatgcca tgaaacactt      4440
tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tgggggaatg gggtcaactc caccagcagt gctgtgaaaa    4620
gtggaccctg gttaatgatg agacccaagc caagatggcc cggatggctg ctgcagctgc    4680
atggggttta ggtcagtggg acagcatgga agaatacacc tgtatgatcc ctcgggacac    4740
ccatgatggg gcatttata gagctgtgct ggcactgcat caggacctct tctccttggc     4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaacttta gtgttgctcc tgggagttga    5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgag aagaagaaac tgcgtcatgc    5580
cagcggggcc aacatcacca cgccaccac tgccgccacc acggccgcca ctgccaccac      5640
cactgccagc accgagggca gcaacagtga gagcgaggcc gagagcaccg agaacagccc    5700
caccccatcg ccgctgcaga agaaggtcac tgaggatctg tccaaaaccc tcctgatgta    5760
cacggtgcct gccgtccagg gcttcttccg ttccatctcc ttgtcacgag caacaacct     5820
ccaggataca ctcagagttc tcaccttatg gtttgattat ggtcactggc cagatgtcaa    5880
tgaggcctta gtgaggggg tgaaagccat ccagattgat acctggctac aggttatacc     5940
tcagctcatt gcaagaattg atacgcccag acccttggtg ggacgtctca ttcaccagct    6000
tctcacagac attggtcggt accaccccca ggccctcatc tacccactga cagtggcttc    6060
taagtctacc acgacagccc ggcacaatgc agccaacaag attctgaaga acatgtgtga    6120
```

```
gcacagcaac accctggtcc agcaggccat gatggtgagc gaggagctga tccgagtggc    6180
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggcccccag actctgaagg aaacatcctt taatcaggcc tatggtcgag atttaatgga    6360
ggcccaagag tggtgcagga agtacatgaa atcagggaat gtcaaggacc tcacccaagc    6420
ctgggacctc tattatcatg tgttccgacg aatctcaaag cagctgcctc agctcacatc    6480
cttagagctg caatatgttt ccccaaaact tctgatgtgc cgggaccttg aattggctgt    6540
gccaggaaca tatgacccca accagccaat cattcgcatt cagtccatag caccgtcttt    6600
gcaagtcatc acatccaagc agaggccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatcccttt atcgaccaac tcgggcctca ttggctgggt    6840
tccccactgt gacacactgc acgccctcat ccgggactac agggagaaga agaagatcct    6900
tctcaacatc gagcatcgca tcatgttgcg gatggctccg gactatgacc acttgactct    6960
gatgcagaag gtggaggtgt tgagcatgc cgtcaataat acagctgggg acgacctggc    7020
caagctgctg tggctgaaaa gccccagctc cgaggtgtgg tttgaccgaa gaaccaatta    7080
tacccgttct ttagcggtca tgtcaatggt tgggtatatt ttaggcctgg gagatagaca    7140
cccatccaac ctgatgctgg accgtctgag tgggaagatc ctgcacattg actttgggga    7200
ctgctttgag gttgctatga cccgagagaa gtttccagag aagattccat ttagactaac    7260
aagaatgttg accaatgcta tggaggttac aggcctggat ggcaactaca gaatcacatg    7320
ccacacagtg atggaggtgc tgcgagagca caaggacagt gtcatggccg tgctggaagc    7380
ctttgtctat gaccccttgc tgaactggag gctgatggac acaaatacca aaggcaacaa    7440
gcgatcccga acgaggacgg attcctactc tgctggccag tcagtcgaaa ttttggacgg    7500
tgtggaactt ggagagccag cccataagaa aacggggacc acagtgccag aatctattca    7560
ttctttcatt ggagacggtt tggtgaaacc agaggcccta aataagaaag ctatccagat    7620
tattaacagg gttcgagata agctcactgg tcgggacttc tctcatgatg acactttgga    7680
tgttccaacg caagttgagc tgctcatcaa acaagcgaca tcccatgaaa acctctgcca    7740
gtgctatatt ggctggtgcc ctttctggta actggaggcc cagatgtgcc catcacgttt    7800
tttctgaggc ttttgtactt tagtaaatgc ttccactaaa ctgaaccat ggtgagaaag    7860 tttgactttg ttaaatattt tgaaatgtaa atgaaaagaa ctactgtata ttaaaagttg    7920
gtttgaacca actttctagc tgctgttgaa gaatatattg tcagaaacac aaggcttgat    7980
ttggttccca ggacagtgaa acatagtaat accacgtaaa tcaagccatt cattttgggg    8040
aacagaagat ccataacttt agaaatacgg gttttgactt aactcacaag agaactcatc    8100
ataagtactt gctgatggaa gaatgaccta gttgctcctc tcaacatggg tacagcaaac    8160
tcagcacagc caagaagcct caggtcgtgg agaacatgga ttaggatcct agactgtaaa    8220
gacacagaag atgctgacct cacccctgcc acctatccca agacctcact ggtctgtgga    8280
cagcagcaga aatgtttgca agataggcca aaatgagtac aaaaggtctg tcttccatca    8340
gacccagtga tgctgcgact cacacgcttc aattcaagac ctgaccgcta gtagggaggt    8400
ttattcagat cgctggcagc ctcggctgag cagatgcaca gagggatca ctgtgcagtg    8460
```

-continued

```
ggaccaccct cactggcctt ctgcagcagg gttctgggat gttttcagtg gtcaaaatac   8520
tctgtttaga gcaagggctc agaaaacaga aatactgtca tggaggtgct gaacacaggg   8580
aaggtctggt acatattgga aattatgagc agaacaaata ctcaactaaa tgcacaaagt   8640
ataaagtgta gccatgtcta gacaccatgt tgtatcagaa taattttttgt gccaataaat  8700 gacatcagaa ttttaaacat atgtaaaaaa aaa                                8733
```

<210> SEQ ID NO 22
<211> LENGTH: 706
<212> TYPE: PRT
<213> ORGANISM: Homo sapiens
<220> FEATURE:
<221> NAME/KEY: MISC_FEATURE
<223> OTHER INFORMATION: HUMAN Protein kinase C theta UniProt No. Q04759

<400> SEQUENCE: 22

```
Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
```

```
              305                 310                 315                 320
              Pro Cys Ser Ile Lys Asn Glu Ala Arg Pro Pro Cys Leu Pro Thr Pro
                              325                 330                 335

Gly Lys Arg Glu Pro Gln Gly Ile Ser Trp Glu Ser Pro Leu Asp Glu
                              340                 345                 350

Val Asp Lys Met Cys His Leu Pro Glu Pro Glu Leu Asn Lys Glu Arg
                              355                 360                 365

Pro Ser Leu Gln Ile Lys Leu Lys Ile Glu Asp Phe Ile Leu His Lys
                              370                 375                 380

Met Leu Gly Lys Gly Ser Phe Gly Lys Val Phe Leu Ala Glu Phe Lys
              385                 390                 395                 400

Lys Thr Asn Gln Phe Phe Ala Ile Lys Ala Leu Lys Lys Asp Val Val
                              405                 410                 415

Leu Met Asp Asp Asp Val Glu Cys Thr Met Val Glu Lys Arg Val Leu
                              420                 425                 430

Ser Leu Ala Trp Glu His Pro Phe Leu Thr His Met Phe Cys Thr Phe
                              435                 440                 445

Gln Thr Lys Glu Asn Leu Phe Phe Val Met Glu Tyr Leu Asn Gly Gly
                              450                 455                 460

Asp Leu Met Tyr His Ile Gln Ser Cys His Lys Phe Asp Leu Ser Arg
              465                 470                 475                 480

Ala Thr Phe Tyr Ala Ala Glu Ile Ile Leu Gly Leu Gln Phe Leu His
                              485                 490                 495

Ser Lys Gly Ile Val Tyr Arg Asp Leu Lys Leu Asp Asn Ile Leu Leu
                              500                 505                 510

Asp Lys Asp Gly His Ile Lys Ile Ala Asp Phe Gly Met Cys Lys Glu
                              515                 520                 525

Asn Met Leu Gly Asp Ala Lys Thr Asn Thr Phe Cys Gly Thr Pro Asp
                              530                 535                 540

Tyr Ile Ala Pro Glu Ile Leu Leu Gly Gln Lys Tyr Asn His Ser Val
              545                 550                 555                 560

Asp Trp Trp Ser Phe Gly Val Leu Leu Tyr Glu Met Leu Ile Gly Gln
                              565                 570                 575

Ser Pro Phe His Gly Gln Asp Glu Glu Leu Phe His Ser Ile Arg
                              580                 585                 590

Met Asp Asn Pro Phe Tyr Pro Arg Trp Leu Glu Lys Glu Ala Lys Asp
                              595                 600                 605

Leu Leu Val Lys Leu Phe Val Arg Glu Pro Glu Lys Arg Leu Gly Val
                              610                 615                 620

Arg Gly Asp Ile Arg Gln His Pro Leu Phe Arg Glu Ile Asn Trp Glu
              625                 630                 635                 640

Glu Leu Glu Arg Lys Glu Ile Asp Pro Pro Phe Arg Pro Lys Val Lys
                              645                 650                 655

Ser Pro Phe Asp Cys Ser Asn Phe Asp Lys Glu Phe Leu Asn Glu Lys
                              660                 665                 670

Pro Arg Leu Ser Phe Ala Asp Arg Ala Leu Ile Asn Ser Met Asp Gln
                              675                 680                 685

Asn Met Phe Arg Asn Phe Ser Phe Met Asn Pro Gly Met Glu Arg Leu
                              690                 695                 700

Ile Ser
              705

<210> SEQ ID NO 23
```

```
<211> LENGTH: 3295
<212> TYPE: DNA
<213> ORGANISM: Homo sapiens
<220> FEATURE:
<221> NAME/KEY: misc_feature
<223> OTHER INFORMATION: Homo sapiens protein kinase C theta (PRKCQ,
      mRNA; Acc. No. NM_006257.4

<400> SEQUENCE: 23
```

| | | | | |
|---|---|---|---|---|
| ccgccagccc | cgccagtccc | cgcgcagtcc | ccgcgcagtc | cccagcgcca | 60 |
| ccgggcagca | gcggcgccgt | gctcgctcca | gggcgcaacc | atgtcgccat | 120 |
| tcttcggat | | | | | |
| tggcttgtcc | aactttgact | gcgggtcctg | ccagtcttgt | cagggcgagg | 180 |
| ctgttaaccc | | | | | |
| ttactgtgct | gtgctcgtca | aagagtatgt | cgaatcagag | aacgggcaga | 240 |
| tgtatatcca | | | | | |
| gaaaaagcct | accatgtacc | caccctggga | cagcactttt | gatgcccata | 300 |
| tcaacaaggg | | | | | |
| aagagtcatg | cagatcattg | tgaaaggcaa | aaacgtggac | ctcatctctg | 360 |
| aaaccaccgt | | | | | |
| ggagctctac | tcgctggctg | agaggtgcag | gaagaacaac | gggaagacag | 420 |
| aaatatggtt | | | | | |
| agagctgaaa | cctcaaggcc | gaatgctaat | gaatgcaaga | tactttctgg | 480 |
| aaatgagtga | | | | | |
| cacaaaggac | atgaatgaat | ttgagacgga | aggcttcttt | gctttgcatc | 540 |
| agcgccgggg | | | | | |
| tgccatcaag | caggcaaagg | tccaccacgt | caagtgccac | gagttcactg | 600 |
| ccaccttctt | | | | | |
| cccacagccc | acattttgct | ctgtctgcca | cgagtttgtc | tggggcctga | 660 |
| caaacagggg | | | | | |
| ctaccagtgc | cgacaatgca | atgcagcaat | tcacaagaag | tgtattgata | 720 |
| agttatagc | | | | | |
| aaagtgcaca | ggatcagcta | tcaatagccg | agaaaccatg | ttccacaagg | 780 |
| agagattcaa | | | | | |
| aattgacatg | ccacacagat | ttaaagtcta | caattacaag | agcccgacct | 840 |
| tctgtgaaca | | | | | |
| ctgtgggacc | ctgctgtggg | gactggcacg | gcaaggactc | aagtgtgatg | 900 |
| catgtggcat | | | | | |
| gaatgtgcat | catagatgcc | agacaaaggt | ggccaacctt | tgtggcataa | 960 |
| accagaagct | | | | | |
| aatggctgaa | gcgctggcca | tgattgagag | cactcaacag | gctcgctgct | 1020 |
| taagagatac | | | | | |
| tgaacagatc | ttcagagaag | gtccggttga | aattggtctc | ccatgctcca | 1080 |
| tcaaaaatga | | | | | |
| agcaaggccg | ccatgtttac | cgacaccggg | aaaagagag | cctcagggca | 1140 |
| tttcctggga | | | | | |
| gtctccgttg | gatgaggtgg | ataaaatgtg | ccatcttcca | gaacctgaac | 1200 |
| tgaacaaaga | | | | | |
| aagaccatct | ctgcagatta | aactaaaaat | tgaggatttt | atcttgcaca | 1260 |
| aaatgttggg | | | | | |
| gaaaggaagt | tttggcaagg | tcttcctggc | agaattcaag | aaaaccaatc | 1320 |
| aattttttcgc | | | | | |
| aataaaggcc | ttaaagaaag | atgtggtctt | gatggacgat | gatgttgagt | 1380 |
| gcacgatggt | | | | | |
| agagaagaga | gttctttcct | tggcctggga | gcatccgttt | ctgacgcaca | 1440 |
| tgttttgtac | | | | | |
| attccagacc | aaggaaaacc | tcttttttgt | gatggagtac | ctcaacggag | 1500 |
| gggacttaat | | | | | |
| gtaccacatc | caaagctgcc | acaagttcga | cctttccaga | gcgacgtttt | 1560 |
| atgctgctga | | | | | |
| aatcattctt | ggtctgcagt | tccttcattc | caaaggaata | gtctacaggg | 1620 |
| acctgaagct | | | | | |
| agataacatc | ctgttagaca | agatggacac | atcaagatc | gcggattttg | 1680 |
| gaatgtgcaa | | | | | |
| ggagaacatg | ttaggagatg | ccaagacgaa | taccttctgt | gggacacctg | 1740 |
| actacatcgc | | | | | |
| cccagagatc | ttgctgggtc | agaaatacaa | ccactctgtg | gactggtggt | 1800 |
| ccttcggggt | | | | | |
| tctcctttat | gaaatgctga | ttggtcagtc | gcctttccac | gggcaggatg | 1860 |
| aggaggagct | | | | | |
| cttccactcc | atccgcatgg | acaatcccct | tacccacgg | tggctggaga | 1920 |
| aggaagcaaa | | | | | |
| ggaccttctg | gtgaagctct | tcgtgcgaga | acctgagaag | aggctgggcg | 1980 |
| tgaggggaga | | | | | |
| catccgccag | cacccttttg | ttcgggagat | caactgggag | gaacttgaac | 2040 |
| ggaaggagat | | | | | |
| tgacccaccg | ttccggccga | aagtgaaatc | accatttgac | tgcagcaatt | 2100 |
| tcgacaaaga | | | | | |

-continued

```
attcttaaac gagaagcccc ggctgtcatt tgccgacaga gcactgatca acagcatgga   2160
ccagaatatg ttcaggaact tttccttcat gaaccccggg atggagcggc tgatatcctg   2220
aatcttgccc ctccagagac aggaaagaat ttgccttctc cctgggaact ggttcaagag   2280
acactgcttg ggttcctttt tcaacttgga aaagaaaga aacactcaac aataaagact   2340
gagacccgtt cgcccccatg tgactttat ctgtagcaga aaccaagtct acttcactaa   2400
```

```
tgacgatgcc gtgtgtctcg tctcctgaca tgtctcacag acgctcctga agttaggtca   2460
ttactaacca tagttattta cttgaaagat gggtctccgc acttggaaag gtttcaagac   2520
ttgatactgc aataaattat ggctcttcac ctgggcgcca actgctgatc aatgaaatgc   2580
ttgttgaatc aggggcaaac ggagtacaga cgtctcaaga ctgaaacggc cccattgcct   2640
ggtctagtag cggatctcac tcagccgcag acaagtaatc actaacccgt tttattctat   2700
tcctatctgt ggatgtgtaa atggctgggg ggccagccct ggataggttt ttatgggaat   2760
tctttacaat aaacatagct tgtaacttga gatctacaaa tccattcatc ctgattgggc   2820
atgaaatcca tggtcaagag gacaagtgga aagtgagagg gaaggtttgc tagacacctt   2880
cgcttgttat cttgtcaaga tagaaaagat agtatcattt cacccttgcc agtaaaaacc   2940
tttccatcca cccattctca gcagactcca gtattggcac agtcactcac tgccattctc   3000
acactataac aagaaaagaa atgaagtgca taagtctcct gggaaaagaa ccttaacccc   3060
ttctcgtgcc atgactggtg atttcatgac tcataagccc ctccgtaggc atcattcaag   3120
atcaatggcc catgcatgct gtttgcagca gtcaattgag ttgaattaga attccaacca   3180
tacattttaa aggtatttgt gctgtgtgta tattttgata aaatgttgtg acttcatggc   3240
aaacaggtgg atgtgtaaaa atggaataaa aaaaaaaaaa gagtcaaaaa aaaaa         3295
```

<210> SEQ ID NO 24
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 24
aagtcggtct ctatgccgct                                                20

<210> SEQ ID NO 25
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 25
ttgctgctct acagttatcc                                                20

<210> SEQ ID NO 26
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 26
aatttcagcg tcagctacac                                                20

<210> SEQ ID NO 27

```
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 27
agaccgactt aatacagagt                                              20

<210> SEQ ID NO 28
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 28
tccgtttctt tcagtagggg                                              20

<210> SEQ ID NO 29
<211> LENGTH: 20
<212> TYPE: DNA
<213> ORGANISM: Artificial Sequence
<220> FEATURE:
<223> OTHER INFORMATION: AHR CRISPR gRNA target sequence

<400> SEQUENCE: 29
agttgtcact acagatgctt                                              20

<210> SEQ ID NO 30
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 30
gtcgccgctt aatagccctc                                              20

<210> SEQ ID NO 31
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 31
tgatcagatg tctaacgata                                              20

<210> SEQ ID NO 32
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 32
gacatcagat gtaccatcac                                              20

<210> SEQ ID NO 33
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 33
```
ctcagcctat tcacagaaac                                                     20

<210> SEQ ID NO 34
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 34
tgaataggct gagctttgtg                                                     20

<210> SEQ ID NO 35
<211> LENGTH: 20
<212> TYPE: DNA
<213> ORGANISM: Artificial Sequence
<220> FEATURE:
<223> OTHER INFORMATION: ARNT CRISPR gRNA target sequence

<400> SEQUENCE: 35
gtggaggagc cattgtccag                                                     20

<210> SEQ ID NO 36
<211> LENGTH: 685
<212> TYPE: PRT
<213> ORGANISM: Homo sapiens
<220> FEATURE:
<221> NAME/KEY: MISC_FEATURE
<223> OTHER INFORMATION: human Neutral and basic amino acid transport
      protein rBAT (SLC3A1) isoform 1 Uniprot Q07837

<400> SEQUENCE: 36

Met Ala Glu Asp Lys Ser Lys Arg Asp Ser Ile Glu Met Ser Met Lys
1               5                   10                  15

Gly Cys Gln Thr Asn Asn Gly Phe Val His Asn Glu Asp Ile Leu Glu
            20                  25                  30

Gln Thr Pro Asp Pro Gly Ser Ser Thr Asp Asn Leu Lys His Ser Thr
        35                  40                  45

Arg Gly Ile Leu Gly Ser Gln Glu Pro Asp Phe Lys Gly Val Gln Pro
    50                  55                  60

Tyr Ala Gly Met Pro Lys Glu Val Leu Phe Gln Phe Ser Gly Gln Ala
65                  70                  75                  80

Arg Tyr Arg Ile Pro Arg Glu Ile Leu Phe Trp Leu Thr Val Ala Ser
                85                  90                  95

Val Leu Val Leu Ile Ala Ala Thr Ile Ala Ile Ala Leu Ser Pro
            100                 105                 110

Lys Cys Leu Asp Trp Trp Gln Glu Gly Pro Met Tyr Gln Ile Tyr Pro
        115                 120                 125

Arg Ser Phe Lys Asp Ser Asn Lys Asp Gly Asn Gly Asp Leu Lys Gly
    130                 135                 140

Ile Gln Asp Lys Leu Asp Tyr Ile Thr Ala Leu Asn Ile Lys Thr Val
145                 150                 155                 160

Trp Ile Thr Ser Phe Tyr Lys Ser Ser Leu Lys Asp Phe Arg Tyr Gly
                165                 170                 175

Val Glu Asp Phe Arg Glu Val Asp Pro Ile Phe Gly Thr Met Glu Asp
            180                 185                 190

Phe Glu Asn Leu Val Ala Ala Ile His Asp Lys Gly Leu Lys Leu Ile
        195                 200                 205

Ile Asp Phe Ile Pro Asn His Thr Ser Asp Lys His Ile Trp Phe Gln

```
            210                 215                 220
Leu Ser Arg Thr Arg Thr Gly Lys Tyr Thr Asp Tyr Ile Trp His
225                 230                 235                 240

Asp Cys Thr His Glu Asn Gly Lys Thr Ile Pro Pro Asn Asn Trp Leu
                    245                 250                 255

Ser Val Tyr Gly Asn Ser Ser Trp His Phe Asp Glu Val Arg Asn Gln
                260                 265                 270

Cys Tyr Phe His Gln Phe Met Lys Glu Gln Pro Asp Leu Asn Phe Arg
            275                 280                 285

Asn Pro Asp Val Gln Glu Ile Lys Glu Ile Leu Arg Phe Trp Leu
290                 295                 300

Thr Lys Gly Val Asp Gly Phe Ser Leu Asp Ala Val Lys Phe Leu Leu
305                 310                 315                 320

Glu Ala Lys His Leu Arg Asp Glu Ile Gln Val Asn Lys Thr Gln Ile
                325                 330                 335

Pro Asp Thr Val Thr Gln Tyr Ser Glu Leu Tyr His Asp Phe Thr Thr
                340                 345                 350

Thr Gln Val Gly Met His Asp Ile Val Arg Ser Phe Arg Gln Thr Met
            355                 360                 365

Asp Gln Tyr Ser Thr Glu Pro Gly Arg Tyr Arg Phe Met Gly Thr Glu
370                 375                 380

Ala Tyr Ala Glu Ser Ile Asp Arg Thr Val Met Tyr Tyr Gly Leu Pro
385                 390                 395                 400

Phe Ile Gln Glu Ala Asp Phe Pro Phe Asn Asn Tyr Leu Ser Met Leu
                405                 410                 415

Asp Thr Val Ser Gly Asn Ser Val Tyr Glu Val Ile Thr Ser Trp Met
                420                 425                 430

Glu Asn Met Pro Glu Gly Lys Trp Pro Asn Trp Met Ile Gly Gly Pro
            435                 440                 445

Asp Ser Ser Arg Leu Thr Ser Arg Leu Gly Asn Gln Tyr Val Asn Val
450                 455                 460

Met Asn Met Leu Leu Phe Thr Leu Pro Gly Thr Pro Ile Thr Tyr Tyr
465                 470                 475                 480

Gly Glu Glu Ile Gly Met Gly Asn Ile Val Ala Ala Asn Leu Asn Glu
                485                 490                 495

Ser Tyr Asp Ile Asn Thr Leu Arg Ser Lys Ser Pro Met Gln Trp Asp
                500                 505                 510

Asn Ser Ser Asn Ala Gly Phe Ser Glu Ala Ser Asn Thr Trp Leu Pro
            515                 520                 525

Thr Asn Ser Asp Tyr His Thr Val Asn Val Asp Val Gln Lys Thr Gln
530                 535                 540

Pro Arg Ser Ala Leu Lys Leu Tyr Gln Asp Leu Ser Leu Leu His Ala
545                 550                 555                 560

Asn Glu Leu Leu Leu Asn Arg Gly Trp Phe Cys His Leu Arg Asn Asp
                565                 570                 575

Ser His Tyr Val Val Tyr Thr Arg Glu Leu Asp Gly Ile Asp Arg Ile
                580                 585                 590

Phe Ile Val Val Leu Asn Phe Gly Glu Ser Thr Leu Leu Asn Leu His
            595                 600                 605

Asn Met Ile Ser Gly Leu Pro Ala Lys Met Arg Ile Arg Leu Ser Thr
610                 615                 620

Asn Ser Ala Asp Lys Gly Ser Lys Val Asp Thr Ser Gly Ile Phe Leu
625                 630                 635                 640
```

```
Asp Lys Gly Glu Gly Leu Ile Phe Glu His Asn Thr Lys Asn Leu Leu
            645                 650                 655

His Arg Gln Thr Ala Phe Arg Asp Arg Cys Phe Val Ser Asn Arg Ala
            660                 665                 670

Cys Tyr Ser Ser Val Leu Asn Ile Leu Tyr Thr Ser Cys
            675                 680                 685

<210> SEQ ID NO 37
<211> LENGTH: 630
<212> TYPE: PRT
<213> ORGANISM: Homo sapiens
<220> FEATURE:
<221> NAME/KEY: MISC_FEATURE
<223> OTHER INFORMATION: human 4F2 cell-surface antigen heavy chain
      (CD98hc; SLC3A2) isoform 1 Uniprot P08195

<400> SEQUENCE: 37

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Leu Gly Ser His Cys Val Ala Gln Thr Gly
        35                  40                  45

Leu Glu Leu Leu Ala Ser Gly Asp Pro Leu Pro Ser Ala Ser Gln Asn
50                  55                  60

Ala Glu Met Ile Glu Thr Gly Ser Asp Cys Val Thr Gln Ala Gly Leu
65                  70                  75                  80

Gln Leu Leu Ala Ser Ser Asp Pro Pro Ala Leu Ala Ser Lys Asn Ala
            85                  90                  95

Glu Val Thr Gly Thr Met Ser Gln Asp Thr Glu Val Asp Met Lys Glu
            100                 105                 110

Val Glu Leu Asn Glu Leu Glu Pro Glu Lys Gln Pro Met Asn Ala Ala
            115                 120                 125

Ser Gly Ala Ala Met Ser Leu Ala Gly Ala Glu Lys Asn Gly Leu Val
        130                 135                 140

Lys Ile Lys Val Ala Glu Asp Glu Ala Glu Ala Ala Ala Ala Ala Lys
145                 150                 155                 160

Phe Thr Gly Leu Ser Lys Glu Glu Leu Leu Lys Val Ala Gly Ser Pro
            165                 170                 175

Gly Trp Val Arg Thr Arg Trp Ala Leu Leu Leu Leu Phe Trp Leu Gly
            180                 185                 190

Trp Leu Gly Met Leu Ala Gly Ala Val Val Ile Ile Val Arg Ala Pro
        195                 200                 205

Arg Cys Arg Glu Leu Pro Ala Gln Lys Trp Trp His Thr Gly Ala Leu
210                 215                 220

Tyr Arg Ile Gly Asp Leu Gln Ala Phe Gln Gly His Gly Ala Gly Asn
225                 230                 235                 240

Leu Ala Gly Leu Lys Gly Arg Leu Asp Tyr Leu Ser Ser Leu Lys Val
            245                 250                 255

Lys Gly Leu Val Leu Gly Pro Ile His Lys Asn Gln Lys Asp Asp Val
            260                 265                 270

Ala Gln Thr Asp Leu Leu Gln Ile Asp Pro Asn Phe Gly Ser Lys Glu
        275                 280                 285

Asp Phe Asp Ser Leu Leu Gln Ser Ala Lys Lys Lys Ser Ile Arg Val
    290                 295                 300
```

```
Ile Leu Asp Leu Thr Pro Asn Tyr Arg Gly Glu Asn Ser Trp Phe Ser
305                 310                 315                 320

Thr Gln Val Asp Thr Val Ala Thr Lys Val Lys Asp Ala Leu Glu Phe
            325                 330                 335

Trp Leu Gln Ala Gly Val Asp Gly Phe Gln Val Arg Asp Ile Glu Asn
            340                 345                 350

Leu Lys Asp Ala Ser Ser Phe Leu Ala Glu Trp Gln Asn Ile Thr Lys
        355                 360                 365

Gly Phe Ser Glu Asp Arg Leu Leu Ile Ala Gly Thr Asn Ser Ser Asp
    370                 375                 380

Leu Gln Gln Ile Leu Ser Leu Leu Glu Ser Asn Lys Asp Leu Leu Leu
385                 390                 395                 400

Thr Ser Ser Tyr Leu Ser Asp Ser Gly Ser Thr Gly Glu His Thr Lys
            405                 410                 415

Ser Leu Val Thr Gln Tyr Leu Asn Ala Thr Gly Asn Arg Trp Cys Ser
            420                 425                 430

Trp Ser Leu Ser Gln Ala Arg Leu Leu Thr Ser Phe Leu Pro Ala Gln
        435                 440                 445

Leu Leu Arg Leu Tyr Gln Leu Met Leu Phe Thr Leu Pro Gly Thr Pro
    450                 455                 460

Val Phe Ser Tyr Gly Asp Glu Ile Gly Leu Asp Ala Ala Ala Leu Pro
465                 470                 475                 480

Gly Gln Pro Met Glu Ala Pro Val Met Leu Trp Asp Glu Ser Ser Phe
            485                 490                 495

Pro Asp Ile Pro Gly Ala Val Ser Ala Asn Met Thr Val Lys Gly Gln
            500                 505                 510

Ser Glu Asp Pro Gly Ser Leu Leu Ser Leu Phe Arg Arg Leu Ser Asp
        515                 520                 525

Gln Arg Ser Lys Glu Arg Ser Leu Leu His Gly Asp Phe His Ala Phe
    530                 535                 540

Ser Ala Gly Pro Gly Leu Phe Ser Tyr Ile Arg His Trp Asp Gln Asn
545                 550                 555                 560

Glu Arg Phe Leu Val Val Leu Asn Phe Gly Asp Val Gly Leu Ser Ala
            565                 570                 575

Gly Leu Gln Ala Ser Asp Leu Pro Ala Ser Ala Ser Leu Pro Ala Lys
            580                 585                 590

Ala Asp Leu Leu Leu Ser Thr Gln Pro Gly Arg Glu Glu Gly Ser Pro
        595                 600                 605

Leu Glu Leu Glu Arg Leu Lys Leu Glu Pro His Glu Gly Leu Leu Leu
    610                 615                 620

Arg Phe Pro Tyr Ala Ala
625                 630

<210> SEQ ID NO 38
<211> LENGTH: 507
<212> TYPE: PRT
<213> ORGANISM: Homo sapiens
<220> FEATURE:
<221> NAME/KEY: MISC_FEATURE
<223> OTHER INFORMATION: human Large neutral amino acids transporter
      small subunit 1 (LAT1; SLC7A5) isoform 1 Uniprot Q01650

<400> SEQUENCE: 38

Met Ala Gly Ala Gly Pro Lys Arg Arg Ala Leu Ala Ala Pro Ala Ala
1               5                   10                  15

Glu Glu Lys Glu Glu Ala Arg Glu Lys Met Leu Ala Ala Lys Ser Ala
```

```
                20                  25                  30
Asp Gly Ser Ala Pro Ala Gly Glu Gly Glu Gly Val Thr Leu Gln Arg
             35                  40                  45
Asn Ile Thr Leu Leu Asn Gly Val Ala Ile Val Gly Thr Ile Ile
 50                  55                  60
Gly Ser Gly Ile Phe Val Thr Pro Thr Gly Val Leu Lys Glu Ala Gly
 65                  70                  75                  80
Ser Pro Gly Leu Ala Leu Val Val Trp Ala Ala Cys Gly Val Phe Ser
             85                  90                  95
Ile Val Gly Ala Leu Cys Tyr Ala Glu Leu Gly Thr Thr Ile Ser Lys
            100                 105                 110
Ser Gly Gly Asp Tyr Ala Tyr Met Leu Glu Val Tyr Gly Ser Leu Pro
            115                 120                 125
Ala Phe Leu Lys Leu Trp Ile Glu Leu Leu Ile Ile Arg Pro Ser Ser
            130                 135                 140
Gln Tyr Ile Val Ala Leu Val Phe Ala Thr Tyr Leu Leu Lys Pro Leu
145                 150                 155                 160
Phe Pro Thr Cys Pro Val Pro Glu Glu Ala Ala Lys Leu Val Ala Cys
            165                 170                 175
Leu Cys Val Leu Leu Leu Thr Ala Val Asn Cys Tyr Ser Val Lys Ala
            180                 185                 190
Ala Thr Arg Val Gln Asp Ala Phe Ala Ala Lys Leu Leu Ala Leu
            195                 200                 205
Ala Leu Ile Ile Leu Leu Gly Phe Val Gln Ile Gly Lys Gly Asp Val
            210                 215                 220
Ser Asn Leu Asp Pro Asn Phe Ser Phe Glu Gly Thr Lys Leu Asp Val
225                 230                 235                 240
Gly Asn Ile Val Leu Ala Leu Tyr Ser Gly Leu Phe Ala Tyr Gly Gly
            245                 250                 255
Trp Asn Tyr Leu Asn Phe Val Thr Glu Glu Met Ile Asn Pro Tyr Arg
            260                 265                 270
Asn Leu Pro Leu Ala Ile Ile Ile Ser Leu Pro Ile Val Thr Leu Val
            275                 280                 285
Tyr Val Leu Thr Asn Leu Ala Tyr Phe Thr Thr Leu Ser Thr Glu Gln
            290                 295                 300
Met Leu Ser Ser Glu Ala Val Ala Val Asp Phe Gly Asn Tyr His Leu
305                 310                 315                 320
Gly Val Met Ser Trp Ile Ile Pro Val Phe Val Gly Leu Ser Cys Phe
            325                 330                 335
Gly Ser Val Asn Gly Ser Leu Phe Thr Ser Ser Arg Leu Phe Phe Val
            340                 345                 350
Gly Ser Arg Glu Gly His Leu Pro Ser Ile Leu Ser Met Ile His Pro
            355                 360                 365
Gln Leu Leu Thr Pro Val Pro Ser Leu Val Phe Thr Cys Val Met Thr
            370                 375                 380
Leu Leu Tyr Ala Phe Ser Lys Asp Ile Phe Ser Val Ile Asn Phe Phe
385                 390                 395                 400
Ser Phe Phe Asn Trp Leu Cys Val Ala Leu Ala Ile Ile Gly Met Ile
            405                 410                 415
Trp Leu Arg His Arg Lys Pro Glu Leu Glu Arg Pro Ile Lys Val Asn
            420                 425                 430
Leu Ala Leu Pro Val Phe Phe Ile Leu Ala Cys Leu Phe Leu Ile Ala
            435                 440                 445
```

```
Val Ser Phe Trp Lys Thr Pro Val Glu Cys Gly Ile Gly Phe Thr Ile
    450                 455                 460

Ile Leu Ser Gly Leu Pro Val Tyr Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
            500                 505

<210> SEQ ID NO 39
<211> LENGTH: 535
<212> TYPE: PRT
<213> ORGANISM: Homo sapiens
<220> FEATURE:
<221> NAME/KEY: MISC_FEATURE
<223> OTHER INFORMATION: human Large neutral amino acids transporter
      small subunit 2 (LAT2; SLC7A8) isoform 1 Uniprot Q9UHI5

<400> SEQUENCE: 39

Met Glu Glu Gly Ala Arg His Arg Asn Asn Thr Glu Lys Lys His Pro
1               5                   10                  15

Gly Gly Gly Glu Ser Asp Ala Ser Pro Glu Ala Gly Ser Gly Gly Gly
            20                  25                  30

Gly Val Ala Leu Lys Lys Glu Ile Gly Leu Val Ser Ala Cys Gly Ile
        35                  40                  45

Ile Val Gly Asn Ile Ile Gly Ser Gly Ile Phe Val Ser Pro Lys Gly
    50                  55                  60

Val Leu Glu Asn Ala Gly Ser Val Gly Leu Ala Leu Ile Val Trp Ile
65              70                  75                  80

Val Thr Gly Phe Ile Thr Val Val Gly Ala Leu Cys Tyr Ala Glu Leu
                85                  90                  95

Gly Val Thr Ile Pro Lys Ser Gly Gly Asp Tyr Ser Tyr Val Lys Asp
            100                 105                 110

Ile Phe Gly Gly Leu Ala Gly Phe Leu Arg Leu Trp Ile Ala Val Leu
        115                 120                 125

Val Ile Tyr Pro Thr Asn Gln Ala Val Ile Ala Leu Thr Phe Ser Asn
    130                 135                 140

Tyr Val Leu Gln Pro Leu Phe Pro Thr Cys Phe Pro Pro Glu Ser Gly
145                 150                 155                 160

Leu Arg Leu Leu Ala Ala Ile Cys Leu Leu Leu Thr Trp Val Asn
                165                 170                 175

Cys Ser Ser Val Arg Trp Ala Thr Arg Val Gln Asp Ile Phe Thr Ala
                180                 185                 190

Gly Lys Leu Leu Ala Leu Ala Leu Ile Ile Met Gly Ile Val Gln
            195                 200                 205

Ile Cys Lys Gly Glu Tyr Phe Trp Leu Glu Pro Lys Asn Ala Phe Glu
    210                 215                 220

Asn Phe Gln Glu Pro Asp Ile Gly Leu Val Ala Leu Ala Phe Leu Gln
225                 230                 235                 240

Gly Ser Phe Ala Tyr Gly Gly Trp Asn Phe Leu Asn Tyr Val Thr Glu
                245                 250                 255

Glu Leu Val Asp Pro Tyr Lys Asn Leu Pro Arg Ala Ile Phe Ile Ser
            260                 265                 270

Ile Pro Leu Val Thr Phe Val Tyr Val Phe Ala Asn Val Ala Tyr Val
        275                 280                 285
```

```
Thr Ala Met Ser Pro Gln Glu Leu Leu Ala Ser Asn Ala Val Ala Val
    290                 295                 300

Thr Phe Gly Glu Lys Leu Leu Gly Val Met Ala Trp Ile Met Pro Ile
305                 310                 315                 320

Ser Val Ala Leu Ser Thr Phe Gly Gly Val Asn Gly Ser Leu Phe Thr
                325                 330                 335

Ser Ser Arg Leu Phe Phe Ala Gly Ala Arg Glu Gly His Leu Pro Ser
            340                 345                 350

Val Leu Ala Met Ile His Val Lys Arg Cys Thr Pro Ile Pro Ala Leu
        355                 360                 365

Leu Phe Thr Cys Ile Ser Thr Leu Leu Met Leu Val Thr Ser Asp Met
370                 375                 380

Tyr Thr Leu Ile Asn Tyr Val Gly Phe Ile Asn Tyr Leu Phe Tyr Gly
385                 390                 395                 400

Val Thr Val Ala Gly Gln Ile Val Leu Arg Trp Lys Lys Pro Asp Ile
                405                 410                 415

Pro Arg Pro Ile Lys Ile Asn Leu Leu Phe Pro Ile Ile Tyr Leu Leu
            420                 425                 430

Phe Trp Ala Phe Leu Leu Val Phe Ser Leu Trp Ser Glu Pro Val Val
        435                 440                 445

Cys Gly Ile Gly Leu Ala Ile Met Leu Thr Gly Val Pro Val Tyr Phe
    450                 455                 460

Leu Gly Val Tyr Trp Gln His Lys Pro Lys Cys Phe Ser Asp Phe Ile
465                 470                 475                 480

Glu Leu Leu Thr Leu Val Ser Gln Lys Met Cys Val Val Val Tyr Pro
                485                 490                 495

Glu Val Glu Arg Gly Ser Gly Thr Glu Glu Ala Asn Glu Asp Met Glu
            500                 505                 510

Glu Gln Gln Gln Pro Met Tyr Gln Pro Thr Pro Thr Lys Asp Lys Asp
        515                 520                 525

Val Ala Gly Gln Pro Gln Pro
    530                 535

<210> SEQ ID NO 40
<211> LENGTH: 523
<212> TYPE: PRT
<213> ORGANISM: Homo sapiens
<220> FEATURE:
<221> NAME/KEY: MISC_FEATURE
<223> OTHER INFORMATION: human Asc-type amino acid transporter 1 (Asc-1;
      SLC7A10) isoform 1 Uniprot Q9NS82

<400> SEQUENCE: 40

Met Ala Gly His Thr Gln Gln Pro Ser Gly Arg Gly Asn Pro Arg Pro
1               5                   10                  15

Ala Pro Ser Pro Ser Pro Val Pro Gly Thr Val Pro Gly Ala Ser Glu
            20                  25                  30

Arg Val Ala Leu Lys Lys Glu Ile Gly Leu Leu Ser Ala Cys Thr Ile
        35                  40                  45

Ile Ile Gly Asn Ile Ile Gly Ser Gly Ile Phe Ile Ser Pro Lys Gly
    50                  55                  60

Val Leu Glu His Ser Gly Ser Val Gly Leu Ala Leu Phe Val Trp Val
65                  70                  75                  80

Leu Gly Gly Gly Val Thr Ala Leu Gly Ser Leu Cys Tyr Ala Glu Leu
                85                  90                  95

Gly Val Ala Ile Pro Lys Ser Gly Gly Asp Tyr Ala Tyr Val Thr Glu
```

```
                100                 105                 110
Ile Phe Gly Gly Leu Ala Gly Phe Leu Leu Leu Trp Ser Ala Val Leu
            115                 120                 125
Ile Met Tyr Pro Thr Ser Leu Ala Val Ile Ser Met Thr Phe Ser Asn
            130                 135                 140
Tyr Val Leu Gln Pro Val Phe Pro Asn Cys Ile Pro Pro Thr Thr Ala
145                 150                 155                 160
Ser Arg Val Leu Ser Met Ala Cys Leu Met Leu Leu Thr Trp Val Asn
            165                 170                 175
Ser Ser Ser Val Arg Trp Ala Thr Arg Ile Gln Asp Met Phe Thr Gly
            180                 185                 190
Gly Lys Leu Leu Ala Leu Ser Leu Ile Ile Gly Val Gly Leu Leu Gln
            195                 200                 205
Ile Phe Gln Gly His Phe Glu Glu Leu Arg Pro Ser Asn Ala Phe Ala
            210                 215                 220
Phe Trp Met Thr Pro Ser Val Gly His Leu Ala Leu Ala Phe Leu Gln
225                 230                 235                 240
Gly Ser Phe Ala Phe Ser Gly Trp Asn Phe Leu Asn Tyr Val Thr Glu
                245                 250                 255
Glu Met Val Asp Ala Arg Lys Asn Leu Pro Arg Ala Ile Phe Ile Ser
            260                 265                 270
Ile Pro Leu Val Thr Phe Val Tyr Thr Phe Thr Asn Ile Ala Tyr Phe
            275                 280                 285
Thr Ala Met Ser Pro Gln Glu Leu Leu Ser Ser Asn Ala Val Ala Val
            290                 295                 300
Thr Phe Gly Glu Lys Leu Leu Gly Tyr Phe Ser Trp Val Met Pro Val
305                 310                 315                 320
Ser Val Ala Leu Ser Thr Phe Gly Gly Ile Asn Gly Tyr Leu Phe Thr
                325                 330                 335
Tyr Ser Arg Leu Cys Phe Ser Gly Ala Arg Glu Gly His Leu Pro Ser
            340                 345                 350
Leu Leu Ala Met Ile His Val Arg His Cys Thr Pro Ile Pro Ala Leu
            355                 360                 365
Leu Val Cys Cys Gly Ala Thr Ala Val Ile Met Leu Val Gly Asp Thr
            370                 375                 380
Tyr Thr Leu Ile Asn Tyr Val Ser Phe Ile Asn Tyr Leu Cys Tyr Gly
385                 390                 395                 400
Val Thr Ile Leu Gly Leu Leu Leu Arg Trp Arg Arg Pro Ala Leu
                405                 410                 415
His Arg Pro Ile Lys Val Asn Leu Leu Ile Pro Val Ala Tyr Leu Val
            420                 425                 430
Phe Trp Ala Phe Leu Leu Val Phe Ser Phe Ile Ser Glu Pro Met Val
            435                 440                 445
Cys Gly Val Gly Val Ile Ile Ile Leu Thr Gly Val Pro Ile Phe Phe
450                 455                 460
Leu Gly Val Phe Trp Arg Ser Lys Pro Lys Cys Val His Arg Leu Thr
465                 470                 475                 480
Glu Ser Met Thr His Trp Gly Gln Glu Leu Cys Phe Val Tyr Pro
                485                 490                 495
Gln Asp Ala Pro Glu Glu Glu Asn Gly Pro Cys Pro Ser Leu
            500                 505                 510
Leu Pro Ala Thr Asp Lys Pro Ser Lys Pro Gln
            515                 520
```

<210> SEQ ID NO 41
<211> LENGTH: 642
<212> TYPE: PRT
<213> ORGANISM: Homo sapiens
<220> FEATURE:
<221> NAME/KEY: MISC_FEATURE
<223> OTHER INFORMATION: human Sodium- and chloride-dependent neutral
    and basic amino acid transporter B(0+)(ATB0,+; SLC6A14) isoform 1
    Uniprot Q9UN76

<400> SEQUENCE: 41

Met Asp Lys Leu Lys Cys Pro Ser Phe Phe Lys Cys Arg Glu Lys Glu
1               5                   10                  15

Lys Val Ser Ala Ser Ser Glu Asn Phe His Val Gly Glu Asn Asp Glu
            20                  25                  30

Asn Gln Asp Arg Gly Asn Trp Ser Lys Lys Ser Asp Tyr Leu Leu Ser
        35                  40                  45

Met Ile Gly Tyr Ala Val Gly Leu Gly Asn Val Trp Arg Phe Pro Tyr
50                  55                  60

Leu Thr Tyr Ser Asn Gly Gly Ala Phe Leu Ile Pro Tyr Ala Ile
65                  70                  75                  80

Met Leu Ala Leu Ala Gly Leu Pro Leu Phe Phe Leu Glu Cys Ser Leu
                85                  90                  95

Gly Gln Phe Ala Ser Leu Gly Pro Val Ser Val Trp Arg Ile Leu Pro
            100                 105                 110

Leu Phe Gln Gly Val Gly Ile Thr Met Val Leu Ile Ser Ile Phe Val
        115                 120                 125

Thr Ile Tyr Tyr Asn Val Ile Ala Tyr Ser Leu Tyr Tyr Met Phe
130                 135                 140

Ala Ser Phe Gln Ser Glu Leu Pro Trp Lys Asn Cys Ser Ser Trp Ser
145                 150                 155                 160

Asp Lys Asn Cys Ser Arg Ser Pro Ile Val Thr His Cys Asn Val Ser
                165                 170                 175

Thr Val Asn Lys Gly Ile Gln Glu Ile Ile Gln Met Asn Lys Ser Trp
            180                 185                 190

Val Asp Ile Asn Asn Phe Thr Cys Ile Asn Gly Ser Glu Ile Tyr Gln
        195                 200                 205

Pro Gly Gln Leu Pro Ser Glu Gln Tyr Trp Asn Lys Val Ala Leu Gln
    210                 215                 220

Arg Ser Ser Gly Met Asn Glu Thr Gly Val Ile Val Trp Tyr Leu Ala
225                 230                 235                 240

Leu Cys Leu Leu Leu Ala Trp Leu Ile Val Gly Ala Ala Leu Phe Lys
                245                 250                 255

Gly Ile Lys Ser Ser Gly Lys Val Val Tyr Phe Thr Ala Leu Phe Pro
            260                 265                 270

Tyr Val Val Leu Leu Ile Leu Leu Val Arg Gly Ala Thr Leu Glu Gly
        275                 280                 285

Ala Ser Lys Gly Ile Ser Tyr Tyr Ile Gly Ala Gln Ser Asn Phe Thr
    290                 295                 300

Lys Leu Lys Glu Ala Glu Val Trp Lys Asp Ala Ala Thr Gln Ile Phe
305                 310                 315                 320

Tyr Ser Leu Ser Val Ala Trp Gly Gly Leu Val Ala Leu Ser Ser Tyr
                325                 330                 335

Asn Lys Phe Lys Asn Asn Cys Phe Ser Asp Ala Ile Val Val Cys Leu
            340                 345                 350

```
Thr Asn Cys Leu Thr Ser Val Phe Ala Gly Phe Ala Ile Phe Ser Ile
            355                 360                 365

Leu Gly His Met Ala His Ile Ser Gly Lys Glu Val Ser Gln Val Val
        370                 375                 380

Lys Ser Gly Phe Asp Leu Ala Phe Ile Ala Tyr Pro Glu Ala Leu Ala
385                 390                 395                 400

Gln Leu Pro Gly Gly Pro Phe Trp Ser Ile Leu Phe Phe Met Leu
                405                 410                 415

Leu Thr Leu Gly Leu Asp Ser Gln Phe Ala Ser Ile Glu Thr Ile Thr
            420                 425                 430

Thr Thr Ile Gln Asp Leu Phe Pro Lys Val Met Lys Lys Met Arg Val
            435                 440                 445

Pro Ile Thr Leu Gly Cys Cys Leu Val Leu Phe Leu Leu Gly Leu Val
            450                 455                 460

Cys Val Thr Gln Ala Gly Ile Tyr Trp Val His Leu Ile Asp His Phe
465                 470                 475                 480

Cys Ala Gly Trp Gly Ile Leu Ile Ala Ala Ile Leu Glu Leu Val Gly
                485                 490                 495

Ile Ile Trp Ile Tyr Gly Gly Asn Arg Phe Ile Glu Asp Thr Glu Met
            500                 505                 510

Met Ile Gly Ala Lys Arg Trp Ile Phe Trp Leu Trp Trp Arg Ala Cys
            515                 520                 525

Trp Phe Val Ile Thr Pro Ile Leu Leu Ile Ala Ile Phe Ile Trp Ser
        530                 535                 540

Leu Val Gln Phe His Arg Pro Asn Tyr Gly Ala Ile Pro Tyr Pro Asp
545                 550                 555                 560

Trp Gly Val Ala Leu Gly Trp Cys Met Ile Val Phe Cys Ile Ile Trp
                565                 570                 575

Ile Pro Ile Met Ala Ile Ile Lys Ile Ile Gln Ala Lys Gly Asn Ile
            580                 585                 590

Phe Gln Arg Leu Ile Ser Cys Cys Arg Pro Ala Ser Asn Trp Gly Pro
        595                 600                 605

Tyr Leu Glu Gln His Arg Gly Glu Arg Tyr Lys Asp Met Val Asp Pro
610                 615                 620

Lys Lys Glu Ala Asp His Glu Ile Pro Thr Val Ser Gly Ser Arg Lys
625                 630                 635                 640

Pro Glu

<210> SEQ ID NO 42
<211> LENGTH: 634
<212> TYPE: PRT
<213> ORGANISM: Homo sapiens
<220> FEATURE:
<221> NAME/KEY: MISC_FEATURE
<223> OTHER INFORMATION: human Sodium-dependent neutral amino acid
      transporter B(0)AT1 (B(0)AT1; SLC6A19) isoform 1 Uniprot Q695T7

<400> SEQUENCE: 42

Met Val Arg Leu Val Leu Pro Asn Pro Gly Leu Asp Ala Arg Ile Pro
1               5                   10                  15

Ser Leu Ala Glu Leu Glu Thr Ile Glu Gln Glu Ala Ser Ser Arg
                20                  25                  30

Pro Lys Trp Asp Asn Lys Ala Gln Tyr Met Leu Thr Cys Leu Gly Phe
            35                  40                  45

Cys Val Gly Leu Gly Asn Val Trp Arg Phe Pro Tyr Leu Cys Gln Ser
```

```
                50               55                60
     His Gly Gly Ala Phe Met Ile Pro Phe Leu Ile Leu Val Leu
     65               70                75                80

Glu Gly Ile Pro Leu Leu Tyr Leu Glu Phe Ala Ile Gly Gln Arg Leu
                      85                90                95

Arg Arg Gly Ser Leu Gly Val Trp Ser Ser Ile His Pro Ala Leu Lys
                     100               105               110

Gly Leu Gly Leu Ala Ser Met Leu Thr Ser Phe Met Val Gly Leu Tyr
                     115               120               125

Tyr Asn Thr Ile Ile Ser Trp Ile Met Trp Tyr Leu Phe Asn Ser Phe
                 130               135               140

Gln Glu Pro Leu Pro Trp Ser Asp Cys Pro Leu Asn Glu Asn Gln Thr
     145               150               155               160

Gly Tyr Val Asp Glu Cys Ala Arg Ser Ser Pro Val Asp Tyr Phe Trp
                     165               170               175

Tyr Arg Glu Thr Leu Asn Ile Ser Thr Ser Ile Ser Asp Ser Gly Ser
                     180               185               190

Ile Gln Trp Trp Met Leu Leu Cys Leu Ala Cys Ala Trp Ser Val Leu
                     195               200               205

Tyr Met Cys Thr Ile Arg Gly Ile Glu Thr Thr Gly Lys Ala Val Tyr
     210               215               220

Ile Thr Ser Thr Leu Pro Tyr Val Val Leu Thr Ile Phe Leu Ile Arg
     225               230               235               240

Gly Leu Thr Leu Lys Gly Ala Thr Asn Gly Ile Val Phe Leu Phe Thr
                     245               250               255

Pro Asn Val Thr Glu Leu Ala Gln Pro Asp Thr Trp Leu Asp Ala Gly
                     260               265               270

Ala Gln Val Phe Phe Ser Phe Ser Leu Ala Phe Gly Gly Leu Ile Ser
                     275               280               285

Phe Ser Ser Tyr Asn Ser Val His Asn Cys Glu Lys Asp Ser Val
                 290               295               300

Ile Val Ser Ile Ile Asn Gly Phe Thr Ser Val Tyr Val Ala Ile Val
     305               310               315               320

Val Tyr Ser Val Ile Gly Phe Arg Ala Thr Gln Arg Tyr Asp Asp Cys
                     325               330               335

Phe Ser Thr Asn Ile Leu Thr Leu Ile Asn Gly Phe Asp Leu Pro Glu
                     340               345               350

Gly Asn Val Thr Gln Glu Asn Phe Val Asp Met Gln Gln Arg Cys Asn
                     355               360               365

Ala Ser Asp Pro Ala Ala Tyr Ala Gln Leu Val Phe Gln Thr Cys Asp
     370               375               380

Ile Asn Ala Phe Leu Ser Glu Ala Val Glu Gly Thr Gly Leu Ala Phe
     385               390               395               400

Ile Val Phe Thr Glu Ala Ile Thr Lys Met Pro Leu Ser Pro Leu Trp
                     405               410               415

Ser Val Leu Phe Phe Ile Met Leu Phe Cys Leu Gly Leu Ser Ser Met
                     420               425               430

Phe Gly Asn Met Glu Gly Val Val Pro Leu Gln Asp Leu Arg Val
                     435               440               445

Ile Pro Pro Lys Trp Pro Lys Glu Val Leu Thr Gly Leu Ile Cys Leu
     450               455               460

Gly Thr Phe Leu Ile Gly Phe Ile Phe Thr Leu Asn Ser Gly Gln Tyr
     465               470               475               480
```

```
Trp Leu Ser Leu Leu Asp Ser Tyr Ala Gly Ser Ile Pro Leu Leu Ile
                485                 490                 495

Ile Ala Phe Cys Glu Met Phe Ser Val Val Tyr Val Tyr Gly Val Asp
            500                 505                 510

Arg Phe Asn Lys Asp Ile Glu Phe Met Ile Gly His Lys Pro Asn Ile
        515                 520                 525

Phe Trp Gln Val Thr Trp Arg Val Val Ser Pro Leu Leu Met Leu Ile
    530                 535                 540

Ile Phe Leu Phe Phe Phe Val Val Glu Val Ser Gln Glu Leu Thr Tyr
545                 550                 555                 560

Ser Ile Trp Asp Pro Gly Tyr Glu Glu Phe Pro Lys Ser Gln Lys Ile
                565                 570                 575

Ser Tyr Pro Asn Trp Val Tyr Val Val Val Ile Val Ala Gly Val
            580                 585                 590

Pro Ser Leu Thr Ile Pro Gly Tyr Ala Ile Tyr Lys Leu Ile Arg Asn
                595                 600                 605

His Cys Gln Lys Pro Gly Asp His Gln Gly Leu Val Ser Thr Leu Ser
        610                 615                 620

Thr Ala Ser Met Asn Gly Asp Leu Lys Tyr
625                 630

<210> SEQ ID NO 43
<211> LENGTH: 515
<212> TYPE: PRT
<213> ORGANISM: Homo sapiens
<220> FEATURE:
<221> NAME/KEY: MISC_FEATURE
<223> OTHER INFORMATION: human Monocarboxylate transporter 10 (TAT1;
      SLC16A10) isoform 1 Uniprot Q8TF71

<400> SEQUENCE: 43

Met Val Leu Ser Gln Glu Glu Pro Asp Ser Ala Arg Gly Thr Ser Glu
1               5                   10                  15

Ala Gln Pro Leu Gly Pro Ala Pro Thr Gly Ala Ala Pro Pro Pro Gly
            20                  25                  30

Pro Gly Pro Ser Asp Ser Pro Glu Ala Ala Val Glu Lys Val Glu Val
        35                  40                  45

Glu Leu Ala Gly Pro Ala Thr Ala Glu Pro His Glu Pro Pro Glu Pro
    50                  55                  60

Pro Glu Gly Gly Trp Gly Trp Leu Val Met Leu Ala Ala Met Trp Cys
65                  70                  75                  80

Asn Gly Ser Val Phe Gly Ile Gln Asn Ala Cys Gly Val Leu Phe Val
                85                  90                  95

Ser Met Leu Glu Thr Phe Gly Ser Lys Asp Asp Asp Lys Met Val Phe
            100                 105                 110

Lys Thr Ala Trp Val Gly Ser Leu Ser Met Gly Met Ile Phe Phe Cys
        115                 120                 125

Cys Pro Ile Val Ser Val Phe Thr Asp Leu Phe Gly Cys Arg Lys Thr
    130                 135                 140

Ala Val Val Gly Ala Ala Val Gly Phe Val Gly Leu Met Ser Ser Ser
145                 150                 155                 160

Phe Val Ser Ser Ile Glu Pro Leu Tyr Leu Thr Tyr Gly Ile Ile Phe
                165                 170                 175

Ala Cys Gly Cys Ser Phe Ala Tyr Gln Pro Ser Leu Val Ile Leu Gly
            180                 185                 190
```

```
His Tyr Phe Lys Lys Arg Leu Gly Leu Val Asn Gly Ile Val Thr Ala
            195                 200                 205

Gly Ser Ser Val Phe Thr Ile Leu Leu Pro Leu Leu Leu Arg Val Leu
210                 215                 220

Ile Asp Ser Val Gly Leu Phe Tyr Thr Leu Arg Val Leu Cys Ile Phe
225                 230                 235                 240

Met Phe Val Leu Phe Leu Ala Gly Phe Thr Tyr Arg Pro Leu Ala Thr
            245                 250                 255

Ser Thr Lys Asp Lys Glu Ser Gly Gly Ser Gly Ser Ser Leu Phe Ser
            260                 265                 270

Arg Lys Lys Phe Ser Pro Pro Lys Lys Ile Phe Asn Phe Ala Ile Phe
            275                 280                 285

Lys Val Thr Ala Tyr Ala Val Trp Ala Val Gly Ile Pro Leu Ala Leu
            290                 295                 300

Phe Gly Tyr Phe Val Pro Tyr Val His Leu Met Lys His Val Asn Glu
305                 310                 315                 320

Arg Phe Gln Asp Glu Lys Asn Lys Glu Val Val Leu Met Cys Ile Gly
            325                 330                 335

Val Thr Ser Gly Val Gly Arg Leu Leu Phe Gly Arg Ile Ala Asp Tyr
            340                 345                 350

Val Pro Gly Val Lys Lys Val Tyr Leu Gln Val Leu Ser Phe Phe Phe
            355                 360                 365

Ile Gly Leu Met Ser Met Met Ile Pro Leu Cys Ser Ile Phe Gly Ala
            370                 375                 380

Leu Ile Ala Val Cys Leu Ile Met Gly Leu Phe Asp Gly Cys Phe Ile
385                 390                 395                 400

Ser Ile Met Ala Pro Ile Ala Phe Glu Leu Val Gly Ala Gln Asp Val
            405                 410                 415

Ser Gln Ala Ile Gly Phe Leu Leu Gly Phe Met Ser Ile Pro Met Thr
            420                 425                 430

Val Gly Pro Pro Ile Ala Gly Leu Leu Arg Asp Lys Leu Gly Ser Tyr
            435                 440                 445

Asp Val Ala Phe Tyr Leu Ala Gly Val Pro Pro Leu Ile Gly Gly Ala
450                 455                 460

Val Leu Cys Phe Ile Pro Trp Ile His Ser Lys Lys Gln Arg Glu Ile
465                 470                 475                 480

Ser Lys Thr Thr Gly Lys Glu Lys Met Glu Lys Met Leu Glu Asn Gln
            485                 490                 495

Asn Ser Leu Leu Ser Ser Ser Gly Met Phe Lys Lys Glu Ser Asp
            500                 505                 510

Ser Ile Ile
        515

<210> SEQ ID NO 44
<211> LENGTH: 504
<212> TYPE: PRT
<213> ORGANISM: Homo sapiens
<220> FEATURE:
<221> NAME/KEY: MISC_FEATURE
<223> OTHER INFORMATION: human Proton-coupled amino acid transporter 4
      (PAT4; SLC36A4) isoform 1 Uniprot Q6YBV0

<400> SEQUENCE: 44

Met Glu Ala Ala Ala Thr Pro Ala Ala Ala Gly Ala Ala Arg Arg Glu
1               5                   10                  15

Glu Leu Asp Met Asp Val Met Arg Pro Leu Ile Asn Glu Gln Asn Phe
```

```
                20              25              30
Asp Gly Thr Ser Asp Glu Glu His Glu Gln Glu Leu Leu Pro Val Gln
                35              40              45
Lys His Tyr Gln Leu Asp Asp Gln Glu Gly Ile Ser Phe Val Gln Thr
            50              55              60
Leu Met His Leu Leu Lys Gly Asn Ile Gly Thr Gly Leu Leu Gly Leu
65              70              75              80
Pro Leu Ala Ile Lys Asn Ala Gly Ile Val Leu Gly Pro Ile Ser Leu
                85              90              95
Val Phe Ile Gly Ile Ile Ser Val His Cys Met His Ile Leu Val Arg
                100             105             110
Cys Ser His Phe Leu Cys Leu Arg Phe Lys Lys Ser Thr Leu Gly Tyr
                115             120             125
Ser Asp Thr Val Ser Phe Ala Met Glu Val Ser Pro Trp Ser Cys Leu
            130             135             140
Gln Lys Gln Ala Ala Trp Gly Arg Ser Val Val Asp Phe Phe Leu Val
145             150             155             160
Ile Thr Gln Leu Gly Phe Cys Ser Val Tyr Ile Val Phe Leu Ala Glu
                165             170             175
Asn Val Lys Gln Val His Glu Gly Phe Leu Glu Ser Lys Val Phe Ile
                180             185             190
Ser Asn Ser Thr Asn Ser Ser Asn Pro Cys Glu Arg Arg Ser Val Asp
            195             200             205
Leu Arg Ile Tyr Met Leu Cys Phe Leu Pro Phe Ile Ile Leu Leu Val
            210             215             220
Phe Ile Arg Glu Leu Lys Asn Leu Phe Val Leu Ser Phe Leu Ala Asn
225             230             235             240
Val Ser Met Ala Val Ser Leu Val Ile Tyr Gln Tyr Val Val Arg
                245             250             255
Asn Met Pro Asp Pro His Asn Leu Pro Ile Val Ala Gly Trp Lys Lys
                260             265             270
Tyr Pro Leu Phe Phe Gly Thr Ala Val Phe Ala Phe Glu Gly Ile Gly
                275             280             285
Val Val Leu Pro Leu Glu Asn Gln Met Lys Glu Ser Lys Arg Phe Pro
            290             295             300
Gln Ala Leu Asn Ile Gly Met Gly Ile Val Thr Thr Leu Tyr Val Thr
305             310             315             320
Leu Ala Thr Leu Gly Tyr Met Cys Phe His Asp Glu Ile Lys Gly Ser
                325             330             335
Ile Thr Leu Asn Leu Pro Gln Asp Val Trp Leu Tyr Gln Ser Val Lys
                340             345             350
Ile Leu Tyr Ser Phe Gly Ile Phe Val Thr Tyr Ser Ile Gln Phe Tyr
                355             360             365
Val Pro Ala Glu Ile Ile Pro Gly Ile Thr Ser Lys Phe His Thr
                370             375             380
Lys Trp Lys Gln Ile Cys Glu Phe Gly Ile Arg Ser Phe Leu Val Ser
385             390             395             400
Ile Thr Cys Ala Gly Ala Ile Leu Ile Pro Arg Leu Asp Ile Val Ile
                405             410             415
Ser Phe Val Gly Ala Val Ser Ser Thr Leu Ala Leu Ile Leu Pro
            420             425             430
Pro Leu Val Glu Ile Leu Thr Phe Ser Lys Glu His Tyr Asn Ile Trp
            435             440             445
```

```
Met Val Leu Lys Asn Ile Ser Ile Ala Phe Thr Gly Val Val Gly Phe
            450                 455                 460

Leu Leu Gly Thr Tyr Ile Thr Val Glu Glu Ile Ile Tyr Pro Thr Pro
465                 470                 475                 480

Lys Val Val Ala Gly Thr Pro Gln Ser Pro Phe Leu Asn Leu Asn Ser
                485                 490                 495

Thr Cys Leu Thr Ser Gly Leu Lys
            500

<210> SEQ ID NO 45
<211> LENGTH: 18
<212> TYPE: PRT
<213> ORGANISM: Artificial Sequence
<220> FEATURE:
<223> OTHER INFORMATION: T2A sequence

<400> SEQUENCE: 45

Glu Gly Arg Gly Ser Leu Leu Thr Cys Gly Asp Val Glu Glu Asn Pro
1               5                   10                  15

Gly Pro

<210> SEQ ID NO 46
<211> LENGTH: 22
<212> TYPE: PRT
<213> ORGANISM: Artificial Sequence
<220> FEATURE:
<223> OTHER INFORMATION: P2A sequence

<400> SEQUENCE: 46

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 47
<211> LENGTH: 19
<212> TYPE: PRT
<213> ORGANISM: Artificial Sequence
<220> FEATURE:
<223> OTHER INFORMATION: P2A sequence

<400> SEQUENCE: 47

Ala Thr Asn Phe Ser Leu Leu Lys Gln Ala Gly Asp Val Glu Glu Asn
1               5                   10                  15

Pro Gly Pro

<210> SEQ ID NO 48
<211> LENGTH: 22
<212> TYPE: PRT
<213> ORGANISM: Artificial Sequence
<220> FEATURE:
<223> OTHER INFORMATION: E2A sequence

<400> SEQUENCE: 48

Gln Cys Thr Asn Tyr Ala Leu Leu Lys Leu Ala Gly Asp Val Glu Ser
1               5                   10                  15

Asn Pro Gly Pro Ser Glu
            20

<210> SEQ ID NO 49
<211> LENGTH: 22
<212> TYPE: PRT
```

```
<213> ORGANISM: Artificial Sequence
<220> FEATURE:
<223> OTHER INFORMATION: F2A sequence

<400> SEQUENCE: 49

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 50
<211> LENGTH: 20
<212> TYPE: DNA
<213> ORGANISM: Artificial Sequence
<220> FEATURE:
<223> OTHER INFORMATION: GCN2 CRISPR gRNA target sequence

<400> SEQUENCE: 50
cgctgagaaa tgactgcacg                                             20

<210> SEQ ID NO 51
<211> LENGTH: 20
<212> TYPE: DNA
<213> ORGANISM: Artificial Sequence
<220> FEATURE:
<223> OTHER INFORMATION: GCN2 CRISPR gRNA target sequence

<400> SEQUENCE: 51
catatacttc ttcaccagtt                                             20

<210> SEQ ID NO 52
<211> LENGTH: 20
<212> TYPE: DNA
<213> ORGANISM: Artificial Sequence
<220> FEATURE:
<223> OTHER INFORMATION: GCN2 CRISPR gRNA target sequence

<400> SEQUENCE: 52
atgtactcac acatctggat                                             20

<210> SEQ ID NO 53
<211> LENGTH: 20
<212> TYPE: DNA
<213> ORGANISM: Artificial Sequence
<220> FEATURE:
<223> OTHER INFORMATION: GCN2 CRISPR gRNA target sequence

<400> SEQUENCE: 53
ttaggtgatg atctttgaac                                             20

<210> SEQ ID NO 54
<211> LENGTH: 20
<212> TYPE: DNA
<213> ORGANISM: Artificial Sequence
<220> FEATURE:
<223> OTHER INFORMATION: GCN2 CRISPR gRNA target sequence

<400> SEQUENCE: 54
tacctcccca cagtgtttct                                             20

<210> SEQ ID NO 55
<211> LENGTH: 20
<212> TYPE: DNA
<213> ORGANISM: Artificial Sequence
<220> FEATURE:
<223> OTHER INFORMATION: GCN2 CRISPR gRNA target sequence
```

-continued

```
<400> SEQUENCE: 55
aaaatctcgc ctagaagaac                                                      20

<210> SEQ ID NO 56
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 56
ccgagctctg attgaccgaa                                                      20

<210> SEQ ID NO 57
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 57
aggaaatcga gcgcctgacc                                                      20

<210> SEQ ID NO 58
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 58
ccagctggac agtgtcccga                                                      20

<210> SEQ ID NO 59
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 59
ctcttgcagg tcctcatacc                                                      20

<210> SEQ ID NO 60
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 60
gcgagtcgcc tctacttccc                                                      20

<210> SEQ ID NO 61
<211> LENGTH: 20
<212> TYPE: DNA
<213> ORGANISM: Artificial Sequence
<220> FEATURE:
<223> OTHER INFORMATION: CHOP CRISPR gRNA target sequence

<400> SEQUENCE: 61
ggctggaaag cagcgcatga                                                      20

<210> SEQ ID NO 62
```

```
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 62
aggatcgtaa ggtttgggac                                             20

<210> SEQ ID NO 63
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 63
taataagcag ccccccaga                                              20

<210> SEQ ID NO 64
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 64
ccactcaccc ttgctgttgt                                             20

<210> SEQ ID NO 65
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 65
tctcttagat gattacctgg                                             20

<210> SEQ ID NO 66
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 66
gcaacgtaag cagtgtagtc                                             20

<210> SEQ ID NO 67
<211> LENGTH: 20
<212> TYPE: DNA
<213> ORGANISM: Artificial Sequence
<220> FEATURE:
<223> OTHER INFORMATION: ATF4 CRISPR gRNA target sequence

<400> SEQUENCE: 67
tttgcagagg atgccttctc                                             20

<210> SEQ ID NO 68
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 68
```

```
caggctgtca aaattcgagc                                            20

<210> SEQ ID NO 69
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 69
cattcttcgt catgttgctg                                            20

<210> SEQ ID NO 70
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 70
gtacttgtca tcaaagaccc                                            20

<210> SEQ ID NO 71
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 71
gtaaaagaag ccctaagagc                                            20

<210> SEQ ID NO 72
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 72
gaccagagac ccatctattt                                            20

<210> SEQ ID NO 73
<211> LENGTH: 20
<212> TYPE: DNA
<213> ORGANISM: Artificial Sequence
<220> FEATURE:
<223> OTHER INFORMATION: eIF2alpha CRISPR gRNA target sequence

<400> SEQUENCE: 73
tacagaaaac atgcccatta                                            20
```